(12) United States Patent
Shimizu et al.

(10) Patent No.: US 7,560,558 B2
(45) Date of Patent: Jul. 14, 2009

(54) COMPOUND HAVING TGFβ INHIBITORY ACTIVITY AND MEDICINAL COMPOSITION CONTAINING THE SAME

(75) Inventors: Kiyoshi Shimizu, Takasaki (JP); Toshiyuki Shimizu, Takasaki (JP); Kaname Kimura, Takasaki (JP); Kazuki Kawakami, Takasaki (JP); Masayoshi Nakoji, Takasaki (JP)

(73) Assignee: Kirin Beer Kabushiki Kaisha, Tokyo-to (JP)

(*) Notice: Subject to any disclaimer, the term of this patent is extended or adjusted under 35 U.S.C. 154(b) by 316 days.

(21) Appl. No.: 10/525,087

(22) PCT Filed: Aug. 22, 2003

(86) PCT No.: PCT/JP03/10647

§ 371 (c)(1), (2), (4) Date: Feb. 23, 2005

(87) PCT Pub. No.: WO2004/018430

PCT Pub. Date: Mar. 4, 2004

(65) Prior Publication Data

US 2006/0111375 A1     May 25, 2006

(30) Foreign Application Priority Data

Aug. 23, 2002 (JP) ............................. 2002-244028

(51) Int. Cl.
C07D 215/44 (2006.01)
C07D 239/72 (2006.01)

(52) U.S. Cl. ..................... 546/160; 544/284; 544/288; 544/293

(58) Field of Classification Search ............... 546/160; 544/284, 288, 293, 405; 514/255, 266.1, 514/253.06
See application file for complete search history.

(56) References Cited

U.S. PATENT DOCUMENTS

| 5,245,036 | A   |   | 9/1993  | Robey et al. |            |
|-----------|-----|---|---------|--------------|------------|
| 6,593,333 | B1  | * | 7/2003  | Cumming      | 514/266.1  |
| 6,716,847 | B2  | * | 4/2004  | Cumming      | 514/253.06 |
| 6,977,259 | B2  | * | 12/2005 | Mortlock et al. | 514/255.05 |
| 2006/0111375 | A1 |   | 5/2006  | Shimizu et al. |          |

FOREIGN PATENT DOCUMENTS

| EP | 0 326 330 | 8/1989 |
|----|-----------|--------|
| EP | 0 602 851 | 6/1994 |
| EP | 0 860 433 | 8/1998 |
| FR | 1 388 756 | 1/1965 |
| JP | 43-23458  | 10/1968 |
| WO | 95/15758  | 6/1995 |
| WO | 96/18299  | 6/1996 |
| WO | 96/39145  | 12/1996 |
| WO | 97/22596  | 6/1997 |
| WO | 98/13350  | 4/1998 |
| WO | 00/12497  | 3/2000 |
| WO | 00/20402  | 4/2000 |
| WO | 00/47212  | 8/2000 |
| WO | 00/50405  | 8/2000 |
| WO | 00/56720  | 9/2000 |
| WO | 01/21594  | 3/2001 |
| WO | 02/30926  | 4/2002 |
| WO | 03/033472 | 4/2003 |
| WO | 2004/013091 | 2/2004 |
| WO | 2004/056812 | 7/2004 |
| WO | 2004/063365 | 7/2004 |

OTHER PUBLICATIONS

Cornea, Mar. 1997, vol. 16(2), pp. 177-187.*
J Am Soc Nephrol, Feb. 2003, vol. 14(2), pp. 377-388.*
J Am Soc Nephrol, Joly 2003, vol. 14(7), pp. 1816-1824.*
Thorax, Sep. 1999, vol. 54(9), pp. 805-812.*
U.S. Appl. No. 10/589,981, filed Aug. 18, 2006, Shimizu, et al.
Bridges, Alexander J. et al. "Tyrosine Kinase Inhibitors. 8. An Unusually Steep Structure-Activity Relationship for Analogues of 4-(3-Bromoanilino)-6,7-dimethoxyquinazoline (PD153035), a Potent Inhibitor of the Epidermal Growth Factor Receptor", J. Med. Chem., vol. 39, No. 1, pp. 267-276 1996.
Database Crossfire Beilstein Beilstein Insitut Zur Foerderung Der Chemischen Wissenschaften, Frankfurt Am Main, DE; XP002485648, Data base accession No. 4510537 abstract & Heterocycles, vol. 40, No. 2, 1995, pp. 653-660.
Database Crossfire Beilstein Beilstein Insitut Zur Foerderung Der Chemischen Wissenschaften, Frankfurt Am Main, DE; XP002485649 Database accession No. 7221863 abstract & Heterocycles, vol. 40, No. 2, 1995, pp. 653-650.

(Continued)

Primary Examiner—D. Margaret Seaman
(74) Attorney, Agent, or Firm—Oblon, Spivak, McClelland, Maier & Neustadt, P.C.

(57) ABSTRACT

The present invention provides compounds represented by formula (I) and pharmaceutically acceptable salts and solvates thereof:

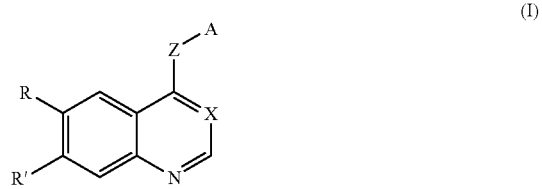

(I)

wherein X represents CH or N; Z represents —O—, —NH— or —C(=O)—; R and R' represent a hydrogen atom, hydroxyl, a halogen atom, optionally substituted alkyl, optionally substituted alkenyl optionally substituted alkoxy, amino, aminocarbonyl, or an optionally substituted heterocyclic group; and A represents an optionally substituted specific carbocyclic or heterocyclic group. The compounds according to the present invention have excellent TGFβ inhibitory activity.

13 Claims, No Drawings

OTHER PUBLICATIONS

Database Crossfire Beilstein Beilstein Insitut Zur Foerderung Der Chemischen Wissenschaften, Frankfurt Am Main, DE; XP002485650 Database accession No. 7225536 abstract & Heterocycles, vol. 40, No. 2, 1995, pp. 653-650.

Laurent F. Hennequin, et al., "Design and Structure-Activity Relationship of a New Class of Potent VEGF Receptor Tyrosine Kinase Inhibitors" J. Med. Chem. 1999, 42, pp. 5369-5389.

Diane H. Boschelli, et al. "Optimization of 4-Phenylamino-3-quinolinecarbonitriles as Potent Inhibitors of Src Kinase Activity", J. Med. Chem. 2001, 44, pp. 3965-3977.

Yanong D. Yang, et al., "Inhibitors of Src Tyrosine Kinase: The Preparation and Structure-Activity Relationship of 4-Anilino-3-cyanoquinolines and 4-Anilinoquinazolines", Bioorganic & Medicinal Chemistry Letters 10 (2000), pp. 2477-2480.

Kazuo Kubo, et al., "A Novel Series of 4-Phenoxyquinolines: Potent and Highly Selective Inhibitors of PDGF Receptor Autophosphorylation" Bioorganic & Medical Chemistry Letters, vol. 7, No. 23, pp. 2935-2940, (1997).

Michael R. Myers, et al. "The Preparation and SAR of 4-(Anilino), 4-(Phenoxy), and 4-(Thiophenoxy)-Quinazolines: Inhibitors of p.56$^{1ck}$ and EGF-R Tyrosine Kinase Activity", Bioorganic & Medicinal Chemistry Letters, vol. 7, No. 4, pp. 417-420, (1997).

\* cited by examiner

COMPOUND HAVING TGFβ INHIBITORY ACTIVITY AND MEDICINAL COMPOSITION CONTAINING THE SAME

BACKGROUND OF THE INVENTION

1. Field of the Invention

The present invention relates to compounds having TGFβ inhibitory activity and more particularly to quinoline derivatives and quinazoline derivatives having TGFβ inhibitory activity. The present invention also relates to a pharmaceutical composition useful for the prophylaxis or therapy of diseases for which TGFβ inhibition is effective therapeutically.

2. Background Art

TGFβ (transforming growth factor-β) is a cytokine which is very important to organisms for regulating growth differentiation of cells and repair and regeneration of cells after tissue disorder. Disruption of its signal is known to cause onset and progression of various diseases.

The relationship between TGFβ and fibrosis of organs or tissues is well known. The fibrosis of an organ or a tissue takes place as a result of excessive accumulation of extracellular matrix proteins within the organ for repair or as a defence mechanism upon damage to the organ or the like by some cause. The extracellular matrix proteins refer to a substance surrounding cells of the tissue. For example, fibrotic proteins such as collagen and elastin, glycoconjugates such as proteoglycan, and glycoproteins such as fibronectin and laminin is included as major extracellular matrix proteins.

When the level of fibrosis of an organ is low, the organ can be recovered to a normal state without leaving any scar. On the other hand, when the level of lesion of the organ is large or when the lesion continues, the fibrosis causes damage to the innate function of the organ. Further, the damage causes new fibrosis to create a vicious cycle. Ultimately, this causes organ failure and, in the worst case, sometimes leads to death.

TGFβ is known to play an important role in the accumulation of the extracellular matrix proteins.

For example, the administration of TGFβ to normal animals is known to cause fibrosis in various tissues (*International Review of Experimental Pathology*, 34B: 43-67, 1993). Further, fibrosis of tissues is also observed in the TGFβ1-highly expressing transgenic mice, and in the normal animals transduced TGFβ1 gene locally (*Proc. Natl. Acad. Sci. USA*, 92: 2572-2576, 1995; *Laboratory Investigation*, 74: 991-1003, 1995).

TGFβ is considered to participate in the fibrosis of tissues through the following mechanism.

1) TGFβ strongly induces mRNA expression of extracellular matrix proteins such as fibronectin (*Journal of Biological Chemistry*, 262: 6443-6446, 1987), collagen (*Proc. Natl. Acad. Sci. USA*, 85 1105-1108, 1988), and proteoglycan (*Journal of Biological Chemistry*, 263: 3039-3045, 1988) in cells.

2) TGFβ lowers the expression of an extracellular degradative enzyme for extracellular matrix proteins (*Journal of Biological Chemistry*, 263: 16999-17005, 1988) and, in addition, highly promotes the expression of an inhibitor of the extracellular matrix degradative enzyme (*Cancer Research*, 49: 2553-2553, 1989). Consequently, the degradation of the extracellular matrix proteins is suppressed.

3) Further, TGFβ increases the expression of integrin as a receptor of extracellular matrix proteins and promotes the deposition of the extracellular matrix proteins around cells (*Journal of Biological Chemistry*, 263: 4586-4592, 1988).

4) Furthermore, TGFβ proliferates cells which produce extracellular matrix proteins, such as fibroblast cells (*American Journal of Physiology*, 264: F199-F205, 1993).

TGFβ is known to be mainly involved in the fibrosis of organs such as kidney, liver, lung, heart, bone marrow, and skin.

For example, the analysis of expression of TGFβ1 clearly demonstrate an increase in expression of TGFβ1 in diseases such as human acute renal diseases, chronic renal diseases, diabetic nephropathy, renal allograft rejection, HIV nephropathy, hepatic fibrosis, cirrhosis, pulmonary fibrosis, scleroderma, and keloid (New Engl. J. Med., 331, 1286-1292, 1994), and the correlation between the TGFb1 expression and the extracellular matrix protein expression.

Further, in pathologic aminal models, such as renal failure diseases, diabetic nephropathy, hepatic fibrosis, pulmonary fibrosis, and scleroderma, it is reported that the administration of soluble receptor comprising the extracellular region of type II receptor and TGFβ-neutralizing antibody can inhibit fibrosis and can improve the pathology (*Nature*, 346: 371-374, 1990; *Journal of the British Thoracic Society*, 54: 805-812, 1999; *Journal of Immunology*, 163: 5693-5699, 1999; *Human Gene Therapy*, 11: 33-42, 2000; *Proc. Natl. Acad. Sci. USA.*, 97: 8015-20, 2000).

These facts show that the inhibition of TGFβ is useful for the prophylaxis and therapy against all diseases involving fibrosis including chronic renal diseases.

Further, TGFβ is also involved in restenosis and arteriosclerosis.

In restenosis model animals, an increase in expression of TGFβ1 and its receptor is observed in a injured blood vessel, and TGFβ1 is suggested to be involved in the formation of new intima after balloon injury is suggested (*Clinical and Experimental Pharmacology and Physiology* 23: 193-200, 1996).

In arteriosclerosis, a highly expression of TGFβ1 is observed in non-foam macrophage infiltrated in an affected region in which matrix proteins synthesis strongly takes place, (*American Journal of Physiology* 146: 1140-1149, 1995), suggesting that the non-foam macrophage participates in matrix protein synthesis in an arteriosclerosis affected region through TGFβ1.

Further, in a cell-migration test, TGFβ1 is also reported to be a potent stimulating factor for migration of smooth muscle cells causative of arteriosclerosis and vascular restenosis (*Biochem Biophys Res Commun.*, 169: 725-729, 1990).

TGFβ1 is also involved in wound repair.

For example, an experiment using a neutralizing antibody against TGFβ1 demonstrates that the inhibition of TGFβ1 suppresses excessive scar after wound and is useful for functional recovery. Specifically, it is also known that the administration of a neutralizing antibody against TGFβ1 or TGFβ2 to rats can suppress scar and promotes dermal cell construction via a mechanism of the suppression of dermal fibronectin and collagen deposition and a reduction in the number of monocytes and macrophages (*Journal of Cellular Science* 108: 985-1002, 1995). In other tissues, the administration of anti-TGFβ neutralizing antibody improves lesions in a rabbit corneal injury model and a rat gastric ulcer model (*Cornea* 16: 177-187, 1997; *An international Journal of gastroenterology & Hepatology* 39: 172-175, 1996).

Further, TGFβ1 is also known to be involved in peritoneal adhesion.

For example, it is suggested that the inhibition of TGFβ is effective in suppressing peritoneal adhesion and subdermal fibrotic adhesion after surgery (*J. Surg. Res.*, 65: 135-138, 1996). A number of articles report that the administration of an anti-TGFβ neutralizing antibody or a soluble type II TGFβ receptor to cancer disease model animals has also beneficial effects on suppression of tumor growth and cancer metastasis (*Journal of Clinical Investigation,* 92: 2569-76, 1993; *Clinical Cancer Research* 7: 2931-2940, 2001; *Cancer Res.* 59: 2210-6, 1999; *Journal of Clinical Investigation* 109: 1551-1559, 2002; *Journal of Clinical Investigation* 109: 1607-1615, 2002).

Tumors usually acquire tumor growth capability and metastatic capability by inducing angiogenesis on host side and by lowering immunity of the host side through TGFβ produced by the tumors per se. The suppression mechanism is based on the evidences that the administration of the anti-TGFβ neutralizing antibody suppress the tumor growth capability and metastatic capability. Thus, the inhibition of TGFβ is considered to be effective in suppressing cancer metastasis and cancer cell growth.

It is also reported that an anti-TGFβ1 neutralizing antibody is effective in in-vitro amplification of hematopoietic stem cells (*Experimental Hematology* 26: 374-381, 1998). Further, TGFβ1 has growth inhibitory activity against a large variety of cells. Accordingly, the inhibition of TGFβ is expected to be effective in in-vitro amplification of a large variety of cells including hematopoietic stem cells.

SUMMARY OF THE INVENTION

The present inventors have now found that a certain group of quinoline derivatives and quinazoline derivatives have inhibitory activity against TGFβ1. The present invention has been made based on such finding.

It is an object of the present invention to provide a compound having potent TGFβ inhibitory activity.

According to the present invention, there is provided a compound represented by formula (I) or a pharmaceutically acceptable salt or solvate thereof:

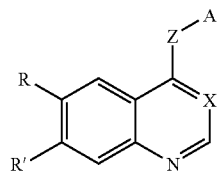

(I)

wherein
X represents CH or N,
Z represents —O—, —NH—, —S—, or —C(=O)—,
R and R', which may be the same or different, represent
1) a hydrogen atom,
2) a halogen atom,
3) $C_{1-6}$ alkyl optionally substituted by hydroxyl, a halogen atom, or a saturated or unsaturated five- or six-membered heterocyclic group,
4) $C_{2-6}$ alkenyl optionally substituted by an oxygen atom or $C_{1-4}$ alkoxy,
5) amino in which one or two hydrogen atoms on the amino group are optionally substituted by $C_{1-6}$ alkyl, and the $C_{1-6}$ alkyl group is optionally substituted by hydroxyl or a saturated or unsaturated five- or six-membered carbocyclic or heterocyclic group,
6) —C(=O)—$NH_2$ wherein one or two hydrogen atoms on the aminocarbonyl group are optionally substituted by $C_{1-6}$ alkyl,
7) —OR" wherein R" represents a hydrogen atom, or —$(CH_2)_m$—$R^a$ wherein $R^a$ represents a hydrogen atom, a halogen atom, hydroxyl, a saturated or unsaturated three- to six-membered carbocyclic or heterocyclic group, $C_{1-4}$ alkoxy, $C_{1-4}$ alkoxycarbonyl, or —$NR^bR^c$ wherein $R^b$ and $R^c$, which may be the same or different, represent a hydrogen atom or $C_{1-6}$ alkyl, in which the $C_{1-6}$ alkyl group is optionally substituted by hydroxyl, an oxygen atom, amino, a nitrogen atom, or $C_{1-4}$ alkyl, and $R^b$ and $R^c$ may combine with a nitrogen atom attached thereto to form a saturated or unsaturated five- or six-membered heterocyclic group, which may further comprise one or more heteroatoms, and in which the heterocyclic group is optionally substituted by $C_{1-4}$ alkyl, optionally substituted by hydroxyl, hydroxyl, an oxygen atom, aminocarbonyl, $C_{1-4}$ alkoxy, $C_{1-4}$ alkoxycarbonyl, or a saturated or unsaturated five- or six-membered heterocyclic group, and the heterocyclic group may condense with another saturated or unsaturated five- or six-membered carbocyclic or heterocyclic group to form a bicyclic group; m is an integer of 1 to 6; and the alkyl chain part in this group, —$(CH_2)m$-, is optionally substituted by hydroxyl, an oxygen atom, —$OR^d$ group, wherein $R^d$ represents $C_{1-4}$ alkyl or $C_{1-4}$ alkylcarbonyl, or $C_{1-4}$ alkyl optionally substituted by hydroxyl or a halogen atom, or
8) a saturated or unsaturated five- or six-membered heterocyclic group, and
A represents any group selected from the group consisting of formulae (a) to (c):
(a) a group of formula (a):

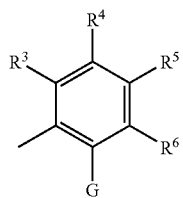

(a)

wherein
$R^3$ to $R^6$, which may be the same or different, represent
a hydrogen atom,
hydroxyl,
a halogen atom,
$C_{1-6}$ alkyl,
$C_{1-10}$ alkoxy optionally substituted by a halogen atom or phenyl,
$C_{2-6}$ alkenylcarbonyloxy,
$C_{1-4}$ alkylcarbonyl,
$C_{1-4}$ alkylthio, or
phenyl optionally substituted by a halogen atom,
$R^3$ and $R^4$, $R^4$ and $R^5$, and $R^5$ and $R^6$ each may combine with a carbon atom attached thereto to form a saturated or unsaturated five- or six-membered carbocyclic or heterocyclic group in which the carbocyclic or heterocyclic group is optionally substituted by a hydrogen atom, a halogen atom, hydroxyl, or $C_{1-4}$ alkyl,
G represents
—C(=O)—$R^7$,
—$CH_2$—N(—$R^{11}$)$R^{12}$, or
—C(—$R^{13}$)(=$NR^{14}$),
wherein
$R^7$ represents
a hydrogen atom, $C_{1-8}$ alkyl optionally substituted by $C_{1-4}$ alkoxy, an oxygen atom, or a saturated or unsaturated five- or six-membered carbocyclic group, $C_{2-6}$ alkenyl optionally substituted by a saturated or unsaturated five- or six-membered carbocyclic group, a saturated or unsaturated five- or six-membered carbocyclic group or heterocyclic group in which the carbocyclic or heterocyclic group is optionally substituted by hydroxyl, $C_{1-4}$ alkyl, or $C_{1-4}$ alkoxy, and the $C_{1-4}$ alkoxy group is optionally substituted by a halogen atom or a saturated or unsaturated five- or six-membered heterocyclic group, group —O—$R^8$, or group —N(—$R^9$)$R^{10}$ wherein $R^8$ represents $C_{1-10}$ alkyl optionally substituted by a saturated or unsaturated five- or six-membered carbocyclic group, $C_{2-8}$ alkenyl, or a saturated or unsaturated five- or six-membered carbocyclic group in which the carbocyclic group is optionally substituted by a halogen atom, $R^9$ and $R^{10}$, and $R^{11}$ and $R^{12}$ which may be the same or different, each represent a hydrogen atom, $C_{1-6}$ alkyl, a saturated or unsaturated five- or six-membered carbocyclic group in which the carbocyclic group is optionally substituted by a halogen atom, or naphthyl optionally substituted by a halogen atom, $R^9$ and $R^{10}$, or $R^{11}$ and $R^{12}$ may combine with a nitrogen atom attached thereto to form a saturated or unsaturated five- or six-membered heterocyclic group which may further comprise one or more heteroatoms and in which the heterocyclic group is optionally substituted by $C_{1-4}$ alkyl optionally substituted by hydroxyl, or a saturated or unsaturated five- or six-membered heterocyclic group, $R^{13}$ represents a hydrogen atom or $C_{1-4}$ alkyl, $R^{14}$ represents a hydrogen atom, hydroxyl, $C_{1-4}$ alkoxy optionally substituted by a saturated or unsaturated six-membered carbocyclic group, $C_{2-6}$ alkenyloxy, phenyloxy, or amino optionally substituted by a saturated or unsaturated six-membered heterocyclic group, (b) a group of formula (b):

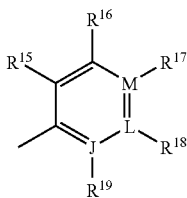

wherein any one of J, L, and M represents a nitrogen atom with the remaining two representing a carbon atom, $R^{15}$ to $R^{19}$, which may be the same or different, represent a hydrogen atom, a halogen atom, nitro, cyano, $C_{1-6}$ alkyl in which the alkyl group is optionally substituted by hydroxyl; phenyl; amino optionally substituted by $C_{1-4}$ alkyl; $C_{1-4}$ alkylcarbonyloxy; or a saturated or unsaturated six-membered heterocyclic group optionally substituted by $C_{1-4}$ alkyl, $C_{1-8}$ alkoxy, $C_{1-4}$ alkylcarbonyl, $C_{2-6}$ alkenyl optionally substituted by a saturated or unsaturated five- or six-membered carbocyclic group, $C_{2-6}$ alkynyl optionally substituted by $C_{1-4}$ alkylsilyl, $C_{1-4}$ alkylthio, a saturated or unsaturated three- to eight-membered carbocyclic oxy group, a saturated or unsaturated six-membered carbocyclic carbonyl or heterocyclic carbonyl group optionally substituted by $C_{1-4}$ alkyl, or a saturated or unsaturated three- to eight-membered carbocyclic or heterocyclic group in which the carbocyclic or heterocyclic group is optionally substituted by hydroxyl; cyano; a halogen atom; $C_{1-4}$ alkoxy; phenyloxy; $C_{1-4}$ alkylcarbonyl; amino optionally substituted by $C_{1-4}$ alkyl or $C_{1-4}$ alkylcarbonyl; aminocarbonyl optionally substituted by $C_{1-4}$ alkyl; or $C_{1-4}$ alkyl optionally substituted by hydroxyl or a halogen atom, $R^{15}$ and $R^{16}$, $R^{16}$ and $R^{17}$, $R^{17}$ and $R^{18}$, and $R^{18}$ and $R^{19}$ each may combine with a carbon atom attached thereto to form a saturated or unsaturated five- or six-membered carbocyclic or heterocyclic group, and the carbocyclic or heterocyclic group is optionally substituted by $C_{1-4}$ alkyl, provided that, among $R^{17}$ to $R^{19}$, those in which J, L, or M attached thereto is a nitrogen atom are absent, and (c) a group of formula (c):

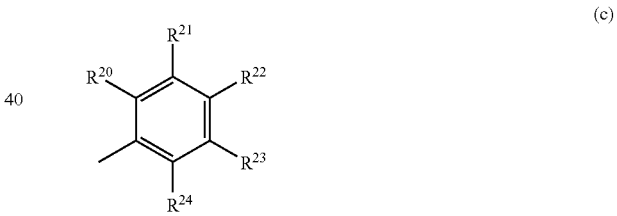

wherein $R^{20}$ to $R^{24}$, which may be the same or different, represent a hydrogen atom, a halogen atom, $C_{1-10}$ alkyl optionally substituted by hydroxyl, a saturated or unsaturated five- or six-membered carbocyclic or heterocyclic group, $C_{1-8}$ alkoxy, $C_{2-6}$ alkenyl optionally substituted by $C_{1-4}$ alkyl, $C_{1-4}$ alkoxy, an oxygen atom or phenyl, phenylcarbonyl optionally substituted by $C_{1-4}$ alkyl, amino optionally substituted by phenyl, nitro, or a saturated or unsaturated five- or six-membered carbocyclic or heterocyclic group in which the carbocyclic or heterocyclic group is optionally substituted by $C_{1-6}$ alkyl, $R^{20}$ and $R^{21}$, or $R^{23}$ and $R^{24}$ may combine with a carbon atom attached thereto to form a saturated or unsaturated five- or six-membered carbocyclic or heterocyclic group, and $R^{21}$ and $R^{22}$ or $R^{22}$ and $R^{23}$ may combine with a carbon atom attached thereto to form a saturated or unsaturated fiveor six-membered carbocyclic or heterocyclic group in which the carbocyclic or heterocyclic group is optionally substituted by a halogen atom, $C_{1-4}$ alkyl, $C_{1-4}$ alkylcarbonyl, $C_{1-6}$ alkoxycarbonyl, or an oxygen atom, and the carbocyclic or heterocyclic group may condense with another saturated or unsaturated five- or six-membered carbocyclic or heterocyclic group to form a tricyclic group together with the six-membered carbocyclic ring of formula (c).

In a preferred embodiment of the present invention, the compound according to the present invention is a compound represented by formula (II), or a pharmaceutically acceptable salt or solvate thereof:

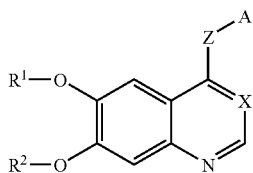

(II)

wherein

X, Z, and A are as defined above, $R^1$ and $R^2$, which may be the same or different, represent a hydrogen atom, or —$(CH_2)m$-$R^a$ wherein $R^a$ represents a hydrogen atom, a halogen atom, hydroxyl, a saturated or unsaturated three- to six-membered carbocyclic or heterocyclic group, $C_{1-4}$ alkoxy, $C_{1-4}$ alkoxycarbonyl, or —$NR^bR^c$ wherein $R^b$ and $R^c$, which may be the same or different, represent a hydrogen atom or $C_{1-6}$ alkyl, in which the $C_{1-6}$ alkyl group is optionally substituted by hydroxyl, an oxygen atom, amino, a nitrogen atom, or $C_{1-4}$ alkyl, and $R^b$ and $R^c$ may combine with a nitrogen atom attached thereto to form a saturated or unsaturated five- or six-membered heterocyclic group, which may further comprise one or more heteroatoms, and in which the heterocyclic group is optionally substituted by $C_{1-4}$ alkyl, optionally substituted by hydroxyl, hydroxyl, an oxygen atom, aminocarbonyl, $C_{1-4}$ alkoxy, $C_{1-4}$ alkoxycarbonyl, or a saturated or unsaturated five- or six-membered heterocyclic group, and the heterocyclic group may condense with another saturated or unsaturated five- or six-membered carbocyclic or heterocyclic group to form a bicyclic group; m is an integer of 1 to 6; and the alkyl chain part in this group, —$(CH_2)m$-, is optionally substituted by hydroxyl, an oxygen atom, —$OR^d$ group, wherein $R^d$ represents $C_{1-4}$ alkyl or $C_{1-4}$ alkylcarbonyl, or $C_{1-4}$ alkyl optionally substituted by hydroxyl or a halogen atom.

The compound according to the present invention can be used for the theraphy or prophylaxis of diseases for which TGFβ inhibition is effective therapeutically or prophylactically.

Diseases for which TGFβ inhibition is effective therapeutically or prophylactically include, for example, chronic renal disease, acute renal disease, hepatic fibrosis, cirrhosis, fibroid lung, scleroderma, wound healing, arthritis, congestive cardiac disease, ulcer, ocular disorder, cornea disorder, diabetic nephropathy, peritoneal sclerosis, arterial sclerosis, peritoneal adhesion, and subdermal adhesion and, further, malignant tumors. Accordingly, the compound according to the present invention is useful for the prophylaxis or therapy of such diseases. The compound according to the present invention is also useful for in-vitro amplification of hematopoietic stem cells.

The pharmaceutical composition according to the present invention comprises as an active ingredient the compound represented by formula (I) according to the present invention.

The TGFβ inhibitor according to the present invention comprises the compound according to the present invention.

The method for treating or preventing a disease for which TGFβ inhibition is effective therapeutically or prophylactically according to the present invention comprises the step of administering a therapeutically or prophylactically effective amount of the compound represented by formula (I) according to the present invention or a pharmaceutically acceptable salt or solvate thereof to a patient who should undergo therapy of a disease for which TGFβ inhibition is effective therapeutically or prophylactically.

The method for amplifying cells in vitro according to the present invention comprises the step of administering, to target cells in vitro, the compound represented by formula (I) according to the present invention or a pharmaceutically acceptable salt or solvate thereof in an amount effective for promoting cell amplification to amplify cells.

DETAILED DESCRIPTION OF THE INVENTION

Compound of Formula (I)

The terms "alkyl," "alkoxy," "alkenyl," and "alkynyl" as used herein as a group or a part of a group respectively mean straight chain or branched chain alkyl, alkoxy, alkenyl, and alkynyl.

The terms "alkylcarbonyl," "alkylsilyl," "alkylthio," "alkoxycarbonyl," "alkenylcarbonyloxy," and "alkenyloxy" as used herein as a group or a part of a group respectively mean straight chain or branched chain alkylcarbonyl, alkylsilyl, alkylthio, alkoxycarbonyl, alkenylcarbonyloxy, and alkenyloxy.

Accordingly, for example, the "$C_{1-10}$ alkyl" and "$C_{1-10}$ alkoxy" as used herein as a group or a part of a group respectively mean straight chain or branched chain alkyl and alkoxy having 1 to 10 carbon atoms.

"$C_{1-10}$ alkyl" is preferably $C_{1-8}$ alkyl, more preferably $C_{1-6}$ alkyl, still more preferably $C_{1-4}$ alkyl. "$C_{1-8}$ alkyl" is preferably $C_{1-6}$ alkyl, more preferably $C_{1-4}$ alkyl. "$C_{1-6}$ alkyl" is preferably $C_{1-4}$ alkyl, more preferably $C_{1-2}$ alkyl. "$C_{1-4}$ alkyl" is preferably $C_{1-2}$ alkyl.

"$C_{1-10}$ alkoxy" is preferably $C_{1-8}$ alkoxy, more preferably $C_{1-6}$ alkoxy, still more preferably $C_{1-4}$ alkoxy. "$C_{1-8}$ alkoxy" is preferably $C_{1-6}$ alkoxy, more preferably $C_{1-4}$ alkoxy. "$C_{1-4}$ alkoxy" is preferably $C_{1-2}$ alkoxy.

"$C_{2-8}$ alkenyl" is preferably $C_{2-6}$ alkenyl, more preferably $C_{2-4}$ alkenyl. "$C_{2-6}$ alkenyl" is preferably $C_{2-4}$ alkenyl. "$C_{2-4}$ alkenyl" is preferably $C_2$ or $C_3$ alkenyl, more preferably $C_2$ alkenyl.

"$C_{2-6}$ alkynyl" is preferably $C_{2-4}$ alkynyl.

"$C_{1-4}$ alkylcarbonyl" is preferably $C_{1-2}$ alkylcarbonyl.

"$C_{1-4}$ alkylsilyl" is preferably $C_{1-2}$ alkylsilyl.

"$C_{1-4}$ alkylthio" is preferably $C_{1-2}$ alkylthio.

"$C_{1-6}$ alkoxycarbonyl" is preferably $C_{1-4}$ alkoxycarbonyl, more preferably $C_{1-2}$ alkoxycarbonyl.

"$C_{2-6}$ alkenylcarbonyloxy" is preferably $C_{2-4}$ alkenylcarbonyloxy.

"$C_{2-6}$ alkenyloxy" is preferably $C_{2-4}$ alkenyloxy.

Examples of $C_{1-10}$ alkyl include methyl, ethyl, n-propyl, isopropyl, n-butyl, i-butyl, s-butyl, t-butyl, n-pentyl, n-hexyl, n-heptyl, n-octyl, n-nonyl, and n-decyl.

Examples of $C_{1-0}$ alkoxy include methoxy, ethoxy, n-propoxy, i-propoxy, n-butoxy, i-butoxy, s-butoxy, and t-butoxy.

Examples of $C_{2-6}$ alkenyl include allyl, butenyl, pentenyl, and hexenyl.

Examples of $C_{2-6}$ alkynyl include 2-propynyl, butynyl, pentynyl, and hexynyl.

Examples of $C_{1-4}$ alkylcarbonyl include aldehyde, methylcarbonyl, ethylcarbonyl, n-propylcarbonyl, isopropylcarbonyl, n-butylcarbonyl, i-butylcarbonyl, and s-butylcarbonyl.

Examples of $C_{1-4}$ alkylsilyl include methylsilyl, ethylsilyl, n-propylsilyl, isopropylsilyl, n-butylsilyl, i-butylsilyl, and s-butylsilyl.

Examples of $C_{1-4}$ alkylthio include methylthio, ethylthio, n-propylthio, isopropylthio, n-butylthio, i-butylthio, and s-butylthio.

Examples of $C_{1-6}$ alkoxycarbonyl include methoxycarbonyl, ethoxycarbonyl, n-propoxycarbonyl, i-propoxycarbonyl, n-butoxycarbonyl, i-butoxycarbonyl, s-butoxycarbonyl, and t-butoxycarbonyl.

Examples of $C_{2-6}$ alkenylcarbonyloxy include allylcarbonyloxy, butenylcarbonyloxy, pentenylcarbonyloxy, and hexenylcarbonyloxy.

Examples of $C_{2-6}$ alkenyloxy include allyloxy, butenyloxy, pentenyloxy, and hexenyloxy.

The expression alkyl "optionally substituted by" as used herein refers to alkyl, in which one or more hydrogen atoms on the alkyl group have been substituted by one or more substituents which may be the same or different, and unsubstituted alkyl. It will be apparent to a person having ordinary skill in the art that the maximum number of substituents may be determined depending upon the number of substitutable hydrogen atoms on the alkyl group. This is true of groups, which may be substituted, other than the alkyl group, for example, alkylsilyl, alkyloxycarbonyl, alkoxy, alkenyl, alkynyl, phenyl, phenylcarbonyl, naphthyl and the like.

The term "halogen atom" as used herein means a fluorine, chlorine, bromine, or iodine atom.

The terms "unsaturated carbocyclic ring" and "unsaturated heterocyclic ring" as used herein respectively mean carbocyclic and heterocyclic rings having one or more unsaturated bonds such as a double bond.

The "saturated or unsaturated three- to eight-membered carbocyclic ring" is preferably a four- to seven-membered, more preferably five- or six-membered, saturated or unsaturated carbocyclic ring. Examples of saturated or unsaturated three- to eight-membered carbocyclic rings include phenyl, cyclopropyl, cyclobutyl, cyclopentyl, cyclohexyl, and cycloheptyl.

The "saturated or unsaturated three- to eight-membered heterocyclic ring" contains at least one hetero-atom selected from oxygen, nitrogen, and sulfur atoms. The saturated or unsaturated three- to eight-membered heterocyclic ring preferably contains one, two or three hetero-atoms with the remaining ring-constituting atoms being carbon atoms. The saturated or unsaturated three- to eight-membered heterocyclic ring is preferably a saturated or unsaturated four- to seven-membered heterocyclic ring, more preferably a saturated or unsaturated five- or six-membered heterocyclic ring. Examples of saturated or unsaturated three- to eight-membered heterocyclic groups include thienyl, pyridyl, 1,2,3-triazolyl, thiazolyl, imidazolyl, isoxazolyl, pyrazolyl, piperazinyl, piperazino, piperidyl, piperidino, morpholinyl, morpholino, homopiperazinyl, homopiperazino, thiomorpholinyl, thiomorpholino, tetrahydropyrrolyl, and azepanyl.

The saturated or unsaturated carboxylic and heterocyclic groups may condense with another saturated or unsaturated five- to seven-membered carbocyclic or heterocyclic ring to form a bicyclic group, preferably a saturated or unsaturated nine- to twelve-membered bicyclic carbocyclic or heterocyclic group. Such bicyclic groups include naphthyl, quinolyl, 1,2,3,4-tetrahydroquinolyl, 1,4-benzoxanyl, indanyl, indolyl, 1,2,3,4-tetrahydronaphthyl, and phthalimide.

When the carbocyclic or heterocyclic group is substituted by two $C_{1-6}$ alkyl groups, the two alkyl groups may combine together to form an alkylene chain, preferably a $C_{1-3}$ alkylene chain. Carbocyclic or heterocyclic groups having this crosslinked structure include azabicyclo[2.2.2]octanyl, bicyclo[2.2.2]octanyl and norbornanyl.

The "saturated or unsaturated five- to six-membered carbocyclic group" as used herein preferably has a six-membered saturated or unsaturated carbocyclic ring. Examples of saturated or unsaturated five- or six-membered carbocyclic rings include phenyl, cyclopentyl, and cyclohexyl.

The "saturated or unsaturated five- or six-membered heterocyclic group" as used herein refers to a saturated or unsaturated five- or six-membered monocyclic heterocyclic group. That is, the saturated or unsaturated five- or six-membered heterocyclic ring may be a heterocyclic ring that contains one to three, preferably one or two hetero-atoms with the remaining ring-constituting atoms being carbon atoms. The heterocyclic group contains at least one hetero-atom selected from oxygen, nitrogen, and sulfur atoms. Examples of heterocyclic groups include pyridyl, furyl, thienyl, pyrrolyl, pyridazyl, pyrimidyl, morpholinyl, morpholino, isoxazolyl, oxazolyl, thiazolyl, imidazoyl, isothiazolyl, and pyrazyl.

This heterocyclic group is optionally substittued by $C_{1-6}$ alkyl; $C_{1-4}$ alkyl optionally substituted by hydroxyl; or a saturated or unsaturated five- or six-membered heterocyclic group, so far as there is no particular description on the substituent.

The "saturated or unsaturated six-membered carbocyclic oxy group" as used herein include phenyloxy and cyclohexyloxy.

The "saturated or unsaturated five- or six-membered carbocyclic carbonyl group" as used herein preferably has a saturated or unsaturated six-membered carbocyclic ring. Examples of saturated or unsaturated five- or six-membered carbocyclic carbonyl groups include phenylcarbonyl, cyclopentylcarbonyl, and cyclohexylcarbonyl.

The "saturated or unsaturated five- or six-membered heterocyclic carbonyl group" as used herein refers to a carbonyl group containing a saturated or unsaturated five- or six-membered monocyclic heterocyclic group. That is, the heterocyclic group part in the saturated or unsaturated five- or six-membered heterocyclic carbonyl group may be a heterocyclic ring that contains one to three, preferably one or two hetero-atoms with the remaining ring-constituting atoms being carbon atoms. The heterocyclic group contains at least one hetero-atom selected from oxygen, nitrogen, and sulfur atoms. Examples of heterocyclic carbonyl groups include pyridylcarbonyl, furylcarbonyl, thienylcarbonyl, pyrrolylcarbonyl, pyridazylcarbonyl, pyrimidylcarbonyl, morpholinylcarbonyl, morpholinocarbonyl, isoxazolylcarbonyl, oxazolylcarbonyl, thiazolylcarbonyl, imidazoylcarbonyl, isothiazolylcarbonyl, and pyrazylcarbonyl.

In one preferred embodiment of the present invention, at least one of R and R' is selected from the group consisting of
1) a hydrogen atom,
2) a halogen atom,
3) $C_{1-6}$ alkyl optionally substituted by hydroxyl, a halogen atom, or a saturated or unsaturated five- or six-membered heterocyclic group,
4) $C_{2-6}$ alkenyl optionally substituted by an oxygen atom or $C_{1-4}$ alkoxy,
5) amino in which one or two hydrogen atoms on the amino group are optionally substituted by $C_{1-6}$ alkyl, and the $C_{1-6}$ alkyl group is optionally substituted by hydroxyl or a saturated or unsaturated five- or six-membered carbocyclic or heterocyclic group, 6) —C(=O)—NH$_2$ wherein one or two hydrogen atoms on the aminocarbonyl group are optionally substituted by C$_{1-6}$ alkyl, or 8) a saturated or unsaturated five- or six-membered heterocyclic group.

In a more preferred embodiment of the present invention, at least one of R and R' is selected from the group consisting of a hydrogen atom, a halogen atom, C$_{1-4}$ alkyl optionally substituted by hydroxyl, a halogen atom, or a saturated or unsaturated five- or six-membered heterocyclic group, C$_{2-4}$ alkenyl optionally substituted by an oxygen atom or C$_{1-4}$ alkoxy, amino in which one or two hydrogen atoms on the amino group are optionally substituted by C$_{1-4}$ alkyl, and the C$_{1-4}$ alkyl group is optionally substituted by hydroxyl or a saturated or unsaturated five- or six-membered heterocyclic group, —C(=O)—NH$_2$, and a saturated or unsaturated five- or six-membered heterocyclic group.

In a still more preferred embodiment of the present invention, R' is selected from the group consisting of a hydrogen atom, a halogen atom, C$_{1-4}$ alkyl optionally substituted by hydroxyl, a halogen atom, or a saturated or unsaturated five- or six-membered heterocyclic group, C$_{2-4}$ alkenyl optionally substituted by an oxygen atom or C$_{1-4}$ alkoxy, amino in which one or two hydrogen atoms on the amino group are optionally substituted by C$_{1-4}$ alkyl, and the C$_{1-4}$ alkyl group is optionally substituted by hydroxyl or a saturated or unsaturated five- or six-membered heterocyclic group, —C(=O)—NH$_2$, and a saturated or unsaturated five- or six-membered heterocyclic group.

In another more preferred embodiment of the present invention, at least one of R and R' is selected from the group consisting of a hydrogen atom, a halogen atom, C$_{1-4}$ alkyl optionally substituted by hydroxyl, a halogen atom, or a saturated six-membered heterocyclic group, C$_{2-4}$ alkenyl optionally substituted by an oxygen atom or C$_{1-4}$ alkoxy, amino in which one of the hydrogen atoms on the amino group is optionally substituted by C$_{1-4}$ alkyl, and the C$_{1-4}$ alkyl group is optionally substituted by a saturated six-membered heterocyclic group, and an unsaturated six-membered heterocyclic group.

In another preferred embodiment of the present invention, R is represented by —OR$^1$, and R' is represented by —OR$^2$. In this case, R$^1$ and R$^2$, which may be the same or different, represent a hydrogen atom, or —(CH$_2$)m-R$^a$ wherein R$^a$ represents a hydrogen atom, a halogen atom, hydroxyl, a saturated or unsaturated three- to six-membered carbocyclic or heterocyclic group, C$_{1-4}$ alkoxy, C$_{1-4}$ alkoxycarbonyl, or —NR$^b$R$^c$ wherein R$^b$ and R$^c$, which may be the same or different, represent a hydrogen atom or C$_{1-6}$ alkyl, in which the C$_{1-6}$ alkyl group may be substituted by hydroxyl, an oxygen atom, amino, a nitrogen atom, or C$_{1-4}$ alkyl, and R$^b$ and R$^c$ may combine with a nitrogen atom attached thereto to form a saturated or unsaturated five- or six-membered heterocyclic group, which may further comprise one or more heteroatoms, and in which the heterocyclic group is optionally substituted by C$_{1-4}$ alkyl optionally substituted by hydroxyl, hydroxyl, an oxygen atom, aminocarbonyl, C$_{1-4}$ alkoxy, C$_{1-4}$ alkoxycarbonyl, or a saturated or unsaturated five- or six-membered heterocyclic group, and the heterocyclic group may condense with another saturated or unsaturated five- or six-membered carbocyclic or heterocyclic group to form a bicyclic group; m is an integer of 1 to 6; and the alkyl chain part in this group, —(CH$_2$)m-, is optionally substituted by hydroxyl, an oxygen atom, —OR$^d$ group, wherein R$^d$ represents C$_{1-4}$ alkyl or C$_{1-4}$ alkylcarbonyl, or C$_{1-4}$ alkyl optionally substituted by hydroxyl or a halogen atom.

Specifically, in a preferred embodiment of the present invention, the compound represented by formula (I) is represented by formula (II).

In R$^a$ in R", R$^1$ or R$^2$, the "saturated or unsaturated three- to six-membered carbocyclic group" is preferably a saturated or unsaturated six-membered carboxylic group.

In R$^a$ in R", R$^1$ or R$^2$, the "saturated or unsaturated three- to six-membered heterocyclic group" contains at least one heteroatom selected from oxygen, nitrogen, and sulfur atoms, preferably an oxygen or nitrogen atom. Preferably, the saturated or unsaturated three- to six-membered heterocyclic group may be a heterocyclic group which contains one or two heteroatoms with the remaining ring atoms being a carbon atom.

In still another preferred embodiment of the present invention, R$^1$ and R$^2$ represent a hydrogen atom, or —(CH$_2$)m-R$^a$ wherein R$^a$ represents a hydrogen atom, a halogen atom, hydroxyl, a saturated or unsaturated three- to six-membered carbocyclic or heterocyclic group, or —NR$^b$R$^c$ wherein R$^b$ and R$^c$, which may be the same or different, represent a hydrogen atom or C$_{1-6}$ alkyl optionally substituted by hydroxyl, and R$^b$ and R$^c$ may combine with a nitrogen atom attached thereto to form a saturated or unsaturated five- or six-membered heterocyclic group, which may further comprise one or more heteroatoms, and in which the heterocyclic group is optionally substituted by C$_{1-4}$ alkyl optionally substituted by hydroxyl, or a saturated or unsaturated five- or six-membered heterocyclic group; m is an integer of 1 to 5; and the alkyl chain part in this group, —(CH$_2$)m-, is optionally substituted by hydroxyl, an oxygen atom, or —OR$^d$ group, wherein R$^d$ represents C$_{1-4}$ alkyl or C$_{1-4}$ alkylcarbonyl.

In a preferred embodiment of the present invention, R$^1$ and R$^2$, which may be the same or different, represent any group selected from the group consisting of a hydrogen atom, C$_{1-6}$ alkyl optionally substituted by phenyl, and groups of formulae (i) to (vi):

(i) a group of formula (i):

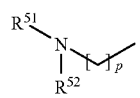

wherein

R$^{51}$ and R$^{52}$, which may be the same or different, represent a hydrogen atom, or C$_{1-8}$ alkyl optionally substituted by hydroxyl, an oxygen atom, amino, or a nitrogen atom, $R^{51}$ and $R^{52}$ may combine with a nitrogen atom attached thereto to form a saturated or unsaturated five- or six-membered heterocyclic group which may further comprise one or more heteroatoms and in which the heterocyclic group is optionally substituted by $C_{1-4}$ alkyl optionally substituted by hydroxyl, hydroxyl, an oxygen atom, aminocarbonyl, $C_{1-4}$ alkoxy, $C_{1-4}$ alkoxycarbonyl, or a saturated or unsaturated five- or six-membered heterocyclic group, and the heterocyclic group optionally formed by allowing $R^{51}$ to combine with $R^{52}$ may condense with another saturated or unsaturated five- or six-membered carbocyclic or heterocyclic group to form a bicyclic group, p is an integer of 2 to 4, preferably 2 or 3, and the alkyl chain part in this group is optionally substituted by hydroxyl, or —$OR^e$ group wherein $R^e$ represents $C_{1-4}$ alkyl or $C_{1-4}$ alkylcarbonyl, (ii) a group of formula (ii):

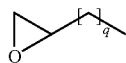

(ii)

wherein q is an integer of 1 to 4, preferably 1 or 2, (iii) a group of formula (iii):

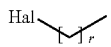

(iii)

wherein Hal represents a halogen atom, preferably a fluorine or chlorine atom, and r represents an integer of 2 to 4, preferably 2 or 3, (iv) a group of formula (iv):

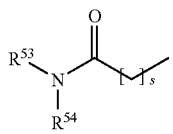

(iv)

wherein $R^{53}$ and $R^{54}$, which may be the same or different, represent a hydrogen atom, or $C_{1-6}$ alkyl optionally substituted by hydroxyl, $R^{53}$ and $R^{54}$ may combine with a nitrogen atom attached thereto to form a saturated or unsaturated five- or six-membered heterocyclic group which may further comprise one or more heteroatoms and in which the heterocyclic group is optionally substituted by $C_{1-4}$ alkyl, optionally substituted by hydroxyl, or a saturated or unsaturated five- or six-membered heterocyclic group, and the heterocyclic group optionally formed by allowing $R^{53}$ to combine with $R^{54}$ may condense with another saturated or unsaturated five- or six-membered carbocyclic or heterocyclic group to form a bicyclic group, and s is an integer of 0 to 3, preferably 0 to 2, (v) a group of formula (v):

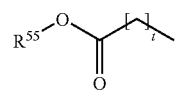

(v)

wherein $R^{55}$ represents $C_{1-4}$ alkyl and t is an integer of 0 (zero) to 3, preferably 0 to 2, and (vi) a group of formula (vi):

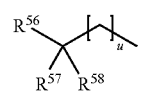

(vi)

wherein $R^{56}$, $R^{57}$ and $R^{58}$, which may be the same or different, represent a hydrogen atom, $C_{1-4}$ alkoxycarbonyl, or $C_{1-4}$ alkyl optionally substituted by hydroxyl or a halogen atom, and u is an integer of 0 (zero) to 4, preferably 0 to 2, more preferably 0 or 1.

In a more preferred embodiment of the present invention, formula (i) is represented by formula (i-a):

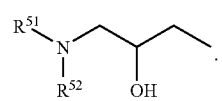

(i-a)

In a still more preferred embodiment of the present invention, $R^1$ and $R^2$, which may be the same or different, represent any group selected from the group consisting of a hydrogen atom, $C_{1-6}$ alkyl, benzyl, groups of formulae (i), (v), and (vi), and groups of formulae (ii-a), (iii-a), and (iv-a):

formula (ii-a):

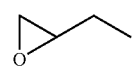

(ii-a)

formula (iii-a):

(iii-a)

wherein r1 is an integer of 2 to 4, preferably 2 or 3, and formula (iv-a):

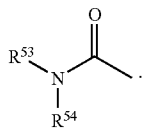

(iv-a)

In a still more preferred embodiment of the present invention, one of $R^1$ and $R^2$ is selected from $C_{1-6}$ alkyl, and the other substituent is selected from the group consisting of a hydrogen atom, benzyl, and groups of formulae (i), (ii-a), (iii-a), (iv-a), (v), and (vi).

When at least one of $R^1$ and $R^2$ represents a group of formula (i), $R^{51}$ and $R^{52}$, which may be the same or different, preferably represent a hydrogen atom, or $C_{1-4}$ alkyl optionally substituted by hydroxyl, an oxygen atom, amino, or a nitrogen atom, $R^{51}$ and $R^{52}$ may combine with a nitrogen atom attached thereto to form a heterocyclic group such as pyridyl, pyrrolyl, pyridazyl, 2-piperidyl, piperidino, piperazyl, pyrimidyl, morpholinyl, morpholino, imidazoyl, or pyrazyl, and the heterocyclic group is optionally substituted by $C_{1-4}$ alkyl optionally substituted by hydroxyl, hydroxyl, an oxygen atom, aminocarbonyl, $C_{1-4}$ alkoxy, $C_{1-4}$ alkoxycarbonyl, or a saturated five- or six-membered heterocyclic group. Further, the heterocyclic group formed by allowing $R^{51}$ to combine with $R^{52}$ may condense with another saturated or unsaturated five- or six-membered carbocyclic or heterocyclic group to form a bicyclic group.

When at least one of $R^1$ and $R^2$ represents a group of formula (i-a), $R^{51}$ and $R^{52}$, which may be the same or different, preferably represent a hydrogen atom, or $C_{1-2}$ alkyl optionally substituted by hydroxyl, or $R^{51}$ and $R^{52}$ may combine with a nitrogen atom attached thereto to form a heterocyclic group such as 2-piperidyl, piperidino, piperazyl, morpholinyl, morpholino, or imidazoyl. This heterocyclic group is optionally substituted by methyl optionally substituted by hydroxyl, or is optionally substituted by pyrrolidyl or piperidino.

When at least one of $R^1$ and $R^2$ represents a group of formula (iv-a), $R^{53}$ and $R^{54}$ preferably combine with a nitrogen atom attached thereto to form a saturated or unsaturated five- or six-membered heterocyclic group, in which the heterocyclic group may further contain one or more heteroatoms, more preferably form morpholine.

When at least one of $R^1$ and $R^2$ represents a group of formula (v), $R^{55}$ preferably represents methyl or ethyl.

When at least one of $R^1$ and $R^2$ represents a group of formula (vi), $R^{56}$, $R^{57}$, and $R^{58}$, which may be the same or different, preferably represent a hydrogen atom, $C_{1-2}$ alkoxycarbonyl, or $C_{1-4}$ alkyl optionally substituted by hydroxyl. When any of $R^{56}$, $R^{57}$, and $R^{58}$ represents $C_{1-4}$ alkyl, the alkyl group is optionally substituted by one or two hydroxyl groups.

In a preferred embodiment of the present invention, at least one of $R^1$ and $R^2$ represents $C_{1-6}$ alkyl. More preferably, $R^1$ represents $C_{1-6}$ alkyl.

When at least one of $R^1$ and $R^2$ represents $C_{1-6}$ alkyl, the $C_{1-6}$ alkyl group preferably represents $C_{1-4}$ alkyl, more preferably methyl or ethyl, most preferably methyl.

In formula (I), the group of formula (a), which A may represent, is preferably represented by any group selected from the group consisting of formulae (a1) to (a3):

(1) a group of formula (a1):

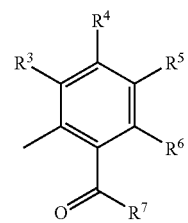

(a1)

wherein $R^3$, $R^4$ and $R^6$, which may be the same or different, represent a hydrogen atom, a halogen atom, $C_{1-6}$ alkyl, $C_{1-10}$ alkoxy optionally substituted by a halogen atom or phenyl, $C_{2-6}$ alkenylcarbonyloxy, $C_{1-4}$ alkylcarbonyl, or phenyl optionally substituted by a halogen atom, $R^5$ is as defined in formula (a), that is, a hydrogen atom, hydroxyl, a halogen atom, $C_{1-6}$ alkyl, $C_{1-10}$ alkoxy optionally substituted by a halogen atom or phenyl, $C_{2-6}$ alkenylcarbonyloxy, $C_{1-4}$ alkylcarbonyl, $C_{1-4}$ alkylthio, or phenyl optionally substituted by a halogen atom, $R^3$ and $R^4$, $R^4$ and $R^5$, and $R^5$ and $R^6$ each may combine with a carbon atom attached thereto to form a saturated or unsaturated five- or six-membered carbocyclic or heterocyclic group, $R^7$ is as defined in formula (a), (2) a group of formula (a2):

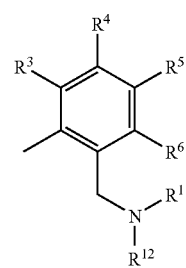

(a2)

wherein $R^3$ to $R^6$ are as defined in formula (a1), $R^{11}$ and $R^{12}$ are as defined in formula (a), and (3) a group of formula (a3):

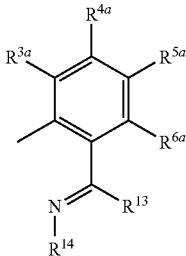

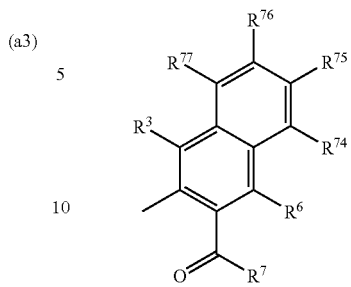

wherein $R^{3a}$ to $R^{6a}$, which may be the same or different, represent
a hydrogen atom,
a halogen atom, or
$C_{1-6}$ alkyl, and
$R^{13}$ and $R^{14}$ are as defined in formula (a).

When A represents a group of formula (a1) and $R^3$ and $R^4$, $R^4$ and $R^5$, or $R^5$ and $R^6$ in formula (a1) form a carbocyclic or heterocyclic group, a cyclic group may be formed at a position of any one of a combination of $R^3$ with $R^4$, a combination of $R^4$ with $R^5$, or a combination of $R^5$ with $R^6$. Alternatively, a cyclic group may be formed at two or more positions of $R^3$ and $R^4$, $R^4$ and $R^5$, and $R^5$ and $R^6$. In this case, A may combine with the carbocyclic ring of formula (a1) to form a tricyclic group.

When A represents the group of formula (a1), $R^3$, $R^4$ and $R^6$ in formula (a1), which may be the same or different, preferably represent
a hydrogen atom,
a halogen atom,
$C_{1-4}$ alkyl, or
$C_{1-4}$ alkoxy optionally substituted by a halogen atom or phenyl.

$R^5$ in formula (a1) preferably represents
a hydrogen atom,
hydroxyl,
a halogen atom,
$C_{1-4}$ alkyl,
$C_{1-4}$ alkoxy optionally substituted by a halogen atom or phenyl,
$C_{2-4}$ alkenylcarbonyloxy,
$C_{1-2}$ alkylcarbonyl,
$C_{1-2}$ alkylthio, or
phenyl optionally substituted by a halogen atom.

In a more preferred embodiment of the present invention, $R^5$ may be represented by $-OR^{73}$ wherein $R^{73}$ represents a hydrogen atom, or $C_{1-4}$ alkyl optionally substituted by phenyl.

In another preferred embodiment of the present invention, $R^5$ is selected from groups other than a hydrogen atom.

In one preferred embodiment of the present invention, at least one of $R^3$ to $R^6$ in formula (a1) is selected from group other than a hydrogen atom.

In another one preferred embodiment of the present invention, $R^4$ combines with $R^5$ to form phenyl as follows, and this phenyl combines with phenyl in formula (a1) to form a bicyclic group.

wherein $R^{74}$ to $R^{77}$ represent a hydrogen atom, a halogen atom, hydroxyl, or $C_{1-4}$ alkyl, preferably a hydrogen atom.

In one preferred embodiment of the present invention, $R^7$ in formula (a1) represents a hydrogen atom, $C_{1-4}$ alkyl, or phenyl in which the phenyl group is optionally substituted by hydroxyl, $C_{1-4}$ alkyl, or $C_{1-4}$ alkoxy. More preferably, $R^7$ represents a hydrogen atom, methyl, ethyl, or phenyl, and the phenyl group is optionally substituted by hydroxyl, $C_{1-4}$ alkyl, or $C_{1-4}$ alkoxy. In this case, more preferably, $R^5$ is selected from groups other than a hydrogen atom.

In another preferred embodiment of the present invention, $R^7$ in formula (a1) represents group $-O-R^8$ or group $-N(-R^9)R^{10}$.

When $R^7$ in formula (a1) represents group $-O-R^8$, $R^8$ preferably represents unsubstituted $C_{1-8}$ alkyl; $C_{1-4}$ alkyl substituted by phenyl; $C_{2-8}$ alkenyl; or phenyl optionally substituted by a halogen atom. More preferably, $R^8$ represents unsubstituted $C_{1-8}$ alkyl; methyl substituted by phenyl; $C_{2-8}$ alkenyl; or phenyl. In this case, more preferably, $R^5$ is selected from groups other than a hydrogen atom.

When $R^7$ in formula (a1) represents group $-N(-R^9)R^{10}$, preferably, at least one of $R^9$ and $R^{10}$ represents a hydrogen atom and the other substituent represents
a hydrogen atom,
$C_{1-6}$ alkyl,
a saturated or unsaturated five- or six-membered carbocyclic group in which the carbocyclic group is optionally substituted by a halogen atom, or
naphthyl optionally substituted by a halogen atom, or
$R^9$ and $R^{10}$ combine with a nitrogen atom attached thereto to form a saturated five- or six-membered heterocyclic group in which the heterocyclic group may further comprise at least one heteroatom. More preferably, at least one of $R^9$ and $R^{10}$ represents a hydrogen atom, and
the other substituent represents a hydrogen atom, $C_{1-4}$ alkyl, a saturated or unsaturated six-membered carbocyclic group in which the carbocyclic group is optionally substituted by a halogen atom, or naphthyl, or
$R^9$ and $R^{10}$ combine with a nitrogen atom attached thereto to form a saturated six-membered heterocyclic group in which the heterocyclic group may further comprise at least one heteroatom. In this case, more preferably, $R^5$ is selected from groups other than a hydrogen atom.

When A represents the group of formula (a2), preferably, $R^{11}$ and $R^{12}$ in formula (a2) combine with a nitrogen atom attached thereto to form a saturated or unsaturated five- or six-membered heterocyclic group in which the heterocyclic group may further comprise one or more heteroatoms and is optionally substituted by $C_{1-4}$ alkyl optionally substituted by hydroxyl; or a saturated five- or six-membered heterocyclic group. In this case, preferably, $R^3$, $R^4$, and $R^6$ in formula (a2)

represent a hydrogen atom, hydroxyl, or a halogen atom, and $R^5$ in formula (a2) represents $C_{1-4}$ alkyl.

More preferably, $R^{11}$ and $R^{12}$ combine with a nitrogen atom attached thereto to form a saturated five- or six-membered heterocyclic group in which the heterocyclic group may further comprise one or more heteroatoms. Still more preferably, $R^{11}$ and $R^{12}$ combine with a nitrogen atom attached thereto to form piperidino, 2-piperidyl, or morpholino.

When A represents the group of formula (a3), preferably, $R^{13}$ represents $C_{1-4}$ alkyl, more preferably methyl or ethyl, still more preferably methyl.

$R^{14}$ in formula (a3) preferably represents hydroxyl; $C_{1-4}$ alkoxy optionally substituted by phenyl; $C_{2-6}$ alkenyloxy; phenyloxy; or amino optionally substituted by a six-membered unsaturated heterocyclic group. In this case, more preferably, $R^{13}$ represents methyl.

Preferably, $R^{3a}$ and $R^{6a}$ in formula (a3) represent a hydrogen atom, and $R^{4a}$ and $R^{5a}$ represent $C_{1-6}$ alkyl. More preferably, $R^{3a}$ and $R^{6a}$ represent a hydrogen atom, and $R^{4a}$ and $R^{5a}$ represent methyl.

In formula (I), the group of formula (b), which A may represent, is preferably any group selected from the group consisting of formulae (b1) to (b3):

(4) a group of formula (b1):

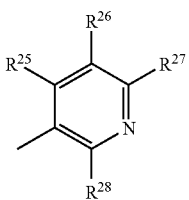
(b1)

wherein
$R^{25}$ to $R^{27}$, which may be the same or different, represent
a hydrogen atom,
a halogen atom,
$C_{1-6}$ alkyl,
$C_{1-8}$ alkoxy,
$C_{1-4}$ alkylcarbonyl,
$C_{1-4}$ alkylthio, or
phenylcarbonyl,
$R^{25}$ and $R^{26}$, and $R^{26}$ and $R^{27}$ each may combine with a carbon atom attached thereto to form a saturated or unsaturated five- or six-membered carbocyclic or heterocyclic group,
$R^{28}$ represents
a hydrogen atom,
a halogen atom,
nitro,
cyano,
$C_{1-6}$ alkyl in which the alkyl group is optionally substituted by hydroxyl; phenyl; amino optionally substituted by $C_{1-4}$ alkyl; $C_{1-4}$ alkylcarbonyloxy; or a saturated or unsaturated six-membered heterocyclic group optionally substituted by $C_{1-4}$ alkyl,
$C_{1-8}$ alkoxy,
$C_{1-4}$ alkylcarbonyl,
$C_{2-6}$ alkenyl optionally substituted by a saturated or unsaturated six-membered carbocyclic group,
$C_{2-6}$ alkynyl optionally substituted by $C_{1-2}$ alkylsilyl,
a saturated or unsaturated three- to eight-membered carbocyclic oxy group, a saturated or unsaturated six-membered carbocyclic carbonyl or heterocyclic carbonyl group optionally substituted by $C_{1-4}$ alkyl, or
a saturated or unsaturated three- to eight-membered carbocyclic or heterocyclic group in which the carbocyclic or heterocyclic group is optionally substituted by hydroxyl; cyano; a halogen atom; $C_{1-4}$ alkoxy; phenyloxy; $C_{1-4}$ alkylcarbonyl; amino optionally substituted by $C_{1-4}$ alkyl or $C_{1-4}$ alkylcarbonyl; aminocarbonyl optionally substituted by $C_{1-4}$ alkyl; or $C_{1-4}$ alkyl optionally substituted by hydroxyl or a halogen atom, (5) a group of formula (b2):

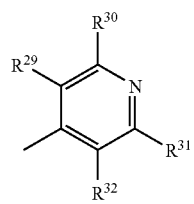
(b2)

wherein
$R^{29}$ to $R^{32}$, which may be the same or different, represent
a hydrogen atom,
a halogen atom, or
$C_{1-6}$ alkyl optionally substituted by hydroxyl,
$R^{29}$ and $R^{30}$, and $R^{31}$ and $R^{32}$ each may combine with a carbon atom attached thereto to form a saturated or unsaturated five- or six-membered carbocyclic or heterocyclic group in which the carbocyclic or heterocyclic group is optionally substituted by a halogen atom or $C_{1-4}$ alkyl, and (6) a group of formula (b3):

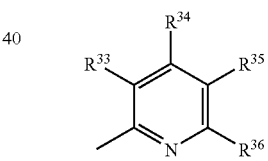
(b3)

wherein
$R^{33}$ to $R^{36}$, which may be the same or different, represent
a hydrogen atom,
a halogen atom, or
$C_{1-6}$ alkyl optionally substituted by hydroxyl,
$R^{33}$ and $R^{34}$, $R^{34}$ and $R^{35}$, and $R^{35}$ and $R^{36}$ each may combine with a carbon atom attached thereto to form a saturated or unsaturated five- or six-membered carbocyclic or heterocyclic group in which the carbocyclic or heterocyclic group is optionally substituted by a halogen atom or $C_{1-4}$ alkyl.

When A represents the group of formula (b1), $R^{25}$ in formula (b1) preferably represents a hydrogen atom or a halogen atom, more preferably a hydrogen atom.

$R^{26}$ in formula (b1) preferably represents a hydrogen atom, a halogen atom, or $C_{1-4}$ alkyl, more preferably a hydrogen atom, a halogen atom, methyl, or ethyl.

$R^{27}$ in formula (b1) preferably represents a hydrogen atom, a halogen atom, $C_{1-4}$ alkyl, $C_{1-4}$ alkoxy, or $C_{1-4}$ alkylthio, more preferably a halogen atom, methyl, ethyl, or methoxy.

In one more preferred embodiment of the present invention, $R^{25}$ represents a hydrogen atom, $R^{26}$ represents a hydrogen atom, a halogen atom, or $C_{1-4}$ alkyl, and $R^{27}$ represents a hydrogen atom, a halogen atom, $C_{1-4}$ alkyl, $C_{1-4}$ alkoxy, or $C_{1-4}$ alkylthio.

In one still more preferred embodiment of the present invention, $R^{25}$ represents a hydrogen atom, $R^{26}$ represents methyl, and $R^{27}$ represents methyl.

In another preferred embodiment of the present invention, $R^{26}$ and $R^{27}$ combine with a carbon atom attached thereto to form an unsaturated six-membered carbocyclic or heterocyclic group. In this case, formula (b1) may be represented by formula.

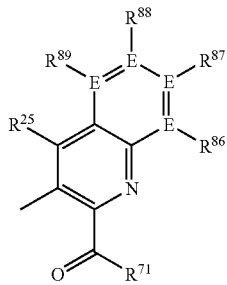

wherein $R^{25}$ is as defined above, $R^{71}$ represents methyl, ethyl, phenyl, or optionally substituted 2-pyridyl, $R^{86}$ to $R^{89}$ represent a hydrogen atom, a halogen atom, or $C_{1-4}$ alkyl, and, preferably, all of $R^{86}$ to $R^{89}$ represent a hydrogen atom, and all of Es represent a carbon atom, or alternatively, any one of Es represents a nitrogen atom with the remaining Es representing a carbon atom.

In the above formula, preferably, all of Es represent a carbon atom, or alternatively, any of Es connected directly to $R^{86}$ or $R^{88}$ represents a nitrogen atom with the remaining Es representing a carbon atom.

$R^{28}$ in formula (b1) preferably represents a hydrogen atom, a halogen atom, nitro, cyano, $C_{1-6}$ alkyl in which the alkyl group is optionally substituted by hydroxyl; phenyl; amino optionally substituted by $C_{1-4}$ alkyl; $C_{1-4}$ alkylcarbonyloxy; or a saturated or unsaturated six-membered heterocyclic group optionally substituted by $C_{1-4}$ alkyl, $C_{1-4}$ alkoxy, $C_{1-4}$ alkylcarbonyl, $C_{2-6}$ alkenyl optionally substituted by phenyl, $C_{2-6}$ alkynyl optionally substituted by $C_{1-2}$ alkylsilyl, a saturated or unsaturated three- to eight-membered carbocyclic oxy group, an unsaturated six-membered heterocyclic carbonyl group optionally substituted by $C_{1-4}$ alkyl, phenylcarbonyl, or a saturated or unsaturated three- to eight-membered carbocyclic or heterocyclic group in which the carbocyclic or heterocyclic group is optionally substituted by hydroxyl; cyano; a halogen atom; $C_{1-4}$ alkoxy; phenyloxy; $C_{1-4}$ alkylcarbonyl; amino optionally substituted by $C_{1-4}$ alkyl or $C_{1-4}$ alkylcarbonyl; aminocarbonyl optionally substituted by $C_{1-4}$ alkyl; or $C_{1-4}$ alkyl optionally substituted by hydroxyl or a halogen atom.

Here when $R^{28}$ represents alkylcarbonyl, carbocyclic carbonyl, or heterocyclic carbonyl group, $R^{28}$ may be represented by $-C(=O)R^{71}$. In this case, $R^{71}$ represents methyl, ethyl, phenyl, or optionally substituted 2-pyridyl.

When $R^{28}$ represents alkyl substituted by alkylcarbonyloxy, $R^{28}$ may be represented by $-C(-R^{71})OR^{72}$ wherein $R^{71}$ is as defined above and $R^{72}$ represents a hydrogen atom or methylcarbonyl.

When $R^{28}$ represents a carbocyclic oxy group, $R^{28}$ may be represented by $-OR^{80}$ wherein $R^{80}$ preferably represents cyclopentyl, cyclohexyl, or phenyl.

When $R^{28}$ represents alkyl substituted by amino, $R^{28}$ may be represented by $-CH_2-N(-R^{84})R^{85}$ wherein $R^{84}$ and $R^{85}$ represent $C_{1-4}$ alkyl, preferably methyl, ethyl, propyl, i-propyl, butyl, t-butyl, or i-butyl.

In a more preferred embodiment of the present invention, $R^{28}$ represents a saturated or unsaturated three- to eight-membered carbocyclic or heterocyclic group in which the carbocyclic or heterocyclic group is optionally substituted by hydroxyl; cyano; a halogen atom; $C_{1-4}$ alkoxy; phenyloxy; $C_{1-4}$ alkylcarbonyl; amino optionally substituted by $C_{1-4}$ alkyl or $C_{1-4}$ alkylcarbonyl; aminocarbonyl optionally substituted by $C_{1-4}$ alkyl; or $C_{1-4}$ alkyl optionally substituted by hydroxyl or a halogen atom.

In a more preferred embodiment of the present invention, $R^{28}$ represents a saturated or unsaturated four- to seven-membered carbocyclic or heterocyclic group, still more preferably a saturated or unsaturated five- or six-membered carbocyclic or heterocyclic group, particularly preferably pyridyl, furyl, thienyl, pyrrolyl, pyridazyl, pyrimidyl, isoxazolyl, isothiazolyl, thiazolyl, or pyrazyl. These rings are optionally substituted.

In another one more preferred embodiment of the present invention, $R^{25}$ represents a hydrogen atom, $R^{26}$ represents a hydrogen atom, a halogen atom, or $C_{1-4}$ alkyl, $R^{27}$ represents a hydrogen atom, a halogen atom, $C_{1-4}$ alkyl, $C_{1-4}$ alkoxy, or $C_{1-4}$ alkylthio, $R^{26}$ and $R^{27}$ may combine with a carbon atom attached thereto to form an unsaturated six-membered carbocyclic or heterocyclic group, and, more preferably, in this case, $R^{28}$ represents a saturated or unsaturated four- to seven-membered carbocyclic or heterocyclic group in which the carbocyclic or heterocyclic group is optionally substituted by hydroxyl; cyano; a halogen atom; $C_{1-4}$ alkoxy; phenyloxy; $C_{1-4}$ alkylcarbonyl; amino optionally substituted by $C_{1-4}$ alkyl or $C_{1-4}$ alkylcarbonyl; aminocarbonyl optionally substituted by $C_{1-4}$ alkyl; or $C_{1-4}$ alkyl optionally substituted by hydroxyl or a halogen atom.

When A represents the group of formula (b2), $R^{29}$ in formula (b2) preferably represents a hydrogen atom. $R^{30}$ in formula (b2) preferably represents a hydrogen atom or $C_{1-4}$ alkyl.

$R^{31}$ and $R^{32}$ in formula (b2) preferably combine with carbon atom attached thereto to from an unsaturated five- or six-membered carbocyclic or heterocyclic group in which the carbocyclic or heterocyclic group is optionally substituted by a halogen atom or $C_{1-4}$ alkyl. More preferably, $R^{31}$ combines with $R^{32}$ to form a phenyl ring or a thienyl ring.

When A represents the group of formula (b3), $R^{33}$ and $R^{34}$ in formula (b3) preferably represent a hydrogen atom, a halogen atom, methyl, or ethyl, more preferably a hydrogen atom.

$R^{35}$ and $R^{36}$ in formula (b3) combine with a carbon atom attached thereto to preferably form an unsaturated five- or six-membered carbocyclic or heterocyclic group, more preferably phenyl.

When A represents the group of formula (c), at least one of $R^{20}$ and $R^{24}$ in formula (c) is preferably selected from a group other than a hydrogen atom.

In formula (c), preferably, $R^{21}$ and $R^{22}$, or $R^{22}$ and $R^{23}$ combine with a carbon atom attached thereto to form a saturated or unsaturated five- or six-membered carbocyclic or heterocyclic group. The carbocyclic or heterocyclic group is optionally substituted by a halogen atom, $C_{1-4}$ alkyl, $C_{1-4}$ alkylcarbonyl, $C_{1-6}$ alkoxycarbonyl, or an oxygen atom and may condense with another saturated or unsaturated five- or six-membered carbocyclic or heterocyclic group to form, together with the six-membered carbocyclic ring in formula (c), a tricyclic group. In this case, preferably, any one of or both $R^{20}$ and $R^{24}$ is selected from groups other than a hydrogen atom.

In another preferred embodiment of the present invention, $R^{22}$ represents $C_{1-10}$ alkyl optionally substituted by hydroxyl or a saturated or unsaturated six-membered carbocyclic or heterocyclic group, $C_{1-8}$ alkoxy, amino optionally substituted by phenyl, nitro, or a saturated or unsaturated five- or six-membered carbocyclic or heterocyclic group in which the carbocyclic or heterocyclic group is optionally substituted by $C_{1-6}$ alkyl. In this case, any one of or both $R^{20}$ and $R^{24}$ is selected from groups other than a hydrogen atom.

When $R^{20}$ or $R^{24}$ is optionally substituted $C_{2-6}$ alkenyl, preferably, $R^{20}$ or $R^{24}$ may be represented by —C═C($R^{61}$)($R^{62}$) wherein $R^{61}$ and $R^{62}$, which may be the same or different, represent a hydrogen atom, $C_{1-4}$ alkyl, $C_{1-4}$ alkoxy, $C_{1-4}$ alkoxycarbonyl, or phenyl. More preferably, $R^{61}$ and $R^{62}$ represent a hydrogen atom, $C_{1-2}$ alkoxycarbonyl, or phenyl.

When $R^{20}$ or $R^{24}$ is amino optionally substituted by phenyl, preferably, $R^{20}$ or $R^{24}$ is represented by formula

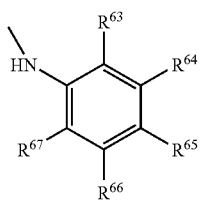

wherein $R^{63}$ to $R^{67}$, which may be the same or different, represent a hydrogen atom, hydroxyl, a halogen atom, or $C_{1-4}$ alkyl.

When $R^{21}$ and $R^{22}$, or $R^{22}$ and $R^{23}$ combine with a carbon atom attached thereto to form a carbocyclic or heterocyclic group, the formed ring combines with the carbocyclic ring of formula (c) to form a bicyclic group. Examples of such bicyclic groups include groups such as naphthyl, indole, benzimidazole, quinoline, isoquinoline, and quinazoline.

For example, when the bicyclic group is in the form of an indole ring, formula (c) may be represented by formula

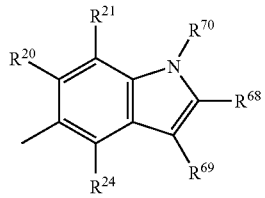

wherein $R^{20}$ and $R^{24}$ are as defined above, $R^{68}$ to $R^{70}$, which may be the same or different, represent a hydrogen atom, a halogen atom, $C_{1-2}$ alkylcarbonyl, $C_{1-2}$ alkoxycarbonyl, or $C_{1-4}$ alkyl, and, preferably, $R^{69}$ represents a hydrogen atom.

When the bicyclic group is in the form of an isoquinoline ring, formula (c) may be represented by formula

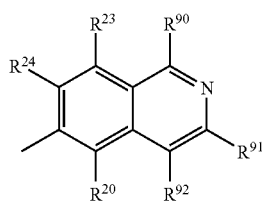

wherein $R^{20}$, $R^{23}$ and $R^{24}$ are as defined above, $R^{90}$ to $R^{92}$, which may be the same or different, represent a hydrogen atom, a halogen atom, $C_{1-2}$ alkylcarbonyl, $C_{1-2}$ alkoxycarbonyl, or $C_{1-4}$ alkyl.

When the bicyclic group is in the form of a quinazoline ring, formula (c) may be represented by formula

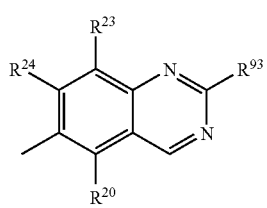

wherein $R^{20}$, $R^{23}$ and $R^{24}$ are as defined above, $R^{93}$ represents a hydrogen atom, a halogen atom, $C_{1-2}$ alkylcarbonyl, $C_{1-2}$ alkoxycarbonyl, or $C_{1-4}$ alkyl, and, preferably, $R^{93}$ represents a hydrogen atom.

In a preferred embodiment of the present invention, A is selected from the group of formula (a) and the group of formula (b).

In one preferred embodiment of the present invention, when one of $R^1$ and $R^2$ is selected from $C_{1-6}$ alkyl with the other substituent being selected from the group consisting of a hydrogen atom, benzyl, and groups of formulae (i), (ii-a), (iii-a), (iv-a), (v), and (vi), A is selected from the group of formula (a1) or the group of formula (b1). In this case, preferably, X represents CH and Z represents —O—.

When A represents the group of formula (a1) and $R^7$ represents a hydrogen atom, $C_{1-4}$ alkyl, or phenyl in which the phenyl group is optionally substituted by hydroxyl, $C_{1-4}$ alkyl, or $C_{1-4}$ alkoxy, preferably, X represents CH or N and Z represents —O—.

When A represents the group of formula (a1) with $R^7$ representing group —O—$R^8$, preferably, X represents CH and Z represents —O—, —S—, or —C(=O)—.

When A represents the group of formula (a1) with $R^7$ representing group —N(—$R^9$)$R^{10}$, preferably, X represents CH and Z represents —O—.

When A represents the group of formula (a2) or formula (a3) with both $R^1$ and $R^2$ being selected from $C_{1-6}$ alkyl, preferably, X represents CH and Z represents —O—.

When A represents the group of formula (b1) with both $R^1$ and $R^2$ being selected from $C_{1-6}$ alkyl, preferably, X represents CH and Z represents —O— or —NH—.

When A represents the group of formula (b2) with both $R^1$ and $R^2$ being selected from $C_{1-6}$ alkyl, preferably, X represents CH and Z represents —O—.

When A represents the group of formula (b3) with both $R^1$ and $R^2$ being selected from $C_{1-6}$ alkyl, preferably, X represents CH and Z represents —O— or —S—.

When A represents the group of formula (c), preferably, $R^1$ and $R^2$, which may be the same or different, are selected from $C_{1-6}$ alkyl. In this case, preferably, X represents CH and Z represents —O—.

In a preferred embodiment of the present invention,
when X represents CH and Z represents —O—, A is selected from the groups of formulae (a) to (c),
when X represents CH and Z represents —NH—, A represents the group of formula (a3),
when X represents CH and Z represents —C(=O)—, A represents the group of formula (a1),
when X represents CH and Z represents —S—, A represents the group of formula (a1) or formula (b3), or
when X represents N and Z represents —O—, A represents the group of formula (a1) or formula (b1).

In one preferred embodiment of the present invention, the compound represented by formula (I) may be a compound represented by formula (100):

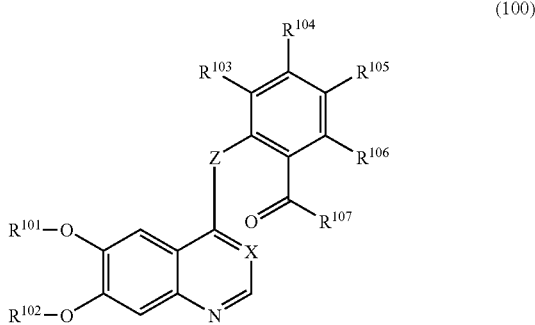

(100)

wherein
X represents CH or N,
Z represents —O—, —NH—, —S—, or —C(=O)—,
$R^{101}$ and $R^{102}$, which may be the same or different, represent any group selected from the group consisting of
a hydrogen atom,
$C_{1-6}$ alkyl,
benzyl, and
groups of formulae (i), (ii-a), (iii-a), (iv-a), (v), and (vi),
$R^{103}$, $R^{104}$ and $R^{106}$, which may be the same or different, represent a hydrogen atom,
a halogen atom,
$C_{1-6}$ alkyl,
$C_{1-10}$ alkoxy optionally substituted by a halogen atom or phenyl,
$C_{2-6}$ alkenylcarbonyloxy,
$C_{1-4}$ alkylcarbonyl, or
phenyl optionally substituted by a halogen atom,
$R^{105}$ represents
hydroxyl,
a halogen atom,
$C_{1-6}$ alkyl,
$C_{1-10}$ alkoxy optionally substituted by a halogen atom or phenyl,
$C_{2-6}$ alkenylcarbonyloxy,
$C_{1-4}$ alkylcarbonyl,
$C_{1-4}$ alkylthio, or
phenyl optionally substituted by a halogen atom,
$R^{103}$ and $R^{104}$, $R^{104}$ and $R^{105}$, and $R^{105}$ and $R^{106}$ each may combine with a carbon atom attached thereto to form a saturated or unsaturated five- or six-membered carbocyclic or heterocyclic group,
$R^{107}$ represents
a hydrogen atom,
$C_{1-4}$ alkyl, or
phenyl optionally substituted by hydroxyl, $C_{1-4}$ alkyl, or $C_{1-4}$ alkoxy.

In one more preferred embodiment of the present invention, in formula (100),
at least one of $R^{101}$ and $R^{102}$ represents methyl, and
$R^{107}$ represents a hydrogen atom, methyl, ethyl, or phenyl optionally substituted by hydroxyl, $C_{1-4}$ alkyl or $C_{1-4}$ alkoxy. In this case, preferably, Z represents —O—.

Specific examples of compounds represented by formula (100) include compounds 26 to 76, 118 to 162, 172 to 192, 200, and 312 to 321.

In one preferred embodiment of the present invention, the compound represented by formula (I) may be a compound represented by formula (200):

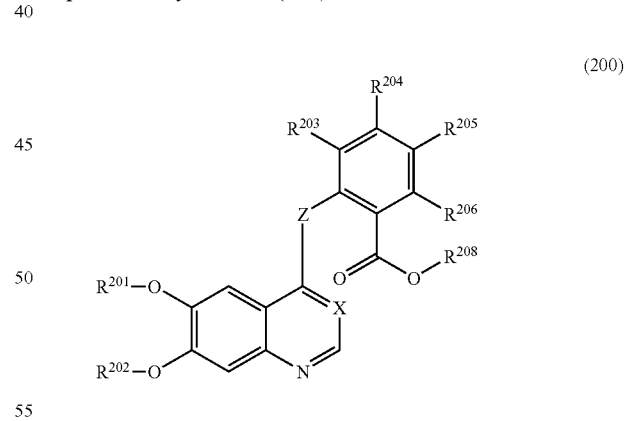

(200)

wherein
X represents CH or N,
Z represents —O—, —NH—, —S—, or —C(=O)—,
$R^{201}$ and $R^{202}$, which may be the same or different, represent any group selected from the group consisting of
a hydrogen atom,
$C_{1-6}$ alkyl,
benzyl, and
groups of formulae (i), (ii-a), (iii-a), (iv-a), (v), and (vi),
$R^{203}$ to $R^{206}$, which may be the same or different, represent
a hydrogen atom, hydroxyl,
a halogen atom,
$C_{1-6}$ alkyl,
$C_{1-10}$ alkoxy optionally substituted by a halogen atom or phenyl,
$C_{2-6}$ alkenylcarbonyloxy,
$C_{1-4}$ alkylcarbonyl,
$C_{1-4}$ alkylthio, or
phenyl optionally substituted by a halogen atom,
$R^{203}$ and $R^{204}$, $R^{204}$ and $R^{205}$, and $R^{205}$ and $R^{206}$ each may combine with a carbon atom attached thereto to form a saturated or unsaturated five- or six-membered carbocyclic or heterocyclic group,
provided that at least one of $R^{203}$ to $R^{206}$ is selected from a group other than a hydrogen atom, and
$R^{208}$ represents unsubstituted $C_{1-8}$ alkyl; $C_{1-4}$ alkyl substituted by phenyl; $C_{2-8}$ alkenyl; or phenyl optionally substituted by a halogen atom.

In one more preferred embodiment of the present invention, in formula (200),
$R^{208}$ represents unsubstituted $C_{1-8}$ alkyl; methyl substituted by phenyl; $C_{2-8}$ alkenyl; or phenyl. In this case, preferably, Z represents —O—, S—, or —C(=O)—.

Specific examples of compounds represented by formula (200) include compounds 79 to 103, 163, 201, 322 to 327, and 419.

In one preferred embodiment of the present invention, the compounds represented by formula (I) may be compounds represented by formula (300):

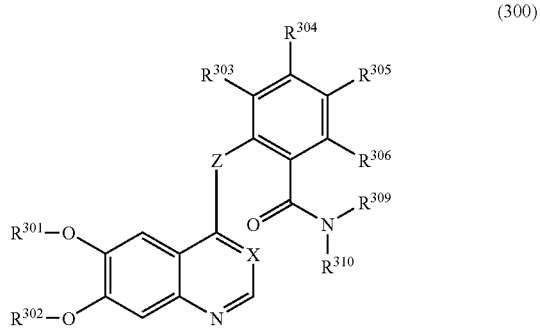

wherein
X represents CH or N,
Z represents —O—, —NH—, —S—, or —C(=O)—,
$R^{301}$ and $R^{302}$, which may be the same or different, represent any group selected from the group consisting of
a hydrogen atom,
$C_{1-6}$ alkyl,
benzyl, and
groups of formulae (i), (ii-a), (iii-a), (iv-a), (v), and (vi),
$R^{303}$ to $R^{306}$, which may be the same or different, represent
a hydrogen atom,
hydroxyl,
a halogen atom,
$C_{1-6}$ alkyl,
$C_{1-10}$ alkoxy optionally substituted by a halogen atom or phenyl,
$C_{2-6}$ alkenylcarbonyloxy,
$C_{1-4}$ alkylcarbonyl,
$C_{1-4}$ alkylthio, or
phenyl optionally substituted by a halogen atom, $R^{303}$ and $R^{304}$, $R^{304}$ and $R^{305}$, and $R^{305}$ and $R^{306}$ each may combine with a carbon atom attached thereto to form a saturated or unsaturated five- or six-membered carbocyclic or heterocyclic group,
provided that at least one of $R^{303}$ to $R^{306}$ is selected from a group other than a hydrogen atom, and
at least one of $R^{309}$ and $R^{310}$ represents a hydrogen atom and the other substituent represents
a hydrogen atom,
$C_{1-6}$ alkyl,
a saturated or unsaturated five- or six-membered carbocyclic group in which the carbocyclic group is optionally substituted by a halogen atom, or
naphthyl optionally substituted by a halogen atom, or
$R^{309}$ and $R^{310}$ combine with a nitrogen atom attached thereto to form a saturated five- or six-membered heterocyclic group which may further comprise one or more heteroatoms.

In one more preferred embodiment of the present invention, in formula (300),
at least one of $R^{309}$ and $R^{310}$ represents a hydrogen atom and
the other substituent represents a hydrogen atom, $C_{1-4}$ alkyl, a saturated or unsaturated six-membered carbocyclic group in which the carbocyclic group is optionally substituted by a halogen atom, or naphthyl, or
$R^{309}$ and $R^{310}$ combine with a nitrogen atom attached thereto to form a saturated six-membered heterocyclic group which may further comprise one or more heteroatoms. In this case, preferably, Z represents —O—.

Specific examples of compounds represented by formula (300) include compounds 104 to 114.

In one preferred embodiment of the present invention, the compound represented by formula (I) may be a compound represented by formula (400):

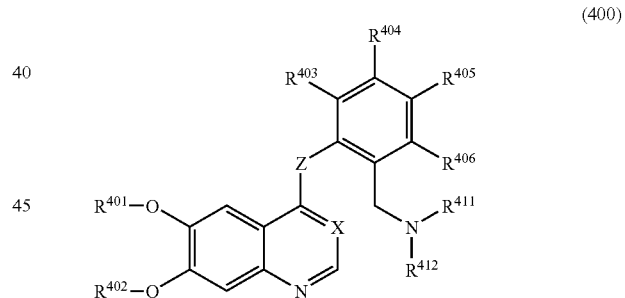

wherein
X represents CH or N,
Z represents —O—, —NH—, —S—, or —C(=O)—,
$R^{401}$ and $R^{402}$, which may be the same or different, represent any group selected from $C_{1-6}$ alkyl,
$R^{403}$, $R^{404}$, and $R^{406}$ represent a hydrogen atom, hydroxyl, or a halogen atom,
$R^{405}$ represents $C_{1-4}$ alkyl,
$R^{411}$ and $R^{412}$ combine with a nitrogen atom attached thereto to form a saturated or unsaturated five- or six-membered heterocyclic group in which the heterocyclic group may further comprise one or more heteroatoms and is optionally substituted by $C_{1-4}$ alkyl optionally substituted by hydroxyl; or a saturated five- or six-membered heterocyclic group.

In one more preferred embodiment of the present invention, in formula (400), $R^{401}$ and $R^{402}$ represent methyl, $R^{411}$ and $R^{412}$ combine with a nitrogen atom attached thereto to form a saturated five- or six-membered heterocyclic group in which the heterocyclic group may further comprise one or more heteroatoms. In this case, preferably, Z represents —O—.

Specific examples of compounds represented by formula (400) include compound 6.

In one preferred embodiment of the present invention, the compound represented by formula (I) may be a compound represented by formula (500):

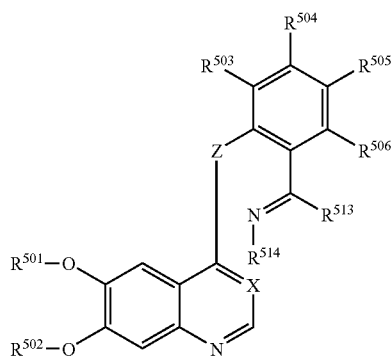

(500)

wherein
X represents CH or N,
Z represents —O—, —NH—, —S—, or —C(=O)—,
$R^{501}$ and $R^{502}$, which may be the same or different, represent any group selected from $C_{1-6}$ alkyl,
$R^{503}$ and $R^{506}$ represent a hydrogen atom,
$R^{504}$ and $R^{505}$ represent $C_{1-6}$ alkyl,
$R^{513}$ represents $C_{1-4}$ alkyl, and
$R^{514}$ represents hydroxyl; $C_{1-4}$ alkoxy optionally substituted by phenyl; $C_{2-6}$ alkenyloxy; phenyloxy; or amino optionally substituted by a six-membered unsaturated heterocyclic group.

In one more preferred embodiment of the present invention, in formula (500),
$R^{501}$ and $R^{502}$ represent methyl,
$R^{503}$ and $R^{506}$ represent a hydrogen atom,
$R^{504}$ and $R^{505}$ represent methyl, and
$R^{513}$ represents methyl. In this case, preferably, Z represents —O—.

Specific examples of compounds represented by formula (500) include compounds 193 to 199.

In one preferred embodiment of the present invention, the compound represented by formula (I) may be a compound represented by formula (600):

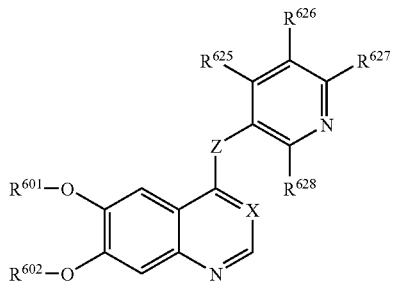

(600)

wherein
X represents CH or N,
Z represents —O—, —NH—, —S—, or —C(=O)—,
$R^{601}$ and $R^{602}$, which may be the same or different, represent any group selected from the group consisting of
a hydrogen atom,
$C_{1-6}$ alkyl,
benzyl, and
groups of formulae (i), (ii-a), (iii-a), (iv-a), (v), and (vi),
$R^{625}$ represents a hydrogen atom,
$R^{626}$ represents a hydrogen atom, a halogen atom, or $C_{1-4}$ alkyl,
$R^{627}$ represents a hydrogen atom, a halogen atom, $C_{1-4}$ alkyl, $C_{1-4}$ alkoxy, or $C_{1-4}$ alkylthio,
$R^{626}$ and $R^{627}$ may combine with a carbon atom attached thereto to form an unsaturated six-membered carbocyclic or heterocyclic group,
$R^{628}$ represents
a hydrogen atom,
a halogen atom,
nitro,
cyano,
$C_{1-6}$ alkyl in which the alkyl group is optionally substituted by hydroxyl; phenyl; amino optionally substituted by $C_{1-4}$ alkyl; $C_{1-4}$ alkylcarbonyloxy; or a saturated or unsaturated six-membered heterocyclic group optionally substituted by $C_{1-4}$ alkyl,
$C_{1-8}$ alkoxy,
$C_{1-4}$ alkylcarbonyl,
$C_{2-6}$ alkenyl optionally substituted by a saturated or unsaturated six-membered carbocyclic group,
$C_{2-6}$ alkynyl optionally substituted by $C_{1-2}$ alkylsilyl,
a saturated or unsaturated three- to eight-membered carbocyclic oxy group,
a saturated or unsaturated six-membered carbocyclic carbonyl or heterocyclic carbonyl group optionally substituted by $C_{1-4}$ alkyl, or
a saturated or unsaturated three- to eight-membered carbocyclic or heterocyclic group in which the carbocyclic or heterocyclic group is optionally substituted by hydroxyl; cyano; a halogen atom; $C_{1-4}$ alkoxy; phenyloxy; $C_{1-4}$ alkylcarbonyl; amino optionally substituted by $C_{1-4}$ alkyl or $C_{1-4}$ alkylcarbonyl; aminocarbonyl optionally substituted by $C_{1-4}$ alkyl; or $C_{1-4}$ alkyl optionally substituted by hydroxyl or a halogen atom.

In one more preferred embodiment of the present invention, in formula (600),
$R^{628}$ represents a saturated or unsaturated four- to seven-membered carbocyclic or heterocyclic group in which the carbocyclic or heterocyclic group is optionally substituted by hydroxyl; cyano; a halogen atom; $C_{1-4}$ alkoxy; phenyloxy;

$C_{1-4}$ alkylcarbonyl; amino optionally substituted by $C_{1-4}$ alkyl or $C_{1-4}$ alkylcarbonyl; aminocarbonyl optionally substituted by $C_{1-4}$ alkyl; or $C_{1-4}$ alkyl optionally substituted by hydroxyl or a halogen atom. In this case, preferably, Z represents —O— or —NH—.

Specific examples of compounds represented by formula (600) include compounds 115 to 117, 202 to 292, 310, 311, 328 to 409, 415 to 418, 421 to 424, and 426 to 469.

In one preferred embodiment of the present invention, the compound represented by formula (I) may be a compound represented by formula (700):

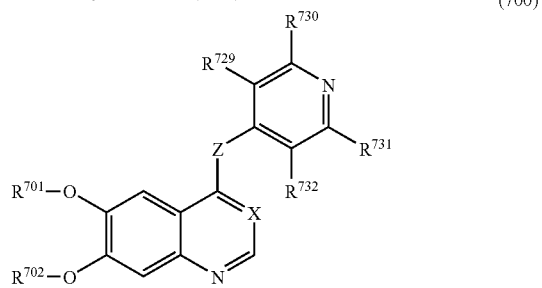

(700)

wherein
X represents CH or N,
Z represents —O—, —NH—, —S—, or —C(=O)—,
$R^{701}$ and $R^{702}$, which may be the same or different, represent any group selected from $C_{1-6}$ alkyl,
$R^{729}$ represents a hydrogen atom,
$R^{730}$ represents a hydrogen atom or $C_{1-4}$ alkyl, and
$R^{731}$ and $R^{732}$ combine with a carbon atom attached thereto to form an unsaturated five- or six-membered carbocyclic or heterocyclic group in which the carbocyclic or heterocyclic group is optionally substituted by a halogen atom or $C_{1-4}$ alkyl.

In one more preferred embodiment of the present invention, in formula (700),
$R^{701}$ and $R^{702}$ represent methyl. In this case, preferably, Z represents —O—.

Specific examples of compounds represented by formula (700) include compounds 307 to 309.

In one preferred embodiment of the present invention, the compound represented by formula (I) may be a compound represented by formula (800):

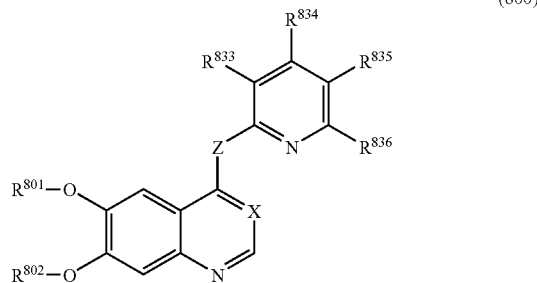

(800)

wherein
X represents CH or N,
Z represents —O—, —NH—, —S—, or —C(=O)—,
$R^{801}$ and $R^{802}$, which may be the same or different, represent any group selected from $C_{1-6}$ alkyl,
$R^{833}$ and $R^{834}$ represent a hydrogen atom, and
$R^{835}$ and $R^{836}$ combine with a carbon atom attached thereto to form an unsaturated five- or six-membered carbocyclic or heterocyclic group.

In one more preferred embodiment of the present invention, in formula (800),

Z represents —O— or —S—,
$R^{801}$ and $R^{802}$ represent methyl,
$R^{835}$ and $R^{836}$ combine with a carbon atom attached thereto to form phenyl.

Specific examples of compounds represented by formula (800) include compound 420.

In one preferred embodiment of the present invention, the compound represented by formula (I) may be a compound represented by formula (900):

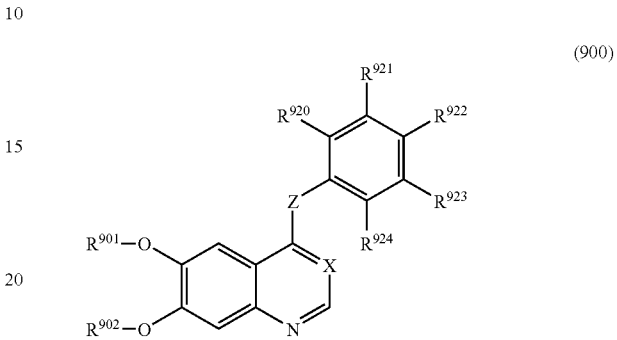

(900)

wherein
X represents CH or N,
Z represents —O—, —NH—, —S—, or —C(=O)—,
$R^{901}$ and $R^{902}$, which may be the same or different, represent any group selected from $C_{1-6}$ alkyl,
$R^{920}$, $R^{921}$, $R^{923}$ and $R^{924}$ which may be the same or different, represent
a hydrogen atom,
a halogen atom,
$C_{1-10}$ alkyl optionally substituted by hydroxyl, a saturated or unsaturated five- or six-membered carbocyclic or heterocyclic group,
$C_{1-8}$ alkoxy,
$C_{2-6}$ alkenyl optionally substituted by $C_{1-4}$ alkyl, $C_{1-4}$ alkoxy, an oxygen atom or phenyl,
phenylcarbonyl optionally substituted by $C_{1-4}$ alkyl,
amino optionally substituted by phenyl,
nitro, or
a saturated or unsaturated five- or six-membered carbocyclic or heterocyclic group in which the carbocyclic or heterocyclic group is optionally substituted by $C_{1-6}$ alkyl,
provided that at least one of $R^{920}$ and $R^{924}$ is selected from a group other than a hydrogen atom,
$R^{922}$ represents
$C_{1-10}$ alkyl optionally substituted by hydroxyl, a saturated or unsaturated six-membered carbocyclic or heterocyclic group,
$C_{1-8}$ alkoxy,
amino optionally substituted by phenyl,
nitro, or
a saturated or unsaturated five- or six-membered carbocyclic or heterocyclic group in which the carbocyclic or heterocyclic group is optionally substituted by $C_{1-6}$ alkyl, and
$R^{921}$ and $R^{922}$, or $R^{922}$ and $R^{923}$ may combine with a carbon atom attached thereto to form a saturated or unsaturated five- or six-membered carbocyclic or heterocyclic group in which the carbocyclic or heterocyclic group is optionally substituted by a halogen atom, $C_{1-4}$ alkyl, $C_{1-4}$ alkylcarbonyl, $C_{1-6}$ alkoxycarbonyl, or an oxygen atom, and the carbocyclic or heterocyclic group may condense with another saturated or unsaturated five- or six-membered carbocyclic or heterocyclic group to form a tricyclic group together with the six-membered carbocyclic ring of formula (c).

In one more preferred embodiment of the present invention, in formula (900), at least one of $R^{920}$ and $R^{924}$ is selected from a group other than a hydrogen atom, and $R^{921}$ and $R^{922}$, or $R^{922}$ and $R^{923}$ combine with a carbon atom attached thereto to form a saturated or unsaturated five- or six-membered carbocyclic or heterocyclic group in which the carbocyclic or heterocyclic group is optionally substituted by a halogen atom, $C_{1-4}$ alkyl, $C_{1-4}$ alkylcarbonyl, $C_{1-6}$ alkoxycarbonyl, or an oxygen atom. In this case, preferably, Z represents —O—.

Specific examples of compounds represented by formula (900) include compounds 1 to 5, 7 to 24, 77, 78, 164 to 171, 293 to 306, and 425.

Examples of preferred compounds according to the present invention include compunds described in the working examples.

More preferred compounds according to the present invention include compounds 195, 207, 260, 261, 270 to 274, 276, 278, 303, 305, 310, 311, 339, 346, 369, 384 to 387, 392, 395, 396, 400, 411, 421, 422, 431, 436, 437, 440, 441, 451, 459, 461, and 469 described in the working examples.

Salts or Solvates of Compounds

The compounds according to the present invention may form pharmaceutically acceptable salts thereof. Preferred examples of such salts include: alkali metal or alkaline earth metal salts such as sodium salts, potassium salts or calcium salts; hydrohalogenic acid salts such as hydrofluoride salts, hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, maleic acid salts, acetic acid salts, malic acid salts, lactic acid salts, or ascorbic acid salts; and amino acid salts such as glycine salts, phenylalanine salts, glutamic acid salts, or aspartic acid salts.

The compounds according to the present invention may form solvates. Such solvates include, for example, hydrates, alcoholates, for example, methanolates and ethanolates, and etherates, for example, diethyl etherate.

Production of Compounds of Formula (I)

Compounds according to the present invention may be produced, for example, according to schemes 1 to 34. Starting compounds necessary for the synthesis of the compounds according to the present invention are commercially available or alternatively may be easily produced by conventional methods.

In the following scheme, quinolone derivatives as an intermediate may be synthesized, for example, according to WO 97/17329.

4-Chloroquinoline derivatives may be synthesized by a conventional method as described, for example, in Org. Synth. Col. Vol. 3, 272 (1955), Acta Chim. Hung., 112, 241 (1983) or WO 98/47873.

4-Chloroquinazoline derivatives may be synthesized by a conventional method as described in J. Am. Chem. Soc., 68, 1299 (1946), J. Am. Chem. Soc., 68, 1305 (1946), and Dai Yuuki Kagaku (Great Organic Chemistry), supervised by Kotake, Vol. 17, p 150, Asakura Publishing Co., Ltd. (published in 1967).

1 and 2) The compound, which is represented by formula (I) and in which formula (I) is represented by formula (II) and A represents a group of formula (c), may be produced, for example, according to scheme 1 and scheme 2 below.

Scheme 1:

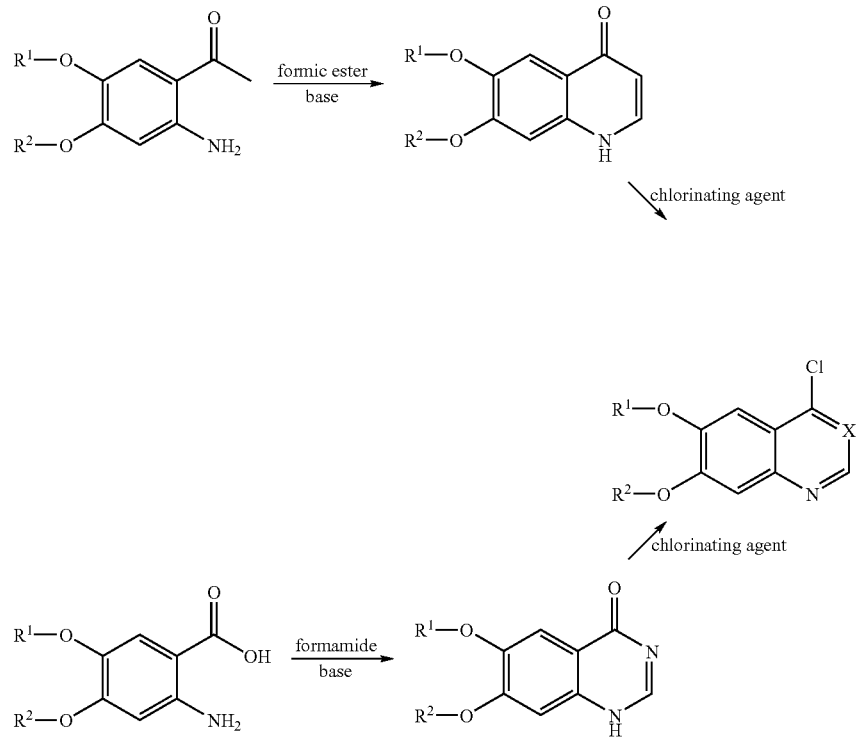

Scheme 2:

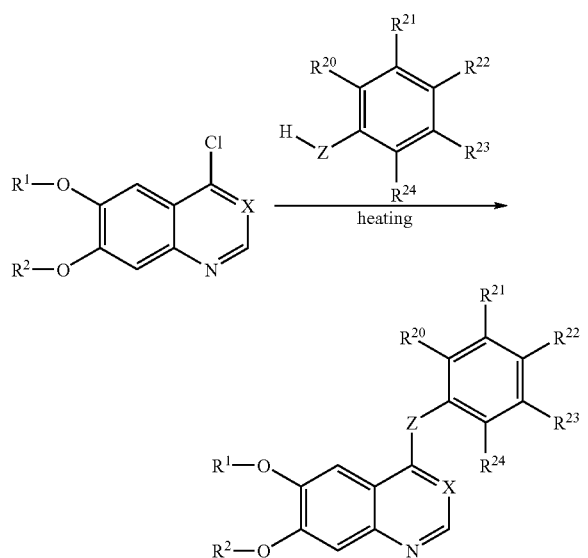

wherein each substituent is as defined above.

The contemplated 4-phenoxyquinoline derivative, 4-anilinoquinoline derivative, or corresponding quinazoline derivative may be synthesized by reacting a phenol derivative or a corresponding aniline derivative with a 4-chloroquinoline derivative or a corresponding quinazoline derivative in a suitable solvent, for example, o-dichlorobenzene, or in the absence of a solvent, for example, at 120 to 180° C. In scheme 1, phosphoryl chloride may be used as the chlorinating agent.

3) The compound, which is represented by formula (I) and in which formula (I) is represented by formula (II) and A represents a group of formulae (a1), (b1) to (b3), and (c), particularly a compound having a substituent of a ketone at the o-position of A, may be produced, for example, according to scheme 3 below.

Scheme 3:

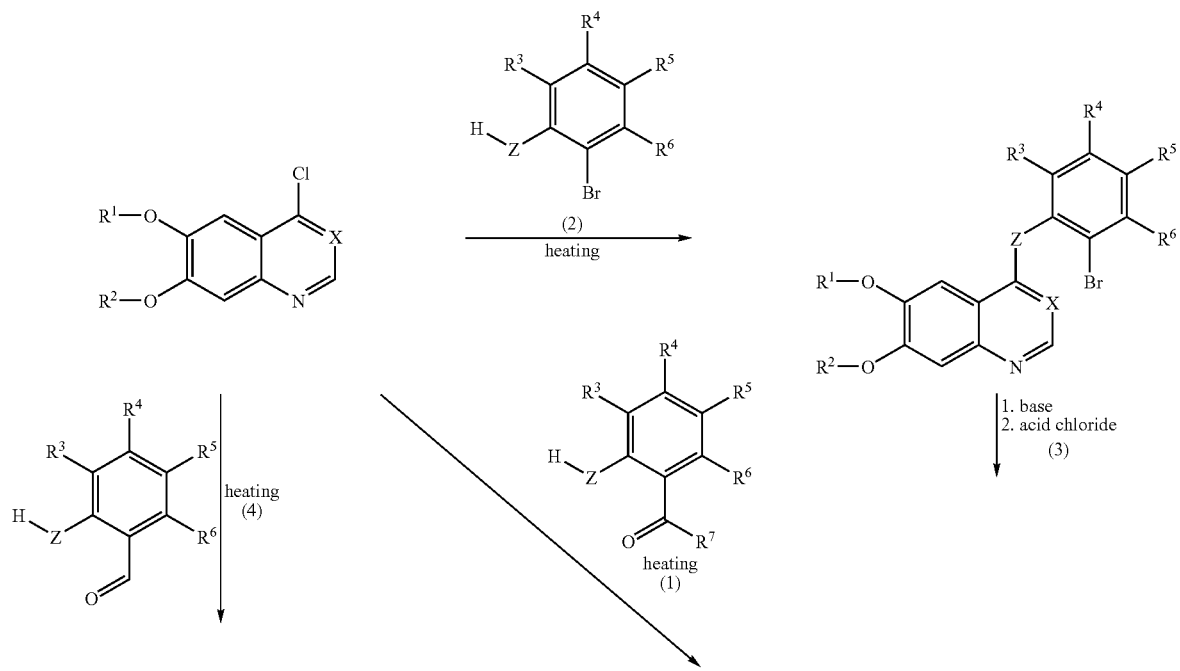

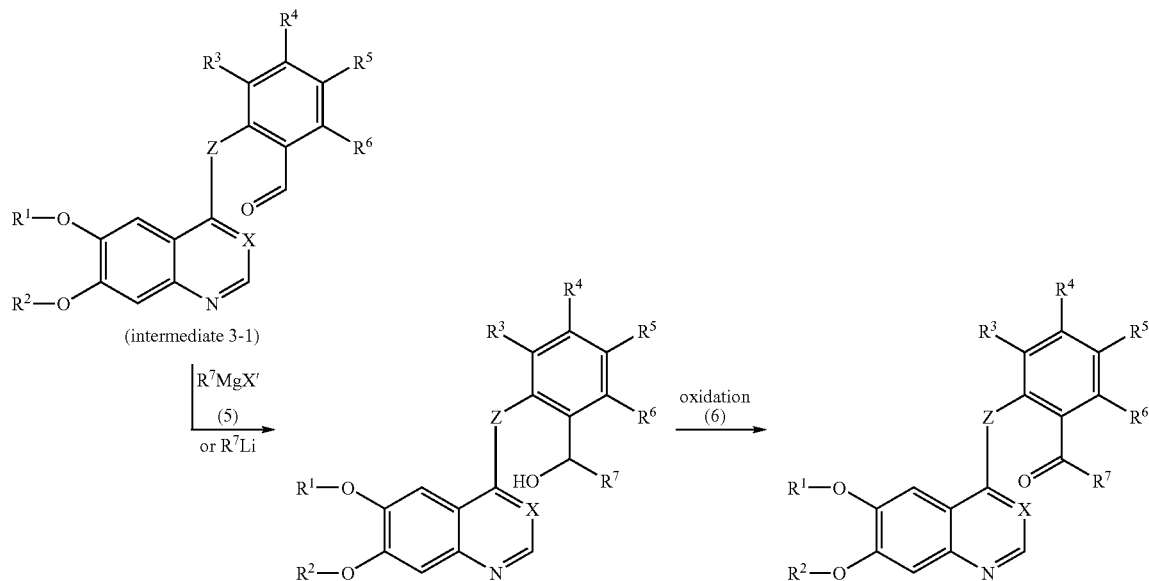

wherein X' represents a halogen atom; and each other substituent is as defined above.

In this scheme, the contemplated compound of formula (I) may be synthesized by any one of the following three routes (i) to (iii).

(i) The contemplated compound of formula (I) may be synthesized by reacting a 4-chloroquinoline derivative or a corresponding quinazoline derivative with a phenol derivative or a corresponding aniline derivative in a suitable solvent, for example, o-dichlorobenzene, or in the absence of a solvent, for example, at 120 to 180° C. (step (1) above).

(ii) The contemplated compound of formula (I) may be synthesized by reacting a 4-chloroquinoline derivative or a corresponding quinazoline derivative with an o-bromophenol derivative or a corresponding o-bromoaniline derivative in a suitable solvent, for example, o-dichlorobenzene, or in the absence of a solvent, for example, at 120 to 180° C. (step (2) above), then subjecting the production products at its bromo site to dipole inversion using a metal base, for example, n-butyllithium, and reacting the produced anion with an acid chloride (step (3) above).

(iii) The contemplated compound of formula (I) may be produced by reacting a 4-chloroquinoline derivative or a corresponding quinazoline derivative with an o-hydroxybenzaldehyde derivative or a corresponding o-aminobenzaldehyde derivative in a suitable solvent, for example, o-dichlorobenzene, or in the absence of a solvent, for example, at 120 to 180° C. (step (4) above), then reacting the reaction product with an alkylating agent, for example, methylmagnesium bromide (step (5) above), and oxidizing the resultant alcohol (step (6) above).

4) The compound, which is represented by formula (I) and in which formula (I) is represented by formula (II) and A represents a group of formula (a1) (particularly an amide compound), may be produced, for example, according to scheme 4 below.

Scheme 4:

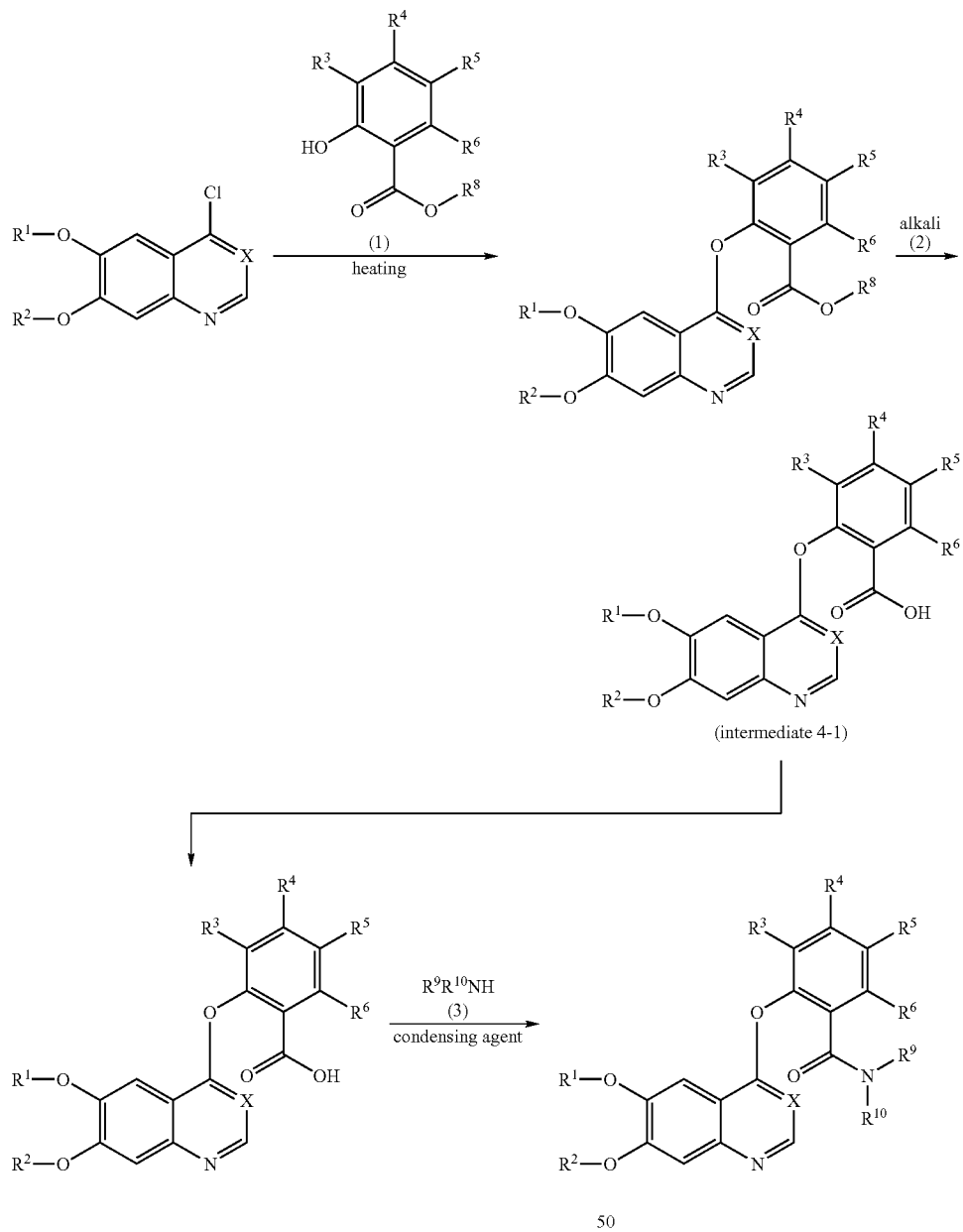

wherein each substituent is as defined above.

The ester-type compound of formula (I) may be produced by reacting a 4-chloroquinoline derivative or a corresponding quinazoline derivative with an o-hydroxybenzoic ester derivative or a corresponding o-aminobenzoic ester derivative in a suitable solvent, for example, o-dichlorobenzene, or in the absence of a solvent, for example, at 120 to 180° C. (step (1) above). Next, the contemplated compound of formula (I) may be synthesized by hydrolyzing the ester-type compound with an alkali (step (2) above) and reacting the hydrolyzation product with an amine using a condensing agent, for example, 1-ethyl-3-(3-dimethylaminopropyl)carbodiimide hydrochloride (step (3) above).

5) The compound, which is represented by formula (I) and in which formula (I) is represented by formula (II) and a desired substituent is present at the 7-position of the quinoline or quinazoline ring in the compound, may be produced, for example, according to scheme 5 below.

Scheme 5:

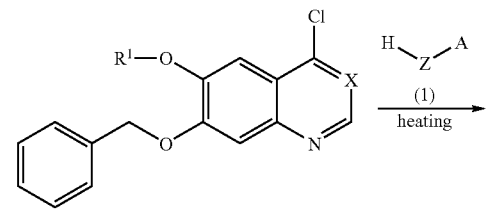

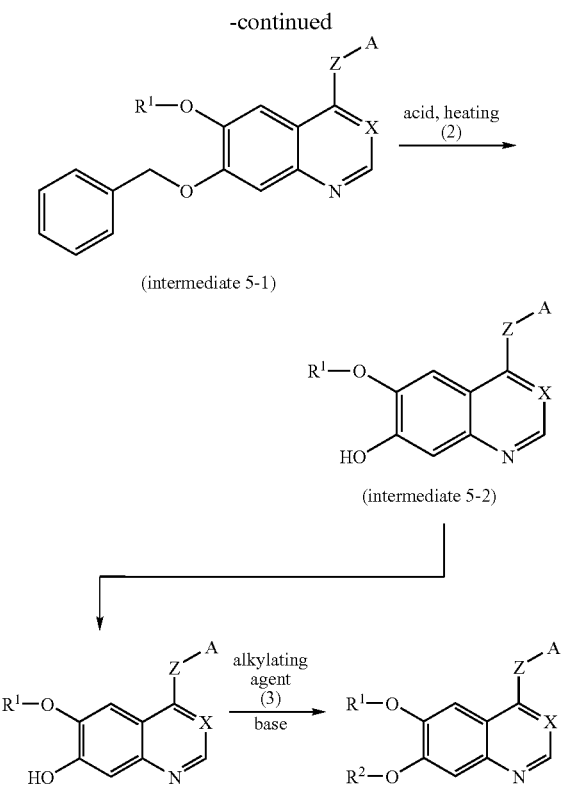

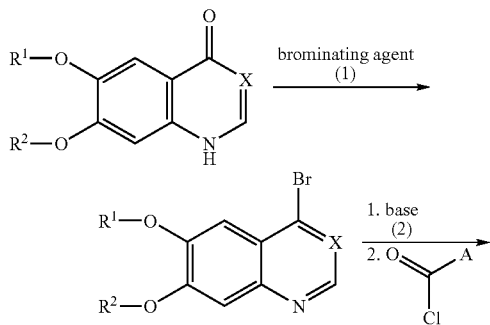

wherein each substituent is as defined above.

The contemplated compound of formula (I) may be synthesized by providing a 7-benzyloxy-4-chloroquinoline derivative or a corresponding quinazoline derivative, reacting the derivative with a phenol derivative or a corresponding aniline derivative in a suitable solvent, for example, o-dichlorobenzene, or in the absence of a solvent, for example, at 120 to 180° C. (step (1) above), then deprotecting a benzyl group in the intermediate 5-1 thus obtained with an acid (step (2) above), and reacting the intermediate 5-2 thus obtained with an alkylating agent, for example, 1-bromo-2-chloroethane, in the presence of a base (step (3) above).

6) The compound, which is represented by formula (I) and in which formula (I) is represented by formula (II) and Z represents —C(=O)—, may be produced, for example, according to scheme 6 below.

Scheme 6:

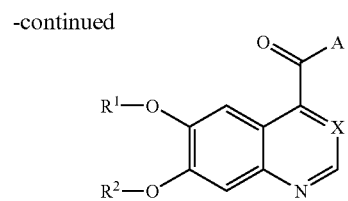

wherein each substituent is as defined above.

The contemplated compound of formula (I) may be produced by reacting a 4-quinolone derivative or a corresponding quinazolone derivative with a brominating agent, for example, phosphoryl bromide (step (1) above) and then subjecting the reaction product at its bromo site to dipole inversion using a metal base, for example, n-butyllithium, and reacting the resultant anion with an acid chloride (step (2) above).

7) The compound, which is represented by formula (I) and in which formula (I) is represented by formula (II) and in which A represents a group of formula (c) and $R^{24}$ represents optionally substituted alkenyl, may be produced, for example, according to scheme 7 below.

Scheme 7:

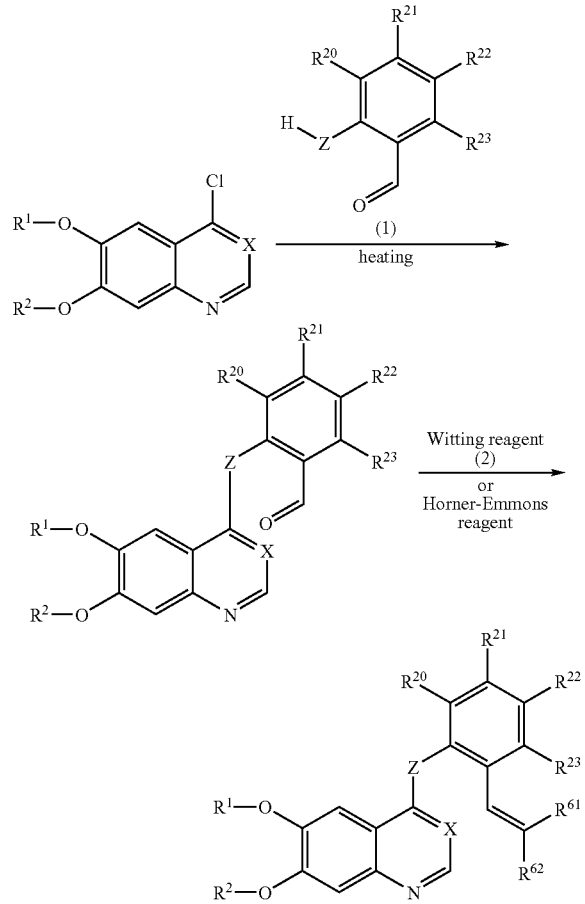

wherein each substituent is as defined above.

The contemplated compound of formula (I) may be synthesized by reacting a 4-chloroquinoline derivative or a corresponding quinazoline derivative with an o-hydroxybenzaldehyde derivative or a corresponding o-aminobenzaldehyde derivative in a suitable solvent, for example, o-dichlorobenzene, or in the absence of a solvent, for example, at 120 to 180° C. (step (1) above) and then reacting the reaction product with a Witting reagent or a Horner-Emmons reagent, for example, phosphorus ylide (step (2) above).

8) The compound, which is represented by formula (I) and in which formula (I) is represented by formula (II) and A represents a group of formula (a2), may be produced, for example, according to scheme 8 below.

Scheme 8:

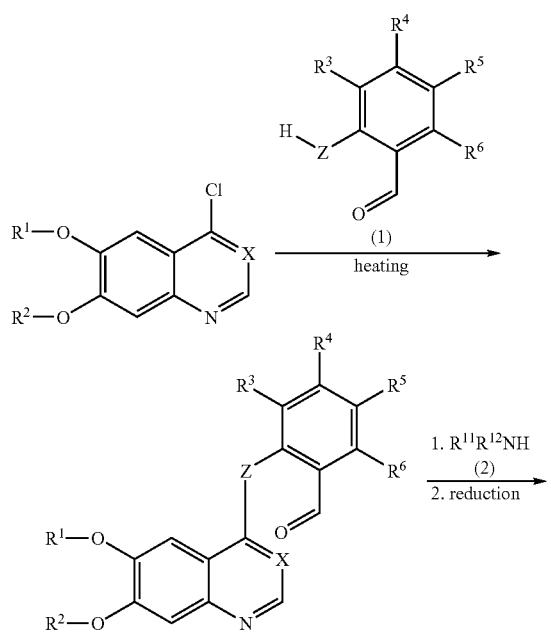

wherein each substituent is as defined above.

The contemplated compound of formula (I) may be synthesized by reacting a 4-chloroquinoline derivative or a corresponding quinazoline derivative with an o-hydroxybenzaldehyde derivative or a corresponding o-aminobenzaldehyde derivative in a suitable solvent, for example, o-dichlorobenzene, or in the absence of a solvent, for example, at 120 to 180° C. (step (1) above) and then reacting the reaction product with an amine ($R^{11}R^{12}NH$) to give an imine which is then reduced (step (2) above).

9) The compound, which is represented by formula (I) and in which formula (I) is represented by formula (II), A represents a group of formula (c) and the group of formula (c) has an amino group substituted by phenyl, may be produced, for example, according to scheme 9 below.

Scheme 9:

-continued

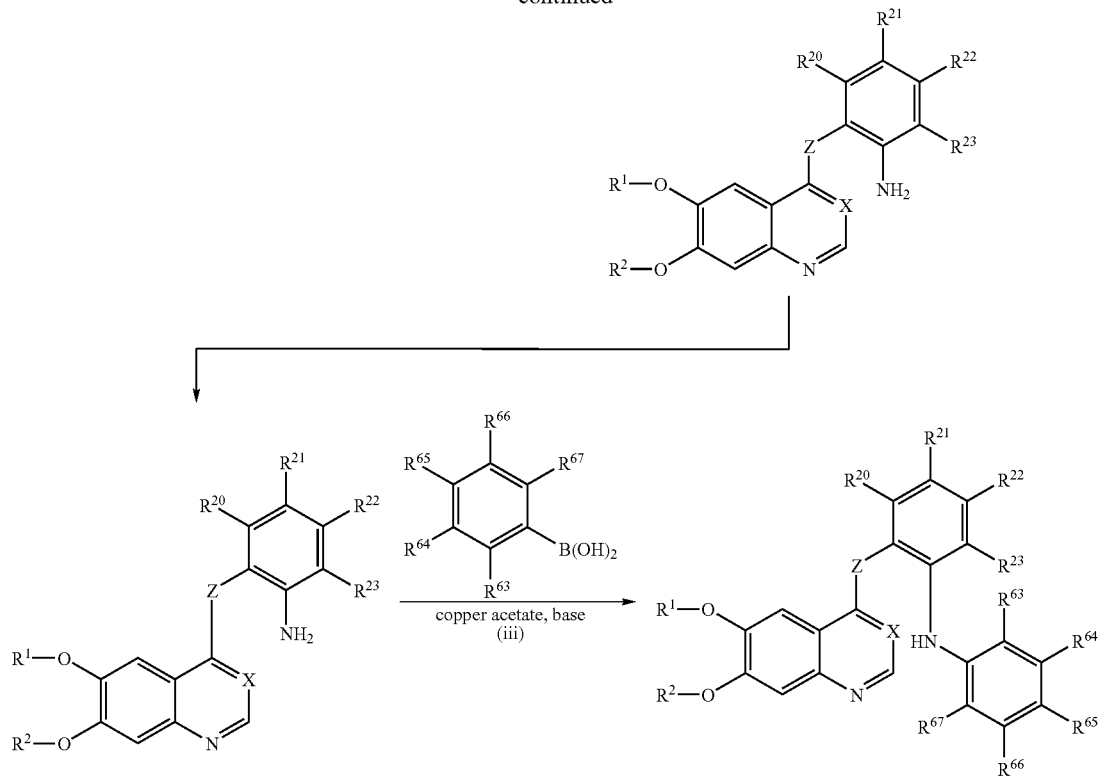

wherein each substituent is as defined above.

The contemplated compound of formula (I) may be synthesized by reacting a 4-chloroquinoline derivative or a corresponding quinazoline derivative with an o-nitrophenol derivative or a corresponding o-nitroaniline derivative in a suitable solvent, for example, o-dichlorobenzene, or in the absence of a solvent, for example, at 120 to 180° C. (step (i) above), then reducing the nitro group (step (ii) above), and reacting the reduction product with a phenylboronic acid derivative (step (iii) above).

10) The compound, which is represented by formula (I) and in which formula (I) is represented by formula (II), A represents a group of formula (c) and the group of formula (c) has a nitrogen-containing five-membered heterocyclic group, may be produced, for example, according to scheme 10 below.

Scheme 10:

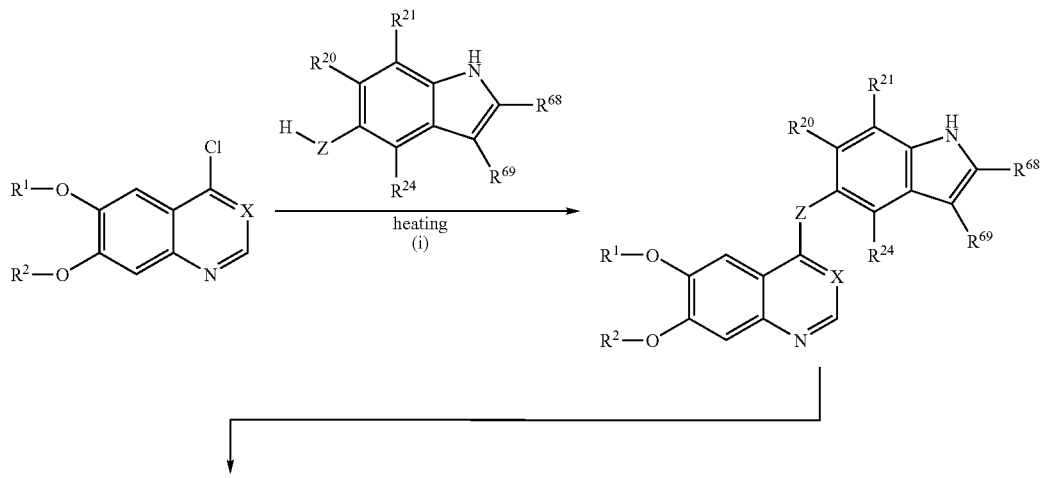

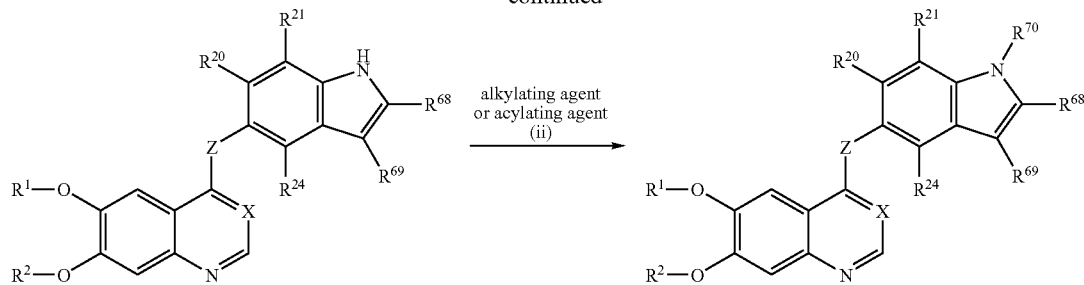

wherein each substituent is as defined above.

The contemplated compound of formula (I) may be synthesized by reacting a 4-chloroquinoline derivative or a corresponding quinazoline derivative with a 5-hydroxyindole derivative or a corresponding 5-aminoindole derivative in a suitable solvent, for example, o-dichlorobenzene, or in the absence of a solvent, for example, at 120 to 180° C. (step (i) above) and then alkylating the amino group with an alkylating agent, for example, methyl iodide, or acylating the amino group with an acylating agent, for example, acetyl chloride (step (ii) above).

11) A given compound, which is represented by formula (I) and in which formula (I) is represented by formula (II) and A represents a group of formula (c), for example, compound 23, may be produced, for example, according to scheme 11 below.

Scheme 11:

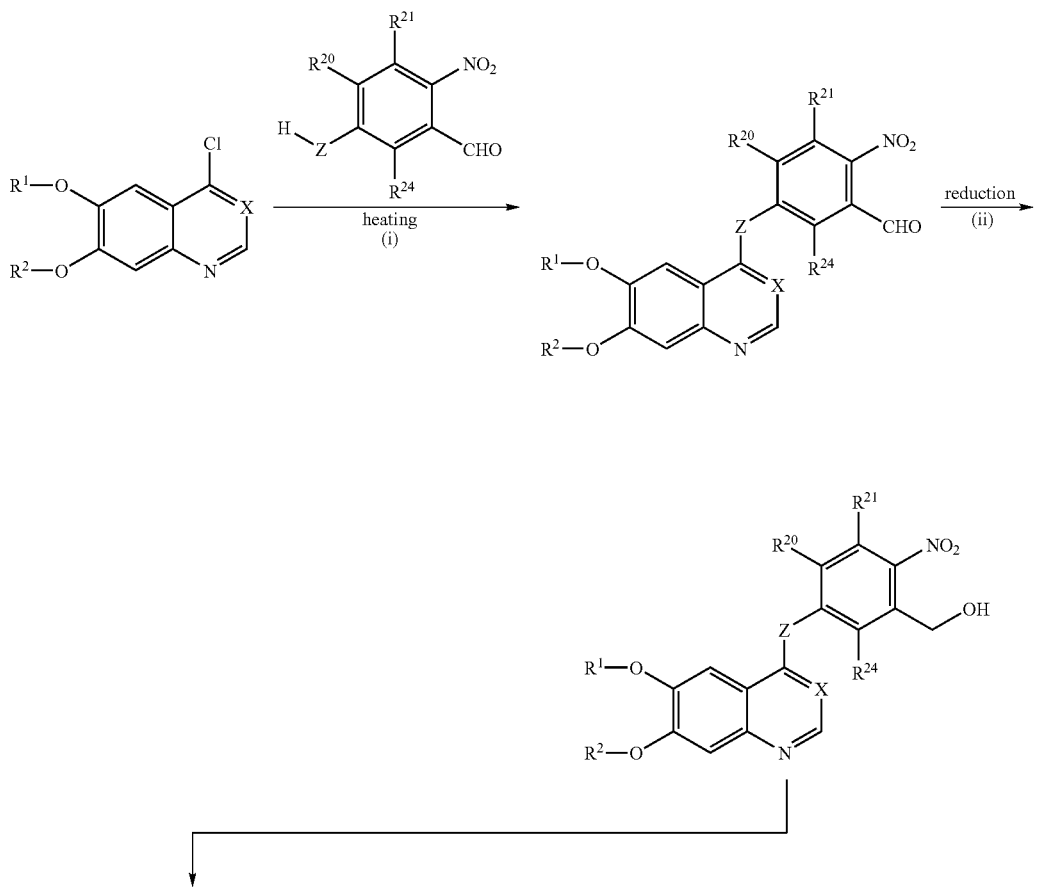

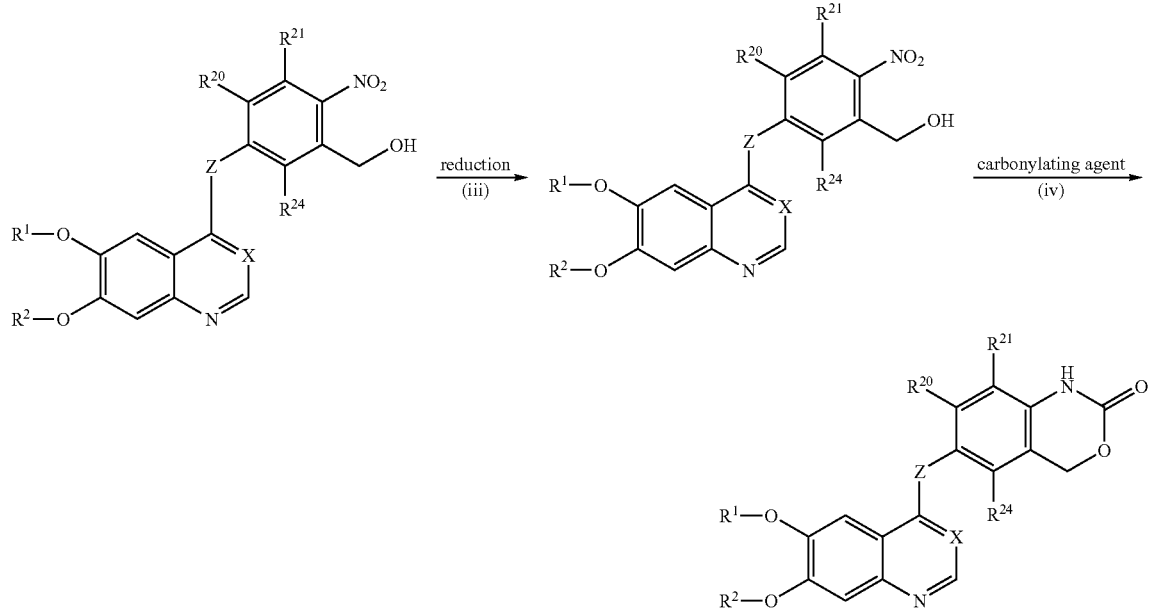

wherein each substituent is as defined above.

The contemplated compound may be synthesized by reacting a 4-chloroquinoline derivative or a corresponding quinazoline derivative with 3-hydroxy-6-nitrobenzaldehyde derivative or a corresponding 5-amino-2-nitrobenzaldehyde derivative in a suitable solvent, for example, o-dichlorobenzene, or in the absence of a solvent (step (i) above), then reducing the formyl group (step (ii) above), then reducing the nitro group of the resultant compound (step (iii) above), and reacting the reduction product with a carbonylating agent, for example, triphosgene (step (iv) above).

12) A given compound, which is represented by formula (I) and in which formula (I) is represented by formula (II) and A represents a group of formula (a1), for example, compound 76, and a given compound in which A represents a group of formula (c), for example, compound 165, may be produced, for example, according to scheme 12 below.

Scheme 12:

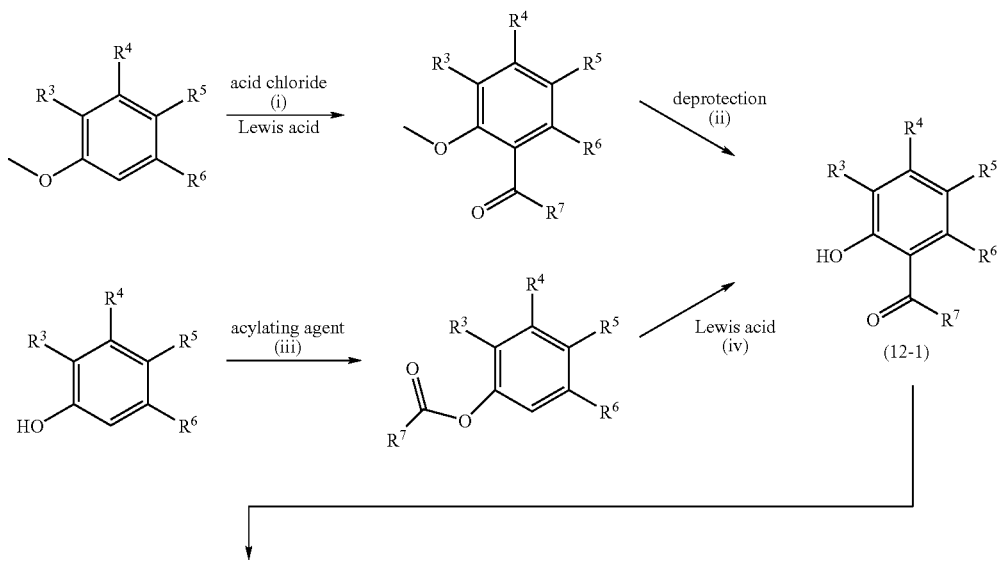

-continued

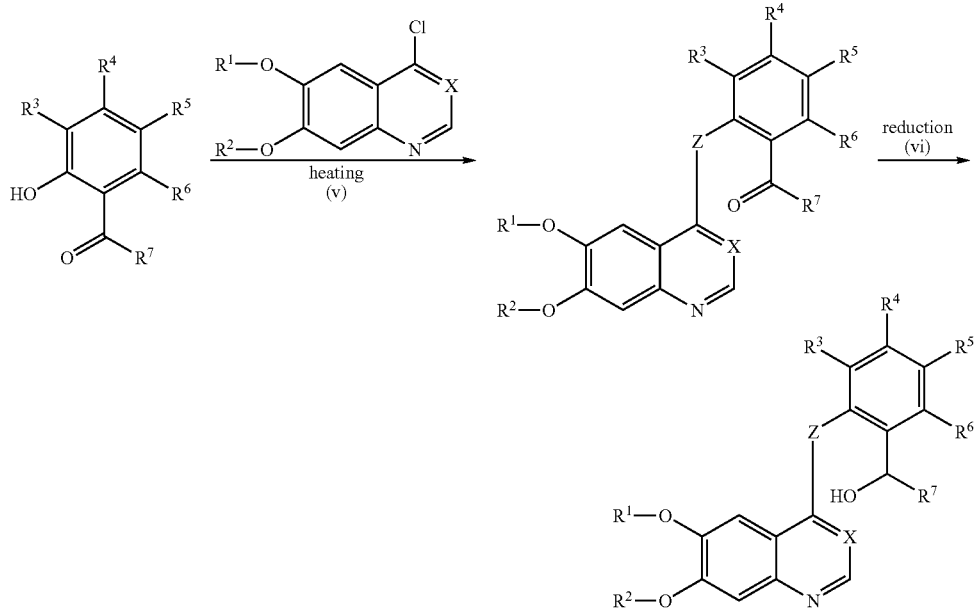

wherein each substituent is as defined above.

The compound of formula (12-1) may be produced by reacting an anisole derivative with an acid chloride in the presence of a Lewis acid (step (i) above) and deprotecting the methoxy group (step (ii) above).

Alternatively, the compound of formula (12-1) may be produced by acylating a phenol derivative with an acylating agent, for example, acetyl chloride or acetic anhydride (step (iii) above) and then reacting the acylation product with a Lewis acid, for example, scandium trifluoromethanesulfonate (step (iv) above).

Next, the contemplated compound, for example, compound 76, may be synthesized by reacting the compound of formula (12-1) with the 4-chloroquinoline derivative or a corresponding quinazoline derivative in a suitable solvent, for example, o-dichlorobenzene, or in the absence of a solvent, for example, at 120 to 180° C. (step (v) above).

The contemplated compound, for example, compound 165, may also be synthesized by reducing the acyl group in the resultant compound (step (vi) above).

13) The compound, which is represented by formula (I) and in which formula (I) is represented by formula (II) and A represents a pyridine ring, that is, a group of formula (b1), may be produced, for example, according to scheme 13 below.

Scheme 13:

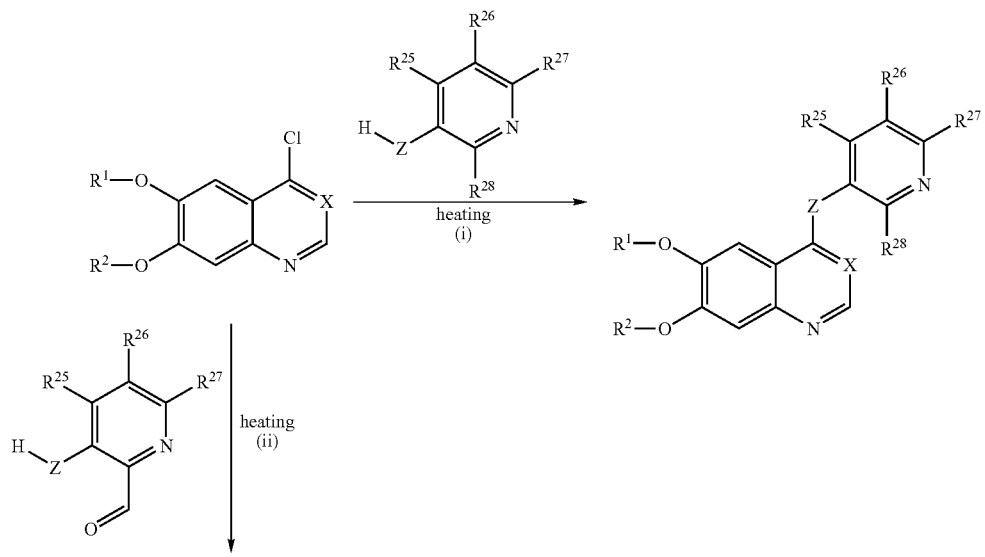

-continued

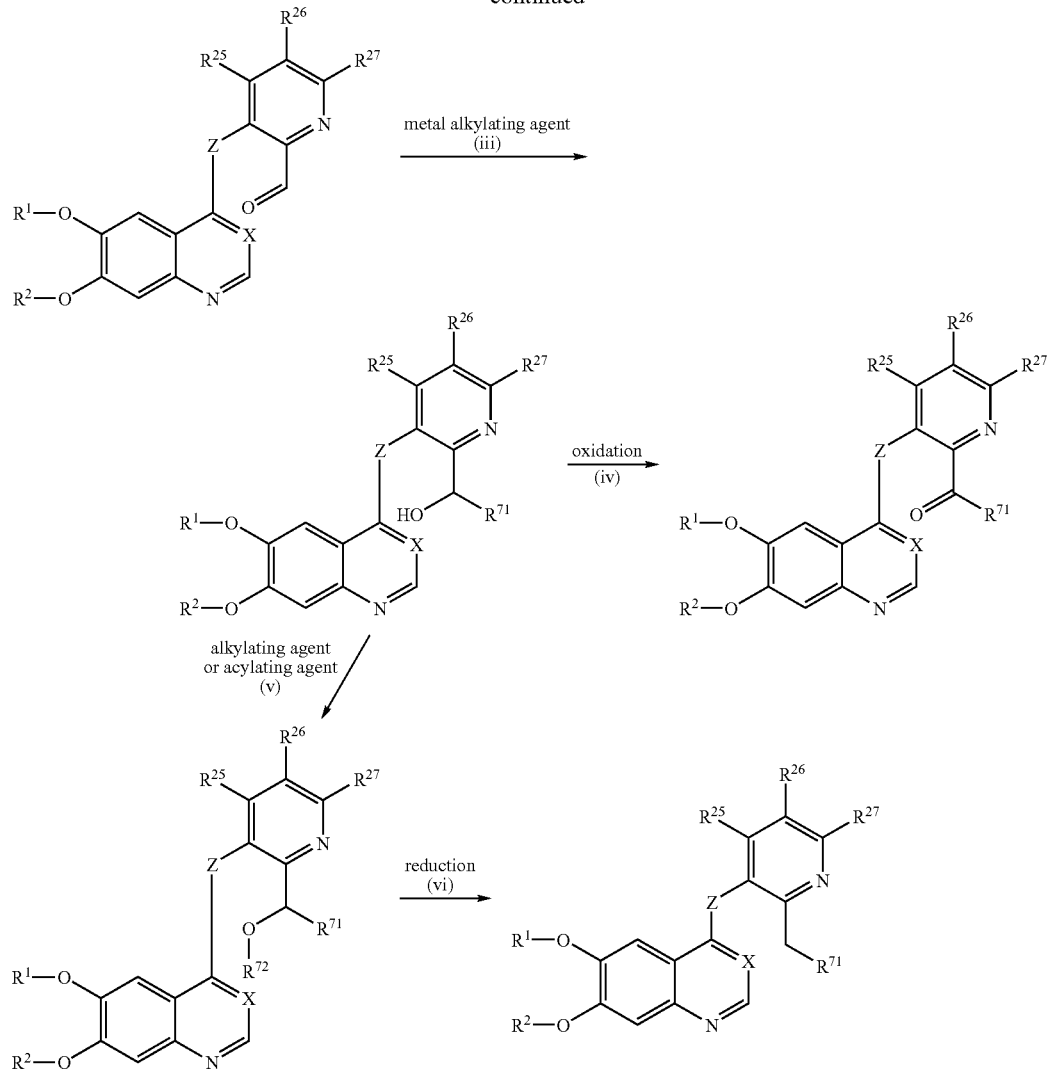

wherein each substituent is as defined above.

The contemplated compound may be synthesized by reacting a 4-chloroquinoline derivative or a corresponding quinazoline derivative with a 3-hydroxypyridine derivative or a corresponding 3-aminopyridine derivative in a suitable solvent, for example, o-dichlorobenzene, in the absence of a solvent, for example, at 120 to 180° C. (step (i) above).

Alternatively, a method may also be adopted in which a 4-chloroquinoline derivative or a corresponding quinazoline derivative is reacted with a 3-hydroxy-2-pyridinecarbaldehyde derivative or a corresponding 3-amino-2-pyridinecarbaldehyde derivative in a suitable solvent, for example, o-dichlorobenzene, or in the absence of a solvent, for example, at 120 to 180° C. (step (ii) above), and the reaction product is then reacted with an alkylating agent, for example, methylmagnesium bromide (step (iii) above).

Next, the contemplated compound, for example, compound 117, may be synthesized by oxidizing the resultant alcoholic compound, for example, with manganese dioxide as an oxidizing agent (step (iv) above).

Alternatively, another contemplated compound, for example, compound 218, may be synthesized by alkylating the hydroxyl group in the resultant alcoholic compound with an alkylating agent, for example, methyl iodide or ethyl iodide, or by acylating the hydroxyl group in the resultant alcoholic compound with an acylating agent, for example, acetyl chloride or acetic anhydride (step (v) above). Further, still another contemplated compound, for example, compound 214, may be synthesized by reducing this compound, for example, with hydrogen gas/palladium hydroxide as a reducing agent (step (vi) above).

14) The compound, which is represented by formula (I) and in which formula (I) is represented by formula (II) and A represents a group of formula (c), particularly a compound in which a substituent such as an iodine atom is present at the o-position of the group of formula (c) represented by A, may be produced, for example, according to scheme 14 below.

Scheme 14:

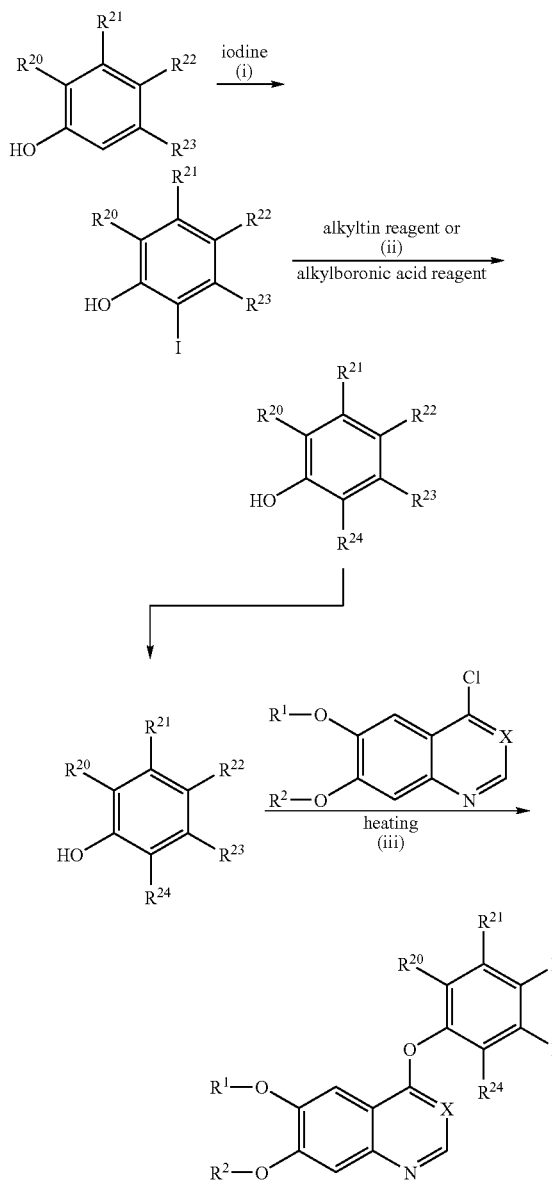

wherein each substituent is as defined above.

The contemplated compound may be produced by reacting a phenol derivative with iodine (step (i) above), then reacting the allyliodine with an alkyltin reagent, for example, tri-n-butyl-(2-pyridyl)-tin, or an alkylboronic acid reagent, for example, 3-pyridylboronic acid, in the presence of a suitable transition metal catalyst, for example, tetrakis triphenylphosphine palladium (step (ii) above), and reacting the resultant phenol derivative with a 4-chloroquinoline derivative or a corresponding quinazolone derivative in a suitable solvent, for example, o-dichlorobenzene, or in the absence of a solvent, for example, at 120 to 180° C. (step (iii) above).

15) The compound, which is represented by formula (I) and in which formula (I) is represented by formula (II) and A represents a group of formula (a1), particularly a compound in which alkoxy is present as a substituent at the 4-position of the group of formula (a1) represented by A may be produced, for example, according to scheme 15 below.

Scheme 15:

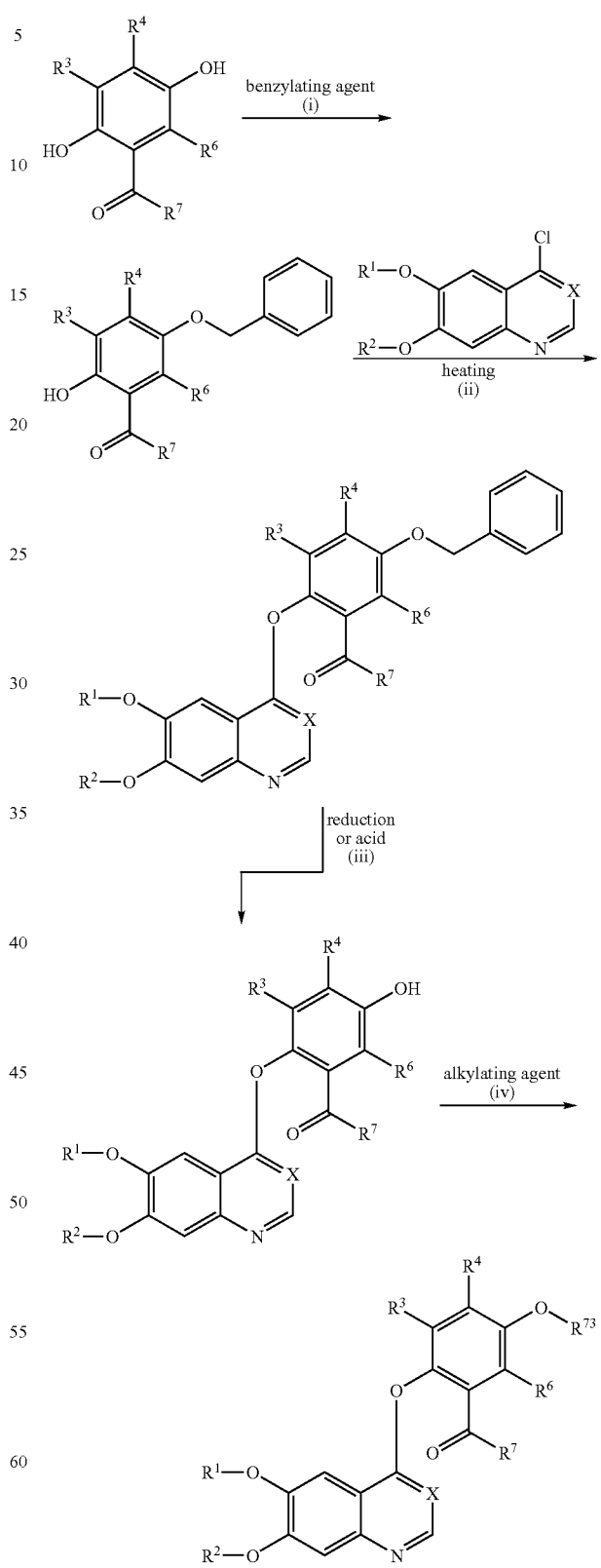

wherein each substituent is as defined above.

The contemplated compound may be produced by reacting a 2,5-dihydroxyphenyl ketone derivative with a benzylating agent, for example, benzyl bromide (step (i) above), reacting the resultant monophenol derivative with a 4-chloroquinoline derivative or a corresponding quinazolone derivative in a suitable solvent, for example, o-dichlorobenzene, or in the absence of a solvent, for example, at 120 to 180° C. (step (ii) above), then deprotecting the benzyl group in the resultant compound with a suitable acid, for example, methanesulfonic acid/trifluoroacetic acid, or by reduction (step (iii) above), and alkylating the phenolic hydroxyl group in the resultant compound with an alkylating agent, for example, ethyl iodide (step (iv) above).

16) The compound, which is represented by formula (I) and in which formula (I) is represented by formula (II) and A represents a group of formula (a1), particularly a compound in which the group of formula (a1) represented by A has a naphthalene structure, may be produced, for example, according to scheme 16 below.

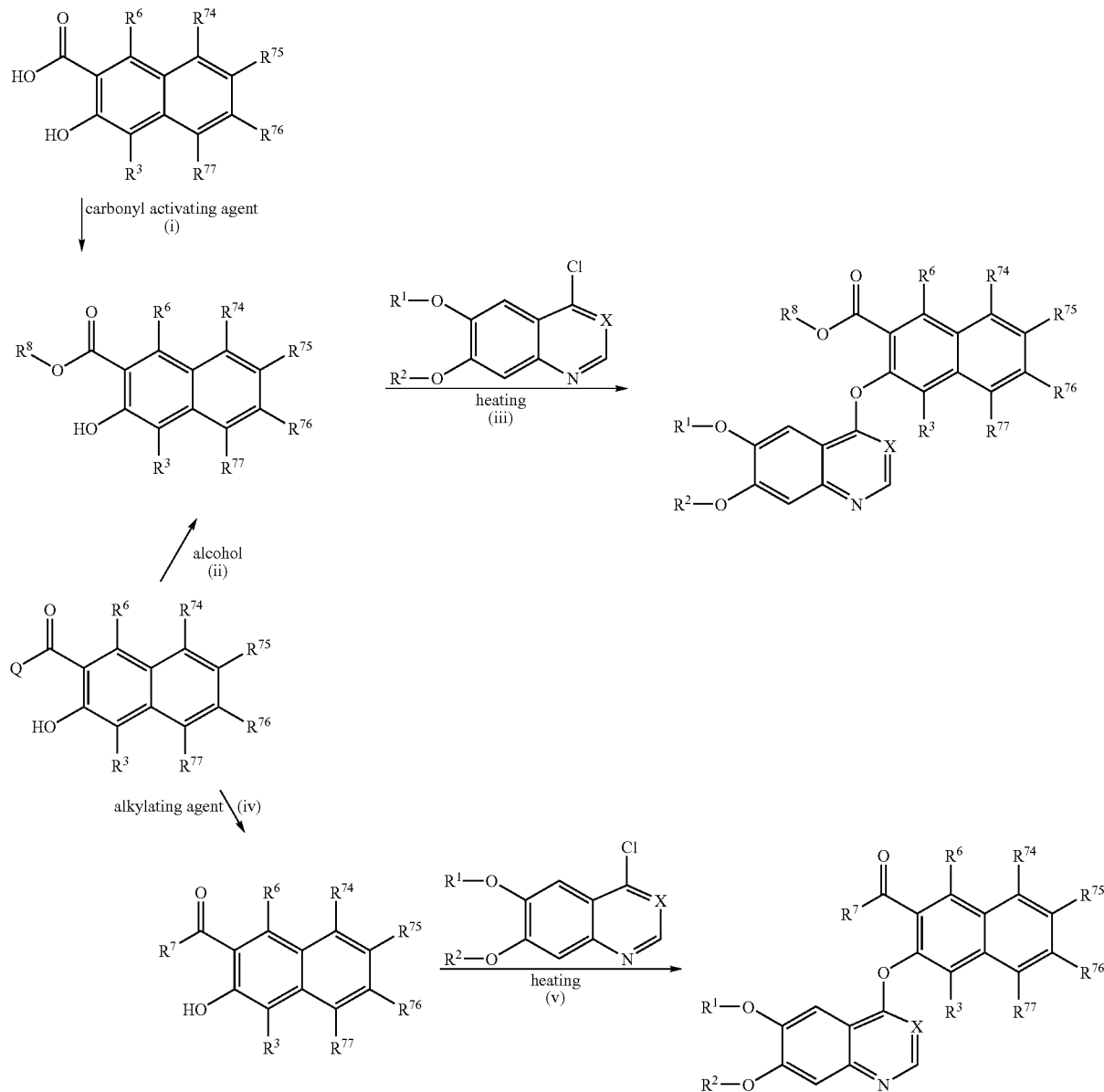

wherein

Q represents, for example, chlorine or N,O-dimethylhydroxyamine and each of the other substituents is as defined above.

In this scheme, the contemplated compound may be synthesized by the following two routes.

(I) An ester derivative is produced by reacting a hydroxynaphthalenecarboxylic acid derivative with a suitable carbonyl activating agent, for example, thionyl chloride (step (i) above) and then reacting the resultant active form of carboxylic acid derivative with an alcohol (step (ii) above). Next, the contemplated compound may be produced by reacting the ester derivative with a 4-chloroquinoline derivative or a corresponding quinazolone derivative in a suitable solvent, for example, o-dichlorobenzene, or in the absence of a solvent, for example, at 120 to 180° C. (step (iii) above).

(II) A ketone derivative is produced by reacting the active form of carboxylic acid derivative produced in step (i) with an alkylating agent, for example, methylmagnesium bromide (step (iv) above). Next, the contemplated compound may be produced by reacting the ketone derivative with a 4-chloroquinoline derivative or a corresponding quinazolone derivative in a suitable solvent, for example, o-dichlorobenzene, or in the absence of a solvent, for example, at 120 to 180° C. (step (v) above).

17) The compound, which is represented by formula (I) and in which formula (I) is represented by formula (II) and A represents a group of formula (b1), particularly a compound in which alkoxy is present at the o-position of the group of formula (b1), can be produced, for example, according to scheme 17 below.

Scheme 17:

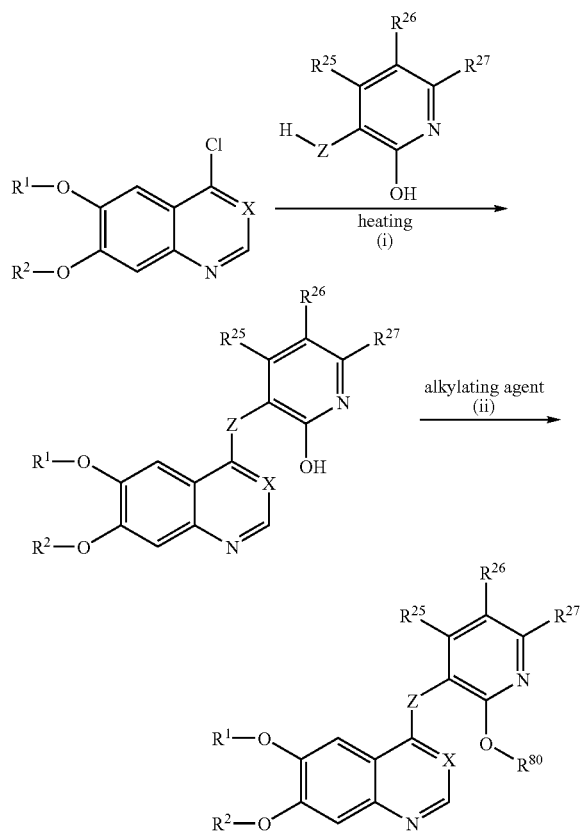

wherein each substituent is as defined above.

The contemplated compound may be produced by reacting a 2-hydroxypyridine derivative with a 4-chloroquinoline derivative or a corresponding quinazolone derivative in a suitable solvent, for example, o-dichlorobenzene, or in the absence of a solvent, for example, at 120 to 180° C. (step (i) above) and alkylating the resultant compound with an alkylating agent, for example, ethyl iodide (step (ii) above).

18) The compound, which is represented by formula (I) and in which formula (I) is represented by formula (II) and A represents a group of formula (b1), particularly a compound in which alkoxy is present at the p-position of the group of formula (b1), can be produced, for example, according to scheme 18 below.

Scheme 18:

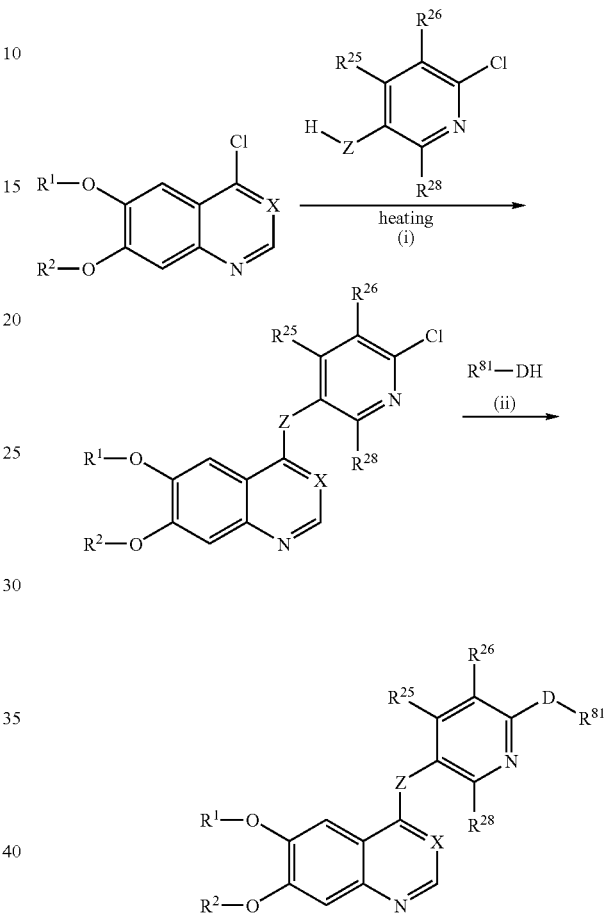

wherein $R^{81}$ represents a hydrogen atom or $C_{1-4}$ alkyl,

D represents an oxygen atom, a nitrogen atom, or a sulfur atom, and each of the other substituents is as defined above.

The contemplated compound may be produced by reacting a 2-chloropyridine derivative with a 4-chloroquinoline derivative or a corresponding quinazolone derivative in a suitable solvent, for example, o-dichlorobenzene, or in the absence of a solvent, for example, at 120 to 180° C. (step (i) above) and reacting the resultant compound with a nucleophilic reagent, for example, methanol (step (ii) above).

19) The compound, which is represented by formula (I) and in which formula (I) is represented by formula (II) and A represents a group of formula (b1), particularly a compound in which a substituent such as an iodine atom or phenyl is present at the opposition of the group of formula (b1), may be produced, for example, according to scheme 19 below.

Scheme 19:

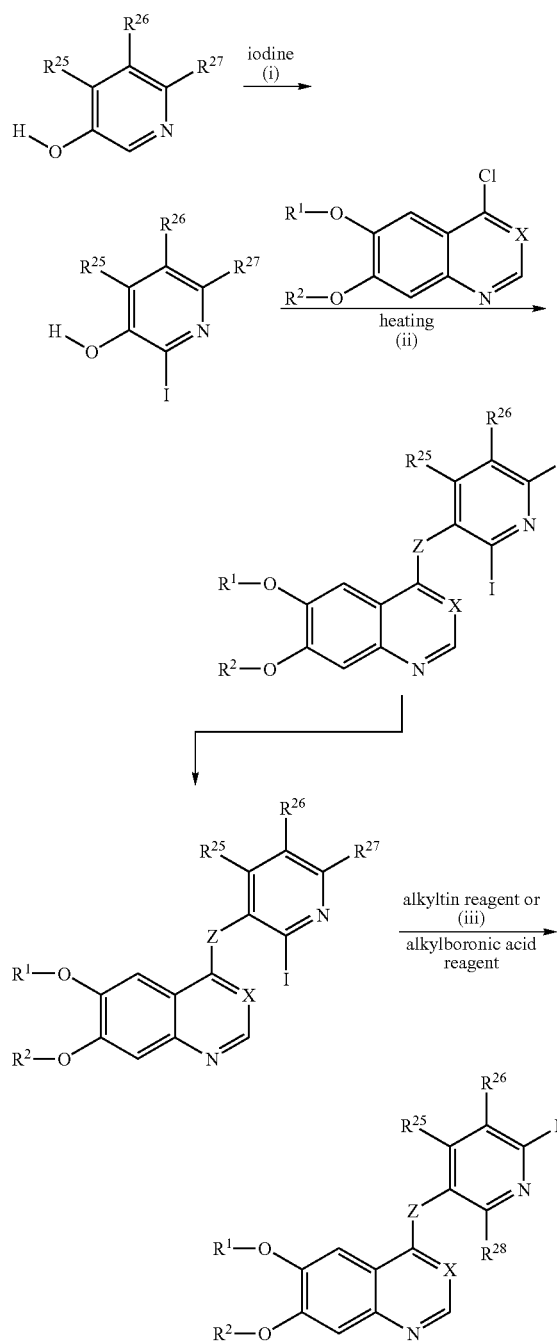

wherein each substituent is as defined above.

The contemplated compound may be produced by reacting a 3-hydroxypyridine derivative with iodine in a suitable solvent, for example, methanol (step (i) above), reacting the resultant 2-iodopyridine derivative with a 4-chloroquinoline derivative or a corresponding quinazolone derivative in a suitable solvent, for example, o-dichlorobenzene, or in the absence of a solvent, for example, at 120 to 180° C. (step (ii) above), and then reacting the resultant compound with an alkyltin reagent, for example, tri-n-butyl-(2-pyridyl)-tin, or an alkylboronic acid reagent, for example, 3-pyridylboronic acid, in the presence of a suitable transition metal catalyst, for example, tetrakis triphenylphosphine palladium (step (iii) above).

20) The compound, which is represented by formula (I) and in which formula (I) is represented by formula (II) and A represents a group of formula (b1), particularly a compound having a cyano group at the o-position of the group of formula (b1), may be produced, for example, according to scheme 20 below.

Scheme 20:

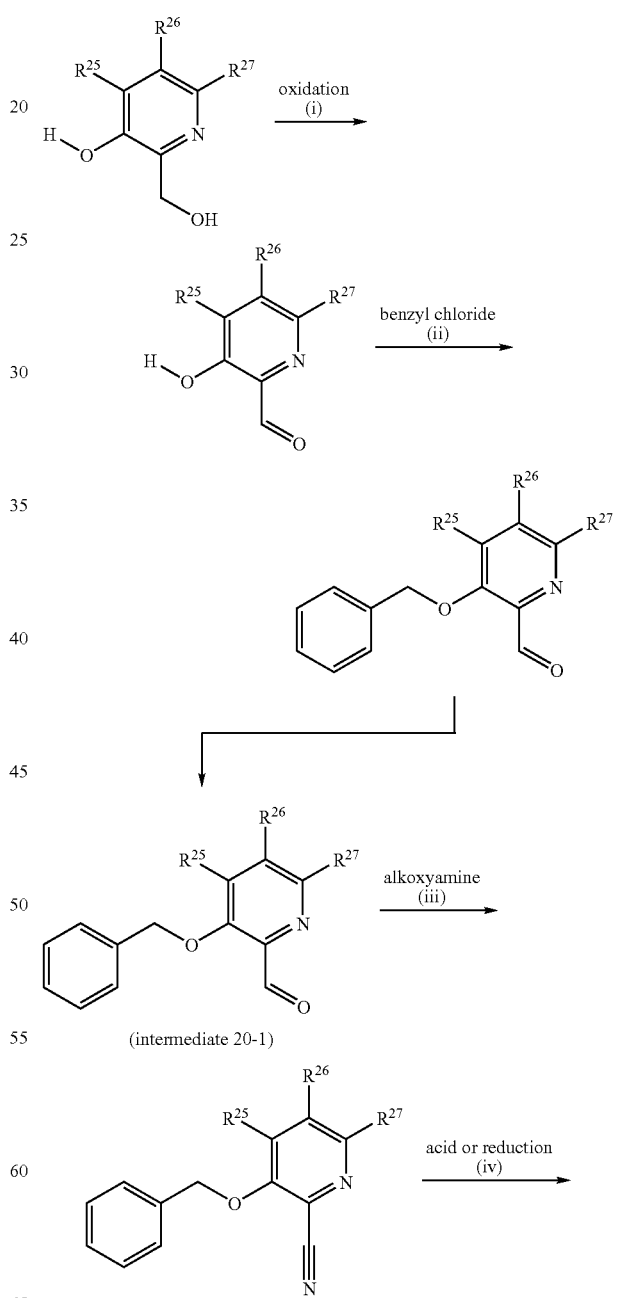

(intermediate 20-1)

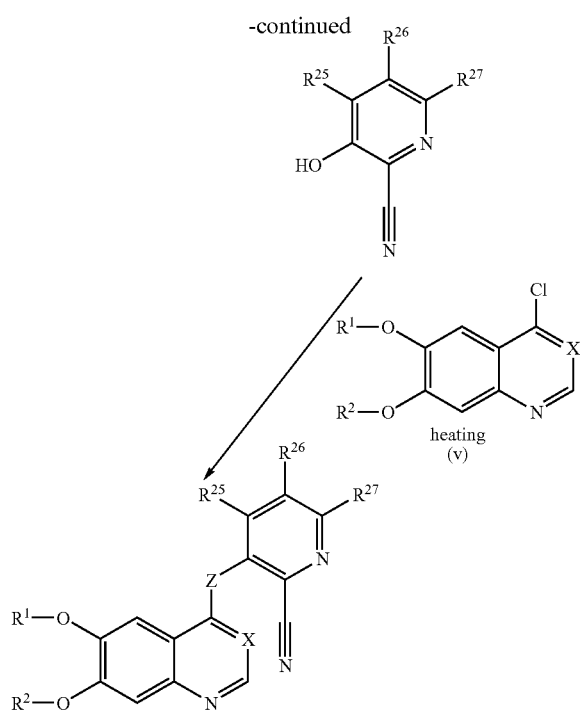

wherein each substituent is as defined above.

Intermediate 20-1 may be produced by reacting the above starting compound with a suitable oxidizing agent, for example, manganese dioxide (step (i) above), then reacting the hydroxyl group, remaining unchanged, in the resultant compound with a suitable benzylating agent, for example, benzyl chloride (step (ii) above). Next, a corresponding cyanopyridine derivative may be produced by reacting intermediate 20-1 with an alkoxyamine (step (iii) above). The cyanopyridine derivative thus obtained is deprotected with a suitable acid, for example, methanesulfonic acid/trifluoroacetic acid, or a suitable reducing agent, for example, hydrogen gas/palladium hydroxide (step (iv) above). The contemplated compound may be produced by reacting the resultant hydroxypyridine derivative with a 4-chloroquinoline derivative or a corresponding quinazolone derivative in a suitable solvent, for example, o-dichlorobenzene, or in the absence of a solvent, for example, at 120 to 180° C. (step (v) above).

n

21) The compound, which is represented by formula (I) and in which formula (I) is represented by formula (II) and A represents a group of formula (b1), particularly a compound having a specific heterocyclic group at the o-position of the group of formula (b1), for example, compound 256, may be produced, for example, according to scheme 21 below.

Scheme 21:

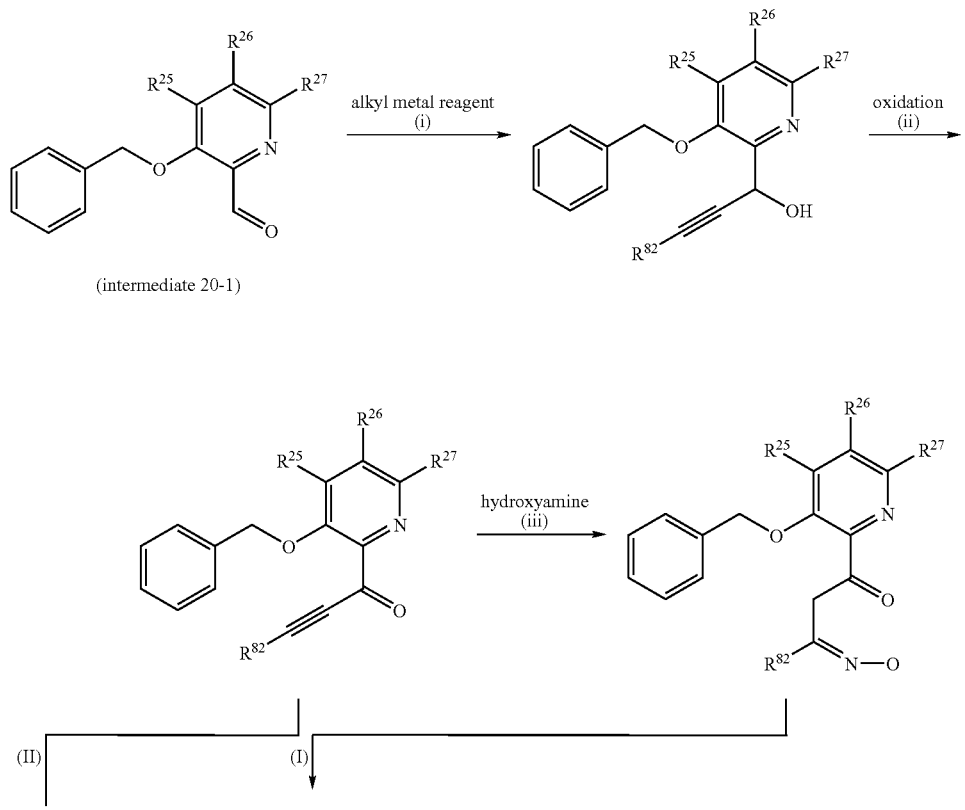

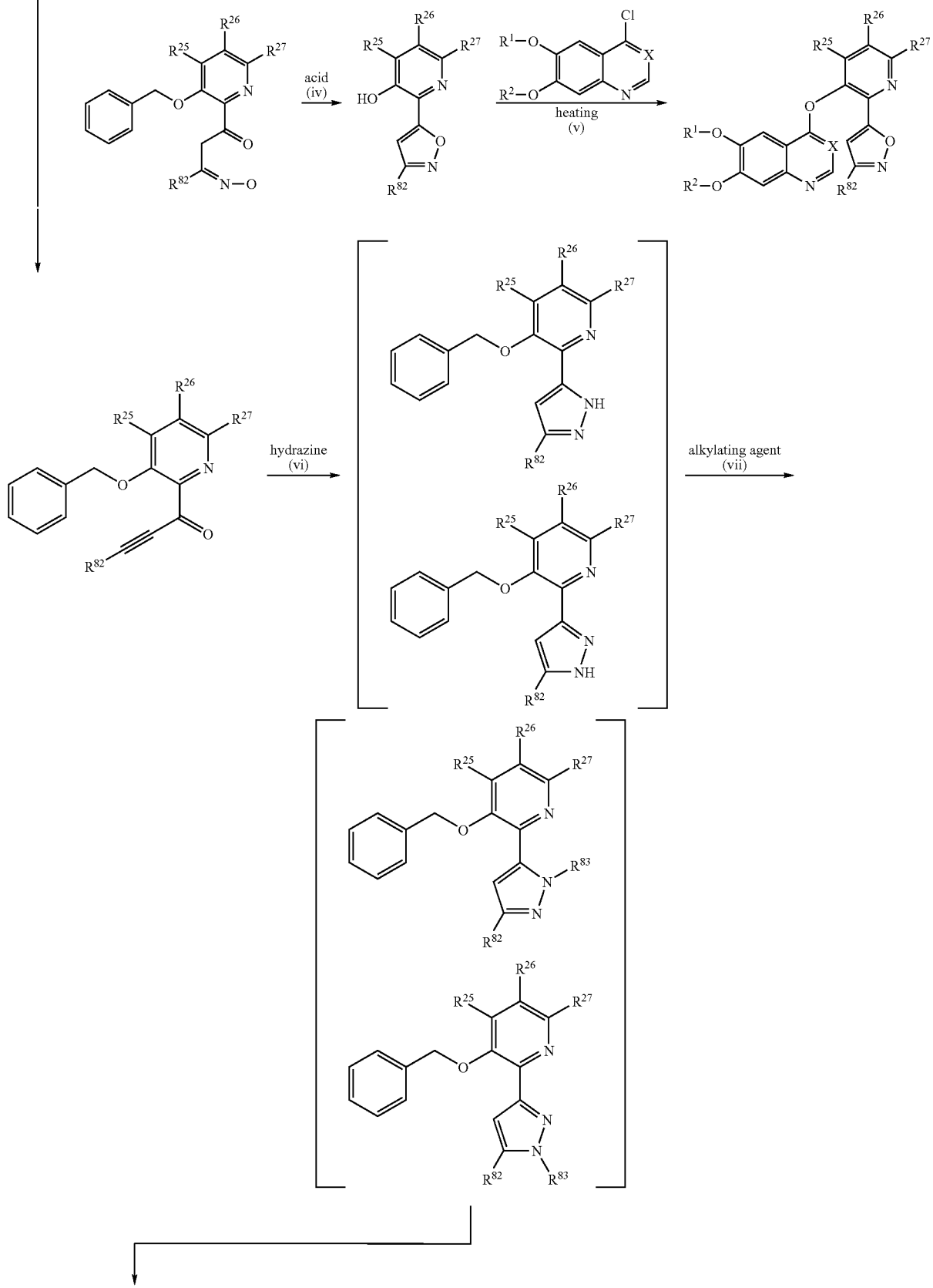

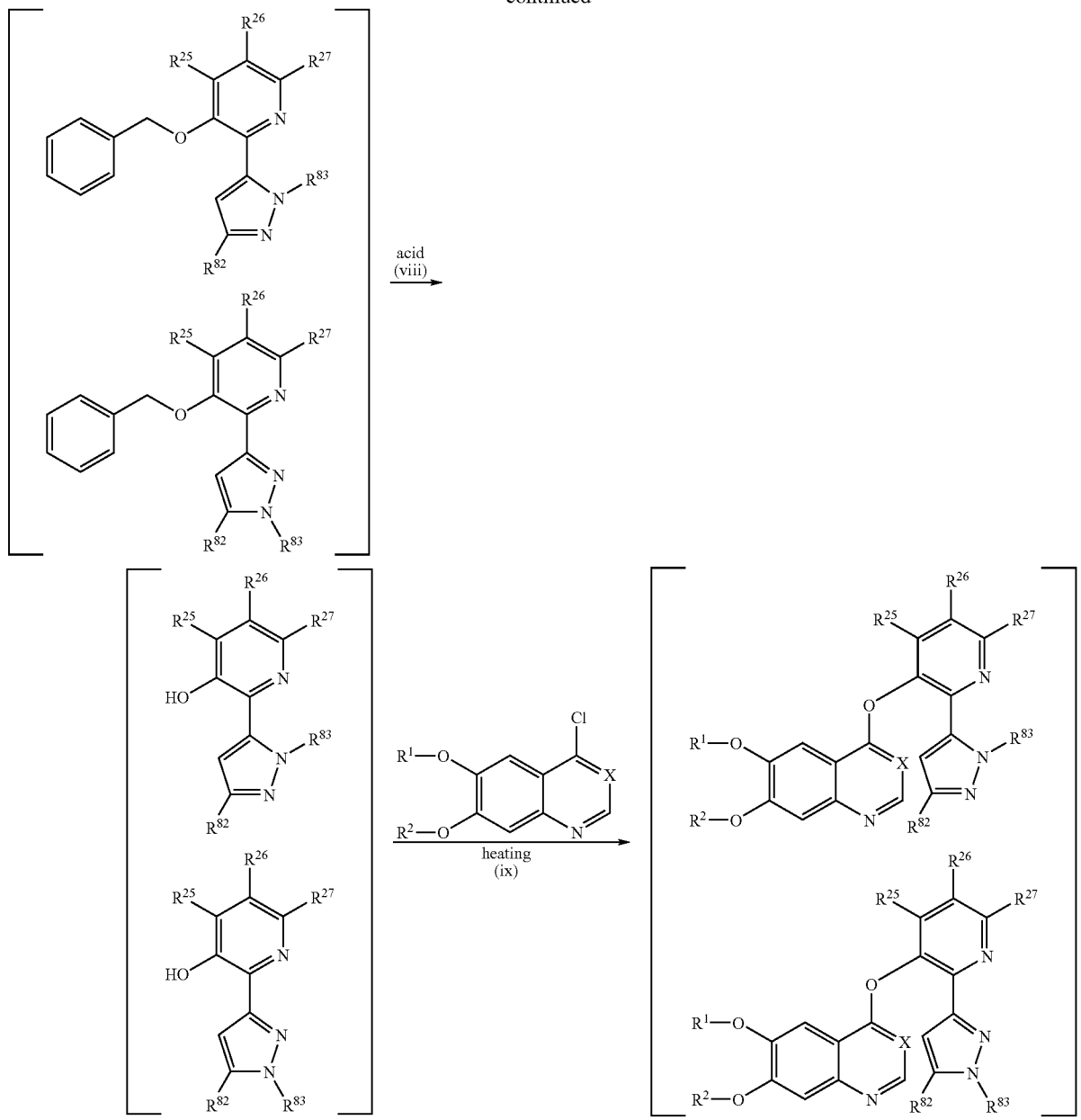

wherein

R[82] and R[83] represent hydroxyl; cyano; a halogen atom; $C_{1-4}$ alkoxy; phenyloxy; $C_{1-4}$ alkylcarbonyl; amino optionally substituted by $C_{1-4}$ alkyl or $C_{1-4}$ alkylcarbonyl; aminocarbonyl optionally substituted by $C_{1-4}$ alkyl; or $C_{1-4}$ alkyl optionally substituted by hydroxyl or a halogen atom, and each of the other substituents is as defined above.

In this scheme, the contemplated compound may be synthesized by the following two routes.

(I) A ketone derivative may be produced by reacting intermediate 20-1 produced according to scheme 20 with an alkyne metal reagent, for example, 1-propynylmagnesium bromide (step (i) above) and then oxidizing the hydroxy group in the resultant compound with a suitable oxidizing agent, for example, manganese oxide (step (ii) above). A 3-hydroxy-2-isoxazoylpyridine derivative may be produced by reacting the resultant ketone derivative with hydroxyamine (step (iii) above) and then reacting the resultant compound with a suitable acid, for example, methanesulfonic acid/trifluoroacetic acid (step (iv) above). The contemplated compound may be produced by reacting the resultant 3-hydroxy-2-isoxazoylpyridine derivative with a 4-chloroquinoline derivative or a corresponding quinazolone derivative in a suitable solvent, for example, o-dichlorobenzene, or in the absence of a solvent, for example, at 120 to 180° C. (step (v) above).

(II) A ketone derivative may be produced by reacting intermediate 20-1 produced according to scheme 20 with an alkyne metal reagent, for example, 1-propynylmagnesium bromide (step (i) above) and then oxidizing the hydroxy group in the resultant compound with a suitable oxidizing agent, for example, manganese oxide (step (ii) above). An N-alkylpyrazole derivative may be produced by reacting the ketone derivative with hydrazine (step (vi) above) and reacting the resultant compound with an alkylating agent, for example, methyl iodide (step (vii) above). A 3-hydroxypyridine derivative may be produced by reacting the resultant N-alkylpyrazole derivative with a suitable acid, for example, methanesulfonic acid/trifluoroacetic acid (step (viii) above). Next, the contemplated compound may be produced by reacting the resultant 3-hydroxypyridine derivative with a 4-chloroquinoline derivative or a corresponding quinazolone derivative in a suitable solvent, for example, o-dichlorobenzene, or in the absence of a solvent, for example, at 120 to 180° C. (step (ix) above).

22) The compound, which is represented by formula (I) and in which formula (I) is represented by formula (II) and A represents a group of formula (b1), particularly a compound in which aminomethyl is present at the o-position of the group of formula (b1), may be produced, for example, according to scheme 22 below.

Scheme 22:

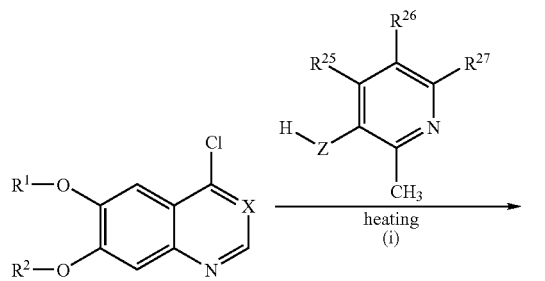

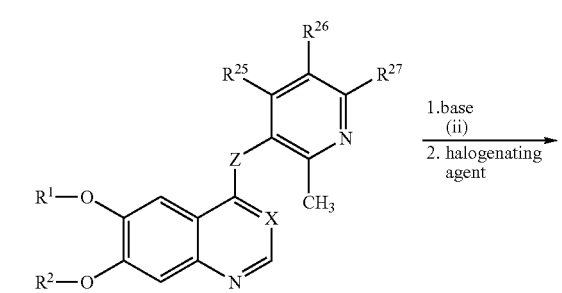

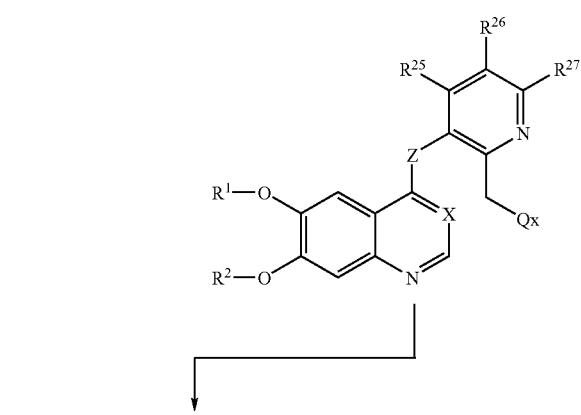

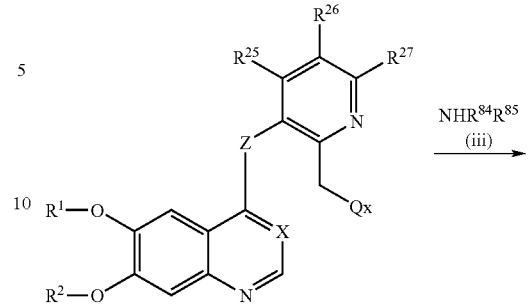

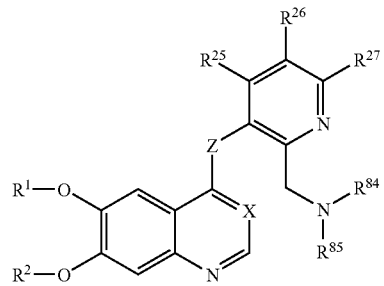

wherein

Qx represents a halogen atom, preferably a chlorine atom or a bromine atom, and each substituent is as defined above.

A quinoline derivative may be produced by reacting a 3-hydroxy-2-methylpyridine derivative with a 4-chloroquinoline derivative or a corresponding quinazolone derivative in a suitable solvent, for example, o-dichlorobenzene, or in the absence of a solvent, for example, at 120 to 180° C. (step (i) above). The contemplated compound may be produced by reacting the resultant compound with a suitable base, for example, lithium diisopropylamide to produce a carbanion, reacting the carbanion with a halogenating agent, for example, N-bromosuccimide (step (ii) above) and then reacting the resultant compound with an amine (step (iii) above).

23 to 25) The compound, which is represented by formula (I) and in which formula (I) is represented by formula (II) and A represents a group of formula (b1), particularly a compound in which carbonyl is present at the o-position of the group of formula (b1), may be produced, for example, by any one of schemes 23 to 25 below.

Scheme 23:

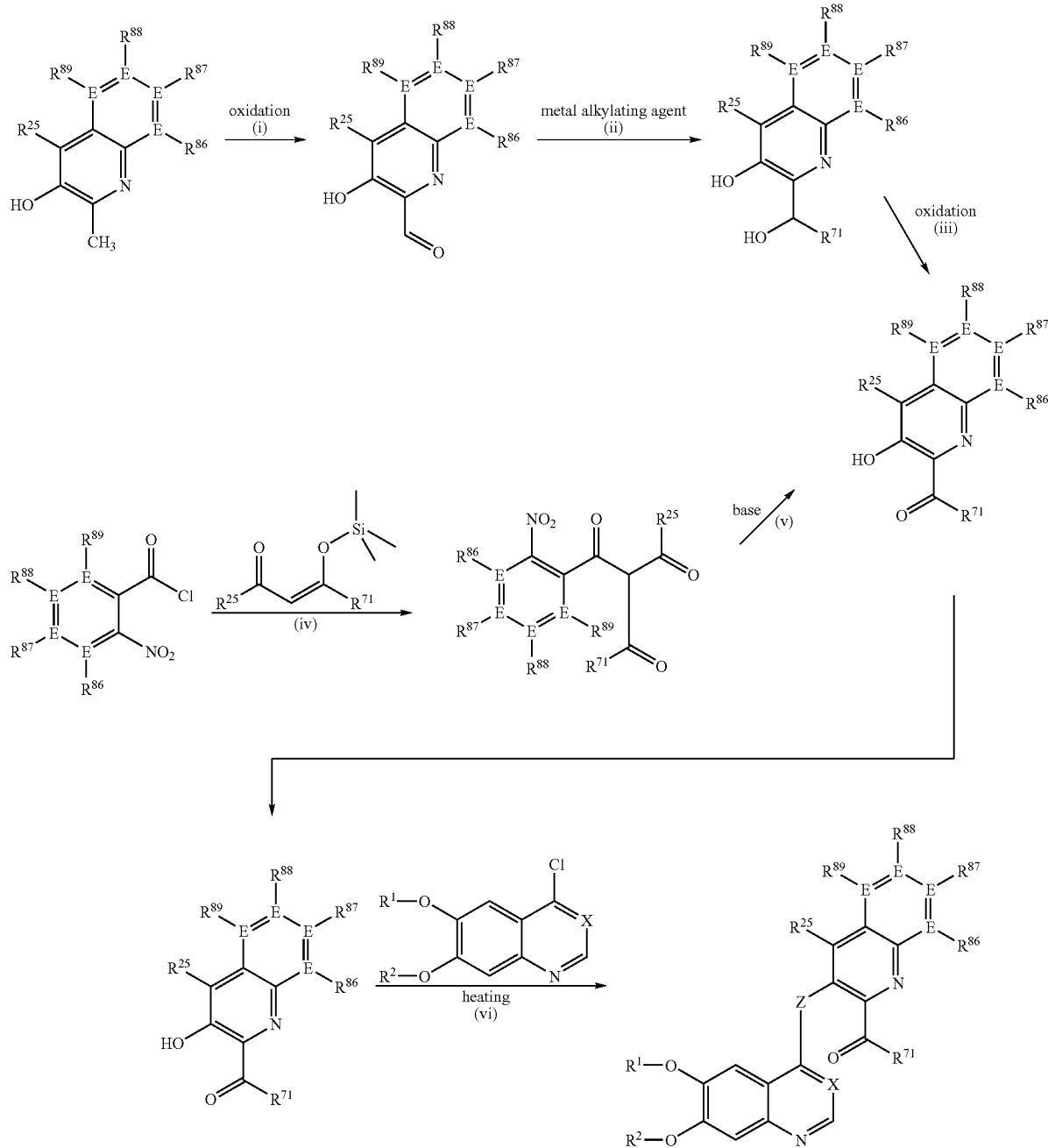

wherein at least one of Es represents a heteroatom such as a nitrogen atom with the remaining Es representing a carbon atom, or all Es represent a carbon atom; and each of the other substituents in the scheme is as defined above.

In this scheme, the contemplated compound may be synthesized by the following two routes.

(I) A ketone derivative may be produced by reacting a 3-hydroxy-2-methylquinoline derivative with a suitable oxidizing agent, for example, selenium dioxide (step (i) above), reacting the resultant aldehyde derivative with a metal alkylating agent, for example, methylmagnesium bromide (step (ii) above), and then oxidizing the resultant alcoholic compound with a suitable oxidizing agent, for example, manganese dioxide (step (iii) above). The contemplated compound may be produced by reacting the resultant ketone derivative with a 4-chloroquinoline derivative or a corresponding quinazolone derivative in a suitable solvent, for example, o-dichlorobenzene, or in the absence of a solvent, for example, at 120 to 180° C. (step (vi) above).

(II) A 3-hydroxyquinoline derivative may be produced by reacting an acid chloride derivative with silyl enol ether, for example, 4-trimethylsilanyloxy-pent-3-en-2-one (step (iv) above) and then reacting the resultant ketone derivative with a suitable base, for example, an aqueous potassium hydroxide solution (step (v) above). The contemplated compound may be produced by reacting the 3-hydroxyquinoline derivative with a 4-chloroquinoline derivative or a corresponding quinazolone derivative in a suitable solvent, for example, o-dichlorobenzene, or in the absence of a solvent, for example, at 120 to 180° C. (step (vi) above).

Scheme 24:

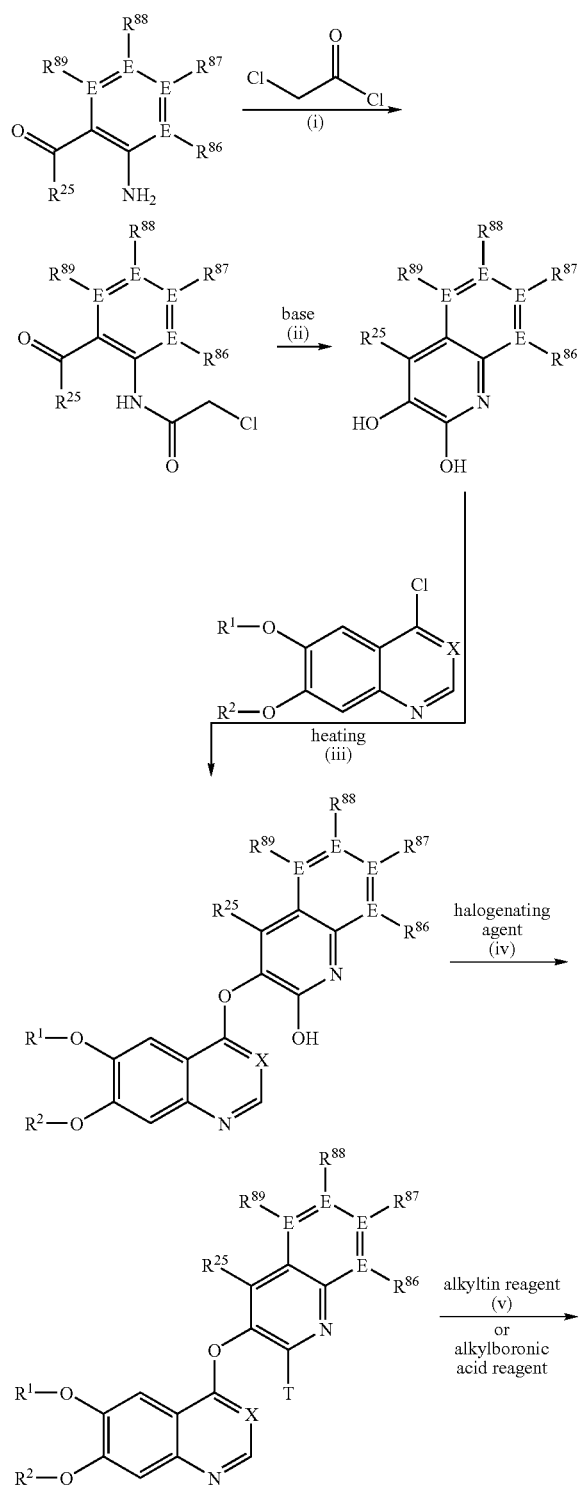

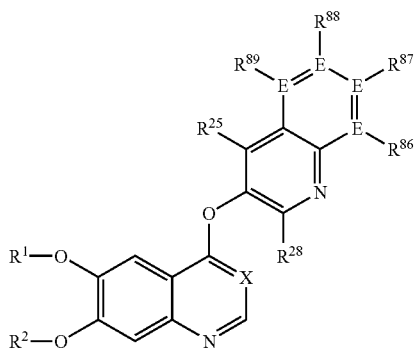

wherein at least any one of Es represents a heteroatom, for example, a nitrogen atom, with the remaining other Es representing a carbon atom, preferably a bromine atom, T represents a halogen atom, preferably a bromine atom, and each of the other substituents in the scheme is as defined above.

A 2,3-dihydroxyquinoline derivative may be produces by reacting an aniline derivative with choloroacetyl chloride (step (i) above) and then reacting the resultant amide derivative with a suitable base, for example, an aqueous potassium hydroxide solution (step (ii) above). A 2-hyroxyquinoline derivative may be produced by reacting the resultant 2,3-dihydroxyquinoline derivative with a 4-chloroquinoline derivative or a corresponding quinazolone derivative in a suitable solvent, for example, o-dichlorobenzene, or in the absence of a solvent, for example, at 120 to 180° C. (step (iii) above). A 2-haloquinoline derivative may be produced by reacting the resultant 2-hydroxyquinoline derivative with a suitable halogenating agent, for example, tetrabutylammonium bromide (ste p (iv) above). The contemplated compound may be produced by reacting the 2-haloquinoline derivative with an alkyltin reagent, for example, tri-n-butyl-(2-pyridyl)-tin, or an alkylboronic acid reagent, for example, 3-pyridylboronic acid, in the presence of a suitable transition metal catalyst, for example, tetrakis triphenylphosphine palladium (step (v) above).

Scheme 25:

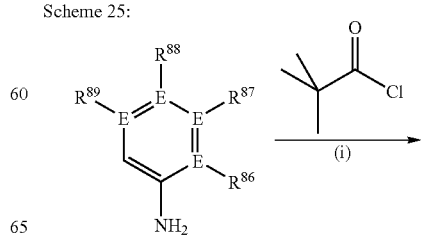

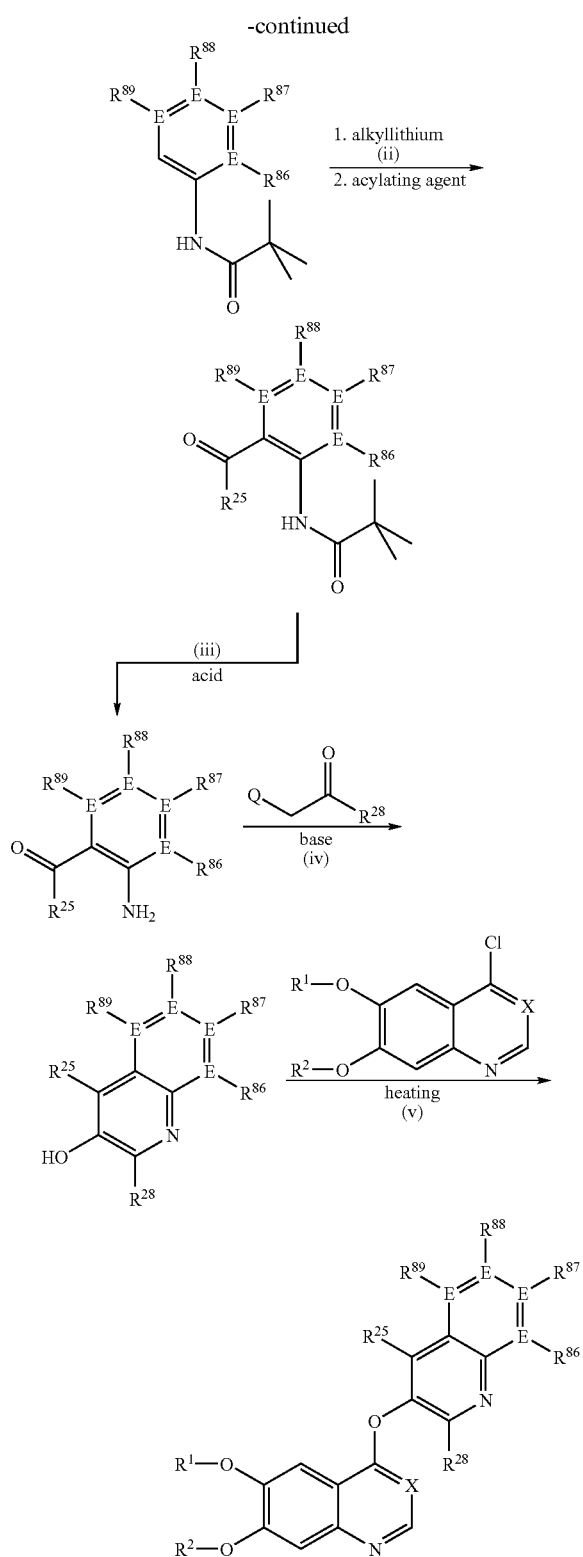

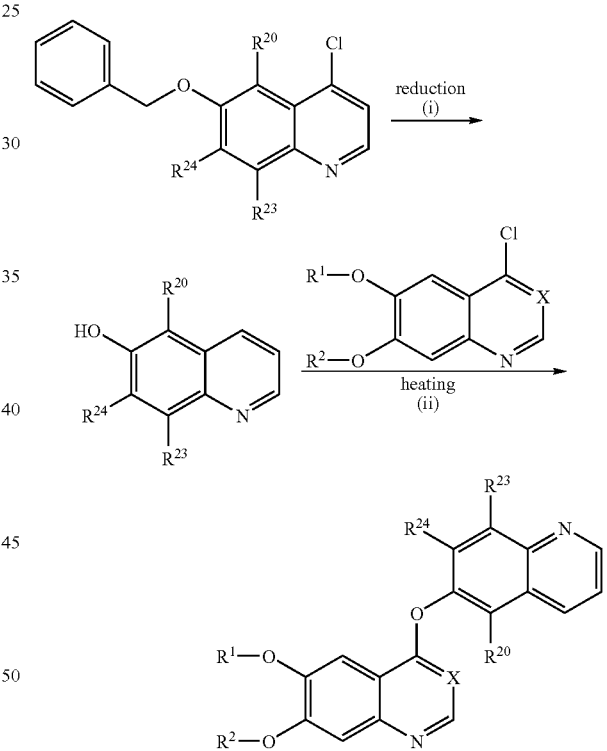

wherein at least any one of Es represents a heteroatom, for example, a nitrogen atom, with the remaining other Es representing a carbon atom, or all Es represent a carbon atom, and each of the other substituents in the scheme is as defined above.

An amide derivative may be produced by reacting an aniline derivative with pivaloyl chloride (step (i) above). Next, an o-acylaniline derivative may be produced by reacting the resultant amide derivative with a suitable alkyllithium, for example, n-butyllithium to give an anion, reacting the anion with an acylating agent, for example, N,N-dimethylformamide (step (ii) above), then deprotecting the pivaloyl group with a suitable acid, for example, hydrochloric acid (step (iii) above). The contemplated compound may be produced by reacting the o-acylaniline derivative with a methyl ketone derivative (step (iv) above) to give a 3-hydroxyquinoline derivative and then reacting the 3-hydroxyquinoline derivative with a 4-chloroquinoline derivative or a corresponding quinazolone derivative in a suitable solvent, for example, o-dichlorobenzene, or in the absence of a solvent, for example, at 120 to 180° C. (step (v) above).

26) The compound, which is represented by formula (I) and in which formula (I) is represented by formula (II) and A represents a group of formula (c), for example, compound 297, may be produced, for example, according to scheme 26 below.

Scheme 26:

wherein each substituent is as defined above.

The contemplated compound may be produced by reacting a 6-benzyloxy-4-chloroquinoline derivative with a suitable reducing agent, for example, hydrogen gas/palladium hydroxide (step (i) above) to give a 6-hydroxyquinoline derivative and reacting the 6-hydroxyquinoline derivative with a 4-chloroquinoline derivative or a corresponding quinazolone derivative in a suitable solvent, for example, o-dichlorobenzene, or in the absence of a solvent, for example, at 120 to 180° C. (step (ii) above).

27) The compound, which is represented by formula (I) and in which formula (I) is represented by formula (II) and A represents a group of formula (c), for example, compound 299, may be produced, for example, according to scheme 27 below.

Scheme 27:

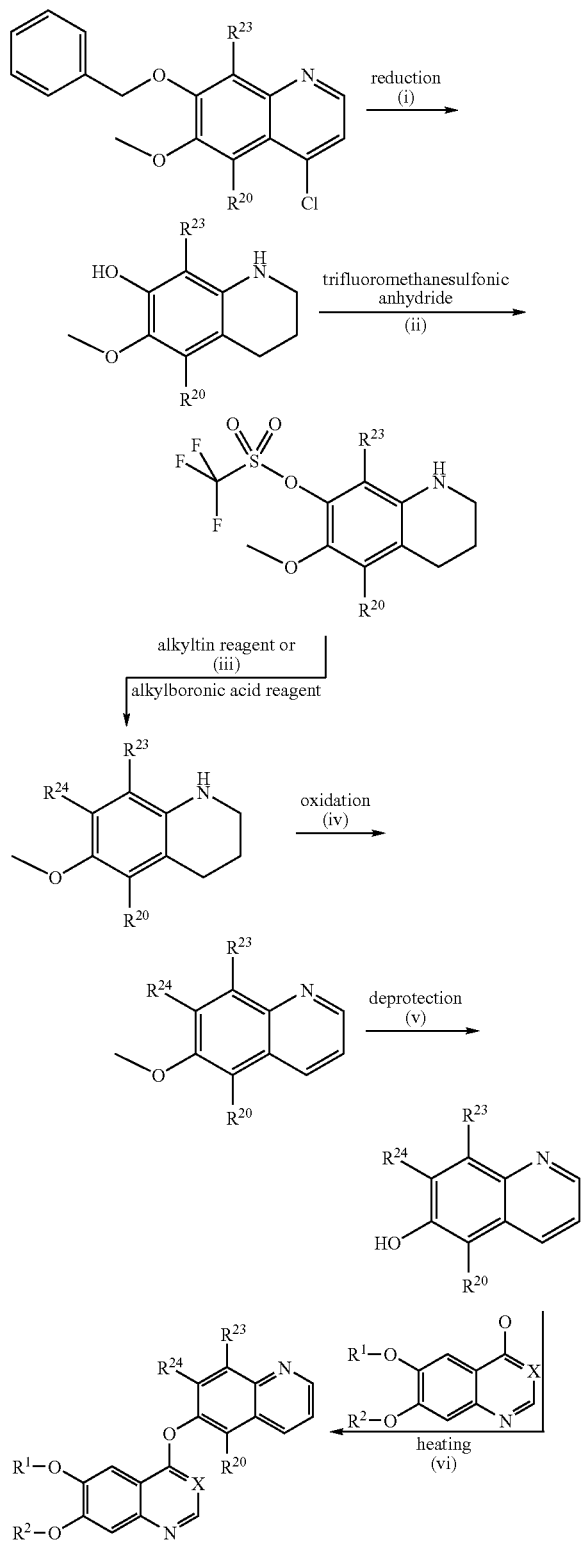

wherein each substituent is as defined above.

A trifluoromethanesulfonate derivative may be produced by reacting a 7-benzyloxy-4-chloroquinoline derivative with a suitable reducing agent, for example, hydrogen gas/palladium hydroxide to give an alcohol (step (i) above) and then reacting the alcohol with trifluoromethanesulfonic anhydride (step (ii) above) to give a trifluoromethanesulfonate derivative. A quinoline derivative may be produced by reacting the trifluoromethanesulfonate derivative with an alkyltin reagent, for example, tri-n-butyl-(2-pyridyl)-tin or an alkylboronic acid reagent, for example, 3-pyridylboronic acid in the presence of a suitable transition metal catalyst, for example, tetrakis triphenylphosphine palladium (step (iii) above) and reacting the resultant compound with a suitable oxidizing agent, for example, 2,3-dichloro-5,6-dicyano-1,4-benzoquinone, to give a quinoline derivative (step (iv) above). Next, a 6-hydroxyquinoline derivative may be produced by reacting the quinoline derivative with a suitable reagent, for example, boron tribromide (step (v) above). The contemplated compound may be produced by reacting the 6-hydroxyquinoline derivative with a 4-chloroquinoline derivative or a corresponding quinazolone derivative in a suitable solvent, for example, o-dichlorobenzene, or in the absence of a solvent, for example, at 120 to 180° C. (step (vi) above).

28 and 29) The compound, which is represented by formula (I) and in which formula (I) is represented by formula (II) and A represents a group of formula (c), particularly a compound in which the group of formula (c) has an isoquinoline structure, may be produced, for example, according to scheme 28 or 29 below.

Scheme 28:

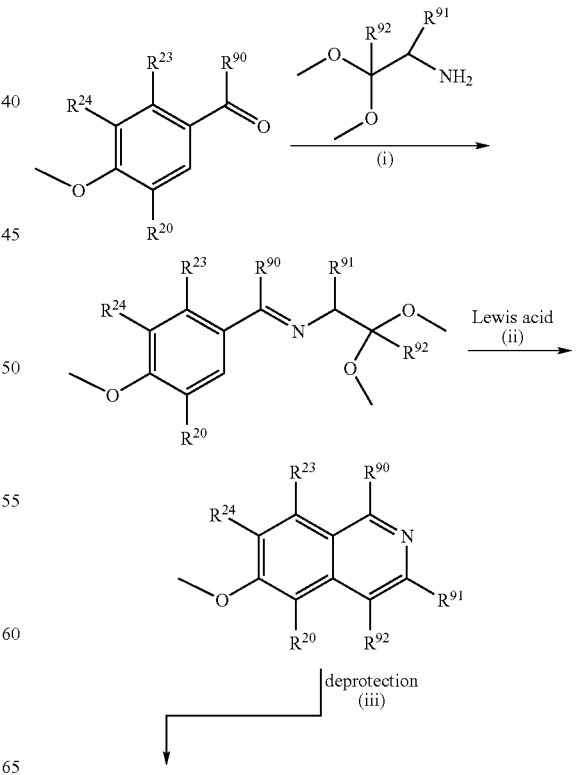

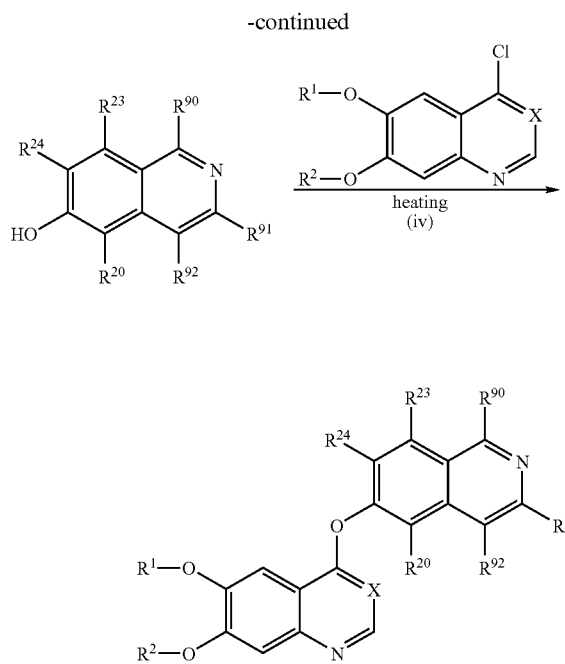

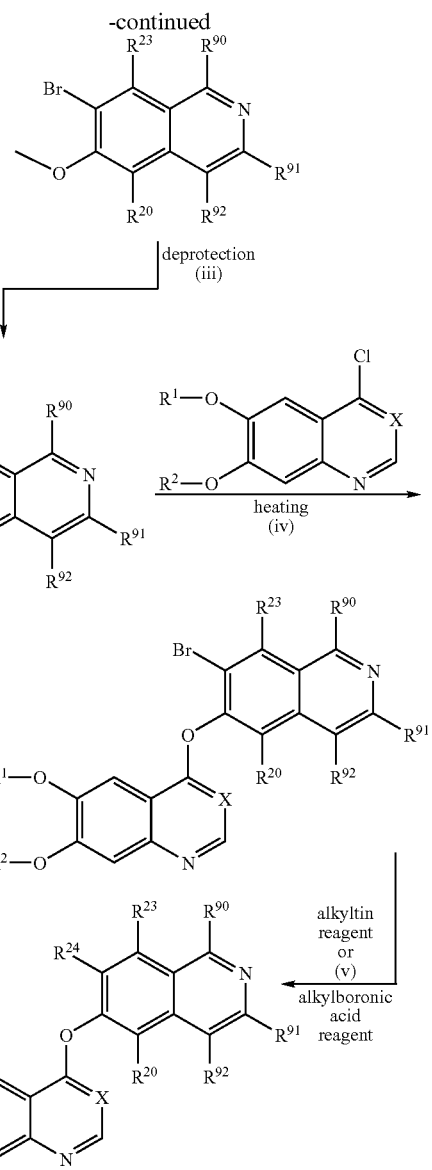

wherein each substituent is as defined above.

A 6-methoxyisoquinoline derivative may be produced by reacting a 4-methoxybenzaldehyde derivative with a dimethoxyalkylamine derivative to give an imine derivative (step (i) above) and reacting the imine derivative with a suitable Lewis acid, for example, titanium tetrachloride, to give a 6-methoxyisoquinoline derivative (step (ii) above). A 6-hydroxyisoquinoline derivative may be produced by reacting the 6-methoxyisoquinoline derivative with a suitable reagent, for example, boron tribromide (step (iii) above). Next, the contemplated compound may be produced by reacting the 6-hydroxyquinoline derivative with a 4-chloroquinoline derivative or a corresponding quinazolone derivative in a suitable solvent, for example, o-dichlorobenzene, or in the absence of a solvent, for example, at 120 to 180° C. (step (iv) above).

Scheme 29:

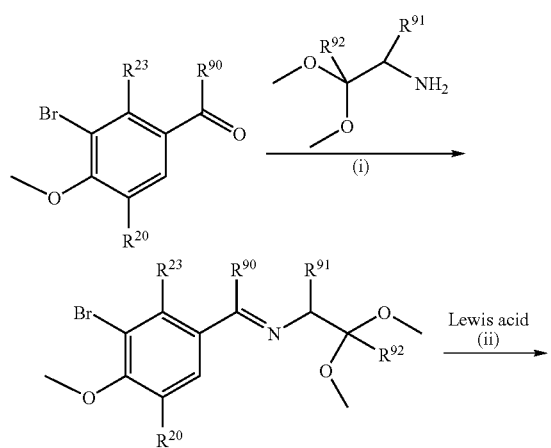

wherein each substituent is as defined above.

A 6-methoxyisoquinoline derivative may be produced by reacting a 3-bromo-4-methoxybenzaldehyde derivative with a dimethoxyalkylamine derivative to give an imine derivative (step (i) above) and then reacting the imine derivative with a suitable Lewis acid, for example, titanium tetrachloride, to give a 6-methoxyisoquinoline derivative (step (ii) above). A 6-hydroxyisoquinoline derivative may be produced by reacting the 6-methoxyisoquinoline derivative with a suitable reagent, for example, boron tribromide (step (iii) above). Next, the 6-hydroxyquinoline derivative is reacted with a 4-chloroquinoline derivative or a corresponding quinazolone derivative in a suitable solvent, for example, o-dichlorobenzene, or in the absence of a solvent, for example, at 120 to 180° C. (step (iv) above). The contemplated compound may be produced by reacting the resultant compound with an alkyltin reagent, for example, tri-n-butyl-(2-pyridyl)-tin, or an alkylboronic acid reagent, for example, 3-pyridylboronic acid, in the presence of a suitable transition metal catalyst, for example, tetrakis triphenylphosphine palladium (step (v) above).

30) The compound, which is represented by formula (I) and in which formula (I) is represented by formula (II) and A represents a group of formula (c), for example, compound 305, may be produced, for example, according to scheme 30 below.

Scheme 30:

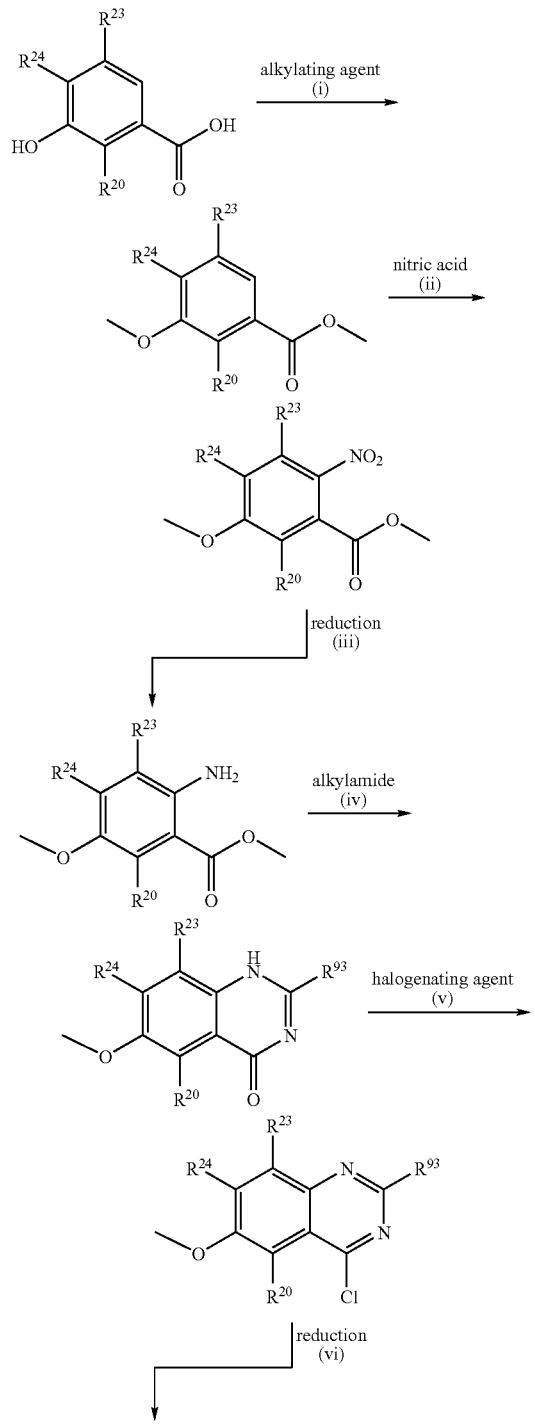

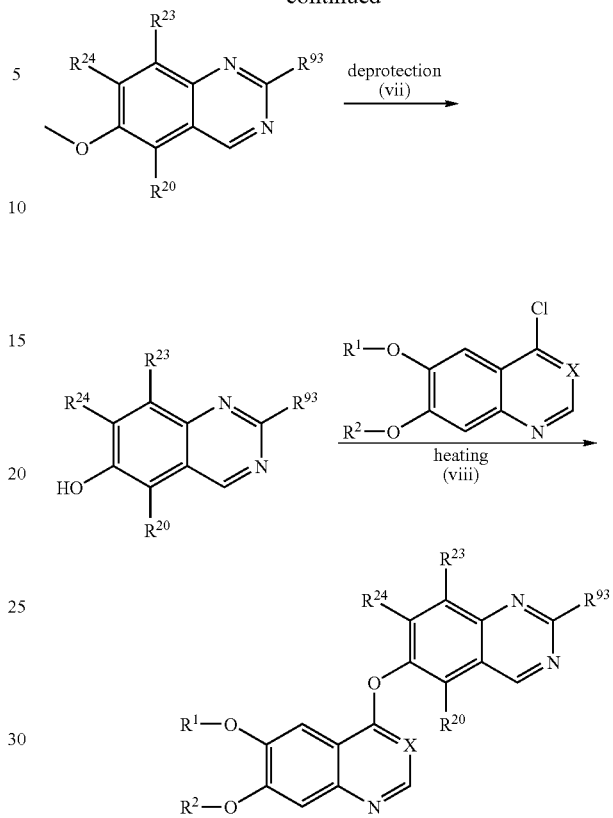

wherein each substituent is as defined above.

An alkyl 3-alkoxybenzoate derivative may be produced by reacting a 3-hydroxybenzoic acid derivative with an alkylating agent, for example, methyl iodide, (step (i) above). An aniline derivative may be produced by reacting the alkyl 3-alkoxybenzoate derivative with nitric acid in the presence of a suitable acid, for example, acetic acid (step (ii) above) and then reducing the resultant nitro group with a suitable reducing agent, for example, hydrogen gas/palladium hydroxide to give an aniline derivative (step (iii) above). A 4-chloroquinazoline derivative may be produced by reacting the amino group in the aniline derivative with an alkylamide (step (iv) above) and then reacting the resultant compound with a suitable halogenating agent, for example, phosphorus oxychloride (step (v) above). Next, a 6-hydroxyquinazoline derivative may be produced by reducing the 4-chloroquinazoline derivative with a suitable reducing agent, for example, hydrogen gas/palladium hydroxide (step (vi) above) and then reacting the resultant compound with a suitable reagent, for example, boron tribromide (step (vii) above). The contemplated compound may be produced by reacting the 6-hydroxyquinazoline derivative with a 4-chloroquinoline derivative or a corresponding quinazolone derivative in a suitable solvent, for example, o-dichlorobenzene, or in the absence of a solvent, for example, at 120 to 180° C. (step (viii) above).

31) The compound, which is represented by formula (I) wherein R' represents a group other than —OR", may be produced, for example, according to scheme 31 below.

Scheme 31:

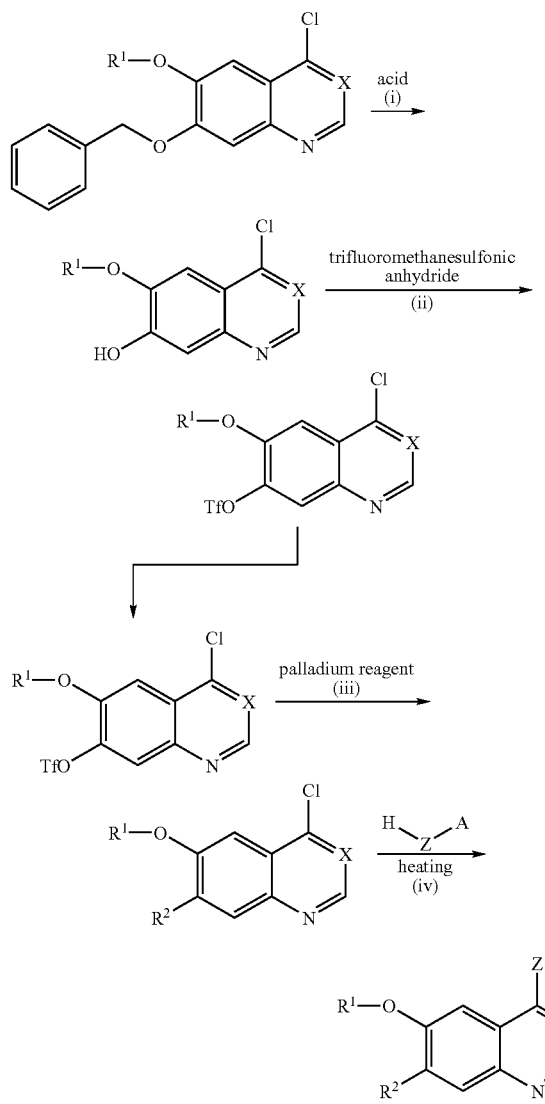

Scheme 32:

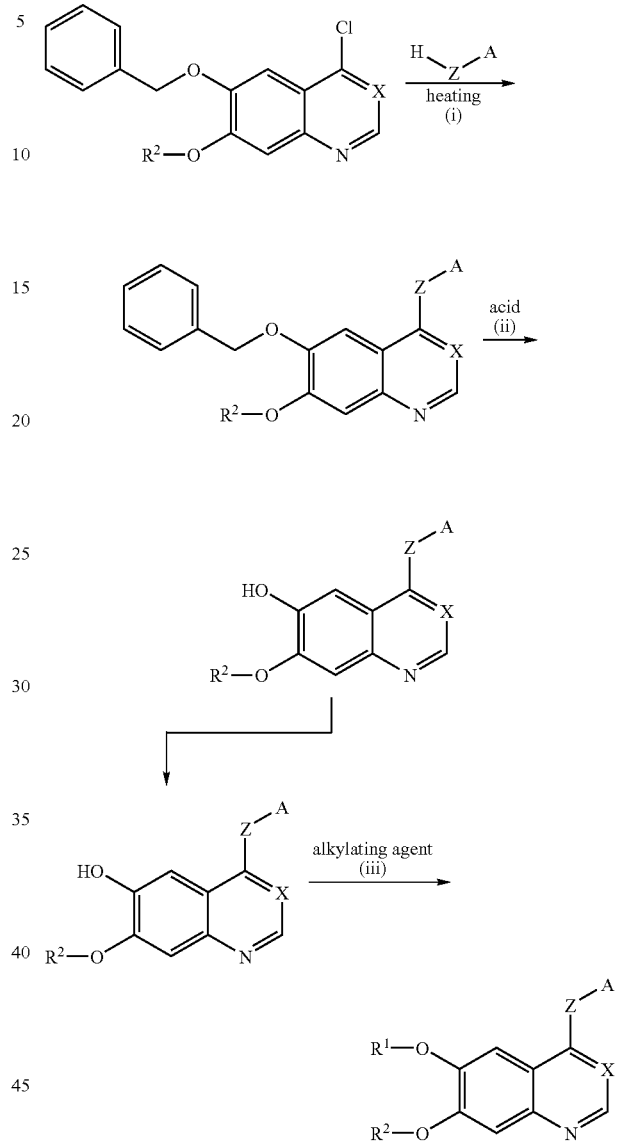

wherein each substituent is as defined above.

A trifluoromethanesulfonate derivative may be produced by reacting a 7-benzyloxy-4-chloroquinoline derivative or a corresponding quinazolone derivative with a suitable acid, for example, methanesulfonic acid/trifluoroacetic acid to give an alcohol (step (i) above) and then reacting the alcohol with trifluoromethanesulfonic anhydride (step (ii) above). The trifluoromethanesulfonate derivative is reacted with an amine or an alkene in the presence of a suitable transition metal catalyst, for example, tetrakis triphenylphosphine palladium (step (iii) above). The contemplated compound may be produced by reacting the resultant compound with a phenol derivative or a corresponding aniline derivative in a suitable solvent, for example, o-dichlorobenzene, or in the absence of a solvent, for example, at 120 to 180° C. (step (iv) above).

32) The compound, which is represented by formula (I) wherein R represents a group other than methoxy, may be produced, for example, according to scheme 32 below.

wherein each substituent is as defined above.

A 6-benzyloxy-4-chloroquinoline derivative or a corresponding quinazolone derivative is reacted with a phenol derivative or a corresponding aniline derivative in a suitable solvent, for example, o-dichlorobenzene, or in the absence of a solvent, for example, at 120 to 180° C. (step (i) above). Next, a 6-hydroxyquinoline derivative may be produced by reacting the resultant compound with a suitable acid, for example, methanesulfonic acid/trifluoroacetic acid (step (ii) above). The contemplated compound may be produced by reacting the 6-hydroxyquinoline derivative with an alkylating agent, for example, 1-bromo-2-chloroethane (step (iii) above).

33) The compound, which is represented by formula (I) and in which formula (I) is represented by formula (II) and A represents a group of formula (a3), may be produced, for example, according to scheme 33 below.

Scheme 33:

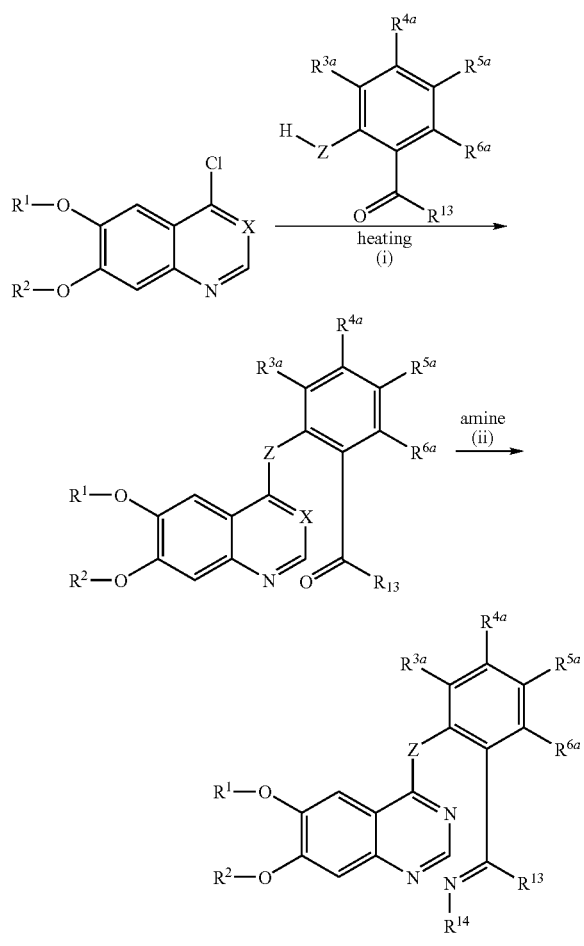

wherein each substituent is as defined above.

The contemplated compound may be produced by reacting a 4-chloroquinoline derivative or a corresponding quinazoline derivative with a phenol derivative or a corresponding aniline derivative in a suitable solvent, for example, o-dichlorobenzene, or in the absence of a solvent, for example, at 120 to 180° C. (step (i) above) and then reacting the resultant compound with an amine derivative (step (ii) above).

34) The compound, which is represented by formula (I) and in which formula (I) is represented by formula (II) and A represents a group of formula (b1), particularly a compound in which an aromatic substituent is present at the o-position of the group of formula (b1) and methyl is present at the m-position and p-position, may be produced, for example, according to scheme 34 below.

Scheme 34:

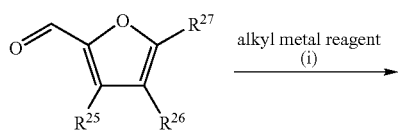

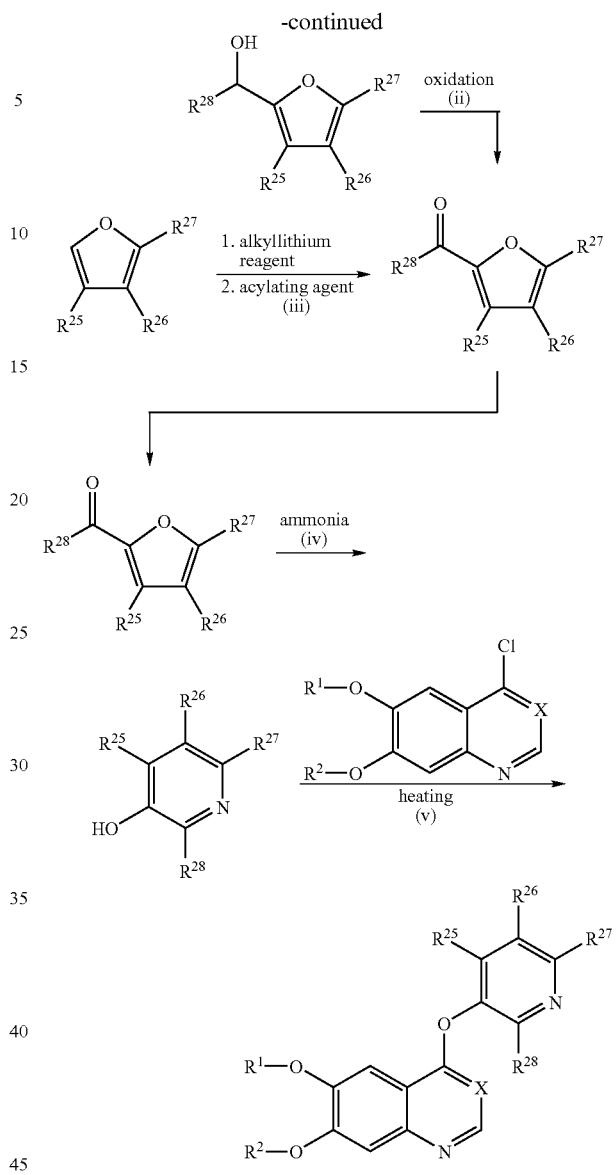

wherein each substituent is as defined above.

In this scheme, the contemplated compound may be synthesized by the following two routes.

(I) An alcohol derivative is produced by reacting a furfural derivative with an alkyl metal reagent, for example, phenylmagnesium bromide (step (i) above). A ketone derivative may be produced by oxidizing the alcohol derivative with a suitable oxidizing agent, for example, manganese dioxide (step (ii) above). Next, a 3-hydroxy-pyridine derivative may be produced by reacting the ketone derivative with ammonia (step (iv) above). Further, the contemplated compound may be produced by reacting the 3-hydroxypyridine derivative with a 4-chloroquinoline derivative or a corresponding quinazolone derivative in a suitable solvent, for example, o-dichlorobenzene, or in the absence of a solvent, for example, at 120 to 180° C.

(II) A ketone derivative may be produced by reacting a furan derivative with an alkyllithium reagent, for example, n-butyllithium, and then reacting the resultant compound with an acylating agent, for example, benzoyl chloride (step (iii) above). A 3-hydroxypyridine derivative may be produced by reacting the ketone derivative with ammonia (step (iv) above). Next, the contemplated compound may be produced by reacting the 3-hydroxypyridine derivative with a 4-chloroquinoline derivative or a corresponding quinazolone derivative in a suitable solvent, for example, o-dichlorobenzene, or in the absence of a solvent, for example, at 120 to 180° C. (step (v) above).

Use of Compounds/Pharmaceutical Composition

Compounds according to the present invention inhibit the action of TGFβ on cells in vitro (see Test Example 1).

As described in the section of the background art, the inhibition of TGFβ has been regarded as useful for the prophylaxis or therapy of all diseases involving fibrosis including chronic renal diseases. Examples of references showing a correlation between TGFβ and these diseases are as described in the section of the background art.

Further, compounds according to the present invention actually exhibited anti-fibrosis activity in vivo (see Test Examples 2 to 4).

Accordingly, the compounds according to the present invention can be used for the prophylaxis or therapy of diseases for which the TGFβ inhibitory activity is effective therapeutically.

The term "TGFβ inhibitory activity" as used herein means that the compound has the activity of inhibition against the activity of TGFβ, a kind of cytokine, within cells or tissues.

According to the present invention, there is provided a method for preventing or treating a disease for which TGFβ inhibition is effective therapeutically, comprising the step of administering a therapeutically or prophylactically effective amount of the compound according to the present invention to a patient. The term "patient" as used herein refers to a patient who should undergo therapy of a disease for which TGFβ inhibition is effective therapeutically or prophylactically.

According to the present invention, there is provided use of the compound according to the present invention, for the manufacture of a therapeutic or prophylactic agent for a disease for which TGFβ inhibition is effective therapeutically or prophylactically.

According to the present invention, there is provided a pharmaceutical composition comprising the compound according to the present invention or a pharmaceutically acceptable salt or solvate thereof. The pharmaceutical composition according to the present invention can be used for the prophylaxis or therapy of diseases for which the TGFβ inhibitory activity is effective therapeutically or prophylactically.

The diseases for which the TGFβ inhibitory activity is effective therapeutically or prophylactically are preferably diseases involving fibrosis of an organ or a tissue.

Diseases for which TGFβ inhibition is effective therapeutically or prophylactically include chronic renal disease, acute renal disease, hepatic fibrosis, cirrhosis, pulmonary fibrosis, scleroderma, wound healing, arthritis, congestive cardiac disease, ulcer, ocular disorder, cornea disorder, diabetic nephropathy, peritoneal sclerosis, arterial sclerosis, peritoneal adhesion, and subdermal adhesion.

In another preferred embodiment of the present invention, the disease for which TGFβ inhibition is effective therapeutically or prophylactically is a malignant tumor.

In still another preferred embodiment of the present invention, the compound or pharmaceutical composition according to the present invention may be used for in vitro amplification of cells. The cells are preferably hematopoietic stem cells.

Accordingly, in a further preferred embodiment of the present invention, there is provided a method for amplifying cells in vitro, comprising the step of addition of the compound according to the present invention or a pharmaceutically acceptable salt or solvate thereof in an amount effective for promoting cell amplification, into targeted cells.

In a still further embodiment of the present invention, there is provided an accelator for in vitro amplification of cells, comprising the compound according to the present invention or a pharmaceutically acceptable salt or solvate thereof.

In another embodiment of the present invention, there is provided a TGFβ inhibitor comprising the compound according to the present invention or a pharmaceutically acceptable salt or solvate thereof.

The compounds according to the present invention can be administered to human and non-human animals either orally or parenterally by administration routes, for example, intravenous administration, intramuscular administration, subcutaneous administration, rectal administration, or percutaneous administration.

Therefore, the pharmaceutical composition comprising the compound according to the present invention is formulated into suitable dosage forms according to the administration routes. Specifically, oral preparations include tablets, capsules, powders, granules, and syrups, and parental preparations include injections, suppositories, tapes, and ointments.

These various drug formulations may be prepared by conventional methods, for example, with pharmaceutically acceptable carriers, that is, commonly used excipients, disintegrants, binders, lubricants, colorants, and diluents.

Excipients include, for example, lactose, glucose, corn starch, sorbit, and crystalline cellulose. Disintegrants include, for example, starch, sodium alginate, gelatin powder, calcium carbonate, calcium citrate, and dextrin. Binders include, for example, dimethylcellulose, polyvinyl alcohol, polyvinyl ether, methylcellulose, ethylcellulose, gum arabic, gelatin, hydroxypropylcellulose, and polyvinyl pyrrolidone. Lubricants include, for example, talc, magnesium stearate, polyethylene glycol, and hydrogenated vegetable oils.

In preparing the injectable solutions, if necessary, for example, buffers, pH adjustors, stabilizers, tonicity agents, and preservatives may be added.

The content of the compound according to the present invention in the pharmaceutical composition according to the present invention may vary depending upon the dosage form. In general, however, the content is 0.5 to 50% by weight, preferably 1 to 20% by weight, based on the whole composition.

The dose may be appropriately determined in consideration of, for example, the age, weight, sex, difference in diseases, and severity of condition of individual patients, for example, in the range of 0.1 to 100 mg/kg, preferably in the range of 0.1 to 30 mg/kg. This dose is administered at a time daily or divided doses of several times daily.

The compound according to the present invention may be administered in combination with other medicament, for example, a carcinostatic agent. In this case, the compound according to the present invention may be administered simultaneously with or after or before the administration of other medicament. The type, administration intervals and the like of the carcinostatic agent may be determined depending upon the type of cancer and the condition of patients.

When the compound according to the present invention is used in in-vitro amplification of cells, a proper medium may be selected or prepared, for example, according to the type of cells. The amount of the compound according to the present invention added to the medium may be properly determined depending upon the type, application and the like of the cells. The addition amount is preferably 0.01 to 50 µM, more preferably 0.1 to 20 µM.

In another one embodiment of the present invention, there is provided a method for inhibiting the action of TGFβ on cells, comprising the step of applying an effective amount of the compound according to the present invention to cells present in vitro or in the body.

EXAMPLES

The present invention is further illustrated by the following Examples that are not intended as a limitation of the invention.

Example 1

In the following Examples, Production Example 1 is Production Example of intermediate 1 in scheme 3, Production Example 2 is Production Example of intermediate 2 in scheme 4, and Production Examples 3 and 4 are respectively Production Examples of intermediates 3 and 4 in scheme 5.

Production Example 1

2-[(6,7-Dimethoxy-4-quinolyl)oxy]-5-methylbenzaldehyde (Intermediate 1)

4-Chloro-6,7-dimethoxyquinoline (113 mg), 2-hydroxy-5-methylbenzaldehyde (344 mg), and 4-dimethylaminopyridine (313 mg) were suspended in o-dichlorobenzene (5 ml), and the suspension was stirred at 160° C. for 2 hr. The reaction solution was cooled to room temperature, and the solvent was then removed therefrom by distillation under the reduced pressure. Chloroform was added to the residue. The organic layer was washed with a 1 N aqueous sodium hydroxide solution and saturated brine and was dried over anhydrous magnesium sulfate. The solvent was removed therefrom by distillation under the reduced pressure. The residue was purified by column chromatography using chloroform to give the title compound (157 mg, yield 96%).

$^1$H-NMR (CDCl$_3$, 400 MHz): δ 2.46 (s, 3H), 4.06 (s, 3H), 4.06 (s, 3H), 6.44 (d, J=5.1 Hz, 1H), 7.10 (d, J=8.3 Hz, 1H), 7.45 (s, 1H), 7.49 (m, 1H), 7.57 (s, 1H), 7.83 (d, J=1.9 Hz, 1H), 8.51 (d, J=1.5 Hz, 1H), 10.28 (s, 1H)

Mass spectrometric value (ESI-MS, m/z): 324 (M+1)$^+$

Production Example 2

2-(6,7-Dimethoxyquinolin-4-yloxy)-5-methoxybenzoic acid (Intermediate 2)

Ethyl 2-(6,7-dimethoxyquinolin-4-yloxy)-5-methoxybenzoate (143 mg) and lithium hydroxide (78 mg) were suspended in a mixed solvent composed of ethanol (10 ml) and water (1 ml), and the suspension was stirred at room temperature overnight. The solvent was then removed therefrom by distillation under the reduced pressure. Water was added to the residue, and the resultant solution was neutralized with 12N hydrochloric acid. The mixture was then extracted with chloroform. The chloroform layer was washed with water and saturated brine and was dried over anhydrous sodium sulfate. The solvent was removed therefrom by distillation under the reduced pressure to give the title compound (140 mg, yield 100%).

$^1$H-NMR (CDCl$_3$-d$_1$, 400 MHz): δ 3.73 (s, 3H), 3.80 (s, 3H), 3.95 (s, 3H), 6.44 (d, J=5.6 Hz, 1H), 6.91-7.19 (m, 3H), 7.34 (s, 1H), 7.46 (s, 1H), 7.60 (s, 1H), 8.10 (d, J=5.6 Hz, 1H), 13.26 (brs, 1H)

Mass spectrometric value (ESI-MS, m/z): 356 (M$^+$+1)

Production Example 3

[2-(7-Benzyloxy-6-methoxyquinolin-4-yloxy)-5-methoxyphenyl]ethanone (Intermediate 3)

7-Benzyloxy-4-chloro-6-methoxyquinoline (3.00 mg), 5-methoxy-2-acetophenone (6.7 g), and 4-dimethylaminopyridine (4.9 g) were suspended in o-dichlorobenzene (30 ml), and the suspension was stirred at 180° C. for 2 hr. The reaction solution was cooled to room temperature. Water was added to the cooled reaction solution, and the mixture was extracted with chloroform. The chloroform layer was washed with water and saturated brine and was dried over anhydrous sodium sulfate. The solvent was removed therefrom by distillation under the reduced pressure, and the residue was purified by thin layer chromatography using acetone-hexane to give the title compound (2.53 g, yield 59%).

$^1$H-NMR (CDCl$_3$-d$_1$, 400 MHz): δ 2.42 (s, 3H), 3.82 (s, 3H), 3.98 (s, 3H), 5.26 (s, 2H), 6.28 (d, J=5.6 Hz, 1H), 7.03-7.08 (m, 1H), 7.23-7.51 (m, 9H), 8.39 (d, J=5.6 Hz, 1H)

Mass spectrometric value (ESI-MS, m/z): 430 (M$^+$+1)

Production Example 4

[2-(7-Hydroxy-6-methoxyquinolin-4-yloxy)-5-methoxyphenyl]ethanone (Intermediate 4)

[2-(7-Benzyloxy-6-methoxyquinolin-4-yloxy)-5-methoxyphenyl]-ethanone (intermediate 3) (2.52 g) was suspended in a mixed solution composed of methanesulfonic acid (3.0 ml) and trifluoroacetic acid (50 ml), and the suspension was stirred at 70° C. for 0.5 hr. The solvent was removed therefrom by distillation under the reduced pressure. Water was added to the residue, and the mixture was neutralized with sodium hydrogencarbonate powder. The mixture was then extracted with chloroform. The chloroform layer was then washed with water and saturated brine and was dried over anhydrous sodium sulfate. The solvent was removed therefrom by distillation under the reduced pressure. The residue was purified by column chromatography using acetone-hexane to give the title compound (1.23 g, yield 62%).

$^1$H-NMR (DMSO-d$_6$, 400 MHz): δ 2.50 (s, 3H), 3.91 (s, 3H), 4.00 (s, 3H), 6.35 (d, J=5.2 Hz, 1H), 7.34 (m, 3H), 7.42 (s, 1H), 7.61 (s, 1H), 8.44 (d, J=5.2 Hz, 1H), 10.24 (brs, 1H)

Mass spectrometric value (ESI-MS, m/z): 338 (M$^+$−1)

Example 2

Compounds of formula (I) according to the present invention were produced as follows.

The compounds thus produced are shown in tables below in relationship to schemes applied to the production thereof.

TABLE A-1

| Scheme | Compound |
|---|---|
| 2 | 1 to 5, 12, 13, 15 to 17, 19, 22, 24, 26 to 42, 57, 62 to 72, 74, 75, 77, 78, 161, 162, and 425 |
| 3 | 9 to 11, 18, 43 to 56, 58 to 61, 73, 166, 172, 181, 188 to 192, 293, 306 to 311, and 418 to 420 |
| 4 | 79 to 114 |
| 5 | 118 to 160, 312 to 409, and 440 to 469 |
| 6 | 163 |

TABLE A-1-continued

| Scheme | Compound |
|---|---|
| 7 | 7, and 8 |
| 8 | 6 |
| 9 | 14 |
| 10 | 20, and 21 |
| 11 | 23 |
| 12 | 76, 165, 173, 174, and 182 to 187 |
| 13 | 115 to 117, 202, 203, 205, 206, 208 to 210, 214, 215, 217 to 221, 275 and 276 |

TABLE A-2

| Scheme | Compound |
|---|---|
| 14 | 164, 167 to 171, 294 to 296, 298, and 302 |
| 15 | 175 to 180 |
| 16 | 200, and 201 |
| 17 | 204, 222, and 280 |
| 18 | 207 |
| 19 | 211, 212, 216, 223 to 255, 259, 261 to 267, 291, 434, and 438 |
| 20 | 213 |
| 21 | 256 to 258 |
| 22 | 277 |
| 23 | 278, and 279 |
| 24 | 281, 282, 284, and 287 to 289 |
| 25 | 283, 285, 286, 290, 292, 421 to 424, 426 to 428, 436, and 439 |
| 26 | 297 |
| 27 | 299 |
| 28 | 300 |
| 29 | 301, 303, and 304 |
| 30 | 305 |
| 31 | 410 to 414 |
| 32 | 415 to 417 |
| 33 | 193 to 199 |
| 34 | 260, 268 to 274, 429 to 433, 435, and 437 |

Compound 1:
4-(2-Benzylphenoxy)-6,7-dimethoxyquinoline

4-Chloro-6,7-dimethoxyquinoline (230 mg) and 2-benzylphenol (254 mg) were suspended in o-dichlorobenzene (1 ml), and the suspension was stirred at 180° C. overnight. The reaction solution was cooled to room temperature, and water was added thereto. The mixture was extracted with ethyl acetate. The ethyl acetate layer was then washed with water and saturated brine and was dried over anhydrous sodium sulfate. The solvent was then removed therefrom by distillation under the reduced pressure, and the residue was purified by thin layer chromatography using ethyl acetate-hexane to give the title compound (40 mg, yield 10%).

$^1$H-NMR (CDCl$_3$, 400 MHz): δ 3.90 (s, 2H), 3.96 (s, 3H), 4.05 (s, 3H), 6.31 (d, J=5.4 Hz, 1H), 7.07-7.37 (m, 9H), 7.40 (s, 1H), 7.44 (s, 1H), 8.42 (d, J=5.1 Hz, 1H)

Mass spectrometric value (ESI-MS, m/z): 372 (M+1)$^+$

Compound 2:
6,7-Dimethoxy-4-[2-(1-propenyl)phenoxy]quinoline

4-Chloro-6,7-dimethoxyquinoline (100 mg), 2-(1-propenyl)phenol (231 μl), and 4-dimethylaminopyridine (220 mg) were suspended in o-dichlorobenzene (1 ml), and the suspension was stirred at 140° C. for 7 hr. The reaction solution was cooled to room temperature, and the solvent was then removed therefrom by distillation under the reduced pressure. Thereafter, water was added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (137 mg, yield 43%).

$^1$H-NMR (CDCl$_3$, 400 MHz): δ 1.76-1.85 (m, 3H), 4.06 (m, 6H), 6.27-6.35 (m, 2H), 6.44-6.48 (m, 1H), 7.06-7.17 (m, 1H), 7.24-7.64 (m, 5H), 8.45 (m, 1H)

Mass spectrometric value (ESI-MS, m/z): 322 (M+1)$^+$

Compound 3: 4-(2-Chloro-4-methylphenoxy)-6,7-dimethoxyquinoline

4-Chloro-6,7-dimethoxyquinoline (0.89 g), 2-chloro-4-methylphenol (1.0 g), and 4-dimethylaminopyridine (1 g) were suspended in o-dichlorobenzene (10 ml), and the mixture was stirred at 160° C. for 2 hr. The reaction solution was cooled to room temperature, and water was then added thereto. The mixture was extracted with ethyl acetate. The ethyl acetate layer was then washed with water and saturated brine, and was dried over anhydrous sodium sulfate. The solvent was removed therefrom by distillation under the reduced pressure, and the residue was purified by column chromatography using acetone-chloroform to give the title compound (0.92 g, yield 70%).

$^1$H-NMR (CDCl$_3$, 400 MHz): δ 2.40 (s, 3H), 4.05 (s, 3H), 4.07 (s, 3H), 6.31 (d, J=5.1 Hz, 1H), 7.13 (d, J=8.1 Hz, 1H), 7.16 (m, 1H), 7.35 (m, 1H), 7.44 (s, 1H), 7.61 (s, 1H), 8.47 (d, J=5.1 Hz, 1H)

Mass spectrometric value (ESI-MS, m/z): 330 (M+1)$^+$

Compound 4:
4-(2-Bromo-4-methylphenoxy)-6,7-dimethoxyquinoline

4-Chloro-6,7-dimethoxyquinoline (1.33 g) and 2-bromo-4-methylphenol (2.5 ml) were dissolved in o-dichlorobenzene (3 ml), and the solution was stirred at 160° C. for 5 hr. The reaction solution was cooled to room temperature, and water was then added to the reaction solution. The mixture was extracted with ethyl acetate. The ethyl acetate layer was then washed with aqueous sodium hydroxide solution and saturated brine and was dried over anhydrous sodium sulfate. The solvent was removed therefrom by distillation under the reduced pressure, and the residue was purified by column chromatography on silica gel using acetone-chloroform to give the title compound (1.83 g, yield 82%).

$^1$H-NMR (CDCl$_3$, 400 MHz): δ 2.38 (s, 3H), 4.03 (s, 3H), 4.04 (s, 3H), 6.28 (d, J=5.4 Hz, 1H), 7.09 (d, J=8.0 Hz, 1H), 7.17 (m, 1H), 7.41 (s, 1H), 7.50 (d, J=1.9 Hz, 1H), 7.58 (s, 1H), 8.45 (d, J=5.1 Hz, 1H)

Mass spectrometric value (ESI-MS, m/z): 374 (M+1)$^+$

Compound 5:
6,7-Dimethoxy-4-(2,4-dimethylphenoxy)quinoline hydrochloride

4-Chloro-6,7-dimethoxyquinoline (200 mg) and 2,4-dimethylphenol (0.267 ml) were suspended in diethylene glycol dimethyl ether (0.1 ml), and the suspension was stirred at 180° C. for 1.5 hr. The reaction solution was cooled to room temperature, and an aqueous sodium hydroxide solution was then added to the reaction solution. The mixture was extracted with chloroform. The chloroform layer was then washed with saturated brine and was dried over anhydrous sodium sulfate.

The solvent was removed therefrom by distillation under the reduced pressure. The residue was purified by column chromatography on silica gel using acetone-chloroform to give 4-(2,4-dimethylphenoxy)-6,7-dimethoxyquinoline (127 mg, yield 46%).

4-(2,4-Dimethylphenoxy)-6,7-dimethoxyquinoline (99 mg) was dissolved in a 10% hydrochloric acid/methanol solution, and the solution was stirred at room temperature for 15 min. The solvent was removed therefrom by distillation under the reduced pressure, and the residue was washed with ethyl acetate to give the title compound (94 mg, yield 85%).

$^1$H-NMR (CD$_3$OD, 400 MHz): δ 2.11 (s, 3H), 2.37 (s, 3H), 4.04 (s, 3H), 4.04 (s, 3H), 6.66 (d, J=6.6 Hz, 1H), 7.21 (m, 1H), 7.23 (m, 1H), 7.31 (m, 1H), 7.63 (s, 1H), 7.78 (s, 1H), 8.75 (d, J=6.6 Hz, 1H)

Compound 6: 6,7-Dimethoxy-4-[4-methyl-2-(piperidinomethyl)phenoxy]-quinoline

2-[(6,7-Dimethoxy-4-quinolyl)oxy]-5-methylbenzaldehyde (88.6 mg) was dissolved in methanol (5 ml). Piperidine (250 mg) was then added to the solution, and the mixture was stirred at room temperature for 10 min. Further, sodium borohydride (17.5 mg) was added thereto, and the mixture was stirred at room temperature for 20 min. Ethyl acetate and water were added to the reaction solution, and the mixture was extracted with ethyl acetate. The ethyl acetate layer was then washed with saturated brine and was dried over anhydrous sodium sulfate. The solvent was removed therefrom by distillation under the reduced pressure, and the residue was purified by thin layer chromatography using acetone-hexane to give the title compound (71 mg, yield 66%).

$^1$H-NMR (CDCl$_3$, 400 MHz): δ 1.25-1.49 (m, 6H), 2.30-2.38 (m, 4H), 2.40 (s, 3H), 3.39 (s, 2H), 4.06 (s, 6H), 6.30 (d, J=5.4 Hz, 1H), 7.01 (d, J=8.1 Hz, 1H), 7.14 (dd, J=1.7 Hz, 8.0 Hz, 1H), 7.39 (d, J=1.4 Hz, 1H), 7.44 (s, 1H), 7.61 (s, 1H), 8.44 (d, J=5.4 Hz, 1H)

Mass spectrometric value (ESI-MS, m/z): 393 (M+1)$^+$

Compound 7: 6,7-Dimethoxy-4-{4-methoxy-2-[(E)-2-phenyl-1-ethenyl]phenoxy}quinoline 4-Chloro-6,7-dimethoxyquinoline (2.23 g), 2-hydroxy-5-methoxybenzaldehyde (6.08 g), and 4-dimethylaminopyridine (4.88 g) were suspended in monochlorobenzene (40 ml), and the suspension was stirred at 130° C. overnight. The reaction solution was cooled to room temperature, and water was then added thereto. The mixture was extracted with ethyl acetate. The ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give 2-[(6,7-dimethoxy-4-quinolyl)oxy]-5-methoxybenzaldehyde (2.72 g).

Sodium hydride (60 wt % oil, 52 mg) was dissolved in anhydrous tetrahydrofuran (1 ml), and a solution (0.5 ml) of benzylphosphonic acid (114 mg) in tetrahydrofuran was added dropwise to the solution at 0° C. under an argon atmosphere. The mixture was stirred at 0° C. for 30 min, and a solution (0.5 ml) of 2-[(6,7-dimethoxy-4-quinolyl)oxy]-5-methoxybenzaldehyde (100 mg) in tetrahydrofuran was then added dropwise thereto. The reaction mixture was stirred at room temperature for one hr, and water (1 ml) was then added dropwise thereto to stop the reaction. The mixture was extracted with ethyl acetate, and the ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give the title compound (100 mg, yield 80%).

$^1$H-NMR (CDCl$_3$, 400 MHz): δ 3.85 (s, 3H), 4.00 (s, 3H), 4.01 (s, 3H), 6.29 (d, J=5.4 Hz, 1H), 6.84 (dd, J=3.2 Hz, 9.0 Hz, 1H), 7.01 (d, J=8.8 Hz, 1H), 7.06 (d, J=7.4 Hz, 1H), 7.11-7.28 (m, 7H), 7.43 (s, 1H), 7.61 (s, 1H), 8.38 (d, J=5.4 Hz, 1H)

Mass spectrometric value (ESI-MS, m/z): 414 (M+1)$^+$

Compound 8: Ethyl (E)-3-{2-[(6,7-dimethoxy-4-quinolyl)oxy]-5-methoxyphenyl}-2-methyl-2-propenoate 4-Chloro-6,7-dimethoxyquinoline (2.23 g), 2-hydroxy-5-methoxybenzaldehyde (6.08 g), and 4-dimethylaminopyridine (4.88 g) were suspended in monochlorobenzene (40 ml), and the suspension was stirred at 130° C. overnight. The reaction solution was cooled to room temperature, and water was then added to the reaction solution. The mixture was extracted with ethyl acetate. The ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give 2-[(6,7-dimethoxy-4-quinolyl)oxy]-5-methoxybenzaldehyde (2.72 g).

Sodium hydride (60 wt % oil, 52 mg) was dissolved in anhydrous tetrahydrofuran (1 ml), and a solution (0.5 ml) of triethyl 2-phosphonopropionate (119 mg) in tetrahydrofuran was added dropwise thereto under an argon atmosphere at 0° C. The mixture was stirred at 0° C. for 30 min, and a solution (0.5 ml) of 2-[(6,7-dimethoxy-4-quinolyl)oxy]-5-methoxybenzaldehyde (100 mg) in tetrahydrofuran was then added dropwise thereto. The reaction mixture was stirred at room temperature for one hr, and water (1 ml) was then added dropwise to stop the reaction. The mixture was extracted with ethyl acetate, and the ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give the title compound (64 mg, yield 50%).

$^1$H-NMR (CDCl$_3$, 400 MHz): δ 1.05 (t, J=7.2 Hz, 3H), 1.99 (s, 3H), 3.80 (s, 3H), 3.98 (s, 6H), 4.00 (q, J=7.2 Hz, 2H), 6.16-6.24 (m, 1H), 6.87-6.94 (m, 2H), 7.05 (d, J=8.5 Hz, 1H), 7.32-7.40 (m, 1H), 7.48 (s, 1H), 7.50 (s, 1H), 8.37 (d, J=5.1 Hz, 1H)

Mass spectrometric value (ESI-MS, m/z): 424 (M+1)$^+$

Compound 9: 1-{2-[(6,7-Dimethoxy-4-quinolyl)oxy]-5-methylphenyl}-1-propanol

Under an argon atmosphere, 2-[(6,7-dimethoxy-4-quinolyl)oxy]-5-methylbenzaldehyde (intermediate 1) (81.6 mg) was dissolved in tetrahydrofuran (3 ml), and the solution was then cooled to −78° C. A 0.96 M tetrahydrofuran solution (0.4 ml) of ethylmagnesium bromide was added dropwise thereto, and the mixture was stirred at −78° C. for 30 min. Water was added to the reaction solution, and the mixture was extracted with ethyl acetate. The ethyl acetate layer was then washed with saturated brine and was dried over anhydrous sodium sulfate. The solvent was removed therefrom by distillation under the reduced pressure. The residue was purified by thin layer chromatography using acetone-hexane to give the title compound (41 mg, yield 46%).

$^1$H-NMR (CDCl$_3$, 400 MHz): δ 0.92 (t, J=7.3 Hz, 3H), 1.80 (m, 2H), 2.42 (s, 3H), 3.99 (s, 3H), 4.02 (s, 3H), 4.75 (t, J=6.3 Hz, 1H), 6.24 (d, J=5.4 Hz, 1H), 6.95 (d, J=8.3 Hz, 1H), 7.14 (dd, J=2.2 Hz, 8.0 Hz, 1H), 7.32 (s, 1H), 7.53 (s, 1H), 7.54 (d, J=1.9 Hz, 1H), 8.13 (d, J=5.4 Hz, 1H)

Mass spectrometric value (ESI-MS, m/z): 354 (M+1)$^+$

Compound 10: 1-{2-[(6,7-Dimethoxy-4-quinolyl)oxy]-5-methylphenyl}-1-pentanol

Under an argon atmosphere, 2-[(6,7-dimethoxy-4-quinolyl)oxy]-5-methylbenzaldehyde (123.2 mg) was dissolved in tetrahydrofuran (3 ml), and the solution was then cooled to −78° C. A 1.56 M n-hexane solution (0.35 ml) of n-butyllithium was added dropwise thereto, and the mixture was stirred at −78° C. for one hr. A saturated aqueous ammonium chloride solution was added to the reaction solution, and the mixture was extracted with ethyl acetate. The ethyl acetate layer was then washed with saturated brine and was dried over anhydrous sodium sulfate. The solvent was removed therefrom by distillation under the reduced pressure, and the residue was purified by thin layer chromatography using acetone-hexane to give the title compound (59.5 mg, yield 41%).

$^1$H-NMR (CDCl$_3$, 400 MHz): δ 0.81 (t, J=7.2 Hz, 3H), 1.20-1.47 (m, 4H), 1.74 (m, 2H), 2.42 (s, 3H), 3.99 (s, 3H), 4.01 (s, 3H), 4.80 (dd, J=5.6 Hz, 7.3 Hz, 1H), 6.20 (d, J=5.4 Hz, 1H), 6.95 (d, J=8.3 Hz, 1H), 7.13 (dd, J=2.2 Hz, 8.3 Hz, 1H), 7.30 (s, 1H), 7.52 (s, 1H), 7.56 (d, J=2.0 Hz, 1H), 8.06 (d, J=5.4 Hz, 1H)

Mass spectrometric value (ESI-MS, m/z): 382 (M+1)$^+$

Compound 11: 1-{2-[(6,7-Dimethoxy-4-quinolyl)oxy]-5-methoxyphenyl}-1-propanol

Under an argon atmosphere, 2-[(6,7-dimethoxy-4-quinolyl)oxy]-5-methoxybenzaldehyde (140 mg) was dissolved in tetrahydrofuran (2 ml), and the solution was then cooled to −78° C. A 0.96 M tetrahydrofuran solution (0.7 ml) of ethylmagnesium bromide was added dropwise thereto, and the mixture was stirred at −78° C. for one hr. A saturated aqueous ammonium chloride solution was added to the reaction solution, and the mixture was extracted with ethyl acetate. The ethyl acetate layer was then washed with saturated brine and was dried over anhydrous magnesium sulfate. The solvent was removed therefrom by distillation under the reduced pressure, and the residue was purified by thin layer chromatography using acetone-hexane to give the title compound (74.5 mg, yield 49%).

$^1$H-NMR (CDCl$_3$, 400 MHz): δ 0.90 (t, J=7.3 Hz, 3H), 1.78 (m, 2H), 3.87 (s, 3H), 4.05 (s, 6H), 4.77 (t, J=6.1 Hz, 1H), 6.35 (d, J=5.4 Hz, 1H), 6.89 (dd, J=3.2 Hz, 8.8 Hz, 1H), 7.03 (d, J=8.8 Hz, 1H), 7.20 (d, J=3.2 Hz, 1H), 7.42 (s, 1H), 7.55 (s, 1H), 8.39 (d, J=5.4 Hz, 1H)

Mass spectrometric value (ESI-MS, m/z): 370 (M+1)$^+$

Compound 12: 5-{2-[6,7-Dimethoxy-4-quinolyl]oxy}-5-methylphenyl}isoxazole

4-Chloro-6,7-dimethoxyquinoline (50 mg) and 2-(5-isoxazoyl)-4-methylphenol (200 mg) were dissolved in N,N-dimethylformamide (2 ml) to prepare a solution which was then stirred at 160° C. for 4 hr. The reaction solution was cooled to room temperature. Water was added thereto, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-chloroform to give the title compound (12 mg, yield 15%).

$^1$H-NMR (CDCl$_3$, 400 MHz): δ 2.42 (s, 3H), 3.98 (s, 3H), 3.99 (s, 3H), 6.32 (d, J=5.1 Hz, 1H), 6.40 (m, 1H), 7.04 (d, J=8.5 Hz, 1H), 7.26 (m, 1H), 7.38 (s, 1H), 7.51 (s, 1H), 7.90 (d, J=1.7 Hz, 1H), 8.07 (m, 1H), 8.38 (d, J=5.4 Hz, 1H)

Mass spectrometric value (ESI-MS, m/z): 363 (M+1)$^+$

Compound 13: 6,7-Dimethoxy-4-(4-methyl-2-nitrophenoxy)quinoline

4-Chloro-6,7-dimethoxyquinoline (1.15 g) and 4-methyl-2-nitrophenol (1.52 g) were suspended in o-dichlorobenzene (7 ml), and the suspension was stirred at 180° C. for 23 hr. The reaction solution was cooled to room temperature. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-chloroform to give the title compound (480 mg, yield 27%).

Mass spectrometric value (ESI-MS, m/z): 341 (M+1)$^+$

Compound 14: N-[2-[(6,7-Dimethoxy-4-quinolyl)oxy]-5-methylphenyl]-N-phenylamine 6,7-Dimethoxy-4-(4-methyl-2-nitrophenoxy)quinoline (480 mg) was dissolved in triethylamine/N,N-dimethylformamide (2 ml/10 ml), and palladium hydroxide (1.2 g) was added to the solution. The mixture was stirred at room temperature in a hydrogen gas atmosphere overnight. The reaction solution was filtered through Celite, and the solvent was removed therefrom by distillation under the reduced pressure. Water was added to the residue, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-chloroform to give 4-(2-amino-4-methylphenoxy)-6,7-dimethoxyquinoline (240 mg, yield 55%).

4-(2-Amino-4-methylphenoxy)-6,7-dimethoxyquinoline (52 mg) was dissolved in triethylamine/N,N-dimethylformamide (0.5 ml/2.5 ml), and phenylboronic acid (100 mg) and copper acetate (250 mg) were added to the solution which was then stirred at room temperature overnight. The reaction solution was filtered, and the solvent was removed therefrom by distillation under the reduced pressure. Water was added to the residue, and the mixture was extracted with ethyl acetate. Next, the ethyl acetate layer was then washed with water and saturated brine and was dried over anhydrous sodium sulfate. The solvent was removed therefrom by distillation under the reduced pressure, and the residue was purified by thin layer chromatography using acetone-chloroform to give the title compound (50 mg, yield 76%).

$^1$H-NMR (CDCl$_3$, 400 MHz): δ 2.35 (s, 3H), 4.03 (s, 3H), 4.04 (s, 3H), 5.77 (s, 1H), 6.51 (d, J=5.4 Hz, 1H), 6.76 (m, 1H), 6.96 (m, 1H), 7.01 (d, J=8.1 Hz, 1H), 7.05 (m, 2H), 7.23-7.27 (m, 3H), 7.43 (s, 1H), 7.54 (s, 1H), 8.46 (d, J=5.1 Hz, 1H)

Mass spectrometric value (ESI-MS, m/z): 387 (M+1)$^+$

Compound 15: 6,7-Dimethoxy-4-(3,4-dimethylphenoxy)quinoline hydrochloride

4-Chloro-6,7-dimethoxyquinoline (200 mg) and 3,4-dimethylphenol (274 mg) were suspended in diethylene glycol dimethyl ether (0.1 ml), and the suspension was stirred at 180° C. for 1.5 hr. The reaction solution was cooled to room temperature, an aqueous sodium hydroxide solution was added to the reaction solution, and the mixture was extracted with chloroform. The chloroform layer was then washed with saturated brine and was dried over anhydrous sodium sulfate. The solvent was removed therefrom by distillation under the reduced pressure, and the residue was purified by column chromatography on silica gel using acetone-chloroform to give 6,7-dimethoxy-4-(3,4-dimethylphenoxy)quinoline (160 mg, yield 58%).

6,7-Dimethoxy-4-(3,4-dimethylphenoxy)quinoline (122 mg) was dissolved in a 10% hydrochloric acid/methanol solution, and the solution was stirred at room temperature for 15 min. The solvent was removed therefrom by distillation under the reduced pressure. The residue was washed with ethyl acetate to give the title compound (118 mg, yield 87%).

$^1$H-NMR (CD$_3$OD, 400 MHz): δ 2.30 (s, 3H), 2.30 (s, 3H), 4.03 (s, 3H), 4.04 (s, 3H), 6.80 (d, J=6.6 Hz, 1H), 7.12 (dd, J=2.5 Hz, 8.3 Hz, 1H), 7.20 (d, J=2.2 Hz, 1H), 7.37 (d, J=8.3 Hz, 1H), 7.64 (s, 1H), 7.72 (s, 1H), 8.77 (d, J=6.6 Hz, 1H)

Compound 16: 6,7-Dimethoxy-4-(1-naphthyloxy)quinoline

4-Chloro-6,7-dimethoxyquinoline (100 mg), 1-hydroxy-2-naphthonic acid (252 mg), and 4-dimethylaminopyridine (164 mg) were suspended in o-dichlorobenzene (3 ml), and the suspension was stirred at 150° C. for 2 hr. The reaction solution was cooled to room temperature, water was then added thereto, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-chloroform to give the title compound (119 mg, yield 80%).

$^1$H-NMR (CDCl$_3$, 400 MHz): δ 3.96 (s, 6H), 6.22 (d, J=5.2 Hz, 1H), 7.22 (m, 1H), 7.31-7.40 (m, 4H), 7.64 (s, 1H), 7.68 (d, J=8.0 Hz, 1H), 7.82 (t, J=8.0 Hz, 2H), 8.31 (d, J=5.2 Hz, 1H)

Mass spectrometric value (ESI-MS, m/z): 332 (M+1)$^+$

Compound 17: 6,7-Dimethoxy-4-(2-naphthyloxy)quinoline

4-Chloro-6,7-dimethoxyquinoline (100 mg), 2-hydroxy-1-naphthonic acid (252 mg), and 4-dimethylaminopyridine (164 mg) were suspended in o-dichlorobenzene (3 ml), and the suspension was stirred at 150° C. for 2 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-chloroform to give the title compound (41 mg, yield 28%).

$^1$H-NMR (DMSO-d$_6$, 400 MHz): δ 3.99 (s, 3H), 4.02 (s, 3H), 6.62 (d, J=5.2 Hz, 1H), 7.49-7.54 (m, 2H), 7.58-7.64 (m, 3H), 7.85 (s, 1H), 7.99 (d, J=7.2 Hz, 1H), 7.07 (d, J=7.2 Hz, 1H), 8.15 (d, J=9.2 Hz, 1H), 8.55 (d, J=5.2 Hz, 1H)

Mass spectrometric value (ESI-MS, m/z): 332 (M+1)$^+$

Compound 18: 4-[(6-Bromo-2-naphthyl)oxy]-6,7-dimethoxyquinoline

4-Chloro-6,7-dimethoxyquinoline (223 mg), 1,6-dibromo-2-naphthol (910 mg), and 4-dimethylaminopyridine (366 mg) were suspended in o-dichlorobenzene (3 ml), and the suspension was stirred at 150° C. for 4 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-chloroform to give 4-[(1,6-dibromo-2-naphthyl)oxy]-6,7-dimethoxyquinoline (326 mg, yield 67%).

4-[(1,6-Dibromo-2-naphthyl)oxy]-6,7-dimethoxyquinoline (65 mg) was dissolved in tetrahydrofuran (3 ml) to prepare a solution which was then cooled to −78° C. A 1.59 M n-butyllithium/hexane solution (0.4 ml) was added thereto, and the mixture was stirred at −78° C. for 20 min. Acetyl chloride (0.2 ml) was added to the reaction solution, and the mixture was stirred at room temperature overnight. Further, water was added to the reaction solution, and the mixture was extracted with ethyl acetate. The ethyl acetate layer was then washed with water and saturated brine and dried over anhydrous sodium sulfate. The solvent was removed therefrom by distillation under the reduced pressure, and the residue was purified by thin layer chromatography using acetone-chloroform to give the title compound (28 mg, yield 51%).

$^1$H-NMR (CDCl$_3$, 400 MHz): δ 4.05 (s, 3H), 4.06 (s, 3H), 6.52 (d, J=5.4 Hz, 1H), 7.27 (s, 1H), 7.50-7.97 (m, 6H), 8.06 (m, 1H), 8.53 (d, J=5.1 Hz, 1H)

Mass spectrometric value (ESI-MS, m/z): 410 (M+1)$^+$

Compound 19: 2-[(6,7-Dimethoxy-4-quinolyl)oxy]fluoren-9-one

4-Chloro-6,7-dimethoxyquinoline (100 mg), 2-hydroxy-9-fluorenone (269 mg), and 4-dimethylaminopyridine (164 mg) were suspended in o-dichlorobenzene (6 ml), and the suspension was stirred at 160° C. for 7 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-chloroform to give the title compound (58 mg, yield 34%).

$^1$H-NMR (CDCl$_3$, 400 MHz): δ 4.03 (s, 3H), 4.04 (s, 3H), 6.56 (d, J=5.2 Hz, 1H), 7.27-7.29 (m, 2H), 7.44-7.67 (m, 7H), 8.51 (d, J=5.2 Hz, 1H)

Mass spectrometric value (ESI-MS, m/z): 384 (M+1)$^+$

Compound 20: 6,7-Dimethoxy-4-[(1-methyl-5-indolyl)oxy]quinoline

A mixture of 4-chloro-6,7-dimethoxyquinoline (1 g) with 5-hydroxyindole (1.19 g) was stirred at 150° C. for 1.5 hr and was cooled to room temperature. Water was then added to the reaction solution, and the mixture was extracted with ethyl acetate. The ethyl acetate layer was then washed with an aqueous sodium hydrogencarbonate solution and saturated brine and was dried over anhydrous sodium sulfate. The solvent was removed therefrom by distillation under the reduced pressure, and the residue was purified by column chromatography using ethyl acetate-hexane to give 6,7-dimethoxy-4-[(1H-5-indolyl)oxy]quinoline (898 mg, yield 63%).

6,7-Dimethoxy-4-[(1H-5-indolyl)oxy]quinoline (50 mg) was dissolved in N,N-dimethylformamide (1 ml), and 60% sodium hydride (7 mg) was added, followed by stirring for 30 min under ice cooling. Methyl iodide (0.0107 ml) was added to the reaction solution, and the mixture was stirred under ice cooling for additional one hr. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (32 mg, yield 62%).

$^1$H-NMR (CDCl$_3$, 500 MHz): δ 3.86 (s, 3H), 4.06 (s, 3H), 4.08 (s, 3H), 6.39 (d, J=5.5 Hz, 1H), 6.50 (d, J=3.1 Hz, 1H), 7.06 (dd, J=2.4 Hz, 8.6 Hz, 1H), 7.15 (d, J=3.1 Hz, 1H), 7.39 (d, J=8.5 Hz, 1H), 7.43 (s, 1H), 7.43 (d, J=2.4 Hz, 1H), 7.6, 7 (s, 1H), 8.43 (d, J=5.5 Hz, 1H)

Mass spectrometric value (FD-MS, m/z): 334 (M$^+$)

Compound 21:
6,7-Dimethoxy-4-[(1-acetyl-5-indolyl)oxy]quinoline 6,7-Dimethoxy-4-[(1H-5-indolyl)oxy]quinoline (50 mg) was dissolved in N,N-dimethylformamide (1 ml), and 60% sodium hydride (7 mg) was added to the solution, followed by stirring under ice cooling for 30 min. Acetyl chloride (16.6 μl) was added to the reaction solution, and the mixture was stirred under ice cooling for additional one hr. Further, water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (23 mg, yield 41%).

$^1$H-NMR (CDCl$_3$, 400 MHz): δ 2.68 (s, 3H), 4.06 (s, 3H), 4.06 (s, 3H), 6.43 (d, J=5.5 Hz, 1H), 6.66 (d, J=4.3 Hz, 1H), 7.20 (dd, J=2.4 Hz, 8.6 Hz, 1H), 7.37 (d, J=2.5 Hz, 1H), 7.44 (s, 1H), 7.51 (d, J=3.7 Hz, 1H), 7.62 (s, 1H), 8.47 (d, J=5.5 Hz, 1H), 8.55 (d, J=9.2 Hz, 1H)

Mass spectrometric value (FD-MS, m/z): 362 (M$^+$)

Compound 22: Ethyl 5-[(6,7-dimethoxy-4-quinolyl) oxy]-1H-2-indolecarboxylate

5-Hydroxy-1H-2-indolecarboxylic acid (328 mg) was dissolved in ethanol (10 ml) to prepare a solution. Concentrated sulfuric acid was added to the solution, and the mixture was heated under reflux for 3 hr. The reaction solution was cooled to room temperature, an aqueous sodium hydrogencarbonate solution was then added thereto, and the mixture was extracted with ethyl acetate. The ethyl acetate layer was then washed with saturated brine and was dried over anhydrous magnesium sulfate. The solvent was removed therefrom by distillation under the reduced pressure, and the residue was purified by column chromatography on silica gel using ethyl acetate-hexane to give ethyl 5-hydroxy-1H-2-indolecarboxylate (336 mg, yield 88%).

4-Chloro-6,7-dimethoxyquinoline (362 mg), ethyl 5-hydroxy-1H-2-indolecarboxylate (277 mg), and 4-dimethylaminopyridine (195 mg) were suspended in o-xylene, and the suspension was heated under reflux overnight. The reaction solution was cooled to room temperature, water was then added to the reaction solution, and the mixture was extracted with ethyl acetate. The ethyl acetate layer was then washed with saturated brine and was dried over anhydrous magnesium sulfate. The solvent was removed therefrom by distillation under the reduced pressure, and the residue was purified by column chromatography using ethyl acetate-hexane on silica gel to give the title compound (161 mg, yield 30%).

$^1$H-NMR (CDCl$_3$, 400 MHz): δ 1.43 (t, J=7.1 Hz, 3H), 4.07 (s, 3H), 4.07 (s, 3H), 4.44 (q, J=7.1 Hz, 2H), 6.43 (d, J=5.4 Hz, 1H), 7.18 (dd, J=2.2 Hz, 9.0 Hz, 1H), 7.24 (m, 1H), 7.47 (s, 1H), 7.50-7.52 (m, 2H), 7.64 (s, 1H), 8.46 (d, J=5.4 Hz, 1H), 9.05 (s, 1H)

Mass spectrometric value (ESI-MS, m/z): 393 (M+1)$^+$

Compound 23: 6-[(6,7-Dimethoxy-4-quinolyl)oxy]-1,4-dihydro-2H-3,1-benzoxazin-2-one 4-Chloro-6,7-dimethoxyquinoline (200 mg) and 5-hydroxy-2-nitrobenzaldehyde (299 mg) were suspended in chlorobenzene (2 ml), and the suspension was heated under reflux for 8 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using ethyl acetate-hexane to give 3-[(6,7-dimethoxy-4-quinolyl)oxy]-6-nitrobenzaldehyde (210 mg, yield 66%).

3-[(6,7-Dimethoxy-4-quinolyl)oxy]-6-nitrobenzaldehyde (201 mg) was dissolved in chloroform/methanol (5 ml/10 ml), and sodium borohydride (127 mg) was added to the solution under ice cooling. The mixture was stirred at room temperature for one hr, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was used in the next reaction without purification.

The residue was dissolved in ethyl acetate/N,N-dimethylformamide (5 ml/5 ml) to prepare a solution. Triethylamine (4 ml) and 20% palladium hydroxide (0.9 g) were added to the solution, and the mixture was stirred under a hydrogen gas atmosphere at room temperature overnight. The reaction solution was filtered through Celite, and the solvent was removed by distillation under the reduced pressure. Water was added to the residue, and the mixture was extracted with ethyl acetate. The ethyl acetate layer was then washed with water and saturated brine and was dried over anhydrous sodium sulfate. The solvent was removed therefrom by distillation under the reduced pressure. The residue was purified by column chromatography on silica gel using acetone-chloroform to give {2-amino-5-[(6,7-dimethoxy-4-quinolyl)oxy] phenyl}methanol (118 mg, yield 64%) (2 steps).

{2-Amino-5-[(6,7-dimethoxy-4-quinolyl)oxy] phenyl}methanol (63 mg) was dissolved in heated triethylamine/toluene (1.2 ml/6 ml) to prepare a solution. Triphosgene (98 mg) was added to the solution and was heated under reflux for 2 min. The reaction solution was cooled to room temperature, water was then added to the reaction solution, and the mixture was extracted with chloroform. The chloroform layer was then washed with water and saturated brine and was dried over anhydrous sodium sulfate. The solvent was removed therefrom by distillation under the reduced pressure, and the residue was purified by column chromatography on silica gel using acetone-chloroform to give the title compound (24 mg, yield 39%).

$^1$H-NMR (CDCl$_3$, 500 MHz): δ 4.06 (s, 3H), 4.09 (s, 3H), 5.36 (s, 2H), 6.47 (d, J=5.1 Hz, 1H), 7.00 (s, 1H), 7.04 (d, J=8.5 Hz, 1H), 7.14 (d, J=8.3 Hz, 1H), 7.52 (s, 1H), 7.53 (s, 1H), 8.53 (m, 1H), 9.13 (s, 1H)

Mass spectrometric value (FD-MS, m/z): 352 (M$^+$)

Compound 24:
6,7-Dimethoxy-4-(6-quinolyloxy)quinoline

A mixture of 4-chloro-6,7-dimethoxyquinoline (90 mg) with 6-hydroxyquinoline (176 mg) was stirred at 180° C. for 30 min. The reaction solution was cooled to room temperature, and was then purified by column chromatography on silica gel using acetone-hexane to give the title compound (62 mg, yield 46%).

$^1$H-NMR (CDCl$_3$, 500 MHz): δ 4.05 (s, 3H), 4.06 (s, 3H), 6.50 (d, J=5.5 Hz, 1H), 7.44-7.62 (m, 5H), 8.13 (d, J=8.5 Hz, 1H), 8.23 (d, J=9.2 Hz, 1H), 8.53 (d, J=4.9 Hz, 1H), 8.94 (d, J=4.3 Hz, 1H)

Mass spectrometric value (FD-MS, m/z): 332 (M$^+$)

Compound 26: 2-[(6,7-Dimethoxy-4-quinolyl)oxy]-5-methoxybenzaldehyde

4-Chloro-6,7-dimethoxyquinoline (115 mg), 2-hydroxy-5-methoxybenzaldehyde (385 mg), and 4-dimethylaminopyridine (321 mg) were suspended in o-dichlorobenzene (5 ml), and the suspension was stirred at 160° C. for 4 hr. The reaction solution was cooled to room temperature, and the solvent was then removed therefrom by distillation under the reduced pressure. Chloroform was added to the residue, and the organic layer was washed with a 1 N aqueous potassium hydroxide solution and saturated brine and was dried over anhydrous sodium sulfate. The solvent was removed therefrom by distillation under the reduced pressure, and the residue was purified by column chromatography using chloroform and by thin layer chromatography using acetone-hexane to quantitatively obtain 180 mg of the title compound.

$^1$H-NMR (CDCl$_3$, 400 MHz): δ 3.91 (s, 3H), 4.07 (s, 3H), 4.07 (s, 3H), 6.39 (d, J=5.1 Hz, 1H), 7.16 (d, J=9.0 Hz, 1H), 7.25 (d, J=3.2 Hz, 1H), 7.45 (s, 1H), 7.49 (d, J=2.9 Hz, 1H), 7.59 (s, 1H), 8.50 (d, J=5.1 Hz, 1H), 10.23 (s, 1H)

Mass spectrometric value (ESI-MS, m/z): 340 (M+1)$^+$

Compound 27: 2-[(6,7-Dimethoxy-4-quinolyl)oxy]naphthalene-1-carbaldehyde

4-Chloro-6,7-dimethoxyquinoline (100 mg), 2-hydroxy-1-naphthoaldehyde (231 mg), and 4-dimethylaminopyridine (164 mg) were suspended in o-dichlorobenzene (6 ml), and the suspension was stirred at 160° C. for 2 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-chloroform to give the title compound (24 mg, yield 15%).

$^1$H-NMR (CDCl$_3$, 400 MHz): δ 3.99 (s, 6H), 6.43 (d, J=5.2 Hz, 1H), 7.19 (m, 1H), 7.42 (s, 1H), 7.51-7.55 (m, 2H), 7.66 (t, J=8.0 Hz, 1H), 7.83 (d, J=8.4 Hz, 1H), 8.07 (d, J=8.4 Hz, 1H), 8.45 (d, J=5.2 Hz, 1H), 9.25 (d, J=8.0 Hz, 1H), 10.73 (s, 1H)

Mass spectrometric value (ESI-MS, m/z): 360 (M+1)$^+$

Compound 28: 9-[(6,7-Dimethoxy-4-quinolyl)oxy]-2,3,6,7-tetrahydro-1H,5H-pyrido[3,2,1-ij]quinoline-8-carbaldehyde 4-Chloro-6,7-dimethoxyquinoline (100 mg), 8-hydroxydurolysine-9-aldehyde (291 mg) and 4-dimethylaminopyridine (164 mg) were suspended in o-dichlorobenzene (6 ml), and the suspension was stirred at 120° C. for 48 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-hexane to give the title compound (7 mg, yield 4%).

$^1$H-NMR (CDCl$_3$, 400 MHz): δ 1.75-1.81 (m, 2H), 1.90-1.96 (m, 2H), 2.12-2.21 (m, 1H), 2.63-2.73 (m, 3H), 3.19-3.27 (m, 4H), 3.98 (s, 3H), 4.01 (s, 3H), 6.27 (d, J=5.2 Hz, 1H), 7.42 (m, 2H), 7.55 (s, 1H), 8.37 (d, J=5.2 Hz, 1H), 9.69 (s, 1H)

Mass spectrometric value (ESI-MS, m/z): 405 (M+1)$^+$

Compound 29: 1-{2-[(6,7-Dimethoxy-4-quinolyl)oxy]phenyl}-1-ethanone

4-Chloro-6,7-dimethoxyquinoline (58.1 mg), 2'-hydroxyacetophenone (361 mg), and 4-dimethylaminopyridine (317 mg) were suspended in o-dichlorobenzene (5 ml), and the suspension was stirred at 160° C. for 11 hr. The reaction solution was cooled to room temperature, and the solvent was then removed therefrom by distillation under the reduced pressure. Chloroform was added to the residue. The organic layer was washed with a 1 N aqueous potassium hydroxide solution and saturated brine and was dried over anhydrous sodium sulfate. The solvent was removed therefrom by distillation under the reduced pressure, and the residue was purified by column chromatography using chloroform and by thin layer chromatography using acetone-hexane to give the title compound (36 mg, yield 43%).

$^1$H-NMR (CDCl$_3$, 400 MHz): δ 2.54 (s, 3H), 4.05 (s, 3H), 4.06 (s, 3H), 6.45 (d, J=5.1 Hz, 1H), 7.16 (dd, J=1.0 Hz, 8.1 Hz, 1H), 7.38 (m, 1H), 7.46 (s, 1H), 7.55 (s, 1H), 7.59 (m, 1H), 7.94 (dd, J=1.7 Hz, 7.8 Hz, 1H), 8.52 (d, J=5.4 Hz, 1H)

Mass spectrometric value (ESI-MS, m/z): 324 (M+1)$^+$

Compound 30: 1-{2-[(6,7-Dimethoxy-4-quinolyl)oxy]-3-methoxyphenyl}-1-ethanone

4-Chloro-6,7-dimethoxyquinoline (100 mg), 2-hydroxy-3-methoxyacetophenone (223 mg), and 4-dimethylaminopyridine (164 mg) were suspended in o-dichlorobenzene (6 ml), and the suspension was stirred at 150° C. for 2 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-chloroform to give the title compound (46 mg, yield 28%).

$^1$H-NMR (CDCl$_3$, 400 MHz): δ 2.41 (s, 3H), 3.85 (s, 3H), 3.98 (s, 3H), 3.99 (s, 3H), 6.52 (d, J=5.2 Hz, 1H), 6.67 (d, J=8.2 Hz, 1H), 6.80 (d, J=8.2 Hz, 1H), 7.33 (t, J=8.2 Hz, 1H), 7.38 (s, 1H), 7.43 (s, 1H), 8.47 (d, J=5.2 Hz, 1H)

Mass spectrometric value (ESI-MS, m/z): 354 (M+1)$^+$

Compound 31: 1-{2-[(6,7-Dimethoxy-4-quinolyl)oxy]-4-methoxyphenyl}-1-ethanone

4-Chloro-6,7-dimethoxyquinoline (112 mg), 2-hydroxy-4-methoxyacetophenone (873 mg), and 4-dimethylaminopyridine (619 mg) were suspended in o-dichlorobenzene (5 ml), and the suspension was stirred at 160° C. for 7 hr. The reaction solution was cooled to room temperature, and the solvent was then removed therefrom by distillation under the reduced pressure. Chloroform was added to the residue, and the organic layer was washed with a 1 N aqueous potassium hydroxide solution and saturated brine and was dried over anhydrous sodium sulfate. The solvent was removed therefrom by distillation under the reduced pressure, and the residue was purified by column chromatography using chloroform and by thin layer chromatography using acetone-hexane to give the title compound (53.9 mg, yield 31%).

$^1$H-NMR (CDCl$_3$, 400 MHz): δ 2.50 (s, 3H), 3.83 (s, 3H), 4.05 (s, 3H), 4.06 (s, 3H), 6.49 (d, J=5.4 Hz, 1H), 6.62 (d, J=2.4 Hz, 1H), 6.89 (dd, J=2.4 Hz, 8.8 Hz, 1H), 7.46 (s, 1H), 7.55 (s, 1H), 8.00 (d, J=8.8 Hz, 1H), 8.53 (d, J=5.1 Hz, 1H)

Mass spectrometric value (ESI-MS, m/z): 354 (M+1)$^+$

Compound 32: 1-{2-[(6,7-Dimethoxy-4-quinolyl)oxy]-4-methylphenyl}-1-ethanone

4-Chloro-6,7-dimethoxyquinoline (116 mg), 2-hydroxy-4-methylacetophenone (300 mg), and 4-dimethylaminopyridine (244 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (37 mg, yield 6%).

$^1$H-NMR (CDCl$_3$, 400 MHz): δ 2.40 (s, 3H), 2.51 (s, 3H), 4.05 (s, 3H), 4.06 (s, 3H), 6.44 (d, J=5.1 Hz, 1H), 6.95 (s, 1H), 7.17 (d, J=8.1 Hz, 1H), 7.45 (s, 1H), 7.55 (s, 1H), 7.87 (d, J=8.1 Hz, 1H), 8.52 (d, J=5.1 Hz, 1H)

Mass spectrometric value (ESI-MS, m/z): 338 (M+1)$^+$

Compound 33: 1-{2-[(6,7-Dimethoxy-4-quinolyl)oxy]-5-fluorophenyl}-1-ethanone

4-Chloro-6,7-dimethoxyquinoline (58.2 mg), 5-fluoro-2-hydroxyacetophenone (409 mg), and 4-dimethylaminopyridine (317 mg) were suspended in o-dichlorobenzene (5 ml), and the suspension was stirred at 160° C. for 8 hr. The reaction solution was cooled to room temperature, and the solvent was then removed therefrom by distillation under the reduced pressure. Chloroform was added to the residue, and the organic layer was washed with a 1 N aqueous potassium hydroxide solution and saturated brine and was dried over anhydrous sodium sulfate. The solvent was removed therefrom by distillation under the reduced pressure, and the residue was purified by column chromatography using chloroform and by thin layer chromatography using acetone-hexane to give the title compound (63.5 mg, yield 72%).

$^1$H-NMR (CDCl$_3$, 400 MHz): δ 2.53 (s, 3H), 4.06 (s, 3H), 4.06 (s, 3H), 6.41 (d, J=5.1 Hz, 1H), 7.17 (dd, J=4.4 Hz, 9.0 Hz, 1H), 7.30 (m, 1H), 7.46 (s, 1H), 7.55 (s, 1H), 7.64 (dd, J=3.2 Hz, 8.8 Hz, 1H), 8.53 (d, J=5.1 Hz, 1H)

Mass spectrometric value (ESI-MS, m/z): 342 (M+1)$^+$

Compound 34: 1-{5-Bromo-2-[(6,7-dimethoxy-4-quinolyl)oxy]phenyl}-1-ethanone

4-Chloro-6,7-dimethoxyquinoline (113 mg), 5-bromo-2-hydroxyacetophenone (550 mg), and 4-dimethylaminopyridine (311 mg) were suspended in o-dichlorobenzene (5 ml), and the suspension was stirred at 160° C. for 4 hr. The reaction solution was cooled to room temperature, and the solvent was then removed therefrom by distillation under the reduced pressure. Chloroform was added to the residue, and the organic layer was washed with a 1 N aqueous potassium hydroxide solution and saturated brine and was dried over anhydrous sodium sulfate. The solvent was removed therefrom by distillation under the reduced pressure, and the residue was purified by column chromatography using chloroform and by thin layer chromatography using acetone-hexane to give the title compound (96.2 mg, yield 47%).

$^1$H-NMR (CDCl$_3$, 400 MHz): δ 2.54 (s, 3H), 4.05 (s, 3H), 4.06 (s, 3H), 6.47 (d, J=5.4 Hz, 1H), 7.05 (d, J=8.6 Hz, 1H), 7.46 (s, 1H), 7.51 (s, 1H), 7.68 (dd, J=2.7 Hz, 8.6 Hz, 1H), 8.05 (d, J=2.7 Hz, 1H), 8.54 (d, J=5.1 Hz, 1H)

Mass spectrometric value (ESI-MS, m/z): 402 (M+1)$^+$

Compound 35: 1-{2-[(6,7-Dimethoxy-4-quinolyl)oxy]-5-methylphenyl}-1-ethanone

4-Chloro-6,7-dimethoxyquinoline (220 mg) and 2-acetyl-4-methylphenol (300 mg) were suspended in o-dichlorobenzene (2 ml), and the suspension was stirred at 170° C. for 6 days. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-chloroform to give the title compound (12 mg, yield 4%).

$^1$H-NMR (CDCl$_3$, 400 MHz): δ 2.37 (s, 3H), 2.43 (s, 3H), 3.98 (s, 3H), 3.99 (s, 3H), 6.34 (d, J=5.1 Hz, 1H), 6.98 (d, J=8.3 Hz, 1H), 7.32 (dd, J=2.0 Hz, 8.3 Hz, 1H), 7.38 (s, 1H), 7.48 (s, 1H), 7.66 (d, J=2.0 Hz, 1H), 8.42 (d, J=5.4 Hz, 1H)

Mass spectrometric value (ESI-MS, m/z): 338 (M+1)$^+$

Compound 36: 1-{2-[(6,7-Dimethoxy-4-quinolyl)oxy]-5-methoxyphenyl}-1-ethanone

4-Chloro-6,7-dimethoxyquinoline (59.4 mg), 2-hydroxy-5-methoxyacetophenone (436 mg), and 4-dimethylaminopyridine (328 mg) were suspended in o-dichlorobenzene (5 ml), and the suspension was stirred at 160° C. for 6 hr. The reaction solution was cooled to room temperature, and the solvent was then removed therefrom by distillation under the reduced pressure. Chloroform was added to the residue, and the organic layer was washed with a 1 N aqueous potassium hydroxide solution and saturated brine and was dried over anhydrous sodium sulfate. The solvent was removed therefrom by distillation under the reduced pressure, and the residue was purified by column chromatography using chloroform and by thin layer chromatography using acetone-hexane to give the title compound (68.6 mg, yield 73%).

$^1$H-NMR (CDCl$_3$, 400 MHz): δ 2.50 (s, 3H), 3.89 (s, 3H), 4.06 (s, 6H), 6.38 (d, J=5.1 Hz, 1H), 7.11 (d, J=8.8 Hz, 1H), 7.15 (dd, J=2.9 Hz, 8.8 Hz, 1H), 7.43 (d, J=3.0 Hz, 1H), 7.45 (s, 1H), 7.58 (s, 1H), 8.50 (d, J=5.4 Hz, 1H)

Mass spectrometric value (ESI-MS, m/z): 354 (M+1)$^+$

Compound 37: 1-{5-Chloro-2-[(6,7-dimethoxy-4-quinolyl)oxy]-4-methylphenyl}-1-ethanone 4-Chloro-6,7-dimethoxyquinoline (100 mg), 5-chloro-2-hydroxy-4-methylacetophenone (248 mg), and 4-dimethylaminopyridine (164 mg) were suspended in o-dichlorobenzene (6 ml), and the suspension was stirred at 150° C. for 2 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-chloroform to give the title compound (71 mg, yield 45%).

$^1$H-NMR (CDCl$_3$, 400 MHz): δ 2.32 (s, 3H), 2.42 (s, 3H), 3.97 (s, 6H), 6.39 (d, J=5.2 Hz, 1H), 6.99 (s, 1H), 7.43 (s, 1H), 7.47 (s, 1H), 7.83 (s, 1H), 8.41 (d, J=5.2 Hz, 1H)

Mass spectrometric value (ESI-MS, m/z): 372 (M+1)$^+$

Compound 38: 1-{2-[(6,7-Dimethoxy-4-quinolyl)oxy]-4,5-dimethylphenyl}-1-ethanone 4-Chloro-6,7-dimethoxyquinoline (100 mg), 4,5-dimethyl-2-hydroxyacetophenone (220 mg), and 4-dimethylaminopyridine (164 mg) were suspended in o-dichlorobenzene (6 ml), and the suspension was stirred at 120° C. for 24 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-hexane to give the title compound (34 mg, yield 22%).

$^1$H-NMR (CDCl$_3$, 400 MHz): δ 2.22 (s, 3H), 2.26 (s, 3H), 2.40 (s, 3H), 3.97 (s, 3H), 3.98 (s, 3H), 6.33 (d, J=5.4 Hz, 1H), 6.85 (s, 1H), 7.37 (s, 1H), 7.48 (s, 1H), 7.65 (s, 1H), 8.41 (d, J=5.4 Hz, 1H)

Mass spectrometric value (ESI-MS, m/z): 352 (M+1)$^+$

Compound 39: 1-{4,5-Dimethoxy-2-[(6,7-dimethoxy-4-quinolyl)oxy]-phenyl}-1-ethanone 4-Chloro-6,7-dimethoxyquinoline (56 mg), 2-hydroxy-4,5-dimethoxyacetophenone (196 mg), and 4-dimethylaminopyridine (122 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure. The residue was purified by column chromatography using acetone-hexane to give the title compound (29 mg, yield 30%).

$^1$H-NMR (CDCl$_3$, 400 MHz): δ 2.47 (s, 3H), 3.87 (s, 3H), 3.99 (s, 3H), 4.07 (s, 6H), 6.40 (d, J=5.3 Hz, 1H), 6.62 (s, 1H), 7.46 (s, 1H), 7.54 (s, 1H), 7.58 (s, 1H), 8.51 (d, J=5.3 Hz, 1H)

Mass spectrometric value (ESI-MS, m/z): 384 (M+1)$^+$

Compound 40: 1-{4,6-Dimethoxy-2-[(6,7-dimethoxy-4-quinolyl)oxy]-phenyl}-1-ethanone 4-Chloro-6,7-dimethoxyquinoline (56 mg), 2-hydroxy-4,6-dimethoxyacetophenone (196 mg), and 4-dimethylaminopyridine (122 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure. The residue was purified by column chromatography using acetone-hexane to give the title compound (25 mg, yield 27%).

$^1$H-NMR (CDCl$_3$, 400 MHz): δ 2.42 (s, 3H), 3.77 (s, 3H), 3.88 (s, 3H), 4.04 (s, 3H), 4.04 (s, 3H), 6.23 (d, J=2.2 Hz, 1H), 6.39 (d, J=2.2 Hz, 1H), 6.56 (d, J=5.1 Hz, 1H), 7.42 (s, 1H), 7.48 (s, 1H), 8.51 (d, J=5.1 Hz, 1H)

Mass spectrometric value (ESI-MS, m/z): 384 (M+1)$^+$

Compound 41: 1-{1-[(6,7-Dimethoxy-4-quinolyl)oxy]-2-naphthyl}-1-ethanone

4-Chloro-6,7-dimethoxyquinoline (100 mg), 1-hydroxy-2-acetonaphthone (250 mg), and 4-dimethylaminopyridine (164 mg) were suspended in o-dichlorobenzene (5 ml), and the suspension was stirred at 160° C. for 2 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-chloroform to give the title compound (5 mg, yield 30%).

$^1$H-NMR (CDCl$_3$, 400 MHz): δ 2.51 (s, 3H), 4.03 (s, 3H), 4.05 (s, 3H), 6.01 (d, J=5.2 Hz, 1H), 7.38 (t, J=8.0 Hz, 1H), 7.51-7.60 (m, 2H), 7.76-7.93 (m, 5H), 8.29 (d, J=5.2 Hz, 1H)

Mass spectrometric value (ESI-MS, m/z): 374 (M+1)$^+$

Compound 42: 1-{2-[(6,7-Dimethoxy-4-quinolyl)oxy]-1-naphthyl}-1-ethanone

4-Chloro-6,7-dimethoxyquinoline (100 mg), 2-hydroxy-1-acetonaphthone (250 mg), and 4-dimethylaminopyridine (164 mg) were suspended in o-dichlorobenzene (6 ml), and the suspension was stirred at 160° C. for 2 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-chloroform to give the title compound (100 mg, yield 60%.

$^1$H-NMR (CDCl$_3$, 400 MHz): δ 2.53 (s, 3H), 3.94 (s, 3H), 3.95 (s, 3H), 6.44 (d, J=5.2 Hz, 1H), 7.44 (d, J=8.8 Hz, 1H), 7.36-7.51 (m, 4H), 7.79-7.86 (m, 3H), 8.42 (d, J=5.2 Hz, 1H)

Mass spectrometric value (ESI-MS, m/z): 374 (M+1)$^+$

Compound 43: 1-{2-[(6,7-Dimethoxy-4-quinolyl)oxy]-3-fluorophenyl}-1-propanone 4-Chloro-6,7-dimethoxyquinoline (111 mg), 3-fluorosalicylaldehyde (280 mg), and 4-dimethylaminopyridine (244 mg) were suspended in monochlorobenzene (2 ml), and the suspension was stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give 2-[(6,7-dimethoxy-4-quinolyl)oxy]-3-fluorobenzaldehyde.

2-[(6,7-Dimethoxy-4-quinolyl)oxy]-3-fluorobenzaldehyde was dissolved in anhydrous tetrahydrofuran (1 ml). A 1 M tetrahydrofuran solution of ethylmagnesium bromide (0.5 ml) was added thereto at 0° C., and the mixture was stirred at 0° C. for one hr. Water (1 ml) was added dropwise to the reaction solution to stop the reaction, followed by extraction with ethyl acetate. The ethyl acetate layer was then washed with water and saturated brine and was dried over anhydrous sodium sulfate. The solvent was removed by distillation under the reduced pressure to give 1-{2-[(6,7-dimethoxy-4-quinolyl)oxy]-3-fluorophenyl}-1-propanol.

1-{2-[(6,7-Dimethoxy-4-quinolyl)oxy]-3-fluorophenyl}-1-propanol was dissolved in anhydrous dimethylsulfoxide (1 ml). Sulfur trioxide trimethylamine complex (70 mg) was added to the solution at 0° C., and the mixture was stirred at room temperature for 18 hr. Water (1 ml) was added dropwise to the reaction solution to stop the reaction. The reaction solution was extracted with ethyl acetate, and the ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give the title compound (2 mg, yield 1%).

$^1$H-NMR (CDCl$_3$, 400 MHz): δ 1.03 (t, J=7.2 Hz, 3H), 2.84 (q, J=7.2 Hz, 2H), 4.05 (s, 6H), 6.34 (d, J=5.4 Hz, 1H), 7.32-7.42 (m, 2H), 7.45 (s, 1H), 7.56 (s, 1H), 7.63-7.67 (m, 1H), 8.48 (d, J=5.4 Hz, 1H)

Mass spectrometric value (ESI-MS, m/z): 356 (M+1)$^+$

Compound 44: 1-{2-[(6,7-Dimethoxy-4-quinolyl)oxy]-4-methoxyphenyl}-1-propanone 4-Chloro-6,7-dimethoxyquinoline (111 mg), 2-hydroxy-4-methoxybenzaldehyde (304 mg), and 4-dimethylaminopyridine (244 mg) were suspended in monochlorobenzene (2 ml), and the suspension was stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give 2-[(6,7-dimethoxy-4-quinolyl)oxy]-4-methoxybenzaldehyde.

2-[(6,7-Dimethoxy-4-quinolyl)oxy]-4-methoxybenzaldehyde was dissolved in anhydrous tetrahydrofuran (1 ml), and a 1 M tetrahydrofuran solution of ethylmagnesium bromide (0.5 ml) was added to the solution at 0° C., and the mixture was stirred at 0° C. for one hr. Water (1 ml) was added dropwise to the reaction solution to stop the reaction. The mixture was extracted with ethyl acetate, and the ethyl acetate layer was then washed with water and saturated brine and was dried over anhydrous sodium sulfate. The solvent was removed by distillation under the reduced pressure to give 1-{2-[(6,7-dimethoxy-4-quinolyl)oxy]-4-methoxyphenyl}-1-propanol.

1-{2-[(6,7-Dimethoxy-4-quinolyl)oxy]-4-methoxyphenyl}-1-propanol was dissolved in anhydrous dimethylsulfoxide (1 ml). A sulfur trioxide trimethylamine complex (70 mg) was added thereto at 0° C., and the mixture was stirred at room temperature for 18 hr. Water (1 ml) was added dropwise to the reaction solution to stop the reaction. The mixture was extracted with ethyl acetate, and the ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give the title compound (25 mg, yield 14%).

$^1$H-NMR (CDCl$_3$, 400 MHz): δ 1.04 (t, J=7.2 Hz, 3H), 2.85 (q, J=7.2 Hz, 2H), 3.80 (s, 3H), 4.02 (s, 3H), 4.04 (s, 3H), 6.46 (d, J=4.6 Hz, 1H), 6.57 (d, J=2.4 Hz, 1H), 6.87 (dd, J=2.4 Hz, 8.8 Hz, 1H), 7.44 (s, 1H), 7.51 (s, 1H), 7.95 (d, J=8.8 Hz, 1H), 8.50 (d, J=5.1 Hz, 1H)

Mass spectrometric value (ESI-MS, m/z): 368 (M+1)$^+$

Compound 45: 1-{4-(Benzyloxy)-2-[(6,7-dimethoxy-4-quinolyl)oxy]-phenyl}-1-propanone 4-Chloro-6,7-dimethoxyquinoline (111 mg), 4-benzyloxy-2-hydroxybenzaldehyde (456 mg), and 4-dimethylaminopyridine (244 mg) were suspended in monochlorobenzene (2 ml), and the suspension was stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give 4-(benzyloxy)-2-[(6,7-dimethoxy-4-quinolyl)oxy]benzaldehyde.

4-(Benzyloxy)-2-[(6,7-dimethoxy-4-quinolyl)oxy]benzaldehyde was dissolved in anhydrous tetrahydrofuran (1 ml). A 1 M tetrahydrofuran solution (0.5 ml) of ethylmagnesium bromide was added thereto at 0° C., and the mixture was stirred at 0° C. for one hr. Water (1 ml) was added dropwise to the reaction solution to stop the reaction. The mixture was extracted with ethyl acetate, and the ethyl acetate layer was then washed with water and saturated brine and was dried over anhydrous sodium sulfate. The solvent was removed by distillation under the reduced pressure to give 1-{4-(benzyloxy)-2-[(6,7-dimethoxy-4-quinolyl)oxy]phenyl}-1-propanol.

1-{4-(Benzyloxy)-2-[(6,7-dimethoxy-4-quinolyl)oxy]phenyl}-1-propanol was dissolved in anhydrous dimethylsulfoxide (1 ml) to prepare a solution. A sulfur trioxide trimethylamine complex (70 mg) was added to the solution at 0° C., and the mixture was stirred at room temperature for 18 hr. Water (1 ml) was added dropwise to the reaction solution to stop the reaction. The reaction solution was extracted with ethyl acetate, and the ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give the title compound (15 mg, yield 7%).

¹H-NMR (CDCl₃, 400 MHz): δ 0.99 (t, J=7.2 Hz, 3H), 2.81 (q, J=7.2 Hz, 2H), 3.96 (s, 3H), 3.99 (s, 3H), 5.00 (s, 2H), 6.37 (d, J=5.4 Hz, 1H), 6.57 (d, J=2.7 Hz, 1H), 6.88 (dd, J=2.4 Hz, 9.0 Hz, 1H), 7.19 (s, 1H), 7.24-7.30 (m, 3H), 7.35 (d, J=5.4 Hz, 1H), 7.38 (s, 1H), 7.43 (s, 1H), 7.89 (d, J=8.8 Hz, 1H), 8.42 (d, J=5.1 Hz, 1H)

Mass spectrometric value (ESI-MS, m/z): 444 (M+1)⁺

Compound 46: 1-{5-Chloro-2-[(6,7-dimethoxy-4-quinolyl)oxy]phenyl}-1-propanone

4-Chloro-6,7-dimethoxyquinoline (111 mg), 5-chlorosalicylaldehyde (360 mg), and 4-dimethylaminopyridine (244 mg) were suspended in monochlorobenzene (2 ml), and the suspension was stirred at 130° C. for overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give 5-chloro-2-[(6,7-dimethoxy-4-quinolyl)oxy]benzaldehyde.

5-Chloro-2-[(6,7-dimethoxy-4-quinolyl)oxy]benzaldehyde was dissolved in anhydrous tetrahydrofuran (1 ml) to prepare a solution. A 1 M tetrahydrofuran solution (0.5 ml) of ethylmagnesium bromide was added to the solution at 0° C., and the mixture was stirred at 0° C. for one hr. Water (1 ml) was added dropwise to the reaction solution to stop the reaction. The mixture was extracted with ethyl acetate, and the ethyl acetate layer was then washed with water and saturated brine and was dried over anhydrous sodium sulfate. The solvent was removed by distillation under the reduced pressure to give 1-{5-chloro-2-[(6,7-dimethoxy-4-quinolyl)oxy]phenyl}-1-propanol.

1-{5-Chloro-2-[(6,7-dimethoxy-4-quinolyl)oxy]phenyl}-1-propanol was dissolved in anhydrous dimethylsulfoxide (1 ml), a sulfur trioxide trimethylamine complex (70 mg) was added to the solution at 0° C., and the mixture was stirred at room temperature for 18 hr. Water (1 ml) was added dropwise to the reaction solution to stop the reaction. The mixture was extracted with ethyl acetate, and the ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give the title compound (11 mg, yield 6%).

¹H-NMR (CDCl₃, 400 MHz): δ 1.00 (t, J=7.2 Hz, 3H), 2.83 (q, J=7.2 Hz, 2H), 4.00 (s, 6H), 6.40 (d, J=5.4 Hz, 1H), 7.02 (d, J=8.8 Hz, 1H), 7.40-7.45 (m, 3H), 7.78 (d, J=2.7 Hz, 1H), 8.46 (d, J=5.2 Hz, 1H)

Mass spectrometric value (ESI-MS, m/z): 372 (M+1)⁺

Compound 47: 1-{2-[(6,7-Dimethoxy-4-quinolyl)oxy]-5-iodophenyl}-1-propanone

4-Chloro-6,7-dimethoxyquinoline (111 mg), 5-iodosalicylaldehyde (496 mg), and 4-dimethylaminopyridine (244 mg) were suspended in monochlorobenzene (2 ml), and the mixture was stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give 2-[(6,7-dimethoxy-4-quinolyl)oxy]-5-iodobenzaldehyde.

2-[(6,7-Dimethoxy-4-quinolyl)oxy]-5-iodobenzaldehyde was dissolved in anhydrous tetrahydrofuran (1 ml) to prepare a solution. A 1 M tetrahydrofuran solution (0.5 ml) of ethylmagnesium bromide was added to the solution at 0° C., and the mixture was stirred at 0° C. for one hr. Water (1 ml) was added dropwise to the reaction solution to stop the reaction. The mixture was extracted with ethyl acetate, and the ethyl acetate layer was then washed with water and saturated brine and was dried over anhydrous sodium sulfate. The solvent was removed by distillation under the reduced pressure to give 1-{2-[(6,7-dimethoxy-4-quinolyl)oxy]-5-iodophenyl}-1-propanol.

1-{2-[(6,7-Dimethoxy-4-quinolyl)oxy]-5-iodophenyl}-1-propanol was dissolved in anhydrous dimethylsulfoxide (1 ml) to prepare a solution. A sulfur trioxide trimethylamine complex (70 mg) was added to the solution at 0° C., and the mixture was stirred at room temperature for 18 hr. Water (1 ml) was added dropwise to the reaction solution to stop the reaction. The mixture was extracted with ethyl acetate, and the ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give the title compound (9 mg, yield 4%).

¹H-NMR (CDCl₃, 400 MHz): δ 1.06 (t, J=7.2 Hz, 3H), 2.89 (q, J=7.2 Hz, 2H), 4.03 (s, 3H), 4.04 (s, 3H), 6.45 (d, J=5.4 Hz, 1H), 7.08 (d, J=8.8 Hz, 1H), 7.45 (s, 1H), 7.48 (s, 1H), 7.50 (dd, J=2.7 Hz, 8.3 Hz, 1H), 7.84 (d, J=2.7 Hz, 1H), 8.52 (d, J=5.1 Hz, 1H)

Mass spectrometric value (ESI-MS, m/z): 464 (M+1)⁺

Compound 48: 1-{2-[(6,7-Dimethoxy-4-quinolyl)oxy]-5-methylphenyl}-1-propanone

Under an argon atmosphere, 1-{2-[(6,7-dimethoxy-4-quinolyl)oxy]-5-methylphenyl}-1-propanol (compound 9) (31.3 mg) was dissolved in methylene chloride (2 ml), and 1,8-diazabicyclo[5.4.0]-7-undecene (30.7 mg) was then added to the solution, followed by cooling to −78° C. N-Tert-butylbenzenesulfineimidoyl chloride (30.4 mg) was dissolved in methylene chloride to prepare a solution, the solution was added thereto, and the mixture was stirred at −78° C. for 50 min. Water was added to the reaction solution, and the mixture was extracted with chloroform. The chloroform layer was then washed with saturated brine and was dried over anhydrous magnesium sulfate. The solvent was removed therefrom by distillation under the reduced pressure, and the residue was purified by thin layer chromatography using acetone-hexane to give the title compound (26.2 mg, yield 84%).

¹H-NMR (CDCl₃, 400 MHz): δ 1.05 (t, J=7.3 Hz, 3H), 2.43 (s, 3H), 2.88 (q, J=7.3 Hz, 2H), 4.05 (s, 3H), 4.06 (s, 3H), 6.42 (d, J=5.1 Hz, 1H), 7.04 (d, J=8.3 Hz, 1H), 7.36 (dd, J=2.2 Hz, 8.3 Hz, 1H), 7.45 (s, 1H), 7.55 (s, 1H), 7.67 (d, J=2.0 Hz, 1H), 8.49 (d, J=5.4 Hz, 1H)

Mass spectrometric value (ESI-MS, m/z): 352 (M+1)⁺

Compound 49: 1-{5-(Tert-butyl)-2-[(6,7-dimethoxy-4-quinolyl)oxy]phenyl}-1-propanone 4-Chloro-6,7-dimethoxyquinoline (111 mg), 5-tert-butyl-2-hydroxybenzaldehyde (356 mg), and 4-dimethylaminopyridine (244 mg) were suspended in monochlorobenzene (2 ml), and the suspension was stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give 5-(tert-butyl)-2-[(6,7-dimethoxy-4-quinolyl)oxy]benzaldehyde.

5-(Tert-butyl)-2-[(6,7-dimethoxy-4-quinolyl)oxy]benzaldehyde was dissolved in anhydrous tetrahydrofuran (1 ml) to prepare a solution. A 1 M tetrahydrofuran solution (0.5 ml) of ethylmagnesium bromide was added to the solution at 0° C., and the mixture was stirred at 0° C. for one hr. Water (1 ml) was added dropwise to the reaction solution to stop the solution. The mixture was extracted with ethyl acetate, and the ethyl acetate layer was then washed with water and saturated brine and was dried over anhydrous sodium sulfate. The solvent was removed by distillation under the reduced pressure to give 1-{5-(tert-butyl)-2-[(6,7-dimethoxy-4-quinolyl)oxy]phenyl}-1-propanol.

1-{5-(Tert-butyl)-2-[(6,7-dimethoxy-4-quinolyl)oxy]phenyl}-1-propanol was dissolved in anhydrous dimethylsulfoxide (1 ml) to prepare a solution. A sulfur trioxide trimethylamine complex (70 mg) was added to the solution at 0° C., and the mixture was stirred at room temperature for 18 hr. Water (1 ml) was added dropwise to the reaction solution to stop the reaction. The mixture was extracted with ethyl acetate, and the ethyl acetate layer was then washed with water and saturated brine and was dried over anhydrous sodium sulfate. The solvent was removed therefrom by distillation under the reduced pressure. The residue was purified by chromatography on silica gel using ethyl acetate-hexane for development to give the title compound (37 mg, yield 19%).

$^1$H-NMR (CDCl$_3$, 400 MHz): δ 1.23 (t, J=7.2 Hz, 3H), 1.36 (s, 9H), 2.88 (q, J=7.2 Hz, 2H), 4.02 (s, 3H), 4.04 (s, 3H), 6.45 (d, J=5.4 Hz, 1H), 7.04 (d, J=8.5 Hz, 1H), 7.44 (s, 1H), 7.52 (s, 1H), 7.56 (dd, J=2.7 Hz, 8.6 Hz, 1H), 7.86 (d, J=2.4 Hz, 1H), 8.49 (d, J=5.1 Hz, 1H)

Mass spectrometric value (ESI-MS, m/z): 394 (M+1)$^+$

Compound 50: 1-{2-[(6,7-Dimethoxy-4-quinolyl)oxy]-5-methoxyphenyl}-1-propanone Under an argon atmosphere, 1-{2-[(6,7-dimethoxy-4-quinolyl)oxy]-5-methoxyphenyl}-1-propanol (compound 11) (65.9 mg) was dissolved in methylene chloride (2 ml) to prepare a solution. 1,8-Diazabicyclo[5.4.0]-7-undecene (72 mg) was then added to the solution, and the mixture was cooled to −78° C. N-Tert-butylbenzenesulfineimidoyl chloride (71.4 mg) was dissolved in methylene chloride to prepare a solution, and the solution was added to the reaction solution. The mixture was stirred at −78° C. for 30 min and at 0° C. for 30 min. Water was added to the reaction solution, and the mixture was extracted with chloroform. The chloroform layer was then washed with saturated brine and was dried over anhydrous magnesium sulfate. The solvent was removed therefrom by distillation under the reduced pressure, and the residue was purified by thin layer chromatography using acetone-hexane to give the title compound (56.2 mg, yield 86%).

$^1$H-NMR (CDCl$_3$, 400 MHz): δ 1.05 (t, J=7.3 Hz, 3H), 2.88 (q, J=7.3 Hz, 2H), 3.89 (s, 3H), 4.06 (s, 6H), 6.39 (d, J=5.1 Hz, 1H), 7.07-7.15 (m, 2H), 7.39 (d, J=2.2 Hz, 1H), 7.45 (s, 1H), 7.57 (s, 1H), 8.49 (d, J=5.1 Hz, 1H)

Mass spectrometric value (ESI-MS, m/z): 368 (M+1)$^+$

Compound 51: 1-[2-(6,7-Dimethoxy-4-quinolyl)oxy]-5-(trifluoromethoxy)phenyl]-1-propanone 4-Chloro-6,7-dimethoxyquinoline (111 mg), 5-trifluoromethoxysalicylaldehyde (412 mg), and 4-dimethylaminopyridine (244 mg) were suspended in monochlorobenzene (2 ml), and the suspension was stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give 2-[(6,7-dimethoxy-4-quinolyl)oxy]-5-trifluoromethoxybenzaldehyde.

2-[(6,7-Dimethoxy-4-quinolyl)oxy]-5-trifluoromethoxybenz-aldehyde was dissolved in anhydrous tetrahydrofuran (1 ml) to prepare a solution. A 1 M tetrahydrofuran solution (0.5 ml) of ethylmagnesium bromide was added to the solution at 0° C., and the mixture was stirred at 0° C. for one hr. Water (1 ml) was added dropwise to the reaction solution to stop the reaction. The mixture was extracted with ethyl acetate, and the ethyl acetate layer was then washed with water and saturated brine and was dried over anhydrous sodium sulfate. The solvent was removed by distillation under the reduced pressure to give 1-{2-[(6,7-dimethoxy-4-quinolyl)oxy]-5-(trifluoromethoxy)phenyl}-1-propanol.

1-{2-[(6,7-Dimethoxy-4-quinolyl)oxy]-5-(trifluoromethoxy)phenyl}-1-propanol was dissolved in anhydrous dimethylsulfoxide (1 ml) to prepare a solution, a sulfur trioxide trimethylamine complex (70 mg) was added to the solution at 0° C., and the mixture was stirred at room temperature for 18 hr. Water (1 ml) was added dropwise to the reaction solution to stop the reaction. The mixture was extracted with ethyl acetate, and the ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give the title compound (18 mg, yield 8%).

$^1$H-NMR (CDCl$_3$, 400 MHz): δ 1.06 (t, J=7.2 Hz, 3H), 2.91 (q, J=7.2 Hz, 2H), 4.02 (s, 3H), 4.04 (s, 3H), 6.47 (d, J=5.1 Hz, 1H), 7.15 (d, J=9.0 Hz, 1H), 7.38 (dd, J=3.0 Hz, 9.0 Hz, 1H), 7.45 (s, 1H), 7.46 (s, 1H), 7.73 (d, J=2.9 Hz, 1H), 8.52 (d, J=5.1 Hz, 1H)

Mass spectrometric value (ESI-MS, m/z): 422 (M+1)$^+$

Compound 52: 1-{2-[(6,7-Dimethoxy-4-quinolyl)oxy]-5-methylphenyl}-1-pentanone Under an argon atmosphere, 1-{2-[(6,7-dimethoxy-4-quinolyl)oxy]-5-methylphenyl}-1-pentanol (compound 10) (45.7 mg) was dissolved in methylene chloride (2 ml) to prepare a solution. 1,8-Diazabicyclo[5.4.0]-7-undecene (37 mg) was then added to the solution, and the mixture was cooled to 0° C. N-Tert-butylbenzenesulfineimidoyl chloride (43 mg) was dissolved in methylene chloride to prepare a solution, the solution was added thereto, and the mixture was stirred at 0° C. for 40 min. Water was added to the reaction solution, and the mixture was extracted with chloroform. The chloroform layer was then washed with saturated brine and was dried over anhydrous sodium sulfate. The solvent was removed therefrom by distillation under the reduced pressure, and the residue was purified by thin layer chromatography using acetone-hexane to give the title compound (27.6 mg, yield 61%).

$^1$H-NMR (CDCl$_3$, 400 MHz): δ 0.75 (t, J=7.3 Hz, 3H), 1.17 (m, 2H), 1.55 (m, 2H), 2.43 (s, 3H), 2.84 (t, J=7.5 Hz, 2H), 4.05 (s, 3H), 4.06 (s, 3H), 6.41 (d, J=5.1 Hz, 1H), 7.05 (d, J=8.3 Hz, 1H), 7.36 (d, J=8.3 Hz, 1H), 7.44 (s, 1H), 7.55 (s, 1H), 7.63 (s, 1H), 8.49 (d, J=5.4 Hz, 1H)

Mass spectrometric value (ESI-MS, m/z): 380 (M+1)$^+$

Compound 53: 1-{2-[(6,7-Dimethoxy-4-quinolyl) oxy]-5-methylphenyl}-2-methyl-1-propanone Under an argon atmosphere, 2-[(6,7-dimethoxy-4-quinolyl)oxy]-5-methylbenzaldehyde (105.3 mg) was dissolved in tetrahydrofuran (3 ml) to prepare a solution, and the solution was then cooled to −78° C. A 0.68 M tetrahydrofuran solution (0.6 ml) of isopropylmagnesium bromide was added dropwise thereto, and the mixture was stirred at −78° C. for one hr. A saturated aqueous ammonium chloride solution was added to the reaction solution, and the mixture was extracted with ethyl acetate. The ethyl acetate layer was then washed with saturated brine and was dried over anhydrous sodium sulfate. The solvent was removed therefrom by distillation under the reduced pressure, and the residue was purified by thin layer chromatography using acetone-hexane to give 1-{2-[(6,7-dimethoxy-4-quinolyl)oxy]-5-methylphenyl}-2-methyl-1-propanol (11.5 mg, yield 10%).

1-{2-[(6,7-Dimethoxy-4-quinolyl)oxy]-5-methylphenyl}-2-methyl-1-propanol (9 mg) thus obtained was then dissolved in 2 ml of methylene chloride under an argon atmosphere to prepare a solution. 1,8-Diazabicyclo[5.4.0]-7-undecene (54 mg) was then added to the solution, and the mixture was cooled to −78° C. N-Tert-butylbenzenesulfineimidoyl chloride (56 mg) was dissolved in methylene chloride, and the solution was added thereto. The mixture was stirred at −78° C. for 3 hr, at 0° C. for one hr, and at room temperature overnight. Water was added to the reaction solution, and the mixture was extracted with chloroform. The chloroform layer was then washed with saturated brine and was dried over anhydrous magnesium sulfate. The solvent was removed therefrom by distillation under the reduced pressure. The residue was purified by thin layer chromatography using acetone-hexane to give the title compound (7.2 mg, yield 80%).

$^1$H-NMR (CDCl$_3$, 400 MHz): δ 1.07 (d, J=6.8 Hz, 6H), 2.43 (s, 3H), 3.29 (m, 1H), 4.03 (s, 3H), 4.06 (s, 3H), 6.46 (d, J=5.4 Hz, 1H), 7.04 (d, J=8.3 Hz, 1H), 7.34 (dd, J=2.2 Hz, 8.3 Hz, 1H), 7.44 (s, 1H), 7.51 (m, 2H), 8.50 (d, J=5.2 Hz, 1H)

Mass spectrometric value (ESI-MS, m/z): 366 (M+1)$^+$

Compound 54: 1-{2-[(6,7-Dimethoxy-4-quinolyl) oxy]-5-methylphenyl}-2,2-dimethyl-1-propanone 4-(2-Bromo-4-methylphenoxy)-6,7-dimethoxyquinoline (compound 4) (100 mg) was dissolved in tetrahydrofuran (6 ml) to prepare a solution which was then cooled to −78° C. A 1.59 M n-butyllithium/hexane solution (0.4 ml) was added thereto, and the mixture was stirred at −78° C. for 20 min. Pivaloyl chloride (0.2 ml) was added to the reaction solution, and the mixture was stirred at room temperature overnight. Further, water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-chloroform to give the title compound (21 mg, yield 21%).

$^1$H-NMR (CDCl$_3$, 400 MHz): δ 1.23 (s, 9H), 2.41 (s, 3H), 4.00 (s, 3H), 4.04 (s, 3H), 6.57 (d, J=5.1 Hz, 1H), 7.02 (d, J=8.3 Hz, 1H), 7.07 (m, 1H), 7.22 (dd, J=1.5 Hz, 8.3 Hz, 1H), 7.43 (s, 1H), 7.44 (s, 1H), 8.51 (d, J=5.1 Hz, 1H)

Mass spectrometric value (ESI-MS, m/z): 380 (M+1)$^+$

Compound 55: 1-{2-[(6,7-Dimethoxy-4-quinolyl) oxy]-5-methylphenyl}-3,3-dimethyl-1-butanone 4-(2-Bromo-4-methylphenoxy)-6,7-dimethoxyquinoline (100 mg) was dissolved in tetrahydrofuran (6 ml) to prepare a solution which was then cooled to −78° C. A 1.59 M n-butyllithium/hexane solution (0.4 ml) was added thereto, and the mixture was stirred at −78° C. for 20 min. Tert-butylacetyl chloride (0.2 ml) was added to the reaction solution, and the mixture was stirred at room temperature overnight. Further, water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-chloroform to give the title compound (15 mg, yield 14%).

$^1$H-NMR (CDCl$_3$, 400 MHz): δ 0.92 (s, 9H), 2.43 (s, 3H), 2.77 (s, 2H), 4.04 (s, 3H), 4.06 (s, 3H), 6.41 (d, J=5.4 Hz, 1H), 7.05 (d, J=8.3 Hz, 1H), 7.35 (dd, J=2.2 Hz, 8.8 Hz, 1H), 7.50 (s, 1H), 7.52 (d, J=2.2 M/Z): 5 Hz, 1H), 7.55 (s, 1H), 8.49 (d, J=4.9 Hz, 1H)

Mass spectrometric value (ESI-MS, m/z): 394 (M+1)$^+$

Compound 56: 3-Cyclopentyl-1-{2-[(6,7-dimethoxy-4-quinolyl)oxy]-5-methylphenyl}-1-propanone 4-(2-Bromo-4-methylphenoxy)-6,7-dimethoxyquinoline (100 mg) was dissolved in tetrahydrofuran (6 ml) to prepare a solution which was then cooled to −78° C. A 1.59 M n-butyllithium/hexane solution (0.4 ml) was added to the cooled solution, and the mixture was stirred at −78° C. for 20 min. 3-Cyclopentylpropionyl chloride (0.2 ml) was added to the reaction solution, and the mixture was stirred at room temperature overnight. Further, water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-chloroform to give the title compound (9 mg, yield 8%).

$^1$H-NMR (CDCl$_3$, 400 MHz): δ 0.88-1.84 (m, 11H), 2.44 (s, 3H), 2.84 (m, 2H), 4.05 (s, 3H), 4.07 (s, 3H), 6.41 (d, J=5.4 Hz, 1H), 7.05 (d, J=8.3 Hz, 1H), 7.38 (dd, J=2.2 Hz, 8.3 Hz, 1H), 7.55 (s, 1H), 7.56 (s, 1H), 7.64 (d, J=1.7 Hz, 1H), 8.50 (d, J=5.4 Hz, 1H)

Mass spectrometric value (ESI-MS, m/z): 420 (M+1)$^+$

Compound 57: 1-{2-[(6,7-Dimethoxy-4-quinolyl)oxy]phenyl}-3-phenyl-2-propen-1-one 4-Chloro-6,7-dimethoxyquinoline (100 mg), 2-hydroxychalcone (300 mg), and 4-dimethylaminopyridine (164 mg) were suspended in o-dichlorobenzene (6 ml), and the suspension was stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-hexane to give the title compound (30 mg, yield 16%).

$^1$H-NMR (CDCl$_3$, 400 MHz): δ 3.74 (s, 3H), 3.88 (s, 1H), 3.97 (s, 3H), 4.01 (s, 1H), 6.41 (d, J=5.4 Hz, 1H), 7.12-7.50 (m, 9H), 7.59 (t, J=8.0 Hz, 1H), 7.80 (d, J=8.0 Hz, 1H), 8.45 (d, J=5.4 Hz, 1H)

Mass spectrometric value (ESI-MS, m/z): 412 (M+1)$^+$

Compound 58: (Cyclopentyl){2-[(6,7-dimethoxy-4-quinolyl)oxy]-5-methylphenyl}methanone 4-(2-Bromo-4-methylphenoxy)-6,7-dimethoxyquinoline (100 mg) was dissolved in tetrahydrofuran (6 ml) to prepare a solution which was then cooled to −78° C. A 1.59 M n-butyllithium/hexane solution (0.35 ml) was added to the cooled solution, and the mixture was stirred at −78° C. for 20 min. Cyclopentanecarbonyl chloride (0.2 ml) was added to the reaction solution, and the mixture was stirred at room temperature for 7 hr. Further, water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-chloroform to give the title compound (14 mg, yield 13%).

$^1$H-NMR (CDCl$_3$, 400 MHz): δ 1.41-1.83 (m, 8H), 2.43 (s, 3H), 3.52 (tt, J=7.1, 8.3 Hz, 1H), 4.03 (s, 3H), 4.06 (s, 3H), 6.45 (d, J=5.2 Hz, 1H), 7.04 (d, J=8.1 Hz, 1H), 7.34 (dd, J=1.7 Hz, 8.3 Hz, 1H), 7.46 (s, 1H), 7.53 (s, 1H), 7.55 (d, J=2.2 Hz, 1H), 8.49 (d, J=5.4 Hz, 1H)

Mass spectrometric value (ESI-MS, m/z): 392 (M+1)$^+$

Compound 59: (Cyclohexyl){2-[(6,7-dimethoxy-4-quinolyl)oxy]-5-methylphenyl}methanone 4-(2-Bromo-4-methylphenoxy)-6,7-dimethoxyquinoline (101 mg) was dissolved in tetrahydrofuran (5 ml) to prepare a solution which was then cooled to −78° C. A 1.59 M n-butyllithium/hexane solution (0.4 ml) was added to the cooled solution, and the mixture was stirred at −78° C. for 20 min. Cyclohexanecarbonyl chloride (0.2 ml) was added to the reaction solution, and the mixture was stirred at room temperature for 3 hr. Further, water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-chloroform to give the title compound (17 mg, yield 16%).

$^1$H-NMR (CDCl$_3$, 400 MHz): δ 0.88-1.70 (m, 10H), 2.35 (s, 3H), 2.94 (m, 1H), 3.97 (s, 3H), 3.99 (s, 3H), 6.35 (d, J=5.4 Hz, 1H), 6.97 (d, J=8.3 Hz, 1H), 7.27 (dd, J=2.2 Hz, 8.3 Hz, 1H), 7.39 (s, 1H), 7.42 (d, J=1.9 Hz, 1H), 7.47 (s, 1H), 8.42 (d, J=5.1 Hz, 1H)

Mass spectrometric value (ESI-MS, m/z): 406 (M+1)$^+$

Compound 60: {2-[(6,7-Dimethoxy-4-quinolyl)oxy]-5-methyl phenyl}(2-furyl)methanone 4-(2-Bromo-4-methylphenoxy)-6,7-dimethoxyquinoline (100 mg) was dissolved in tetrahydrofuran (6 ml) to prepare a solution which was then cooled to −78° C. A 1.59 M n-butyllithium/hexane solution (0.35 ml) was added to the cooled solution, and the mixture was stirred at −78° C. for 20 min. 2-Furancarbonyl chloride (0.2 ml) was added to the reaction solution, and the mixture was stirred at room temperature for 7 hr. Further, water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-chloroform to give the title compound (34 mg, yield 33%).

$^1$H-NMR (CDCl$_3$, 400 MHz): δ 2.49 (s, 3H), 3.99 (s, 3H), 4.09 (s, 3H), 6.49-6.51 (m, 2H), 6.64 (d, J=6.1 Hz, 1H), 7.18 (d, J=8.3 Hz, 1H), 7.37 (s, 1H), 7.46 (dd, J=2.2 Hz, 8.3 Hz, 1H), 7.53 (m, 1H), 7.57 (m, 1H), 7.86 (s, 1H), 8.72 (d, J=5.9 Hz, 1H)

Mass spectrometric value (ESI-MS, m/z): 390 (M+1)$^+$

Compound 61: {2-[(6,7-Dimethoxy-4-quinolyl)oxy]-5-methylphenyl}(5-isoxazolyl)methanone 4-(2-Bromo-4-methylphenoxy)-6,7-dimethoxyquinoline (100 mg) was dissolved in tetrahydrofuran (6 ml) to prepare a solution which was then cooled to −78° C. A 1.59 M n-butyllithium/hexane solution (0.4 ml) was added to the solution, and the mixture was stirred at −78° C. for 20 min. Isoxazole-5-carbonyl chloride (0.2 ml) was added to the reaction solution, and the mixture was stirred at room temperature overnight. Further, water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-chloroform to give the title compound (27 mg, yield 26%).

$^1$H-NMR (CDCl$_3$, 400 MHz): δ 2.48 (s, 3H), 4.01 (s, 3H), 4.02 (s, 3H), 6.46 (d, J=5.4 Hz, 1H), 6.81 (d, J=1.9 Hz, 1H), 7.13 (d, J=8.3 Hz, 1H), 7.24 (s, 1H), 7.40 (s, 1H), 7.49 (dd, J=1.9, 8.3 Hz, 1H), 7.59 (d, J=1.7 Hz, 1H), 8.25 (d, J=1.9 Hz, 1H), 8.46 (d, J=5.4 Hz, 1H)

Mass spectrometric value (ESI-MS, m/z): 391 (M+1)$^+$

Compound 62: {2-[(6,7-Dimethoxy-4-quinolyl)oxy]phenyl}(phenyl)-methanone

4-Chloro-6,7-dimethoxyquinoline (58 mg), 2-hydroxybenzophenone (271 mg), and 4-dimethylaminopyridine (166 mg) were suspended in o-dichlorobenzene (5 ml), and the suspension was stirred at 160° C. for 4 hr. The reaction solution was cooled to room temperature, and the solvent was then removed therefrom by distillation under the reduced pressure. Chloroform was added to the residue, and the mixture was washed with a 1 N aqueous potassium hydroxide solution and saturated brine and was dried over anhydrous sodium sulfate.

The solvent was removed therefrom by distillation under the reduced pressure, and the residue was purified by column chromatography using chloroform and by thin layer chromatography using acetone-hexane to quantitatively give 110.4 mg of the title compound.

$^1$H-NMR (CDCl$_3$, 400 MHz): δ 3.82 (s, 3H), 3.99 (s, 3H), 6.43 (d, J=5.1 Hz, 1H), 6.93 (s, 1H), 7.26 (d, J=8.3 Hz, 1H), 7.28-7.34 (m, 3H), 7.39-7.48 (m, 2H), 7.59-7.72 (m, 4H), 8.44 (d, J=5.4 Hz, 1H)

Mass spectrometric value (ESI-MS, m/z): 386 (M+1)$^+$

Compound 63: {2-[(6,7-Dimethoxy-4-quinolyl)oxy]-phenyl}(phenyl)-methanone hydrochloride 4-Chloro-6,7-dimethoxyquinoline (0.92 g) and 2-hydroxybenzophenone (1.64 g) were stirred at 180° C. for one hr, and the reaction solution was cooled to room temperature. Chloroform was then added to the reaction solution, and separation was carried out with a 10% aqueous sodium hydroxide solution. The organic layer was washed with a saturated aqueous sodium hydrogencarbonate solution and saturated brine and was dried over anhydrous magnesium sulfate. The solvent was removed therefrom by distillation under the reduced pressure, and the residue was purified by column chromatography on silica gel using hexane-acetone. Thereafter, 10% hydrochloric acid-methanol (10 ml) was added to the product, followed by concentration. The concentrate was suspended in ether. The suspension was filtered to give the title compound (174 mg, yield 10%).

$^1$H-NMR (CDCl$_3$, 400 MHz): δ 3.92 (s, 3H), 4.13 (s, 3H), 6.66 (d, J=6.4 Hz, 1H), 7.15 (s, 1H), 7.35-7.41 (m, 3H), 7.52-7.61 (m, 2H), 7.67-7.79 (m, 4H), 8.08 (s, 1H), 8.44 (dd, J=6.6 Hz, 6.6 Hz, 1H)

Mass spectrometric value (ESI-MS, m/z): 386 (M−HCl+1)$^+$

Compound 64: {2-[(6,7-Dimethoxy-4-quinolyl)oxy]-4-methoxyphenyl}-(phenyl)methanone 4-Chloro-6,7-dimethoxyquinoline (56.5 mg), 2-hydroxy-4-methoxybenzophenone (286 mg), and 4-dimethylaminopyridine (163 mg) were suspended in o-dichlorobenzene (5 ml), and the suspensioon was stirred at 160° C. for 4 hr. The reaction solution was cooled to room temperature, and the solvent was then removed therefrom by distillation under the reduced pressure. Chloroform was added to the residue, and the mixture was washed with a 1 N aqueous potassium hydroxide solution and saturated brine and was dried over anhydrous sodium sulfate. The solvent was removed therefrom by distillation under the reduced pressure, and the residue was purified by column chromatography using chloroform and by thin layer chromatography using acetone-hexane to give the title compound (14.5 mg, yield 14%).

$^1$H-NMR (CDCl$_3$, 400 MHz): δ 3.87 (s, 3H), 3.89 (s, 3H), 3.99 (s, 3H), 6.42 (d, J=5.4 Hz, 1H), 6.76 (d, J=2.4 Hz, 1H), 6.92 (s, 1H), 6.96 (dd, J=2.4 Hz, 8.8 Hz, 1H), 7.24-7.33 (m, 3H), 7.41 (m, 1H), 7.61-7.66 (m, 2H), 7.69 (d, J=8.8 Hz, 1H), 8.43 (d, J=5.1 Hz, 1H)

Mass spectrometric value (ESI-MS, m/z): 416 (M+1)$^+$

Compound 65: {2-[(6,7-Dimethoxy-4-quinolyl)oxy]-4-methoxyphenyl}(4-methylphenyl)methanone 4-Chloro-6,7-dimethoxyquinoline (56 mg), 2-hydroxy-4-methoxy-4'-methylbenzophenone (242 mg), and 4-dimethylaminopyridine (122 mg) were suspended in o-dichlorobenzene (1 ml), and the suspension was stirred at 140° C. for 4 hr. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure. The residue was purified by thin layer chromatography using acetone-hexane to give the title compound (46 mg, yield 43%).

$^1$H-NMR (CDCl$_3$, 400 MHz): δ 2.31 (s, 3H), 3.88 (s, 3H), 3.89 (s, 3H), 4.01 (s, 3H), 6.43 (d, J=5.3 Hz, 1H), 6.77 (d, J=2.4 Hz, 1H), 6.95 (dd, J=8.5 Hz, 2.4 Hz, 1H), 6.98 (s, 1H), 7.07 (d, J=8.0 Hz, 2H), 7.35 (s, 1H), 7.54 (d, J=8.0 Hz, 2H), 7.66 (d, J=8.5 Hz, 1H), 8.43 (d, J=5.3 Hz, 1H)

Mass spectrometric value (ESI-MS, m/z): 430 (M+1)$^+$

Compound 66: {2-[(6,7-Dimethoxy-4-quinolyl)oxy]-4-octoxyphenyl}-(phenyl)methanone 4-Chloro-6,7-dimethoxyquinoline (100 mg), 2-hydroxy-4-n-octoxybenzophenone (652 mg), and 4-dimethylaminopyridine (244 mg) were suspended in o-dichlorobenzene (1 ml), and the suspension was stirred at 120° C. for 6 hr. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (85 mg, yield 33%).

$^1$H-NMR (CDCl$_3$, 400 MHz): δ 0.89 (t, J=6.8 Hz, 3H), 1.23-1.50 (m, 10H), 1.82 (m, 2H), 3.87 (s, 3H), 3.99-4.06 (m, 5H), 6.42 (d, J=5.3 Hz, 1H), 6.74 (d, J=2.2 Hz, 1H), 6.92 (s, 1H), 6.94 (dd, J=2.2 Hz, 8.6 Hz, 1H), 7.27 (m, 2H), 7.30 (s, 1H), 7.39 (m, 1H), 7.63 (m, 2H), 7.67 (d, J=8.6 Hz, 1H), 8.43 (d, J=5.3 Hz, 1H)

Mass spectrometric value (ESI-MS, m/z): 514 (M+1)$^+$

Compound 67: 4-Benzoyl-3-[(6,7-dimethoxy-4-quinolyl)oxy]phenyl-2-methylacrylate 4-Chloro-6,7-dimethoxyquinoline (56 mg), 4-methacryloxy-2-hydroxybenzophenone (282 mg), and 4-dimethylaminopyridine (122 mg) were suspended in o-dichlorobenzene (1 ml), and the suspension was stirred at 140° C. for 4 hr. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by thin layer chromatography using acetone-hexane to give the title compound (21 mg, yield 18%).

$^1$H-NMR (CDCl$_3$, 400 MHz): δ 1.78 (s, 3H), 4.04 (s, 3H), 4.06 (s, 3H), 5.52 (m, 1H), 5.82 (m, 1H), 6.75 (d, J=5.1 Hz, 1H), 7.10 (d, J=2.0 Hz, 1H), 7.16 (dd, J=8.6 Hz, 2.2 Hz, 1H), 7.31-8.48 (m, 8H), 8.61 (d, J=5.1 Hz, 1H)

Mass spectrometric value (ESI-MS, m/z): 470 (M+1)$^+$

Compound 68: {5-Chloro-2-[(6,7-dimethoxy-4-quinolyl)oxy]phenyl}-(phenyl)methanone 4-Chloro-6,7-dimethoxyquinoline (57.5 mg), 5-chloro-2-hydroxybenzophenone (309 mg), and 4-dimethylaminopyridine (173 mg) were suspended in o-dichlorobenzene (5 ml), and the suspension was stirred at 160° C. for 5 hr. The mixture was cooled to room temperature, and the solvent was then removed therefrom by distillation under the reduced pressure, and chloroform was added to the residue. The mixture was washed with a 1 N aqueous potassium hydroxide solution and saturated brine and was dried over anhydrous magnesium sulfate. The solvent was removed therefrom by distillation under the reduced pressure, and the residue was purified by column chromatography using chloroform and by thin layer chromatography using acetone-hexane to quantitatively give 114 mg of the title compound.

$^1$H-NMR (CDCl$_3$, 400 MHz): δ 3.82 (s, 3H), 3.99 (s, 3H), 6.44 (d, J=5.1 Hz, 1H), 6.90 (s, 1H), 7.21 (d, J=8.8 Hz, 1H), 7.31-7.37 (m, 3H), 7.46-7.51 (m, 1H), 7.58 (dd, J=2.7 Hz, 8.8 Hz, 1H), 7.63 (d, J=2.7 Hz, 1H), 7.68-7.72 (m, 2H), 8.45 (d, J=5.4 Hz, 1H)

Mass spectrometric value (ESI-MS, m/z): 420 (M+1)$^+$

Compound 69: {5-Chloro-2-[(6,7-dimethoxy-4-quinolyl)oxy]phenyl}-(phenyl)methanone hydrochloride 4-Chloro-6,7-dimethoxyquinoline (1.00 g) and 5-chloro-2-hydroxybenzophenone (1.46 g) were stirred at 170° C. for one hr, and the reaction solution was cooled to room temperature. Chloroform was then added to the reaction solution, and separation was carried out with a 10% aqueous sodium hydroxide solution. The organic layer was washed with a saturated aqueous sodium hydrogencarbonate solution and saturated brine and was dried over anhydrous magnesium sulfate. The solvent was removed therefrom by distillation under the reduced pressure, and the residue was purified by column chromatography on silica gel using hexane-acetone. Thereafter, 10% hydrochloric acid-methanol (10 ml) was added to the product, followed by concentration. The concentrate was suspended in ether, and the suspension was filtered to give the title compound (225 mg, yield 11%).

$^1$H-NMR (CDCl$_3$, 400 MHz): δ 3.91 (s, 3H), 4.12 (s, 3H), 6.68 (d, J=5.6 Hz, 1H), 7.11 (s, 1H), 7.32 (d, J=8.5 Hz, 1H), 7.38-7.43 (m, 2H), 7.54-7.60 (m, 1H), 7.66-7.74 (m, 4H), 8.08 (s, 1H), 8.48 (brs, 1H)

Mass spectrometric value (ESI-MS, m/z): 420 (M-HCl+1)$^+$

Compound 70: {5-Bromo-2-[(6,7-dimethoxy-4-quinolyl)oxy]phenyl}-(phenyl)methanone 4-Chloro-6,7-dimethoxyquinoline (56.1 mg), 5-bromo-2-hydroxybenzophenone (361 mg), and 4-dimethylaminopyridine (168 mg) were suspended in o-dichlorobenzene (5 ml), and the suspension was stirred at 160° C. for 7 hr. The reaction solution was cooled to room temperature, and the solvent was then removed therefrom by distillation under the reduced pressure. Chloroform was added to the residue, and mixture was washed with a 1 N aqueous potassium hydroxide solution and saturated brine and was dried over anhydrous magnesium sulfate. The solvent was removed therefrom by distillation under the reduced pressure, and the residue was purified by column chromatography using chloroform and by thin layer chromatography using acetone-hexane to give the title compound (110 mg, yield 94%).

$^1$H-NMR (CDCl$_3$, 400 MHz): δ 3.82 (s, 3H), 3.99 (s, 3H), 6.45 (d, J=5.4 Hz, 1H), 6.83 (s, 1H), 7.15 (d, J=8.6 Hz, 1H), 7.31-7.37 (m, 3H), 7.46-7.51 (m, 1H), 7.67-7.75 (m, 3H), 7.78 (d, J=2.4 Hz, 1H), 8.45 (d, J=5.4 Hz, 1H)

Mass spectrometric value (ESI-MS, m/z): 465 (M+1)$^+$

Compound 71: {2-[(6,7-Dimethoxy-4-quinolyl)oxy]-5-methylphenyl}-(phenyl)methanone 4-Chloro-6,7-dimethoxyquinoline (58.6 mg), 2-hydroxy-5-methylbenzophenone (276 mg), and 4-dimethylaminopyridine (156 mg) were suspended in o-dichlorobenzene (5 ml), and the suspension was stirred at 160° C. for 5 hr. The reaction solution was cooled to room temperature, and the solvent was then removed therefrom by distillation under the reduced pressure. Chloroform was added to the residue, and the mixture was washed with a 1 N aqueous potassium hydroxide solution and saturated brine and was dried over anhydrous sodium sulfate. The solvent was removed therefrom by distillation under the reduced pressure, and the residue was purified by column chromatography using chloroform and by thin layer chromatography using acetone-hexane to give the title compound (98.9 mg, yield 95%).

$^1$H-NMR (CDCl$_3$, 400 MHz): δ 2.46 (s, 3H), 3.81 (s, 3H), 3.98 (s, 3H), 6.40 (d, J=5.4 Hz, 1H), 6.89 (s, 1H), 7.16 (d, J=8.3 Hz, 1H), 7.27-7.33 (m, 3H), 7.40-7.48 (m, 3H), 7.67-7.71 (m, 2H), 8.42 (d, J=5.1 Hz, 1H)

Mass spectrometric value (ESI-MS, m/z): 400 (M+1)$^+$

Compound 72: {2-[(6,7-Dimethoxy-4-quinolyl)oxy]-5-methylphenyl}-(phenyl)methanone hydrochloride 4-Chloro-6,7-dimethoxyquinoline (1.00 g) and 2-hydroxy-5-methylbenzophenone (1.14 g) were stirred at 170° C. for one hr. The reaction solution was cooled to room temperature. Chloroform was then added to the reaction solution, and separation was carried out with a 10% aqueous sodium hydroxide solution. The organic layer was washed with a saturated aqueous sodium hydrogencarbonate solution and saturated brine and was dried over anhydrous magnesium sulfate. The solvent was removed therefrom by distillation under the reduced pressure, and the residue was purified by column chromatography on silica gel using hexane-acetone. Thereafter, 10% hydrochloric acid-methanol (10 ml) was added to the product, followed by concentration. The concentrate was suspended in ether, and the suspension was filtered to give the title compound (234 mg, yield 12%).

$^1$H-NMR (CDCl$_3$, 400 MHz): δ 2.51 (s, 3H), 3.91 (s, 3H), 4.12 (s, 3H), 6.66 (d, J=6.4 Hz, 1H), 7.11 (s, 1H), 7.23 (d, J=8.3 Hz, 1H), 7.38 (t, J=7.6 Hz, 1H), 7.50-7.57 (m, 4H), 7.65-7.70 (m, 2H), 8.06 (s, 1H), 8.43 (brs, 1H)

Mass spectrometric value (ESI-MS, m/z): 400 (M-HCl+1)$^+$

Compound 73: [4-(Tert-butyl)phenyl]{2-[(6,7-dimethoxy-4-quinolyl)oxy]-5-methylphenyl}methanone 4-(2-Bromo-4-methylphenoxy)-6,7-dimethoxyquinoline (100 mg) was dissolved in tetrahydrofuran (6 ml) to prepare a solution which was then cooled to −78° C. A 1.59 M n-butyl-lithium/hexane solution (0.35 ml) was added to the cooled solution, and the mixture was stirred at −78° C. for 20 min. 4-Tert-butylphenylcarbonyl chloride (0.15 ml) was added to the reaction solution, and the mixture was stirred at room temperature for 30 min. Further, water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-chloroform to give the title compound (31 mg, yield 25%).

¹H-NMR (CDCl₃, 400 MHz): δ 1.23 (s, 9H), 2.46 (s, 3H), 3.84 (s, 3H), 3.98 (s, 3H), 6.48 (d, J=5.1 Hz, 1H), 7.07 (s, 1H), 7.16 (d, J=8.3 Hz, 1H), 7.28 (d, J=8.8 Hz, 2H), 7.30 (s, 1H), 7.41 (m, 1H), 7.43 (s, 1H), 7.64 (d, J=8.6 Hz, 2H), 8.43 (d, J=4.9 Hz, 1H)

Mass spectrometric value (ESI-MS, m/z): 456 (M+1)⁺

Compound 74: {2-[(6,7-Dimethoxy-4-quinolyl)oxy]-5-methoxyphenyl}-(phenyl)methanone A mixture of 4-chloro-6,7-dimethoxyquinoline (93 mg) with 2-hydroxy-5-methoxybenzophenone (462 mg) was stirred at 180° C. for 9 hr. The reaction solution was cooled to room temperature and was purified by column chromatography on silica gel using acetone-hexane to give the title compound (14 mg, yield 8%).

¹H-NMR (CDCl₃, 500 MHz): δ 3.87 (s, 3H), 3.89 (s, 3H), 4.00 (s, 3H), 6.42 (d, J=5.5 Hz, 1H), 6.76 (d, J=2.4 Hz, 1H), 6.92 (s, 1H), 6.96 (dd, J=2.4 Hz, 8.6 Hz, 1H), 7.26-7.29 (m, 3H), 7.31 (s, 1H), 7.41 (t, J=7.3 Hz, 1H), 7.63 (d, J=6.7 Hz, 1H), 7.69 (d, J=8.6 Hz, 1H), 8.43 (d, J=5.5 Hz, 1H)

Mass spectrometric value (FD-MS, m/z): 415 (M⁺)

Compound 75: {5-Chloro-2-[(6,7-dimethoxy-4-quinolyl)oxy]-4-methylphenyl}(phenyl)methanone 4-Chloro-6,7-dimethoxyquinoline (100 mg), 5-chloro-2-hydroxy-4-methylbenzophenone (443 mg), and 4-dimethylaminopyridine (220 mg) were suspended in o-dichlorobenzene (1 ml), and the mixture was stirred at 140° C. for 7 hr. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (175 mg, yield 90%).

¹H-NMR (CDCl₃, 400 MHz): δ 2.48 (s, 3H), 3.84 (s, 3H), 4.00 (s, 3H), 6.43 (d, J=5.4 Hz, 1H), 6.91 (s, 1H), 7.14 (s, 1H), 7.32 (m, 3H), 7.46 (m, 1H), 7.67 (m, 3H), 7.44 (d, J=5.4 Hz, 1H)

Mass spectrometric value (ESI-MS, m/z): 434 (M+1)⁺

Compound 76: {2-[(6,7-Dimethoxy-4-quinolyl)oxy]-4,5-dimethylphenyl}-(phenyl)methanone hydrochloride Commercially available 3,4-dimethylanisole (409 mg) was dissolved in nitromethane (6 ml) to prepare a solution. Lithium perchlorate (1.9 g) and benzoyl chloride (843 mg) were added to the solution, scandium trifluoromethanesulfonate (148 mg) was then added thereto, and the mixture was stirred at room temperature for 3 days. A saturated aqueous sodium hydrogencarbonate solution was added to the reaction solution, and the mixture was extracted with chloroform. The organic layer was washed with saturated brine, was dried over sodium sulfate and was concentrated. The residue was subjected to separation and purification by column chromatography on silica gel using hexane/ethyl acetate as a solvent to give (4,5-dimethyl-2-methoxyphenyl)(phenyl) methanone (667 mg, yield 93%).

(4,5-Dimethyl-2-methoxyphenyl)(phenyl)methanone (650 mg) was dissolved in dimethylformamide (10 ml) to prepare a solution. Sodium thiomethoxide (379 mg) was added to the solution, and the mixture was stirred while heating under reflux overnight. The reaction solution was cooled to room temperature, water was added thereto, and the mixture was extracted with ethyl acetate. The organic layer was washed with saturated brine, was dried over sodium sulfate and was concentrated. The residue was subjected to separation and purification by column chromatography on silica gel using hexane/ethyl acetate as a solvent to give (4,5-dimethyl-2-hydroxy-phenyl)(phenyl)methanone. The (4,5-dimethyl-2-hydroxy-phenyl)(phenyl)methanone (40 mg) thus obtained and 4-chloro-6,7-dimethoxyquinoline (150 mg) were added to o-dichlorobenzene (0.2 ml), and the mixture was heated at 180° C. for two days. The reaction solution was concentrated and was subjected to separation and purification by column chromatography on silica gel using hexane-ethyl acetate. Subsequently, a hydrochloric acid-methanol mixed solution was added thereto, the solvent was removed by distillation, and the residue was suspended in ethyl acetate. The solid thus obtained was collected by filtration, was washed with ethyl acetate, and was then dried to give the title compound (9.2 mg, yield 11%).

¹H-NMR (CDCl₃, 400 MHz): δ 2.40 (s, 3H), 2.43 (s, 3H), 3.93 (s, 3H), 4.12 (s, 3H), 6.65 (d, J=6.6 Hz, 1H), 7.11 (s, 1H), 7.13 (s, 1H), 7.36 (dd, J=7.6 Hz, 7.6 Hz, 2H), 7.49 (s, 1H), 7.51 (dd, J=7.3 Hz, 7.3 Hz, 1H), 7.66 (d, J=7.1 Hz, 2H), 8.06 (s, 1H), 8.42 (dd, J=6.6 Hz, 6.6 Hz, 1H)

Mass spectrometric value (ESI-MS, m/z): 414 (M-HCl+1)⁺

Compound 77: {3-[(6,7-Dimethoxy-4-quinolyl)oxy] phenyl}(phenyl)-methanone

4-Chloro-6,7-dimethoxyquinoline (112 mg) and 3-hydroxybenzophenone (297 mg) were mixed together, and the mixture was heated at 170° C. for 10 min. A saturated aqueous sodium hydrogencarbonate solution was added thereto, and the mixture was extracted with ethyl acetate. The organic layer was washed with saturated brine, was dried over sodium sulfate, and was then concentrated. The residue was subjected to separation and purification by column chromatography on silica gel using hexane-acetone as a solvent to give the title compound (126 mg, yield 65%).

¹H-NMR (CDCl₃, 400 MHz): δ 4.05 (s, 3H), 4.07 (s, 3H), 6.53 (d, J=5.4 Hz, 1H), 7.42-7.65 (m, 8H), 7.72 (dd, J=1.5 Hz, 6.3 Hz, 1H), 7.83 (dd, J=1.2 Hz, 8.3 Hz, 2H), 8.53 (d, J=5.1 Hz, 1H)

Mass spectrometric value (FD-MS, m/z): 385 (M+)

Compound 78: Synthesis of {4-[(6,7-dimethoxy-4-quinolyl)oxy]phenyl}(3-methylphenyl)methanone Commercially available anisole (541 mg) and 3-methylbenzoyl chloride (773 mg) were dissolved in nitromethane (5 ml) to prepare a solution. Scandium trifluoromethanesulfonate (49 mg) was added to the solution, and the mixture was stirred at 60° C. overnight. A saturated aqueous sodium hydrogencarbonate solution was added thereto, and the mixture was extracted with chloroform. The organic layer was washed with saturated brine, was dried over sodium sulfate, and was then concentrated. The residue was subjected to separation and purification by column chromatography on silica gel using hexane-acetone as a solvent to give (4-methoxyphenyl)(3-methylphenyl)methanone (633 mg, yield 56%).

(4-Methoxyphenyl)(3-methylphenyl)methanone (603 mg) was dissolved in dichloromethane (3 ml) to prepare a solution. A boron tribromide-dichloromethane solution (1.0 M) (11 ml) was added to the solution, and the mixture was stirred at room temperature for 2 days. The reaction solution was poured into ice-cooled water, and the mixture was extracted with chloroform. The organic layer was washed with saturated brine, was dried over sodium sulfate, and was then concentrated. The residue was subjected to separation and purification by column chromatography on silica gel using hexane/ethyl acetate as a solvent to give (4-hydroxyphenyl) (3-methylphenyl)methanone (1.50 g, yield 56%).

(4-Hydroxyphenyl)(3-methylphenyl)methanone (307 mg) was dissolved in xylene to prepare a solution. 4-Dimethylaminopyridine (194 mg) and 4-chloro-6,7-dimethoxyquinoline (342 mg) were added to the solution, and the mixture was heated under reflux for 23 hr. A saturated aqueous sodium hydrogencarbonate solution was added thereto, and the mixture was extracted with chloroform. The organic layer was dried over sodium sulfate and was then concentrated. The residue was subjected to separation and purification by column chromatography on silica gel using hexane-ethyl acetate, chloroform, and hexane-acetone as solvents to give the title compound (262 mg, yield 45%).

$^1$H-NMR (CDCl$_3$, 400 MHz): δ 2.44 (s, 3H), 4.03 (s, 3H), 4.06 (s, 3H), 6.66 (d, J=4.9 Hz, 1H), 7.27 (d, J=8.6 Hz, 2H), 7.38 (t, J=7.3 Hz, 1H), 7.41 (d, J=7.3 Hz, 1H), 7.46 (s, 1H), 7.49 (s, 1H), 7.59 (d, J=7.3 Hz, 1H), 7.64 (s, 1H), 7.93 (d, J=8.6 Hz, 2H), 8.57 (d, J=5.5 Hz, 1H)

Mass spectrometric value (FD-MS, m/z): 399 (M$^+$)

Compound 79: Methyl 3-[(6,7-dimethoxy-4-quinolyl)oxy]naphthalene-2-carboxylate

4-Chloro-6,7-dimethoxyquinoline (100 mg), methyl 2-hydroxy-3-naphthoate (271 mg), and 4-dimethylaminopyridine (164 mg) were suspended in o-dichlorobenzene (6 ml), and the suspension was stirred at 150° C. for 2 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-chloroform to give the title compound (7 mg, yield 4%).

$^1$H-NMR (CDCl$_3$, 400 MHz): δ 3.57 (s, 3H), 4.01 (s, 6H), 6.28 (d, J=5.4 Hz, 1H), 7.46-7.61 (m, 5H), 7.77 (d, J=8.0 Hz, 1H), 7.93 (d, J=8.0 Hz, 1H), 8.37 (d, J=5.4 Hz, 1H), 8.59 (s, 1H)

Mass spectrometric value (ESI-MS, m/z): 390 (M+1)$^+$

Compound 80: Ethyl 2-[(6,7-dimethoxy-4-quinolyl)oxy]benzoate

4-Chloro-6,7-dimethoxyquinoline (100 mg), ethyl salicylate (336 mg), and 4-dimethylaminopyridine (244 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (100 mg, yield 56%).

$^1$H-NMR (CDCl$_3$, 400 MHz): δ 0.87 (t, 3H), 4.06 (m, 8H), 6.28 (d, J=5.4 Hz, 1H), 7.23-7.42 (m, 3H), 7.64 (m, 2H), 8.07 (dd, J=7.8 Hz, 1.7 Hz, 1H), 8.45 (d, J=5.4 Hz, 1H)

Mass spectrometric value (ESI-MS, m/z): 354 (M+1)$^+$

Compound 81: Ethyl 4-chloro-2-[(6,7-dimethoxy-4-quinolyl)oxy]benzoate

4-Chlorosalicylic acid (344 mg), 1-ethyl-3-(3-dimethylaminopropylcarbodiimide hydrochloride (420 mg), 1-hydroxybenzotriazole hydrate (337 mg), and ethanol (2 ml) were dissolved in N,N-dimethylformamide to prepare a solution which was then stirred at room temperature overnight. Water was added to the reaction solution, and the mixture was extracted with ethyl acetate. The ethyl acetate layer was then washed with water and was dried over anhydrous sodium sulfate. The solvent was removed therefrom by distillation under the reduced pressure, and the residue was purified by column chromatography using acetone-hexane to give ethyl 4-chlorosalicylate (174 mg, yield 43%).

Ethyl 4-chlorosalicylate (174 mg), 4-chloro-6,7-dimethoxyquinoline (195 mg), and 4-dimethylaminopyridine (320 mg) were suspended in o-dichlorobenzene (1 ml), and the suspension was stirred at 120° C. overnight. The reaction solution was cooled to room temperature, and the solvent was removed therefrom by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (26 mg, yield 8%).

$^1$H-NMR (CDCl$_3$, 400 MHz): δ 0.88 (t, J=7.1 Hz, 3H), 4.06 (m, 8H), 6.31 (d, J=5.1 Hz, 1H), 7.26 (d, J=2.0 Hz, 1H), 7.37 (dd, J=8.4 Hz, 2.0 Hz, 1H), 7.43 (s, 1H), 7.56 (s, 1H), 8.02 (d, J=8.4 Hz, 1H), 8.48 (d, J=5.1 Hz, 1H)

Mass spectrometric value (ESI-MS, m/z): 388 (M+1)$^+$

Compound 82: Ethyl 2-[(6,7-dimethoxy-4-quinolyl)oxy]-4-methyl benzoate

4-Methylsalicylic acid (304 mg), 1-ethyl-3-(3-dimethylaminopropylcarbodiimide hydrochloride (420 mg), 1-hydroxybenzotriazole hydrate (337 mg), and ethanol (2 ml) were dissolved in N,N-dimethylformamide to prepare a solution which was then stirred at room temperature overnight. Water was added to the reaction solution, and the mixture was extracted with ethyl acetate. The ethyl acetate layer was then washed with water and was dried over anhydrous sodium sulfate. The solvent was removed therefrom by distillation under the reduced pressure, and the residue was purified by column chromatography using acetone-hexane to give ethyl 4-methylsalicylate (175 mg, yield 49%).

Ethyl 4-methylsalicylate (175 mg), 4-chloro-6,7-dimethoxyquinoline (216 mg), and 4-dimethylaminopyridine (355 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (28 mg, yield 9%).

$^1$H-NMR (CDCl$_3$, 400 MHz): δ 0.84 (t, J=7.1 Hz, 3H), 2.44 (s, 3H), 4.04 (m, 8H), 6.27 (d, J=5.4 Hz, 1H), 7.05 (s, 1H), 7.19 (d, J=7.9 Hz, 1H), 7.42 (s, 1H), 7.61 (s, 1H), 7.98 (d, J=7.9 Hz, 1H), 8.45 (d, J=5.4 Hz, 1H)

Mass spectrometric value (ESI-MS, m/z): 368 (M+1)$^+$

Compound 83: Ethyl 2-[(6,7-dimethoxy-4-quinolyl)oxy]-5-fluorobenzoate

5-Fluoro-2-hydroxybenzoic acid (344 mg), 1-ethyl-3-(3-dimethylaminopropylcarbodiimide hydrochloride (420 mg), 1-hydroxybenzotriazole hydrate (337 mg), and ethanol (2 ml) were dissolved in N,N-dimethylformamide to prepare a solution which was then stirred at room temperature overnight. Water was added to the reaction solution, and the mixture was extracted with ethyl acetate. The ethyl acetate layer was then washed with water and was dried over anhydrous sodium sulfate. The solvent was removed therefrom by distillation under the reduced pressure, and the residue was purified by column chromatography using acetone-hexane to give ethyl 5-fluorosalicylate (191 mg, yield 28%).

Ethyl 5-fluorosalicylate (191 mg), 4-chloro-6,7-dimethoxyquinoline (125 mg), and 4-dimethylaminopyridine (205 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (64 mg, yield 22%).

$^1$H-NMR (CDCl$_3$, 400 MHz): δ 0.87 (t, J=7.1 Hz, 3H), 4.07 (m, 8H), 6.24 (d, J=5.3 Hz, 1H), 7.22-7.37 (m, 2H), 7.42 (s, 1H), 7.60 (s, 1H), 7.77 (dd, J=5.8 Hz, 3.2 Hz, 1H), 8.46 (d, J=5.3 Hz, 1H)

Mass spectrometric value (ESI-MS, m/z): 372 (M+1)$^+$

Compound 84: Ethyl 5-chloro-2-[(6,7-dimethoxy-4-quinolyl)oxy]benzoate

5-Chlorosalicylic acid (344 mg), 1-ethyl-3-(3-dimethylaminopropylcarbodiimide hydrochloride (420 mg), 1-hydroxybenzotriazole hydrate (337 mg), and ethanol (2 ml) were dissolved in N,N-dimethylformamide to prepare a solution which was then stirred at room temperature overnight. Water was added to the reaction solution, and the mixture was extracted with ethyl acetate. The ethyl acetate layer was then washed with water and was dried over anhydrous sodium sulfate. The solvent was removed therefrom by distillation under the reduced pressure, and the residue was purified by column chromatography using acetone-hexane to give ethyl 5-chlorosalicylate (147 mg, yield 37%).

Ethyl 5-chlorosalicylate (147 mg), 4-chloro-6,7-dimethoxyquinoline (165 mg), and 4-dimethylaminopyridine (270 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (41 mg, yield 15%).

$^1$H-NMR (CDCl$_3$, 400 MHz): δ 0.90 (t, J=7.1 Hz, 3H), 4.08 (m, 8H), 6.28 (d, J=5.8 Hz, 1H), 7.19 (d, J=8.6 Hz, 1H), 7.42 (s, 1H), 7.59 (m, 2H), 8.04 (d, J=2.4 Hz, 1H), 8.46 (d, J=5.3 Hz, 1H)

Mass spectrometric value (ESI-MS, m/z): 388 (M+1)$^+$

Compound 85: Ethyl 5-bromo-2-[(6,7-dimethoxy-4-quinolyl)oxy]benzoate

5-Bromosalicylic acid (434 mg), 1-ethyl-3-(3-dimethylaminopropylcarbodiimide hydrochloride (420 mg), 1-hydroxybenzotriazole hydrate (337 mg), and ethanol (2 ml) were dissolved in N,N-dimethylformamide to prepare a solution which was then stirred at room temperature overnight. Water was added to the reaction solution, and the mixture was extracted with ethyl acetate. The ethyl acetate layer was then washed with water and was dried over anhydrous sodium sulfate. The solvent was removed therefrom by distillation under the reduced pressure, and the residue was purified by column chromatography using acetone-hexane to give ethyl 5-bromosalicylate (299 mg, yield 61%).

Ethyl 5-bromosalicylate (299 mg), 4-chloro-6,7-dimethoxyquinoline (270 mg), and 4-dimethylaminopyridine (440 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (40 mg, yield 8%).

$^1$H-NMR (CDCl$_3$, 400 MHz): δ 0.91 (t, J=7.1 Hz, 3H), 4.07 (m, 8H), 6.28 (d, J=5.3 Hz, 1H), 7.13 (d, J=8.8 Hz, 1H), 7.43 (s, 1H), 7.57 (s, 1H), 7.73 (dd, J=8.8 Hz, 2.4 Hz, 1H), 8.19 (d, J=2.4 Hz, 1H), 8.47 (d, J=5.3 Hz, 1H)

Mass spectrometric value (ESI-MS, m/z): 432 (M+1)$^+$

Compound 86: Ethyl 2-[(6,7-dimethoxy-4-quinolyl)oxy]-5-iodobenzoate

5-Iodosalicylic acid (528 mg), 1-ethyl-3-(3-dimethylaminopropylcarbodiimide hydrochloride (420 mg), 1-hydroxybenzotriazole hydrate (337 mg), and ethanol (2 ml) were dissolved in N,N-dimethylformamide to prepare a solution which was then stirred at room temperature overnight. Water was added to the reaction solution, and the mixture was extracted with ethyl acetate. The ethyl acetate layer was then washed with water and was dried over anhydrous sodium sulfate. The solvent was removed therefrom by distillation under the reduced pressure, and the residue was purified by column chromatography using acetone-hexane to give ethyl 5-iodosalicylate (457 mg, yield 78%).

Ethyl 5-iodosalicylate (457 mg), 4-chloro-6,7-dimethoxyquinoline (348 mg), and 4-dimethylaminopyridine (573 mg) were suspended in o-dichlorobenzene (1 ml), and the suspension was stirred at 120° C. overnight. The reaction solution was cooled to room temperature, and the solvent was removed by distillation under the reduced pressure. Water was then added to the reaction solution, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (31 mg, yield 4%).

$^1$H-NMR (CDCl$_3$, 400 MHz): δ 0.90 (t, J=7.1 Hz, 3H), 4.07 (m, 8H), 6.29 (d, J=5.3 Hz, 1H), 7.00 (d, J=8.6 Hz, 1H), 7.42

(s, 1H), 7.56 (s, 1H), 7.91 (dd, J=8.6 Hz, 2.3 Hz, 1H), 8.36 (d, J=2.3 Hz, 1H), 8.46 (d, J=5.3 Hz, 1H)

Mass spectrometric value (ESI-MS, m/z): 480 (M+1)$^+$

Compound 87: Ethyl 2-[(6,7-dimethoxy-4-quinolyl)oxy]-5-methylbenzoate

4-Chloro-6,7-dimethoxyquinoline (113 mg), ethyl 5-methylsalicylate (632 mg), and 4-dimethylaminopyridine (435 mg) were suspended in o-dichlorobenzene (5 ml), and the suspension was stirred at 160° C. overnight. The reaction solution was cooled to room temperature, and the solvent was then removed therefrom by distillation under the reduced pressure. Chloroform was added to the residue, and the mixture was washed with a 1 N aqueous sodium hydroxide solution and saturated brine and was dried over anhydrous magnesium sulfate. The solvent was removed therefrom by distillation under the reduced pressure, and the residue was purified by column chromatography using chloroform and by thin layer chromatography using acetone-hexane to give the title compound (64.1 mg, yield 35%).

$^1$H-NMR (CDCl$_3$, 400 MHz): δ 0.84 (t, J=7.1 Hz, 3H), 2.45 (s, 3H), 4.04 (m, 2H), 4.05 (s, 3H), 4.06 (s, 3H), 6.26 (d, J=5.4 Hz, 1H), 7.14 (d, J=8.3 Hz, 1H), 7.42 (s, 1H), 7.41-7.44 (m, 1H), 7.63 (s, 1H), 7.87 (d, J=1.4 Hz, 1H), 8.44 (d, J=5.4 Hz, 1H)

Mass spectrometric value (ESI-MS, m/z): 368 (M+1)$^+$

Compound 88: Ethyl 5-acetyl-2-[(6,7-dimethoxy-4-quinolyl)oxy]benzoate

5-Acetylsalicylic acid (200 mg), 1-ethyl-3-(3-dimethylaminopropylcarbodiimide hydrochloride (382 mg), 1-hydroxybenzotriazole hydrate (306 mg), and ethanol (2 ml) were dissolved in N,N-dimethylformamide to prepare a solution which was then stirred at room temperature overnight. Water was added to the reaction solution, and the mixture was extracted with ethyl acetate. The ethyl acetate layer was then washed with water and was dried over anhydrous sodium sulfate. The solvent was removed therefrom by distillation under the reduced pressure, and the residue was purified by column chromatography using acetone-hexane to give ethyl 5-acetylsalicylate (211 mg, yield 92%).

Ethyl 5-acetylsalicylate (211 mg), 4-chloro-6,7-dimethoxyquinoline (111 mg), and 4-dimethylaminopyridine (183 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (19 mg, yield 5%).

$^1$H-NMR (CDCl$_3$, 400 MHz): δ 0.97 (t, J=7.1 Hz, 3H), 2.68 (s, 3H), 4.04 (s, 3H), 4.06 (s, 3H), 4.14 (q, J=7.1 Hz, 2H), 6.37 (d, J=5.2 Hz, 1H), 7.28 (d, J=8.5 Hz, 1H), 7.44 (s, 1H), 7.55 (s, 1H), 8.20 (dd, J=8.5 Hz, 2.2 Hz, 1H), 8.50 (d, J=5.2 Hz, 1H), 8.62 (d, J=2.2 Hz, 1H)

Mass spectrometric value (ESI-MS, m/z): 396 (M+1)$^+$

Compound 89: Ethyl 2-[(6,7-dimethoxy-4-quinolyl)oxy]-5-(2,4-difluorophenyl)benzoate Diflunisal (250 mg), 1-ethyl-3-(3-dimethylaminopropyl-carbodiimide hydrochloride (382 mg), 1-hydroxybenzotriazole hydrate (306 mg), and ethanol (2 ml) were dissolved in N,N-dimethylformamide to prepare a solution which was then stirred at room temperature overnight. Water was added to the reaction solution, and the mixture was extracted with ethyl acetate. The ethyl acetate layer was then washed with water and was dried over anhydrous sodium sulfate. The solvent was removed therefrom by distillation under the reduced pressure, and the residue was purified by column chromatography using acetone-hexane to give ethyl 5-(2,4-difluorophenyl)salicylate (188 mg, yield 34%).

Ethyl 5-(2,4-difluorophenyl)salicylate (188 mg), 4-chloro-6,7-dimethoxyquinoline (57 mg), and 4-dimethylaminopyridine (93 mg) were suspended in o-dichlorobenzene (1 ml), and the suspension was stirred at 120° C. overnight. The reaction solution was cooled to room temperature, and the solvent was removed by distillation under the reduced pressure. Water was then added to the reaction solution, and the mixture was extracted with chloroform. The chloroform layer was washed with water and was dried over anhydrous sodium sulfate. The solvent was removed therefrom by distillation under the reduced pressure. The residue was purified by column chromatography using acetone-hexane to give the title compound (13 mg, yield 24%).

$^1$H-NMR (CDCl$_3$, 400 MHz): δ 0.89 (t, J=7.3 Hz, 3H), 4.09 (m, 8H), 6.38 (d, J=5.3 Hz, 1H), 6.99 (m, 2H), 7.31 (d, J=8.6 Hz, 1H), 7.44-7.51 (m, 2H), 7.62 (s, 1H), 7.77 (m, 1H), 8.18 (m, 1H), 8.49 (d, J=5.3 Hz, 1H)

Mass spectrometric value (ESI-MS, m/z): 466 (M+1)$^+$

Compound 90: Ethyl 2-[(6,7-dimethoxy-4-quinolyl)oxy]-5-(pyrrol-1-yl)benzoate

2-Hydroxy-5-(pyrrol-1-yl)benzoic acid (406 mg), 1-ethyl-3-(3-dimethylaminopropylcarbodiimide hydrochloride (420 mg), 1-hydroxybenzotriazole hydrate (337 mg), and ethanol (2 ml) were dissolved in N,N-dimethylformamide to prepare a solution which was then stirred at room temperature overnight. Water was added to the reaction solution, and the mixture was extracted with ethyl acetate. The ethyl acetate layer was then washed with water and was dried over anhydrous sodium sulfate. The solvent was removed therefrom by distillation under the reduced pressure, and the residue was purified by column chromatography using acetone-hexane to give ethyl 5-(pyrrol-1-yl)salicylate (170 mg, yield 20%).

Ethyl 5-(pyrrol-1-yl)salicylate (170 mg), 4-chloro-6,7-dimethoxyquinoline (87 mg), and 4-dimethylaminopyridine (143 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (36 mg, yield 15%).

$^1$H-NMR (CDCl$_3$, 400 MHz): δ 0.87 (t, J=7.3 Hz, 3H), 4.09 (m, 8H), 6.32 (d, J=5.4 Hz, 1H), 6.4 (t, J=2.2 Hz, 2H), 7.15 (t, J=2.2 Hz, 2H), 7.31 (d, J=8.7 Hz, 1H), 7.43 (s, 1H), 7.61 (s, 1H), 7.64 (dd, J=8.7 Hz, 3.0 Hz, 1H), 8.09 (d, J=3.0 Hz, 1H), 8.47 (d, J=5.4 Hz, 1H)

Mass spectrometric value (ESI-MS, m/z): 419 (M+1)$^+$

Compound 91: Ethyl 2-[(6,7-dimethoxy-4-quinolyl)oxy]-5-methoxybenzoate

5-Methoxysalicylic acid (2.00 g) was suspended in ethanol (28 ml), and thionyl chloride (2.11 g) was gradually added dropwise to the suspension. Thereafter, the mixture was heated under reflux for 2 hr. The solvent was removed therefrom by distillation under the reduced pressure. Water was added to the residue, and the mixture was neutralized with a 20% aqueous sodium hydroxide solution and was then extracted with chloroform. The chloroform layer was then washed with water and saturated brine and was dried over anhydrous sodium sulfate. The solvent was removed therefrom by distillation under the reduced pressure, and the residue was purified by column chromatography using acetone-hexane to give ethyl 5-methoxysalicylic acid (1.37 g, yield 58%).

4-Chloro-6,7-dimethoxyquinoline (514 mg), ethyl 5-methoxysalicylic acid (1.35 g), and 4-dimethylaminopyridine (843 mg) were suspended in o-dichlorobenzene (8 ml), and the suspension was stirred at 180° C. for 4 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-hexane to give the title compound (152 mg, yield 170%).

$^1$H-NMR (CDCl$_3$, 400 MHz): δ 0.73 (t, J=7.2 Hz, 3H), 3.82 (s, 3H), 3.94-3.98 (m, 8H), 6.17 (d, J=5.2 Hz, 1H), 7.10 (m, 2H), 7.38 (s, 1H), 7.49 (s, 1H), 7.54 (s, 1H), 8.36 (d, J=5.2 Hz, 1H)

Mass spectrometric value (ESI-MS, m/z): 384 (M+1)$^+$

Compound 92: Ethyl 2-[(6,7-dimethoxy-4-quinolyl)oxy]-6-methylbenzoate

4-Chloro-6,7-dimethoxyquinoline (112 mg), ethyl 6-methylsalicylate (360 mg), and 4-dimethylaminopyridine (244 mg) were suspended in o-dichlorobenzene (1 ml), and the suspension was stirred at 120° C. overnight and was further stirred at 140° C. for 2 hr. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (168 mg, yield 91%).

$^1$H-NMR (CDCl$_3$, 400 MHz): δ 0.96 (t, J=7.1 Hz, 3H), 2.44 (s, 3H), 4.03 (s, 3H), 4.05 (s, 3H), 4.10 (q, J=7.1 Hz, 2H), 6.50 (d, J=5.2 Hz, 1H), 6.99 (d, J=7.9 Hz, 1H), 7.15 (d, J=7.9 Hz, 1H), 7.37 (t, J=7.9 Hz, 1H), 7.42 (s, 1H), 7.52 (s, 1H), 8.50 (d, J=5.2 Hz, 1H)

Mass spectrometric value (ESI-MS, m/z): 368 (M+1)$^+$

Compound 93: Isopropyl 2-[(6,7-dimethoxy-4-quinolyl)oxy]benzoate

4-Chloro-6,7-dimethoxyquinoline (112 mg), isopropyl salicylate (360 mg), and 4-dimethylaminopyridine (244 mg) were suspended in o-dichlorobenzene (1 ml), and the suspension was stirred at 120° C. overnight. The reaction solution was cooled to room temperature, and the solvent was removed under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (38 mg, yield 21%).

$^1$H-NMR (CDCl$_3$, 400 MHz): δ 0.84 (m, 6H), 4.06 (m, 6H), 5.00 (m, 1H), 6.25 (d, J=5.4 Hz, 1H), 7.27 (m, 1H), 7.41 (m, 2H), 7.64 (m, 2H), 8.07 (m, 1H), 8.44 (d, J=5.4 Hz, 1H)

Mass spectrometric value (ESI-MS, m/z): 368 (M+1)$^+$

Compound 94: Propyl 2-[(6,7-dimethoxy-4-quinolyl)oxy]benzoate

4-Chloro-6,7-dimethoxyquinoline (112 mg), n-propyl salicylate (360 mg), and 4-dimethylaminopyridine (244 mg) were suspended in o-dichlorobenzene (1 ml), and the suspension was stirred at 120° C. overnight and at 140° C. for 2 hr. The reaction solution was cooled to room temperature, and the solvent was removed by distillation under the reduced pressure. Water was then added to the reaction solution, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (104 mg, yield 57%).

$^1$H-NMR (CDCl$_3$, 400 MHz): δ 0.67 (t, J=7.6 Hz, 3H), 1.30 (m, 2H), 4.00 (t, J=6.6 Hz, 2H), 4.05 (s, 3H), 4.06 (s, 3H), 6.29 (d, J=5.1 Hz, 1H), 7.23 (dd, J=8.3 Hz, 1.0 Hz, 1H), 7.39 (td, J=7.8 Hz, 1.0 Hz, 1H), 7.42 (s, 1H), 7.63 (m, 2H), 8.08 (dd, J=7.8 Hz, 1.7 Hz, 1H), 8.46 (d, J=5.1 Hz, 1H)

Mass spectrometric value (ESI-MS, m/z): 368 (M+1)$^+$

Compound 95: Propyl 2-[(6,7-dimethoxy-4-quinolyl)oxy]-5-acetylbenzoate

5-Acetylsalicylic acid (360 mg), 1-ethyl-3-(3-dimethylaminopropylcarbodiimide hydrochloride (458 mg), 1-hydroxybenzotriazole hydrate (36.7 mg), and propanol (2 ml) were dissolved in N,N-dimethylformamide to prepare a solution which was then stirred at room temperature overnight. Water was added to the reaction solution, and the mixture was extracted with ethyl acetate. The ethyl acetate layer was then washed with water and was dried over anhydrous sodium sulfate. The solvent was removed therefrom by distillation under the reduced pressure, and the residue was purified by column chromatography using acetone-hexane to give propyl 5-acetylsalicylate (202 mg, yield 45%).

Propyl 5-acetylsalicylate (202 mg), 4-chloro-6,7-dimethoxyquinoline (101 mg), and 4-dimethylaminopyridine (164 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure. The residue was purified by column chromatography using acetone-hexane to give the title compound (35 mg, yield 9%).

$^1$H-NMR (CDCl$_3$, 400 MHz): δ 0.73 (t, J=7.3 Hz, 3H), 1.39 (m, 2H), 2.68 (s, 3H), 4.07 (m, 8H), 6.39 (d, J=5.4 Hz, 1H), 7.26 (d, J=8.5 Hz, 1H), 7.44 (s, 1H), 7.54 (s, 1H), 8.19 (dd, J=8.5 Hz, 2.3 Hz, 1H), 8.50 (d, J=5.4 Hz, 1H), 8.62 (d, J=2.3 Hz, 1H)

Mass spectrometric value (ESI-MS, m/z): 410 (M+1)$^+$

Compound 96: Propyl 2-[(6,7-dimethoxy-4-quinolyl)oxy]-5-(2,4-difluorophenyl)benzoate Diflunisal (500 mg), 1-ethyl-3-(3-dimethylaminopropyl-carbodiimide hydrochloride (458 mg), 1-hydroxybenzotriazole hydrate (36.7 mg), and propanol (2 ml) were dissolved in N,N-dimethylformamide to prepare a solution which was then stirred at room temperature overnight. Water was added to the reaction solution, and the mixture was extracted with ethyl acetate. The ethyl acetate layer was then washed with water and was dried over anhydrous sodium sulfate. The solvent was removed therefrom by distillation under the reduced pressure, and the residue was purified by column chromatography using acetone-hexane to give propyl 5-(2,4-difluorophenyl)salicylate (179 mg, yield 30%).

Propyl 5-(2,4-difluorophenyl)salicylate (179 mg), 4-chloro-6,7-dimethoxyquinoline (70 mg), and 4-dimethylaminopyridine (110 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (30 mg, yield 10%).

$^1$H-NMR (CDCl$_3$, 400 MHz): δ 0.67 (t, J=7.3 Hz, 3H), 1.31 (m, 2H), 4.04 (m, 8H), 6.40 (d, J=5.2 Hz, 1H), 6.99 (m, 2H), 7.30 (d, J=8.3 Hz, 1H), 7.47 (m, 2H), 7.61 (s, 1H), 7.76 (m, 1H), 8.19 (m, 1H), 8.49 (d, J=5.2 Hz, 1H)

Mass spectrometric value (ESI-MS, m/z): 480 (M+1)$^+$

Compound 97: Isobutyl 2-[(6,7-dimethoxy-4-quinolyl)oxy]benzoate

4-Chloro-6,7-dimethoxyquinoline (100 mg), isobutyl salicylate (388 mg), and 4-dimethylaminopyridine (244 mg) were suspended in o-dichlorobenzene (1 ml), and the suspension was stirred at 120° C. overnight and at 140° C. for 3 hr. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (47 mg, yield 25%).

$^1$H-NMR (CDCl$_3$, 400 MHz): δ 0.67 (m, 6H), 1.59 (m, 1H), 3.83 (m, 2H), 4.02 (m, 6H), 6.28 (m, 1H), 7.14-7.64 (m, 5H), 8.05 (m, 1H), 8.43 (m, 1H)

Mass spectrometric value (ESI-MS, m/z): 382 (M+1)$^+$

Compound 98: Butyl 2-[(6,7-dimethoxy-4-quinolyl)oxy]benzoate

4-Chloro-6,7-dimethoxyquinoline (100 mg), butyl salicylate (388 mg), and 4-dimethylaminopyridine (244 mg) were suspended in o-dichlorobenzene (1 ml), and the suspension was stirred at 120° C. overnight and at 140° C. for 3 hr. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (106 mg, yield 57%).

$^1$H-NMR (CDCl$_3$, 400 MHz): δ 0.66 (t, J=7.3 Hz, 3H), 1.06 (m, 2H), 1.24 (m, 2H), 4.03 (m, 8H), 6.28 (d, J=5.3 Hz, 1H), 7.23 (d, J=8.0 Hz, 1H), 7.37-7.43 (m, 2H), 7.63 (m, 2H), 8.07 (dd, J=7.8 Hz, 1.4 Hz, 1H), 8.45 (d, J=5.3 Hz, 1H)

Mass spectrometric value (ESI-MS, m/z): 382 (M+1)$^+$

Compound 99: Isoamyl 2-[(6,7-dimethoxy-4-quinolyl)oxy]benzoate

4-Chloro-6,7-dimethoxyquinoline (100 mg), isoamyl salicylate (416 mg), and 4-dimethylaminopyridine (244 mg) were suspended in o-dichlorobenzene (1 ml), and the suspension was stirred at 120° C. overnight and at 140° C. for 3 hr. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (110 mg, yield 56%).

$^1$H-NMR (CDCl$_3$, 400 MHz): δ 0.67 (m, 6H), 1.13 (m, 2H), 1.34 (m, 1H), 4.06 (m, 8H), 6.29 (d, J=5.2 Hz, 1H), 7.23 (m, 1H), 7.40 (m, 2H), 7.62 (m, 2H), 8.07 (m, 1H), 8.46 (d, J=5.2 Hz, 1H)

Mass spectrometric value (ESI-MS, m/z): 396 (M+1)$^+$

Compound 100: (Z)-3-Hexenyl 2-[(6,7-dimethoxy-4-quinolyl)oxy]benzoate

4-Chloro-6,7-dimethoxyquinoline (112 mg), (Z)-3-hexenyl salicylate (440 mg), and 4-dimethylaminopyridine (244 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (130 mg, yield 64%).

$^1$H-NMR (CDCl$_3$, 400 MHz): δ 0.86 (t, J=7.6 Hz, 3H), 1.82 (m, 2H), 2.00 (m, 2H), 4.00 (t, J=7.1 Hz, 2H), 4.05 (s, 3H), 4.06 (s, 3H), 5.03 (m, 1H), 5.30 (m, 1H), 6.28 (d, J=5.1 Hz, 1H), 7.23 (m, 1H), 7.40 (m, 2H), 7.63 (m, 2H), 8.07 (dd, J=7.8 Hz, 1.7 Hz, 1H), 8.45 (d, J=5.1 Hz, 1H)

Mass spectrometric value (ESI-MS, m/z): 408 (M+1)$^+$

Compound 101: 2-Ethylhexyl 2-[(6,7-dimethoxy-4-quinolyl)oxy]benzoate

4-Chloro-6,7-dimethoxyquinoline (100 mg), 2-ethylhexylsalicylate (500 mg), and 4-dimethylaminopyridine (244 mg) were suspended in o-dichlorobenzene (1 ml), and the suspension was stirred at 120° C. overnight and at 140° C. for 3 hr.

The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (38 mg, yield 18%).

$^1$H-NMR (CDCl$_3$, 400 MHz): δ 0.64 (t, J=7.3 Hz, 3H), 0.79 (t, J=6.8 Hz, 3H), 1.07 (m, 8H), 1.25 (m, 1H), 4.02 (s, 8H), 6.31 (d, J=5.2 Hz, 1H), 7.20 (m, 1H), 7.39 (m, 2H), 7.61 (m, 2H), 8.06 (dd, J=7.8 Hz, 1.7 Hz, 1H), 8.46 (d, J=5.2 Hz, 1H)

Mass spectrometric value (ESI-MS, m/z): 438 (M+1)$^+$

Compound 102: Phenyl 3-[(6,7-dimethoxy-4-quinolyl)oxy]naphthalene-2-carboxylate

4-Chloro-6,7-dimethoxyquinoline (100 mg), 3-phenyl 2-hydroxynaphthoate (354 mg), and 4-dimethylaminopyridine (164 mg) were suspended in o-dichlorobenzene (5 ml), and the suspension was stirred at 150° C. for 2 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-chloroform to give the title compound (45 mg, yield 22%).

$^1$H-NMR (CDCl$_3$, 400 MHz): δ 3.89 (s, 3H), 3.92 (s, 3H), 6.35 (d, J=5.2 Hz, 1H), 6.73 (d, J=7.8 Hz, 2H), 7.05-7.18 (m, 3H), 7.34 (s, 1H), 7.52-7.62 (m, 3H), 7.66 (s, 1H), 7.78 (d, J=8.0 Hz, 1H), 7.96 (d, J=8.0 Hz, 1H), 8.40 (d, J=5.2 Hz, 1H), 8.73 (s, 1H)

Mass spectrometric value (ESI-MS, m/z): 452 (M+1)$^+$

Compound 103: Benzyl 2-[(6,7-dimethoxy-4-quinolyl)oxy]benzoate

4-Chloro-6,7-dimethoxyquinoline (100 mg), benzylsalicylate (456 mg), and 4-dimethylaminopyridine (244 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (68 mg, yield 33%).

$^1$H-NMR (CDCl$_3$, 400 MHz): δ 3.93 (s, 3H), 4.09 (s, 3H), 5.02 (s, 2H), 6.28 (d, J=5.5 Hz, 1H), 6.92 (m, 2H), 7.06-7.24 (m, 4H), 7.35-7.45 (m, 2H), 7.57 (s, 1H), 7.65 (td, J=7.6, 1.7 Hz, 1H), 8.14 (dd, J=7.8 Hz, 1.7 Hz, 1H), 8.47 (d, J=5.5 Hz, 1H)

Mass spectrometric value (ESI-MS, m/z): 416 (M+1)$^+$

Compound 104: N-Phenyl-2-[(6,7-dimethoxy-4-quinolyl)oxy]benzamide

4-Chloro-6,7-dimethoxyquinoline (56 mg), salicylanilide (213 mg), and 4-dimethylaminopyridine (122 mg) were suspended in o-dichlorobenzene (1 ml), and the suspension was stirred at 140° C. for 4 hr. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by thin layer chromatography using acetone-hexane to give the title compound (86 mg, yield 86%).

$^1$H-NMR (CDCl$_3$, 400 MHz): δ 3.82 (s, 3H), 4.02 (s, 3H), 6.41 (m, 1H), 6.98 (m, 2H), 7.06 (d, J=4.9 Hz, 1H), 7.09 (s, 1H), 7.18-7.28 (m, 4H), 7.33-7.38 (m, 2H), 7.45 (s, 1H), 8.66 (d, J=4.9 Hz, 1H), 10.50 (s, 1H)

Mass spectrometric value (ESI-MS, m/z): 399 (M−1)$^−$

Compound 105: N-Phenyl-5-chloro-2-[(6,7-dimethoxy-4-quinolyl)oxy]-benzamide

4-Chloro-6,7-dimethoxyquinoline (100 mg), 4'-chlorosalicylanilide (445 mg), and 4-dimethylaminopyridine (220 mg) were suspended in o-dichlorobenzene (1 ml), and the suspension was stirred at 140° C. for 4 hr. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (38 mg, yield 20%).

$^1$H-NMR (CDCl$_3$, 400 MHz): δ 3.85 (s, 3H), 4.02 (s, 3H), 6.90-7.45 (m, 11H), 8.69 (d, J=4.6 Hz, 1H), 10.46 (s, 1H)

Mass spectrometric value (ESI-MS, m/z): 433 (M−1)$^−$

Compound 106: 5-Chloro-2-[(6,7-dimethoxy-4-quinolyl)oxy]benzamide

4-Chloro-6,7-dimethoxyquinoline (100 mg), 5-chloro-2-hydroxybenzamide (343 mg), and 4-dimethylaminopyridine (244 mg) were suspended in o-dichlorobenzene (1 ml), and the suspension was stirred at 120° C. overnight. The reaction solution was cooled to room temperature, and the solvent was removed therefrom by distillation under the reduced pressure. The residue was purified by column chromatography using acetone-hexane to give the title compound (265 mg, yield 100%).

$^1$H-NMR (CDCl$_3$, 400 MHz): δ 3.68 (s, 3H), 3.86 (s, 3H), 6.22-6.61 (m, 1H), 6.97 (d, J=8.8 Hz, 1H), 7.23 (dd, J=8.8 Hz, 2.7 Hz, 1H), 7.31 (s, 1H), 7.44 (s, 1H), 8.10 (m, 1H), 8.20 (d, J=2.7 Hz, 1H), 8.58-8.62 (m, 2H)

Mass spectrometric value (ESI-MS, m/z): 359 (M+1)$^+$

Compound 107: N-(3,4-Dichlorophenyl)-5-chloro-2-[(6,7-dimethoxy-4-quinolyl)oxy]benzamide 4-Chloro-6,7-dimethoxyquinoline (116 mg), 3',4',5-trichlorosalicylanilide (632 mg), and 4-dimethylaminopyridine (244 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (14 mg, yield 6%).

¹H-NMR (CDCl₃, 400 MHz): δ 3.87 (s, 3H), 4.03 (s, 3H), 6.88-7.49 (m, 9H), 8.70 (d, J=4.9 Hz, 1H)

Mass spectrometric value (ESI-MS, m/z): 502 (M−1)⁻

Compound 108: N-(4-Chlorophenyl)-5-bromo-2-[(6,7-dimethoxy-4-quinolyl)oxy]benzamide 4-Chloro-6,7-dimethoxyquinoline (100 mg), 5-bromo-4′-chlorosalicylanilide (653 mg), and 4-dimethylaminopyridine (244 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (59 mg, yield 23%).

¹H-NMR (CDCl₃, 400 MHz): δ 3.85 (s, 3H), 4.02 (s, 3H), 6.83 (d, J=5.1 Hz, 1H), 6.99-7.47 (m, 9H), 8.68 (d, J=4.9 Hz, 1H)

Mass spectrometric value (ESI-MS, m/z): 513 (M−1)⁻

Compound 109: {2-[(6,7-Dimethoxy-4-quinolyl)oxy]-5-methylphenyl}-(piperidino)methanone 2-[(6,7-Dimethoxy-4-quinolyl)oxy]-5-methylbenzoic acid (80 mg) was dissolved in a 20% thionyl chloride/dichloromethane mixed solvent (3 ml), and the solution was heated under reflux overnight. The solvent was removed therefrom by distillation under the reduced pressure. 1,4-Dioxane (3 ml) was added to the residue, a solution of piperidine (201 mg) in a 2 N aqueous sodium hydroxide solution (3 ml) was added dropwise thereto, and the mixture was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-hexane to give the title compound (58 mg, yield 61%).

¹H-NMR (CDCl₃, 400 MHz): δ 1.27-1.50 (m, 6H), 2.35 (s, 3H), 3.18-3.43 (m, 4H), 3.94 (s, 3H), 3.96 (s, 3H), 6.48 (d, J=5.2 Hz, 1H), 6.96 (d, J=8.2 Hz, 1H), 7.17 (m, 2H), 7.34 (s, 1H), 7.47 (s, 1H), 8.41 (d, J=5.2 Hz, 1H)

Mass spectrometric value (ESI-MS, m/z): 429 (M+Na)⁺

Compound 110: N-Methyl-2-[(6,7-dimethoxy-4-quinolyl)oxy]-5-methoxybenzamide

2-[(6,7-Dimethoxy-4-quinolyl)oxy]-5-methoxybenzoic acid (intermediate 2) (74 mg) was dissolved in a 20% thionyl chloride/dichloromethane mixed solvent (3 ml), and the solution was heated under reflux overnight. The solvent was removed therefrom by distillation under the reduced pressure. 1,4-Dioxane (3 ml) was added to the residue, a solution of monomethyl ammonium chloride (425 mg) in a 2 N aqueous sodium hydroxide solution (3 ml) was added dropwise thereto, and the mixture was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-hexane to give the title compound (33 mg, yield 43%).

¹H-NMR (CDCl₃, 400 MHz): δ 2.78 (s, 3H), 3.81 (s, 3H), 3.97 (s, 3H), 3.98 (s, 3H), 6.38 (d, J=5.2 Hz, 1H), 6.91-7.05 (m, 3H), 7.38 (s, 1H), 7.42 (s, 1H), 7.64 (d, J=2.8 Hz, 1H), 8.43 (d, J=5.2 Hz, 1H)

Mass spectrometric value (ESI-MS, m/z): 369 (M+1)⁺

Compound 111: N-Isopropyl-2-[(6,7-dimethoxy-4-quinolyl)oxy]-5-methoxybenzamide

2-[(6,7-Dimethoxyquinolyl)oxy]-5-methoxybenzoic acid (74 mg) was dissolved in a 20% thionyl chloride/dichloromethane mixed solvent (3 ml), and the solution was heated under reflux overnight. The solvent was removed therefrom by distillation under the reduced pressure. 1,4-Dioxane (3 ml) was added to the residue, a solution of isopropyl ammonium chloride (514 mg) in a 2 N aqueous sodium hydroxide solution (3 ml) was added dropwise thereto, and the mixture was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-hexane to give the title compound (57 mg, yield 71%).

¹H-NMR (CDCl₃, 400 MHz): δ 0.74 (d, J=6.0 Hz, 6H), 3.82 (s, 3H), 3.98 (m, 7H), 6.28 (d, J=5.2 Hz, 1H), 6.74 (brs, 1H), 7.01 (s, 1H), 7.41 (s, 1H), 7.49 (s, 1H), 7.63 (s, 1H), 8.41 (d, J=5.2 Hz, 1H)

Mass spectrometric value (ESI-MS, m/z): 397 (M+1)⁺

Compound 112: N-Cyclohexyl-2-[(6,7-dimethoxy-4-quinolyl)oxy]-5-methoxybenzamide

2-[(6,7-Dimethoxyquinolyl)oxy]-5-methoxybenzoic acid (74 mg) was dissolved in a 20% thionyl chloride/dichloromethane mixed solvent (3 ml), and the solution was heated under reflux overnight. The solvent was removed therefrom by distillation under the reduced pressure. 1,4-Dioxane (3 ml) was added to the residue, a solution of cyclohexylamine (208 mg) in a 2 N aqueous sodium hydroxide solution (3 ml) was added dropwise thereto, and the mixture was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-hexane to give the title compound (27 mg, yield 29%).

¹H-NMR (CDCl₃, 400 MHz): δ 0.65-0.73 (m, 2H), 0.80-0.89 (m, 1H), 1.08-1.18 (m, 2H), 1.32-1.40 (m, 3H), 1.53-1.57 (m, 2H), 3.67-3.78 (m, 1H), 3.82 (s, 3H), 4.02 (s, 6H), 6.30 (d, J=5.2 Hz, 1H), 6.85 (brs, 1H), 6.99 (m, 2H), 7.38 (s, 1H), 7.47 (s, 1H), 7.62 (s, 1H), 8.41 (d, J=5.2 Hz, 1H)

Mass spectrometric value (ESI-MS, m/z): 437 (M+1)⁺

Compound 113: N-(4-Bromophenyl)-3,5-dibromo-2-[(6,7-dimethoxy-4-quinolyl)oxy]benzamide 4-Chloro-6,7-dimethoxyquinoline (116 mg), 3,5,4′-tribromosalicylanilide (900 mg), and 4-dimethylaminopyridine (244 mg) were suspended in o-dichlorobenzene (1 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed therefrom by distillation under the reduced pressure, and the residue was purified by column chromatography using acetone-hexane to give the title compound (17 mg, yield 6%).

$^1$H-NMR (CDCl$_3$, 400 MHz): δ 3.86 (s, 3H), 4.03 (s, 3H), 6.98 (s, 1H), 7.06 (m, 4H), 7.48 (m, 3H), 7.60 (d, J=2.4 Hz, 1H), 8.70 (d, J=4.9 Hz, 1H)

Mass spectrometric value (ESI-MS, m/z): 636 (M−1)$^-$

Compound 114: N-(1-Naphthalenyl)-3-[(6,7-dimethoxy-4-quinolyl)oxy]-2-naphthamide 4-Chloro-6,7-dimethoxyquinoline (111 mg), naphthol AS-BO (626 mg), and 4-dimethylaminopyridine (244 mg) were suspended in monochlorobenzene (2 ml), and the suspension was stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by chromatography on silica gel using ethyl acetate-hexane for development to give the title compound (43 mg, yield 17%).

Mass spectrometric value (ESI-MS, m/z): 501 (M+1)$^+$

Compound 115: 4-[(6-Methyl-3-pyridyl)oxy]-6,7-dimethoxyquinoline

4-Chloro-6,7-dimethoxyquinoline (229 mg), 3-hydroxy-2-iodo-6-methylpyridine (486 mg), and 4-dimethylaminopyridine (390 mg) were suspended in o-dichlorobenzene (5 ml), and the suspension was stirred at 140° C. overnight. The reaction solution was cooled to room temperature and was then purified by column chromatography using acetone-chloroform to give the title compound (186 mg, yield 61%).

$^1$H-NMR (CDCl$_3$, 400 MHz): δ 2.63 (s, 3H), 4.06 (s, 3H), 4.06 (s, 3H), 6.44 (d, J=5.4 Hz, 1H), 7.26 (d, J=8.3 Hz, 1H), 7.42 (dd, J=2.7 Hz, 8.6 Hz, 1H), 7.44 (s, 1H), 7.54 (s, 1H), 8.46 (d, J=2.7 Hz, 1H), 8.51 (d, J=5.1 Hz, 1H)

Mass spectrometric value (ESI-MS, m/z): 297 (M+1)$^+$

Compound 116: 4-[(2-Iodo-6-methyl-3-pyridyl)oxy]-6,7-dimethoxy-quinoline

4-Chloro-6,7-dimethoxyquinoline (229 mg), 3-hydroxy-2-iodo-6-methylpyridine (486 mg), and 4-dimethylaminopyridine (390 mg) were suspended in o-dichlorobenzene (5 ml), and the suspension was stirred at 140° C. overnight. The reaction solution was cooled to room temperature and was then purified by column chromatography using acetone-chloroform to give the title compound (47 mg, yield 11%).

$^1$H-NMR (CDCl$_3$, 400 MHz): δ 2.62 (s, 3H), 4.06 (s, 3H), 4.07 (s, 3H), 6.35 (d, J=5.4 Hz, 1H), 7.19 (d, J=8.1 Hz, 1H), 7.31 (d, J=8.1 Hz, 1H), 7.46 (s, 1H), 7.58 (s, 1H), 8.51 (d, J=5.4 Hz, 1H)

Mass spectrometric value (ESI-MS, m/z): 423 (M+1)$^+$

Compound 117: 1-{[3-(6,7-Dimethoxy-4-quinolyl)oxy]-6-methyl-2-pyridyl}-1-ethanone 2,6-Lutidine-α$^2$,3-diol (0.75 g) was dissolved in methanol/methylene chloride (5 ml/15 ml) to prepare a solution. Manganese dioxide (2.78 g) was added to the solution, and the mixture was stirred at room temperature overnight. The reaction solution was filtered through Celite, and the solvent was removed therefrom by distillation under the reduced pressure. The residue was purified by column chromatography using acetone-chloroform to give 3-hydroxy-6-methyl-2-pyridinecarbaldehyde (642 mg, yield 87%).

4-Chloro-6,7-dimethoxyquinoline (330 mg), 3-hydroxy-6-methyl-2-pyridinecarbaldehyde (200 mg), and 4-dimethylaminopyridine (360 mg) were suspended in o-dichlorobenzene (7 ml), and the suspension was stirred at 150° C. for 3 hr. The reaction solution was cooled to room temperature and was then purified by column chromatography using acetone-chloroform to give 3-[6,7-dimethoxy-4-quinolyl]oxy}-6-methyl-2-pyridinecarbaldehyde (24 mg, yield 5%).

3-[6,7-Dimethoxy-4-quinolyl]oxy}-6-methyl-2-pyridinecarbaldehyde (24 mg) was dissolved in tetrahydrofuran (4 ml) to prepare a solution which was then cooled to 0° C. A 0.94 M methylmagnesium bromide/tetrahydrofuran solution (0.5 ml) was added to the cooled solution, and the mixture was stirred at room temperature for one hr. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was used in the next reaction without purification.

The residue was dissolved in methylene chloride (4 ml) to prepare a solution. Manganese dioxide (0.7 g) was added to the solution, and the mixture was stirred at room temperature overnight. The reaction solution was filtered through Celite, and the solvent was removed therefrom by distillation under the reduced pressure. The residue was purified by column chromatography using acetone-chloroform to give the title compound (7 mg, yield 29%) (2 steps).

$^1$H-NMR (CDCl$_3$, 400 MHz): δ 2.63 (s, 3H), 2.67 (s, 3H), 4.05 (s, 3H), 4.05 (s, 3H), 6.28 (d, J=5.1 Hz, 1H), 7.40 (d, J=8.6 Hz, 1H), 7.44 (s, 1H), 7.46 (d, J=8.3 Hz, 1H), 7.57 (s, 1H), 8.47 (d, J=5.2 Hz, 1H)

Mass spectrometric value (ESI-MS, m/z): 339 (M+1)$^+$

Compound 118: 4-(2-Acetyl-4-methoxyphenoxy)-6-methoxy-7-quinolyl 4-morpholine carboxylate 1-{2-[(7-Hydroxy-6-methoxy-4-quinolyl)oxy]-5-methoxyphenyl}-1-ethanone (intermediate 4) (86 mg), morpholine-4-carbonyl chloride (114 mg), and potassium carbonate (175 mg) were suspended in N,N-dimethylformamide (2 ml), and the suspension was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (17 mg, yield 15%).

$^1$H-NMR (CDCl$_3$, 400 MHz): δ 2.42 (s, 3H), 3.29 (m, 4H), 3.60 (m, 4H), 3.82 (s, 3H), 3.95 (s, 3H), 6.32 (d, J=5.2 Hz, 1H), 7.02-7.09 (m, 2H), 7.36 (d, J=2.8 Hz, 1H), 7.54 (s, 1H), 7.87 (s, 1H), 8.43 (d, J=5.2 Hz, 1H)

Mass spectrometric value (ESI-MS, m/z): 453 (M+1)$^+$

Compound 119: 1-(2-{[7-(2-Chloroethoxy)-6-methoxy-4-quinolyl]oxy}-5-methoxyphenyl)-1-ethanone 1-{2-[(7-Hydroxy-6-methoxy-4-quinolyl)oxy]-5-methoxyphenyl}-1-ethanone (100 mg), 1-bromo-2-chloroethane (127 mg), and potassium carbonate (204 mg) were suspended in N,N-dimethylformamide (3 ml), and the mixture was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-hexane to give the title compound (107 mg, yield 30%).

$^1$H-NMR (CDCl$_3$, 400 MHz): δ 2.41 (s, 3H), 3.82 (s, 3H), 3.88 (t, J=6.4 Hz, 2H), 3.97 (s, 3H), 4.39 (t, J=6.4 Hz, 2H), 6.31 (d, J=5.4 Hz, 1H), 7.02-7.08 (m, 2H), 7.28-7.38 (m, 2H), 7.52 (s, 1H), 8.42 (d, J=5.4 Hz, 1H)

Mass spectrometric value (ESI-MS, m/z): 402 (M+1)$^+$

Compound 120: 1-(5-Methoxy-2-{[6-methoxy-7-(2-morpholinoethoxy)-4-quinolyl]oxy}phenyl)-1-ethanone 1-(2-{[7-(2-Chloroethoxy)-6-methoxy-4-quinolyl]oxy}-5-methoxyphenyl)-1-ethanone (compound 119) (89 mg), morpholine (57 mg), and potassium carbonate (152 mg) were suspended in N,N-dimethylformamide (2 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (24 mg, yield 24%).

$^1$H-NMR (CDCl$_3$, 400 MHz): δ 2.42 (s, 3H), 2.58 (m, 4H), 2.89 (t, J=5.8 Hz, 2H), 3.68 (m, 4H), 3.81 (s, 3H), 3.95 (s, 3H), 4.28 (t, J=5.8 Hz, 2H), 6.30 (d, J=5.2 Hz, 1H), 7.01-7.08 (m, 2H), 7.35 (d, J=2.8 Hz, 1H), 7.37 (s, 1H), 7.49 (s, 1H), 8.41 (d, J=5.2 Hz, 1H)

Mass spectrometric value (ESI-MS, m/z): 453 (M+1)$^+$

Compound 121: 1-(2-{[7-(3-Chloropropoxy)-6-methoxy-4-quinolyl]oxy}-5-methoxyphenyl)-1-ethanone 1-{2-[(7-Hydroxy-6-methoxy-4-quinolyl)oxy]-5-methoxyphenyl}-1-ethanone (100 mg), 1-bromo-3-chloropropane (138 mg), and potassium carbonate (204 mg) were suspended in N,N-dimethylformamide (3 ml), and the suspension was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-hexane to give the title compound (123 mg, yield 34%).

$^1$H-NMR (CDCl$_3$, 400 MHz): δ 2.32 (m, 2H), 2.41 (s, 3H), 3.72 (t, J=6.4 Hz, 2H), 3.81 (s, 3H), 3.97 (s, 3H), 4.28 (t, J=6.4 Hz, 2H), 6.31 (d, J=5.3 Hz, 1H), 7.01-7.08 (m, 2H), 7.29 (d, J=2.8 Hz, 1H), 7.35 (s, 1H), 7.49 (s, 1H), 8.41 (d, J=5.3 Hz, 1H)

Mass spectrometric value (ESI-MS, m/z): 416 (M+1)+

Compound 122: 1-(5-Methoxy-2-{[6-methoxy-7-(3-morpholinopropoxy)-4-quinolyl]oxy}phenyl)-1-ethanone 1-(2-{[7-(3-Chloropropoxy)-6-methoxy-4-quinolyl]oxy}-5-methoxyphenyl)-1-ethanone (compound 121) (100 mg), morpholine (63 mg), and potassium carbonate (166 mg) were suspended in N,N-dimethylformamide (2 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (55 mg, yield 49%).

$^1$H-NMR (CDCl$_3$, 400 MHz): δ 2.06 (m, 2H), 2.41 (m, 7H), 2.51 (t, J=6.8 Hz, 2H), 3.65 (m, 4H), 3.80 (s, 3H), 3.95 (s, 3H), 4.20 (t, J=6.8 Hz, 2H), 6.30 (d, J=5.2 Hz, 1H), 7.01-7.08 (m, 2H), 7.34 (d, J=2.8 Hz, 1H), 7.37 (s, 1H), 7.45 (s, 1H), 8.40 (d, J=5.2 Hz, 1H)

Mass spectrometric value (ESI-MS, m/z): 467 (M+1)$^+$

Compound 123: (2-{[7-(2-Chloroethoxy)-6-methoxy-4-quinolyl]oxy}-5-methylphenyl)(phenyl)methanone {2-[(7-Hydroxy-6-methoxy-4-quinolyl)oxy]-5-methylphenyl}-(phenyl)methanone (500 mg), 1-bromo-2-chloroethane (245 mg), and potassium carbonate (897 mg) were suspended in N,N-dimethylformamide (20 ml), and the suspension was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-hexane to give the title compound (465 mg, yield 80%).

$^1$H-NMR (CDCl$_3$, 400 MHz): δ 2.41 (s, 3H), 3.75 (s, 3H), 3.85 (t, J=6.0 Hz, 2H), 4.34 (t, J=6.0 Hz, 2H), 6.38 (d, J=5.2 Hz, 1H), 6.88 (s, 1H), 7.10 (d, J=7.2 Hz, 1H), 7.25 (m, 3H), 7.41 (m, 3H), 7.61 (m, 2H), 8.34 (d, J=5.2 Hz, 1H)

Mass spectrometric value (ESI-MS, m/z): 448 (M+1)$^+$

Compound 124: {2-[(7-{2-[(2-Hydroxyethyl)amino]ethoxy}-6-methoxy-4-quinolyl)oxy]-5-methylphenyl}(phenyl)methanone (2-{[7-(2-Chloroethoxy)-6-methoxy-4-quinolyl]oxy}-5-methylphenyl)(phenyl)methanone (compound 123) (50 mg), 2-aminoethanol (20 mg), and potassium carbonate (76 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (23 mg, yield 44%).

$^1$H-NMR (CDCl$_3$, 400 MHz): δ 2.39 (s, 3H), 2.81 (m, 2H), 3.08 (m, 2H), 3.62 (m, 2H), 3.70 (s, 3H), 4.18 (m, 2H), 6.31 (d, J=5.4 Hz, 1H), 6.80 (s, 1H), 7.07 (d, J=7.2 Hz, 1H), 7.22-7.26 (m, 3H), 7.34-7.39 (m, 3H), 7.62 (m, 2H), 8.32 (d, J=5.4 Hz, 1H)

Mass spectrometric value (ESI-MS, m/z): 495 (M+Na)$^+$

Compound 125: [2-({7-[2-(Diethylamino)ethoxy]-6-methoxy-4-quinolyl}oxy)-5-methylphenyl](phenyl)methanone (2-{[7-(2-Chloroethoxy)-6-methoxy-4-quinolyl]oxy}-5-methylphenyl)(phenyl)methanone (50 mg), diethylamine (24 mg), and potassium carbonate (76 mg) were suspended in N,N-dimethylformamide (3 ml), and the suspension was stirred at 80° C. overnight. The reaction solution was cooled to room temperature, water was then added to the cooled reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (7 mg, yield 13%).

$^1$H-NMR (CDCl$_3$, 400 MHz): δ 1.11-1.20 (m, 6H), 2.40 (s, 3H), 2.60-3.13 (m, 6H), 3.71 (s, 3H), 4.24 (m, 2H), 6.32 (d, J=5.4 Hz, 1H), 6.80 (s, 1H), 7.08 (d, J=7.2 Hz, 1H), 7.22-7.26 (m, 3H), 7.34-7.39 (m, 3H), 7.61 (m, 2H), 8.34 (d, J=5.4 Hz, 1H)

Mass spectrometric value (ESI-MS, m/z): 485 (M+1)$^+$

Compound 126: {2-[(7-{2-[4-(Hydroxymethyl)piperidino]ethoxy}-6-methoxy-4-quinolyl)oxy]-5-methylphenyl}(phenyl)methanone (2-{[7-(2-Chloroethoxy)-6-methoxy-4-quinolyl]oxy}-5-methylphenyl)(phenyl)methanone (50 mg), 4-piperidine methanol (38 mg), and potassium carbonate (76 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (31 mg, yield 54%).

$^1$H-NMR (CDCl$_3$, 400 MHz): δ 1.18-1.35 (m, 2H), 1.41-1.51 (m, 1H), 1.68 (m, 2H), 2.11 (m, 2H), 2.39 (s, 3H), 2.86 (t, J=6.4 Hz, 2H), 2.99 (m, 2H), 3.43 (d, J=6.2 Hz, 2H), 3.71 (s, 3H), 4.21 (t, J=6.2 Hz, 2H), 6.31 (d, J=5.2 Hz, 1H), 6.80 (s, 1H), 7.07 (d, J=7.2 Hz, 1H), 7.22-7.26 (m, 3H), 7.34-7.39 (m, 3H), 7.62 (m, 2H), 8.32 (d, J=5.2 Hz, 1H)

Mass spectrometric value (ESI-MS, m/z): 549 (M+Na)$^+$

Compound 127: [5-Methyl-2-({6-methoxy-7-[2-(4-tetrahydro-1-pyrrolylpiperidino)ethoxy]-4-quinolyl}oxy)phenyl](phenyl)methanone (2-{[7-(2-Chloroethoxy)-6-methoxy-4-quinolyl]oxy}-5-methylphenyl)(phenyl)methanone (96 mg), 4-(1-pyrrolidinyl)piperidine (97 mg), and potassium carbonate (145 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (43 mg, yield 41%).

$^1$H-NMR (CDCl$_3$, 400 MHz): δ 1.47-1.57 (m, 2H), 1.69-1.82 (m, 6H), 1.98 (m, 1H), 2.10 (m, 2H), 2.38 (s, 3H), 2.51 (m, 4H), 2.82 (t, J=6.4 Hz, 2H), 2.96 (m, 2H), 3.70 (s, 3H), 4.18 (t, J=6.4 Hz, 2H), 6.30 (d, J=5.4 Hz, 1H), 6.79 (s, 1H), 7.07 (d, J=7.2 Hz, 1H), 7.20-7.25 (m, 3H), 7.34-7.38 (m, 3H), 7.60 (m, 2H), 8.32 (d, J=5.4 Hz, 1H)

Mass spectrometric value (ESI-MS, m/z): 566 (M+1)$^+$

Compound 128: [2-({6-Methoxy-7-[2-(1-piperazino)ethoxy]-4-quinolyl}oxy)-5-methylphenyl](phenyl)methanone (2-{[7-(2-Chloroethoxy)-6-methoxy-4-quinolyl]oxy}-5-methylphenyl)(phenyl)methanone (50 mg), piperazine (28 mg), and potassium carbonate (76 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (91 mg, yield 93%).

$^1$H-NMR (CDCl$_3$, 400 MHz): δ 2.39 (s, 3H), 2.51 (m, 4H), 2.84 (m, 6H), 3.71 (s, 3H), 4.18 (t, J=6.1 Hz, 2H), 6.31 (d, J=5.3 Hz, 1H), 6.80 (s, 1H), 7.07 (d, J=7.2 Hz, 1H), 7.22-7.26 (m, 3H), 7.34-7.39 (m, 3H), 7.62 (m, 2H), 8.32 (d, J=5.3 Hz, 1H)

Mass spectrometric value (ESI-MS, m/z): 520 (M+Na)$^+$

Compound 129: [2-({6-Methoxy-7-[2-(4-methylpiperazino)ethoxy]-4-quinolyl}oxy)-5-methylphenyl](phenyl)methanone (2-{[7-(2-Chloroethoxy)-6-methoxy-4-quinolyl]oxy}-5-methylphenyl)(phenyl)methanone (50 mg), 4-methylpiperazine (33 mg), and potassium carbonate (76 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (29 mg, yield 52%).

$^1$H-NMR (CDCl$_3$, 400 MHz): δ 2.24 (s, 3H), 2.39-2.44 (m, 7H), 2.59 (m, 4H), 2.85 (t, J=6.1 Hz, 2H), 3.70 (s, 3H), 4.20 (t, J=6.1 Hz, 2H), 6.31 (d, J=5.2 Hz, 1H), 6.80 (s, 1H), 7.07 (d, J=7.3 Hz, 1H), 7.22-7.26 (m, 3H), 7.34-7.39 (m, 3H), 7.62 (m, 2H), 8.33 (d, J=5.2 Hz, 1H)

Mass spectrometric value (ESI-MS, m/z): 534 (M+Na)$^+$

Compound 130: (5-Methyl-2-{[6-methoxy-7-(2-morpholinoethoxy)-4-quinolyl]oxy}phenyl)(phenyl)methanone (2-{[7-(2-Chloroethoxy)-6-methoxy-4-quinolyl]oxy}-5-methylphenyl)(phenyl)methanone (50 mg), morpholine (29 mg), and potassium carbonate (76 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (35 mg, yield 64%).

$^1$H-NMR (CDCl$_3$, 400 MHz): δ 2.39 (s, 3H), 2.54 (m, 4H), 2.84 (t, J=6.1 Hz, 2H), 3.65-3.71 (m, 7H), 4.16 (t, J=6.1 Hz, 2H), 6.32 (d, J=5.3 Hz, 1H), 6.81 (s, 1H), 7.07 (d, J=7.2 Hz, 1H), 7.22-7.26 (m, 3H), 7.34-7.39 (m, 3H), 7.62 (m, 2H), 8.33 (d, J=5.3 Hz, 1H)

Mass spectrometric value (ESI-MS, m/z): 521 (M+Na)$^+$

Compound 131: [2-({7-[2-(1-Imidazoyl)ethoxy]-6-methoxy-4-quinolyl}-oxy)-5-methyl phenyl](phenyl)methanone (2-{[7-(2-Chloroethoxy)-6-methoxy-4-quinolyl]oxy}-5-methylphenyl)(phenyl)methanone (50 mg), imidazole (22 mg), and potassium carbonate (76 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (33 mg, yield 63%).

$^1$H-NMR (CDCl$_3$, 400 MHz): δ 2.39 (s, 3H), 3.71 (s, 3H), 4.25 (m, 2H), 4.33 (m, 2H), 6.32 (d, J=5.2 Hz, 1H), 6.82 (s, 1H), 6.98-7.40 (m, 9H), 7.60 (m, 3H), 8.32 (d, J=5.2 Hz, 1H)

Mass spectrometric value (ESI-MS, m/z): 502 (M+Na)$^+$

Compound 132: (2-{[7-(3-Chloropropoxy)-6-methoxy-4-quinolyl]oxy}-5-methylphenyl)(phenyl)methanone {2-[(7-Hydroxy-6-methoxy-4-quinolyl)oxy]-5-methylphenyl}-(phenyl)methanone (200 mg), 1-bromo-3-chloropropane (245 mg), and potassium carbonate (358 mg) were suspended in N,N-dimethylformamide (5 ml), and the suspension was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-hexane to give the title compound (210 mg, yield 87%).

$^1$H-NMR (CDCl$_3$, 400 MHz): δ 2.25 (m, 2H), 2.38 (s, 3H), 3.69 (m, 5H), 4.18 (t, J=6.2 Hz, 2H), 6.30 (d, J=5.3 Hz, 1H), 6.80 (s, 1H), 7.02 (d, J=7.2 Hz, 1H), 7.23-7.26 (m, 3H), 7.31-7.37 (m, 3H), 7.59 (m, 2H), 8.31 (d, J=5.3 Hz, 1H)

Mass spectrometric value (ESI-MS, m/z): 462 (M+1)$^+$

Compound 133: {2-[(7-{3-[(2-Hydroxyethyl)amino]propoxy}-6-methoxy-4-quinolyl)oxy]-5-methylphenyl}(phenyl)methanone (2-{[7-(3-Chloropropoxy)-6-methoxy-4-quinolyl]oxy}-5-methylphenyl)(phenyl)methanone (compound 132) (68 mg), 4-aminoethanol (25 mg), and potassium carbonate (95 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (36 mg, yield 54%).

$^1$H-NMR (CDCl$_3$, 400 MHz): δ 2.01 (m, 2H), 2.39 (s, 3H), 2.72-2.80 (m, 4H), 3.60 (m, 2H), 3.71 (s, 3H), 4.17 (t, J=6.1 Hz, 2H), 6.31 (d, J=5.2 Hz, 1H), 6.80 (s, 1H), 7.07 (d, J=7.2 Hz, 1H), 7.22-7.26 (m, 3H), 7.34-7.39 (m, 3H), 7.62 (m, 2H), 8.32 (d, J=5.2 Hz, 1H)

Mass spectrometric value (ESI-MS, m/z): 509 (M+Na)$^+$

Compound 134: [2-({7-[3-(Diethylamino)propoxy]-6-methoxy-4-quinolyl}oxy)-5-methylphenyl](phenyl)methanone (2-{[7-(3-Chloropropoxy)-6-methoxy-4-quinolyl]oxy}-5-methylphenyl)(phenyl)methanone (68 mg), diethylamine (30 mg), and potassium carbonate (95 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (26 mg, yield 38%).

$^1$H-NMR (CDCl$_3$, 400 MHz): δ 0.97 (t, J=7.2 Hz, 6H), 1.99 (m, 2H), 2.39 (s, 3H), 2.49 (m, 4H), 2.56 (t, J=7.6 Hz, 2H), 3.71 (s, 3H), 4.11 (t, J=6.8 Hz, 2H), 6.30 (d, J=5.4 Hz, 1H), 6.79 (s, 1H), 7.07 (d, J=7.2 Hz, 1H), 7.19-7.24 (m, 3H), 7.33-7.39 (m, 3H), 7.62 (m, 2H), 8.32 (d, J=5.4 Hz, 1H)

Mass spectrometric value (ESI-MS, m/z): 499 (M+1)$^+$

Compound 135: {2-[(7-{3-[4-(Hydroxymethyl)piperidino]propoxy}-6-methoxy-4-quinolyl)oxy]-5-methylphenyl}(phenyl)methanone (2-{[7-(3-Chloropropoxy)-6-methoxy-4-quinolyl]oxy}-5-methylphenyl)(phenyl)methanone (62 mg), 4-piperidine ethanol (25 mg), and potassium carbonate (100 mg) were suspended in N,N-dimethylformamide (4 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (55 mg, yield 75%).

$^1$H-NMR (CDCl$_3$, 400 MHz): δ 1.48 (m, 2H), 1.76 (m, 2H), 1.73 (m, 2H), 2.16-2.29 (m, 4H), 2.39 (s, 3H), 2.79 (m, 2H), 3.22 (m, 2H), 3.44 (m, 2H), 3.70 (s, 3H), 4.06 (m, 1H), 6.32 (d, J=5.4 Hz, 1H), 6.81 (s, 1H), 7.07 (d, J=7.2 Hz, 1H), 7.20-7.26 (m, 3H), 7.34-7.40 (m, 3H), 7.62 (m, 2H), 8.32 (d, J=5.4 Hz, 1H)

Mass spectrometric value (ESI-MS, m/z): 541 (M+1)$^+$

Compound 136: [5-Methyl-2-({6-methoxy-7-[3-(4-tetrahydro-1-pyrrolylpiperidino)propoxy]-4-quinolyl}oxy)phenyl](phenyl)methanone (2-{[7-(3-Chloropropoxy)-6-methoxy-4-quinolyl]oxy}-5-methylphenyl)(phenyl)methanone (112 mg), 4-(1-pyrrolidinyl)piperidine (111 mg), and potassium carbonate (166 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (47 mg, yield 35%).

$^1$H-NMR (CDCl$_3$, 400 MHz): δ 1.44-1.54 (m, 2H), 1.69-2.22 (m, 11H), 2.38-2.50 (m, 9H), 2.85 (m, 2H), 3.70 (s, 3H), 4.10 (t, J=6.8 Hz, 2H), 6.30 (d, J=5.4 Hz, 1H), 6.79 (s, 1H), 7.07 (d, J=7.2 Hz, 1H), 7.20-7.25 (m, 3H), 7.34-7.38 (m, 3H), 7.61 (m, 2H), 8.31 (d, J=5.4 Hz, 1H)

Mass spectrometric value (ESI-MS, m/z): 580 (M+1)$^+$

Compound 137: [2-({6-Methoxy-7-[3-(1-piperazino)propoxy]-4-quinolyl}oxy)-5-methylphenyl](phenyl)methanone (2-{[7-(3-Chloropropoxy)-6-methoxy-4-quinolyl]oxy}-5-methylphenyl)(phenyl)methanone (68 mg), piperazine (36 mg), and potassium carbonate (95 mg) were suspended in N,N-dimethylformamide (3 ml), and the suspension was stirred at 80° C. overnight. The reaction solution was cooled to room temperature, water was then added to the cooled reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (43 mg, yield 61%).

$^1$H-NMR (CDCl$_3$, 400 MHz): δ 2.01 (m, 2H), 2.39-2.47 (m, 9H), 2.82 (m, 4H), 3.73 (s, 3H), 4.12 (t, J=6.4 Hz, 2H), 6.31 (d, J=5.2 Hz, 1H), 6.80 (s, 1H), 7.07 (d, J=7.2 Hz, 1H), 7.22-7.26 (m, 3H), 7.34-7.39 (m, 3H), 7.62 (m, 2H), 8.32 (d, J=5.2 Hz, 1H)

Mass spectrometric value (ESI-MS, m/z): 512 (M+1)$^+$

Compound 138: [2-({6-Methoxy-7-[3-(4-methylpiperazino)propoxy]-4-quinolyl}oxy)-5-methylphenyl](phenyl)methanone (2-{[7-(3-Chloropropoxy)-6-methoxy-4-quinolyl]oxy}-5-methylphenyl)(phenyl)methanone (68 mg), 4-methylpiperazine (42 mg), and potassium carbonate (95 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (54 mg, yield 75%).

$^1$H-NMR (CDCl$_3$, 400 MHz): δ 2.01 (m, 2H), 2.21 (s, 3H), 2.38-2.49 (m, 13H), 3.70 (s, 3H), 4.11 (t, J=6.4 Hz, 2H), 6.30 (d, J=5.2 Hz, 1H), 6.79 (s, 1H), 7.07 (d, J=7.2 Hz, 1H), 7.20-7.25 (m, 3H), 7.33-7.42 (m, 3H), 7.61 (m, 2H), 8.32 (d, J=5.2 Hz, 1H)

Mass spectrometric value (ESI-MS, m/z): 526 (M+1)$^+$

Compound 139: (5-Methyl-2-{[6-methoxy-7-(3-morpholinopropoxy)-4-quinolyl]oxy}phenyl)(phenyl)methanone (2-{[7-(3-Chloropropoxy)-6-methoxy-4-quinolyl]oxy}-5-methylphenyl)(phenyl)methanone (62 mg), morpholine (40 mg), and potassium carbonate (100 mg) were suspended in N,N-dimethylformamide (4 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (45 mg, yield 66%).

$^1$H-NMR (CDCl$_3$, 400 MHz): δ 2.02 (m, 2H), 2.39-2.54 (m, 9H), 3.63-3.71 (m, 7H), 4.04 (m, 2H), 6.31 (d, J=5.3 Hz, 1H), 6.81 (s, 1H), 7.07 (d, J=7.2 Hz, 1H), 7.19-7.25 (m, 3H), 7.33-7.39 (m, 3H), 7.62 (m, 2H), 8.32 (d, J=5.3 Hz, 1H)

Mass spectrometric value (ESI-MS, m/z): 513 (M+1)$^+$

Compound 140: [2-({7-[3-(1-Imidazoyl)propoxy]-6-methoxy-4-quinolyl}oxy)-5-methylphenyl](phenyl)methanone (2-{[7-(3-Chloropropoxy)-6-methoxy-4-quinolyl]oxy}-5-methylphenyl)(phenyl)methanone (68 mg), imidazole (28 mg), and potassium carbonate (95 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (59 mg, yield 87%).

$^1$H-NMR (CDCl$_3$, 400 MHz): δ 2.23 (m, 2H), 2.38 (s, 3H), 3.73 (s, 3H), 3.99 (t, J=6.0 Hz, 2H), 4.14 (t, J=6.8 Hz, 2H), 6.32 (d, J=5.2 Hz, 1H), 6.84 (m, 2H), 6.96 (s, 1H), 7.07 (d, J=7.2 Hz, 1H), 7.17-7.26 (m, 3H), 7.33-7.41 (m, 4H), 7.61 (m, 2H), 8.32 (d, J=5.2 Hz, 1H)

Mass spectrometric value (ESI-MS, m/z): 516 (M+Na)$^+$

Compound 141: (2-{[7-(4-Chlorobutoxy)-6-methoxy-4-quinolyl]oxy}-5-methylphenyl)(phenyl)methanone {2-[(7-Hydroxy-6-methoxy-4-quinolyl)oxy]-5-methylphenyl}-(phenyl)methanone (500 mg), 1-bromo-3-chlorobutane (668 mg), and potassium carbonate (896 mg) were suspended in N,N-dimethylformamide (20 ml), and the suspension was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-hexane to give the title compound (584 mg, yield 95%).

¹H-NMR (CDCl₃, 400 MHz): δ 1.95 (m, 4H), 2.40 (s, 3H), 3.57 (t, J=6.4 Hz, 2H), 3.72 (s, 3H), 4.11 (t, J=6.4 Hz, 2H), 6.34 (d, J=5.4 Hz, 1H), 6.83 (s, 1H), 7.09 (d, J=7.2 Hz, 1H), 7.22-7.28 (m, 3H), 7.35-7.40 (m, 3H), 7.61 (m, 2H), 8.33 (d, J=5.4 Hz, 1H)

Mass spectrometric value (ESI-MS, m/z): 476 (M+1)⁺

Compound 142: {2-[(7-{4-[(2-Hydroxyethyl)amino]butoxy}-6-methoxy-4-quinolyl)oxy]-5-methylphenyl}(phenyl)methanone (2-{[7-(4-Chlorobutoxy)-6-methoxy-4-quinolyl]oxy}-5-methylphenyl)(phenyl)methanone (compound 142) (60 mg), 4-aminoethanol (24 mg), and potassium carbonate (90 mg) were suspended in N,N-dimethylformamide (2 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate, and the solvent was removed therefrom by distillation under the reduced pressure. The residue was purified by thin layer chromatography using methanol-chloroform to give the title compound (33 mg, yield 51%).

¹H-NMR (CDCl₃, 400 MHz): δ 1.62 (m, 2H), 1.88 (m, 2H), 2.39 (s, 3H), 2.65 (t, J=6.8 Hz, 2H), 2.72 (t, J=5.2 Hz, 2H), 3.59 (t, J=5.2 Hz, 2H), 3.71 (s, 3H), 4.09 (t, J=6.8 Hz, 2H), 6.30 (d, J=5.4 Hz, 1H), 6.80 (s, 1H), 7.07 (d, J=7.2 Hz, 1H), 7.22-7.26 (m, 3H), 7.34-7.39 (m, 3H), 7.61 (m, 2H), 8.31 (d, J=5.4 Hz, 1H)

Mass spectrometric value (ESI-MS, m/z): 501 (M+1)⁺

Compound 143: [2-({7-[4-(Diethylamino)butoxy]-6-methoxy-4-quinolyl}oxy)-5-methylphenyl](phenyl)methanone (2-{[7-(4-Chlorobutoxy)-6-methoxy-4-quinolyl]oxy}-5-methylphenyl)(phenyl)methanone (60 mg), diethylamine (29 mg), and potassium carbonate (90 mg) were suspended in N,N-dimethylformamide (2 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (27 mg, yield 41%).

¹H-NMR (CDCl₃, 400 MHz): δ 0.96 (t, J=7.2 Hz, 6H), 1.59 (m, 2H), 1.84 (m, 2H), 2.39 (s, 3H), 2.48 (m, 4H), 2.56 (t, J=7.6 Hz, 2H), 3.71 (s, 3H), 4.07 (t, J=6.8 Hz, 2H), 6.30 (d, J=5.4 Hz, 1H), 6.79 (s, 1H), 7.07 (d, J=7.2 Hz, 1H), 7.19-7.24 (m, 3H), 7.33-7.39 (m, 3H), 7.61 (m, 2H), 8.32 (d, J=5.2 Hz, 1H)

Mass spectrometric value (ESI-MS, m/z): 513 (M+1)⁺

Compound 144: {2-[(7-{4-[4-(Hydroxymethyl)piperidino]butoxy}-6-methoxy-4-quinolyl)oxy]-5-methylphenyl}(phenyl)methanone (2-{[7-(4-Chlorobutoxy)-6-methoxy-4-quinolyl]oxy}-5-methylphenyl)(phenyl)methanone (60 mg), 4-piperidine ethanol (45 mg), and potassium carbonate (90 mg) were suspended in N,N-dimethylformamide (2 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (32 mg, yield 41%).

¹H-NMR (CDCl₃, 400 MHz): δ 1.17-1.27 (m, 2H), 1.38-1.46 (m, 1H), 1.59-1.66 (m, 4H), 1.80-1.95 (m, 4H), 2.31-2.38 (m, 5H), 2.88 (m, 2H), 3.39 (d, J=6.4 Hz, 2H), 3.70 (s, 3H), 4.05 (t, J=6.4 Hz, 2H), 6.31 (d, J=5.2 Hz, 1H), 6.79 (s, 1H), 7.07 (d, J=7.2 Hz, 1H), 7.22-7.26 (m, 3H), 7.34-7.39 (m, 3H), 7.60 (m, 2H), 8.31 (d, J=5.2 Hz, 1H)

Mass spectrometric value (ESI-MS, m/z): 577 (M+Na)⁺

Compound 145: [5-Methyl-2-({6-methoxy-7-[4-(4-tetrahydro-1-pyrrolylpiperidino)butoxy]-4-quinolyl}oxy)phenyl](phenyl)methanone (2-{[7-(4-Chlorobutoxy)-6-methoxy-4-quinolyl]oxy}-5-methylphenyl)(phenyl)methanone (60 mg), 4-(1-pyrrolidinyl)piperidine (60 mg), and potassium carbonate (90 mg) was suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (69 mg, yield 90%).

¹H-NMR (CDCl₃, 400 MHz): δ 1.44-1.97 (m, 15H), 2.30 (m, 2H), 2.38 (s, 3H), 2.50 (m, 4H), 2.85 (m, 2H), 3.70 (s, 3H), 4.07 (t, J=6.8 Hz, 2H), 6.30 (d, J=5.4 Hz, 1H), 6.78 (s, 1H), 7.07 (d, J=7.2 Hz, 1H), 7.20-7.25 (m, 3H), 7.34-7.38 (m, 3H), 7.61 (m, 2H), 8.32 (d, J=5.4 Hz, 1H)

Mass spectrometric value (ESI-MS, m/z): 594 (M+1)⁺

Compound 146: [5-Methyl-2-({6-methoxy-7-[4-(4-piperidylpiperidino)-butoxy]-4-quinolyl}oxy)phenyl](phenyl)methanone (2-{[7-(4-Chlorobutoxy)-6-methoxy-4-quinolyl]oxy}-5-methylphenyl)(phenyl)methanone (60 mg), 4-piperidinopiperidine (66 mg), and potassium carbonate (90 mg) were suspended in N,N-dimethylformamide (2 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (34 mg, yield 43%).

¹H-NMR (CDCl₃, 400 MHz): δ 1.34-1.85 (m, 16H), 2.20 (m, 1H), 2.30 (m, 2H), 2.38-2.44 (m, 7H), 2.91 (m, 2H), 3.70 (s, 3H), 4.07 (t, J=6.8 Hz, 2H), 6.30 (d, J=5.4 Hz, 1H), 6.78 (s, 1H), 7.07 (d, J=7.2 Hz, 1H), 7.20-7.25 (m, 3H), 7.34-7.38 (m, 3H), 7.61 (m, 2H), 8.31 (d, J=5.4 Hz, 1H)

Mass spectrometric value (ESI-MS, m/z): 608 (M+1)⁺

Compound 147: [2-({6-Methoxy-7-[4-(1-piperazino)butoxy]-4-quinolyl}-oxy)-5-methylphenyl](phenyl)methanone (2-{[7-(4-Chlorobutoxy)-6-methoxy-4-quinolyl]oxy}-5-methylphenyl)(phenyl)methanone (60 mg), piperazine (34 mg), and potassium carbonate (90 mg) were suspended in N,N-dimethylformamide (2 ml), and the suspensioon was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate, and the solvent was removed therefrom by distillation under the reduced pressure. The residue was purified by thin layer chromatography using methanol-chloroform to give the title compound (41 mg, yield 60%).

$^1$H-NMR (CDCl$_3$, 400 MHz): δ 1.61 (m, 2H), 1.85 (m, 2H), 2.30-2.38 (m, 9H) 2.82 (m, 4H), 3.70 (s, 3H), 4.07 (t, J=6.4 Hz, 2H), 6.30 (d, J=5.2 Hz, 1H), 6.79 (s, 1H), 7.07 (d, J=7.2 Hz, 1H), 7.22-7.26 (m, 3H), 7.34-7.39 (m, 3H), 7.61 (m, 2H), 8.32 (d, J=5.2 Hz, 1H)

Mass spectrometric value (ESI-MS, m/z): 526 (M+1)$^+$

Compound 148: [2-({6-Methoxy-7-[4-(4-methylpiperazino)butoxy]-4-quinolyl}oxy)-5-methylphenyl](phenyl)methanone (2-{[7-(4-Chlorobutoxy)-6-methoxy-4-quinolyl]oxy}-5-methylphenyl)(phenyl)methanone (60 mg), 4-methylpiperazine (39 mg), and potassium carbonate (90 mg) were suspended in N,N-dimethylformamide (2 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (41 mg, yield 60%).

$^1$H-NMR (CDCl$_3$, 400 MHz): δ 1.61 (m, 2H), 1.85 (m, 2H), 2.21 (s, 3H), 2.29-2.38 (m, 13H), 3.70 (s, 3H), 4.05 (t, J=6.8 Hz, 2H), 6.30 (d, J=5.2 Hz, 1H), 6.79 (s, 1H), 7.07 (d, J=7.2 Hz, 1H), 7.20-7.25 (m, 3H), 7.33-7.42 (m, 3H), 7.61 (m, 2H), 8.31 (d, J=5.2 Hz, 1H)

Mass spectrometric value (ESI-MS, m/z): 562 (M+Na)$^+$

Compound 149: (5-Methyl-2-{[6-methoxy-7-(4-morpholinobutoxy)-4-quinolyl]oxy}phenyl)(phenyl)methanone (2-{[7-(4-Chlorobutoxy)-6-methoxy-4-quinolyl]oxy}-5-methylphenyl)(phenyl)methanone (60 mg), morpholine (34 mg), and potassium carbonate (90 mg) were suspended in N,N-dimethylformamide (2 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (36 mg, yield 55%).

$^1$H-NMR (CDCl$_3$, 400 MHz): δ 1.62 (m, 2H), 1.86 (m, 2H), 2.25-2.39 (m, 9H), 3.63 (m, 4H), 3.70 (s, 3H), 4.07 (t, J=7.2 Hz, 2H), 6.30 (d, J=5.2 Hz, 1H), 6.81 (s, 1H), 7.07 (d, J=7.4 Hz, 1H), 7.22-7.26 (m, 3H), 7.34-7.39 (m, 3H), 7.62 (m, 2H), 8.32 (d, J=5.2 Hz, 1H)

Mass spectrometric value (ESI-MS, m/z): 527 (M+1)$^+$

Compound 150: [2-({7-[4-(1-Imidazoyl)butoxy]-6-methoxy-4-quinolyl}-oxy)-5-methylphenyl](phenyl)methanone (2-{[7-(4-Chlorobutoxy)-6-methoxy-4-quinolyl]oxy}-5-methylphenyl)(phenyl)methanone (60 mg), imidazole (27 mg), and potassium carbonate (90 mg) were suspended in N,N-dimethylformamide (2 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (16 mg, yield 24%).

$^1$H-NMR (CDCl$_3$, 400 MHz): δ 1.77 (m, 2H), 1.91 (m, 2H), 2.37 (s, 3H), 3.70 (s, 3H), 3.99 (t, J=6.8 Hz, 2H), 4.14 (t, J=6.8 Hz, 2H), 6.30 (d, J=5.2 Hz, 1H), 6.81 (s, 1H), 6.88 (s, 1H), 6.98 (s, 1H), 7.07 (d, J=7.2 Hz, 1H), 7.17-7.26 (m, 3H), 7.33-7.41 (m, 3H), 7.47 (m, 1H), 7.62 (m, 2H), 8.30 (d, J=5.2 Hz, 1H)

Mass spectrometric value (ESI-MS, m/z): 530 (M+Na)$^+$

Compound 151: (2-{[6-Methoxy-7-(2-oxiranylmethoxy)-4-quinolyl]oxy}-5-methylphenyl)(phenyl)methanone {2-[(7-Hydroxy-6-methoxy-4-quinolyl)oxy]-5-methylphenyl}-(phenyl)methanone (200 mg), epibromohydrin (213 mg), and potassium carbonate (358 mg) were suspended in N,N-dimethylformamide (5 ml), and the suspension was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-hexane to give the title compound (176 mg, yield 75%).

$^1$H-NMR (CDCl$_3$, 400 MHz): δ 2.38 (s, 3H), 2.54-2.91 (m, 2H), 3.38 (m, 1H), 3.72 (s, 3H), 4.00-4.30 (m, 2H), 6.31 (d, J=5.3 Hz, 1H), 6.81 (s, 1H), 7.06 (d, J=7.2 Hz, 1H), 7.19-7.24 (m, 3H), 7.33-7.38 (m, 3H), 7.59 (m, 2H), 8.33 (d, J=5.3 Hz, 1H)

Mass spectrometric value (ESI-MS, m/z): 442 (M+1)$^+$

Compound 152: {2-[(7-{2-Hydroxy-3-[(2-hydroxyethyl)amino]propoxy}-6-methoxy-4-quinolyl)oxy]-5-methyl phenyl}(phenyl)methanone (2-{[6-Methoxy-7-(2-oxiranylmethoxy)-4-quinolyl]oxy}-5-methylphenyl)(phenyl)methanone (compound 151) (39 mg) and 4-aminoethanol (16 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (29 mg, yield 66%).

$^1$H-NMR (CDCl$_3$, 400 MHz): δ 2.39 (s, 3H), 2.76-2.87 (m, 4H), 3.62-3.76 (m, 5H), 4.06 (m, 2H), 4.19 (m, 1H), 6.31 (d, J=5.3 Hz, 1H), 6.79 (s, 1H), 7.07 (d, J=7.2 Hz, 1H), 7.20-7.25 (m, 3H), 7.34-7.38 (m, 3H), 7.60 (m, 2H), 8.31 (d, J=5.3 Hz, 1H)

Mass spectrometric value (ESI-MS, m/z): 525 (M+Na)$^+$

Compound 153: [2-({7-[3-(Diethylamino)-2-hydroxypropoxy]-6-methoxy-4-quinolyl}oxy)-5-methylphenyl](phenyl)methanone (2-{[6-Methoxy-7-(2-oxiranylmethoxy)-4-quinolyl]oxy}-5-methylphenyl)(phenyl)methanone (39 mg) and diethylamine (19 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (21 mg, yield 46%).

$^1$H-NMR (CDCl$_3$, 400 MHz): δ 1.02 (m, 6H), 2.39 (s, 3H), 2.48-2.70 (m, 6H), 3.70 (s, 3H), 4.03 (m, 2H), 4.12 (m, 1H), 6.31 (d, J=5.4 Hz, 1H), 6.81 (s, 1H), 7.07 (d, J=7.2 Hz, 1H), 7.20-7.26 (m, 3H), 7.34-7.40 (m, 3H), 7.61 (m, 2H), 8.32 (d, J=5.4 Hz, 1H)

Mass spectrometric value (ESI-MS, m/z): 515 (M+1)$^+$

Compound 154: {2-[(7-{2-Hydroxy-3-[4-(hydroxymethyl)piperidino]-propoxy}-6-methoxy-4-quinolyl)oxy]-5-methylphenyl}(phenyl)methanone (2-{[6-Methoxy-7-(2-oxiranylmethoxy)-4-quinolyl]oxy}-5-methylphenyl)(phenyl)methanone (41 mg) and 4-piperidine ethanol (32 mg) were suspended in N,N-dimethylformamide (4 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (48 mg, yield 93%).

$^1$H-NMR (CDCl$_3$, 400 MHz): δ 1.68 (m, 2H), 1.99 (m, 2H), 2.25 (m, 1H), 2.39 (s, 3H), 2.50 (m, 2H), 2.85-3.02 (m, 4H), 3.39-3.43 (m, 2H), 3.69 (s, 3H), 4.02 (m, 2H), 4.17 (m, 1H), 6.31 (d, J=5.4 Hz, 1H), 6.79 (s, 1H), 7.07 (d, J=7.3 Hz, 1H), 7.20-7.26 (m, 3H), 7.34-7.40 (m, 3H), 7.61 (m, 2H), 8.32 (d, J=5.4 Hz, 1H)

Mass spectrometric value (ESI-MS, m/z): 557 (M+1)$^+$

Compound 155: [2-({7-[2-Hydroxy-3-(4-tetrahydro-1-pyrrolylpiperidino)-propoxy]-6-methoxy-4-quinolyl}oxy)-5-methylphenyl](phenyl)methanone (2-{[6-Methoxy-7-(2-oxiranylmethoxy)-4-quinolyl]oxy}-5-methylphenyl)(phenyl)methanone (39 mg) and 4-(1-pyrrolidinyl)piperidine (41 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (38 mg, yield 73%).

$^1$H-NMR (CDCl$_3$, 400 MHz): δ 1.46-1.59 (m, 2H), 1.72 (m, 4H), 1.82 (m, 2H), 1.97 (m, 2H), 2.26 (m, 1H), 2.39 (s, 3H), 2.42-2.52 (m, 6H), 2.78-2.96 (m, 2H), 3.69 (s, 3H), 4.03 (m, 2H), 4.11 (m, 1H), 6.30 (d, J=5.3 Hz, 1H), 6.79 (s, 1H), 7.07 (d, J=7.2 Hz, 1H), 7.20-7.25 (m, 3H), 7.34-7.38 (m, 3H), 7.61 (m, 2H), 8.32 (d, J=5.3 Hz, 1H)

Mass spectrometric value (ESI-MS, m/z): 596 (M+1)$^+$

Compound 156: [2-({7-[2-Hydroxy-3-(4-piperidylpiperidino)propoxy]-6-methoxy-4-quinolyl}oxy)-5-methylphenyl](phenyl)methanone (2-{[6-Methoxy-7-(2-oxiranylmethoxy)-4-quinolyl]oxy}-5-methylphenyl)(phenyl)methanone (39 mg) and 4-piperidinopiperidine (45 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (49 mg, yield 91%).

$^1$H-NMR (CDCl$_3$, 400 MHz): δ 1.36 (m, 2H), 1.45-1.54 (m, 6H), 1.74 (m, 2H), 1.93 (m, 1H), 2.21 (m, 2H), 2.39-2.50 (m, 9H), 2.83-3.00 (m, 2H), 3.69 (s, 3H), 4.02 (m, 2H), 4.11 (m, 1H), 6.30 (d, J=5.4 Hz, 1H), 6.79 (s, 1H), 7.07 (d, J=7.2 Hz, 1H), 7.20-7.25 (m, 3H), 7.34-7.38 (m, 3H), 7.61 (m, 2H), 8.31 (d, J=5.4 Hz, 1H)

Mass spectrometric value (ESI-MS, m/z): 610 (M+1)$^+$

Compound 157: [2-({7-[2-Hydroxy-3-(1-piperazino)propoxy]-6-methoxy-4-quinolyl}oxy)-5-methylphenyl](phenyl)methanone (2-{[6-Methoxy-7-(2-oxiranylmethoxy)-4-quinolyl]oxy}-5-methylphenyl)(phenyl)methanone (39 mg) and piperazine (23 mg) were suspended in N,N-dimethylformamide (3 ml), and the suspensioon was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (22 mg, yield 47%).

$^1$H-NMR (CDCl$_3$, 400 MHz): δ 2.39-2.59 (m, 9H), 2.80-2.90 (m, 4H), 3.70 (s, 3H), 4.04 (m, 2H), 4.15 (m, 1H), 6.31 (d, J=5.4 Hz, 1H), 6.80 (s, 1H), 7.07 (d, J=7.2 Hz, 1H), 7.20-7.25 (m, 3H), 7.34-7.38 (m, 3H), 7.62 (m, 2H), 8.32 (d, J=5.4 Hz, 1H)

Mass spectrometric value (ESI-MS, m/z): 528 (M+1)$^+$

Compound 158: [2-({7-[2-Hydroxy-3-(4-methylpiperazino)propoxy]-6-methoxy-4-quinolyl}oxy)-5-methylphenyl](phenyl)methanone (2-{[6-Methoxy-7-(2-oxiranylmethoxy)-4-quinolyl]oxy}-5-methylphenyl)(phenyl)methanone (39 mg) and 4-methylpiperazine (27 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (40 mg, yield 84%).

$^1$H-NMR (CDCl$_3$, 400 MHz): δ 2.24 (s, 3H), 2.39-2.64 (m, 13H), 3.69 (s, 3H), 4.04 (m, 2H), 4.15 (m, 1H), 6.31 (d, J=5.3 Hz, 1H), 6.79 (s, 1H), 7.09 (d, J=7.2 Hz, 1H), 7.20-7.25 (m, 3H), 7.34-7.38 (m, 3H), 7.61 (m, 2H), 8.32 (d, J=5.3 Hz, 1H)

Mass spectrometric value (ESI-MS, m/z): 564 (M+Na)$^+$

Compound 159: (2-{[7-(2-Hydroxy-3-morpholinopropoxy)-6-methoxy-4-quinolyl]oxy}-5-methylphenyl)(phenyl)methanone (2-{[6-Methoxy-7-(2-oxiranylmethoxy)-4-quinolyl]oxy}-5-methylphenyl)(phenyl)methanone (41 mg) and morpholine (53 mg) were suspended in N,N-dimethylformamide (4 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (34 mg, yield 69%).

$^1$H-NMR (CDCl$_3$, 400 MHz): δ 2.39-2.62 (m, 9H), 3.62-3.70 (m, 7H), 4.05 (m, 2H), 4.17 (m, 1H), 6.32 (d, J=5.4 Hz, 1H), 6.81 (s, 1H), 7.08 (d, J=7.3 Hz, 1H), 7.20-7.26 (m, 3H), 7.34-7.40 (m, 3H), 7.61 (m, 2H), 8.32 (d, J=5.4 Hz, 1H)

Mass spectrometric value (ESI-MS, m/z): 551 (M+Na)$^+$

Compound 160: [2-({7-[2-Hydroxy-3-(1-imidazoyl)propoxy]-6-methoxy-4-quinolyl}oxy)-5-methylphenyl](phenyl)methanone (2-{[6-Methoxy-7-(2-oxiranylmethoxy)-4-quinolyl]oxy}-5-methylphenyl)(phenyl)methanone (39 mg) and imidazole (18 mg) were suspended in N,N-dimethylformamide (3 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using methanol-chloroform to give the title compound (36 mg, yield 80%).

$^1$H-NMR (CDCl$_3$, 400 MHz): δ 2.39 (s, 3H), 3.70 (s, 3H), 3.86 (m, 1H), 4.01-4.31 (m, 4H), 6.32 (d, J=5.3 Hz, 1H), 6.84-7.69 (m, 13H), 8.31 (d, J=5.3 Hz, 1H)

Mass spectrometric value (ESI-MS, m/z): 532 (M+Na)$^+$

Compound 161: {2-[(6,7-Dimethoxy-4-quinazolyl)oxy]-5-methylphenyl}-(phenyl)methanone 4-Chloro-6,7-dimethoxyquinazoline (59 mg), 2-hydroxy-5-methylbenzophenone (279 mg), and 4-dimethylaminopyridine (168 mg) were suspended in o-dichlorobenzene (5 ml), and the suspension was stirred at 160° C. for 10 min. The reaction solution was cooled to room temperature, the solvent was then removed therefrom by distillation under the reduced pressure, and chloroform was added to the residue. The mixture was washed with a 1 N aqueous potassium hydroxide solution and saturated brine and was dried over anhydrous magnesium sulfate. The solvent was removed therefrom by distillation under the reduced pressure, and the residue was purified by column chromatography using chloroform and by thin layer chromatography using acetone-hexane to give the title compound (97 mg, yield 92%).

$^1$H-NMR (CDCl$_3$, 400 MHz): δ 2.46 (s, 3H), 3.90 (s, 3H), 4.01 (s, 3H), 7.03 (s, 1H), 7.19 (s, 1H), 7.22-7.27 (m, 2H), 7.31 (d, J=8.6 Hz, 1H), 7.33-7.39 (m, 1H), 7.43-7.49 (m, 2H), 7.67-7.73 (m, 2H), 8.49 (s, 1H)

Mass spectrometric value (ESI-MS, m/z): 401 (M+1)$^+$

Compound 162: 1-{2-[(6,7-Dimethoxy-4-quinazolyl)oxy]-5-methoxyphenyl}-1-ethanone 4-Chloro-6,7-dimethoxyquinazoline (59 mg), 2-hydroxy-5-methoxyacetophenone (213 mg), and 4-dimethylaminopyridine (173 mg) were suspended in o-dichlorobenzene (5 ml), and the suspension was stirred at 160° C. for 10 min. The reaction solution was cooled to room temperature, the solvent was then removed therefrom by distillation under the reduced pressure, and chloroform was added to the residue. The mixture was washed with a 1 N aqueous potassium hydroxide solution and saturated brine and was dried over anhydrous magnesium sulfate. The solvent was removed therefrom by distillation under the reduced pressure, and the residue was purified by column chromatography using chloroform and by thin layer chromatography using acetone-hexane to give the title compound (46.5 mg, yield 50%).

$^1$H-NMR (CDCl$_3$, 400 MHz): δ 2.45 (s, 3H), 3.89 (s, 3H), 4.07 (s, 6H), 7.13-7.20 (m, 2H), 7.34 (s, 1H), 7.40 (d, J=2.4 Hz, 1H), 7.56 (s, 1H), 8.60 (s, 1H)

Mass spectrometric value (ESI-MS, m/z): 355 (M+1)$^+$

Compound 163: Ethyl 2-[(6,7-dimethoxy-4-quinolyl)carbonyl]benzoate 6,7-Dimethoxyquinolone (0.79 g) was dissolved in chlorobenzene (7 ml) to prepare a solution. Phosphorus oxybromide (3.34 g) was added to the solution, and the mixture was stirred at 150° C. for 6 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography on silica gel using acetone-chloroform to give 4-bromo-6,7-dimethoxyquinoline (429 mg, yield 42%).

4-Bromo-6,7-dimethoxyquinoline (138 mg) was dissolved in tetrahydrofuran (6 ml) to prepare a solution which was then cooled to −78° C. A 1.59 M n-butyllithium/hexane solution (0.3 ml) was added to the cooled solution, and the mixture was stirred at −78° C. for 20 min. A solution of phthalic anhydride (250 mg) in tetrahydrofuran (2 ml) was added to the reaction solution, and the mixture was stirred at room temperature for one hr. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was used in the next reaction without purification.

The residue provided by the above reaction was dissolved in N,N-dimethylformamide (1 ml) to prepare a solution, cesium carbonate (100 mg) and ethyl iodide (0.05 ml) were added to the solution, and the mixture was stirred at room temperature for one hr. Water was added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-chloroform to give the title compound (3 mg, yield 2%) (2 steps).

$^1$H-NMR (CDCl$_3$, 400 MHz): δ 1.01 (t, J=7.1 Hz, 3H), 3.98 (q, J=7.1 Hz, 2H), 4.07 (s, 3H), 4.07 (s, 3H), 7.07 (d, J=4.6 Hz, 1H), 7.51 (s, 1H), 7.53 (dd, J=1.4 Hz, 7.3 Hz, 1H), 7.64 (m, 1H), 7.66 (m, 1H), 8.02 (m, 1H), 8.33 (s, 1H), 8.69 (d, J=4.6 Hz, 1H)

Mass spectrometric value (ESI-MS, m/z): 366 (M+1)$^+$

Compound 164: 4-(2-Iodo-4,5-dimethyl-phenoxy)-6,7-dimethoxy-quinoline 3,4-Dimethylphenol (0.68 g) and iodine (1.82 g) were dissolved in methanol/water (10 ml/5 ml), and the mixture was stirred at room temperature overnight. An aqueous sodium sulfite solution was added to the reaction solution, and the mixture was extracted with ethyl acetate. The ethyl acetate layer was then washed with water and was dried over anhydrous sodium sulfate. The solvent was removed by distillation under the reduced pressure. The residue was purified by column chromatography using ethyl acetate-hexane to give 2-iodo-4,5-dimethylphenol (833 mg, yield 64%).

2-Iodo-4,5-dimethylphenol (447 mg), 4-chloro-6,7-dimethoxyquinoline (466 mg), and 4-dimethylaminopyridine (539 mg) were suspended in o-dichlorobenzene (20 ml), and the mixture was stirred at 130° C. for 4 hr. The reaction solution was cooled to room temperature, and the solvent was then removed by distillation under the reduced pressure. Water was then added to the residue, and the mixture was extracted with chloroform. The chloroform layer was washed with water and was dried over anhydrous sodium sulfate. The solvent was removed by distillation under the reduced pressure. The residue was purified by column chromatography using acetone-chloroform to give the title compound (452 mg, yield 50%).

$^1$H-NMR (CDCl$_3$, 400 MHz): δ 2.25 (s, 3H), 2.28 (s, 3H), 4.05 (s, 3H), 4.07 (s, 3H), 6.32 (d, J=5.4 Hz, 1H), 6.97 (s, 1H), 7.44 (s, 1H), 7.61 (s, 1H), 7.68 (s, 1H), 8.48 (d, J=5.1 Hz, 1H)

Mass spectrometric value (ESI-MS, m/z): 436 (M+1)$^+$

Compound 165: 1-[2-(6,7-Dimethoxy-quinolin-4-yloxy)-5-methyl-phenyl]-decane-1,10-diol 4-Methylanisole (732 mg) was dissolved in nitromethane (30 ml) to prepare a solution. Anhydrous lithium perchlorate (3.8 g), methyl 10-chloro-10-oxodecanoate (2 ml), and scandium triflate (300 mg) were added to the solution, and the mixture was stirred at room temperature for 4 hr. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by column chromatography using acetone-hexane to give methyl 10-(2-methoxy-5-methylphenyl)-10-oxo-decanoate (1.6 g, yield 83%).

Methyl 10-(2-methoxy-5-methyl-phenyl)-10-oxo-decanoate (1.6 g) was dissolved in methylene chloride (30 ml), 1 M boron tribromide (7.5 ml) was added to the solution at −78° C., and the mixture was stirred at room temperature for 30 min. Water was added to the reaction solution, and the mixture was extracted with chloroform, and the chloroform layer was then washed with water and was dried over anhydrous sodium sulfate. The solvent was removed by distillation under the reduced pressure, and the residue was purified by column chromatography using acetone-hexane to give methyl 10-(2-hydroxy-5-methyl-phenyl)-10-oxo-decanoate (546 mg, yield 34%).

Methyl 10-(2-hydroxy-5-methyl-phenyl)-10-oxo-decanoate (546 mg), 4-chloro-6,7-dimethoxyquinoline (397 mg), and 4-dimethylaminopyridine (434 mg) were suspended in o-dichlorobenzene (20 ml), and the suspension was stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate, and the solvent was removed by distillation under the reduced pressure. The residue was purified by column chromatography using acetone-hexane to give methyl 10-[2-(6,7-dimethoxy-quinolin-4-yloxy)-5-methylphenyl]-10-oxo-decanoate (90 mg, yield 1.0%).

Methyl 10-[2-(6,7-dimethoxy-quinolin-4-yloxy)-5-methyl-phenyl]-10-oxo-decanoate (40 mg) was dissolved in tetrahydrofuran (3 ml), 0.93 M diisobutylaluminum hydride (1 ml) was added to the solution at 0° C., and the mixture was stirred at room temperature for 5 hr. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using methanol-chloroform to give the title compound (4.9 mg, yield 13%).

$^1$H-NMR (CDCl$_3$, 400 MHz): δ 1.02-1.78 (m, 16H), 2.42 (s, 3H), 3.61 (t, J=6.6 Hz, 2H), 4.05 (s, 6H), 4.86 (m, 1H), 6.38 (d, J=5.4 Hz, 1H), 6.98 (d, J=8.3 Hz, 1H), 7.16 (m, 1H), 7.45 (m, 2H), 7.56 (s, 1H), 8.39 (d, J=5.4 Hz, 1H)

Mass spectrometric value (ESI-MS, m/z): 468 (M+1)$^+$

Compound 166: 1-[2-(6,7-Dimethoxy-quinolin-4-yloxy)-5-methoxyphenyl]-2-pyridin-2-yl-ethanol 2-Picoline (40 μl) was dissolved in tetrahydrofuran (2 ml), and the solution was cooled to −78° C. under an argon atmosphere. n-Butyllithium (1.56 M hexane solution) (260 μl) was added to the cooled solution, and the mixture was stirred for 2 hr. A solution of 2-(6,7-dimethoxy-quinolin-4-yloxy)-5-methoxy-benzaldehyde (100 mg) in tetrahydrofuran (2 ml) was then added to the reaction solution, and the mixture was stirred at −78° C. for one hr. A saturated ammonium chloride solution was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by column chromatography using acetone-hexane to give the title compound (37 mg, yield 29%).

¹H-NMR (CDCl₃, 400 MHz): δ 3.01-3.14 (m, 2H), 3.86 (s, 3H), 4.02 (s, 3H), 4.05 (s, 3H), 5.28 (m, 1H), 6.08 (brs, 1H), 6.45 (m, 1H), 6.80 (m, 1H), 6.89 (m, 1H), 7.03 (m, 1H), 7.12 (m, 1H), 7.31 (d, J=3.0 Hz, 1H), 7.43-7.53 (m, 2H), 7.57 (m, 1H), 8.46 (m, 2H)

Mass spectrometric value (ESI-MS, m/z): 433 (M+1)⁺

Compound 167: 6,7-Dimethoxy-4-(4-methyl-2-pyridin-2-yl-phenoxy)-quinoline

N,N-dimethylformamide (1 ml) was added to 4-(2-bromo-4-methyl-phenoxy)-6,7-dimethoxy-quinoline (compound 4) (50 mg), tetrakistriphenylphosphine palladium (15 mg), tri-n-butyl-(2-pyridyl)-tin (59 mg), and copper(II) oxide (2.1 mg) under an argon atmosphere, and the mixture was stirred at 100° C. for 4 hr. The reaction solution was cooled to room temperature, water was then added thereto, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using acetone-hexane to give the title compound (37 mg, yield 75%).

¹H-NMR (CDCl₃, 400 MHz): δ 2.48 (s, 3H), 4.04 (s, 3H), 4.05 (s, 3H), 6.45 (d, J=5.6 Hz, 1H), 7.06-7.12 (m, 1H), 7.14 (d, J=8.0 Hz, 1H), 7.32 (dd, J=2.2, 10.0 Hz, 1H), 7.45-7.58 (m, 3H), 7.60 (d, J=8.0 Hz, 1H), 7.76 (s, 1H), 8.37 (d, J=5.6 Hz, 1H), 8.57 (d, J=4.6 Hz, 1H)

Mass spectrometric value (ESI-MS, m/z): 373 (M+1)⁺

Compound 168: 6,7-Dimethoxy-4-(4-methyl-2-pyridin-3-yl-phenoxy)-quinoline

N,N-Dimethylformamide (1 ml) and a 2 M aqueous potassium carbonate solution (1 ml) were added to 4-(2-bromo-4-methyl-phenoxy)-6,7-dimethoxy-quinoline (compound 4) (50 mg), tetrakistriphenylphosphine palladium (15 mg), and 3-pyridylboronic acid (33 mg) under an argon atmosphere, and the mixture was stirred at 70° C. for 5 hr. The reaction solution was cooled to room temperature, water was then added to the cooled reaction solution, and the mixture was extracted with ethyl acetate. The ethyl acetate layer was then washed with water and was dried over anhydrous sodium sulfate. The solvent was removed therefrom by distillation under the reduced pressure. The residue was purified by thin layer chromatography using chloroform-methanol to give the title compound (24.7 mg, yield 50%).

¹H-NMR (CDCl₃, 400 MHz): δ 2.47 (s, 3H), 4.01 (s, 3H), 4.01 (s, 3H), 6.37 (d, J=5.1 Hz, 1H), 7.15 (d, J=8.1 Hz, 1H), 7.16 (s, 1H), 7.69 (dd, J=1.5, 8.1 Hz, 1H), 7.34 (s, 1H), 7.36 (s, 1H), 7.43 (s, 1H), 7.76 (d, J=8.1 Hz, 1H), 8.28-8.58 (m, 2H), 8.77 (brs, 1H)

Mass spectrometric value (ESI-MS, m/z): 373 (M+1)⁺

Compound 169: 4-(4,5-Dimethyl-2-pyridin-2-yl-phenoxy)-6,7-dimethoxy-quinoline 4-(2-Iodo-4,5-dimethyl-phenoxy)-6,7-dimethoxyquinoline (compound 164) (95 mg), tri-n-butyl(2-pyridyl)tin (0.25 ml), and tetrakistriphenylphosphine palladium (64 mg) were dissolved in N,N-dimethylformamide (7 ml), lithium chloride (102 mg) was added to the reaction system, and the mixture was stirred at 100° C. for one hr. Water was added to the reaction solution, and the mixture was extracted with ethyl acetate. The ethyl acetate layer was then washed with water and was dried over anhydrous sodium sulfate. The solvent was removed by distillation under the reduced pressure. The residue was purified by thin layer chromatography using acetone-chloroform to give the title compound (3 mg, yield 4%).

¹H-NMR (CDCl₃, 400 MHz): δ 2.33 (s, 3H), 2.38 (s, 3H), 4.03 (s, 3H), 4.03 (s, 3H), 6.42 (d, J=5.4 Hz, 1H), 7.00 (s, 1H), 7.07 (dd, J=4.9, 7.6 Hz, 1H), 7.39 (s, 1H), 7.45 (ddd, J=1.7, 7.6, 8.1 Hz, 1H), 7.54 (s, 1H), 7.63 (d, J=8.1 Hz, 1H), 7.76 (s, 1H), 8.39 (d, J=5.4 Hz, 1H), 8.60 (d, J=4.9 Hz, 1H)

Mass spectrometric value (ESI-MS, m/z): 387 (M+1)⁺

Compound 170: 4-(4,5-Dimethyl-2-pyridin-3-yl-phenoxy)-6,7-dimethoxy-quinoline 4-(2-Iodo-4,5-dimethyl-phenoxy)-6,7-dimethoxyquinoline (compound 164) (59 mg), pyridine-3-boronic acid (33 mg), and tetrakistriphenylphosphine palladium (10 mg) were dissolved in N,N-dimethylformamide (4 ml), a 2 M aqueous potassium carbonate solution (0.5 ml) was added to the reaction system, and the mixture was stirred at 100° C. for 30 min. Water was added to the reaction solution, and the mixture was extracted with ethyl acetate. The ethyl acetate layer was then washed with water and was dried over anhydrous sodium sulfate. The solvent was removed therefrom by distillation under the reduced pressure. The residue was purified by thin layer chromatography using acetone-chloroform to give the title compound (13 mg, yield 25%).

¹H-NMR (CDCl₃, 400 MHz): δ 2.33 (s, 3H), 2.37 (s, 3H), 4.01 (s, 3H), 4.02 (s, 3H), 6.38 (d, J=5.4 Hz, 1H), 7.04 (s, 1H), 7.13 (dd, J=4.9, 8.1 Hz, 1H), 7.30 (s, 1H), 7.36 (s, 1H), 7.44 (s, 1H), 7.55 (ddd, J=2.0, 2.0, 7.8 Hz, 1H), 8.40-8.42 (m, 2H), 8.75 (d, J=2.2 Hz, 1H)

Mass spectrometric value (ESI-MS, m/z): 387 (M+1)⁺

Compound 171: 4-(4-Imidazol-1-yl-2-iodo-phenoxy)-6,7-dimethoxy-quinoline 4-(Imidazol-1-yl)phenol (500 mg) was dissolved in water (6 ml), methanol (18 ml), and dichloromethane (6 ml) to prepare a solution. Iodine (1.58 g) was added to the solution, and the mixture was stirred at room temperature for 8 days. An aqueous sodium thiosulfate solution and methanol were added to the reaction solution, and the mixture was stirred and was then concentrated. The concentrate was extracted with chloroform, and the chloroform layer was then washed with water and saturated brine and was dried over anhydrous sodium sulfate. The solvent was removed therefrom by distillation under the reduced pressure, and the residue was purified by thin layer chromatography using chloroform-methanol to give 4-(imidazol-1-yl)-2-iodophenol (123 mg, yield 14%).

4-(Imidazol-1-yl)-2-iodophenol (123 mg), 4-chloro-6,7-dimethoxyquinoline (288 mg), and 4-dimethylaminopyridine (158 mg) were suspended in o-dichlorobenzene (3 ml), and the suspension was stirred at 140° C. for 7.5 hr. The reaction solution was cooled to room temperature, water was then added thereto, and the mixture was extracted with chloroform. The chloroform layer was washed with saturated brine and was dried over anhydrous sodium sulfate. The solvent was removed therefrom by distillation under the reduced pressure. The residue was purified by thin layer chromatography using chloroform-methanol to give the title compound (92 mg, yield 45%).

¹H-NMR (CDCl₃, 400 MHz): δ 4.07 (s, 3H), 4.08 (s, 3H), 6.42 (d, J=5.4 Hz, 1H), 7.26-7.30 (m, 3H), 7.47-7.51 (m, 2H), 7.59 (s, 1H), 7.88 (s, 1H), 7.99 (d, J=2.4 Hz, 1H), 8.53 (dd, J=0.7 Hz, 5.1 Hz, 1H)

Mass spectrometric value (ESI-MS, m/z): 474 (M+1)⁺

Compound 172: 1-[2-(6,7-Dimethoxy-quinolin-4-yloxy)-5-ethyl-phenyl]-ethanone 3-Ethyl-6-hydroxyacetophenone (341 mg), 4-chloro-6,7-dimethoxyquinoline (154 mg), and 4-dimethylaminopyridine (254 mg) were suspended in o-dichlorobenzene (6.5 ml), and the suspension was stirred at 130° C. for 8 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by thin layer chromatography using acetone-hexane to give the title compound (48 mg, yield 20%).

$^1$H-NMR (CDCl$_3$, 400 MHz): δ 1.21 (t, J=7.6 Hz, 3H), 2.44 (s, 3H), 2.65 (q, J=7.6 Hz, 2H), 3.96 (s, 3H), 3.97 (s, 3H), 6.35 (d, J=5.6 Hz, 1H), 7.00 (d, J=8.0 Hz, 1H), 7.32-7.37 (m, 2H), 7.48 (s, 1H), 7.67 (s, 1H), 8.42 (d, J=5.6 Hz, 1H)

Mass spectrometric value (ESI-MS, m/z): 352 (M+1)$^+$

Compound 173: 1-[2-(6,7-Dimethoxy-quinolin-4-yloxy)-5-propyl-phenyl]-ethanone 4-n-Propylphenol (1.00 g) was dissolved in dichloromethane (10 ml) to prepare a solution. Pyridine (862 mg) and acetyl chloride (692 mg) were added to the solution, and the mixture was stirred at room temperature overnight. The solvent was removed therefrom by distillation under the reduced pressure. Water was then added to the residue, and the mixture was extracted with chloroform. The chloroform layer was washed with water and was dried over anhydrous magnesium sulfate. The solvent was removed therefrom by distillation under the reduced pressure, and the residue was purified by column chromatography using chloroform to give 4-n-propylphenyl acetate (1.09 g, yield 100%).

4-n-Propylphenyl acetate (1.07 g) and scandium trifluoromethanesulfonate (345 mg) were suspended in toluene (10 ml), and the suspension was stirred at 120° C. for 7 hr. The reaction solution was cooled to room temperature, and the cooled reaction solution was then filtered. The solvent was removed from the filtrate by distillation under the reduced pressure. Water was then added to the residue, and the mixture was extracted with ethyl acetate. The ethyl acetate layer was then washed with water and saturated brine and was dried over anhydrous sodium sulfate. The solvent was removed therefrom by distillation under the reduced pressure, and the residue was purified by column chromatography using acetone-hexane to give 2-hydroxy-5-n-propylacetophenone (276 mg, yield 26%).

2-Hydroxy-5-n-propylacetophenone (276 mg), 4-chloro-6,7-dimethoxyquinoline (117 mg), and 4-dimethylaminopyridine (191 mg) were suspended in o-dichlorobenzene (6.5 ml), and the suspension was stirred at 130° C. for 8 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure. The residue was purified by thin layer chromatography using acetone-hexane to give the title compound (50 mg, yield 26%).

$^1$H-NMR (CDCl$_3$, 400 MHz): δ 0.90 (t, J=7.2 Hz, 3H), 1.61 (qt, J=7.2 Hz, J=7.6 Hz, 2H), 2.44 (s, 3H), 2.59 (t, J=7.6 Hz, 2H), 3.96 (s, 3H), 3.97 (s, 3H), 6.35 (d, J=5.2 Hz, 1H), 7.00 (d, J=8.0 Hz, 1H), 7.30-7.37 (m, 2H), 7.48 (s, 1H), 7.65 (s, 1H), 8.43 (d, J=5.2 Hz, 1H)

Mass spectrometric value (ESI-MS, m/z): 366 (M+1)$^+$

Compound 174: 1-[5-Butyl-2-(6,7-dimethoxy-quinolin-4-yloxy)-phenyl]-ethanone 4-n-Butylphenol (1.00 g) was dissolved in dichloromethane (10 ml) to prepare a solution. Pyridine (783 mg) and acetyl chloride (675 mg) were added to the solution, and the mixture was stirred at room temperature overnight. The solvent was removed by distillation under the reduced pressure. Water was then added to the residue, and the mixture was extracted with ethyl acetate. The ethyl acetate layer was then washed with water and was dried over anhydrous magnesium sulfate. The solvent was removed by distillation under the reduced pressure. The residue was purified by column chromatography using chloroform to give 4-n-butylphenyl acetate (1.03 g, yield 80%).

4-n-Butylphenyl acetate (1.01 g) and scandium trifluoromethane sulfonate (307 mg) were suspended in toluene (10 ml) to prepare a suspension which was then stirred at 120° C. overnight. The reaction solution was cooled to room temperature and was then filtered. The solvent was removed from the filtrate by distillation under the reduced pressure, water was then added to the residue, and the mixture was extracted with ethyl acetate. The ethyl acetate layer was then washed with water and saturated brine and was dried over anhydrous sodium sulfate. The solvent was removed by distillation under the reduced pressure. The residue was purified by column chromatography using acetone-hexane to give 3-n-butyl-6-hydroxyacetophenone (370 mg, yield 37%).

3-n-Butyl-6-hydroxyacetophenone (370 mg), 4-chloro-6,7-dimethoxyquinoline (860 mg), and 4-dimethylaminopyridine (354 mg) were suspended in o-dichlorobenzene (5 ml) to prepare a suspension which was then stirred at 120° C. for 10 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure. The residue was purified by thin layer chromatography using acetone-hexane to give the title compound (31 mg, yield 4%).

$^1$H-NMR (CDCl$_3$, 400 MHz): δ 0.88 (t, J=7.6 Hz, 3H), 1.31 (qt, J=7.6 Hz, J=7.6 Hz, 2H), 1.56 (tt, J=7.6 Hz, J=7.6 Hz, 2H), 2.44 (s, 3H), 2.61 (t, J=7.6 Hz, 2H), 3.96 (s, 3H), 3.98 (s, 3H), 6.35 (d, J=5.2 Hz, 1H), 6.99 (d, J=7.8 Hz, 1H), 7.32 (dd, J=7.8 Hz, J=2.4 Hz, 1H), 7.37 (s, 1H), 7.48 (s, 1H), 7.66 (d, J=2.4 Hz, 1H), 8.43 (d, J=5.2 Hz, 1H)

Mass spectrometric value (ESI-MS, m/z): 380 (M+1)$^+$

Compound 175: 1-[5-Benzyloxy-2-(6,7-dimethoxy-quinolin-4-yloxy)-phenyl]-ethanone 2,5-Dihydroxyacetophenone (3.00 g), benzyl bromide (2.48 g), and potassium carbonate (8.16 g) were suspended in acetonitrile (30 ml) to prepare a suspension which was heated under reflux overnight. The reaction solution was cooled to room temperature, and the solvent was then removed by distillation under the reduced pressure. Water was then added to the residue, and the mixture was extracted with chloroform. The chloroform layer was washed with water and was dried over anhydrous magnesium sulfate. The solvent was removed by distillation under the reduced pressure. The residue was purified by column chromatography using acetone-hexane to give 3-benzyloxy-6-hydroxyacetophenone (1.88 g, yield 39%).

3-Benzyloxy-6-hydroxyacetophenone (1.88 g), 4-chloro-6,7-dimethoxyquinoline (3.43 g), and 4-dimethylaminopyridine (1.41 g) were suspended in o-dichlorobenzene (20 ml) to prepare a suspension which was then stirred at 130° C. for 10 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by column chromatography using acetone-hexane to give the title compound (188 mg, yield 6%).

$^1$H-NMR (CDCl$_3$, 400 MHz): δ 2.41 (s, 3H), 3.97 (s, 6H), 5.06 (s, 2H), 6.31 (d, J=5.2 Hz, 1H), 7.02 (d, J=8.8 Hz, 1H), 7.13 (dd, J=8.8 Hz, J=3.2 Hz, 1H), 7.25-7.41 (m, 6H), 7.45 (d, J=3.2 Hz, 1H), 7.49 (s, 1H), 8.41 (d, J=5.2 Hz, 1H)

Mass spectrometric value (ESI-MS, m/z): 430 (M+1)$^+$

Compound 176: 1-[2-(6,7-Dimethoxy-quinolin-4-yloxy)-5-hydroxy-phenyl]-ethanone

1-[5-Benzyloxy-2-(6,7-dimethoxy-quinolin-4-yloxy)-phenyl]-ethanone (compound 175) (188 mg) was suspended in a mixed solution composed of methanesulfonic acid (0.3 ml) and trifluoroacetic acid (4 ml) to prepare a suspension which was then stirred at 70° C. for 1.5 hr. The solvent was removed by distillation under the reduced pressure, water was added to the residue, and the mixture was neutralized with sodium hydrogencarbonate powder and was then extracted with chloroform. The chloroform layer was then washed with water and saturated brine and was dried over anhydrous magnesium sulfate. The solvent was removed by distillation under the reduced pressure. The residue was purified by column chromatography using acetone-hexane to give the title compound (145 mg, yield 100%).

$^1$H-NMR (CDCl$_3$, 400 MHz): δ 2.42 (s, 3H), 3.99 (s, 3H), 4.00 (s, 3H), 6.41 (d, J=5.2 Hz, 1H), 7.01 (d, J=8.8 Hz, 1H), 7.12 (dd, J=8.8 Hz, J=2.8 Hz, 1H), 7.24 (s, 1H), 7.42 (m, 2H), 7.58 (s, 1H), 8.46 (d, J=5.2 Hz, 1H)

Mass spectrometric value (ESI-MS, m/z): 340 (M+1)$^+$

Compound 177: 1-[2-(6,7-Dimethoxy-quinolin-4-yloxy)-5-methoxy-phenyl]-ethanone hydrochloride 2-Hydroxy-5-methoxyacetophenone (11.1 g), 4-chloro-6,7-dimethoxyquinoline (5.00 g), and 4-dimethylaminopyridine (8.10 g) were suspended in o-dichlorobenzene (40 ml) to prepare a suspension which was then stirred at 120° C. for 48 hr. The reaction solution was cooled to room temperature, and the solvent was then removed by distillation under the reduced pressure. Water was added to the residue, and the mixture was extracted with chloroform. The chloroform layer was then washed with water and saturated brine and was dried over anhydrous magnesium sulfate. The solvent was removed by distillation under the reduced pressure. The residue was purified by column chromatography using acetone-hexane to give 1-[2-(6,7-dimethoxy-quinolin-4-yloxy)-5-methoxy-phenyl]-ethanone (802 mg, yield 10%).

1-[2-(6,7-Dimethoxy-quinolin-4-yloxy)-5-methoxy-phenyl]-ethanone (802 mg) was dissolved in a hydrochloric acid-methanol solution (20 ml) to prepare a solution which was then stirred at room temperature overnight. The solvent was removed by distillation under the reduced pressure, and the residue was washed with ethyl acetate and was dried in vacuo to give the title compound (885 mg, yield 10%).

$^1$H-NMR (CD$_3$OD, 400 MHz): δ 2.52 (s, 3H), 3.93 (s, 3H), 4.06 (s, 3H), 4.12 (s, 3H), 6.78 (d, J=6.8 Hz, 1H), 7.38 (m, 2H), 7.45 (s, 1H), 7.59 (d, J=2.8 Hz, 1H), 7.81 (s, 1H), 8.60 (d, J=6.8 Hz, 1H)

Mass spectrometric value (ESI-MS, m/z): 354 (M+1-HCl)$^+$

Compound 178: 1-[2-(6,7-Dimethoxy-quinolin-4-yloxy)-5-ethoxy-phenyl]-ethanone

1-[2-(6,7-Dimethoxy-quinolin-4-yloxy)-5-hydroxy-phenyl]-ethanone (compound 176) (75 mg) was dissolved in N,N-dimethylformamide (2 ml) to prepare a solution. Ethyl iodide (103 mg) and potassium carbonate (153 mg) were added to the solution, and the mixture was stirred at room temperature overnight. The solvent was removed by distillation under the reduced pressure, water was then added to the residue, and the mixture was extracted with ethyl acetate. The ethyl acetate layer was then washed with water and was dried over anhydrous magnesium sulfate. The solvent was removed by distillation under the reduced pressure, and the residue was purified by thin layer chromatography using acetone-hexane to give the title compound (50 mg, yield 62%).

$^1$H-NMR (CDCl$_3$, 400 MHz): δ 1.38 (t, J=6.8 Hz, 3H), 2.41 (s, 3H), 3.98 (s, 6H), 4.04 (q, J=6.8 Hz, 2H), 6.30 (d, J=5.2 Hz, 1H), 7.00-7.07 (m, 2H), 7.34 (d, J=2.8 Hz, 1H), 7.36 (s, 1H), 7.49 (s, 1H), 8.41 (d, J=5.2 Hz, 1H)

Mass spectrometric value (ESI-MS, m/z): 368 (M+1)$^+$

Compound 179: 1-[2-(6,7-Dimethoxy-quinolin-4-yloxy)-5-propoxy-phenyl]-ethanone

1-[2-(6,7-Dimethoxy-quinolin-4-yloxy)-5-hydroxy-phenyl]-ethanone (compound 176) (75 mg) was dissolved in N,N-dimethylformamide (2 ml) to prepare a solution. Propyl iodide (113 mg) and potassium carbonate (153 mg) were added to the solution, and the mixture was stirred at room temperature overnight. The solvent was removed by distillation under the reduced pressure, water was then added to the residue, and the mixture was extracted with ethyl acetate. The ethyl acetate layer was then washed with water and was dried over anhydrous magnesium sulfate. The solvent was removed by distillation under the reduced pressure, and the residue was purified by thin layer chromatography using acetone-hexane to give the title compound (22 mg, yield 26%).

$^1$H-NMR (CDCl$_3$, 400 MHz): δ 0.99 (t, J=7.4 Hz, 3H), 1.77 (m, 2H), 2.41 (s, 3H), 3.92 (t, J=6.4 Hz, 2H), 3.98 (s, 6H), 6.30 (d, J=5.2 Hz, 1H), 6.99-7.08 (m, 2H), 7.34 (d, J=2.8 Hz, 1H), 7.37 (s, 1H), 7.50 (s, 1H), 8.41 (d, J=5.2 Hz, 1H)

Mass spectrometric value (ESI-MS, m/z): 382 (M$^+$+1)

Compound 180: 1-[5-Butoxy-2-(6,7-dimethoxy-quinolin-4-yloxy)-phenyl]-ethanone

1-[2-(6,7-Dimethoxy-quinolin-4-yloxy)-5-hydroxy-phenyl]-ethanone (compound 176) (54 mg) was dissolved in N,N-dimethylformamide (2 ml) to prepare a solution. Butyl iodide (88 mg) and potassium carbonate (110 mg) were added to the solution, and the mixture was stirred at room temperature for 3 hr. The solvent was removed by distillation under the reduced pressure, water was then added to the residue, and the mixture was extracted with ethyl acetate. The ethyl acetate layer was then washed with water and was dried over anhydrous magnesium sulfate. The solvent was removed by distillation under the reduced pressure, and the residue was purified by thin layer chromatography using acetone-hexane to give the title compound (41 mg, yield 65%).

¹H-NMR (CDCl₃, 400 MHz): δ 0.92 (t, J=7.4 Hz, 3H), 1.44 (m, 2H), 1.74 (m, 2H), 2.41 (s, 3H), 3.93-4.05 (m, 8H), 6.30 (d, J=5.2 Hz, 1H), 6.98-7.12 (m, 2H), 7.34 (d, J=3.2 Hz, 1H), 7.37 (s, 1H), 7.49 (s, 1H), 8.41 (d, J=5.2 Hz, 1H)

Mass spectrometric value (ESI-MS, m/z): 396 (M+1)⁺

Compound 181: 1-[4-Chloro-2-(6,7-dimethoxy-quinolin-4-yloxy)-phenyl]-ethanone

4-Chloro-2-hydroxyacetophenone (45 mg), 4-chloro-6,7-dimethoxyquinoline (60 mg), and 4-dimethylaminopyridine (95 mg) are suspended in o-dichlorobenzene (10 ml) to prepare a suspension which was then stirred at 120° C. overnight and then at 140° C. for 5 hr. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate, and the solvent was removed by distillation under the reduced pressure, and the residue was purified by thin layer chromatography using acetone-hexane to give the title compound (11 mg, yield 12%).

¹H-NMR (CDCl₃, 400 MHz): δ 2.54 (s, 3H), 4.04 (s, 3H), 4.07 (s, 3H), 6.51 (d, J=5.4 Hz, 1H), 7.14 (d, J=2.0 Hz, 1H), 7.35 (dd, J=2.0 Hz, 8.6 Hz, 1H), 7.48 (m, 2H), 7.91 (d, J=8.5 Hz, 1H), 8.57 (d, J=5.4 Hz, 1H)

Mass spectrometric value (ESI-MS, m/z): 358 (M+1)⁺

Compound 182: 1-[6-(6,7-Dimethoxy-quinolin-4-yloxy)-indan-5-yl]-ethanone

5-Indanol (500 mg) was dissolved in dichloromethane (5 ml) to prepare a solution. Pyridine (439 mg) and acetyl chloride (349 mg) were added to the solution, and the mixture was stirred at room temperature for 6 hr. The solvent was removed by distillation under the reduced pressure, water was then added to the residue, and the mixture was extracted with ethyl acetate. The ethyl acetate layer was then washed with water and was dried over anhydrous magnesium sulfate. The solvent was removed by distillation under the reduced pressure, and the residue was purified by column chromatography using chloroform to give indan-5-yl acetate (599 mg, yield 92%).

Indan-5-yl acetate (599 mg) and scandium trifluoromethane sulfonate (201 mg) were suspended in toluene (5 ml), and the suspension was stirred at 140° C. overnight. The reaction solution was cooled to room temperature and was then filtered. The solvent was removed from the filtrate by distillation under the reduced pressure, water was then added to the residue, and the mixture was extracted with ethyl acetate. The ethyl acetate layer was then washed with water and saturated brine and was dried over anhydrous sodium sulfate. The solvent was removed by distillation under the reduced pressure, and the residue was purified by column chromatography using acetone-hexane to give 1-(6-hydroxy-indan-5-yl)-ethanone (275 mg, yield 46%).

1-(6-Hydroxyindan-5-yl)-ethanone (275 mg), 4-chloro-6,7-dimethoxyquinoline (173 mg), and 4-dimethylaminopyridine (286 mg) were suspended in o-dichlorobenzene (5 ml) to prepare a suspension which was stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using acetone-hexane to give the title compound (37 mg, yield 13%).

¹H-NMR (CDCl₃, 400 MHz): δ 2.09 (m, 2H), 2.41 (s, 3H), 2.82-2.92 (m, 4H), 3.97 (s, 6H), 6.35 (d, J=5.2 Hz, 1H), 6.91 (s, 1H), 7.37 (s, 1H), 7.48 (s, 1H), 7.70 (s, 1H), 8.42 (d, J=5.2 Hz, 1H)

Mass spectrometric value (ESI-MS, m/z): 364 (M+1)⁺

Compound 183: 1-[2-(6,7-Dimethoxy-quinolin-4-yloxy)-5-isopropyl-4-methyl-phenyl]-ethanone 4-Isopropyl-3-methylphenol (1.00 g) was dissolved in dichloromethane (10 ml) to prepare a solution. Pyridine (724 mg) and acetyl chloride (615 mg) were added to the solution, and the mixture was stirred at room temperature overnight. The solvent was removed by distillation under the reduced pressure, water was then added to the residue, and the mixture was extracted with chloroform. The chloroform layer was washed with water and was dried over anhydrous magnesium sulfate, and the solvent was removed by distillation under the reduced pressure. The residue was dried under the reduced pressure to give 4-isopropyl-3-methylphenyl acetate (1.41 g, yield 100%).

4-Isopropyl-3-methylphenyl acetate (1.41 g) and scandium trifluoromethane sulfonate (433 mg) were suspended in toluene (5 ml) to prepare a suspension which was then stirred at 140° C. overnight. The reaction solution was cooled to room temperature and was filtered, and the solvent was then removed from the filtrate by distillation under the reduced pressure. Water was then added to the residue, and the mixture was extracted with ethyl acetate. The ethyl acetate layer was then washed with water and saturated brine and was dried over anhydrous sodium sulfate. The solvent was removed by distillation under the reduced pressure, and the residue was purified by column chromatography using acetone-hexane to give 1-(2-hydroxy-5-isopropyl-4-methyl-phenyl)ethanone (13 mg, yield 1%).

1-(2-Hydroxy-5-isopropyl-4-methyl-phenyl)-ethanone (13 mg), 4-chloro-6,7-dimethoxyquinoline (30 mg), and 4-dimethylaminopyridine (25 mg) were suspended in o-dichlorobenzene (3 ml) to prepare a suspension which was then stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using acetone-hexane to give the title compound (2 mg, yield 7%).

¹H-NMR (CDCl₃, 400 MHz): δ 1.23 (d, J=7.2 Hz, 6H), 2.33 (s, 3H), 2.42 (s, 3H), 3.10 (m, 1H), 3.98 (s, 3H), 4.03 (s, 3H), 6.42 (d, J=5.6 Hz, 1H), 6.88 (s, 1H), 7.19 (s, 1H), 7.47 (s, 1H), 7.77 (s, 1H), 8.41 (d, J=5.6 Hz, 1H)

Mass spectrometric value (ESI-MS, m/z): 380 (M+1)⁺

Compound 184: 1-[4-Chloro-2-(6,7-dimethoxy-quinolin-4-yloxy)-5-methyl-phenyl]-ethanone 3-Chloro-4-methylphenol (1.00 g) was dissolved in dichloromethane (10 ml) to prepare a solution. Pyridine (747 mg) and acetyl chloride (656 mg) were added to the solution, and the mixture was stirred at room temperature overnight. The solvent was removed by distillation under the reduced pressure, water was then added to the residue, and the mixture was extracted with chloroform. The chloroform layer was washed with water and was dried over anhydrous magnesium sulfate, and the solvent was then removed by distillation under the reduced pressure. The residue was dried under the reduced pressure. Scandium trifluoromethanesulfonate (414 mg) was added to the compound thus obtained, and the mixture was suspended in toluene (5 ml) to prepare a suspension which was then heated under reflux overnight. The reaction solution was cooled to room temperature, and the reaction solution was then filtered. The solvent was removed from the filtrate by distillation under the reduced pressure, water was then added to the residue, and the mixture was extracted with ethyl acetate. The ethyl acetate layer was then washed with water and saturated brine and was dried over anhydrous sodium sulfate. The solvent was removed by distillation under the reduced pressure, and the residue was purified by column chromatography using acetone-hexane to give 1-(4-chloro-2-hydroxy-5-methyl-phenyl)-ethanone (193 mg, yield 15%).

1-(4-Chloro-2-hydroxy-5-methyl-phenyl)-ethanone (193 mg), 4-chloro-6,7-dimethoxyquinoline (468 mg), and 4-dimethylaminopyridine (385 mg) were suspended in o-dichlorobenzene (5 ml) to prepare a suspension which was then stirred at 140° C. for 24 hr. The reaction solution was cooled to room temperature, water was then added to the reaction solution, and the mixture was extracted with ethyl acetate. The ethyl acetate layer was then washed with water and saturated brine and was dried over anhydrous magnesium sulfate. The solvent was removed by distillation under the reduced pressure, and the residue was purified by thin layer chromatography using acetone-hexane to give the title compound (39 mg, yield 10%).

$^1$H-NMR (CDCl$_3$, 400 MHz): δ 2.36 (s, 3H), 2.43 (s, 3H), 3.96 (s, 3H), 3.98 (s, 3H), 6.39 (d, J=5.2 Hz, 1H), 7.09 (s, 1H), 7.39 (s, 1H), 7.43 (s, 1H), 7.75 (s, 1H), 8.46 (d, J=5.2 Hz, 1H)

Mass spectrometric value (ESI-MS, m/z): 372 (M+1)$^+$

Compound 185: 1-[4-Tert-butyl-2-(6,7-dimethoxy-quinolin-4-yloxy)-5-methoxyphenyl]-ethanone 3-Tert-butyl-4-methoxyphenol (1.00 g) was dissolved in dichloromethane (10 ml) to prepare a solution. Pyridine (658 mg) and acetyl chloride (599 mg) were added to the solution, and the mixture was stirred at room temperature overnight. The solvent was removed by distillation under the reduced pressure, water was then added to the residue, and the mixture was extracted with chloroform. The chloroform layer was washed with water and was dried over anhydrous magnesium sulfate, and the solvent was then removed by distillation under the reduced pressure. The residue was dried under the reduced pressure. Scandium trifluoromethane sulfonate (327 mg) was added to the compound thus obtained, the mixture was suspended in toluene (5 ml), and the suspension was heated under reflux overnight. The reaction solution was cooled to room temperature, and the reaction solution was then filtered. The solvent was removed from the filtrate by distillation under the reduced pressure, water was then added to the residue, and the mixture was extracted with ethyl acetate. The ethyl acetate layer was then washed with water and saturated brine and was dried over anhydrous sodium sulfate. The solvent was removed by distillation under the reduced pressure, and the residue was purified by column chromatography using acetone-hexane to give 1-(4-tert-butyl-2-hydroxy-5-methoxy-phenyl)-ethanone (30 mg, yield 5%).

1-(4-Tert-butyl-2-hydroxy-5-methoxyphenyl)-ethanone (30 mg), 4-chloro-6,7-dimethoxyquinoline (87 mg), and 4-dimethylaminopyridine (48 mg) were suspended in o-dichlorobenzene (4 ml) to prepare a suspension which was then stirred at 140° C. for 24 hr. The reaction solution was cooled to room temperature, water was then added to the reaction solution, and the mixture was extracted with ethyl acetate. The ethyl acetate layer was then washed with water and saturated brine and was dried over anhydrous magnesium sulfate. The solvent was removed by distillation under the reduced pressure, and the residue was purified by thin layer chromatography using acetone-hexane to give the title compound (7 mg, yield 13%).

$^1$H-NMR (CDCl$_3$, 400 MHz): δ 1.29 (s, 9H), 2.39 (s, 3H), 3.87 (s, 3H), 3.99 (s, 6H), 6.29 (d, J=5.6 Hz, 1H), 7.00 (s, 1H), 7.39 (s, 1H), 7.44 (s, 1H), 7.53 (s, 1H), 8.42 (d, J=5.6 Hz, 1H)

Mass spectrometric value (ESI-MS, m/z): 410 (M+1)$^+$

Compound 186: 1-[2-(6,7-Dimethoxy-quinolin-4-yloxy)-4-methyl-5-methylsulfanyl-phenyl]-ethanone 3-Methyl-4-methylsulfanylphenol (1.00 g) was dissolved in dichloromethane (10 ml) to prepare a solution. Pyridine (724 mg) and acetyl chloride (615 mg) were added to the solution, and the mixture was stirred at room temperature overnight. The solvent was removed by distillation under the reduced pressure. Water was then added to the residue, and the mixture was extracted with chloroform. The chloroform layer was washed with water and was dried over anhydrous magnesium sulfate. The solvent was removed by distillation under the reduced pressure. The residue was purified by column chromatography using chloroform to give 3-methyl-4-methylsulfanyl-phenyl acetate (1.00 g, yield 80%).

3-Methyl-4-methylsulfanyl-phenyl acetate (1.00 g) and scandium trifluoromethane sulfonate (300 mg) were suspended in toluene (5 ml) to prepare a suspension which was heated under reflux overnight. The suspension was cooled to room temperature, and the reaction solution was then filtered. The solvent was removed from the filtrate by distillation under the reduced pressure, water was then added to the residue, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using acetone-hexane to give 1-(2-hydroxy-4-methyl-5-methylsulfanyl-phenyl)-ethanone (150 mg, yield 15%).

1-(2-Hydroxy-4-methyl-5-methylsulfanyl-phenyl)ethanone (29 mg), 4-chloro-6,7-dimethoxyquinoline (66 mg), and 4-dimethylaminopyridine (54 mg) were suspended in o-dichlorobenzene (2 ml) to prepare a suspension which was then stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous magnesium sulfate. The solvent was removed by distillation under the reduced pressure, and the residue was purified by thin layer chromatography using acetone-hexane to give the title compound (17 mg, yield 30%).

$^1$H-NMR (CDCl$_3$, 400 MHz): δ 2.27 (s, 3H), 2.35 (s, 3H), 2.46 (s, 3H), 3.98 (s, 6H), 6.30 (d, J=5.6 Hz, 1H), 6.88 (s, 1H), 7.11 (s, 1H), 7.39 (s, 1H), 7.53 (s, 1H), 8.49 (d, J=5.6 Hz, 1H)

Mass spectrometric value (ESI-MS, m/z): 767 (2M+1)$^+$

Compound 187: Methyl 8-[2-(6,7-dimethoxy-quinolin-4-yloxy)-5-methyl-phenyl]-8-oxo-octanoate 4-Methylanisole (732 mg) was dissolved in nitromethane (30 ml) to prepare a solution. Anhydrous lithium perchlorate (3.8 g), methyl 7-chlorocarbonyl-heptanoate (1.28 ml), and scandium triflate (300 mg) were added to the solution, and the mixture was stirred at room temperature for 4 hr. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by column chromatography using acetone-hexane to give methyl 8-(2-methoxy-5-methylphenyl)-8-oxo-octanoate (992 mg, yield 57%).

Methyl 8-(2-methoxy-5-methyl-phenyl)-8-oxo-octanoate (992 mg) was dissolved in methylene chloride (30 ml) to prepare a solution. 1 M boron tribromide (5.0 ml) was added at −78° C. to the solution, and the mixture was stirred at room temperature for 30 min. Water was added to the reaction solution, and the mixture was extracted with chloroform. The chloroform layer was then washed with water and was dried over anhydrous sodium sulfate. The solvent was removed by distillation under the reduced pressure. The residue was purified by column chromatography using acetone-hexane to give methyl 8-(2-hydroxy-5-methyl-phenyl)-8-oxo-octanoate (271 mg, yield 29%).

Methyl 8-(2-hydroxy-5-methyl-phenyl)-8-oxo-octanoate (271 mg), 4-chloro-6,7-dimethoxyquinoline (220 mg), and 4-dimethylaminopyridine (237 mg) were suspended in o-dichlorobenzene (20 ml) to prepare a suspension which was then stirred at 120° C. overnight. The reaction solution was cooled to room temperature, and the solvent was removed by distillation under the reduced pressure. Water was then added to the residue, and the mixture was extracted with chloroform. The chloroform layer was washed with water and was dried over anhydrous sodium sulfate. The solvent was removed by distillation under the reduced pressure, and the residue was purified by column chromatography using acetone-hexane to give the title compound (16 mg, yield 3.5%).

$^1$H-NMR (CDCl$_3$, 400 MHz): δ 1.13 (m, 4H), 1.47 (m, 2H), 1.56 (m, 2H), 2.17 (t, J=7.6 Hz, 2H), 2.44 (s, 3H), 2.83 (t, J=7.3 Hz, 2H), 3.63 (s, 3H), 4.05 (s, 3H), 4.06 (s, 3H), 6.40 (d, J=5.4 Hz, 1H), 7.05 (d, J=8.3 Hz, 1H), 7.37 (dd, J=2.2 Hz, 8.3 Hz, 1H), 7.45 (s, 1H), 7.54 (s, 1H), 7.63 (d, J=2.0 Hz, 1H), 8.49 (d, J=5.4 Hz, 1H)

Mass spectrometric value (ESI-MS, m/z): 466 (M+1)$^+$

Compound 188: [2-(6,7-Dimethoxy-quinolin-4-yloxy)-5-methyl-phenyl]-(4-hydroxy-phenyl)-methanone 4-Bromophenol (1.00 g) was dissolved in N,N-dimethylformamide (20 ml) to prepare a solution. Imidazole (0.95 g) and tert-butylchlorodimethylsilane (1.05 g) were added to the solution, and the mixture was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by column chromatography using chloroform to give (4-bromo-phenoxy)-tert-butyl-dimethyl-silane (1.586 g, yield 96%).

2-Hydroxy-5-methyl-benzaldehyde (344 mg), 4-chloro-6,7-dimethoxyquinoline (113 mg), and 4-dimethylaminopyridine (313 mg) were suspended in o-dichlorobenzene (5 ml), and the suspension was stirred at 160° C. for 2 hr. The reaction solution was cooled to room temperature, and the solvent was removed by distillation under the reduced pressure. Water was then added to the residue, and the mixture was extracted with chloroform. The chloroform layer was washed with aqueous sodium hydroxide solution and saturated brine and was dried over anhydrous magnesium sulfate. The solvent was removed by distillation under the reduced pressure, and the residue was purified by column chromatography using chloroform to give 2-(6,7-dimethoxy-quinolin-4-yloxy)-5-methyl-benzaldehyde (157 mg, yield 96%).

(4-Bromo-phenoxy)-tert-butyl-dimethyl-silane (175 mg) was dissolved in tetrahydrofuran (3 ml) to prepare a solution which was cooled to −78° C. A 1.41 M n-pentane solution (0.86 ml) of tert-butyllithium was added dropwise to the cooled solution, and the mixture was stirred at −78° C. for 20 min. A solution of 2-(6,7-dimethoxy-quinolin-4-yloxy)-5-methylbenzaldehyde (164 mg) in tetrahydrofuran was added dropwise thereto, and the mixture was stirred at −78° C. for one hr and then at 0° C. for 30 min. A saturated ammonium chloride solution was added thereto to stop the reaction, and the mixture was then extracted with ethyl acetate. The ethyl acetate layer was then washed with saturated brine and was dried over anhydrous sodium sulfate. The solvent was removed by distillation under the reduced pressure, and the residue as such was used for the next reaction.

The residue (252 mg) of the reaction was dissolved in methylene chloride (5 ml) to prepare a solution. A solution of 1,8-diazabicyclo[5.4.0]undeca-7-ene (154 mg) in methylene chloride was added to the solution, and the mixture was cooled to −78° C. A solution of N-tert-butylbenzenesulfineimidoyl (164 mg) in methylene chloride was added thereto, and the mixture was stirred at −78° C. for one hr. Further, a solution of N-tert-butylbenzenesulfineimidoyl (55 mg) in methylene chloride was added thereto, and the mixture was stirred at −78° C. for 30 min and then at 0° C. for 20 min. Water was added to the reaction solution, and the mixture was extracted with chloroform. The chloroform layer was then washed with saturated brine and was dried over anhydrous sodium sulfate. The solvent was removed by distillation under the reduced pressure, and the residue as such was used for the next reaction.

A part (384 mg) of the residue of the reaction was dissolved in tetrahydrofuran (5 ml) to prepare a solution which was cooled to 0° C. A solution (1 ml) of tetrabutylammonium fluoride in tetrahydrofuran was then added thereto, and the mixture was stirred for 30 min. Water was added to the reaction solution, and the mixture was extracted with ethyl acetate. The ethyl acetate layer was then washed with saturated brine and was dried over anhydrous magnesium sulfate. The solvent was removed by distillation under the reduced pressure, and the residue was purified by column chromatography using acetone-hexane to give the title compound (128 mg, yield 61%) (3 steps).

$^1$H-NMR (CDCl$_3$, 400 MHz): δ 2.45 (s, 3H), 3.86 (s, 3H), 3.88 (s, 3H), 6.44 (d, J=5.4 Hz, 1H), 6.77 (d, J=8.8 Hz, 2H), 7.07 (s, 1H), 7.14 (d, J=8.0 Hz, 1H), 7.25 (s, 1H), 7.38-7.41 (m, 2H), 7.62 (d, J=8.8 Hz, 2H), 8.33 (d, J=5.4 Hz, 1H)

Mass spectrometric value (ESI-MS, m/z): 416 (M+1)$^+$

Compound 189: [4-(2-Chloro-ethoxy)-phenyl]-[2-(6,7-dimethoxy-quinolin-4-yloxy)-5-methyl-phenyl]-methanone

[2-(6,7-Dimethoxy-quinolin-4-yloxy)-5-methyl-phenyl]-(4-hydroxy-phenyl)-methanone (compound 188) (128 mg) was dissolved in N,N-dimethylformamide to prepare a solution. Potassium carbonate (215 mg) and 1-bromo-2-chloroethane (134 mg) were then added to the solution, and the mixture was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by column chromatography using acetone-hexane to give the title compound (99 mg, yield 69%).

$^1$H-NMR (CDCl$_3$, 400 MHz): δ 2.46 (s, 3H), 3.79 (t, J=5.9 Hz, 2H), 3.84 (s, 3H), 3.99 (s, 3H), 4.19 (t, J=5.9 Hz, 2H), 6.40 (d, J=5.4 Hz, 1H), 6.80 (d, J=8.8 Hz, 2H), 6.94 (s, 1H), 7.16 (d, J=8.1 Hz, 1H), 7.32 (s, 1H), 7.40-7.44 (m, 2H), 7.68 (d, J=8.8 Hz, 2H), 8.41 (d, J=5.4 Hz, 1H)

Mass spectrometric value (ESI-MS, m/z): 478 (M+1)$^+$

Compound 190: [2-(6,7-Dimethoxy-quinolin-4-yloxy)-5-methyl-phenyl]-[4-(2-piperidin-1-yl-ethoxy)-phenyl]-methanone

[4-(2-Chloro-ethoxy)-phenyl]-[2-(6,7-dimethoxy-quinolin-4-yloxy)-5-methyl-phenyl]-methanone (compound 189) (48 mg) was dissolved in N,N-dimethylformamide to prepare a solution. Potassium carbonate (86 mg) and piperidine (52 mg) were then added to the solution, and the mixture was stirred at 80° C. overnight. The reaction solution was cooled to room temperature, and water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by column chromatography using chloroform methanol to give the title compound (31 mg, yield 58%).

$^1$H-NMR (CDCl$_3$, 400 MHz): δ 1.40-1.73 (m, 6H), 2.46 (s, 3H), 3.33-3.48 (m, 4H), 3.83 (s, 3H), 3.99 (s, 3H), 4.17 (t, J=4.6 Hz, 2H), 4.41 (t, J=4.6 Hz, 2H), 6.42 (d, J=5.4 Hz, 1H), 6.84 (d, J=8.8 Hz, 2H), 6.98 (s, 1H), 7.15 (d, J=8.6 Hz, 1H), 7.33 (s, 1H), 7.38-7.43 (m, 2H), 7.71 (d, J=8.8 Hz, 2H), 8.41 (d, J=5.4 Hz, 1H)

Compound 191: [2-(6,7-Dimethoxy-quinolin-4-yloxy)-5-methyl-phenyl]-[4-(2-morpholin-4-yl-ethoxy)-phenyl]-methanone

[4-(2-Chloro-ethoxy)-phenyl]-[2-(6,7-dimethoxy-quinolin-4-yloxy)-5-methyl-phenyl]-methanone (compound 189) (51 mg) was dissolved in N,N-dimethylformamide to prepare a solution. Potassium carbonate (84 mg) and morpholine (46 mg) were then added to the solution, and the mixture was stirred at 80° C. overnight. The reaction solution was cooled to room temperature, and water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by column chromatography using chloroform-methanol to give the title compound (38 mg, yield 68%).

$^1$H-NMR (CDCl$_3$, 400 MHz): δ 2.49 (s, 3H), 3.46 (brs, 4H), 3.64 (brs, 4H), 3.84 (s, 3H), 3.99 (s, 3H), 4.16 (t, d=4.9 Hz, 2H), 4.44 (t, d=4.9 Hz, 2H), 6.41 (d, J=5.4 Hz, 1H), 6.82 (d, J=8.8 Hz, 2H), 6.98 (s, 1H), 7.15 (d, J=7.8 Hz, 1H), 7.32 (s, 1H), 7.41 (d, J=7.8 Hz, 1H), 7.42 (s, 1H), 7.70 (d, J=8.8 Hz, 2H), 8.41 (d, J=5.4 Hz, 1H)

Compound 192: [2-(6,7-Dimethoxy-quinolin-4-yloxy)-5-methoxy-phenyl]-thiazol-2-yl-methanone Thiazole (30 μl) was dissolved in tetrahydrofuran (1 ml) to prepare a solution which was cooled under an argon atmosphere to −78° C. n-Butyllithium (1.56 M hexane solution) (260 μl) was added to the cooled solution, and the mixture was stirred for 2 hr. A solution (2 ml) of 2-(6,7-dimethoxy-quinolin-4-yloxy)-5-methoxy-benzaldehyde (compound 26) (138 mg) in tetrahydrofuran was then added to the reaction solution, and the mixture was stirred at −78° C. for one hr. A saturated ammonium chloride solution was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by column chromatography using acetone-hexane to give [2-(6,7-dimethoxy-quinolin-4-yloxy)-5-methoxy-phenyl]-thiazol-2-yl-methanol (90 mg, yield 52%).

[2-(6,7-Dimethoxy-quinolin-4-yloxy)-5-methoxy-phenyl]-thiazol-2-yl-methanol (90 mg) was dissolved in methanol/methylene chloride (3 ml/9 ml) to prepare a solution, manganese dioxide (90 mg) was added to the solution, and the mixture was stirred at room temperature overnight. The reaction solution was filtered through Celite, water was added to the filtrate, and the mixture was extracted with ethyl acetate. The solvent was removed by distillation under the reduced pressure, and the residue was purified by column chromatography using acetone-hexane to give the title compound (65 mg, yield 74%).

$^1$H-NMR (CDCl$_3$, 400 MHz): δ 3.90 (s, 3H), 3.95 (s, 3H), 4.01 (s, 3H), 6.53 (d, J=5.4 Hz, 1H), 7.14-7.28 (m, 3H), 7.34 (s, 1H), 7.39 (d, J=2.9 Hz, 1H), 7.56 (d, J=3.2 Hz, 1H), 7.87 (d, J=3.2 Hz, 1H), 8.44 (d, J=5.4 Hz, 1H)

Mass spectrometric value (ESI-MS, m/z): 423 (M+1)$^+$

Compound 193: {1-[2-(6,7-Dimethoxy-quinolin-4-yloxy)-4,5-dimethylphenyl]-ethylidene}-hydrazine 1-[2-(6,7-Dimethoxy-quinolin-4-yloxy)-4,5-dimethylphenyl]-1-ethanone (compound 38) (50 mg) was dissolved in ethanol (1.5 ml) to prepare a solution. Hydrazine monohydrate (20 mg) and triethylamine (45 mg) were added to the solution, and the mixture was stirred under reflux for 3 hr. The solvent was removed by distillation under the reduced pressure, water was added to the residue, and the mixture was extracted with ethyl acetate. The ethyl acetate layer was then washed with water and was dried over anhydrous sodium sulfate. The solvent was removed by distillation under the reduced pressure. The residue was purified by thin layer chromatography using hexane-acetone to give the title compound (36 mg, yield 67%).

$^1$H-NMR (CDCl$_3$, 400 MHz): δ 1.96 (s, 3H), 2.27 (s, 3H), 2.31 (s, 3H), 4.05 (s, 3H), 4.06 (s, 3H), 5.17 (brs, 2H), 6.38 (d, J=5.4 Hz, 1H), 6.91 (s, 1H), 7.37 (s, 1H), 7.45 (s, 1H), 7.56 (s, 1H), 8.44 (d, J=5.4 Hz, 1H)

Mass spectrometric value (ESI-MS, m/z): 388 (M+Na)$^+$

Compound 194: N-{1-[2-(6,7-Dimethoxy-quinolin-4-yloxy)-4,5-dimethyl-phenyl]-ethylidene}-N'-pyridin-2-yl-hydrazine 1-[2-(6,7-Dimethoxy-quinolin-4-yloxy)-4,5-dimethylphenyl]-1-ethanone (compound 38) (30 mg) was dissolved in ethanol (1 ml) to prepare a solution. (2-Pyridyl)hydrazine (28 mg) was added to the solution, and the mixture was stirred at 60° C. overnight. Ytterbium triflate (1 mg) was added to the reaction solution, and the mixture was stirred at 60° C. for 5 days. The reaction solution was cooled to room temperature, water was then added to the cooled solution, and the mixture was extracted with ethyl acetate. The ethyl acetate layer was then washed with water and was dried over anhydrous sodium sulfate. The solvent was removed by distillation under the reduced pressure. The residue was purified by thin layer chromatography using hexane-acetone to give the title compound (13 mg, yield 39%).

$^1$H-NMR (CDCl$_3$, 400 MHz): δ 2.08-2.16 (m, 3H), 2.28-2.59 (m, 6H), 3.99-4.07 (m, 6H), 6.38-6.40 (m, 1H), 6.67-6.75 (m, 1H), 6.92-7.57 (m, 6H), 8.01-8.09 (m, 2H), 8.41-8.49 (m, 1H)

Mass spectrometric value (ESI-MS, m/z): 465 (M+Na)$^+$

Compound 195: 1-[2-(6,7-Dimethoxy-quinolin-4-yloxy)-4,5-dimethyl-phenyl]-ethanone oxime 1-[2-(6,7-Dimethoxy-quinolin-4-yloxy)-4,5-dimethylphenyl]-1-ethanone (compound 38) (30 mg) was dissolved in ethanol (1 ml) to prepare a solution. Hydroxylamine hydrochloride (12 mg) and triethylamine (27 mg) were added to the solution, and the mixture was stirred at room temperature overnight. Further, hydroxylamine hydrochloride (12 mg) and triethylamine (27 mg) were then added to the reaction solution, and the mixture was stirred at room temperature for 5 hr. The solvent was removed by distillation under the reduced pressure, water was added to the residue, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using hexane-acetone to give the title compound (10 mg, yield 31%).

$^1$H-NMR (CDCl$_3$, 400 MHz): δ 2.13 (s, 3H), 2.28 (s, 3H), 2.31 (s, 3H), 4.02 (s, 3H), 4.03 (s, 3H), 6.37 (d, J=5.4 Hz, 1H), 6.93 (s, 1H), 7.31 (s, 1H), 7.41 (s, 1H), 7.52 (s, 1H), 8.39 (d, J=5.4 Hz, 1H)

Mass spectrometric value (ESI-MS, m/z): 389 (M+Na)$^+$

Compound 196: 1-[2-(6,7-Dimethoxy-quinolin-4-yloxy)-4,5-dimethyl-phenyl]-ethanone o-methyl-oxime 1-[2-(6,7-Dimethoxy-quinolin-4-yloxy)-4,5-dimethylphenyl]-1-ethanone (compound 38) (30 mg) was dissolved in ethanol (1 ml) to prepare a solution. Methoxyamine hydrochloride (22 mg) and triethylamine (27 mg) were added to the solution, and the mixture was stirred at room temperature for 4 hr. The solvent was removed by distillation under the reduced pressure, and the residue was purified by column chromatography using hexane-acetone to give the title compound (33 mg, yield 98%).

$^1$H-NMR (CDCl$_3$, 400 MHz): δ 2.05 (s, 3H), 2.27 (s, 3H), 2.31 (s, 3H), 3.79 (s, 3H), 4.04 (s, 3H), 4.07 (s, 3H), 6.38 (d, J=5.1 Hz, 1H), 6.93 (s, 1H), 7.32 (s, 1H), 7.41 (s, 1H), 7.54 (s, 1H), 8.45 (d, J=5.4 Hz, 1H)

Mass spectrometric value (ESI-MS, m/z): 403 (M+Na)$^+$

Compound 197: 1-[2-(6,7-Dimethoxy-quinolin-4-yloxy)-4,5-dimethyl-phenyl]-ethanone o-allyl-oxime 1-[2-(6,7-Dimethoxy-quinolin-4-yloxy)-4,5-dimethylphenyl]-1-ethanone (compound 38) (30 mg) was dissolved in ethanol (1 ml) to prepare a solution. Allyloxyamine hydrochloride (29 mg) and triethylamine (27 mg) were added to the solution, and the mixture was stirred at room temperature for 4 hr. The solvent was removed by distillation under the reduced pressure, and the residue was purified by column chromatography using hexane-acetone to give the title compound (32 mg, yield 88%).

$^1$H-NMR (CDCl$_3$, 400 MHz): δ 2.10 (s, 3H), 2.27 (s, 3H), 2.31 (s, 3H), 4.04 (s, 3H), 4.05 (s, 3H), 4.50 (ddd, J=1.4, 1.4, 5.6 Hz, 2H), 5.04-5.16 (m, 2H), 5.79-5.91 (m, 1H), 6.38 (d, J=5.1 Hz, 1H), 6.93 (s, 1H), 7.31 (s, 1H), 7.41 (s, 1H), 7.54 (s, 1H), 8.45 (d, J=5.1 Hz, 1H)

Mass spectrometric value (ESI-MS, m/z): 407 (M+1)$^+$

Compound 198: 1-[2-(6,7-Dimethoxy-quinolin-4-yloxy)-4,5-dimethyl-phenyl]-ethanone o-benzyl-oxime 1-[2-(6,7-Dimethoxy-quinolin-4-yloxy)-4,5-dimethylphenyl]-1-ethanone (compound 38) (30 mg) was dissolved in ethanol (1 ml) to prepare a solution. Benzyloxyamine hydrochloride (43 mg) and triethylamine (27 mg) were added to the solution, and the mixture was stirred at room temperature for 4 hr. The mixture was then stirred at 50° C. for 3 days. The reaction solution was cooled to room temperature, the solvent was then removed by distillation under the reduced pressure, and the residue was purified by thin layer chromatography using hexane-acetone to give the title compound (38 mg, yield 94%).

$^1$H-NMR (CDCl$_3$, 400 MHz): δ 2.15 (s, 3H), 2.30 (s, 3H), 2.33 (s, 3H), 4.04 (s, 3H), 4.08 (s, 3H), 5.07 (s, 2H), 6.39 (d, J=5.4 Hz, 1H), 6.95 (s, 1H), 7.19-7.31 (m, 5H), 7.33 (s, 1H), 7.45 (s, 1H), 7.55 (s, 1H), 8.46 (d, J=5.4 Hz, 1H)

Mass spectrometric value (ESI-MS, m/z): 457 (M+1)$^+$

Compound 199: 1-[2-(6,7-Dimethoxy-quinolin-4-yloxy)-4,5-dimethyl-phenyl]-ethanone o-phenyl-oxime 1-[2-(6,7-Dimethoxy-quinolin-4-yloxy)-4,5-dimethylphenyl]-1-ethanone (compound 38) (30 mg) was dissolved in ethanol (1 ml) to prepare a solution. Phenoxyamine hydrochloride (39 mg) and triethylamine (27 mg) were added to the solution, and the mixture was stirred at room temperature for 4 hr. The reaction solution was then stirred at 50° C. for 3 days. The reaction solution was cooled to room temperature, and the solvent was then removed by distillation under the reduced pressure. The residue was purified by thin layer chromatography using hexane-acetone to give the title compound (10 mg, yield 26%).

$^1$H-NMR (CDCl$_3$, 400 MHz): δ 2.30 (s, 6H), 2.34 (s, 3H), 3.99 (s, 3H), 4.04 (s, 3H), 6.45 (d, J=5.1 Hz, 1H), 6.96 (t, J=7.3 Hz, 1H), 6.97 (s, 1H), 7.03 (s, 1H), 7.05 (s, 1H), 7.20 (dd, J=8.8, 8.8 Hz, 2H), 7.42 (d, J=4.4 Hz, 2H), 7.53 (s, 1H), 8.46 (d, J=5.4 Hz, 1H)

Mass spectrometric value (ESI-MS, m/z): 443 (M+1)$^+$

Compound 200: 1-[3-(6,7-Dimethoxy-quinolin-4-yloxy)-naphthalen-2-yl]-ethanone

Dichloromethane (304 ml) and thionyl chloride (76 ml) were added to 3-hydroxynaphthalene-2-carboxylic acid (5 g), and the mixture was stirred under reflux for 4 hr. The solvent was then removed by distillation under the reduced pressure. Dioxane (200 ml) was added to the residue to prepare a solution. A solution of O,N-dimethylhydroxylamine hydrochloride (7.8 g) in a 2 N aqueous sodium hydroxide solution was added thereto, and the mixture was stirred at room temperature for one hr. Under ice cooling, the reaction solution was acidified by the addition of 4 N hydrochloric acid, and the mixture was extracted with ethyl acetate. The ethyl acetate layer was then washed with an aqueous potassium carbonate solution and water and was dried over anhydrous sodium sulfate. The solvent was removed by distillation under the reduced pressure to give 3-hydroxynaphthalene-2-carboxylic acid methoxymethylamide (660 mg, yield 11%).

3-Hydroxynaphthalene-2-carboxylic acid methoxymethylamide (600 mg) was dissolved in tetrahydrofuran (36 ml) to prepare a solution. A solution (9.8 ml) of 0.93 M methylmagnesium bromide in tetrahydrofuran was added thereto at −78° C., temperature of the mixture was raised to room temperature, and the mixture was stirred for 1.5 hr. A saturated aqueous ammonium chloride solution was added to stop the reaction, water was added thereto, and the mixture was extracted with ethyl acetate. The ethyl acetate layer was then washed with an aqueous potassium carbonate solution, was washed with water and was dried over anhydrous sodium sulfate. The solvent was removed by distillation under the reduced pressure, and the residue was purified by column chromatography using hexane-ethyl acetate to give 1-(3-hydroxynaphthalen-2-yl)-ethanone (378 mg, yield 78%).

1-(3-Hydroxynaphthalen-2-yl)-ethanone (249 mg), 4-chloro-6,7-dimethoxyquinoline (100 mg), and 4-(N,N-dimethylamino)-pyridine (164 mg) were dissolved in 1,2-dichlorobenzene (5 ml) to prepare a solution which was then stirred at 130° C. overnight. The reaction solution was cooled to room temperature, and the solvent was then removed by distillation under the reduced pressure. Water was added to the residue, and the mixture was extracted with ethyl acetate. The ethyl acetate layer was then washed with water and was dried over anhydrous sodium sulfate. The solvent was removed by distillation under the reduced pressure. The residue was purified by thin layer chromatography using hexane-acetone to give the title compound (27 mg, yield 16%).

$^1$H-NMR (CDCl$_3$, 400 MHz): δ 2.60 (s, 3H), 4.05 (s, 3H), 4.06 (s, 3H), 6.46 (d, J=5.2 Hz, 1H), 7.46 (s, 1H), 7.51-7.62 (m, 4H), 7.77 (d, J=8 Hz, 1H), 7.99 (d, J=7.6 Hz, 1H), 8.44 (s, 1H), 8.49 (d, J=5.6 Hz, 1H)

Mass spectrometric value (ESI-MS, m/z): 374 (M+1)$^+$

Compound 201: Propyl 3-(6,7-dimethoxy-quinolin-4-yloxy)-naphthalene-2-carboxylate 2-Hydroxy-naphthalene-3-carboxylic acid (2 g) was dissolved in 1-propanol (10 ml) to prepare a solution. The solution was brought to 0° C., and thionyl chloride (1.16 ml) was gradually added dropwise. The mixture was stirred at 120° C. for 2 hr. The reaction solution was cooled to room temperature, and the solvent was removed by distillation under the reduced pressure. Water was then added to the residue, and the mixture was extracted with chloroform. The chloroform layer was washed with saturated brine and was dried over anhydrous sodium sulfate. The solvent was removed by distillation under the reduced pressure, and the residue was purified by column chromatography using chloroform to give propyl 2-hydroxy-3-naphthoate (2.15 g, yield 88%).

Propyl 2-hydroxy-3-naphthoate (400 mg), 4-chloro-6,7-dimethoxyquinoline (130 mg), and 4-dimethylaminopyridine (213 mg) were suspended in o-dichlorobenzene (4 ml), and the suspension was stirred at 140° C. for 12.5 hr. The reaction solution was cooled to room temperature, water was then added thereto, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (108 mg, yield 44%).

$^1$H-NMR (CDCl$_3$, 400 MHz): δ 0.71 (t, J=7.6 Hz, 3H), 1.29-1.38 (m, 2H), 4.03 (t, J=6.8 Hz, 2H), 4.08 (s, 3H), 4.08 (s, 3H), 6.35 (d, J=5.4 Hz, 1H), 7.53 (s, 1H), 7.57-7.68 (m, 4H), 7.84 (d, J=8.3 Hz, 1H), 8.02 (d, J=8.3 Hz, 1H), 8.44 (d, J=5.4 Hz, 1H), 8.67 (s, 1H)

Mass spectrometric value (ESI-MS, m/z): 418 (M+1)$^+$

Compound 202: 6,7-Dimethoxy-4-(2-methyl-pyridin-3-yloxy)-quinoline

4-Chloro-6,7-dimethoxyquinoline (245 mg), 2-methyl-3-pyridinol (227 mg), and 4-dimethylaminopyridine (420 mg) were suspended in o-dichlorobenzene (13 ml), and the suspension was stirred at 135° C. for 2 days. The reaction solution was cooled to room temperature. The solvent was then removed by distillation under the reduced pressure. The residue was purified by column chromatography using acetone-chloroform to give the title compound (324 mg, yield 100%).

$^1$H-NMR (CDCl$_3$, 400 MHz): δ 2.48 (s, 3H), 4.07 (s, 3H), 4.07 (s, 3H), 6.28 (d, J=5.4 Hz, 1H), 7.27 (m, 1H), 7.42-7.46 (m, 2H), 7.56 (d, J=1.7 Hz, 1H), 8.48-8.50 (m, 2H)

Mass spectrometric value (ESI-MS, m/z): 297 (M+1)$^+$

Compound 203: 4-(2-Bromo-pyridin-3-yloxy)-6,7-dimethoxyquinoline

4-Chloro-6,7-dimethoxyquinoline (226 mg), 2-bromo-3-pyridinol (250 mg), and 4-dimethylaminopyridine (400 mg) were suspended in o-dichlorobenzene (10 ml), and the suspension was stirred at 140° C. for 2 hr. The reaction solution was cooled to room temperature, the solvent was then removed by distillation under the reduced pressure, and the residue was purified by column chromatography using acetone-chloroform to give the title compound (21 mg, yield 6%).

$^1$H-NMR (CDCl$_3$, 400 MHz): δ 4.06 (s, 3H), 4.06 (s, 3H), 6.38 (d, J=5.4 Hz, 1H), 7.39 (dd, J=4.6, 7.8 Hz, 1H), 7.46 (s, 1H), 7.53 (dd, J=1.7, 8.1 Hz, 1H), 7.54 (s, 1H), 8.37 (dd, J=1.6, 4.6 Hz, 1H), 8.54 (d, J=5.1 Hz, 1H)

Mass spectrometric value (ESI-MS, m/z): 361 (M+1)$^+$

Compound 204: 4-(2-Cyclopentyloxy-pyridin-3-yloxy)-6,7-dimethoxy-quinoline

4-Chloro-6,7-dimethoxyquinoline (252 mg), 2,3-dihydroxypyridine (396 mg), and 4-dimethylaminopyridine (400 mg) were suspended in o-dichlorobenzene (13 ml), and the suspension was stirred at 160° C. overnight. The reaction solution was cooled to room temperature, the solvent was then removed by distillation under the reduced pressure, and the residue was purified by column chromatography using acetone-chloroform to give 6,7-dimethoxy-4-(2-hydroxy-pyridin-3-yloxy)-quinoline (84 mg, yield 25%).

6,7-Dimethoxy-4-(2-hydroxy-pyridin-3-yloxy)-quinoline (21 mg) was dissolved in chloroform (7 ml) to prepare a solution. Potassium carbonate (300 mg) and cyclopentyl bromide (0.2 ml) were added to the solution. The mixture was stirred at room temperature overnight, water was added to the reaction solution, and the mixture was extracted with ethyl acetate. The organic layer was washed with water and was dried over anhydrous sodium sulfate. The solvent was removed by distillation under the reduced pressure, and the residue was purified by column chromatography using acetone-chloroform to give the title compound (14 mg, yield 55%).

$^1$H-NMR (CDCl$_3$, 400 MHz): δ 1.23-1.81 (m, 8H), 4.06 (s, 3H), 4.06 (s, 3H), 5.43 (m, 1H), 6.31 (d, J=5.1 Hz, 1H), 6.95 (dd, J=1.1, 7.6 Hz, 1H), 7.43 (s, 1H), 7.49 (m, 1H), 7.58 (s, 1H), 8.10 (m, 1H), 8.46 (d, J=5.1 Hz, 1H)

Mass spectrometric value (ESI-MS, m/z): 367 (M+1)$^+$

Compound 205: 4-(6-Fluoro-pyridin-3-yloxy)-6,7-dimethoxyquinoline

6-Fluoro-3-hydroxypyridine (10 mg), 4-chloro-6,7-dimethoxyquinoline (59 mg), and 4-dimethylaminopyridine (32 mg) were suspended in o-dichlorobenzene (2 ml), and the suspension was stirred at 140° C. for 3.5 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using acetone-chloroform to give the title compound (20 mg, yield 76%).

$^1$H-NMR (CDCl$_3$, 400 MHz): δ 3.98 (s, 6H), 6.35 (d, J=5.2 Hz, 1H), 6.99 (dd, J=8.8 Hz, 3.6 Hz, 1H), 7.36 (s, 1H), 7.44 (s, 1H), 7.56 (m, 1H), 8.09 (s, 1H), 8.46 (d, J=5.2 Hz, 1H)

Mass spectrometric value (ESI-MS, m/z): 301 (M+1)$^+$

Compound 206: 4-(6-Chloro-pyridin-3-yloxy)-6,7-dimethoxyquinoline

2-Chloro-5-hydroxypyridine (100 mg), 4-chloro-6,7-dimethoxyquinoline (861 mg), and 4-dimethylaminopyridine (283 mg) were suspended in o-dichlorobenzene (5 ml), and the suspension was stirred at 140° C. for 2 hr. The reaction solution was cooled to room temperature, water was then added to the reaction solution, and the mixture was extracted with ethyl acetate. The ethyl acetate layer was then washed with water and saturated brine and was dried over anhydrous magnesium sulfate. The solvent was removed by distillation under the reduced pressure, and the residue was purified by column chromatography using acetone-hexane to give the title compound (164 mg, yield 67%).

$^1$H-NMR (CDCl$_3$, 400 MHz): δ 4.00 (s, 3H), 4.02 (s, 3H), 6.45 (d, J=5.2 Hz, 1H), 7.31-7.49 (m, 4H), 8.31 (d, J=3.2 Hz, 1H), 8.51 (d, J=5.2 Hz, 1H)

Mass spectrometric value (ESI-MS, m/z): 317 (M+1)$^+$

Compound 207: 6,7-Dimethoxy-4-(6-methoxy-pyridin-3-yloxy)quinoline 4-(6-Chloro-pyridin-3-yloxy)-6,7-dimethoxy-quinoline (compound 206) (145 mg) and sodium methoxide (87 mg) were suspended in toluene (1.2 ml), and the suspension was heated under reflux for 20 hr. The reaction solution was cooled to room temperature, water was then added to the reaction solution, and the mixture was extracted with chloroform. The chloroform layer was then washed with water and saturated brine and was dried over anhydrous magnesium sulfate. The solvent was removed by distillation under the reduced pressure, and the residue was purified by thin layer chromatography using acetone-hexane to give the title compound (88 mg, yield 61%).

$^1$H-NMR (CDCl$_3$, 400 MHz): δ 3.89 (s, 3H), 3.96 (s, 3H), 3.97 (s, 3H), 6.31 (d, J=5.2 Hz, 1H), 6.76 (d, J=9.2 Hz, 1H), 7.31-7.39 (m, 2H), 7.47 (s, 1H), 8.02 (d, J=2.8 Hz, 1H), 8.41 (d, J=5.2 Hz, 1H)

Mass spectrometric value (ESI-MS, m/z): 313 (M+1)$^+$

Compound 208: 4-(5-Chloro-pyridin-3-yloxy)-6,7-dimethoxyquinoline

4-Chloro-6,7-dimethoxyquinoline (245 mg), 3-chloro-5-pyridinol (277 mg), and 4-dimethylaminopyridine (377 mg) were suspended in o-dichlorobenzene (13 ml), and the mixture was stirred at 140° C. for 6 hr. Water was added to the reaction solution, and the mixture was extracted with ethyl acetate. The organic layer was washed with an aqueous sodium hydroxide solution and water and was dried over anhydrous sodium sulfate. The solvent was removed by distillation under the reduced pressure, and the residue was purified by column chromatography using acetone-chloroform to give the title compound (283 mg, yield 81%).

$^1$H-NMR (CDCl$_3$, 400 MHz): δ 4.04 (s, 3H), 4.06 (s, 3H), 6.56 (d, J=5.1 Hz, 1H), 7.44 (s, 1H), 7.46 (s, 1H), 7.53 (m, 1H), 8.47 (d, J=2.4 Hz, 1H), 8.51 (d, J=1.9 Hz, 1H), 8.58 (d, J=5.1 Hz, 1H)

Mass spectrometric value (ESI-MS, m/z): 317 (M+1)$^+$

Compound 209: 4-(2,6-Dimethyl-pyridin-3-yloxy)-6,7-dimethoxy-quinoline 2,6-Dimethylpyridin-3-ol (165 mg), 4-chloro-6,7-dimethoxyquinoline (100 mg), and 4-(N,N-dimethylamino)pyridine (164 mg) were dissolved in 1,2-dichlorobenzene (4.5 ml) to prepare a solution which was then stirred at 130° C. overnight. The reaction solution was cooled to room temperature, and the solvent was then removed by distillation under the reduced pressure. Water was added to the residue, the mixture was extracted with ethyl acetate, and the ethyl acetate layer was then washed with water and was dried over anhydrous sodium sulfate. The solvent was removed by distillation under the reduced pressure, and the residue was purified by column chromatography using hexane-acetone to give the title compound (116 mg, yield 83%).

$^1$H-NMR (CDCl$_3$, 400 MHz): δ 2.41 (s, 3H), 2.60 (s, 3H), 4.08 (s, 6H), 6.30 (d, J=5.6 Hz, 1H), 7.12 (d, J=8.3 Hz, 1H), 7.33 (d, J=8.3 Hz, 1H), 7.56 (s, 1H), 7.59 (s, 1H), 8.47 (d, J=5.6 Hz, 1H)

Mass spectrometric value (ESI-MS, m/z): 311 (M+1)$^+$

Compound 210: 6,7-Dimethoxy-4-(6-methyl-2-nitro-pyridin-3-yloxy)-quinoline

2-Nitro-6-methylpyridin-3-ol (4.1 g), 4-chloro-6,7-dimethoxyquinoline (2 g), and 4-(N,N-dimethylamino)-pyridine (3.3 g) were dissolved in 1,2-dichlorobenzene (90 ml) to prepare a solution which was then stirred at 130° C. overnight. The reaction solution was cooled to room temperature, and the solvent was then removed by distillation under the reduced pressure. A 1 N aqueous sodium hydroxide solution was added to the residue, the mixture was extracted with ethyl acetate, and the ethyl acetate layer was then washed with water and was dried over anhydrous sodium sulfate. The solvent was removed by distillation under the reduced pressure, and the residue was purified by column chromatography using hexane-acetone to give the title compound (732 mg, yield 24%).

$^1$H-NMR (CDCl$_3$, 400 MHz): δ 2.67 (s, 3H), 4.02 (s, 3H), 4.05 (s, 3H), 6.52 (d, J=5.4 Hz, 1H), 7.43 (s, 1H), 7.44 (s, 1H), 7.49 (d, J=8.5 Hz, 1H), 7.59 (d, J=8.5 Hz, 1H), 8.56 (d, J=5.1 Hz, 1H)

Mass spectrometric value (ESI-MS, m/z): 364 (M+Na)$^+$

Compound 211: 4-(6-Fluoro-2-iodo-pyridin-3-yloxy)-6,7-dimethoxy-quinoline

6-Fluoro-3-hydroxypyridine (870 mg) and iodine (9.76 g) were dissolved in a mixed solvent composed of methanol (20 ml) and water (10 ml) to prepare a solution which was then stirred at room temperature for 120 hr. Thereafter, sodium sulfite was added until the solution became transparent.

Methanol in the reaction solution was removed under the reduced pressure, water was added to the residue, and the mixture was extracted with chloroform. The chloroform layer was washed with water and saturated brine and was dried over anhydrous magnesium sulfate. The solvent was removed by distillation under the reduced pressure, and the residue was purified by column chromatography using acetone-chloroform to give 6-fluoro-2-iodo-pyridin-3-ol (350 mg, yield 19%).

6-Fluoro-2-iodo-pyridin-3-ol (20 mg), 4-chloro-6,7-dimethoxyquinoline (56 mg), and 4-dimethylaminopyridine (31 mg) were suspended in o-dichlorobenzene (2 ml), and the suspension was stirred at 140° C. for 5 hr. The reaction solution was cooled to room temperature, water was then added to the reaction solution, and the mixture was extracted with ethyl acetate. The ethyl acetate layer was then washed with water and saturated brine and was dried over anhydrous magnesium sulfate. The solvent was removed by distillation under the reduced pressure, and the residue was purified by thin layer chromatography using acetone-chloroform to give the title compound (2 mg, yield 6%).

$^1$H-NMR (CDCl$_3$, 400 MHz): δ 3.99 (s, 3H), 4.00 (s, 3H), 6.27 (d, J=5.6 Hz, 1H), 6.95 (dd, J=8.4 Hz, 3.6 Hz, 1H), 7.37-7.50 (m, 3H), 8.47 (d, J=5.2 Hz, 1H)

Mass spectrometric value (ESI-MS, m/z): 875 (2M+Na)$^+$

Compound 212: 6,7-Dimethoxy-4-(6-methyl-2-trimethylsilanylethynyl-pyridin-3-yloxy)-quinoline 4-[(2-Iodo-6-methyl-3-pyridyl)oxy]-6,7-dimethoxyquinoline (compound 116) (84 mg), trimethylsilylacetylene (39 mg), and bis(triphenylphosphine)palladium(II) chloride (14 mg) were dissolved in tetrahydrofuran (1 ml) to prepare a solution. Diisopropylethylamine (0.2 ml) and copper iodide (3.8 mg) were added to the solution, and the mixture was stirred at room temperature for 18 hr. The reaction solution was filtered, the solvent was then removed by distillation under the reduced pressure, and the residue was purified by column chromatography using chloroform to give the title compound (45 mg, yield 58%).

$^1$H-NMR (CDCl$_3$, 400 MHz): δ −0.17 (s, 9H), 2.62 (s, 3H), 4.06 (s, 3H), 4.06 (s, 3H), 6.33 (d, J=5.6 Hz, 1H), 7.24 (d, J=8.4 Hz, 1H), 7.48 (d, J=8.4 Hz, 1H), 7.50 (s, 1H), 7.60 (s, 1H), 8.51 (d, J=5.2 Hz, 1H)

Mass spectrometric value (ESI-MS, m/z): 393 (M+1)$^+$

Compound 213: 3-(6,7-Dimethoxy-quinolin-4-yloxy)-6-methyl-pyridin-2-carbonitrile 2-Hydroxymethyl-6-methyl-pyridin-3-ol (1.03 g) was suspended in dichloromethane (50 ml), manganese dioxide (5.53 g) was added to the suspension, and the mixture was stirred at room temperature for 3 days. The reaction solution was filtered, and the solvent was removed by distillation under the reduced pressure. The residue was used in the next reaction without purification.

The residue was dissolved in N,N-dimethylformamide (40 ml) to prepare a solution. Potassium carbonate (2.35 g) and benzyl chloride (0.8 ml) were added to the solution, and the mixture was stirred at room temperature overnight. Water was added to the reaction solution, and the mixture was extracted with ethyl acetate. The organic layer was washed with water and was dried over anhydrous sodium sulfate. The solvent was removed by distillation under the reduced pressure, and the residue was purified by column chromatography using ethyl acetate-hexane to give 3-benzyloxy-6-methyl-pyridine-2-carbaldehyde (881 mg, yield 52%) (2 steps).

3-Benzyloxy-6-methyl-pyridine-2-carbaldehyde (100 mg) was dissolved in acetonitrile (5 ml) to prepare a solution. Hydroxylamine hydrochloride (72 mg) and triethylamine (0.25 ml) were added to the solution, and the mixture was stirred at room temperature for one hr. 4-Nitrophthalic anhydride was added to the reaction solution, and the mixture was stirred at 100° C. overnight. Water was added to the reaction solution, and the mixture was extracted with ethyl acetate. The organic layer was washed with water and was dried over anhydrous sodium sulfate. The solvent was removed by distillation under the reduced pressure, and the residue was purified by column chromatography using ethyl acetate-hexane to give 3-benzyloxy-6-methylpyridine-2-carbonitrile (53 mg, yield 54%).

Trifluoroacetic acid (1.5 ml) and methanesulfonic acid (0.15 ml) were added to 3-benzyloxy-6-methylpyridine-2-carbonitrile (50 mg) to prepare a solution which was then stirred at room temperature for one hr. The solvent was removed by distillation under the reduced pressure, water was then added to the reaction solution, and the mixture was extracted with ethyl acetate. The organic layer was washed with an aqueous sodium hydrogencarbonate solution and water and was dried over anhydrous sodium sulfate. The solvent was removed by distillation under the reduced pressure, and the residue was used in the next reaction without purification.

The residue, 4-chloro-6,7-dimethoxyquinoline (94 mg), and 4-dimethylaminopyridine (90 mg) were suspended in o-dichlorobenzene (4 ml), and the suspension was stirred at 140° C. for 6 hr. The reaction solution was cooled to room temperature, and the solvent was then removed by distillation under the reduced pressure. The residue was purified by column chromatography using acetone-chloroform to give the title compound (12 mg, yield 17%) (2 steps).

$^1$H-NMR (CDCl$_3$, 400 MHz): δ 2.65 (s, 3H), 4.05 (s, 3H), 4.06 (s, 3H), 6.54 (d, J=5.1 Hz, 1H), 7.41 (d, J=8.8 Hz, 1H), 7.44 (d, J=8.8 Hz, 1H), 7.46 (s, 1H), 7.46 (s, 1H), 8.59 (d, J=5.1 Hz, 1H)

Mass spectrometric value (ESI-MS, m/z): 344 (M+Na)$^+$

Compound 214: 4-(2-Benzyl-6-methyl-pyridin-3-yloxy)-6,7-dimethoxy-quinoline

[3-(6,7-Dimethoxy-quinolin-4-yloxy)-6-methyl-pyridin-2-yl]-phenyl methyl acetate (compound 218) (40 mg) was dissolved in N,N-dimethylformamide (5 ml) to prepare a solution. Triethylamine (0.3 ml) and 20% palladium hydroxide (10 mg) were added to the solution, and the mixture was stirred under hydrogen pressure at room temperature overnight. The reaction solution was filtered through Celite and was then washed with chloroform and methanol. The solvent was removed by distillation under the reduced pressure, and the residue was purified by thin layer chromatography using chloroform-acetone to give the title compound (32 mg, yield 92%).

$^1$H-NMR (CDCl$_3$, 400 MHz): δ 2.64 (s, 3H), 3.96 (s, 3H), 4.07 (s, 3H), 4.10 (s, 2H), 6.19 (d, J=5.6 Hz, 1H), 7.10-7.15 (m, 6H), 7.30 (d, J=8.3 Hz, 1H), 7.36 (s, 1H), 7.51 (s, 1H), 8.38 (d, J=5.4 Hz, 1H)

Mass spectrometric value (ESI-MS, m/z): 387 (M+1)$^+$

Compound 215: 6,7-Dimethoxy-4-[6-methyl-2-(6-methyl-pyridin-2-ylmethyl)-pyridin-3-yloxy]-quinoline 3-(6,7-Dimethoxy-quinolin-4-yloxy)-6-methyl-pyridin-2-yl]-(6-methyl-pyridin-2-yl)-methyl acetate (compound 219) (25 mg) was dissolved in N,N-dimethylformamide (1 ml) to prepare a solution. Triethylamine (0.2 ml) and 20% palladium hydroxide (14 mg) were added to the solution, and the mixture was stirred under hydrogen pressure at room temperature overnight. The reaction solution was filtered through Celite and was then washed with chloroform and methanol. The solvent was removed by distillation under the reduced pressure, and the residue was purified by thin layer chromatography using chloroform-acetone to give the title compound (13 mg, yield 59%).

$^1$H-NMR (CDCl$_3$, 400 MHz): δ 2.23 (s, 3H), 2.64 (s, 3H), 3.97 (s, 3H), 4.04 (s, 3H), 4.33 (s, 2H), 6.15 (d, J=5.4 Hz, 1H), 6.80 (d, J=7.6 Hz, 1H), 6.85 (d, J=7.8 Hz, 1H), 7.16 (d, J=8.1 Hz, 1H), 7.28-7.34 (m, 3H), 7.40 (s, 1H), 8.34 (d, J=5.1 Hz, 1H)

Mass spectrometric value (ESI-MS, m/z): 402 (M+1)$^+$

Compound 216: 6,7-Dimethoxy-4-(6-methyl-2-styryl-pyridin-3-yloxy)-quinoline

4-[(2-Iodo-6-methyl-3-pyridyl)oxy]-6,7-dimethoxyquinoline (compound 116) (84 mg), trans-2-phenylvinylboronic acid (148 mg), and tetrakistriphenylphosphine palladium (12 mg) were dissolved in toluene (1 ml) to prepare a solution. A saturated aqueous sodium hydrogencarbonate solution (1 ml) was added to the solution, and the mixture was stirred at 80° C. for 3 hr. The reaction solution was filtered, and the solvent was then removed by distillation under the reduced pressure. The residue was purified by column chromatography using methanol-chloroform to give the title compound (53 mg, yield 67%).

$^1$H-NMR (CDCl$_3$, 400 MHz): δ 2.64 (s, 3H), 4.05 (s, 3H), 4.06 (s, 3H), 6.33 (d, J=5.4 Hz, 1H), 7.10 (d, J=8.3 Hz, 1H), 7.18-7.26 (m, 4H), 7.31 (d, J=8.3 Hz, 1H), 7.40 (m, 2H), 7.45 (s, 1H), 7.62 (s, 1H), 7.88 (d, J=15.8 Hz, 1H), 8.45 (d, J=5.4 Hz, 1H)

Mass spectrometric value (ESI-MS, m/z): 399 (M+1)$^+$

Compound 217: [3-(6,7-Dimethoxy-quinolin-4-yloxy)-6-methyl-pyridin-2-yl]-phenyl-methanol

[3-(6,7-Dimethoxy-quinolin-4-yloxy)-6-methyl-pyridin-2-yl]-phenyl-methanone (55 mg) (compound 220) was dissolved in methanol (3 ml) to prepare a solution. Sodium borohydride (26 mg) was added to the solution at 0° C., and the mixture was stirred at room temperature for 2 hr. The solvent was removed by distillation under the reduced pressure, water was added to the residue, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-acetone to give the title compound (52 mg, yield 92%).

$^1$H-NMR (CDCl$_3$, 400 MHz): δ 2.70 (s, 3H), 3.95 (s, 3H), 4.08 (s, 3H), 5.74-5.79 (m, 2H), 6.07 (d, J=5.4 Hz, 1H), 7.07-7.31 (m, 8H), 7.52 (s, 1H), 8.31 (d, J=5.4 Hz, 1H)

Mass spectrometric value (ESI-MS, m/z): 403 (M+1)$^+$

Compound 218: [3-(6,7-Dimethoxy-quinolin-4-yloxy)-6-methyl-pyridin-2-yl]-phenyl-methyl acetate

[3-(6,7-Dimethoxy-quinolin-4-yloxy)-6-methyl-pyridin-2-yl]-phenyl-methanol (47 mg) (compound 217) was dissolved in chloroform (7 ml) to prepare a solution. Triethylamine (1 ml), acetic anhydride (0.8 ml), and 4-dimethylaminopyridine (20 mg) were added to the solution, and the mixture was stirred at room temperature overnight. Water was added to the reaction solution, and the mixture was extracted with chloroform. The chloroform layer was washed with saturated brine and was dried over anhydrous sodium sulfate, and the solvent was removed by distillation under the reduced pressure. The residue was purified by thin layer chromatography using chloroform-acetone to give the title compound (48 mg, yield 89%).

$^1$H-NMR (CDCl$_3$, 400 MHz): δ 2.01 (s, 3H), 2.65 (s, 3H), 3.98 (s, 3H), 4.08 (s, 3H), 6.28 (d, J=5.4 Hz, 1H), 6.91 (s, 1H), 7.16-7.35 (m, 7H), 7.40 (s, 1H), 7.56 (s, 1H), 8.40 (d, J=5.4 Hz, 1H)

Mass spectrometric value (ESI-MS, m/z): 445 (M+1)$^+$

Compound 219: [3-(6,7-Dimethoxy-quinolin-4-yloxy)-6-methyl-pyridin-2-yl]-(6-methyl-pyridin-2-yl)-methyl acetate 4-(2-Iodo-6-methyl-pyridin-3-yloxy)-6,7-dimethoxyquinoline (compound 116) (100 mg) was dissolved in tetrahydrofuran (7 ml) to prepare a solution which was then brought to −78° C. n-Butyllithium hexane solution (0.22 ml) was slowly added dropwise thereto, and the mixture was stirred at −78° C. for 20 min. 6-Methyl-2-pyridine-carbaldehyde (57 mg) was dissolved in tetrahydrofuran (7 ml) to prepare a solution which was then added dropwise to the reaction solution, followed by stirring at room temperature for 5 hr. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-acetone to give [3-(6,7-dimethoxy-quinolin-4-yloxy)-6-methyl-pyridin-2-yl]-(6-methyl-pyridin-2-yl)-methanol (73 mg, yield 73%).

[3-(6,7-Dimethoxy-quinolin-4-yloxy)-6-methyl-pyridin-2-yl]-(6-methyl-pyridin-2-yl)-methanol (43 mg) was dissolved in chloroform (6 ml) to prepare a solution. Triethylamine (0.9 ml) and acetic anhydride (0.45 ml) were added to the solution, and the mixture was stirred at room temperature overnight. Water was added to the reaction solution, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (28 mg, yield 61%).

$^1$H-NMR (CDCl$_3$, 400 MHz): δ 2.10 (s, 3H), 2.27 (s, 3H), 2.62 (s, 3H), 4.03 (s, 3H), 4.07 (s, 3H), 6.28 (d, J=5.6 Hz, 1H), 6.91 (d, J=7.6 Hz, 1H), 7.07 (s, 1H), 7.16-7.19 (m, 2H), 7.30-7.55 (m, 4H), 8.37 (d, J=5.4 Hz, 1H)

Mass spectrometric value (ESI-MS, m/z): 460 (M+1)$^+$

Compound 220: [3-(6,7-Dimethoxy-quinolin-4-yloxy)-6-methyl-pyridin-2-yl]-phenyl-methanone 2,6-Lutidine-a2,3-diol (2.25 g) was dissolved in methanol (15 ml) and dichloromethane (45 ml) to prepare a solution. Manganese dioxide (8.34 g) was added to the solution, and the mixture was stirred at room temperature overnight. The reaction solution was filtered through Celite and was then washed with chloroform and methanol. The solvent was removed by distillation under the reduced pressure, and the residue was purified by column chromatography using chloroform-acetone to give 3-hydroxy-6-methyl-pyridine-2-carbaldehyde (1.88 g, yield 85%).

3-Hydroxy-6-methyl-pyridine-2-carbaldehyde (350 mg) was dissolved in tetrahydrofuran (13 ml) to prepare a solution which was brought to −78° C. Phenylmagnesium bromide (7.4 ml) was slowly added dropwise thereto, and the mixture was stirred at room temperature for one hr. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-acetone to give 2-(hydroxyphenyl-methyl)-6-methyl-pyridin-3-ol (553 mg, yield 100%).

2-(Hydroxy-phenyl-methyl)-6-methyl-pyridin-3-ol (553 mg) was dissolved in methanol (3 ml) and dichloromethane (9 ml) to prepare a solution. Manganese dioxide (2.05 g) was added to the solution, and the mixture was stirred at room temperature overnight. The reaction solution was filtered through Celite and was then washed with chloroform and methanol. The solvent was removed by distillation under the reduced pressure, and the residue was purified by thin layer chromatography using chloroform-acetone to give (3-hydroxy-6-methyl-pyridin-2-yl)-phenyl-methanone (439 mg, yield 80%).

(3-Hydroxy-6-methyl-pyridin-2-yl)-phenyl-methanone (213 mg), 4-chloro-6,7-dimethoxyquinoline (223 mg), and 4-dimethylaminopyridine (366 mg) were suspended in o-dichlorobenzene (3 ml), and the suspension was stirred at 120° C. overnight. The reaction solution was cooled to room temperature, water was then added thereto, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (89 mg, yield 22%).

$^1$H-NMR (CDCl$_3$, 400 MHz): δ 2.68 (s, 3H), 3.89 (s, 3H), 4.03 (s, 3H), 6.52 (d, J=5.4 Hz, 1H), 7.19 (s, 1H), 7.39-7.45 (m, 4H), 7.51-7.55 (m, 2H), 7.85 (d, J=7.1 Hz, 2H), 8.47 (d, J=5.6 Hz, 1H)

Mass spectrometric value (ESI-MS, m/z): 401 (M+1)$^+$

Compound 221: [3-(6,7-Dimethoxy-quinolin-4-yloxy)-6-methyl-pyridin-2-yl]-(6-methyl-pyridin-2-yl)-methanone

[3-(6,7-Dimethoxy-quinolin-4-yloxy)-6-methyl-pyridin-2-yl]-(6-methyl-pyridin-2-yl)-methanol (20 mg) was dissolved in methanol (0.4 ml) and dichloromethane (1.2 ml) to prepare a solution. Manganese dioxide (300 mg) was added to the solution, and the mixture was stirred at room temperature for 6 days. The reaction solution was filtered through Celite and was then washed with chloroform and methanol. The solvent was removed by distillation under the reduced pressure, and the residue was purified by thin layer chromatography using chloroform-acetone to give the title compound (6 mg, yield 28%).

$^1$H-NMR (CDCl$_3$, 400 MHz): δ 2.28 (s, 3H), 2.70 (s, 3H), 3.89 (s, 3H), 4.01 (s, 3H), 6.77 (d, J=5.4 Hz, 1H), 7.06 (s, 1H), 7.08 (s, 1H), 7.35-7.39 (m, 2H), 7.48 (d, J=8.3 Hz, 1H), 7.56 (t, J=7.8 Hz, 1H), 7.82 (d, J=7.1 Hz, 1H), 8.50 (d, J=5.4 Hz, 1H)

Mass spectrometric value (ESI-MS, m/z): 438 (M+Na)$^+$

Compound 222: 4-(5-Chloro-2-cyclopentyloxy-pyridin-3-yloxy)-6,7-dimethoxy-quinoline 4-Chloro-6,7-dimethoxyquinoline (226 mg), 3-chloro-5,6-dihydroxypyridine (290 mg), and 4-dimethylaminopyridine (360 mg) were suspended in o-dichlorobenzene (13 ml), and the suspension was stirred at 160° C. for 3 hr. The reaction solution was cooled to room temperature, water was then added to the residue, and the mixture was extracted with chloroform. The chloroform layer was washed with water and was dried over anhydrous sodium sulfate. The solvent was removed by distillation under the reduced pressure, and the residue was purified by column chromatography using methanol-chloroform to give 4-(5-chloro-2-hydroxy-pyridin-3-yloxy)-6,7-dimethoxyquinoline (83 mg, yield 25%).

4-(5-Chloro-2-hydroxy-pyridin-3-yloxy)-6,7-dimethoxyquinoline (39 mg) was suspended in N,N-dimethylformamide (7 ml). Cyclopentyl bromide (0.3 ml) and potassium carbonate (300 mg) were added to the suspension, and the mixture was stirred at room temperature for 2 hr. Water was added to the reaction solution, and the mixture was extracted with ethyl acetate. The organic layer was washed with an aqueous sodium hydrogencarbonate solution and water and was dried over anhydrous sodium sulfate. The solvent was removed by distillation under the reduced pressure, and the residue was purified by column chromatography using acetone-chloroform to give the title compound (29 mg, yield 62%).

$^1$H-NMR (CDCl$_3$, 400 MHz): δ 1.24-1.78 (m, 8H), 4.05 (s, 3H), 4.06 (s, 3H), 5.38 (m, 1H), 6.35 (d, J=5.1 Hz, 1H), 7.44 (s, 1H), 7.51 (m, 2H), 8.05 (m, 1H), 8.50 (d, J=5.1 Hz, 1H)

Mass spectrometric value (ESI-MS, m/z): 401 (M+1)$^+$

Compound 223: 6,7-Dimethoxy-4-(6-methyl-2-phenyl-pyridin-3-yloxy)-quinoline

4-[(2-Iodo-6-methyl-3-pyridyl)oxy]-6,7-dimethoxyquinoline (compound 116) (84 mg), phenylboronic acid (121 mg), and tetrakistriphenylphosphine palladium (23 mg) were dissolved in toluene (1 ml) to prepare a solution. A saturated aqueous sodium hydrogencarbonate solution (0.5 ml) was added to the solution, and the mixture was stirred at 80° C. for 3 hr. The reaction solution was filtered, the solvent was then removed by distillation under the reduced pressure, and the residue was purified by column chromatography using methanol-chloroform to give the title compound (74 mg, yield 100%).

$^1$H-NMR (CDCl$_3$, 400 MHz): δ 2.69 (s, 3H), 4.03 (s, 3H), 4.05 (s, 3H), 6.39 (d, J=5.4 Hz, 1H), 7.22-7.59 (m, 5H), 7.65-7.70 (m, 2H), 7.81-7.84 (m, 2H), 8.42 (dd, J=2.0, 5.6 Hz, 1H)

Mass spectrometric value (ESI-MS, m/z): 373 (M+1)$^+$

Compound 224: 6,7-Dimethoxy-4-(6-methyl-2-o-tolyl-pyridin-3-yloxy)-quinoline

4-[(2-Iodo-6-methyl-3-pyridyl)oxy]-6,7-dimethoxyquinoline (compound 116) (84 mg), 2-methylphenylboronic acid (136 mg), and tetrakistriphenylphosphine palladium (12 mg) were dissolved in toluene (1 ml) to prepare a solution. A saturated aqueous sodium hydrogencarbonate solution (1 ml) was added to the solution, and the mixture was stirred at 80° C. for 3 hr. The reaction solution was filtered, the solvent was then removed by distillation under the reduced pressure, and the residue was purified by column chromatography using methanol-chloroform to give the title compound (68 mg, yield 89%).

$^1$H-NMR (CDCl$_3$, 400 MHz): δ 2.25 (s, 3H), 2.64 (s, 3H), 3.93 (s, 3H), 3.96 (s, 3H), 6.33 (d, J=5.4 Hz, 1H), 6.97-7.70 (m, 4H), 7.20-7.27 (m, 2H), 7.29 (s, 1H), 7.47 (d, J=8.3 Hz, 1H), 8.38 (d, J=5.4 Hz, 1H)

Mass spectrometric value (ESI-MS, m/z): 387 (M+1)$^+$

Compound 225: 1-{2-[3-(6,7-Dimethoxy-quinolin-4-yloxy)-6-methyl-pyridin-2-yl]-phenyl}-ethanone Toluene (1 ml) and a saturated aqueous sodium hydrogencarbonate solution (0.5 ml) were added to 4-(2-iodo-6-methyl-pyridin-3-yloxy)-6,7-dimethoxy-quinoline (compound 116) (50 mg), tetrakistriphenylphosphine palladium (14 mg), and 2-acetylphenylboronic acid (97 mg) under an argon atmosphere, and the mixture was stirred at 80° C. overnight. The reaction solution was cooled to room temperature, a 1 N aqueous sodium hydroxide solution was then added, and the mixture was extracted with chloroform. The chloroform layer was then washed with water and was dried over anhydrous sodium sulfate. The solvent was removed by distillation under the reduced pressure, and the residue was purified by thin layer chromatography using chloroform-methanol to give the title compound (10 mg, yield 20%).

$^1$H-NMR (CDCl$_3$, 400 MHz): δ 2.38 (s, 3H), 2.64 (s, 3H), 4.01 (s, 3H), 4.03 (s, 3H), 6.47 (d, J=5.4 Hz, 1H), 7.23 (d, J=8.3 Hz, 1H), 7.32-7.42 (m, 5H), 7.52-7.59 (m, 2H), 8.41 (d, J=5.4 Hz, 1H)

Mass spectrometric value (ESI-MS, m/z): 415 (M+1)$^+$

Compound 226: 2-[3-(6,7-Dimethoxy-quinolin-4-yloxy)-6-methyl-pyridin-2-yl]-phenol Toluene (1 ml) and a saturated aqueous sodium hydrogencarbonate solution (0.5 ml) were added to 4-(2-iodo-6-methyl-pyridin-3-yloxy)-6,7-dimethoxy-quinoline (compound 116) (50 mg), tetrakistriphenylphosphine palladium (14 mg), and 2-hydroxyphenylboronic acid (81 mg) under an argon atmosphere, and the mixture was stirred at 80° C. overnight. The reaction solution was cooled to room temperature, water was then added to the reaction solution, and the mixture was extracted with chloroform. The chloroform layer was then washed with water and was dried over anhydrous sodium sulfate. The solvent was removed by distillation under the reduced pressure, and the residue was purified by thin layer chromatography using chloroform-methanol to give the title compound (45 mg, yield 93%).

$^1$H-NMR (CDCl$_3$, 400 MHz): δ 2.68 (s, 3H), 4.03 (s, 3H), 4.05 (s, 3H), 6.43 (d, J=5.4 Hz, 1H), 6.56 (dd, J=8.0, 8.0 Hz, 1H), 6.86-7.62 (m, 7H), 8.07 (d, J=8, 3 Hz, 1H), 8.46 (d, J=5.4 Hz, 1H)

Mass spectrometric value (ESI-MS, m/z): 389 (M+1)$^+$

Compound 227: 6,7-Dimethoxy-4-[2-(2-methoxy-phenyl)-6-methyl-pyridin-3-yloxy]-quinoline 4-(2-Iodo-6-methyl-pyridin-3-yloxy)-6,7-dimethoxyquinoline (compound 116) (84 mg), 2-methoxyphenylboronic acid (152 mg), and tetrakistriphenylphosphine palladium (12 mg) were disssolved in toluene (1 ml) to prepare a solution. A saturated aqueous sodium hydrogencarbonate solution (1 ml) was added to the solution, and the mixture was stirred at 80° C. for 3 hr. The reaction solution was filtered, the solvent was then removed by distillation under the reduced pressure, and the residue was purified by column chromatography using methanol-chloroform to give the title compound (23 mg, yield 29%).

$^1$H-NMR (CDCl$_3$, 400 MHz): δ 2.65 (s, 3H), 3.32 (s, 3H), 3.87 (s, 3H), 3.99 (s, 3H), 6.57 (d, J=5.4 Hz, 1H), 6.67 (d, J=8.3 Hz, 1H), 6.92 (ddd, J=1.0, 7.3, 7.6 Hz, 1H), 7.18-7.26 (m, 3H), 7.35 (dd, J=1.7, 7.6 Hz, 1H), 7.36 (s, 1H), 7.46 (d, J=8.3 Hz, 1H), 8.45 (d, J=5.4 Hz, 1H)

Mass spectrometric value (ESI-MS, m/z): 403 (M+1)$^+$

Compound 228: 4-[2-(2-Chloro-phenyl)-6-methyl-pyridin-3-yloxy]-6,7-dimethoxy-quinoline Toluene (0.7 ml) and a saturated aqueous sodium hydrogencarbonate solution (0.35 ml) were added to 4-(2-iodo-6-methyl-pyridin-3-yloxy)-6,7-dimethoxy-quinoline (compound 116) (50 mg), tetrakistriphenylphosphine palladium (14 mg), and 2-chlorophenyl boronic acid (81 mg) under an argon atmosphere, and the mixture was stirred at 80° C. for 3 days. The reaction solution was cooled to room temperature, water was then added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-acetone to give the title compound (43 mg, yield 90%).

$^1$H-NMR (CDCl$_3$, 400 MHz): δ 2.68 (s, 3H), 4.00 (s, 3H), 4.00 (s, 3H), 6.41 (d, J=5.4 Hz, 1H), 7.10-7.17 (m, 2H), 7.17-7.29 (m, 4H), 7.44 (s, 1H), 7.52 (d, J=5.6 Hz, 1H), 8.42 (d, J=5.1 Hz, 1H)

Mass spectrometric value (ESI-MS, m/z): 407 (M+1)$^+$

Compound 229: 6,7-Dimethoxy-4-(6-methyl-2-m-tolyl-pyridin-3-yloxy)-quinoline 4-[(2-Iodo-6-methyl-3-pyridyl)oxy]-6,7-dimethoxyquinoline (compound 116) (84 mg), 3-methylphenylboronic acid (136 mg), and tetrakistriphenylphosphine palladium (12 mg) were dissolved in toluene (1 ml) to prepare a solution. A saturated aqueous sodium hydrogencarbonate solution (1 ml) was added to the solution, and the mixture was stirred at +80° C. for 3 hr. The reaction solution was filtered, the solvent was then removed by distillation under the reduced pressure, and the residue was purified by column chromatography using methanol-chloroform to give the title compound (72 mg, yield 94%).

$^1$H-NMR (CDCl$_3$, 400 MHz): δ 2.22 (s, 3H), 2.65 (s, 3H), 4.00 (s, 3H), 4.00 (s, 3H), 6.32 (d, J=5.4 Hz, 1H), 7.03 (d, J=7.6 Hz, 1H), 7.11 (m, 1H), 7.17 (d, J=8.3 Hz, 1H), 7.36 (s, 1H), 7.41 (d, J=8.3 Hz, 1H), 7.48 (s, 1H), 7.58-7.67 (m, 2H), 8.38 (d, J=5.1 Hz, 1H)

Mass spectrometric value (ESI-MS, m/z): 387 (M+1)$^+$

Compound 230: 6,7-Dimethoxy-4-[6-methyl-2-(3-trifluoromethyl-phenyl)-pyridin-3-yloxy]-quinoline N,N-Dimethylformamide (1 ml), ethanol (0.5 ml), and a 2 M aqueous potassium carbonate solution (1 ml) were added to 4-(2-iodo-6-methyl-pyridin-3-yloxy)-6,7-dimethoxy-quinoline (compound 116) (50 mg), tetrakistriphenylphosphine palladium (14 mg), and 3-trifluoromethylphenylboronic acid (67 mg) under an argon atmosphere, and the mixture was stirred at 80° C. for 3 hr. The reaction solution was cooled to room temperature, water was then added to the solution, and the mixture was extracted with ethyl acetate. The ethyl acetate layer was then washed with water and was dried over anhydrous sodium sulfate, the solvent was removed by distillation under the reduced pressure, and the residue was purified by thin layer chromatography using chloroform-acetone to give the title compound (50 mg, yield 95%).

$^1$H-NMR (CDCl$_3$, 400 MHz): δ 2.71 (s, 3H), 4.05 (s, 6H), 6.33 (d, J=5.4 Hz, 1H), 7.29 (d, J=8.3 Hz, 1H), 7.38-7.60 (m, 5H), 8.04 (d, J=8.3 Hz, 1H), 8.23 (s, 1H), 8.40 (d, J=5.1 Hz, 1H)

Mass spectrometric value (ESI-MS, m/z): 441 (M+1)$^+$

Compound 231: {3-[3-(6,7-Dimethoxy-quinolin-4-yloxy)-6-methyl-pyridin-2-yl]-phenyl}-methanol Toluene (1 ml) and a saturated aqueous sodium hydrogencarbonate solution (0.5 ml) were added to 4-(2-iodo-6-methyl-pyridin-3-yloxy)-6,7-dimethoxy-quinoline (compound 116) (50 mg), tetrakis-triphenylphosphine palladium (14 mg), and (3-hydroxymethyl)-phenylboronic acid (90 mg) under an argon atmosphere, and the mixture was stirred 80° C. overnight. The reaction solution was cooled to room temperature, a 1 N aqueous sodium hydroxide solution was then added thereto, and the mixture was extracted with chloroform. The chloroform layer was then washed with water and was dried over anhydrous sodium sulfate. The solvent was removed by distillation under the reduced pressure, and the residue was purified by thin layer chromatography using chloroform-methanol to give the title compound (20 mg, yield 43%).

$^1$H-NMR (CDCl$_3$, 400 MHz): δ 2.69 (s, 3H), 4.03 (s, 3H), 4.03 (s, 3H), 4.63 (s, 2H), 6.35 (d, J=5.4 Hz, 1H), 7.17-7.34 (m, 4H), 7.43 (d, J=8.3 Hz, 1H), 7.50 (s, 1H), 7.71-7.80 (m, 1H), 7.86 (s, 1H), 8.22 (d, J=5.2 Hz, 1H)

Mass spectrometric value (ESI-MS, m/z): 403 (M+1)$^+$

Compound 232: 1-{3-[3-(6,7-Dimethoxy-quinolin-4-yloxy)-6-methyl-pyridin-2-yl]-phenyl}-ethanone N,N-dimethylformamide (1 ml) and a 2 M aqueous potassium carbonate solution (1 ml) were added to 4-(2-iodo-6-methyl-pyridin-3-yloxy)-6,7-dimethoxy-quinoline (compound 116) (50 mg), tetrakistriphenylphosphine palladium (14 mg), and 3-acetylphenylboronic acid (67 mg) under an argon atmosphere, and the mixture was stirred at 70° C. overnight. The reaction solution was cooled to room temperature, water was then added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-methanol to give the title compound (49 mg, yield 99%).

$^1$H-NMR (CDCl$_3$, 400 MHz): δ 2.44 (s, 3H), 2.71 (s, 3H), 4.04 (s, 3H), 4.08 (s, 3H), 6.33 (d, J=5.4 Hz, 1H), 7.28 (d, J=7.8 Hz, 1H), 7.37-7.58 (m, 4H), 7.85 (d, J=7.8 Hz, 1H), 8.05 (d, J=7.8 Hz, 1H), 8.40 (d, J=5.4 Hz, 1H), 8.51 (s, 1H)

Mass spectrometric value (ESI-MS, m/z): 415 (M+1)$^+$

Compound 233: 3-[3-(6,7-Dimethoxy-quinolin-4-yloxy)-6-methyl-pyridin-2-yl]-benzamide N,N-Dimethylformamide (1 ml) and a 2 M aqueous potassium carbonate solution (1 ml) were added to 4-(2-iodo-6-methyl-pyridin-3-yloxy)-6,7-dimethoxy-quinoline (compound 116) (50 mg), tetrakistriphenylphosphine palladium (14 mg), and (3-aminocarbonyl)phenylboronic acid (58 mg) under an argon atmosphere, and the mixture was stirred at 70° C. for 5 hr. The reaction solution was cooled to room temperature, water was then added thereto, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-methanol to give the title compound (49 mg, yield 100%).

$^1$H-NMR (CDCl$_3$, 400 MHz): δ 2.70 (s, 3H), 4.03 (s, 3H), 4.07 (s, 3H), 6.34 (d, J=5.1 Hz, 1H), 7.29 (s, 1H), 7.37 (dd, J=7.8, 7.8 Hz, 1H), 7.42 (s, 1H), 7.50 (d, J=8.0 Hz, 1H), 7.53 (s, 1H), 7.70 (dd, J=1.4, 8.0 Hz, 1H), 8.01 (d, J=8.0 Hz, 1H), 8.38-8.44 (m, 2H)

Mass spectrometric value (ESI-MS, m/z): 414 (M−1)$^-$

Compound 234: 3-[3-(6,7-Dimethoxy-quinolin-4-yloxy)-6-methyl-pyridin-2-yl]-benzonitrile N,N-Dimethylformamide (1 ml) and a 2 M aqueous potassium carbonate solution (1 ml) were added to 4-(2-iodo-6-methyl-pyridin-3-yloxy)-6,7-dimethoxy-quinoline (compound 116) (50 mg), tetrakistriphenylphosphine palladium (14 mg) and 3-cyanophenylboronic acid (52 mg) under an argon atmosphere, and the mixture was stirred at 70° C. for 5 hr. The reaction solution was cooled to room temperature, water was then added thereto, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-methanol to give the title compound (43 mg, yield 92%).

$^1$H-NMR (CDCl$_3$, 400 MHz): δ 2.70 (s, 3H), 4.04 (s, 3H), 4.07 (s, 3H), 6.35 (d, J=5.4 Hz, 1H), 7.30 (d, J=8.3 Hz, 1H), 7.34-7.52 (m, 4H), 7.56 (d, J=7.6 Hz, 1H), 8.10 (d, J=8.1 Hz, 1H), 8.30 (s, 1H), 8.43 (d, J=5.4 Hz, 1H)

Mass spectrometric value (ESI-MS, m/z): 398 (M+1)+

Compound 235: 3-[3-(6,7-Dimethoxy-quinolin-4-yloxy)-6-methyl-pyridin-2-yl]-phenylamine Toluene (1 ml), N,N-dimethylformamide (0.5 ml), and a saturated aqueous sodium hydrogencarbonate solution (0.5 ml) were added to 4-(2-iodo-6-methyl-pyridin-3-yloxy)-6,7-dimethoxy-quinoline (compound 116) (50 mg), tetrakistriphenylphosphine palladium (28 mg), and 3-aminophenylboronic acid (162 mg) under an argon atmosphere, and the mixture was stirred at 80° C. overnight. The reaction solution was cooled to room temperature, water was then added to the reaction solution, and the mixture was extracted with chloroform. The ethyl acetate layer was then washed with water and was dried over anhydrous magnesium sulfate. The solvent was removed by distillation under the reduced pressure, and the residue was purified by thin layer chromatography using chloroform-methanol to give the title compound (39 mg, yield 85%).

$^1$H-NMR (CDCl$_3$, 400 MHz): δ 2.69 (s, 3H), 4.04 (s, 3H), 4.05 (s, 3H), 6.39 (d, J=5.4 Hz, 1H), 6.59 (dd, J=2.2, 7.8 Hz, 1H), 7.02 (dd, J=7.8, 7.8 Hz, 1H), 7.14-7.25 (m, 3H), 7.44 (d, J=8.3 Hz, 1H), 7.48-7.57 (m, 2H), 8.42 (d, J=5.4 Hz, 1H)

Mass spectrometric value (ESI-MS, m/z): 388 (M+1)$^+$

Compound 236: N-{3-[3-(6,7-Dimethoxy-quinolin-4-yloxy)-6-methyl-pyridin-2-yl]-phenyl}-acetamide Toluene (1 ml) and a saturated aqueous sodium hydrogencarbonate solution (0.5 ml) were added to 4-(2-iodo-6-methyl-pyridin-3-yloxy)-6,7-dimethoxy-quinoline (compound 116) (50 mg), tetrakistriphenylphosphine palladium (14 mg), and (3-acetylamino)-phenylboronic acid (97 mg) under an argon atmosphere, and the mixture was stirred at 80° C. overnight. The reaction solution was cooled to room temperature, a 1 N aqueous sodium hydroxide solution was then added thereto, and the mixture was extracted with chloroform. The chloroform layer was then washed with water and was dried over anhydrous sodium sulfate. The solvent was removed by distillation under the reduced pressure, and the residue was purified by thin layer chromatography using chloroform-methanol to give the title compound (3.6 mg, yield 7%).

$^1$H-NMR (CDCl$_3$, 400 MHz): δ 2.09 (s, 3H), 2.69 (s, 3H), 4.04 (s, 3H), 4.08 (s, 3H), 6.35 (d, J=5.4 Hz, 1H), 7.12-7.29 (m, 3H), 7.33 (d, J=7.6 Hz, 1H), 7.46 (d, J=8.3 Hz, 1H), 7.49 (s, 1H), 7.54 (d, J=7.6 Hz, 1H), 7.58 (s, 1H), 8.17 (s, 1H), 8.40 (d, J=5.6 Hz, 1H)

Mass spectrometric value (ESI-MS, m/z): 430 (M+1)$^+$

Compound 237: 3-[3-(6,7-Dimethoxy-quinolin-4-yloxy)-6-methyl-pyridin-2-yl]-phenol Toluene (1 ml) and a saturated aqueous sodium hydrogencarbonate solution (0.5 ml) were added to 4-(2-iodo-6-methyl-pyridin-3-yloxy)-6,7-dimethoxy-quinoline (compound 116) (50 mg), tetrakistriphenylphosphine palladium (14 mg), and 3-hydroxyphenylboronic acid (81 mg) under an argon atmosphere, and the mixture was stirred at 80° C. overnight. The reaction solution was cooled to room temperature, water was then added thereto, and the mixture was extracted with chloroform. The chloroform layer was then washed with water and was dried over anhydrous sodium sulfate. The solvent was removed by distillation under the reduced pressure, and the residue was purified by thin layer chromatography using chloroform-methanol to give the title compound (6.8 mg, yield 15%).

$^1$H-NMR (CDCl$_3$, 400 MHz): δ 2.67 (s, 3H), 3.82 (s, 3H), 3.98 (s, 3H), 6.36 (d, J=5.4 Hz, 1H), 6.92 (dd, J=1.7, 7.8 Hz, 1H), 6.97 (s, 1H), 7.17 (d, J=8.3 Hz, 1H), 7.23-7.32 (m, 2H), 7.34 (d, J=7.8 Hz, 1H), 7.37 (s, 1H), 7.44 (s, 1H), 7.48 (d, J=7.8 Hz, 1H), 7.94 (d, J=5.6 Hz, 1H)

Mass spectrometric value (ESI-MS, m/z): 389 (M+1)$^+$

Compound 238: 6,7-Dimethoxy-4-[2-(3-methoxy-phenyl)-6-methyl-pyridin-3-yloxy]-quinoline 4-[(2-Iodo-6-methyl-3-pyridyl)oxy]-6,7-dimethoxyquinoline (compound 116) (84 mg), 3-methoxyphenylboronic acid (152 mg), and tetrakistriphenylphosphine palladium (12 mg) were dissolved in toluene (1 ml) to prepare a solution. A saturated aqueous sodium hydrogencarbonate solution (1 ml) was added to the solution, and the mixture was stirred at 80° C. for 3 hr. The reaction solution was filtered, the solvent was then removed by distillation under the reduced pressure, and the residue was purified by column chromatography using methanol-chloroform to give the title compound (79 mg, yield 99%).

$^1$H-NMR (CDCl$_3$, 400 MHz): δ 2.65 (s, 3H), 3.62 (s, 3H), 3.99 (s, 3H), 4.00 (s, 3H), 6.33 (d, J=5.4 Hz, 1H), 6.78 (m, 1H), 7.14-7.19 (m, 2H), 7.36-7.45 (m, 4H), 7.48 (s, 1H), 8.39 (d, J=5.4 Hz, 1H)

Mass spectrometric value (ESI-MS, m/z): 403 (M+1)$^+$

Compound 239: 4-[2-(3-Ethoxy-phenyl)-6-methyl-pyridin-3-yloxy]-6,7-dimethoxy-quinoline N,N-Dimethylformamide (1 ml) and a 2 M aqueous potassium carbonate solution (1 ml) were added to 4-(2-iodo-6-methyl-pyridin-3-yloxy)-6,7-dimethoxy-quinoline (compound 116) (50 mg), tetrakistriphenylphosphine palladium (14 mg), and 3-ethoxyphenylboronic acid (59 mg) under an argon atmosphere, and the mixture was stirred at 70° C. for 5 hr. The reaction solution was cooled to room temperature, water was then added thereto, and the mixture was extracted with ethyl acetate. The ethyl acetate layer was then washed with water and was dried over anhydrous sodium sulfate, the solvent was removed by distillation under the reduced pressure, and the residue was purified by thin layer chromatography using chloroform-methanol to give the title compound (43 mg, yield 87%).

$^1$H-NMR (CDCl$_3$, 400 MHz): δ 1.28 (t, J=6.8 Hz, 3H), 2.69 (s, 3H), 3.87 (q, J=6.8 Hz, 2H), 4.04 (s, 3H), 4.05 (s, 3H), 6.36 (d, J=5.4 Hz, 1H), 6.79 (dd, J=1.7, 7.1 Hz, 1H), 7.17 (dd, J=8.3, 8.3 Hz, 1H), 7.16 (d, J=8.3 Hz, 1H), 7.36-7.51 (m, 4H), 7.53 (s, 1H), 8.42 (d, J=5.4 Hz, 1H)

Mass spectrometric value (ESI-MS, m/z): 439 (M+Na)$^+$

Compound 240: 4-[2-(3-Fluoro-phenyl)-6-methyl-pyridin-3-yloxy]-6,7-dimethoxy-quinoline N,N-Dimethylformamide (1 ml) and a 2 M aqueous potassium carbonate solution (1 ml) were added to 4-(2-iodo-6-methyl-pyridin-3-yloxy)-6,7-dimethoxy-quinoline (compound 116) (50 mg), tetrakistriphenylphosphine palladium (14 mg), and 3-fluorophenylboronic acid (50 mg) under an argon atmosphere, and the mixture was stirred at 70° C. for 5 hr. The reaction solution was cooled to room temperature, water was then added thereto, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-methanol to give the title compound (43 mg, yield 87%).

$^1$H-NMR (CDCl$_3$, 400 MHz): δ 2.70 (s, 3H), 4.06 (s, 3H), 4.06 (s, 3H), 6.39 (d, J=5.4 Hz, 1H), 6.94-7.00 (m, 1H), 7.20-7.32 (m, 2H), 7.44-7.72 (m, 5H), 8.44 (d, J=5.6 Hz, 1H)

Mass spectrometric value (ESI-MS, m/z): 413 (M+Na)$^+$

Compound 241: 4-[2-(3-Chloro-phenyl)-6-methyl-pyridin-3-yloxy]-6,7-dimethoxy-quinoline 4-[(2-Iodo-6-methyl-3-pyridyl)oxy]-6,7-dimethoxyquinoline (compound 116) (84 mg), 3-chlorophenylboronic acid (156 mg), tetrakistriphenylphosphine palladium (12 mg) were dissolved in toluene (1 ml) to prepare a solution. A saturated aqueous sodium hydrogencarbonate solution (1 ml) was added to the solution, and the mixture was stirred at 80° C. for 3 hr. The reaction solution was filtered, and the solvent was then removed by distillation under the reduced pressure. The residue was purified by column chromatography using methanol-chloroform to give the title compound (59 mg, yield 73%).

$^1$H-NMR (CDCl$_3$, 400 MHz): δ 2.65 (s, 3H), 4.01 (s, 3H), 4.02 (s, 3H), 6.30 (d, J=5.4 Hz, 1H), 7.15-7.22 (m, 3H), 7.37 (s, 1H), 7.44 (d, J=8.3 Hz, 1H), 7.48 (s, 1H), 7.70 (m, 1H), 7.92 (m, 1H), 8.39 (d, J=5.4 Hz, 1H)

Mass spectrometric value (ESI-MS, m/z): 407 (M+1)$^+$

Compound 242: 6,7-Dimethoxy-4-(6-methyl-2-p-tolyl-pyridin-3-yloxy)-quinoline 4-[(2-Iodo-6-methyl-3-pyridyl)oxy]-6,7-dimethoxyquinoline (compound 116) (84 mg), 4-methylphenylboronic acid (136 mg), and tetrakistriphenylphosphine palladium (12 mg) were dissolved in toluene (1 ml) to prepare a solution. A saturated aqueous sodium hydrogencarbonate solution (1 ml) was added to the solution, and the mixture was stirred at 80° C. for 3 hr. The reaction solution was filtered, then the solvent was removed by distillation under the reduced pressure, and the residue was purified by column chromatography using methanol-chloroform to give the title compound (77 mg, yield 100%).

¹H-NMR (CDCl₃, 400 MHz): δ 2.24 (s, 3H), 2.64 (s, 3H), 4.00 (s, 3H), 4.01 (s, 3H), 6.33 (d, J=5.1 Hz, 1H), 7.06 (d, J=8.0 Hz, 2H), 7.15 (d, J=8.3 Hz, 1H), 7.37 (s, 1H), 7.38 (d, J=8.1 Hz, 1H), 7.49 (s, 1H), 7.74 (d, J=8.3 Hz, 2H), 8.39 (d, J=5.4 Hz, 1H)

Mass spectrometric value (ESI-MS, m/z): 387 (M+1)⁺

Compound 243: 4-[2-(4-Isopropyl-phenyl)-6-methyl-pyridin-3-yloxy]-6,7-dimethoxy-quinoline 4-[(2-Iodo-6-methyl-3-pyridyl)oxy]-6,7-dimethoxyquinoline (compound 116) (84 mg), 4-isopropylphenylboronic acid (164 mg), and tetrakistriphenylphosphine palladium (12 mg) were dissolved in toluene (1 ml) to prepare a solution. A saturated aqueous sodium hydrogencarbonate solution (1 ml) was added to the solution, and the mixture was stirred at 80° C. for 3 hr. The reaction solution was filtered, the solvent was then removed by distillation under the reduced pressure, and the residue was purified by column chromatography using methanol-chloroform to give the title compound (59 mg, yield 72%).

¹H-NMR (CDCl₃, 400 MHz): δ 1.10 (d, J=6.8 Hz, 6H), 2.60 (s, 3H), 2.76 (m, 1H), 3.95 (s, 3H), 3.96 (s, 3H), 6.32 (d, J=5.4 Hz, 1H), 7.07-7.11 (m, 3H), 7.33 (d, J=8.3 Hz, 1H), 7.34 (s, 1H), 7.44 (s, 1H), 7.72 (d, J=8.3 Hz, 2H), 8.36 (d, J=5.1 Hz, 1H)

Mass spectrometric value (ESI-MS, m/z): 415 (M+1)⁺

Compound 244: 4-[2-(4-Butyl-phenyl)-6-methyl-pyridin-3-yloxy]-6,7-dimethoxy-quinoline 4-[(2-Iodo-6-methyl-3-pyridyl)oxy]-6,7-dimethoxyquinoline (compound 116) (84 mg), 4-n-butylphenylboronic acid (178 mg), and tetrakistriphenylphosphine palladium (12 mg) were dissolved in toluene (1 ml) to prepare a solution. A saturated aqueous sodium hydrogencarbonate solution (1 ml) was added to the solution, and the mixture was stirred at 80° C. for 3 hr. The reaction solution was filtered, the solvent was then removed by distillation under the reduced pressure, and the residue was purified by column chromatography using methanol-chloroform to give the title compound (55 mg, yield 64%).

¹H-NMR (CDCl₃, 400 MHz): δ 0.79 (t, J=7.3 Hz, 3H), 1.18 (m, 2H), 1.44 (m, 2H), 2.46 (t, J=7.6 Hz, 2H), 2.60 (s, 3H), 3.95 (s, 3H), 3.96 (s, 3H), 6.30 (d, J=5.4 Hz, 1H), 7.02 (d, J=8.1 Hz, 2H), 7.11 (d, J=8.3 Hz, 1H), 7.34-7.35 (m, 2H), 7.44 (s, 1H), 7.70 (d, J=8.3 Hz, 2H), 8.35 (d, J=5.4 Hz, 1H)

Mass spectrometric value (ESI-MS, m/z): 429 (M+1)⁺

Compound 245: {4-[3-(6,7-Dimethoxy-quinolin-4-yloxy)-6-methyl-pyridin-2-yl]-phenyl}-methanol Toluene (1 ml) and a saturated aqueous sodium hydrogencarbonate solution (0.5 ml) were added to 4-(2-iodo-6-methyl-pyridin-3-yloxy)-6,7-dimethoxy-quinoline (compound 116) (50 mg), tetrakistriphenylphosphine palladium (14 mg), and (4-hydroxymethyl)phenylboronic acid (90 mg) under an argon atmosphere, and the mixture was stirred at 80° C. for 5 hr. The reaction solution was cooled to room temperature, an aqueous sodium hydroxide solution was then added thereto, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-methanol to give the title compound (11 mg, yield 24%).

¹H-NMR (CDCl₃, 400 MHz): δ 2.69 (s, 3H), 4.03 (s, 3H), 4.03 (s, 3H), 4.63 (s, 2H), 6.35 (d, J=5.4 Hz, 1H), 7.22 (d, J=8.3 Hz, 1H), 7.28 (d, J=8.6 Hz, 1H), 7.40-7.48 (m, 2H), 7.51 (s, 1H), 7.58 (d, J=8.3 Hz, 1H), 7.85 (d, J=8.6 Hz, 2H), 8.41 (d, J=5.4 Hz, 1H)

Mass spectrometric value (ESI-MS, m/z): 403 (M+1)⁺

Compound 246: 1-{4-[3-(6,7-Dimethoxy-quinolin-4-yloxy)-6-methyl-pyridin-2-yl]-phenyl}-ethanone N,N-Dimethylformamide (1 ml) and a 2 M aqueous potassium carbonate solution (0.5 ml) were added to 4-(2-iodo-6-methyl-pyridin-3-yloxy)-6,7-dimethoxy-quinoline (compound 116) (50 mg), tetrakistriphenylphosphine palladium (14 mg), and 4-acetylphenylboronic acid (97 mg) under an argon atmosphere, and the mixture was stirred at 70° C. overnight. The reaction solution was cooled to room temperature, water was then added thereto, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-methanol to give the title compound (26 mg, yield 52%).

¹H-NMR (CDCl₃, 400 MHz): δ 2.55 (s, 3H), 2.71 (s, 3H), 4.05 (s, 3H), 4.06 (s, 3H), 6.38 (d, J=5.4 Hz, 1H), 7.29 (d, J=8.5 Hz, 1H), 7.34-7.60 (m, 3H), 7.88 (d, J=8.3 Hz, 2H), 7.97 (d, J=8.3 Hz, 2H), 8.42 (d, J=5.6 Hz, 1H)

Mass spectrometric value (ESI-MS, m/z): 437 (M+Na)⁺

Compound 247: {4-[3-(6,7-Dimethoxy-quinolin-4-yloxy)-6-methyl-pyridin-2-yl]-phenyl}-dimethyl-amine Toluene (1 ml), N,N-dimethylformamide (0.5 ml) and a saturated aqueous sodium hydrogencarbonate solution (0.5 ml) were added to 4-(2-iodo-6-methyl-pyridin-3-yloxy)-6,7-dimethoxy-quinoline (compound 116) (50 mg), tetrakistriphenylphosphine palladium (28 mg), and 4-dimethylaminophenylboronic acid (196 mg) under an argon atmosphere, and the mixture was stirred at 80° C. overnight. The reaction solution was cooled to room temperature, water was then added thereto, and the mixture was extracted with chloroform. The chloroform layer was then washed with water and was dried over anhydrous magnesium sulfate. The solvent was removed by distillation under the reduced pressure, and the residue was purified by column chromatography using chloroform-methanol to give the title compound (39 mg, yield 80%).

¹H-NMR (CDCl₃, 400 MHz): δ 2.66 (s, 3H), 2.91 (s, 6H), 4.05 (s, 6H), 6.37 (d, J=5.4 Hz, 1H), 6.59 (d, J=9.0 Hz, 2H), 7.09 (d, J=8.3 Hz, 1H), 7.38 (d, J=8.3 Hz, 1H), 7.48 (s, 1H), 7.59 (s, 1H), 7.84 (d, J=9.0 Hz, 2H), 8.41 (d, J=5.4 Hz, 1H)

Mass spectrometric value (ESI-MS, m/z): 438 (M+Na)⁺

Compound 248: {4-[3-(6,7-Dimethoxy-quinolin-4-yloxy)-6-methyl-pyridin-2-yl]-phenol N,N-Dimethylformamide (1 ml) and a 2 M aqueous potassium carbonate solution (0.5 ml) were added to 4-(2-iodo-6-methyl-pyridin-3-yloxy)-6,7-dimethoxy-quinoline (compound 116) (50 mg), tetrakistriphenylphosphine palladium (14 mg), and 4-hydroxyphenylboronic acid (81 mg) under an argon atmosphere, and the mixture was stirred at 70° C. overnight. The reaction solution was cooled to room temperature, water was then added thereto, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-methanol to give the title compound (34 mg, yield 75%).

$^1$H-NMR (CDCl$_3$, 400 MHz): δ 2.66 (s, 3H), 3.99 (s, 3H), 4.03 (s, 3H), 6.34 (d, J=5.6 Hz, 1H), 6.69 (d, J=8.8 Hz, 2H), 7.17 (d, J=8.3 Hz, 1H), 7.40-7.46 (m, 2H), 7.52 (s, 1H), 7.68 (d, J=8.8 Hz, 2H), 8.38 (d, J=5.4 Hz, 1H)

Mass spectrometric value (ESI-MS, m/z): 389 (M+1)$^+$

Compound 249: 6,7-Dimethoxy-4-[2-(4-methoxyphenyl)-6-methyl-pyridin-3-yloxy]-quinoline 4-[(2-Iodo-6-methyl-3-pyridyl)oxy]-6,7-dimethoxyquinoline (compound 116) (84 mg), 4-methoxyphenylboronic acid (152 mg), and tetrakistriphenylphosphine palladium (12 mg) were dissolved in toluene (1 ml) to prepare a solution. A saturated aqueous sodium hydrogencarbonate solution (1 ml) was added to the solution, and the mixture was stirred at 80° C. for 3 hr. The reaction solution was filtered, and the solvent was then removed by distillation under the reduced pressure. The residue was purified by column chromatography using methanol-chloroform to give the title compound (64 mg, yield 80%).

$^1$H-NMR (CDCl$_3$, 400 MHz): δ 2.59 (s, 3H), 3.66 (s, 3H), 3.96 (s, 3H), 3.96 (s, 3H), 6.28 (d, J=5.1 Hz, 1H), 6.73 (d, J=8.8 Hz, 2H), 7.08 (d, J=8.1 Hz, 1H), 7.31-7.34 (m, 2H), 7.46 (s, 1H), 7.77 (d, J=8.8 Hz, 2H), 8.34 (d, J=5.4 Hz, 1H)

Mass spectrometric value (ESI-MS, m/z): 403 (M+1)$^+$

Compound 250: 6,7-Dimethoxy-4-[6-methyl-2-(4-phenoxyphenyl)-pyridin-3-yloxy]-quinoline Toluene (1 ml) and a saturated aqueous sodium hydrogencarbonate solution (0.5 ml) were added to 4-(2-iodo-6-methyl-pyridin-3-yloxy)-6,7-dimethoxy-quinoline (compound 116) (50 mg), tetrakistriphenylphosphine palladium (14 mg), and 4-phenoxyphenylboronic acid (81 mg) under an argon atmosphere, and the mixture was stirred at 70° C. overnight. The reaction solution was cooled to room temperature, water was then added thereto, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-methanol to give the title compound (53 mg, yield 96%).

$^1$H-NMR (CDCl$_3$, 400 MHz): δ 2.68 (s, 3H), 4.02 (s, 3H), 4.05 (s, 3H), 6.37 (d, J=5.1 Hz, 1H), 6.85-6.91 (m, 4H), 7.08 (t, J=7.6 Hz, 1H), 7.20 (d, J=8.0 Hz, 1H), 7.25-7.33 (m, 2H), 7.38-7.52 (m, 3H), 7.84 (d, J=8.8 Hz, 2H), 8.43 (d, J=5.4 Hz, 1H)

Mass spectrometric value (ESI-MS, m/z): 465 (M+1)$^+$

Compound 251: 4-[2-(4-Fluoro-phenyl)-6-methyl-pyridin-3-yloxy]-6,7-dimethoxy-quinoline 4-[(2-Iodo-6-methyl-3-pyridyl)oxy]-6,7-dimethoxyquinoline (compound 116) (84 mg), 4-fluorophenylboronic acid (140 mg), and tetrakistriphenylphosphine palladium (12 mg) were dissolved in toluene (1 ml) to prepare a solution. A saturated aqueous sodium hydrogencarbonate solution (1 ml) was added to the solution, and the mixture was stirred at 80° C. for 3 hr. The reaction solution was filtered, the solvent was then removed by distillation under the reduced pressure, and the residue was purified by column chromatography using methanol-chloroform to give the title compound (64 mg, yield 82%).

$^1$H-NMR (CDCl$_3$, 400 MHz): δ 2.60 (s, 3H), 3.95 (s, 3H), 3.96 (s, 3H), 6.28 (d, J=5.4 Hz, 1H), 6.90 (m, 2H), 7.14 (d, J=8.3 Hz, 1H), 7.34 (s, 1H), 7.36 (d, J=8.0 Hz, 1H), 7.41 (s, 1H), 7.79 (m, 2H), 8.36 (d, J=5.1 Hz, 1H)

Mass spectrometric value (ESI-MS, m/z): 391 (M+1)$^+$

Compound 252: 4-[2-(4-Chlorophenyl)-6-methyl-pyridin-3-yloxy]-6,7-dimethoxy-quinoline 4-[(2-Iodo-6-methyl-3-pyridyl)oxy]-6,7-dimethoxyquinoline (compound 116) (84 mg), 4-chlorophenylboronic acid (156 mg), and tetrakistriphenylphosphine palladium (12 mg) were dissolved in toluene (1 ml) to prepare a solution. A saturated aqueous sodium hydrogencarbonate solution (1 ml) was added to the solution, and the mixture was stirred at 80° C. for 3 hr. The reaction solution was filtered, the solvent was then removed by distillation under the reduced pressure, and the residue was purified by column chromatography using methanol-chloroform to give the title compound (74 mg, yield 91%).

$^1$H-NMR (CDCl$_3$, 400 MHz): δ 2.60 (s, 3H), 3.95 (s, 3H), 3.96 (s, 3H), 6.27 (d, J=5.4 Hz, 1H), 7.14 (d, J=8.3 Hz, 1H), 7.19 (m, 2H), 7.34-7.40 (m, 3H), 7.75 (m, 2H), 8.36 (d, J=5.4 Hz, 1H)

Mass spectrometric value (ESI-MS, m/z): 407 (M+1)$^+$

Compound 253: 4-[2-(2,6-Dichloro-phenyl)-6-methyl-pyridin-3-yloxy]-6,7-dimethoxy-quinoline 4-[(2-Iodo-6-methyl-3-pyridyl)oxy]-6,7-dimethoxyquinoline (compound 116) (84 mg), 2,6-dichlorophenylboronic acid (191 mg), and tetrakistriphenylphosphine palladium (12 mg) were dissolved in toluene (1 ml) to prepare a solution. A saturated aqueous sodium hydrogencarbonate solution (1 ml) was added to the solution, and the mixture was stirred at 80° C. for 3 hr. The reaction solution was filtered, the solvent was then removed by distillation under the reduced pressure, and the residue was purified by column chromatography using methanol-chloroform to give the title compound (79 mg, yield 90%).

$^1$H-NMR (CDCl$_3$, 400 MHz): δ 2.64 (s, 3H), 3.97 (s, 3H), 3.97 (s, 3H), 6.38 (d, J=5.4 Hz, 1H), 7.09 (dd, J=2.7, 8.6 Hz, 1H), 7.19 (d, J=8.6 Hz, 1H), 7.28 (d, J=8.8 Hz, 1H), 7.31 (s, 1H), 7.35 (d, J=2.7 Hz, 1H), 7.39 (s, 1H), 7.49 (d, J=8.3 Hz, 1H), 8.41 (d, J=5.1 Hz, 1H)

Mass spectrometric value (ESI-MS, m/z): 441 (M+1)$^+$

Compound 254: 4-[2-(3,5-Difluoro-phenyl)-6-methyl-pyridin-3-yloxy]-6,7-dimethoxy-quinoline N,N-Dimethylformamide (1 ml) and a 2 M aqueous potassium carbonate solution (1 ml) were added to 4-(2-iodo-6-methyl-pyridin-3-yloxy)-6,7-dimethoxy-quinoline (compound 116) (50 mg), tetrakistriphenylphosphine palladium (14 mg), and 3,5-difluorophenylboronic acid (56 mg) under an argon atmosphere, and the mixture was stirred at 70° C. for 5 hr. The reaction solution was cooled to room temperature, water was then added thereto, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-methanol to give the title compound (23 mg, yield 47%).

¹H-NMR (CDCl₃, 400 MHz): δ 2.70 (s, 3H), 4.07 (s, 6H), 6.36 (d, J=5.6 Hz, 1H), 6.68-6.79 (m, 1H), 7.29 (d, J=8.3 Hz, 1H), 7.41-7.63 (m, 5H), 8.43 (d, J=5.4 Hz, 1H)

Mass spectrometric value (ESI-MS, m/z): 409 (M+1)⁺

Compound 255: 6,7-Dimethoxy-4-(6-methyl-2-thiophen-3-yl-pyridin-3-yloxy)-quinoline 4-[(2-Iodo-6-methyl-3-pyridyl)oxy]-6,7-dimethoxyquinoline (compound 116) (84 mg), 3-thiopheneboronic acid (128 mg), and tetrakistriphenylphosphine palladium (12 mg) were dissolved in toluene (1 ml) to prepare a solution. A saturated aqueous sodium hydrogencarbonate solution (1 ml) was added to the solution, and the mixture was stirred at 80° C. for 3 hr. The reaction solution was filtered, the solvent was then removed by distillation under the reduced pressure, and the residue was purified by column chromatography using methanol-chloroform to give the title compound (58 mg, yield 77%).

¹H-NMR (CDCl₃, 400 MHz): δ 2.65 (s, 3H), 4.06 (s, 3H), 4.08 (s, 3H), 6.42 (d, J=5.6 Hz, 1H), 7.16 (d, J=8.3 Hz, 1H), 7.23 (m, 1H), 7.24 (s, 1H), 7.39 (d, J=8.3 Hz, 1H), 7.61 (s, 1H), 7.69 (d, J=5.1 Hz, 1H), 7.88 (d, J=2.7 Hz, 1H), 8.41 (d, J=5.6 Hz, 1H)

Mass spectrometric value (ESI-MS, m/z): 379 (M+1)⁺

Compound 256: 4-[2-(1,5-Dimethyl-1H-pyrazol-3-yl)-6-methyl-pyridin-3-yloxy]-6,7-dimethoxy-quinoline 3-Benzyloxy-6-methyl-pyridine-2-carbaldehyde (452 mg) was dissolved in tetrahydrofuran (15 ml) to prepare a solution. A 1-propynylmagnesium bromide/0.5 M tetrahydrofuran solution (6 ml) was added to the solution at −78° C., and the mixture was stirred at room temperature for 2 hr. Water was added to the reaction solution, and the mixture was extracted with ethyl acetate. The ethyl acetate layer was then washed with water and was dried over anhydrous sodium sulfate, and the solvent was removed by distillation under the reduced pressure. The residue was used in the next reaction without purification.

The residue was dissolved in chloroform (15 ml) to prepare a solution. Manganese dioxide (1.36 g) was added to the solution, and the mixture was stirred at room temperature overnight. The reaction solution was filtered, and the solvent was removed by distillation under the reduced pressure. The residue (563 mg) was used in the next reaction without purification.

A part (240 mg) of the residue was dissolved in N,N-dimethylformamide (7 ml) to prepare a solution. Hydrazine monohydrate (0.15 ml) was added to the solution, and the mixture was stirred at room temperature overnight. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was used in the next reaction without purification.

The residue was dissolved in N,N-dimethylformamide (5 ml) to prepare a solution. Potassium carbonate (339 mg) and methyl iodide (0.15 ml) were added to the solution under ice cooling, and the mixture was stirred at room temperature overnight. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was used in the next reaction without purification.

Trifluoroacetic acid (3 ml) and methanesulfonic acid (0.3 ml) were added to the residue, and the mixture was stirred at room temperature overnight. The solvent was removed by distillation under the reduced pressure. Water was then added to the reaction solution, and the mixture was extracted with ethyl acetate. The organic layer was washed with an aqueous sodium hydrogencarbonate solution and water and was dried over anhydrous sodium sulfate. The solvent was removed by distillation under the reduced pressure, and the residue was purified by column chromatography using acetone-chloroform to give 2-(1,5-dimethyl-1H-pyrazol-3-yl)-6-methyl-pyridin-3-ol (60 mg, yield 32%) (5 steps).

2-(1,5-Dimethyl-1H-pyrazol-3-yl)-6-methyl-pyridin-3-ol (111 mg), 4-chloro-6,7-dimethoxyquinoline (218 mg), and 4-dimethylaminopyridine (130 mg) were suspended in o-dichlorobenzene (5 ml), and the suspension was stirred at 160° C. for 2 days. The reaction solution was cooled to room temperature, and the solvent was then removed by distillation under the reduced pressure. The residue was purified by thin layer chromatography using methanol-chloroform to give the title compound (9 mg, yield 4%).

¹H-NMR (CDCl₃, 400 MHz): δ 2.13 (s, 3H), 2.71 (s, 3H), 3.75 (s, 3H), 4.06 (s, 3H), 4.07 (s, 3H), 6.33 (d, J=5.4 Hz, 1H), 6.41 (s, 1H), 7.17 (d, J=8.3 Hz, 1H), 7.39 (d, J=8.0 Hz, 1H), 7.44 (s, 1H), 7.65 (s, 1H), 8.42 (d, J=5.1 Hz, 1H)

Mass spectrometric value (ESI-MS, m/z): 413 (M+Na)⁺

Compound 257: 4-[2-(2,5-Dimethyl-2H-pyrazol-3-yl)-6-methyl-pyridin-3-yloxy]-6,7-dimethoxy-quinoline 3-Benzyloxy-6-methyl-pyridine-2-carbaldehyde (452 mg) was dissolved in tetrahydrofuran (15 ml) to prepare a solution. A 1-propynylmagnesium bromide/0.5 M tetrahydrofuran solution (6 ml) was added to the solution at −78° C., and the mixture was stirred at room temperature for 2 hr. Water was added to the reaction solution, and the mixture was extracted with ethyl acetate, and the ethyl acetate layer was then washed with water and was dried over anhydrous sodium sulfate. The solvent was removed by distillation under the reduced pressure, and the residue was used in the next reaction without purification.

The residue was dissolved in chloroform (15 ml) to prepare a solution. Manganese dioxide (1.36 g) was added to the solution, and the mixture was stirred at room temperature overnight. The reaction solution was filtered, and the solvent was removed by distillation under the reduced pressure. The residue (563 mg) was used in the next reaction without purification.

A part (240 mg) of the residue was dissolved in N,N-dimethylformamide (7 ml) to prepare a solution. Hydrazine monohydrate (0.15 ml) was added to the solution, and the mixture was stirred at room temperature overnight. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was used in the next reaction without purification.

The residue was dissolved in N,N-dimethylformamide (5 ml) to prepare a solution. Potassium carbonate (339 mg) and methyl iodide (0.15 ml) were added to the solution under ice cooling, and the mixture was stirred at room temperature overnight. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was used in the next reaction without purification.

Trifluoroacetic acid (3 ml) and methanesulfonic acid (0.3 ml) were added to the residue, and the mixture was stirred at room temperature overnight. The solvent was removed by distillation under the reduced pressure. Water was then added to the reaction solution, and the mixture was extracted with ethyl acetate. The organic layer was washed with an aqueous sodium hydrogencarbonate solution and was washed with water and was dried over anhydrous sodium sulfate. The solvent was removed by distillation under the reduced pressure, and the residue was purified by column chromatography using acetone-chloroform to give 2-(2,5-dimethyl-2H-pyrazol-3-yl)-6-methyl-pyridin-3-ol (38 mg, yield 21%) (5 steps).

2-(2,5-Dimethyl-2H-pyrazol-3-yl)-6-methyl-pyridin-3-ol (33 mg), 4-chloro-6,7-dimethoxyquinoline (109 mg), and 4-dimethylaminopyridine (66 mg) were dissolved in dimethyl sulfoxide (5 ml) to prepare a solution. Cesium carbonate (165 mg) was added to the solution, and the mixture was stirred at 140° C. for 4 hr. The reaction solution was cooled to room temperature, water was then added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using methanol-chloroform to give the title compound (15 mg, yield 23%).

$^1$H-NMR (CDCl$_3$, 400 MHz): δ 2.12 (s, 3H), 2.66 (s, 3H), 4.03 (s, 3H), 4.06 (s, 3H), 4.08 (s, 3H), 6.27 (s, 1H), 6.37 (d, J=5.4 Hz, 1H), 7.22 (d, J=8.3 Hz, 1H), 7.43 (d, J=8.3 Hz, 1H), 7.45 (s, 1H), 7.48 (s, 1H), 8.48 (d, J=5.1 Hz, 1H)

Mass spectrometric value (ESI-MS, m/z): 413 (M+Na)$^+$

Compound 258: 6,7-Dimethoxy-4-[6-methyl-2-(3-methylisoxazol-5-yl)-pyridin-3-yloxy]-quinoline 3-Benzyloxy-6-methyl-pyridine-2-carbaldehyde (452 mg) was dissolved in tetrahydrofuran (15 ml) to prepare a solution. A 1-propynylmagnesium bromide/0.5 M tetrahydrofuran solution (6 ml) was added to the solution at −78° C., and the mixture was stirred at room temperature for 2 hr. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was used in the next reaction without purification.

The residue was dissolved in chloroform (15 ml) to prepare a solution. Manganese dioxide (1.36 g) was added to the solution, and the mixture was stirred at room temperature overnight. The reaction solution was filtered, the solvent was removed by distillation under the reduced pressure, and the residue (563 mg) was used in the next reaction without purification.

A part (117 mg) of the residue was dissolved in N,N-dimethylformamide (4 ml) to prepare a solution. Hydroxyamine hydrochloride (298 mg) and triethylamine (0.6 ml) were added to the solution, and the mixture was stirred at room temperature for 4 hr. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was used in the next reaction without purification.

Trifluoroacetic acid (2 ml) and methanesulfonic acid (0.2 ml) were added to the residue, and the mixture was stirred at room temperature overnight. The solvent was removed by distillation under the reduced pressure, water was then added to the reaction solution, and the mixture was extracted with ethyl acetate. The organic layer was washed with an aqueous sodium hydrogencarbonate solution and water and was dried over anhydrous sodium sulfate. The solvent was removed by distillation under the reduced pressure, and the residue (84 mg) was used in the next reaction without purification.

A part (56 mg) of the residue, 4-chloro-6,7-dimethoxyquinoline (200 mg), and 4-dimethylaminopyridine (158 mg) were dissolved in o-dichlorobenzene (4 ml) to prepare a solution which was then stirred at 140° C. for 5 hr. The reaction solution was cooled to room temperature, the solvent was then removed by distillation under the reduced pressure, and the residue was purified by thin layer chromatography using methanol-chloroform to give the title compound (16 mg, yield 10%) (5 steps).

$^1$H-NMR (CDCl$_3$, 400 MHz): δ 2.26 (s, 3H), 2.71 (s, 3H), 4.05 (s, 3H), 4.07 (s, 3H), 6.41 (d, J=5.4 Hz, 1H), 6.62 (s, 1H), 7.30 (d, J=8.5 Hz, 1H), 7.45 (d, J=8.3 Hz, 1H), 7.47 (s, 1H), 7.57 (s, 1H), 8.49 (d, J=5.4 Hz, 1H)

Mass spectrometric value (ESI-MS, m/z): 400 (M+Na)$^+$

Compound 259: 6,7-Dimethoxy-4-(6-methyl-2-thiazol-2-yl-pyridin-3-yloxy)-quinoline N,N-Dimethylformamide (1 ml) was added to 4-(2-iodo-6-methyl-pyridin-3-yloxy)-6,7-dimethoxy-quinoline (compound 116) (50 mg), tetrakistriphenylphosphine palladium (14 mg), tri-n-butyl-(thiazol-2-yl)-tin (132 mg), and copper (II) oxide (1.9 mg) under an argon atmosphere, and the mixture was stirred at 70° C. overnight. The reaction solution was cooled to room temperature, water was then added thereto, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using hexane-acetone to give the title compound (5.2 mg, yield 12%).

$^1$H-NMR (CDCl$_3$, 400 MHz): δ 2.73 (s, 3H), 4.06 (s, 3H), 4.08 (s, 3H), 6.41 (d, J=5.4 Hz, 1H), 7.31 (d, J=8.5 Hz, 1H), 7.36 (d, J=3.2 Hz, 1H), 7.51 (d, J=8.5 Hz, 1H), 7.53 (s, 1H), 7.70 (s, 1H), 7.79 (d, J=3.2 Hz, 1H), 8.44 (d, J=5.4 Hz, 1H)

Mass spectrometric value (ESI-MS, m/z): 380 (M+1)$^+$

Compound 260: 4-[2-(4,5-Dimethylthiazol-2-yl)-5,6-dimethyl-pyridin-3-yloxy]-6,7-dimethoxy-quinoline 4,5-Dimethylthiazole (1.0 g) was dissolved in tetrahydrofuran (40 ml) under an argon atmosphere to prepare a solution. A 1.6M hexane solution (5.6 ml) of n-butyllithium was added dropwise at −78° C., and the mixture was then stirred at −78° C. for 30 min. A solution of 4,5-dimethylfurfural (1 g) in tetrahydrofuran (20 ml) was added dropwise thereto, and the temperature of the mixture was raised to room temperature with stirring. Water was added to the reaction solution to stop the reaction. The solvent was removed by distillation under the reduced pressure, water was added to the residue, and the mixture was extracted with ethyl acetate. The ethyl acetate layer was then washed with water and was dried over anhydrous sodium sulfate. The solvent was removed by distillation under the reduced pressure, and the residue was purified by column chromatography using hexane-acetone to give (4,5-dimethylfuran-2-yl)-(4,5-dimethylthiazol-2-yl)methanol (945 mg, yield 50%).

(4,5-Dimethylfuran-2-yl)-(4,5-dimethylthiazol-2-yl) methanol (945 mg) was dissolved in chloroform (20 ml) to prepare a solution. Manganese dioxide (3.5 g) was added to the solution, and the mixture was stirred at room temperature overnight. The reaction solution was filtered through Celite, and the solvent was removed from the filtrate by distillation under the reduced pressure to give (4,5-dimethylfuran-2-yl) (4,5-dimethylthiazol-2-yl)-methanone (910 mg, yield 97%).

(4,5-Dimethylfuran-2-yl)-(4,5-dimethylthiazol-2-yl) methanone (910 mg), methanol (7 ml), and 8 ml of a 28% aqueous ammonia solution were placed in a sealed tube, and the mixture was stirred at 160° C. overnight. The reaction solution was cooled to room temperature, the solvent was then removed by distillation under the reduced pressure, and the residue was purified by column chromatography using hexane-ethyl acetate to give 5,6-dimethyl-2-(4,5-dimethylthiazol-2-yl)pyridin-3-ol (782 mg, yield 86%).

Dimethyl sulfoxide (2 ml) was added to 5,6-dimethyl-2-(4,5-dimethylthiazol-2-yl)-pyridin-3-ol (50 mg), 4-chloro-6,7-dimethoxyquinoline (143 mg), cesium carbonate (209 mg), and 4-(N,N-dimethylamino)-pyridine (78 mg), and the mixture was stirred at 140° C. overnight. The reaction solution was cooled to room temperature, water was then added to the cooled solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using hexane-acetone to give the title compound (7.7 mg, yield 9%).

$^{1}$H-NMR (CDCl$_{3}$, 400 MHz): δ 2.13 (s, 3H), 2.27 (s, 3H), 2.35 (s, 3H), 2.64 (s, 3H), 4.07 (s, 3H), 4.07 (s, 3H), 6.33 (d, J=5.1 Hz, 1H), 7.33 (s, 1H), 7.45 (s, 1H), 7.71 (s, 1H), 8.42 (d, J=5.4 Hz, 1H)

Mass spectrometric value (ESI-MS, m/z): 444 (M+Na)$^{+}$

Compound 261: 3-(6,7-Dimethoxy-quinolin-4-yloxy)-6-methyl-[2,2']-bipyridine

N,N-Dimethylformamide (1.2 ml) was added to 4-(2-iodo-6-methyl-pyridin-3-yloxy)-6,7-dimethoxy-quinoline (compound 116) (50 mg), tetrakistriphenylphosphine palladium (14 mg), tri-n-butyl-(2-pyridyl)-tin (65 mg), and cesium fluoride (36 mg) under an argon atmosphere, and the mixture was stirred at 70° C. for three nights. The reaction solution was cooled to room temperature, water was then added thereto, and the mixture was extracted with ethyl acetate. The ethyl acetate layer was then washed with water and was dried over anhydrous sodium sulfate.

Likewise, N,N-dimethylformamide (1.2 ml) was added to 4-(2-iodo-6-methyl-pyridin-3-yloxy)-6,7-dimethoxy-quinoline (compound 116) (50 mg), tris(dibenzylideneacetone) (chloroform)dipalladium(0) (6.1 mg), (±)-2,2'-(diphenylphosphino)-binaphthyl (3.7 mg), tri-n-butyl-(2-pyridyl)-tin (65 mg), and cesium fluoride (36 mg) under an argon atmosphere, and the mixture was stirred at 70° C. for 3 nights. The reaction solution was cooled to room temperature, water was then added thereto, and the mixture was extracted with ethyl acetate. The ethyl acetate layer was then washed with water and was dried over anhydrous sodium sulfate.

The above two ethyl acetate layers were combined, and the solvent was removed by distillation under the reduced pressure. The residue was purified by thin layer chromatography using ether-methanol to give the title compound (14 mg, yield 32%).

$^{1}$H-NMR (CDCl$_{3}$, 400 MHz): δ 2.72 (s, 3H), 4.02 (s, 3H), 4.03 (s, 3H), 6.37 (d, J=5.4 Hz, 1H), 7.13 (dd, J=4.9, 7.3 Hz, 1H), 7.31 (d, J=8.5 Hz, 1H), 7.40 (s, 1H), 7.52 (d, J=8.5 Hz, 1H), 7.53 (s, 1H), 7.55-7.63 (m, 1H), 7.79 (d, J=7.8 Hz, 1H), 8.39 (d, J=5.4 Hz, 1H), 8.50 (d, J=4.6 Hz, 1H)

Mass spectrometric value (ESI-MS, m/z): 374 (M+1)$^{+}$

Compound 262: 3-(6,7-Dimethoxy-quinolin-4-yloxy)-6-methyl-[2,3']bipyridine

N,N-Dimethylformamide (1 ml), ethanol (0.5 ml), and a 2 M aqueous potassium carbonate solution (1 ml) were added to 4-(2-iodo-6-methyl-pyridin-3-yloxy)-6,7-dimethoxy-quinoline (compound 116) (50 mg), tetrakistriphenylphosphine palladium (14 mg), and 3-pyridylboronic acid (44 mg) under an argon atmosphere, and the mixture was stirred at 70° C. for 3 hr. The reaction solution was cooled to room temperature, water was then added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-methanol to give the title compound (33 mg, yield 75%).

$^{1}$H-NMR (CDCl$_{3}$, 400 MHz): δ 2.71 (s, 3H), 4.05 (s, 3H), 4.06 (s, 3H), 6.40 (d, J=5.4 Hz, 1H), 7.22-7.32 (m, 2H), 7.46-7.57 (m, 3H), 8.16 (d, J=8.0 Hz, 1H), 8.44 (d, J=5.4 Hz, 1H), 8.52 (dd, J=3.2, 1.5 Hz, 1H), 9.06 (s, 1H)

Mass spectrometric value (ESI-MS, m/z): 374 (M+1)$^{+}$

Compound 263: 3-(6,7-Dimethoxy-quinolin-4-yloxy)-6-methyl-[2,4']bipyridine

N,N-Dimethylformamide (1 ml), ethanol (0.5 ml), and a 2 M aqueous potassium carbonate solution (1 ml) were added to 4-(2-iodo-6-methyl-pyridin-3-yloxy)-6,7-dimethoxy-quinoline (compound 116) (50 mg), tetrakistriphenylphosphine palladium (14 mg) and 4-pyridylboronic acid (44 mg) under an argon atmosphere, and the mixture was stirred at 70° C. for 3 hr. The reaction solution was cooled to room temperature, water was then added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-methanol to give the title compound (29 mg, yield 66%).

$^{1}$H-NMR (CDCl$_{3}$, 400 MHz): δ 2.71 (s, 3H), 4.04 (s, 3H), 4.07 (s, 3H), 6.42 (d, J=5.4 Hz, 1H), 7.33 (d, J=8.3 Hz, 1H), 7.49 (d, J=8.3 Hz, 1H), 7.49 (s, 1H), 7.55 (s, 1H), 7.79 (d, J=6.1 Hz, 2H), 8.46 (d, J=5.4 Hz, 1H), 8.58 (d, J=6.1 Hz, 2H)

Mass spectrometric value (ESI-MS, m/z): 374 (M+1)$^{+}$

Compound 264: 3-(6,7-Dimethoxy-quinolin-4-yloxy)-6.6°-dimethyl-[2,2']bipyridine

2-Bromo-6-methylpyridine (191 mg) was dissolved in tetrahydrofuran (5 ml) to prepare a solution which was then cooled to −78° C. A 1.57 M n-butyllithium/hexane solution (1 ml) was added to the reaction solution, and the mixture was stirred at −78° C. for 10 min. Tributyltin chloride (0.4 ml) was added to the reaction solution, and the mixture was stirred at room temperature for one hr. Water was then added to the reaction solution, and the mixture was extracted with ethyl acetate. The ethyl acetate layer was washed with water and was dried over anhydrous sodium sulfate. The solvent was removed by distillation under the reduced pressure, and the residue was used in the next reaction without purification.

The residue, 4-(2-iodo-6-methyl-pyridin-3-yloxy)-6,7-dimethoxy-quinoline (compound 116) (205 mg), and tetrakistriphenylphosphine palladium (48 mg) were dissolved in N,N-dimethylformamide (25 ml), copper(II) oxide (28 mg) was added to the solution, and the mixture was stirred at 100° C. overnight. The reaction solution was cooled to room temperature, water was then added to the reaction solution, and the mixture was extracted with ethyl acetate. The ethyl acetate layer was then washed with water and was dried over anhydrous sodium sulfate, the solvent was removed by distillation under the reduced pressure, and the residue was purified by thin layer chromatography using acetone-chloroform to give the title compound (11 mg, yield 6%).

$^1$H-NMR (CDCl$_3$, 400 MHz): δ 2.22 (s, 3H), 2.71 (s, 3H), 4.03 (s, 3H), 4.03 (s, 3H), 6.32 (d, J=5.1 Hz, 1H), 6.95 (d, J=7.6 Hz, 1H), 7.31 (d, J=8.1 Hz, 1H), 7.37 (s, 1H), 7.49 (dd, J=7.6, 7.8 Hz, 1H), 7.54 (d, J=8.3 Hz, 1H), 7.55 (s, 1H), 7.63 (d, J=7.3 Hz, 1H), 8.36 (d, J=5.2 Hz, 1H)

Mass spectrometric value (ESI-MS, m/z): 410 (M+Na)$^+$

Compound 265: 6,7-Dimethoxy-4-(6-methyl-2-pyrimidin-5-yl-pyridin-3-yloxy)-quinoline N,N-Dimethylformamide. (1 ml) and a 2 M aqueous potassium carbonate solution (1 ml) were added to 4-(2-iodo-6-methyl-pyridin-3-yloxy)-6,7-dimethoxy-quinoline (compound 116) (50 mg), tetrakistriphenylphosphine palladium (14 mg), and 5-piperidylboronic acid (44 mg) under an argon atmosphere, and the mixture was stirred at 70° C. for 5 hr. The reaction solution was cooled to room temperature, water was then added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-methanol to give the title compound (38 mg, yield 86%).

$^1$H-NMR (CDCl$_3$, 400 MHz): δ 2.70 (s, 3H), 4.03 (s, 3H), 4.05 (s, 3H), 6.39 (d, J=5.1 Hz, 1H), 7.31 (d, J=8.3 Hz, 1H), 7.43 (s, 1H), 7.46 (s, 1H), 7.48 (d, J=8.3 Hz, 1H), 8.47 (d, J=5.4 Hz, 1H), 9.14 (s, 1H), 9.30 (s, 2H)

Mass spectrometric value (ESI-MS, m/z): 397 (M+Na)$^+$

Compound 266: 3-(6,7-Dimethoxy-quinolin-4-yloxy)-6-methylsulfanyl-[2,2']bipyridine 6-Fluoro-2-iodo-pyridin-3-ol (50 mg) was dissolved in acetonitrile (2 ml) to prepare a solution. Methyl iodide (148 mg) and potassium carbonate (87 mg) were added to the solution, and the mixture was stirred at room temperature overnight. The solvent was removed by distillation under the reduced pressure, water was then added to the residue, and the mixture was extracted with chloroform. The chloroform layer was washed with water and was dried over anhydrous magnesium sulfate, the solvent was removed by distillation under the reduced pressure, and the residue was purified by thin layer chromatography using chloroform to give 6-fluoro-2-iodo-3-methoxypyridine (52 mg, yield 100%).

6-Fluoro-2-iodo-3-methoxypyridine (84 mg), tetrakistriphenylphosphine palladium (0) (38 mg), and copper(II) oxide (53 mg) were suspended in N,N-dimethylformamide (2 ml). 2-Tributylstannylpyridine (244 mg) was added to the suspension, and the mixture was stirred at 100° C. overnight. The reaction solution was cooled to room temperature. The reaction solution was then filtered, the solvent was removed from the filtrate by distillation under the reduced pressure. Water was then added to the residue, and the mixture was extracted with dichloromethane. The dichloromethane layer was washed with water and saturated brine and was dried over anhydrous magnesium sulfate. The solvent was removed by distillation under the reduced pressure, and the residue was purified by thin layer chromatography using chloroform-methanol to give 6-fluoro-3-methoxy-[2,2']bipyridine (12 mg, yield 18%).

6-Fluoro-3-methoxy-[2,2']bipyridine (12 mg) and sodium thiomethoxide (41 mg) were suspended in N,N-dimethylformamide (1.5 ml), and the suspension was stirred at 160° C. overnight. The reaction solution was cooled to room temperature, the reaction solution was then filtered, and the solvent was removed from the filtrate by distillation under the reduced pressure. The residue was purified by thin layer chromatography using acetone-chloroform to give 6-methylsulfanyl-[2,2']bipyridin-3-ol (6 mg, yield 47%).

6-Methylsulfanyl-[2,2']bipyridin-3-ol (6 mg), 4-chloro-6,7-dimethoxyquinoline (18 mg), 4-dimethylaminopyridine (10 mg), and cesium carbonate (27 mg) were suspended in N,N-dimethyl sulfoxide (1 ml), and the suspension was stirred at 140° C. overnight. The reaction solution was cooled to room temperature, water was then added to the reaction solution, and the mixture was extracted with ethyl acetate. The ethyl acetate layer was then washed with water and saturated brine and was dried over anhydrous magnesium sulfate. The solvent was removed by distillation under the reduced pressure, and the residue was purified by thin layer chromatography using acetone-hexane to give the title compound (1 mg, yield 8%).

$^1$H-NMR (CDCl$_3$, 400 MHz): δ 2.61 (s, 3H), 3.96 (s, 6H), 6.27 (d, J=5.6 Hz, 1H), 7.05 (m, 1H), 7.26 (d, J=8.4 Hz, 1H), 7.31 (s, 1H), 7.41 (d, J=8.4 Hz, 1H), 7.52 (s, 1H), 7.59 (dd, J=8.0, 1.6 Hz, 1H), 7.86 (d, J=7.6 Hz, 1H), 8.27 (d, J=7.6 Hz, 1H), 8.31 (d, J=5.6 Hz, 1H)

Mass spectrometric value (ESI-MS, m/z): 428 (M+Na)$^+$

Compound 267: 3-(6,7-Dimethoxy-quinolin-4-yloxy)-6-methylsulfanyl-[2,3']bipyridine 6-Fluoro-2-iodo-3-methoxypyridine (52 mg), tetrakistriphenylphosphine palladium(0) (24 mg), and 3-pyridineboronic acid (76 mg) were suspended in a mixed solvent composed of N,N-dimethylformamide (0.75 ml) and a 2 N aqueous potassium carbonate solution (0.75 ml), and the suspension was stirred at 80° C. for 4 hr. The reaction solution was cooled to room temperature, the reaction solution was then filtered, and the solvent was removed from the filtrate by distillation under the reduced pressure. Water was then added to the residue, and the mixture was extracted with dichloromethane. The dichloromethane layer was washed with water and saturated brine and was dried over anhydrous magnesium sulfate. The solvent was removed by distillation under the reduced pressure, and the residue was purified by thin layer chromatography using acetone-chloroform to give 6-fluoro-3-methoxy-[2,3']bipyridine (31 mg, yield 72%).

6-Fluoro-3-methoxy-[2,3']bipyridine (30 mg) and sodium thiomethoxide (103 mg) were suspended in N,N-dimethylformamide (1.5 ml), and the suspension was stirred at 160° C. for 4 hr. The reaction solution was cooled to room temperature, the reaction solution was filtered, and the solvent was removed from the filtrate by distillation under the reduced pressure. The residue was purified by thin layer chromatography using chloroform-methanol to give 6-methylsulfanyl-[2,3']bipyridin-3-ol (13 mg, yield 45%).

6-Methylsulfanyl-[2,3']bipyridin-3-ol (13 mg), 4-chloro-6,7-dimethoxyquinoline (46 mg), and 4-dimethylaminopyridine (29 mg) were suspended in o-dichlorobenzene (2 ml), and the suspension was stirred at 140° C. for 4 hr. The reaction solution was cooled to room temperature, water was then added to the reaction solution, and the mixture was extracted with ethyl acetate. The ethyl acetate layer was then washed with water and saturated brine and was dried over anhydrous magnesium sulfate. The solvent was removed by distillation under the reduced pressure, and the residue was purified by thin layer chromatography using acetone-chloroform to give the title compound (25 mg, yield 91%).

$^1$H-NMR (CDCl$_3$, 400 MHz): δ 2.61 (s, 3H), 3.96 (s, 6H), 6.32 (d, J=5.2 Hz, 1H), 7.15-7.25 (m, 2H), 7.30-7.37 (m, 2H), 7.43 (s, 1H), 8.17 (m, 1H), 8.37 (d, J=5.2 Hz, 1H), 8.46 (m, 1H), 9.17 (s, 1H)

Mass spectrometric value (ESI-MS, m/z): 428 (M+Na)$^+$

Compound 268: 4-(5,6-Dimethyl-2-phenyl-pyridin-3-yloxy)-6,7-dimethoxy-quinoline

Carbon disulfide (35 ml) was added to benzoyl chloride (7.3 g) and anhydrous aluminum chloride (7.0 g) under an argon atmosphere, and a solution of 2,3-dimethylfuran (5.0 g) in carbon disulfide (35 ml) was added dropwise thereto at 10° C. The mixture was then stirred for 30 min while raising the temperature to room temperature. 10% Hydrochloric acid (200 ml) was added to the reaction solution, and the mixture was extracted with dichloromethane. The dichloromethane layer was then washed with water and a 5% aqueous sodium bicarbonate solution and was dried over anhydrous sodium sulfate. The solvent was removed by distillation under the reduced pressure, and the residue was purified by column chromatography using hexane-ethyl acetate to give (4,5-dimethylfuran-2-yl)-phenyl-methanone (2.5 g, yield 25%).

(4,5-Dimethylfuran-2-yl)-phenyl-methanone (1 g) and ammonium acetate (910 mg) were placed in a sealed tube, and the mixture was stirred at 250° C. for 10 hr. The reaction solution was cooled to room temperature, the solvent was then removed by distillation under the reduced pressure, and the residue was purified by column chromatography using hexane-ethyl acetate to give 5,6-dimethyl-2-phenyl-pyridin-3-ol (160 g, yield 16%).

1,2-Dichlorobenzene (4.5 ml) was added to 5,6-dimethyl-2-phenyl-pyridin-3-ol (267 mg), 4-chloro-6,7-dimethoxyquinoline (100 mg), and 4-(N,N-dimethylamino)pyridine (164 mg), and the mixture was stirred at 140° C. for 8 hr. The reaction solution was cooled to room temperature, and the solvent was then removed by distillation under the reduced pressure. Water was added to the residue, and the mixture was extracted with chloroform. The chloroform layer was washed with water and was dried over anhydrous sodium sulfate. The solvent was removed by distillation under the reduced pressure, and the residue was purified by thin layer chromatography using hexane-acetone to give the title compound (159 mg, yield 92%).

$^1$H-NMR (CDCl$_3$, 400 MHz): δ 2.40 (s, 3H), 2.67 (s, 3H), 4.07 (s, 3H), 4.09 (s, 3H), 6.43 (d, J=5.1 Hz, 1H), 7.28-7.36 (m, 4H), 7.46 (s, 1H), 7.55 (s, 1H), 7.89 (dd, J=3.2, 6.4 Hz, 2H), 8.41 (d, J=5.1 Hz, 1H)

Mass spectrometric value (ESI-MS, m/z): 409 (M+Na)$^+$

Compound 269: 3-(6,7-Dimethoxy-quinolin-4-yloxy)-5,6-dimethyl-[2,2']bipyridine 2,3-Dimethylfuran (5 g) was dissolved in diethyl ether (75 ml) under an argon atmosphere. A 1.6 M hexane solution (35.7 ml) of n-butyllithium was added dropwise thereto at 0° C., and the mixture was stirred under reflux for 2.5 hr. Thereafter, the reaction solution was cooled to −78° C., a solution of 2-cyanopyridine (6.0 g) in diethyl ether (20 ml) was added dropwise thereto, and the mixture was stirred at room temperature for 3 hr. The reaction solution was poured into ice to stop the reaction. The reaction solution was adjusted to pH 5 by the addition of 2 M hydrochloric acid and was then extracted with chloroform. The chloroform layer was then washed with water and was dried over anhydrous sodium sulfate. The solvent was removed by distillation under the reduced pressure, and the residue was purified by column chromatography using hexane-ethyl acetate to give (4,5-dimethylfuran-2-yl)-(2-pyridyl)-methanone (1.8 g, yield 17%).

(4,5-Dimethylfuran-2-yl)-(2-pyridyl)-methanone (1.6 g), methanol (15 ml), and a 28% aqueous ammonia solution (15 ml) were placed in a sealed tube, and the mixture was stirred at 160° C. overnight. The reaction solution was cooled to room temperature, the solvent was then removed by distillation under the reduced pressure, and the residue was purified by column chromatography using hexane-ethyl acetate to give 5,6-dimethyl-[2,2']-bipyridin-3-ol (1.2 g, yield 75%).

Dimethyl sulfoxide (1.5 ml) was added to 5,6-dimethyl-[2,2']-bipyridin-3-ol (30 mg), 4-chloro-6,7-dimethoxyquinoline (101 mg), and cesium carbonate (147 mg), and the mixture was stirred at 130° C. for 7 hr. The reaction solution was cooled to room temperature, water was then added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using hexane-acetone to give the title compound (12 mg, yield 20%).

$^1$H-NMR (CDCl$_3$, 400 MHz): δ 2.37 (s, 3H), 2.65 (s, 3H), 4.02 (s, 3H), 4.02 (s, 3H), 6.36 (d, J=5.4 Hz, 1H), 7.10 (dd, J=5.6, 7.3 Hz, 1H), 7.35 (s, 1H), 7.37 (s, 1H), 7.53 (s, 1H), 7.57 (ddd, J=1.7, 1.7, 7.8 Hz, 1H), 7.78 (d, J=7.8 Hz, 1H), 8.39 (d, J=5.4 Hz, 1H), 8.51 (d, J=4.1 Hz, 1H)

Mass spectrometric value (ESI-MS, m/z): 410 (M+Na)$^+$

Compound 270: 3-(6,7-Dimethoxy-quinolin-4-yloxy)-5,6-dimethyl-[2,3']bipyridine 2,3-Dimethylfuran (5 g) was dissolved in diethyl ether (75 ml) under an argon atmosphere, a 1.6 M hexane solution (35.7 ml) of n-butyllithium was added dropwise thereto at 0° C., and the mixture was stirred under reflux for 2.5 hr. Thereafter, the reaction solution was cooled to −78° C., a solution of 3-cyanopyridine (6.0 g) in diethyl ether (20 ml) was added dropwise thereto, and the mixture was stirred at room temperature for 3 hr. The reaction solution was poured into ice to stop the reaction solution. The reaction solution was adjusted to pH 5 by the addition of 2 M hydrochloric acid and was extracted with chloroform. The chloroform layer was then washed with water and was dried over anhydrous sodium sulfate. The solvent was removed by distillation under the reduced pressure, and the residue was purified by column chromatography using hexane-ethyl acetate to give (4,5-dimethylfuran-2-yl)-(3-pyridyl)-methanone (1.9 g, yield 18%).

(4,5-Dimethylfuran-2-yl)-(3-pyridyl)-methanone (1.8 g), methanol (30 ml), and a 28% aqueous ammonia solution (30 ml) were placed in a sealed tube and were stirred at 160° C. overnight. The reaction solution was cooled to room temperature, and the solvent was then removed by distillation under the reduced pressure. The residue was purified by column chromatography using hexane-ethyl acetate to give 5,6-dimethyl-[2,3']-bipyridin-3-ol (1.1 g, yield 63%).

5,6-Dimethyl-[2,3']-bipyridin-3-ol (50 mg), 4-chloro-6,7-dimethoxyquinoline (168 mg), and 4-(N,N-dimethylamino)

pyridine (92 mg) were dissolved in 1,2-dichlorobenzene (2.5 ml), and the mixture was stirred at 140° C. overnight. The reaction solution was cooled to room temperature, and the solvent was then removed by distillation under the reduced pressure. The residue was purified by thin layer chromatography using hexane-acetone to give the title compound (81 mg, yield 84%).

$^1$H-NMR (CDCl$_3$, 400 MHz): δ 2.35 (s, 3H), 2.61 (s, 3H), 4.01 (s, 3H), 4.02 (s, 3H), 6.36 (d, J=5.4 Hz, 1H), 7.22 (dd, J=4.6, 7.8 Hz, 1H), 7.30 (s, 1H), 7.39 (s, 1H), 7.47 (s, 1H), 8.16 (ddd, J=2.0, 2.0, 8.0 Hz, 1H), 8.43 (d, J=5.1 Hz, 1H), 8.48 (dd, J=1.5, 4.9 Hz, 1H), 9.13 (d, J=1.7 Hz, 1H)

Mass spectrometric value (ESI-MS, m/z): 410 (M+Na)$^+$

Compound 271: 3-(6,7-Dimethoxy-quinolin-4-yloxy)-5,6,6'-trimethyl-[2,2']bipyridine 2-Bromo-6-picoline (1.5 g) was dissolved in tetrahydrofuran (40 ml) under an argon atmosphere to prepare a solution. A 1.6 M hexane solution (5.6 ml) of n-butyllithium was added dropwise to the solution at −78° C., and the mixture was then stirred at −78° C. for 30 min. A solution of 4,5-dimethylfurfural (1 g) in tetrahydrofuran (20 ml) was added dropwise thereto, and the temperature of the mixture was raised to room temperature while stirring. Water was added to the reaction solution to stop the reaction, and the solvent was removed by distillation under the reduced pressure. Water was added to the residue, and the mixture was extracted with ethyl acetate. The ethyl acetate layer was then washed with water and was dried over anhydrous sodium sulfate. The solvent was removed by distillation under the reduced pressure, and the residue was purified by column chromatography using hexane-acetone to give (4,5-dimethylfuran-2-yl)-(6-methyl-pyridin-2-yl)-methanol (1.4 g, yield 74%).

(4,5-Dimethylfuran-2-yl)-(6-methyl-pyridin-2-yl)-methanol (1.4 g) was dissolved in chloroform (30 ml) to prepare a solution. Manganese dioxide (5.7 g) was added to the solution, and the mixture was stirred at room temperature overnight. Further, manganese dioxide (1.8 g) was then added thereto, and the mixture was stirred overnight. The reaction solution was filtered through Celite. The solvent was removed from the filtrate by distillation under the reduced pressure to give (4,5-dimethylfuran-2-yl)-(6-methyl-pyridin-2-yl)-methanone (815 mg, yield 58%).

(4,5-Dimethylfuran-2-yl)-(6-methyl-pyridin-2-yl)-methanone (810 mg), methanol (7 ml), and a 28% aqueous ammonia solution (7 ml) were placed in a sealed tube, and the mixture was stirred at 160° C. overnight. The reaction solution was cooled to room temperature, the solvent was then removed by distillation under the reduced pressure, and the residue was purified by column chromatography using hexane-ethyl acetate to give 5,6,6'-trimethyl-[2,2']bipyridin-3-ol (753 mg, yield 93%).

Dimethyl sulfoxide (2 ml) was added to 5,6,6'-trimethyl-[2,2']bipyridin-3-ol (50 mg), 4-chloro-6,7-dimethoxyquinoline (157 mg), cesium carbonate (229 mg), and 4-(N,N-dimethylamino)-pyridine (86 mg), and the mixture was stirred at 140° C. overnight. The reaction solution was cooled to room temperature, water was then added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using hexane-acetone to give the title compound (17 mg, yield 18%).

$^1$H-NMR (CDCl$_3$, 400 MHz): δ 2.21 (s, 3H), 2.38 (s, 3H), 2.64 (s, 3H), 4.03 (s, 6H), 6.32 (d, J=5.4 Hz, 1H), 6.93 (d, J=7.6 Hz, 1H), 7.38 (s, 2H), 7.47 (t, J=5.9 Hz, 1H), 7.57 (s, 1H), 7.63 (d, J=7.8 Hz, 1H), 8.36 (d, J=5.4 Hz, 1H)

Mass spectrometric value (ESI-MS, m/z): 402 (M+1)$^+$

Compound 272: 3-(6,7-Dimethoxy-quinolin-4-yloxy)-5,6,5'-trimethyl-[2,2']bipyridine 2-Bromo-5-picoline (1.5 g) was dissolved in tetrahydrofuran (40 ml) under an argon atmosphere to prepare a solution. A 1.6 M hexane solution (5.6 ml) of n-butyllithium was added dropwise to the solution at −78° C. The reaction solution was then stirred at −78° C. for 30 min. A solution of 4,5-dimethylfurfural (1 g) in tetrahydrofuran (20 ml) was added dropwise thereto, and the temperature of the mixture was raise to room temperature with stirring. Water was added to the reaction solution to stop the reaction. The solvent was removed by distillation under the reduced pressure, water was added to the residue, and the mixture was extracted with ethyl acetate. The ethyl acetate layer was then washed with water and was dried over anhydrous sodium sulfate. The solvent was removed by distillation under the reduced pressure, and the residue was purified by column chromatography using hexane-ethyl acetate to give (4,5-dimethylfuran-2-yl)-(5-methyl-pyridin-2-yl)-methanol (855 mg, yield 44%).

(4,5-Dimethylfuran-2-yl)-(5-methyl-pyridin-2-yl)methanol (850 mg) was dissolved in chloroform (40 ml) to prepare a solution. Manganese dioxide (3.4 g) was added to the solution, and the mixture was stirred at room temperature overnight. The reaction solution was filtered through Celite. The solvent was removed from the filtrate by distillation under the reduced pressure, and the residue was purified by column chromatography using hexane-ethyl acetate to give (4,5-dimethylfuran-2-yl)-(5-methyl-pyridin-2-yl)-methanone (788 mg, yield 93%).

(4,5-Dimethylfuran-2-yl)-(6-methyl-pyridin-2-yl)-methanone (780 mg), methanol (7 ml), and a 28% aqueous ammonia solution (7 ml) were placed in a sealed tube and were stirred at 160° C. overnight. The reaction solution was cooled to room temperature, the solvent was then removed by distillation under the reduced pressure, and the residue was purified by column chromatography using hexane-ethyl acetate to give 5,6,5'-trimethyl-[2,2']bipyridin-3-ol (529 mg, yield 68%).

Dimethyl sulfoxide (2.8 ml) was added to 5,6,5'-trimethyl-[2,2']bipyridin-3-ol (60 mg), 4-chloro-6,7-dimethoxyquinoline (184 mg), cesium carbonate (274 mg), 4-(N,N-dimethylamino)-pyridine (51 mg), and cesium fluoride (64 mg) to prepare a solution which was then stirred at 140° C. overnight. The reaction solution was cooled to room temperature, water was then added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using chloroform-methanol to give the title compound (33 mg, yield 29%).

$^1$H-NMR (CDCl$_3$, 400 MHz): δ 2.24 (s, 3H), 2.37 (s, 3H), 2.65 (s, 3H), 4.04 (s, 6H), 6.35 (d, J=5.4 Hz, 1H), 7.34 (s, 1H), 7.36-7.41 (m, 2H), 7.56 (s, 1H), 7.70 (d, J=8.1 Hz, 1H), 8.36 (d, J=2.2 Hz, 1H), 8.39 (d, J=5.1 Hz, 1H)

Mass spectrometric value (ESI-MS, m/z): 424 (M+Na)$^+$

Compound 273: 3-(6,7-Dimethoxy-quinolin-4-yloxy)-5,6,4'-trimethyl-[2,2']bipyridine 2-Bromo-4-picoline (1.5 g) was dissolved in tetrahydrofuran (40 ml) under an argon atmosphere to prepare a solution.

A 1.6 M hexane solution (5.6 ml) of n-butyllithium was added dropwise to the solution at −78° C., and the mixture was then stirred at −78° C. for 30 min. A solution of 4,5-dimethylfurfural (1 g) in tetrahydrofuran (20 ml) was added dropwise thereto, and the temperature of the mixture was raised to room temperature with stirring. Water was added to the reaction solution to stop the reaction. The solvent was removed by distillation under the reduced pressure. Water was added to the residue, the mixture was extracted with ethyl acetate, and the ethyl acetate layer was then washed with water and was dried over anhydrous sodium sulfate. The solvent was removed by distillation under the reduced pressure, and the residue was purified by column chromatography using hexane-ethyl acetate to give (4,5-dimethylfuran-2-yl)-(4-methyl-pyridin-2-yl)-methanol (904 mg, yield 47%).

(4,5-Dimethylfuran-2-yl)-(4-methyl-pyridin-2-yl)-methanol (900 mg) was dissolved in chloroform (20 ml) to prepare a solution. Manganese dioxide (3.6 g) was added to the solution, and the mixture was stirred at room temperature overnight. Further, manganese dioxide (1.8 g) was then added to the reaction solution, and the mixture was stirred at room temperature for 5 hr. The reaction solution was filtered through Celite, and the solvent was removed from the filtrate by distillation under the reduced pressure, and the residue was purified by column chromatography using hexane-ethyl acetate to give (4,5-dimethylfuran-2-yl)-(4-methyl-pyridin-2-yl)-methanone (690 mg, yield 77%).

(4,5-Dimethylfuran-2-yl)-(6-methyl-pyridin-2-yl)methanone (690 mg), methanol (6 ml), and a 28% aqueous ammonia solution (6 ml) were placed in a sealed tube and were stirred at 160° C. overnight. The reaction solution was cooled to room temperature, the solvent was then removed by distillation under the reduced pressure, and the residue was purified by column chromatography using hexane-ethyl acetate to give 5,6,4'-trimethyl-[2,2']bipyridin-3-ol (611 mg, yield 89%).

Dimethyl sulfoxide (2 ml) was added to 5,6,4'-trimethyl-[2,2']bipyridin-3-ol (50 mg), 4-chloro-6,7-dimethoxyquinoline (157 mg), and cesium carbonate (229 mg), and the mixture was stirred at 130° C. overnight. The reaction solution was cooled to room temperature, water was then added to the solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using hexane-acetone to give the title compound (42 mg, yield 45%).

$^1$H-NMR (CDCl$_3$, 400 MHz): δ 2.21 (s, 3H), 2.38 (s, 3H), 2.65 (s, 3H), 4.03 (s, 3H), 4.04 (s, 3H), 6.33 (d, J=5.4 Hz, 1H), 6.89-6.96 (m, 1H), 7.36 (s, 2H), 7.57 (s, 1H), 7.61-7.64 (m, 1H), 8.35 (d, J=5.1 Hz, 1H), 8.37 (d, J=5.1 Hz, 1H)

Mass spectrometric value (ESI-MS, m/z): 402 (M+1)$^+$

Compound 274: 4-(5,6-Dimethyl-2-pyrimidin-2-yl-pyridin-3-yloxy)-6,7-dimethoxy-quinoline 2,3-Dimethylfuran (1.5 g) was dissolved in diethyl ether (20 ml) under an argon atmosphere to prepare a solution. A 1.6 M hexane solution (10.9 ml) of n-butyllithium was added dropwise to the solution at 0° C., and the mixture was stirred under reflux for 2.5 hr. Thereafter, the reaction solution was cooled to −78° C., a solution of 2-cyanopyrimidine (1.8 g) in diethyl ether (8 ml) was added dropwise thereto, and the mixture was stirred at room temperature overnight. The reaction solution was poured into ice to stop the reaction. The mixture was acidified with 1 M hydrochloric acid and was extracted with ethyl acetate. The ethyl acetate layer was then washed with water and was dried over anhydrous sodium sulfate. The solvent was removed by distillation under the reduced pressure, and the residue was purified by column chromatography using chloroform-acetone to give (4,5-dimethylfuran-2-yl)-(2-pyrimidyl)-methanone (226 mg, yield 7%).

(4,5-Dimethylfuran-2-yl)-(2-pyrimidyl)-methanone (220 mg), methanol (2 ml), and a 28% aqueous ammonia solution (2 ml) were placed in a sealed tube, and the mixture was stirred at 160° C. overnight. The reaction solution was cooled to room temperature, the solvent was removed by distillation under the reduced pressure, and the residue was purified by column chromatography using hexane-acetone to give 5,6-dimethyl-2-pyrimidin-2-yl-pyridin-3-ol (129 mg, yield 59%).

Dimethyl sulfoxide (2.5 ml) was added to 5,6-dimethyl-2-pyrimidin-2-yl-pyridin-3-ol (50 mg), 4-chloro-6,7-dimethoxyquinoline (167 mg), and cesium carbonate (243 mg), and the mixture was stirred at 130° C. overnight. The reaction solution was cooled to room temperature, water was then added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using hexane-acetone to give the title compound (54 mg, yield 55%).

$^1$H-NMR (CDCl$_3$, 400 MHz): δ 2.41 (s, 3H), 2.68 (s, 3H), 4.02 (s, 3H), 4.03 (s, 3H), 6.40 (d, J=5.2 Hz, 1H), 7.09 (t, J=4.9 Hz, 1H), 7.36 (s, 1H), 7.41 (s, 1H), 7.56 (s, 1H), 8.38 (d, J=5.4 Hz, 1H), 8.64 (d, J=4.9 Hz, 2H)

Mass spectrometric value (ESI-MS, m/z): 389 (M+1)$^+$

Compound 275: 6,7-Dimethoxy-4-(quinolin-3-yloxy)-quinoline

4-Chloro-6,7-dimethoxyquinoline (243 mg), 3-hydroxyquinoline (100 mg), and 4-dimethylaminopyridine (348 mg) were dissolved in o-dichlorobenzene (13 ml) to prepare a solution which was stirred at 140° C. overnight. The reaction solution was cooled to room temperature, water was then added to the reaction solution, and the mixture was extracted with ethyl acetate. The ethyl acetate layer was then washed with water and was dried over anhydrous sodium sulfate, the solvent was removed by distillation under the reduced pressure, and the residue was purified by thin layer chromatography using acetone-chloroform to give the title compound (213 mg, yield 93%).

$^1$H-NMR (CDCl$_3$, 400 MHz): δ 4.06 (s, 3H), 4.08 (s, 3H), 6.54 (d, J=5.1 Hz, 1H), 7.47 (d, J=0.9 Hz, 1H), 7.56 (d, J=1.6 Hz, 1H), 7.61 (m, 1H), 7.74 (m, 1H), 7.80 (d, J=8.1 Hz, 1H), 7.88 (m, 1H), 8.18 (d, J=8.7 Hz, 1H), 8.53 (dd, J=0.7, 5.1 Hz, 1H), 8.89 (d, J=2.9 Hz, 1H)

Mass spectrometric value (ESI-MS, m/z): 333 (M+1)$^+$

Compound 276: 6,7-Dimethoxy-4-(2-methyl-quinolin-3-yloxy)-quinoline

4-Chloro-6,7-dimethoxyquinoline (240 mg), 3-hydroxy-2-methyl-quinoline-4-carboxylic acid (232 mg), and 4-dimethylaminopyridine (372 mg) were dissolved in o-dichlorobenzene (10 ml) to prepare a solution which was stirred at 160° C. overnight. The reaction solution was cooled to room temperature, water was then added to the reaction solution, and the mixture was extracted with ethyl acetate. The ethyl acetate layer was then washed with water and was dried over anhydrous sodium sulfate, the solvent was removed by distillation under the reduced pressure, and the residue was purified by column chromatography using acetone-chloroform to give the title compound (37 mg, yield 11%).

$^1$H-NMR (CDCl$_3$, 400 MHz): δ 2.67 (s, 3H), 4.07 (s, 3H), 4.08 (s, 3H), 6.39 (d, J=5.1 Hz, 1H), 7.48 (s, 1H), 7.54 (m, 1H), 7.59 (d, J=1.7 Hz, 1H), 7.70-7.76 (m, 2H), 7.81 (s, 1H), 8.10 (d, J=8.5 Hz, 1H), 8.50 (dd, J=0.7, 5.1 Hz, 1H)

Mass spectrometric value (ESI-MS, m/z): 347 (M+1)$^+$

Compound 277: [3-(6,7-Dimethoxy-quinolin-4-yloxy)-quinolin-2-ylmethyl]-diisopropyl-amine 6,7-Dimethoxy-4-(2-methyl-quinolin-3-yloxy)-quinoline (compound 276) (108 mg) was dissolved in tetrahydrofuran (5 ml) to prepare a solution. A lithiumdiisopropylamide/1.8 M heptane-tetrahydrofuran-ethylbenzene solution (0.3 ml) was added to the solution at −78° C., and the mixture was stirred for 10 min. N-Bromosuccimide (180 mg) was added to the reaction solution, and the mixture was stirred at room temperature for 5 hr. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using methanol-chloroform to give the title compound (23 mg, yield 16%).

$^1$H-NMR (CDCl$_3$, 400 MHz): δ 0.91-0.95 (m, 12H), 3.06 (m, 2H), 4.05 (s, 3H), 4.06 (s, 3H), 4.10 (s, 2H), 6.48 (d, J=5.4 Hz, 1H), 7.46 (s, 1H), 7.54 (m, 1H), 7.61 (s, 1H), 7.70-7.73 (m, 2H), 7.73 (s, 1H), 8.17 (d, J=8.5 Hz, 1H), 8.51 (d, J=5.4 Hz, 1H)

Mass spectrometric value (ESI-MS, m/z): 446 (M+1)$^+$

Compound 278: 1-[3-(6,7-Dimethoxy-quinolin-4-yloxy)-quinolin-2-yl]-ethanone

A mixture of 2-nitrobenzoyl chloride (500 mg) with 4-trimethylsilanyloxy-pent-3-en-2-one (540 mg) was stirred at 140° C. for 5 min. The reaction solution was cooled to room temperature and was then purified by column chromatography using acetone-hexane to give 3-(2-nitro-benzoyl)-pentane-2,4-dione (143 mg, yield 20%).

3-(2-Nitro-benzoyl)-pentane-2,4-dione (143 mg) was suspended in a 20% aqueous potassium hydroxide solution (10 ml), and the suspension was heated under reflux for 45 min. The reaction solution was cooled to room temperature, was then neutralized with a 1 N aqueous hydrochloric acid solution, and was extracted with chloroform. The chloroform layer was washed with water and saturated brine and was dried over anhydrous magnesium sulfate. The solvent was removed by distillation under the reduced pressure. The residue was purified by thin layer chromatography using chloroform to give 2-acetyl-3-quinolinol (22 mg, yield 21%).

2-Acetyl-3-quinolinol (22 mg), 4-chloro-6,7-dimethoxyquinoline (54 mg), and 4-dimethylaminopyridine (88 mg) were suspended in o-dichlorobenzene (5 ml), and the suspension was stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous magnesium sulfate. The solvent was removed by distillation under the reduced pressure, and the residue was purified by thin layer chromatography using acetone-hexane to give the title compound (6 mg, yield 13%).

$^1$H-NMR (CDCl$_3$, 400 MHz): δ 2.70 (s, 3H), 3.99 (s, 6H), 6.30 (d, J=5.2 Hz, 1H), 7.42 (s, 1H), 7.53-7.66 (m, 2H), 7.76 (m, 2H), 7.90 (s, 1H), 8.16 (d, J=9.2 Hz, 1H), 8.41 (d, J=5.2 Hz, 1H)

Mass spectrometric value (ESI-MS, m/z): 375 (M+1)$^+$

Compound 279: [3-(6,7-Dimethoxy-quinolin-4-yloxy)-quinolin-2-yl]-phenyl-methanone Ethyl 3-hydroxy-2-methyl-quinoline-4-carboxylate (2.10 g) was suspended in o-dichlorobenzene (50 ml), and the mixture was stirred at 150° C. overnight and was further stirred at 160° C. for one day. The reaction solution was cooled to room temperature, and the solvent was then removed by distillation under the reduced pressure. The residue was purified by column chromatography using methanol-chloroform to give 3-hydroxy-2-methyl-quinoline (976 mg, yield 60%).

3-Hydroxy-2-methyl-quinoline (0.46 g) was suspended in xylene (30 ml), zelene dioxide (2.55 g) was added to the suspension, and the mixture was stirred at 130° C. for 30 min. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by column chromatography using acetone-chloroform to give 3-hydroxyquinoline-2-carbaldehyde (124 mg, yield 25%).

3-Hydroxy-quinoline-2-carbaldehyde (124 mg) was dissolved in tetrahydrofuran (20 ml) to prepare a solution. A phenylmagnesium bromide/1.04 M tetrahydrofuran solution (4 ml) was added to the solution under ice cooling, and the mixture was stirred at room temperature for one hr. Water was added to the reaction solution, the mixture was extracted with ethyl acetate. The ethyl acetate layer was then washed with water and was dried over anhydrous sodium sulfate. The solvent was removed by distillation under the reduced pressure, and the residue was used in the next reaction without purification.

The residue was dissolved in chloroform (15 ml), manganese dioxide (2.56 g) was added to the solution, and the mixture was stirred at room temperature overnight. The reaction solution was filtered, the solvent was removed by distillation under the reduced pressure, and the residue was purified by column chromatography using ethyl acetate-hexane to give (3-hydroxy-quinolin-2-yl)-phenyl-methanone (28 mg, yield 16%) (2 steps).

(3-Hydroxy-quinolin-2-yl)-phenyl-methanone (27 mg), 4-chloro-6,7-dimethoxyquinoline (120 mg), and 4-dimethylaminopyridine (147 mg) were suspended in o-dichlorobenzene (5 ml), and the suspension was stirred at 150° C. for 2 hr. The reaction solution was cooled to room temperature, and the solvent was removed by distillation under the reduced pressure. Water was then added to the residue, and the mixture was extracted with ethyl acetate. The organic layer was washed with water and was dried over anhydrous sodium sulfate, the solvent was removed by distillation under the reduced pressure, and the residue was purified by thin layer chromatography using acetone-chloroform to give the title compound (20 mg, yield 42%).

$^1$H-NMR (CDCl$_3$, 400 MHz): δ 3.89 (s, 3H), 4.03 (s, 3H), 6.67 (d, J=5.2 Hz, 1H), 7.27 (s, 1H), 7.40 (s, 1H), 7.44 (dd, J=7.8, 7.8 Hz, 2H), 7.58 (m, 1H), 7.67 (m, 1H), 7.78 (dd, J=7.1, 7.1 Hz, 1H), 7.82 (d, J=8.0 Hz, 1H), 7.92-7.94 (m, 3H), 8.22 (d, J=8.5 Hz, 1H), 8.52 (d, J=5.1 Hz, 1H)

Mass spectrometric value (ESI-MS, m/z): 437 (M+1)$^+$

Compound 280: 4-(2-Cyclopentyloxy-quinolin-3-yloxy)-6,7-dimethoxy-quinoline

4-Chloro-6,7-dimethoxyquinoline (106 mg), 2,3-dihydroxyquinoline (50 mg), and 4-dimethylaminopyridine (124 mg) were suspended in o-dichlorobenzene (5 ml), and the suspension was stirred at 150° C. for 8 hr. The reaction solution was cooled to room temperature, water was then added thereto, and the mixture was extracted with ethyl acetate. The organic layer was washed with water and was dried over anhydrous sodium sulfate. The solvent was removed by distillation under the reduced pressure, and the residue was purified by column chromatography using methanol-chloroform to give 6,7-dimethoxy-4-(2-hydroxy-quinolin-3-yloxy)-quinoline (40 mg, yield 37%).

6,7-Dimethoxy-4-(2-hydroxy-quinolin-3-yloxy)-quinoline (19 mg) was dissolved in N,N-dimethylformamide (4 ml) to prepare a solution. Potassium carbonate (180 mg) and cyclopentyl bromide (0.1 ml) were added to the solution, and the mixture was stirred at room temperature overnight. Water was added to the reaction solution, and the mixture was extracted with ethyl acetate. The organic layer was washed with water and was dried over anhydrous sodium sulfate, and the solvent was removed by distillation under the reduced pressure. The residue was purified by column chromatography using acetone-chloroform to give the title compound (14 mg, yield 60%).

$^1$H-NMR (CDCl$_3$, 400 MHz): δ 1.23-1.86 (m, 8H), 4.07 (s, 3H), 4.07 (s, 3H), 5.65 (m, 1H), 6.39 (d, J=5.4 Hz, 1H), 7.43 (m, 1H), 7.46 (s, 1H), 7.62 (s, 1H), 7.64 (m, 1H), 7.72 (d, J=7.8 Hz, 1H), 7.85 (s, 1H), 7.88 (d, J=8.5 Hz, 1H), 8.46 (d, J=5.4 Hz, 1H)

Mass spectrometric value (ESI-MS, m/z): 417 (M+1)$^+$

Compound 281: 4-(2-Bromo-quinolin-3-yloxy)-6,7-dimethoxyquinoline

2-Aminobenzaldehyde (650 mg) was dissolved in dichloromethane (20 ml) to prepare a solution. Chloroacetyl chloride (728 mg) was added to the solution, and the mixture was stirred at room temperature overnight. Water was added thereto, and the mixture was extracted with dichloromethane. The dichloromethane layer was washed with water and saturated brine and was dried over anhydrous sodium sulfate. The solvent was removed by distillation under the reduced pressure, and the residue was purified by column chromatography using chloroform to give 2-chloro-N-(2-formylphenyl)-acetamide (1.05 g, yield 99%).

2-Chloro-N-(2-formyl-phenyl)-acetamide (960 mg) was dissolved in a mixed solvent composed of water (60 ml) and methanol (24 ml) at 100° C. A 10% aqueous potassium hydroxide solution (12 ml) was added dropwise to the solution and was then heated under reflux for one hr. The reaction solution was cooled to room temperature, methanol was then removed under the reduced pressure, and the residue was neutralized with a 1 N aqueous hydrochloric acid solution. The precipitate was collected by filtration, was washed with ethyl acetate, and was dried under the reduced pressure to give 2,3-dihydroxyquinoline (450 mg, yield 26%).

2,3-Dihydroxyquinoline (450 mg), 4-chloro-6,7-dimethoxyquinoline (575 mg), and 4-dimethylaminopyridine (472 mg) were suspended in o-dichlorobenzene (12 ml), and the mixture was stirred at 135° C. for 5.5 hr. The reaction solution was cooled to room temperature, water was then added to the reaction solution, and the mixture was extracted with ethyl acetate. The ethyl acetate layer was then washed with water and saturated brine and was dried over anhydrous magnesium sulfate. The solvent was removed by distillation under the reduced pressure. The residue was purified by column chromatography using acetone-chloroform to give 3-(6,7-dimethoxy-quinolin-4-yloxy)-quinolin-2-ol (344 mg, yield 77%).

3-(6,7-Dimethoxy-quinolin-4-yloxy)-quinolin-2-ol (50 mg), diphosphorus pentaoxide (51 mg), and tetrabutylammonium bromide (69 mg) were suspended in o-dichlorobenzene (1 ml), and the suspension was stirred at 140° C. for 1.5 hr. The reaction solution was cooled to room temperature. A 10% aqueous sodium hydrogencarbonate solution was then added to the reaction solution, and the mixture was extracted with chloroform. The chloroform layer was then washed with water and saturated brine and was dried over anhydrous magnesium sulfate. The solvent was removed by distillation under the reduced pressure, and the residue was purified by thin layer chromatography using chloroform-methanol to give the title compound (5 mg, yield 8%).

$^1$H-NMR (CDCl$_3$, 400 MHz): δ 4.05 (s, 6H), 6.44 (d, J=5.2 Hz, 1H), 7.50 (s, 1H), 7.54-7.65 (m, 2H), 7.70-7.79 (m, 2H), 7.89 (s, 1H), 8.11 (d, J=8.4 Hz, 1H), 8.51 (d, J=5.2 Hz, 1H)

Mass spectrometric value (ESI-MS, m/z): 411 (M+1)$^+$

Compound 282: 4-(2-Iodo-quinolin-3-yloxy)-6,7-dimethoxyquinoline 3-(6,7-Dimethoxy-quinolin-4-yloxy)-quinolin-2-ol (50 mg), diphosphorus pentaoxide (51 mg), and tetrabutylammonium iodide (80 mg) were suspended in o-dichlorobenzene (1 ml), and the mixture was stirred at 140° C. for 3.5 hr. The reaction solution was cooled to room temperature, a 10% aqueous sodium hydrogencarbonate solution was then added to the reaction solution, and the mixture was extracted with chloroform. The chloroform layer was then washed with water and saturated brine and was dried over anhydrous magnesium sulfate. The solvent was removed therefrom by distillation under the reduced pressure, and the residue was purified by thin layer chromatography using chloroform-methanol to give the title compound (1 mg, yield 2%).

$^1$H-NMR (CDCl$_3$, 400 MHz): δ 4.03 (s, 6H), 6.43 (d, J=5.2 Hz, 1H), 7.50-7.79 (m, 6H), 8.09 (d, J=8.8 Hz, 1H), 8.47 (d, J=5.2 Hz, 1H)

Mass spectrometric value (ESI-MS, m/z): 459 (M+1)$^+$

Compound 283: 6,7-Dimethoxy-4-(2-phenyl-quinolin-3-yloxy)-quinoline

4-Chloro-6,7-dimethoxyquinoline (222 mg), 2-phenylquinolin-3-ol (107 mg), and 4-dimethylaminopyridine (340 mg) were suspended in o-dichlorobenzene (11 ml), and the suspension was stirred at 145° C. for 7 hr. The reaction solution was cooled to room temperature, water was added to the reaction solution, and the mixture was extracted with ethyl acetate. The organic layer was washed with water and was dried over anhydrous sodium sulfate. The solvent was removed by distillation under the reduced pressure. The residue was purified by thin layer chromatography using acetone-chloroform to give the title compound (134 mg, yield 68%).

$^1$H-NMR (CDCl$_3$, 400 MHz): δ 4.02 (s, 3H), 4.05 (s, 3H), 6.47 (d, J=5.1 Hz, 1H), 7.32-7.36 (m, 3H), 7.41 (s, 1H), 7.50 (s, 1H), 7.59 (m, 1H), 7.76 (m, 1H), 7.80 (d, J=8.1 Hz, 1H), 7.95-7.98 (m, 3H), 8.24 (d, J=8.6 Hz, 1H), 8.45 (d, J=5.1 Hz, 1H)

Mass spectrometric value (ESI-MS, m/z): 409 (M+1)$^+$

Compound 284: {3-[3-(6,7-Dimethoxy-quinolin-4-yloxy)-quinolin-2-yl]-phenyl}-methanol 4-(2-Bromo-quinolin-3-yloxy)-6,7-dimethoxy-quinoline (compound 281) (50 mg), tetrakistriphenylphosphine palladium(0) (14 mg), and (3-hydroxymethylphenyl)boranic acid (55 mg) were suspended in a mixed solvent composed of N,N-dimethylformamide (1 ml) and a 2 N aqueous potassium carbonate solution (1 ml), and the suspension was stirred at 80° C. for 2.5 hr. The reaction solution was cooled to room temperature, the reaction solution was then filtered, and the solvent was removed from the filtrate by distillation under the reduced pressure. Water was then added to the residue, and the mixture was extracted with ethyl acetate. The ethyl acetate layer was then washed with water and saturated brine and was dried over anhydrous magnesium sulfate. The solvent was removed by distillation under the reduced pressure, and the residue was purified by thin layer chromatography using acetone-hexane to give the title compound (54 mg, yield 97%).

$^1$H-NMR (CDCl$_3$, 400 MHz): δ 3.86 (s, 3H), 3.95 (s, 3H), 4.56 (s, 2H), 6.24 (d, J=5.2 Hz, 1H), 7.16-7.24 (m, 3H), 7.42 (s, 1H), 7.49 (m, 1H), 7.68 (m, 2H), 7.80 (d, J=5.2 Hz, 1H), 7.84 (s, 1H), 8.01 (s, 1H), 8.12 (m, 2H)

Mass spectrometric value (ESI-MS, m/z): 437 (M−1)$^−$

Compound 285: 4-[2-(4-Fluoro-phenyl)-quinolin-3-yloxy]-6,7-dimethoxy-quinoline 2-Aminobenzaldehyde (118 mg) and 2-bromo-1-(4-fluoro-phenyl)-ethanone (225 mg) were dissolved in methanol (5 ml) to prepare a solution. Sodium hydroxide (100 mg) and water (5 ml) were added to the solution, and the mixture was stirred at room temperature overnight. Dilute hydrochloric acid was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using ethyl acetate-hexane to give 2-(4-fluorophenyl)-quinolin-3-ol (53 mg, yield 22%).

2-(4-Fluoro-phenyl)-quinolin-3-ol (52 mg), 4-chloro-6,7-dimethoxyquinoline (145 mg), and 4-dimethylaminopyridine (214 mg) were suspended in o-dichlorobenzene (6 ml), and the suspension was stirred at 145° C. for 5 hr. The reaction solution was cooled to room temperature, water was then added to the reaction solution, and the mixture was extracted with ethyl acetate. The organic layer was washed with water and was dried over anhydrous sodium sulfate. The solvent was removed by distillation under the reduced pressure, and the residue was purified by thin layer chromatography using acetone-chloroform to give the title compound (59 mg, yield 64%).

$^1$H-NMR (CDCl$_3$, 400 MHz): δ 4.03 (s, 3H), 4.05 (s, 3H), 6.43 (d, J=5.1 Hz, 1H), 7.03 (m, 2H), 7.42 (s, 1H), 7.49 (d, J=2.2 Hz, 1H), 7.59 (m, 1H), 7.74-7.80 (m, 2H), 7.94 (d, J=2.0 Hz, 1H), 8.00 (m, 2H), 8.21 (d, J=8.6 Hz, 1H), 8.45 (d, J=5.4 Hz, 1H)

Mass spectrometric value (ESI-MS, m/z): 427 (M+1)$^+$

Compound 286: 4-[2-(2,4-Difluoro-phenyl)-quinolin-3-yloxy]-6,7-dimethoxy-quinoline 2-Aminobenzaldehyde (360 mg) and 2-chloro-1-(2,4-difluoro-phenyl)-ethanone (585 mg) were dissolved in methanol (15 ml) to prepare a solution. Sodium hydroxide (310 mg) and water (3 ml) were added to the solution, and the mixture was stirred at room temperature overnight. A dilute hydrochloric acid was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by column chromatography using ethyl acetate-hexane to give 2-(2,4-difluoro-phenyl)-quinolin-3-ol (237 mg, yield 41%).

2-(2,4-Difluoro-phenyl)-quinolin-3-ol (220 mg), 4-chloro-6,7-dimethoxyquinoline (237 mg), and 4-dimethylaminopyridine (380 mg) were suspended in o-dichlorobenzene (10 ml), and the suspension was stirred at 145° C. for 8 hr. The reaction solution was cooled to room temperature, water was then added to the reaction solution, and the mixture was extracted with ethyl acetate. The organic layer was washed with water and was dried over anhydrous sodium sulfate. The solvent was removed by distillation under the reduced pressure. The residue was purified by thin layer chromatography using acetone-chloroform to give the title compound (104 mg, yield 27%).

$^1$H-NMR (CDCl$_3$, 400 MHz): δ 4.00 (s, 3H), 4.04 (s, 3H), 6.54 (d, J=5.4 Hz, 1H), 6.79 (m, 1H), 6.92 (m, 1H), 7.40 (s, 1H), 7.46 (s, 1H), 7.59-7.65 (m, 2H), 7.75 (m, 1H), 7.79 (d, J=8.3 Hz, 1H), 7.89 (s, 1H), 8.21 (d, J=8.5 Hz, 1H), 8.49 (d, J=5.1 Hz, 1H)

Mass spectrometric value (ESI-MS, m/z): 445 (M+1)$^+$

Compound 287: 6,7-Dimethoxy-4-(2-pyridin-2-yl-quinolin-3-yloxy)-quinoline

N,N-Dimethylformamide (1 ml) was added to 4-(2-bromo-quinolin-3-yloxy)-6,7-dimethoxy-quinoline (35 mg), tetrakistriphenylphosphine palladium (9.8 mg), tri-n-butyl-(2-pyridyl)-tin (63 mg), and copper(II) oxide (14 mg) under an argon atmosphere, and the mixture was stirred at 100° C. overnight. The reaction solution was cooled to room temperature, water was then added thereto, and the mixture was extracted with ethyl acetate. The ethyl acetate layer was then washed with water and was dried over anhydrous sodium sulfate. The solvent was removed by distillation under the reduced pressure, and the residue was purified by column chromatography using hexane-acetone. The purification product was then dissolved in methanol, and the solution was added dropwise to water. The precipitate was collected by filtration to give the title compound (5.1 mg, yield 15%).

$^1$H-NMR (CDCl$_3$, 400 MHz): δ 4.04 (s, 3H), 4.05 (s, 3H), 6.46 (d, J=5.4 Hz, 1H), 7.19 (dd, J=5.9, 5.9 Hz, 1H), 7.43 (s, 1H), 7.60 (s, 1H), 7.60-7.77 (m, 2H), 7.78 (dd, J=8.5, 8.5 Hz, 1H), 7.85 (d, J=8.6 Hz, 1H), 7.96 (d, J=7.6 Hz, 1H), 8.05 (s, 1H), 8.30 (d, J=8.3 Hz, 1H), 8.31 (d, J=5.4 Hz, 1H), 8.51 (d, J=4.2 Hz, 1H)

Mass spectrometric value (ESI-MS, m/z): 432 (M+Na)$^+$

Compound 288: 6,7-Dimethoxy-4-(2-pyridin-3-yl-quinolin-3-yloxy)-quinoline 4-(2-Bromo-quinolin-3-yloxy)-6,7-dimethoxy-quinoline (compound 281) (50 mg), tetrakistriphenylphosphine palladium(0) (14 mg), and 3-pyridineboronic acid (42 mg) were suspended in a mixed solvent composed of N,N-dimethylformamide (1 ml) and a 2 N aqueous potassium carbonate solution (1 ml), and the mixture was stirred at 80° C. for 3 hr. The reaction solution was cooled to room temperature, the reaction solution was then filtered, and the solvent was removed from the filtrate by distillation under the reduced pressure. Water was then added to the residue, and the mixture was extracted with ethyl acetate. The ethyl acetate layer was then washed with water and saturated brine and was dried over anhydrous magnesium sulfate. The solvent was removed by distillation under the reduced pressure, and the residue was purified by thin layer chromatography using acetone-chloroform to give the title compound (16 mg, yield 33%).

$^1$H-NMR (CDCl$_3$, 400 MHz): δ 3.96 (s, 3H), 3.97 (s, 3H), 6.40 (d, J=5.2 Hz, 1H), 7.23 (dd, J=8.0 Hz, 3.2 Hz, 1H), 7.37 (s, 1H), 7.42 (s, 1H), 7.55 (m, 1H), 7.73 (m, 2H), 7.90 (s, 1H), 8.17 (d, J=8.4 Hz, 1H), 8.23 (d, J=8.4 Hz, 1H), 8.39 (d, J=5.2 Hz, 1H), 8.50 (dd, J=4.8 Hz, 1.6 Hz, 1H), 9.20 (d, J=1.6 Hz, 1H)

Mass spectrometric value (ESI-MS, m/z): 410 (M+1)$^+$

Compound 289: 6,7-Dimethoxy-4-(2-pyridin-4-yl-quinolin-3-yloxy)-quinoline 4-(2-Bromo-quinolin-3-yloxy)-6,7-dimethoxy-quinoline (compound 281) (50 mg), tetrakistriphenylphosphine palladium(0) (14 mg), and 4-pyridineboronic acid (42 mg) were suspended in a mixed solvent composed of N,N-dimethylformamide (1 ml) and a 2 N aqueous potassium carbonate solution (1 ml), and the suspension was stirred at 80° C. for 2.5 hr. The reaction solution was cooled to room temperature, the reaction solution was then filtered, and the solvent was removed from the filtrate by distillation under the reduced pressure. Water was then added to the residue, and the mixture was extracted with ethyl acetate. The ethyl acetate layer was then washed with water and saturated brine and was dried over anhydrous magnesium sulfate. The solvent was removed by distillation under the reduced pressure, and the residue was purified by thin layer chromatography using acetone-chloroform to give the title compound (13 mg, yield 26%).

$^1$H-NMR (CDCl$_3$, 400 MHz): δ 3.95 (s, 3H), 3.98 (s, 3H), 6.41 (d, J=5.6 Hz, 1H), 7.39 (s, 1H), 7.40 (s, 1H), 7.56 (m, 1H), 7.73 (m, 2H), 7.84 (d, J=4.8 Hz, 2H), 7.91 (s, 1H), 8.18 (d, J=8.8 Hz, 1H), 8.41 (d, J=5.6 Hz, 1H), 8.56 (d, J=4.8 Hz, 2H)

Mass spectrometric value (ESI-MS, m/z): 432 (M+Na)$^+$

Compound 290: 4-[2-(5-Chloro-4-methyl-thiophen-2-yl)-quinolin-3-yloxy]-6,7-dimethoxy-quinoline 2-Aminobenzaldehyde (184 mg) and 2-bromo-1-(4-bromo-5-chloro-thiophen-2-yl)-ethanone (442 mg) were dissolved in methanol (10 ml) to prepare a solution. Sodium hydroxide (210 mg) and water (5 ml) were added to the solution, and the mixture was stirred at room temperature for 2 days. Dilute hydrochloric acid was added to the reaction solution, and the mixture was extracted with chloroform. The organic layer was then washed with water and was dried over anhydrous sodium sulfate. The solvent was removed by distillation under the reduced pressure, and the residue was used in the next reaction without further purification.

The residue, 4-chloro-6,7-dimethoxyquinoline (174 mg), and 4-dimethylaminopyridine (102 mg) were suspended in o-dichlorobenzene (7 ml), and the suspension was stirred at 140° C. for 4 hr and further at 160° C. for 3 hr. The reaction solution was cooled to room temperature, and the solvent was then removed by distillation under the reduced pressure. The residue was purified by thin layer chromatography using acetone-chloroform to give 4-[2-(4-bromo-5-chloro-thiophen-2-yl)-quinolin-3-yloxy]-6,7-dimethoxy-quinoline (32 mg, yield 4%) (2 steps).

4-[2-(4-Bromo-5-chloro-thiophen-2-yl)-quinolin-3-yloxy]-6,7-dimethoxy-quinoline (20 mg) was dissolved in dioxane (3 ml) to prepare a solution. Tetrakistriphenylphosphine palladium (25 mg), methylboronic acid (0.1 ml), water (0.3 ml), and cesium carbonate (182 mg) were added to the solution, and the mixture was stirred at 100° C. for 4 days. The reaction solution was filtered, and the solvent was removed by distillation under the reduced pressure. The residue was purified by thin layer chromatography using methanol-chloroform to give the title compound (13 mg, yield 76%).

$^1$H-NMR (CDCl$_3$, 400 MHz): δ 2.10 (s, 3H), 4.05 (s, 3H), 4.09 (s, 3H), 6.59 (d, J=5.1 Hz, 1H), 7.50 (s, 1H), 7.52 (m, 1H), 7.62 (s, 1H), 7.67-7.72 (m, 3H), 7.79 (s, 1H), 8.11 (d, J=8.5 Hz, 1H), 8.54 (d, J=5.4 Hz, 1H)

Mass spectrometric value (ESI-MS, m/z): 485 (M+Na)$^+$

Compound 291: 4-(4-Bromo-2-methyl-quinolin-3-yloxy)-6,7-dimethoxy-quinoline

3-Hydroxy-2-methyl-quinoline (76 mg) was dissolved in chlorobenzene (7 ml) to prepare a solution. N-Bromosuccimide (180 mg) and 2,2'-azobisisobutyronitrile (23 mg) were added to the solution, and the mixture was stirred at 80° C. for one hr. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using acetone-chloroform to give 4-bromo-3-hydroxy-2-methyl-quinoline (35 mg, yield 31%).

4-Bromo-3-hydroxy-2-methyl-quinoline (35 mg), 4-chloro-6,7-dimethoxyquinoline (110 mg), and 4-dimethylaminopyridine (89 mg) were suspended in o-dichlorobenzene (5 ml), and the suspension was stirred at 140° C. for 5 hr. The reaction solution was cooled to room temperature, and the solvent was removed by distillation under the reduced pressure. The residue was purified by thin layer chromatography using acetone-chloroform to give the title compound (20 mg, yield 32%).

$^1$H-NMR (CDCl$_3$, 400 MHz): δ 2.64 (s, 3H), 4.08 (s, 3H), 4.12 (s, 3H), 6.18 (d, J=5.1 Hz, 1H), 7.49 (s, 1H), 7.68 (m, 1H), 7.71 (s, 1H), 7.79 (m, 1H), 8.12 (dd, J=3.2, 8.3 Hz, 1H), 8.18 (d, J=9.0 Hz, 1H), 8.46 (d, J=5.4 Hz, 1H)

Mass spectrometric value (ESI-MS, m/z): 871 (2M+Na)$^+$

Compound 292: 4-(6-Fluoro-2-phenyl-quinolin-3-yloxy)-6,7-dimethoxy-quinoline

5-Fluoro-1H-indole-2,3-dione (1.19 g) and 2-hydroxy-1-phenyl-ethanone (2.25 g) were dissolved in methanol (70 ml) to prepare a solution. Sodium hydroxide (4.82 g) and water (30 ml) were added to the solution, and the mixture was stirred at room temperature overnight. Dilute hydrochloric acid was added to the reaction solution, and the precipitated crystal was washed with methanol and water to give 6-fluoro-3-hydroxy-2-phenyl-quinoline-4-carboxylic acid (427 mg, yield 21%).

6-Fluoro-3-hydroxy-2-phenyl-quinoline-4-carboxylic acid (118 mg), 4-chloro-6,7-dimethoxyquinoline (330 mg), and 4-dimethylaminopyridine (310 mg) were suspended in o-dichlorobenzene (8 ml), and the mixture was stirred at 160° C. for 11 hr. The reaction solution was cooled to room temperature, water was then added to the reaction solution, and the mixture was extracted with ethyl acetate. The organic layer was washed with water and was dried over anhydrous sodium sulfate. The solvent was removed by distillation under the reduced pressure, and the residue was purified by thin layer chromatography using acetone-chloroform to give the title compound (32 mg, yield 18%).

$^1$H-NMR (CDCl$_3$, 400 MHz): δ 4.01 (s, 3H), 4.05 (s, 3H), 6.48 (d, J=5.1 Hz, 1H), 7.34-7.53 (m, 7H), 7.87 (s, 1H), 7.96 (m, 2H), 8.22 (dd, J=5.1, 9.3 Hz, 1H), 8.47 (d, J=5.4 Hz, 1H)

Mass spectrometric value (ESI-MS, m/z): 427 (M+1)$^+$

Compound 293: 4-(1H-Indol-5-yloxy)-6,7-dimethoxy-quinoline

5-Hydoroxyindole (180 mg), 4-chloro-6,7-dimethoxyquinoline (100 mg), and 4-dimethylaminopyridine (110 mg) were suspended in o-dichlorobenzene (6 ml), and the mixture was stirred at 130° C. for 8 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using acetone-hexane to give the title compound (10 mg, yield 7%).

$^1$H-NMR (CDCl$_3$, 400 MHz): δ 3.97 (s, 3H), 3.99 (s, 3H), 6.35 (d, J=5.6 Hz, 1H), 6.51 (s, 1H), 6.96 (dd, J=8.8 Hz, 2.4 Hz, 1H), 7.25 (m, 1H), 7.38 (m, 3H), 7.59 (s, 1H), 8.36 (d, J=5.6 Hz, 1H), 8.43 (brs, 1H)

Mass spectrometric value (ESI-MS, m/z): 321 (M+1)$^+$

Compound 294: 4-(7-Iodo-benzothiazol-6-yloxy)-6,7-dimethoxy-quinoline

6-Hydroxy-benzothiazole (0.39 g) and iodine (1.32 g) were dissolved in methanol/water (15 ml/5 ml) to prepare a solution which was then stirred at room temperature for 2 days. An aqueous sodium sulfite solution was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by column chromatography using acetone-chloroform to give 6-hydroxy-7-iodo-benzothiazole (211 mg, yield 29%).

6-Hydroxy-7-iodo-benzothiazole (210 mg), 4-chloro-6,7-dimethoxyquinoline (567 mg), and 4-dimethylaminopyridine (390 mg) were suspended in o-dichlorobenzene (15 ml), and the suspension was stirred at 140° C. for 3 hr. The reaction solution was cooled to room temperature, and the solvent was removed by distillation under the reduced pressure. Water was then added to the residue, and the mixture was extracted with ethyl acetate. The ethyl acetate layer was then washed with water and was dried over anhydrous sodium sulfate. The solvent was removed by distillation under the reduced pressure, and the residue was purified by column chromatography using acetone-chloroform to give the title compound (151 mg, yield 43%).

$^1$H-NMR (CDCl$_3$, 400 MHz): δ 4.07 (s, 3H), 4.09 (s, 3H), 6.34 (d, J=5.1 Hz, 1H), 7.34 (d, J=8.8 Hz, 1H), 7.47 (s, 1H), 7.64 (s, 1H), 8.18 (d, J=8.8 Hz, 1H), 8.50 (d, J=5.1 Hz, 1H), 9.14 (s, 1H)

Mass spectrometric value (ESI-MS, m/z): 465 (M+1)$^+$

Compound 295: 6,7-Dimethoxy-4-(7-phenyl-benzothiazol-6-yloxy)-quinoline 4-(7-Iodo-benzothiazol-6-yloxy)-6,7-dimethoxy-quinoline (compound 294) (40 mg), phenylboronic acid (40 mg), and tetrakistriphenylphosphine palladium (20 mg) were dissolved in N,N-dimethylformamide (5 ml) to prepare a solution. A 2 M aqueous potassium carbonate solution (0.3 ml) was added to the reaction system, and the mixture was stirred at 80° C. for 20 min. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using acetone-chloroform to give the title compound (35 mg, yield 98%).

$^1$H-NMR (CDCl$_3$, 400 MHz): δ 3.99 (s, 3H), 4.02 (s, 3H), 6.45 (d, J=5.1 Hz, 1H), 7.28-7.33 (m, 3H), 7.40 (s, 1H), 7.40 (s, 1H), 7.45 (d, J=8.8 Hz, 1H), 7.53 (m, 2H), 8.19 (d, J=8.8 Hz, 1H), 8.46 (d, J=5.4 Hz, 1H), 9.03 (s, 1H)

Mass spectrometric value (ESI-MS, m/z): 415 (M+1)$^+$

Compound 296: 6,7-Dimethoxy-4-(7-methyl-quinolin-6-yloxy)-quinoline

4-Methoxy-3-methylaniline (45.2 g) was dissolved in isopropanol (100 ml) to prepare a solution. Diethyl ethoxymethylenemalonate (71.3 g) was added to the solution, and the mixture was heated under reflux for 5 min. The reaction solution was cooled, and the solvent was then removed by distillation under the reduced pressure. The residue was washed with ether-hexane to give diethyl 2-[(4-methoxy-3-methyl-phenylamino)-methylene]-malonate (76.9 g, yield 76%).

Diethyl 2-[(4-methoxy-3-methyl-phenylamino)-methylene]-malonate (73.9 g) was dissolved in diphenyl ether (200 ml) to prepare a solution which was then stirred at 220° C. for 2 hr. The reaction solution was cooled to room temperature, hexane was then added to the reaction solution, and the precipitated crystal was collected by filtration to give ethyl 6-methoxy-7-methyl-4-oxo-1,4-dihydro-quinoline-3-carboxylate (25.5 g, yield 35%).

Ethyl 6-methoxy-7-methyl-4-oxo-1,4-dihydro-quinoline-3-carboxylate (25.5 g) was suspended in a 2 M aqueous sodium hydroxide solution (250 ml), and the mixture was heated under reflux for 4 hr. The reaction solution was cooled to room temperature, the aqueous layer was then washed with chloroform and was neutralized with dilute hydrochloric acid. The precipitated crystal was collected by filtration and was washed with water, isopropanol, and hexane in that order to give 6-methoxy-7-methyl-4-oxo-1,4-dihydro-quinoline-3-carboxylic acid (22.1 g, yield 98%).

6-Methoxy-7-methyl-4-oxo-1,4-dihydro-quinoline-3-carboxylic acid (22 g) was suspended in diphenyl ether (200 ml), and the suspension was heated under reflux overnight. The reaction solution was cooled to room temperature, hexane was then added to the reaction solution, and the precipitated crystal was collected by filtration to give 6-methoxy-7-methyl-1H-quinolin-4-one (16.6 g, yield 93%).

6-Methoxy-7-methyl-1H-quinolin-4-one (73.9 g) was added to phosphorus oxychloride (160 ml), and the mixture was heated under reflux for 2 hr. The reaction solution was cooled to room temperature, and the solvent was then removed by distillation under the reduced pressure. Chloroform and water were added to the reaction solution, and the aqueous layer was neutralized with an aqueous potassium hydroxide solution. The organic layer was washed with water and saturated brine and was dried over anhydrous sodium sulfate. The solvent was removed by distillation under the reduced pressure, hexane was added to the residue, and the precipitated crystal was collected by filtration to give 4-chloro-6-methoxy-7-methyl-quinoline (12.7 g, yield 71%).

4-Chloro-6-methoxy-7-methyl-quinoline (10.8 g) was dissolved in diisopropylethylamine/IMS (7.4 g/100 ml), 5% palladium carbon (0.5 g) was added to the solution, and the mixture was stirred under a hydrogen gas atmosphere at room temperature overnight. The reaction solution was filtered, and the solvent was then removed by distillation under the reduced pressure to give 6-methoxy-7-methyl-quinoline (3 g, yield 33%).

6-Methoxy-7-methyl-quinoline (3 g) was added to an aqueous bromic acid solution (30 ml), and the mixture was heated under reflux for 7 hr. The reaction solution was cooled to room temperature, the aqueous layer was then neutralized with an aqueous sodium hydroxide solution and an aqueous sodium hydrogencarbonate solution. The organic layer was extracted with ether, the solvent was removed by distillation under the reduced pressure, and the residue was washed with cooled ether to give 6-hydroxy-7-methylquinoline (1.3 g, yield 47%).

6-Hydroxy-7-methylquinoline (180 mg), 4-chloro-6,7-dimethoxyquinoline (126 mg), and 4-dimethylaminopyridine (69 mg) were suspended in o-dichlorobenzene (3 ml), and the suspension was stirred at 140° C. for 3 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using acetone-chloroform to give the title compound (36 mg, yield 60%).

$^1$H-NMR (CDCl$_3$, 400 MHz): δ 2.36 (s, 3H), 3.99 (s, 6H), 6.31 (d, J=5.2 Hz, 1H), 7.31 (dd, J=8.4 Hz, 4.0 Hz, 1H), 7.42 (s, 1H), 7.44 (s, 1H), 7.54 (s, 1H), 8.00 (m, 2H), 8.41 (d, J=5.2 Hz, 1H), 8.83 (dd, J=8.4 Hz, 4.0 Hz, 1H)

Mass spectrometric value (ESI-MS, m/z): 347 (M+1)$^+$

Compound 297: 6,7-Dimethoxy-4-(7-methoxy-quinolin-6-yloxy)-quinoline

6-Benzyloxy-4-chloro-7-methoxy-quinoline (525 mg) was dissolved in triethylamine/N,N-dimethylformamide (5 ml/20 ml) to prepare a solution. 20% palladium hydroxide (1.52 g) was added to the solution, and the mixture was stirred at room temperature under a hydrogen gas atmosphere for 6 hr. The reaction solution was filtered, and the solvent was then removed by distillation under the reduced pressure. Water was added to the residue, the mixture was extracted with chloroform, and the chloroform layer was then washed with water and was dried over anhydrous sodium sulfate. The solvent was removed by distillation under the reduced pressure, and the residue was purified by column chromatography using acetone-chloroform to give 6-hydroxy-7-methoxyquinoline (258 mg, yield 84%).

6-Hydroxy-7-methoxyquinoline (65 mg), 4-chloro-6,7-dimethoxyquinoline (100 mg), and 4-dimethylaminopyridine (148 mg) were suspended in o-dichlorobenzene (5 ml), and the suspension was stirred at 155° C. overnight. The reaction solution was cooled to room temperature. Water was then added thereto, and the mixture was extracted with ethyl acetate. The ethyl acetate layer was washed with water and was dried over anhydrous sodium sulfate. The solvent was removed by distillation under the reduced pressure, and the residue was purified by column chromatography using acetone-chloroform to give the title compound (134 mg, yield 100%).

$^1$H-NMR (CDCl$_3$, 400 MHz): δ 3.93 (s, 3H), 4.06 (s, 3H), 4.07 (s, 3H), 6.38 (d, J=5.1 Hz, 1H), 7.34 (dd, J=4.4, 8.3 Hz, 1H), 7.45 (s, 1H), 7.56 (s, 1H), 7.63 (s, 1H), 7.63 (s, 1H), 8.05 (d, J=8.1 Hz, 1H), 8.48 (d, J=5.1 Hz, 1H), 8.88 (dd, J=1.4, 4.4 Hz, 1H)

Mass spectrometric value (ESI-MS, m/z): 363 (M+1)$^+$

Compound 298: 4-(5-Chloro-quinolin-6-yloxy)-6,7-dimethoxyquinoline

6-Hydroxyquinoline (0.5 g) and iodine (1.24 g) were dissolved in methanol/water (15 ml/7.5 ml) to prepare a solution which was then stirred at room temperature for 2 hr. The solvent was removed by distillation under the reduced pressure, water was added to the residue, and the mixture was extracted with ethyl acetate. The ethyl acetate layer was then washed with water and was dried over anhydrous sodium sulfate. The solvent was removed by distillation under the reduced pressure, and the residue was washed with ethyl acetate to give 6-hydroxy-5-iodo-quinoline (419 mg, yield 45%).

6-Hydroxy-5-iodo-quinoline (100 mg), 4-chloro-6,7-dimethoxyquinoline (215 mg), and 4-dimethylaminopyridine (367 mg) were suspended in o-dichlorobenzene (12 ml), and the suspension was stirred at 120° C. for 5 hr. The reaction solution was cooled to room temperature, and the solvent was removed by distillation under the reduced pressure. Water was then added to the residue, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using acetone-chloroform to give the title compound (20 mg, yield 12%).

$^1$H-NMR (CDCl$_3$, 400 MHz): δ 4.08 (s, 3H), 4.09 (s, 3H), 6.35 (d, J=5.4 Hz, 1H), 7.49 (s, 1H), 7.55-7.68 (m, 3H), 8.16 (d, J=9.0 Hz, 1H), 8.49 (d, J=5.1 Hz, 1H), 8.65 (m, 1H), 9.01 (dd, J=1.7, 4.1 Hz, 1H)

Mass spectrometric value (ESI-MS, m/z): 367 (M+1)$^+$

Compound 299: 6,7-Dimethoxy-4-(7-phenyl-quinolin-6-yloxy)-quinoline

Trifluoroacetic acid (15 ml) and methanesulfonic acid (1.5 ml) were added to 7-benzyloxy-4-chloro-6-methoxy-quinoline (1.02 g), and the mixture was stirred at room temperature for one hr. The solvent was removed by distillation under the reduced pressure, water was then added to the reaction solution, and the mixture was extracted with ethyl acetate. The organic layer was washed with an aqueous sodium hydrogencarbonate solution and water and was dried over anhydrous sodium sulfate. The solvent was removed by distillation under the reduced pressure, and the residue (0.8 g) was used in the next reaction without purification.

A part (545 g) of the residue was suspended in triethylamine/dichloromethane (5 ml/20 ml), trifluoromethanesulfonic anhydride (2 ml) was added to the suspension under ice cooling, and the mixture was stirred at room temperature for 2 hr. The solvent was removed by distillation under the reduced pressure. Water was then added to the reaction solution, and the mixture was extracted with ethyl acetate. The organic layer was washed with an aqueous sodium hydrogencarbonate solution and water and was dried over anhydrous sodium sulfate. The solvent was removed by distillation under the reduced pressure, and the residue was purified by column chromatography using ethyl acetate-hexane to give 4-chloro-6-methoxy-quinolin-7-yl trifluoro-methanesulfonate (228 mg, yield 29%) (2 steps).

4-Chloro-6-methoxy-quinolin-7-yl trifluoro-methanesulfonate (114 mg), phenylboronic acid (150 mg), and tetrakistriphenylphosphine palladium (25 mg) were dissolved in N,N-dimethylformamide (3 ml), a 2 M aqueous potassium carbonate solution (0.3 ml) was added to the reaction system, and the mixture was stirred at 80° C. for one hr. Water was added to the reaction solution, and the mixture was extracted with ethyl acetate, and the ethyl acetate layer was then washed with water and was dried over anhydrous sodium sulfate. The solvent was removed by distillation under the reduced pressure, and the residue was used in the next reaction without purification.

The residue was dissolved in triethylamine/N,N-dimethylformamide (2 ml/10 ml) to prepare a solution, palladium hydroxide (0.83 g) was added to the solution, and the mixture was stirred at room temperature under a hydrogen gas atmosphere overnight. The reaction solution was filtered, and the solvent was then removed by distillation under the reduced pressure. Water was added to the residue, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using ethyl acetate-hexane to give 6-methoxy-7-phenyl-1,2,3,4-tetrahydro-quinoline (63 mg, yield 79%).

6-Methoxy-7-phenyl-1,2,3,4-tetrahydro-quinoline (62 mg) was dissolved in o-dichlorobenzene (20 ml) to prepare a solution. 2,3-Dichloro-5,6-dicyano-1,4-benzoquinone (227 mg) was added to the solution, and the mixture was stirred at 120° C. for 30 min. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was used in the next reaction without purification.

The residue was dissolved in dichloromethane (3 ml) to prepare a solution, a boron tribromide/1 M dichloromethane solution (0.3 ml) was added to the solution under ice cooling, and the mixture was stirred for 2 days. The solvent was removed by distillation under the reduced pressure, water was then added to the residue, and the mixture was extracted with ethyl acetate. The ethyl acetate layer was washed with water and was dried over anhydrous sodium sulfate. The solvent was removed by distillation under the reduced pressure, and the residue was used in the next reaction without purification.

The residue, 4-chloro-6,7-dimethoxyquinoline (62 mg), and 4-dimethylaminopyridine (49 mg) were suspended in o-dichlorobenzene (2 ml), and the suspension was stirred at 150° C. for 4 hr. The reaction solution was cooled to room temperature, and the solvent was removed by distillation under the reduced pressure. The residue was purified by thin layer chromatography using acetone-chloroform to give the title compound (24 mg, yield 23%) (3 steps).

$^1$H-NMR (CDCl$_3$, 400 MHz): δ 4.01 (s, 3H), 4.03 (s, 3H), 6.47 (d, J=5.4 Hz, 1H), 7.23-7.32 (m, 3H), 7.38 (s, 1H), 7.44-7.47 (m, 2H), 7.61-7.63 (m, 3H), 8.12 (d, J=7.8 Hz, 1H), 8.30 (s, 1H), 8.43 (d, J=5.1 Hz, 1H), 8.97 (dd, J=1.7, 4.2 Hz, 1H)

Mass spectrometric value (ESI-MS, m/z): 409 (M+1)$^+$

Compound 300: 6,7-Dimethoxy-4-(7-methyl-isoquinolin-6-yloxy)-quinoline

4-Methoxy-3-methylbenzaldehyde (3.00 g) was dissolved in benzene (30 ml) to prepare a solution. 2,2-Dimethoxyethylamine (2.10 g) was added to the solution, and the mixture was heated under reflux overnight. The solvent was removed by distillation under the reduced pressure, the residue was then dissolved in tetrahydrofuran (30 ml), and the mixture was cooled to −10° C. Ethyl chloroformate (2.17 g) and trimethyl phosphite (2.97 g) were added thereto, and mixture was stirred at room temperature overnight. The solvent was removed by distillation under the reduced pressure, the residue was then dissolved in dichloromethane (30 ml), titanium tetrachloride (22.7 g) was added to the solution, and the mixture was heated under reflux for 36 hr. The reaction solution was cooled to room temperature, was then neutralized with a 1 N aqueous sodium hydroxide solution, and was extracted with 3 N hydrochloric acid. The aqueous layer was made basic by the addition of a 3 N aqueous sodium hydroxide solution and was then extracted with dichloromethane. The solvent was removed by distillation under the reduced pressure to give 6-methoxy-7-methylisoquinoline (764 mg, yield 22%).

6-Methoxy-7-methylisoquinoline (239 mg) and sodium thiomethoxide (1.58 g) were suspended in N,N-dimethylformamide (12 ml), and the suspension was stirred at 160° C. for 2 hr. The reaction solution was cooled to room temperature, the reaction solution was then filtered, and the solvent was removed from the filtrate by distillation under the reduced pressure. The residue was purified by thin layer chromatography using chloroform-methanol to give 6-hydroxy-7-methylisoquinoline (21 mg, yield 1%).

6-Hydroxy-7-methylisoquinoline (21 mg), 4-chloro-6,7-dimethoxyquinoline (81 mg), and 4-dimethylaminopyridine (44 mg) were suspended in o-dichlorobenzene (2.5 ml), and the suspension was stirred at 140° C. for 6 hr. The reaction solution was cooled to room temperature, water was then added to reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using acetone-chloroform to give the title compound (24 mg, yield 58%).

$^1$H-NMR (CDCl$_3$, 400 MHz): δ 2.37 (s, 3H), 3.96 (s, 3H), 3.99 (s, 3H), 6.35 (d, J=5.2 Hz, 1H), 7.36 (s, 1H), 7.39 (s, 1H), 7.47 (m, 2H), 7.86 (s, 1H), 8.41 (d, J=5.6 Hz, 1H), 8.44 (d, J=5.2 Hz, 1H), 9.15 (s, 1H)

Mass spectrometric value (ESI-MS, m/z): 347 (M+1)$^+$

Compound 301: 4-(7-Bromo-isoquinolin-6-yloxy)-6,7-dimethoxy-quinoline

3-Bromo-4-methoxybenzaldehyde (10.0 g) was dissolved in benzene (100 ml) to prepare a solution. 2,2-Dimethoxyethylamine (4.89 g) was added to the solution, and the mixture was heated under reflux overnight. The solvent was removed by distillation under the reduced pressure, and the residue was then dissolved in tetrahydrofuran (100 ml) to prepare a solution which was then cooled to −10° C. Ethyl chloroformate (5.05 g) and trimethyl phosphite (6.92 g) were added thereto, and the mixture was stirred at room temperature overnight. The solvent was removed by distillation under the reduced pressure, the residue was then dissolved in dichloromethane (100 ml) to prepare a solution. Titanium tetrachloride (53.0 g) was added to the solution, and the mixture was heated under reflux for 36 hr. The reaction solution was cooled to room temperature, was then neutralized with a 1 N aqueous sodium hydroxide solution, and was extracted with 3 N hydrochloric acid. The aqueous layer was made basic with a 3 N aqueous sodium hydroxide solution, was then extracted with dichloromethane, and the solvent was removed by distillation under the reduced pressure to give 7-bromo-6-methoxyisoquinoline (2.90 g, yield 26%).

7-Bromo-6-methoxyisoquinoline (50 mg) and sodium thiomethoxide (147 mg) were suspended in N,N-dimethylformamide (2 ml), and the suspensioin was stirred at 150° C. for 2 hr. The reaction solution was cooled to room temperature, the reaction solution was then filtered, and the solvent was removed from the filtrate by distillation under the reduced pressure. The residue was purified by thin layer chromatography using chloroform-methanol to give 7-bromo-6-hydroxyisoquinoline (11 mg, yield 22%).

7-Bromo-6-hydroxyisoquinoline (11 mg), 4-chloro-6,7-dimethoxyquinoline (31 mg), and 4-dimethylaminopyridine (17 mg) were suspended in o-dichlorobenzene (2 ml), and the mixture was stirred at 140° C. for 7 hr. The reaction solution was cooled to room temperature, water was then added to the reaction solution, and the mixture was extracted with ethyl acetate. The ethyl acetate layer was then washed with water and saturated brine and was dried over anhydrous magnesium sulfate. The solvent was removed by distillation under the reduced pressure, and the residue was purified by thin layer chromatography using chloroform-methanol to give the title compound (9 mg, yield 48%).

$^1$H-NMR (CDCl$_3$, 400 MHz): δ 3.97 (s, 3H), 3.99 (s, 3H), 6.44 (d, J=5.2 Hz, 1H), 7.40 (s, 1H), 7.49 (m, 3H), 8.32 (s, 1H), 8.50 (m, 2H), 9.17 (s, 1H)

Mass spectrometric value (ESI-MS, m/z): 412 (M+1)$^+$

Compound 302: 4-(5-Chloro-7-methyl-quinolin-6-yloxy)-6,7-dimethoxy-quinoline

6-Hydroxy-7-methylquinoline (76 mg) was dissolved in chlorobenzene (7 ml) to prepare a solution. N-Bromosuccimide (180 mg) and 2,2'-azobisisobutyronitrile (23 mg) were added to the solution, and the mixture was stirred at 80° C. for one hr. Water was added to the reaction solution, and the mixture was extracted with ethyl acetate. The ethyl acetate layer was then washed with water and was dried over anhydrous sodium sulfate, the solvent was removed by distillation under the reduced pressure, and the residue was purified by thin layer chromatography using acetone-chloroform to give 5-bromo-6-hydroxy-7-methyl-quinoline (111 mg, yield 97%).

5-Bromo-6-hydroxy-7-methyl-quinoline (110 mg), 4-chloro-6,7-dimethoxyquinoline (330 mg), and 4-dimethylaminopyridine (240 mg) were suspended in o-dichlorobenzene (10 ml), and the mixture was stirred at 140° C. for 6 hr. The reaction solution was cooled to room temperature, and the solvent was removed therefrom by distillation under the reduced pressure. The residue was purified by thin layer chromatography using acetone-chloroform to give the title compound (19 mg, yield 10%).

$^1$H-NMR (CDCl$_3$, 400 MHz): δ 2.42 (s, 3H), 4.08 (s, 3H), 4.12 (s, 3H), 6.18 (d, J=5.4 Hz, 1H), 7.49 (s, 1H), 7.53 (dd, J=4.3, 8.6 Hz, 1H), 7.72 (s, 1H), 8.04 (s, 1H), 8.44 (d, J=5.1 Hz, 1H), 8.56 (d, J=8.6 Hz, 1H), 8.98 (dd, J=1.3, 4.4 Hz, 1H)

Mass spectrometric value (ESI-MS, m/z): 783 (2M+Na)$^+$

Compound 303: 6,7-Dimethoxy-4-(7-pyridin-2-yl-isoquinolin-6-yloxy)-quinoline

7-Bromo-6-methoxyisoquinoline (200 mg), tetrakistriphenylphosphine palladium(0) (97 mg), and copper(II) oxide (134 mg) were suspended in N,N-dimethylformamide (5 ml), tri-n-butyl-(2-pyridyl)-tin (618 mg) was added to the suspension, and the mixture was stirred at 100° C. overnight. The reaction solution was cooled to room temperature, the reaction solution was then fitlered, and the solvent was removed from the filtrate by distillation under the reduced pressure. Water was then added to the residue, and the mixture was extracted with dichloromethane. The dichloromethane layer was washed with water and saturated brine and was dried over anhydrous magnesium sulfate. The solvent was removed by distillation under the reduced pressure, and the residue was purified by thin layer chromatography using chloroform-methanol to give 6-methoxy-7-pyridin-2-yl-isoquinoline (122 mg, yield 62%).

6-Methoxy-7-pyridin-2-yl-isoquinoline (118 mg) and sodium thiomethoxide (350 mg) were suspended in N,N-dimethylformamide (3 ml), and the mixture was stirred at 150° C. for 4 hr. The reaction solution was cooled to room temperature, the reaction solution was then filtered, and the solvent was removed from the filtrate by distillation under the reduced pressure. The residue was purified by thin layer chromatography using chloroform-methanol to give 7-pyridin-2-yl-isoquinolin-6-ol (30 mg, yield 27%).

7-Pyridin-2-yl-isoquinolin-6-ol (20 mg), 4-chloro-6,7-dimethoxyquinoline (50 mg), and 4-dimethylaminopyridine (33 mg) were suspended in o-dichlorobenzene (3 ml), and the mixture was stirred at 140° C. for 24 hr. The reaction solution was cooled to room temperature, water was then added to the reaction solution, and the mixture was extracted with ethyl acetate. The ethyl acetate layer was then washed with water and saturated brine and was dried over anhydrous magnesium sulfate. The solvent was removed by distillation under the reduced pressure, and the residue was purified by thin layer chromatography using chloroform-methanol to give the title compound (8 mg, yield 22%).

$^1$H-NMR (CDCl$_3$, 400 MHz): δ 3.93 (s, 3H), 3.97 (s, 3H), 6.27 (d, J=5.2 Hz, 1H), 7.12 (m, 1H), 7.34 (s, 1H), 7.41 (s, 1H), 7.51 (m, 3H), 7.71 (d, J=7.6 Hz, 1H), 8.40 (d, J=5.2 Hz, 1H), 8.49 (d, J=6.0 Hz, 1H), 8.52 (s, 1H), 8.60 (d, J=4.4 Hz, 1H), 9.31 (s, 1H)

Mass spectrometric value (ESI-MS, m/z): 432 (M+Na)$^+$

Compound 304: 6,7-Dimethoxy-4-(7-pyridin-3-yl-isoquinolin-6-yloxy)-quinoline

7-Bromo-6-methoxyisoquinoline (100 mg), tetrakistriphenylphosphine palladium(0) (49 mg), and 3-pyridineboronic acid (155 mg) were suspended in a mixed solvent composed of N,N-dimethylformamide (1.5 ml) and a 2 N aqueous potassium carbonate solution (1.5 ml), and the mixture was stirred at 80° C. for 4.5 hr. The reaction was cooled to room temperature, the reaction solution was then filtered, and the solvent was removed from the filtrate by distillation under the reduced pressure. Water was then added to the residue, and the mixture was extracted with dichloromethane. The dichloromethane layer was washed with water and saturated brine and was dried over anhydrous magnesium sulfate. The solvent was removed by distillation under the reduced pressure, and the residue was purified by thin layer chromatography using chloroform-methanol to give 6-methoxy-7-pyridin-3-yl-isoquinoline (42 mg, yield 85%).

6-Methoxy-7-pyridin-3-yl-isoquinoline (42 mg) and sodium thiomethoxide (126 mg) were suspended in N,N-dimethylformamide (1.5 ml), and the mixture was stirred at 160° C. for 2 hr. The reaction solution was cooled to room temperature, the reaction solution was then filtered, and the solvent was removed from the filtrate by distillation under the reduced pressure. The residue was purified by thin layer chromatography using chloroform-methanol to give 7-pyridin-3-yl-isoquinolin-6-ol (7 mg, yield 17%).

7-Pyridin-3-yl-isoquinolin-6-ol (7 mg), 4-chloro-6,7-dimethoxyquinoline (21 mg), and 4-dimethylaminopyridine (12 mg) were suspended in o-dichlorobenzene (1.5 ml), and the suspension was stirred at 140° C. for 4 hr. The reaction solution was cooled to room temperature, water was then added to the reaction solution, and the mixture was extracted with ethyl acetate. The ethyl acetate layer was then washed with water and saturated brine and was dried over anhydrous magnesium sulfate. The solvent was removed by distillation under the reduced pressure, and the residue was purified by thin layer chromatography using chloroform-methanol to give the title compound (7 mg, yield 55%).

$^1$H-NMR (CDCl$_3$, 400 MHz): δ 3.91 (s, 3H), 3.96 (s, 3H), 6.48 (d, J=5.2 Hz, 1H), 7.19 (m, 1H), 7.28 (s, 1H), 7.34 (s, 1H), 7.50 (s, 1H), 7.54 (d, J=5.6 Hz, 1H), 7.85 (d, J=7.6 Hz, 1H), 8.08 (s, 1H), 8.46 (m, 3H), 8.83 (s, 1H), 9.28 (s, 1H)

Mass spectrometric value (ESI-MS, m/z): 432 (M+Na)$^+$

Compound 305: 6-(6,7-Dimethoxy-quinolin-4-yloxy)-7-methyl-quinazoline

3-Hydroxy-4-methylbenzoic acid (3 g) was dissolved in N,N-dimethylformamide (60 ml) to prepare a solution. Potassium carbonate (6.81 g) and methyl iodide (6.14 ml) were added to the solution, and the mixture was stirred at room temperature overnight. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by column chromatography using acetone-hexane to give methyl 3-methoxy-4-methylbenzoate (3.48 g, yield 98%).

Methyl 3-methoxy-4-methylbenzoate (1 g) was dissolved in acetic acid (1 ml) to prepare a solution which was then cooled to 0° C. Fuming nitric acid (1 ml) was added to the solution in small portions. The mixture was stirred at room temperature overnight. The reaction solution was added in small portions to water of 0° C., and the mixture was neutralized with a 10% aqueous sodium hydroxide solution, followed by extraction with chloroform. The chloroform layer was then washed with saturated brine and was dried over anhydrous sodium sulfate. The solvent was removed by distillation under the reduced pressure, and the residue was used in the next reaction without purification.

The residue (1.02 g) was dissolved in N,N-dimethylformamide (15 ml) to prepare a solution. Triethylamine (3 ml) and 20% palladium hydroxide (150 mg) were added to the solution, and the mixture was stirred under hydrogen pressure at room temperature overnight. The reaction solution was filtered through Celite and was then washed with chloroform and methanol. The solvent was removed by distillation under the reduced pressure, and the residue was purified by column chromatography using acetone-hexane to give methyl 2-amino-5-methoxy-4-methylbenzoate (522 mg, yield 48%).

Methyl 2-amino-5-methoxy-4-methylbenzoate (510 mg) was suspended in formamide (5 ml), and the suspension was stirred at 140° C. overnight. The precipitated crystal was washed with ether to give 6-methoxy-7-methyl-1H-quinazolin-4-one (275 mg, yield 55%).

6-Methoxy-7-methyl-1H-quinazolin-4-one (275 mg) was suspended in N,N-diisopropylethylamine (3.78 ml), phosphorus oxychloride (0.3 ml) was added to the suspension, and the mixture was stirred at 100° C. for 6 hr. The reaction solution was added in small portions to water of 0° C., an aqueous sodium hydrogencarbonate solution was further added thereto, and the mixture was extracted with chloroform. The chloroform layer was then washed with saturated brine and was dried over anhydrous sodium sulfate. The solvent was removed by distillation under the reduced pressure, and the residue was purified by thin layer chromatography using chloroform-methanol to give 4-chloro-6-methoxy-7-methyl-quinazoline (199 mg, yield 66%).

4-Chloro-6-methoxy-7-methyl-quinazoline (99 mg) was dissolved in N,N-dimethylformamide (6 ml) to prepare a solution. Triethylamine (0.6 ml) and 20% palladium hydroxide (4 mg) were added to the solution, and the mixture was stirred under hydrogen pressure at room temperature overnight. The reaction solution was filtered through Celite and was then washed with chloroform and methanol, and the solvent was removed by distillation under the reduced pressure. Water was added to the residue, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give 6-methoxy-7-methyl-quinazoline (76 mg, yield 93%).

6-Methoxy-7-methyl-quinazoline (94 mg) was dissolved in N,N-dimethylformamide (5 ml) to prepare a solution, sodium thiomethoxide (376 mg) was added to the solution, and the mixture was stirred at 140° C. for one hr. The solvent was removed by distillation under the reduced pressure, and the residue was purified by thin layer chromatography using chloroform-methanol to give 6-hydroxy-7-methyl-quinazoline (64 mg, yield 73%).

6-Hydroxy-7-methyl-quinazoline (38 mg), 4-chloro-6,7-dimethoxyquinoline (159 mg), and 4-dimethylaminopyridine (87 mg) were suspended in o-dichlorobenzene (2 ml), and the suspension was stirred at 150° C. overnight. The reaction solution was cooled to room temperature, water was then added to the solution, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (71 mg, yield 86%).

$^1$H-NMR (CDCl$_3$, 400 MHz): δ 2.51 (s, 3H), 4.07 (s, 3H), 4.10 (s, 3H), 6.45 (d, J=5.4 Hz, 1H), 7.57-7.59 (m, 3H), 8.06 (s, 1H), 8.53 (d, J=5.4 Hz, 1H), 9.31 (s, 1H), 9.34 (s, 1H)

Mass spectrometric value (ESI-MS, m/z): 348 (M+1)$^+$

Compound 306: 6-(6,7-Dimethoxy-quinolin-4-yloxy)-4-methyl-chromen-2-one

6-Hydroxy-4-methyl-chromen-2-one (238 mg), 4-chloro-6,7-dimethoxyquinoline (100 mg), and 4-dimethylaminopyridine (165 mg) were suspended in o-dichlorobenzene (5 ml), and the suspension was stirred at 140° C. for 3.5 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using acetone-chloroform to give the title compound (24 mg, yield 5%).

$^1$H-NMR (CDCl$_3$, 400 MHz): δ 2.34 (s, 3H), 3.98 (s, 6H), 6.30 (s, 1H), 6.35 (d, J=5.2 Hz, 1H), 7.28-7.42 (m, 4H), 7.48 (s, 1H), 8.43 (d, J=5.2 Hz, 1H)

Mass spectrometric value (ESI-MS, m/z): 749 (2M+Na)$^+$

Compound 307: 6,7-Dimethoxy-4-(thieno[3,2-b]pyridin-7-yloxy)-quinoline

Thieno[3,2-b]pyridin-7-ol (203 mg), 4-chloro-6,7-dimethoxyquinoline (100 mg), and 4-dimethylaminopyridine (110 mg) were suspended in o-dichlorobenzene (6 ml), and the suspension was stirred at 130° C. for 8 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using acetone-hexane to give the title compound (4 mg, yield 1%).

$^1$H-NMR (CDCl$_3$, 400 MHz): δ 3.89 (s, 3H), 4.00 (s, 3H), 6.77 (m, 2H), 7.31 (s, 1H), 7.44 (s, 1H), 7.57 (d, J=5.6 Hz, 1H), 7.73 (d, J=5.6 Hz, 1H), 8.57 (m, 2H)

Mass spectrometric value (ESI-MS, m/z): 339 (M+1)$^+$

Compound 308: 6,7-Dimethoxy-4-(6-fluoro-2-methyl-quinolin-4-yloxy)-quinoline

6-Fluoro-2-methyl-quinolin-4-ol (237 mg), 4-chloro-6,7-dimethoxyquinoline (100 mg), and 4-dimethylaminopyridine (164 mg) were suspended in o-dichlorobenzene (6 ml), and the suspension was stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using acetone-chloroform to give the title compound (11 mg, yield 7%).

$^1$H-NMR (CDCl$_3$, 400 MHz): δ 2.57 (s, 3H), 3.88 (s, 3H), 4.00 (s, 3H), 6.69 (m, 2H), 7.29 (s, 1H), 7.45 (m, 2H), 7.72 (dd, J=8.8 Hz, 2.8 Hz, 1H), 8.00 (m, 1H), 8.57 (s, 1H)

Mass spectrometric value (ESI-MS, m/z): 365 (M+1)$^+$

Compound 309: 6,7-Dimethoxy-4-(2-methyl-quinolin-4-yloxy)-quinoline

2-Methyl-quinolin-4-ol (213 mg), 4-chloro-6,7-dimethoxyquinoline (100 mg), and 4-dimethylaminopyridine (110 mg) were suspended in o-dichlorobenzene (6 ml), and the suspension was stirred at 130° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using acetone-hexane to give the title compound (7 mg, yield 2%).

$^1$H-NMR (CDCl$_3$, 400 MHz): δ 2.60 (s, 3H), 3.88 (s, 3H), 4.00 (s, 3H), 6.68 (d, J=5.2 Hz, 1H), 6.70 (s, 1H), 7.34 (s, 1H), 7.45 (m, 2H), 7.70 (m, 1H), 8.02 (d, J=8.4 Hz, 1H), 8.11 (d, J=8.4 Hz, 1H), 8.55 (d, J=5.2 Hz, 1H)

Mass spectrometric value (ESI-MS, m/z): 347 (M+1)$^+$

Compound 310: 3-(6,7-Dimethoxy-quinolin-4-yloxy)-2-methyl-[1,8]naphthyridine

2-Aminopyridine (14.1 g) and triethylamine (19.0 g) were dissolved in dichloromethane (200 ml) to prepare a solution which was then cooled at 0° C. A solution of pivaloylic acid chloride (19.9 g) in dichloromethane (30 ml) was gradually added dropwise to the solution, and the mixture was stirred at 0° C. for 15 min. Thereafter, the mixture was stirred at room temperature for 4 hr, and the reaction solution was poured into water (150 ml). The dichloromethane layer was washed with a dilute aqueous sodium hydrogencarbonate solution and was dried over anhydrous sodium sulfate. The solvent was removed by distillation under the reduced pressure. The residue was purified by column chromatography using chloroform to give 2,2-dimethyl-N-pyridin-2-yl-propionamide (25.2 g, yield 95%).

2,2-Dimethyl-N-pyridin-2-yl-propionamide (20.3 g) was dissolved in tetrahydrofuran (230 ml) to prepare a solution which was then cooled to −78° C. A 2.44 M n-butyllithium/n-hexane solution (100 ml) was gradually added dropwise thereto, and the mixture was stirred at −78° C. for 15 min. The reaction solution was stirred at 0° C. for 2 hr and was then again cooled to −78° C. A solution of N,N-dimethylformamide (25.0 g) in tetrahydrofuran (25 ml) was gradually added dropwise thereto. The temperature of the mixture was raised to room temperature. The reaction solution was then poured into a mixture of ice (50 g) and 6 N hydrochloric acid (150 ml), and the mixture was stirred at room temperature for 20 min. The aqueous layer was neutralized with potassium carbonate powder and was extracted with diethyl ether. The diethyl ether layer was then washed with water and saturated brine and was dried over magnesium sulfate. The solvent was removed by distillation under the reduced pressure, and the residue was purified by column chromatography using acetone-chloroform to give N-(3-formyl-pyridin-2-yl)-2,2-dimethyl-propionamide (11.8 g, yield 50%).

N-(3-Formyl-pyridin-2-yl)-2,2-dimethyl-propionamide (9.68 g) was dissolved in 3 N hydrochloric acid (140 ml) to prepare a solution which was then stirred under reflux overnight. The reaction solution was cooled to room temperature, the reaction solution was washed with diethyl ether, and was neutralized with potassium carbonate powder. Diethyl ether was added thereto for extraction. The diethyl ether layer was dried over potassium carbonate. The solvent was removed by distillation under the reduced pressure, and the residue was purified by column chromatography using acetone-chloroform to give 2-amino-pyridine-3-carbaldehyde (5.03 g, yield 88%).

2-Amino-pyridine-3-carbaldehyde (2.0 g) and chloroacetone (1.5 g) were suspended in a 5 N aqueous sodium hydroxide solution (10 ml) and was allowed to stand in a hermetically sealed state for 3 days. The reaction solution was neutralized with 10% hydrochloric acid, and the precipitated crystal was then collected by filtration. Isopropanol was added to the crystal, and the mixture was heated under reflux. The reaction solution was cooled to room temperature, and the solvent was then removed by distillation. Hexane was added to the residue, and the precipitated crystal was collected by filtration and was washed with hexane to give 2-methyl-[1,8]naphthyridin-3-ol (1.05 g, yield 40%).

2-Methyl-[1,8]naphthyridin-3-ol (20 mg), 4-chloro-6,7-dimethoxyquinoline (84 mg), and 4-dimethylaminopyridine (46 mg) were suspended in o-dichlorobenzene (2 ml), and the suspension was stirred at 140° C. for 3 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using chloroform-methanol to give the title compound (41 mg, yield 100%).

$^1$H-NMR (CDCl$_3$, 400 MHz): δ 2.68 (s, 3H), 3.97 (s, 3H), 3.99 (s, 3H), 6.36 (d, J=5.2 Hz, 1H), 7.40 (m, 2H), 7.46 (s, 1H), 7.70 (s, 1H), 8.03 (dd, J=8.4 Hz, 2.0 Hz, 1H), 8.46 (d, J=5.2 Hz, 1H), 9.01 (d, J=2.0 Hz, 1H)

Mass spectrometric value (ESI-MS, m/z): 370 (M+Na)$^+$

Compound 311: 3-(6,7-Dimethoxy-quinolin-4-yloxy)-2-methyl-[1,6]naphthyridine 4-Aminopyridine (4.70 g) and triethylamine (6.31 g) were dissolved in dichloromethane (75 ml) to prepare a solution which was cooled to 0° C. A solution of pivaloylic acid chloride (6.63 g) in dichloromethane (10 ml) was gradually added dropwise thereto, and the mixture was stirred at 0° C. for 15 min. Thereafter, the mixture was stirred at room temperature overnight, and the reaction solution was poured into water (50 ml). The dichloromethane layer was washed with a dilute aqueous sodium hydrogencarbonate solution and was dried over anhydrous sodium sulfate. The solvent was removed by distillation under the reduced pressure, and the residue was purified by column chromatography using chloroform to give 2,2-dimethyl-N-pyridin-4-yl-propionamide (7.70 g, yield 87%).

2,2-Dimethyl-N-pyridin-4-yl-propionamide (5.60 g) was dissolved in tetrahydrofuran (70 ml) to prepare a solution which was then cooled to −78° C. A 1.57 M n-butyllithium/n-hexane solution (62 ml) was gradually added dropwise thereto, and the mixture was stirred at −78° C. for 15 min. The reaction solution was stirred at 0° C. for 4 hr and was then again cooled to −78° C. A solution of N,N-dimethylformamide (6.69 g) in tetrahydrofuran (7 ml) was gradually added dropwise thereto. The temperature of the reaction solution was raised to room temperature, the reaction solution was then poured into a mixture composed of ice (10 g) and 6 N hydrochloric acid (30 ml), and the mixture was stirred at room temperature for 15 min. The aqueous layer was neutralized with potassium carbonate powder and was extracted with diethyl ether. The diethyl ether layer was then washed with water and saturated brine and was dried over magnesium sulfate. The solvent was removed by distillation under the reduced pressure, and the residue was purified by column chromatography using acetone-chloroform to give N-(3-formyl-pyridin-4-yl)-2,2-dimethyl-propionamide (3.35 g, yield 52%).

N-(3-Formyl-pyridin-4-yl)-2,2-dimethyl-propionamide (3.35 g) was dissolved in 3 N hydrochloric acid (50 ml) to prepare a solution which was stirred under reflux for 5.5 hr. The reaction solution was cooled to room temperature, the reaction solution was then washed with diethyl ether and was neutralized with potassium carbonate powder. Diethyl ether was added thereto, and the mixture was extracted. The diethyl ether layer was dried over potassium carbonate. The solvent was removed by distillation under the reduced pressure, and the residue was purified by column chromatography using acetone-chloroform to give 4-amino-pyridine-3-carbaldehyde (1.12 g, yield 58%).

4-Amino-pyridine-3-carbaldehyde (1.0 g) and chloroacetone (0.7 g) were suspended in a 5 N aqueous sodium hydroxide solution (5 ml), and the suspension was allowed to stand in a sealed tube for 3 days. The reaction solution was neutralized with 10% hydrochloric acid, and the precipitated crystal was then collected by filtration. Isopropanol was added to the collected crystal, and the mixture was heated under reflux. The reaction solution was cooled to room temperature, and the solvent was then removed by distillation. Hexane was added to the residue, and the precipitated crystal was collected by filtration and was washed with hexane to give 2-methyl-[1,6]naphthyridin-3-ol (0.60 g, yield 46%).

2-Methyl-[1,6]naphthyridin-3-ol (20 mg), 4-chloro-6,7-dimethoxyquinoline (84 mg), and 4-dimethylaminopyridine (46 mg) were suspended in o-dichlorobenzene (2 ml), and the suspension was stirred at 140° C. for 3 hr. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using chloroform-methanol to give the title compound (23 mg, yield 55%).

$^1$H-NMR (CDCl$_3$, 400 MHz): δ 2.67 (s, 3H), 3.98 (s, 3H), 4.00 (s, 3H), 6.37 (d, J=5.2 Hz, 1H), 7.41 (s, 1H), 7.45 (s, 1H), 7.79 (s, 1H), 7.83 (d, J=6.0 Hz, 1H), 8.48 (d, J=5.2 Hz, 1H), 8.68 (d, J=6.0 Hz, 1H), 9.10 (s, 1H)

Mass spectrometric value (ESI-MS, m/z): 348 (M+1)$^+$

Compound 312: 1-[2-(7-Hydroxy-6-methoxy-quinolin-4-yloxy)-5-methoxy-phenyl]-ethanone 2-Hydroxy-5-methoxyacetophenone (3.00 g), 7-benzyloxy-4-chloro-6-methoxyquinoline (6.65 g), and 4-dimethylaminopyridine (4.90 g) were suspended in o-dichlorobenzene (30 ml), and the suspension was stirred at 180° C. for 2 hr. The reaction solution was cooled to room temperature, and the solvent was then removed by distillation under the reduced pressure. Water was added to the residue, and the mixture was extracted with chloroform. The chloroform layer was then washed with water and saturated brine and was dried over anhydrous magnesium sulfate. The solvent was removed by distillation under the reduced pressure, and the residue was purified by column chromatography using acetone-chloroform to give 1-[2-(7-benzyloxy-6-methoxy-quinolin-4-yloxy)-5-methoxy-phenyl]-ethanone (2.53 g, yield 59%).

1-[2-(7-Benzyloxy-6-methoxy-quinolin-4-yloxy)-5-methoxy-phenyl]-ethanone (2.52 g) was suspended in a mixed solution composed of methanesulfonic acid (3 ml) and trifluoroacetic acid (50 ml), and the suspension was stirred at 70° C. for 30 min. The solvent was removed by distillation under the reduced pressure, water was added to the residue, and the mixture was neutralized with sodium hydrogencarbonate powder and was then extracted with chloroform. The chloroform layer was then washed with water and saturated brine and was dried over anhydrous magnesium sulfate, the solvent was removed by distillation under the reduced pressure, and the residue was purified by column chromatography using chloroform-methanol to give the title compound (1.23 g, yield 62%).

$^1$H-NMR (DMSO-d$_6$, 400 MHz): δ 2.50 (s, 3H), 3.91 (s, 3H), 4.00 (s, 3H), 6.35 (d, J=5.2 Hz, 1H), 7.34 (m, 3H), 7.42 (s, 1H), 7.61 (s, 1H), 8.45 (d, J=5.2 Hz, 1H), 10.23 (brs, 1H)

Mass spectrometric value (ESI-MS, m/z): 338 (M−1)$^-$

Compound 313: 1-[2-(7-Benzyloxy-6-methoxy-quinolin-4-yloxy)-4,5-dimethyl-phenyl]-ethanone 2-Hydroxy-4,5-dimethylacetophenone (3.63 g), 7-benzyloxy-4-chloro-6-methoxyquinoline (1.50 g), and 4-dimethylaminopyridine (2.71 g) were suspended in o-dichlorobenzene (15 ml), and the suspension was stirred at 130° C. overnight. The reaction solution was cooled to room temperature, and the solvent was then removed by distillation under the reduced pressure. Water was added to the residue, and the mixture was extracted with chloroform, and the chloroform layer was then washed with water and saturated brine and was dried over anhydrous magnesium sulfate. The solvent was removed by distillation under the reduced pressure, and the residue was purified by column chromatography using acetone-hexane to give the title compound (1.10 g, yield 37%).

¹H-NMR (CDCl₃, 400 MHz): δ 2.23 (s, 3H), 2.26 (s, 3H), 2.43 (s, 3H), 3.98 (s, 3H), 5.24 (s, 2H), 6.35 (d, J=5.2 Hz, 1H), 6.87 (s, 1H), 7.22-7.36 (m, 3H), 7.47 (m, 3H), 7.54 (s, 1H), 7.68 (s, 1H), 8.42 (d, J=5.2 Hz, 1H)

Mass spectrometric value (ESI-MS, m/z): 428 (M+1)⁺

Compound 314: 1-[2-(7-Hydroxy-6-methoxy-quinolin-4-yloxy)-4,5-dimethyl-phenyl]-ethanone 1-[2-(7-Benzyloxy-6-methoxy-quinolin-4-yloxy)-4,5-dimethyl-phenyl]-ethanone (compound 313) (1.10 g) was suspended in a mixed solution composed of methanesulfonic acid (0.8 ml) and trifluoroacetic acid (10 ml), and the mixture was stirred at 70° C. for one hr. The solvent was removed by distillation under the reduced pressure, water was added to the residue, and the mixture was neutralized with sodium hydrogencarbonate powder and was then extracted with chloroform. Next, the chloroform layer was washed with water and saturated brine and was dried over anhydrous magnesium sulfate. The solvent was removed by distillation under the reduced pressure, and the residue was purified by column chromatography using chloroform-methanol to give the title compound (700 mg, yield 83%).

¹H-NMR (CDCl₃, 400 MHz): δ 2.29 (s, 3H), 2.33 (s, 3H), 2.45 (s, 3H), 3.98 (s, 3H), 6.35 (d, J=5.2 Hz, 1H), 7.70 (s, 1H), 7.52 (s, 1H), 7.56 (s, 1H), 7.72 (s, 1H), 8.45 (d, J=5.2 Hz, 1H)

Mass spectrometric value (ESI-MS, m/z): 336 (M−1)⁻

Compound 315: 1-{2-[7-(2-Chloro-ethoxy)-6-methoxy-quinolin-4-yloxy]-4,5-dimethyl-phenyl}-ethanone 1-[2-(7-Hydroxy-6-methoxy-quinolin-4-yloxy)-4,5-dimethyl-phenyl]-ethanone (compound 314) (150 mg), 1-bromo-2-chloroethane (191 mg), and potassium carbonate (307 mg) were suspended in N,N-dimethylformamide (6 ml). The mixture was stirred at room temperature overnight, water was added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by column chromatography using acetone-hexane to give the title compound (122 mg, 68%).

¹H-NMR (CDCl₃, 400 MHz): δ 2.22 (s, 3H), 2.25 (s, 3H), 2.39 (s, 3H), 3.88 (t, J=6.4 Hz, 2H), 3.95 (s, 3H), 4.38 (t, J=6.4 Hz, 2H), 6.33 (d, J=5.2 Hz, 1H), 6.85 (s, 1H), 7.35 (s, 1H), 7.50 (s, 1H), 7.64 (s, 1H), 8.42 (d, J=5.2 Hz, 1H)

Mass spectrometric value (ESI-MS, m/z): 400 (M+1)⁺

Compound 316: 1-{2-[6-Methoxy-7-(2-morpholin-4-yl-ethoxy)-quinolin-4-yloxy]-4,5-dimethyl-phenyl}-ethanone 1-{2-[7-(2-Chloro-ethoxy)-6-methoxy-quinolin-4-yloxy]-4,5-dimethyl-phenyl}-ethanone (compound 315) (52 mg), morpholine (34 mg), and potassium carbonate (90 mg) were suspended in N,N-dimethylformamide (2 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using chloroform-methanol to give the title compound (18 mg, 31%).

¹H-NMR (CDCl₃, 400 MHz): δ 2.22 (s, 3H), 2.26 (s, 3H), 2.40 (s, 3H), 2.57 (m, 4H), 2.88 (t, J=6.0 Hz, 2H), 3.68 (m, 4H), 3.94 (s, 3H), 4.26 (t, J=6.0 Hz, 2H), 6.32 (d, J=5.2 Hz, 1H), 6.85 (s, 1H), 7.36 (s, 1H), 7.49 (s, 1H), 7.65 (s, 1H), 8.41 (d, J=5.2 Hz, 1H)

Mass spectrometric value (ESI-MS, m/z): 451 (M+1)⁺

Compound 317: 1-{2-[7-(2-Imidazol-1-yl-ethoxy)-6-methoxy-quinolin-4-yloxy]-4,5-dimethyl-phenyl}-ethanone 1-{2-[7-(2-Chloro-ethoxy)-6-methoxy-quinolin-4-yloxy]-4,5-dimethyl-phenyl}-ethanone (compound 315) (52 mg), imidazole (27 mg), and potassium carbonate (90 mg) were suspended in N,N-dimethylformamide (2 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using chloroform-methanol to give the title compound (18 mg, 31%).

¹H-NMR (CDCl₃, 400 MHz): δ 2.22 (s, 3H), 2.25 (s, 3H), 2.39 (s, 3H), 3.95 (s, 3H), 4.34 (m, 2H), 4.40 (m, 2H), 6.32 (d, J=5.2 Hz, 1H), 6.85 (s, 1H), 7.00 (s, 1H), 7.07 (s, 1H), 7.29 (s, 1H), 7.49 (s, 1H), 7.64 (m, 2H), 8.40 (d, J=5.2 Hz, 1H)

Mass spectrometric value (ESI-MS, m/z): 432 (M+1)⁺

Compound 318: 1-{2-[7-(3-Chloro-propoxy)-6-methoxy-quinolin-4-yloxy]-4,5-dimethyl-phenyl}-ethanone 1-[2-(7-Hydroxy-6-methoxy-quinolin-4-yloxy)-4,5-dimethyl-phenyl]-ethanone (compound 314) (150 mg), 1-bromo-3-chloropropane (210 mg), and potassium carbonate (307 mg) were suspended in N,N-dimethylformamide (6 ml), and the mixture was stirred at room temperature overnight. Water was added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by column chromatography using acetone-hexane to give the title compound (174 mg, 94%).

¹H-NMR (CDCl₃, 400 MHz): δ 2.20 (s, 3H), 2.23 (s, 3H), 2.30 (m, 2H), 2.38 (s, 3H), 3.70 (t, J=6.4 Hz, 2H), 3.92 (s, 3H), 4.25 (t, J=6.4 Hz, 2H), 6.31 (d, J=5.2 Hz, 1H), 6.84 (s, 1H), 7.36 (s, 1H), 7.47 (s, 1H), 7.63 (s, 1H), 8.40 (d, J=5.2 Hz, 1H)

Mass spectrometric value (ESI-MS, m/z): 414 (M+1)⁺

Compound 319: 1-{2-[6-Methoxy-7-(3-morpholin-4-yl-propoxy)-quinolin-4-yloxy]-4,5-dimethyl-phenyl}-ethanone 1-{2-[7-(3-Chloro-propoxy)-6-methoxy-quinolin-4-yloxy]-4,5-dimethyl-phenyl}-ethanone (compound 318) (77 mg), morpholine (49 mg), and potassium carbonate (131 mg) were suspended in N,N-dimethylformamide (2 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by column chromatography using chloroform-methanol to give the title compound (60 mg, 68%).

$^1$H-NMR (CDCl$_3$, 400 MHz): δ 2.05 (m, 2H), 2.21 (s, 3H), 2.25 (s, 3H), 2.41 (m, 7H), 2.50 (t, J=7.2 Hz, 2H), 3.64 (m, 4H), 3.94 (s, 3H), 4.22 (t, J=6.8 Hz, 2H), 6.32 (d, J=5.2 Hz, 1H), 6.85 (s, 1H), 7.35 (s, 1H), 7.47 (s, 1H), 7.64 (s, 1H), 8.40 (d, J=5.2 Hz, 1H)

Mass spectrometric value (ESI-MS, m/z): 465 (M+1)$^+$

Compound 320: 1-{2-[6-Methoxy-7-(3-morpholin-4-yl-propoxy)-quinolin-4-yloxy]-4,5-dimethyl-phenyl}-ethanone hydrochloride 1-{2-[6-Methoxy-7-(3-morpholin-4-yl-propoxy)-quinolin-4-yloxy]-4,5-dimethyl-phenyl}-ethanone (compound 319) (344 mg) was dissolved in a hydrochloric acid-methanol solution (10 ml), and the solution was stirred at room temperature overnight. The solvent was removed by distillation under the reduced pressure, and the residue was washed with ethyl acetate and was dried under the reduced pressure to give the title compound (398 mg, yield 100%).

$^1$H-NMR (CD$_3$OD, 400 MHz): δ 2.25-2.55 (m, 11H), 3.22 (m, 2H), 3.49 (m, 2H), 3.67 (d, J=12.0 Hz, 2H), 3.86 (t, J=12.0 Hz, 2H), 4.02-4.18 (m, 5H), 4.47 (m, 2H), 6.76 (d, J=5.2 Hz, 1H), 7.22 (s, 1H), 7.52 (s, 1H), 7.84 (s, 1H), 7.92 (s, 1H), 8.60 (d, J=5.2 Hz, 1H)

Mass spectrometric value (ESI-MS, m/z): 465 (M+1-2HCl)$^+$

Compound 321: 1-{2-[7-(3-Imidazol-1-yl-propoxy)-6-methoxy-quinolin-4-yloxy]-4,5-dimethyl-phenyl}-ethanone 1-{2-[7-(3-Chloro-propoxy)-6-methoxy-quinolin-4-yloxy]-4,5-dimethyl-phenyl}-ethanone (compound 318) (77 mg), imidazole (38 mg), and potassium carbonate (131 mg) were suspended in N,N-dimethylformamide (2 ml), and the suspension was stirred at 80° C. overnight. The reaction solution was cooled to room temperature, water was then added to the reaction solution, and the mixture was extracted with ethyl acetate. The ethyl acetate layer was then washed with water and saturated brine and was dried over anhydrous sodium sulfate. The solvent was removed by distillation under the reduced pressure, and the residue was purified by thin layer chromatography using chloroform-methanol to give the title compound (52 mg, 61%).

$^1$H-NMR (CDCl$_3$, 400 MHz): δ 2.22 (s, 3H), 2.25 (s, 3H), 2.30 (m, 2H), 2.41 (s, 3H), 3.97 (s, 3H), 4.07 (t, J=6.4 Hz, 2H), 4.21 (t, J=6.4 Hz, 2H), 6.32 (d, J=5.2 Hz, 1H), 6.85 (s, 1H), 6.88 (s, 1H), 6.97 (s, 1H), 7.30 (s, 1H), 7.44 (s, 1H), 7.50 (s, 1H), 7.65 (s, 1H), 8.40 (d, J=5.2 Hz, 1H)

Mass spectrometric value (ESI-MS, m/z): 446 (M+1)$^+$

Compound 322: Propyl 3-[7-(2-chloro-ethoxy)-6-methoxy-quinolin-4-yloxy]-naphthalene-2-carboxylate 3-Hydroxy-naphthalene-2-carboxylic acid (2 g) was dissolved in 1-propanol (10 ml) to prepare a solution which was then brought to 0° C. Thionyl chloride (1.16 ml) was gradually added dropwise to the solution, and the mixture was stirred at 120° C. for 2 hr. The reaction solution was cooled to room temperature, and the solvent was removed by distillation under the reduced pressure. Water was then added to the residue, and the mixture was extracted with chloroform. The chloroform layer was washed with saturated brine and was dried over anhydrous sodium sulfate. The solvent was removed by distillation under the reduced pressure, and the residue was purified by column chromatography using chloroform to give propyl 3-hydroxy-naphthalene-2-carboxylate (2.15 g, yield 88%).

Propyl 3-hydroxy-naphthalene-2-carboxylate (460 mg), 7-benzyloxy-4-chloro-6-methoxyquinoline (200 mg), and 4-dimethylaminopyridine (244 mg) were suspended in o-dichlorobenzene (4 ml), and the mixture was stirred at 120° C. for 5 hr. The reaction solution was cooled to room temperature, water was then added to the reaction solution, and the mixture was extracted with chloroform. The chloroform layer was washed with saturated brine and was dried over anhydrous sodium sulfate, the solvent was removed by distillation under the reduced pressure, and the residue was purified by thin layer chromatography using chloroform-acetone to give propyl 3-(7-benzyloxy-6-methoxy-quinolin-4-yloxy)-naphthalene-2-carboxylate (165 mg, yield 50%).

Propyl 3-(7-benzyloxy-6-methoxy-quinolin-4-yloxy) naphthalene-2-carboxylate (160 mg) was dissolved in trifluoroacetic acid (1.5 ml) to prepare a solution. Methanesulfonic acid (0.15 ml) was added to the solution, and the mixture was stirred at 70° C. for one hr. The reaction solution was cooled to room temperature, and the solvent was removed by distillation under the reduced pressure. An aqueous sodium hydrogencarbonate solution was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give propyl 3-(7-hydroxy-6-methoxy-quinolin-4-yloxy)-naphthalene-2-carboxylate (87 mg, yield 68%).

Propyl 3-(7-hydroxy-6-methoxy-quinolin-4-yloxy)-naphthalene-2-carboxylate (80 mg) and 1-bromo-2-chloroethane (0.082 ml) were dissolved in N,N-dimethylformamide (2 ml) to prepare a solution. Potassium carbonate (274 mg) was added to the solution, and the mixture was stirred at room temperature overnight. Water was then added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by column chromatography using acetone-chloroform to give the title compound (85 mg, yield 91%).

$^1$H-NMR (CDCl$_3$, 400 MHz): δ 0.71 (t, J=7.3 Hz, 3H), 1.26-1.38 (m, 2H), 3.97-4.05 (m, 4H), 4.07 (s, 3H), 4.50 (t, J=6.1 Hz, 2H), 6.37 (d, J=5.4 Hz, 1H), 7.52-7.70 (m, 5H), 7.84 (d, J=8.3 Hz, 1H), 8.02 (d, J=8.1 Hz, 1H), 8.44 (d, J=5.4 Hz, 1H), 8.67 (s, 1H)

Mass spectrometric value (ESI-MS, m/z): 466 (M+1)$^+$

Compound 323: Propyl 3-[6-methoxy-7-(2-morpholin-4-yl-ethoxy)-quinolin-4-yloxy]-naphthalene-2-carboxylate Propyl 3-[7-(2-chloro-ethoxy)-6-methoxy-quinolin-4-yloxy]-naphthalene-2-carboxylate (compound 322) (80 mg) was dissolved in N,N-dimethylformamide (2 ml) to prepare a solution. Potassium carbonate (484 mg) and morpholine (0.15 ml) were added to the solution, and the mixture was stirred at 60° C. for 2 days. The reaction solution was cooled to room temperature, water was then added thereto, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using hexane-acetone to give the title compound (52 mg, yield 59%).

$^1$H-NMR (CDCl$_3$, 400 MHz): δ 0.70-0.73 (m, 3H), 1.30-1.39 (m, 2H), 2.69 (s, 4H), 2.98-3.01 (m, 2H), 3.79 (t, J=4.6 Hz, 4H), 4.02-4.04 (m, 2H), 4.05 (s, 3H), 4.40 (t, J=5.9 Hz, 2H), 6.36 (d, J=5.6 Hz, 1H), 7.52-7.68 (m, 5H), 7.84 (d, J=8.1 Hz, 1H), 8.02 (d, J=8.3 Hz, 1H), 8.43 (d, J=5.4 Hz, 1H), 8.67 (s, 1H)

Mass spectrometric value (ESI-MS, m/z): 517 (M+1)$^+$

Compound 324: Propyl 3-[7-(2-imidazol-1-yl-ethoxy)-6-methoxy-quinolin-4-yloxy]-naphthalene-2-carboxylate Propyl 3-[7-(2-chloro-ethoxy)-6-methoxy-quinolin-4-yloxy]-naphthalene-2-carboxylate (compound 322) (138 mg) was dissolved in N,N-dimethylformamide (2 ml) to prepare a solution. Potassium carbonate (274 mg) and imidazole (101 mg) were added to the solution, and the mixture was stirred at 60° C. overnight. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was pufified by thin layer chromatography using chloroform-methanol to give the title compound (105 mg, yield 70%).

$^1$H-NMR (CDCl$_3$, 400 MHz): δ 0.71 (t, J=7.6 Hz, 3H), 1.30-1.39 (m, 2H), 4.04 (t, J=6.6 Hz, 2H), 4.07 (s, 3H), 4.45-4.51 (m, 4H), 6.37 (d, J=5.4 Hz, 1H), 7.10 (s, 1H), 7.17 (s, 1H), 7.52 (s, 1H), 7.58-7.69 (m, 4H), 7.76 (s, 1H), 7.84 (d, J=8.1 Hz, 1H), 8.02 (d, J=8.1 Hz, 1H), 8.42 (d, J=5.6 Hz, 1H), 8.67 (s, 1H)

Mass spectrometric value (ESI-MS, m/z): 498 (M+1)$^+$

Compound 325: Propyl 3-[7-(3-chloro-propoxy)-6-methoxy-quinolin-4-yloxy]-naphthalene-2-carboxylate Propyl 3-(7-hydroxy-6-methoxy-quinolin-4-yloxy)-naphthalene-2-carboxylate (240 mg) was dissolved in N,N-dimethylformamide (6 ml) to prepare a solution. Potassium carbonate (822 mg) and 1-bromo-3-chloropropane (0.29 ml) were added to the solution, and the mixture was stirred at room temperature overnight. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using acetone-chloroform to give the title compound (230 mg, yield 81%).

$^1$H-NMR (CDCl$_3$, 400 MHz): δ 0.71 (t, J=7.3 Hz, 3H), 1.30-1.39 (m, 2H), 2.39-2.45 (m, 2H), 3.83 (t, J=6.3 Hz, 2H), 4.02-4.04 (m, 2H), 4.05 (s, 3H), 4.39 (t, J=6.1 Hz, 2H), 6.35 (d, J=5.6 Hz, 1H), 7.56-7.68 (m, 5H), 7.84 (d, J=8.1 Hz, 1H), 8.02 (d, J=8.1 Hz, 1H), 8.43 (d, J=5.4 Hz, 1H), 8.67 (s, 1H)

Mass spectrometric value (ESI-MS, m/z): 480 (M+1)$^+$

Compound 326: Propyl 3-[6-methoxy-7-(3-morpholin-4-yl-propoxy)-quinolin-4-yloxy]-naphthalene-2-carboxylate Propyl 3-[7-(3-chloro-propoxy)-6-methoxy-quinolin-4-yloxy]-naphthalene-2-carboxylate (compound 325) (110 mg) was dissolved in N,N-dimethylformamide (3 ml) to prepare a solution. Potassium carbonate (317 mg) and morpholine (0.1 ml) were added to the solution, and the mixture was stirred at 60° C. overnight. Water was added to the reaction solution, the mixture was extracted with chloroform, and the chloroform layer was then washed with saturated brine and was dried over anhydrous sodium sulfate. The solvent was removed by distillation under the reduced pressure, and the residue was pufified by thin layer chromatography using chloroform-methanol to give the title compound (106 mg, yield 87%).

$^1$H-NMR (CDCl$_3$, 400 MHz): δ 0.70 (t, J=7.6 Hz, 3H), 1.29-1.38 (m, 2H), 2.17-2.20 (m, 2H), 2.56-2.65 (m, 6H), 3.76-3.78 (m, 4H), 4.02-4.03 (m, 2H), 4.05 (s, 3H), 4.30 (t, J=6.6 Hz, 2H), 6.33 (d, J=5.4 Hz, 1H), 7.50 (s, 1H), 7.57-7.67 (m, 4H), 7.83 (d, J=7.8 Hz, 1H), 8.02 (d, J=8.1 Hz, 1H), 8.43 (d, J=5.4 Hz, 1H), 8.66 (s, 1H)

Mass spectrometric value (ESI-MS, m/z): 531 (M+1)$^+$

Compound 327: Propyl 3-[7-(3-imidazol-1-yl-propoxy)-6-methoxy-quinolin-4-yloxy]-naphthalene-2-carboxylate Propyl 3-[7-(3-chloro-propoxy)-6-methoxy-quinolin-4-yloxy]-naphthalene-2-carboxylate (compound 325) (110 mg) was dissolved in N,N-dimethylformamide (3 ml) to prepare a solution. Potassium carbonate (317 mg) and imidazole (78 mg) were added to the solution, and the mixture was stirred at 60° C. overnight. Water was added to the reaction solution, and the mixture was extracted with chloroform. The chloroform layer was then washed with saturated brine and was dried over anhydrous sodium sulfate. The solvent was removed by distillation under the reduced pressure, and the residue was purified by thin layer chromatography using chloroform-methanol to give the title compound (97 mg, yield 82%).

$^1$H-NMR (CDCl$_3$, 400 MHz): δ 0.73 (t, J=7.6 Hz, 3H), 1.32-1.41 (m, 2H), 2.38-2.44 (m, 2H), 4.05 (t, J=6.6 Hz, 2H), 4.08 (s, 3H), 4.19 (t, J=5.9 Hz, 2H), 4.29 (t, J=6.8 Hz, 2H), 6.36 (d, J=5.6 Hz, 1H), 6.98 (s, 1H), 7.08 (s, 1H), 7.50 (s, 1H), 7.57-7.70 (m, 5H), 7.84 (d, J=8.1 Hz, 1H), 8.02 (d, J=8.3 Hz, 1H), 8.43 (d, J=5.6 Hz, 1H), 8.67 (s, 1H)

Mass spectrometric value (ESI-MS, m/z): 512 (M+1)$^+$

Compound 328: 7-Benzyloxy-6-methoxy-4-(6-methyl-2-thiazol-2-yl-pyridin-3-yloxy)-quinoline 2-Iodo-6-picolin-3-ol (10 g), 4-chloro-7-benzyloxy-6-methoxyquinoline (6.8 g), and 4-(N,N-dimethylamino)-pyridine (12.2 g) were dissolved in 1,2-dichlorobenzene (400 ml) to prepare a solution, and the mixture was stirred at 125° C. overnight. The reaction solution was cooled to room temperature, and the solvent was then removed by distillation under the reduced pressure. Water was added to the residue, the mixture was extracted with chloroform, and the chloroform layer was then washed with water and was dried over anhydrous sodium sulfate. The solvent was removed by distillation under the reduced pressure. The residue was purified by column chromatography using chloroform-acetone to give 7-benzyloxy-4-(2-iodo-6-methyl-pyridin-3-yloxy)-6-methoxy-quinoline (5.2 g, yield 31%).

N,N-Dimethylformamide (2 ml) was added to 7-benzyloxy-4-(2-iodo-6-methyl-pyridin-3-yloxy)-6-methoxyquinoline (100 mg), tetrakistriphenylphosphine palladium (23 mg), tri-n-butyl-(thiazol-2-yl)-tin (113 mg), and copper (II) oxide (32 mg) under an argon atmosphere, and the mixture was stirred at 100° C. overnight. The reaction solution was cooled to room temperature, water was then added thereto, and the mixture was extracted with ethyl acetate. The ethyl acetate layer was then washed with water and was dried over anhydrous sodium sulfate. The solvent was removed by distillation under the reduced pressure, and the residue was purified by column chromatography using hexane-acetone to give the title compound (43 mg, yield 46%).

$^1$H-NMR (CDCl$_3$, 400 MHz): δ 2.63 (s, 3H), 3.96 (s, 3H), 5.25 (s, 2H), 6.29 (d, J=5.4 Hz, 1H), 7.17-7.48 (m, 9H), 7.62 (s, 1H), 7.74 (d, J=3.2 Hz, 1H), 8.34 (d, J=5.4 Hz, 1H)

Mass spectrometric value (ESI-MS, m/z): 478 (M+Na)$^+$

Compound 329: 6-Methoxy-4-(6-methyl-2-thiazol-2-yl-pyridin-3-yloxy)-quinolin-7-ol Trifluoroacetic acid (1 ml) and methanesulfonic acid (0.1 ml) were added to 7-benzyloxy-6-methoxy-4-(6-methyl-2-thiazol-2-yl-pyridin-3-yloxy)-quinoline (compound 328) (40 mg), and the mixture was stirred at 80° C. for 1.5 hr. The reaction solution was cooled to room temperature, and a saturated aqueous sodium hydrogencarbonate solution was then added to the reaction solution. The mixture was made alkaline, and the mixture was then extracted with chloroform. The chloroform layer was washed with water and was dried over anhydrous sodium sulfate. The solvent was removed by distillation under the reduced pressure, and the residue was purified by thin layer chromatography using chloroform-methanol to give the title compound (23 mg, yield 70%).

$^1$H-NMR (CDCl$_3$, 400 MHz): δ 2.70 (s, 3H), 4.06 (s, 3H), 6.35 (d, J=5.4 Hz, 1H), 7.28 (d, J=8.3 Hz, 1H), 7.34 (d, J=3.2 Hz, 1H), 7.48 (d, J=8.3 Hz, 1H), 7.57 (s, 1H), 7.69 (s, 1H), 7.79 (d, J=3.2 Hz, 1H), 8.43 (d, J=5.4 Hz, 1H)

Mass spectrometric value (ESI-MS, m/z): 388 (M+Na)$^+$

Compound 330: 2-[6-Methoxy-4-(6-methyl-2-thiazol-2-yl-pyridin-3-yloxy)-quinolin-7-yloxymethyl]-propane-1,3-diol A solution of 2-methoxypropene (1 g) in N,N-dimethylformamide (150 ml) was added to 2-(hydroxymethyl)-1,3-propanediol (500 mg). p-Toluenesulfonic acid (10 mg) was added thereto, and the mixture was stirred at room temperature overnight. The solvent was removed by distillation under the reduced pressure, water was added to the residue, and the mixture was extracted with n-butanol. The n-butanol layer was then washed with water and was dried over anhydrous sodium sulfate. The solvent was removed by distillation under the reduced pressure, and the residue was purified by column chromatography using hexane-acetone to give (2,2-dimethyl[1,3]dioxan-5-yl)-methanol (378 mg, yield 55%).

Toluene (0.4 ml) was added to 6-methoxy-4-(6-methyl-2-thiazol-2-yl-pyridin-3-yloxy)-quinolin-7-ol (compound 329) (20 mg) and (2,2-dimethyl[1,3]dioxan-5-yl)-methanol (24 mg). Triphenylphosphine (43 mg) and a solution of diethylazocarbodiimide (29 mg) in toluene (0.2 ml) were added in that order to the mixture, and the mixture was stirred at room temperature for 4 hr. A 1 N aqueous sulfuric acid solution (1 ml) was added to the reaction solution, and the mixture was stirred at room temperature overnight. Water was added to the reaction solution, the mixture was washed with ethyl acetate, and the ethyl acetate layer was extracted with 1 N hydrochloric acid. Aqueous layers were combined, the combined aqueous layers were made alkaline by the addition of potassium carbonate, and the mixture was extracted with ethyl acetate. The ethyl acetate layer was washed with water and was dried over anhydrous sodium sulfate. The solvent was removed by distillation under the reduced pressure, and the residue was purified by thin layer chromatography using chloroform-methanol to give the title compound (4.7 mg, yield 19%).

$^1$H-NMR (CDCl$_3$, 400 MHz): δ 2.34-2.47 (m, 1H), 2.63 (s, 3H), 3.96-4.05 (m, 7H), 4.41 (d, J=5.6 Hz, 2H), 6.38 (d, J=5.1 Hz, 1H), 7.30 (d, J=8.3 Hz, 1H), 7.36 (d, J=3.2 Hz, 1H), 7.47 (s, 1H), 7.50 (d, J=8.6 Hz, 1H), 7.67 (s, 1H), 7.81 (d, J=3.2 Hz, 1H), 8.43 (d, J=5.1 Hz, 1H)

Mass spectrometric value (ESI-MS, m/z): 454 (M+1)$^+$

Compound 331: 7-Benzyloxy-4-(5,6-dimethyl-2-phenyl-pyridin-3-yloxy)-6-methoxy-quinoline 5,6-Dimethyl-2-phenyl-pyridin-3-ol (400 mg), 7-benzyloxy-4-chloro-6-methoxyquinoline (1.81 g), and 4-dimethylaminopyridine (736 mg) were suspended in o-dichlorobenzene (10 ml), and the suspension was stirred at 140° C. for 4 hr. The reaction solution was cooled to room temperature, water was then added to the reaction solution, and the mixture was extracted with chloroform. The chloroform layer was washed with saturated brine and was dried over anhydrous sodium sulfate. The solvent was removed by distillation under the reduced pressure, and the residue was purified by column chromatography using chloroform-methanol to give the title compound (965 mg, yield 100%).

$^1$H-NMR (CDCl$_3$, 400 MHz): δ 2.35 (s, 3H), 2.62 (s, 3H), 4.02 (s, 3H), 5.31 (s, 2H), 6.37 (d, J=5.4 Hz, 1H), 7.25-7.52 (m, 11H), 7.82-7.85 (m, 2H), 8.40 (d, J=5.4 Hz, 1H)

Mass spectrometric value (ESI-MS, m/z): 463 (M+1)$^+$

Compound 332: 4-(5,6-Dimethyl-2-phenyl-pyridin-3-yloxy)-6-methoxy-quinolin-7-ol 7-Benzyloxy-4-(5,6-dimethyl-2-phenyl-pyridin-3-yloxy)-6-methoxy-quinoline (compound 331) (958 mg) was dissolved in trifluoroacetic acid (9.5 ml) to prepare a solution. Methanesulfonic acid (0.95 ml) was added to the solution, and the mixture was stirred at 70° C. for one hr. The reaction solution was cooled to room temperature, and the solvent was removed by distillation under the reduced pressure. An aqueous sodium hydrogencarbonate solution was then added to the residue, and the mixture was extracted with chloroform. The chloroform layer was washed with saturated brine and was dried over anhydrous sodium sulfate. The solvent was removed by distillation under the reduced pressure, and the residue was purified by column chromatography using chloroform-methanol to give the title compound (848 mg, yield 100%).

$^1$H-NMR (CDCl$_3$, 400 MHz): δ 2.35 (s, 3H), 2.62 (s, 3H), 4.04 (s, 3H), 6.37 (d, J=5.1 Hz, 1H), 7.25-7.31 (m, 4H), 7.52 (d, J=4.4 Hz, 2H), 7.82-7.85 (m, 2H), 8.44 (d, J=5.1 Hz, 1H)

Mass spectrometric value (ESI-MS, m/z): 373 (M+1)$^+$

Compound 333: 2-[4-(5,6-Dimethyl-2-phenyl-pyridin-3-yloxy)-6-methoxy-quinolin-7-yloxy]-ethanol 4-(5,6-Dimethyl-2-phenyl-pyridin-3-yloxy)-6-methoxy-quinolin-7-ol (compound 332) (162 mg) was dissolved in N,N-dimethylformamide (3 ml) to prepare a solution. Potassium carbonate (180 mg) and 2-bromoethanol (0.1 ml) were added to the solution, and the mixture was stirred at 70° C. overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (135 mg, yield 76%).

¹H-NMR (CDCl₃, 400 MHz): δ 2.36 (s, 3H), 2.63 (s, 3H), 4.00 (s, 3H), 4.09 (t, J=4.4 Hz, 2H), 4.29 (t, J=4.9 Hz, 2H), 6.39 (d, J=5.4 Hz, 1H), 7.24-7.29 (m, 4H), 7.44 (s, 1H), 7.51 (s, 1H), 7.82-7.85 (m, 2H), 8.42 (d, J=5.4 Hz, 1H)

Mass spectrometric value (ESI-MS, m/z): 417 (M+1)⁺

Compound 334: 4-(5,6-Dimethyl-2-phenyl-pyridin-3-yloxy)-6-methoxy-7-oxiranylmethoxy-quinoline 4-(5,6-Dimethyl-2-phenyl-pyridin-3-yloxy)-6-methoxy-quinolin-7-ol (compound 332) (150 mg) was dissolved in N,N-dimethylformamide (4 ml) to prepare a solution, potassium carbonate (167 mg) and epibromohydrin (0.1 ml) were added to the solution, and the mixture was stirred at room temperature overnight. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (140 mg, yield 82%).

¹H-NMR (CDCl₃, 400 MHz): δ 2.35 (s, 3H), 2.62 (s, 3H), 2.84 (dd, J=2.7 Hz, 4.9 Hz, 1H), 2.95-2.97 (m, 1H), 3.48-3.52 (m, 1H), 4.01 (s, 3H), 4.17 (dd, J=5.6 Hz, 11.2 Hz, 1H), 4.42 (dd, J=3.2 Hz, 11.2 Hz, 1H), 6.38 (d, J=5.1 Hz, 1H), 7.22-7.30 (m, 4H), 7.41 (s, 1H), 7.51 (s, 1H), 7.82-7.85 (m, 2H), 8.42 (d, J=5.1 Hz, 1H)

Mass spectrometric value (ESI-MS, m/z): 429 (M+1)⁺

Compound 335: 3-[4-(5,6-Dimethyl-2-phenyl-pyridin-3-yloxy)-6-methoxy-quinolin-7-yloxy]-propane-1,2-diol 4-(5,6-Dimethyl-2-phenyl-pyridin-3-yloxy)-6-methoxy-7-oxiranylmethoxy-quinoline (compound 334) (130 mg) was dissolved in methylene chloride (2 ml) to prepare a solution which was then brought to 0° C. Trifluoroacetic acid (1 ml) was added to the solution, and the mixture was stirred at 0° C. for 30 min and was then stirred at room temperature for 3 hr. The reaction solution was brought to 0° C., was stirred, and was made alkaline by the addition of a 10% aqueous sodium hydroxide solution. Water was added to the reaction solution, and the mixture was extracted with chloroform. The chloroform layer was then washed with saturated brine and was dried over anhydrous sodium sulfate. The solvent was removed by distillation under the reduced pressure, and the residue was purified by thin layer chromatography using chloroform-methanol to give the title compound (89 mg, yield 66%).

¹H-NMR (CD₃OD, 400 MHz): δ 2.41 (s, 3H), 2.60 (s, 3H), 3.69-3.78 (m, 2H), 3.99 (s, 3H), 4.08-4.16 (m, 2H), 4.21-4.25 (m, 1H), 6.38 (d, J=5.4 Hz, 1H), 7.24-7.31 (m, 4H), 7.56 (d, J=3.4 Hz, 2H), 7.69-7.72 (m, 2H), 8.30 (d, J=5.4 Hz, 1H)

Mass spectrometric value (ESI-MS, m/z): 447 (M+1)⁺

Compound 336: 2-[4-(5,6-Dimethyl-2-phenyl-pyridin-3-yloxy)-6-methoxy-quinolin-7-yloxymethyl]-propane-1,3-diol 4-(5,6-Dimethyl-2-phenyl-pyridin-3-yloxy)-6-methoxy-quinolin-7-ol (compound 332) (85 mg) was dissolved in tetrahydrofuran (2 ml) to prepare a solution. Triphenylphosphine (120 mg), (2,2-dimethyl-[1,3]dioxan-5-yl)-methanol (40 mg), and diethylazodicarboxylic acid (0.083 ml) were added to the solution, and the mixture was stirred at room temperature for 4 hr. Further, 1 N sulfuric acid (4 ml) was added thereto, and the mixture was stirred at room temperature overnight. The reaction solution was brought to 0° C., was stirred, and was made alkaline by the addition of a 10% aqueous sodium hydroxide solution. Water was added thereto, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (80 mg, yield 76%).

¹H-NMR (CDCl₃, 400 MHz): δ 2.35-2.40 (m, 4H), 2.63 (s, 3H), 3.94-4.02 (m, 7H), 4.38 (d, J=5.6 Hz, 2H), 6.38 (d, J=5.4 Hz, 1H), 7.22-7.30 (m, 4H), 7.43 (s, 1H), 7.47 (s, 1H), 7.82-7.84 (m, 2H), 8.41 (d, J=5.4 Hz, 1H)

Mass spectrometric value (ESI-MS, m/z): 461 (M+1)⁺

Compound 337: 3-(7-Benzyloxy-6-methoxy-quinolin-4-yloxy)-5,6-dimethyl-[2,2']bipyridine 5,6-Dimethyl-3-hydroxy-[2,2']bipyridine (241 mg), 7-benzyloxy-4-chloro-6-methoxyquinoline (1.08 g), 4-dimethylaminopyridine (441 mg), and cesium carbonate (1.18 g) were suspended in dimethyl sulfoxide (6 ml), and the mixture was stirred at 130° C. overnight. The reaction solution was cooled to room temperature, water was then added to the reaction solution, and the mixture was extracted with chloroform. The chloroform layer was washed with saturated brine and was dried over anhydrous sodium sulfate. The solvent was removed by distillation under the reduced pressure, and the residue was purified by column chromatography using chloroform-methanol to give the title compound (408 mg, yield 73%).

¹H-NMR (CDCl₃, 400 MHz): δ 2.38 (s, 3H), 2.66 (s, 3H), 4.02 (s, 3H), 5.31 (s, 2H), 6.37 (d, J=5.4 Hz, 1H), 7.10-7.13 (m, 1H), 7.25-7.61 (m, 9H), 7.80 (d, J=7.8 Hz, 1H), 8.37 (d, J=5.4 Hz, 1H), 8.51 (d, J=4.4 Hz, 1H)

Mass spectrometric value (ESI-MS, m/z): 464 (M+1)⁺

Compound 338: 4-(5,6-Dimethyl-[2,2']bipyridin-3-yloxy)-6-methoxy-quinolin-7-ol 3-(7-Benzyloxy-6-methoxy-quinolin-4-yloxy)-5,6-dimethyl-[2,2']bipyridine (compound 337) (497 mg) was dissolved in trifluoroacetic acid (5 ml) to prepare a solution. Methanesulfonic acid (0.5 ml) was added to the solution, and the mixture was stirred at 70° C. for 1.5 hr. The reaction solution was cooled to room temperature, and the solvent was removed by distillation under the reduced pressure. An aqueous sodium hydrogencarbonate solution was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (437 mg, yield 100%).

¹H-NMR (CDCl₃, 400 MHz): δ 2.38 (s, 3H), 2.65 (s, 3H), 4.05 (s, 3H), 6.36 (d, J=5.4 Hz, 1H), 7.11-7.14 (m, 1H), 7.35 (s, 1H), 7.52 (s, 1H), 7.57-7.62 (m, 2H), 7.78-7.81 (m, 1H), 8.40 (d, J=5.4 Hz, 1H), 8.49-8.52 (m, 1H)

Mass spectrometric value (ESI-MS, m/z): 374 (M+1)⁺

Compound 339: 2-[4-(5,6-Dimethyl-[2,2']bipyridin-3-yloxy)-6-methoxy-quinolin-7-yloxy]-ethanol 4-(5,6-Dimethyl-[2,2']bipyridin-3-yloxy)-6-methoxy-quinolin-7-ol (compound 338) (80 mg) was dissolved in N,N-dimethylformamide (2 ml) to prepare a solution. Potassium carbonate (89 mg) and 2-bromoethanol (0.05 ml) were added to the solution, and the mixture was stirred at 70° C. overnight. The solvent was removed by distillation under the reduced pressure, water was then added to the residue, and the mixture was extracted with chloroform. The chloroform layer was washed with saturated brine and was dried over anhydrous sodium sulfate, the solvent was removed by distillation under the reduced pressure, and the residue was purified by thin layer chromatography using chloroform-methanol to give the title compound (77 mg, yield 88%).

$^1$H-NMR (CDCl$_3$, 400 MHz): δ 2.39 (s, 3H), 2.66 (s, 3H), 4.00 (s, 3H), 4.08 (t, J=4.4 Hz, 2H), 4.29 (t, J=4.6 Hz, 2H), 6.38 (dd, J=0.5 Hz, 5.4 Hz, 1H), 7.10-7.13 (m, 1H), 7.37 (s, 1H), 7.43 (s, 1H), 7.56 (s, 1H), 7.57-7.61 (m, 1H), 7.81 (dd, J=1.0 Hz, 8.1 Hz, 1H), 8.39 (d, J=5.4 Hz, 1H), 8.48-8.49 (m, 1H)

Mass spectrometric value (ESI-MS, m/z): 418 (M+1)$^+$

Compound 340: 3-[4-(5,6-Dimethyl-[2,2']bipyridin-3-yloxy)-6-methoxy-quinolin-7-yloxy]-propan-1-ol 4-(5,6-Dimethyl-[2,2']bipyridin-3-yloxy)-6-methoxy-quinolin-7-ol (compound 338) (45 mg) was suspended in N,N-dimethylformamide (5 ml), potassium carbonate (50 mg) and 3-bromo-1-propanol (0.03 ml) were added to the suspension, and the mixture was stirred at room temperature overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (22 mg, yield 42%).

$^1$H-NMR (CDCl$_3$, 400 MHz): δ 2.16-2.22 (m, 2H), 2.39 (s, 3H), 2.66 (s, 3H), 3.93 (t, J=5.4 Hz, 2H), 4.00 (s, 3H), 4.38 (t, J=6.1 Hz, 2H), 6.38 (d, J=5.4 Hz, 1H), 7.10-7.13 (m, 1H), 7.37 (s, 1H), 7.44 (s, 1H), 7.54 (s, 1H), 7.57-7.61 (m, 1H), 7.81 (d, J=7.8 Hz, 1H), 8.38 (d, J=5.4 Hz, 1H), 8.47-8.49 (m, 1H)

Mass spectrometric value (ESI-MS, m/z): 432 (M+1)$^+$

Compound 341: 3-(6-Methoxy-7-oxiranylmethoxy-quinolin-4-yloxy)-5,6-dimethyl-[2,2']bipyridine 4-(5,6-Dimethyl-[2,2']bipyridin-3-yloxy)-6-methoxy-quinolin-7-ol (compound 338) (97 mg) was dissolved in N,N-dimethylformamide (4 ml), potassium carbonate (107 mg) and epibromohydrin (0.07 ml) were added to the solution, and the mixture was stirred at room temperature overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (99 mg, yield 89%).

$^1$H-NMR (CDCl$_3$, 400 MHz): δ 2.39 (s, 3H), 2.66 (s, 3H), 2.84 (dd, J=2.4 Hz, 4.9 Hz, 1H), 2.95-2.97 (m, 1H), 3.48-3.52 (m, 1H), 4.02 (s, 3H), 4.17 (dd, J=5.6 Hz, 11.2 Hz, 1H), 4.43 (dd, J=3.2 Hz, 11.2 Hz, 1H), 6.38 (d, J=5.1 Hz, 1H), 7.10-7.13 (m, 1H), 7.37 (s, 1H), 7.41 (s, 1H), 7.56 (s, 1H), 7.56-7.61 (m, 1H), 7.80 (d, J=8.1 Hz, 1H), 8.39 (d, J=5.4 Hz, 1H), 8.48-8.50 (m, 1H)

Mass spectrometric value (ESI-MS, m/z): 430 (M+1)$^+$

Compound 342: 3-[4-(5,6-Dimethyl-[2,2']bipyridin-3-yloxy)-6-methoxy-quinolin-7-yloxy]-propane-1,2-diol 3-(6-Methoxy-7-oxiranylmethoxy-quinolin-4-yloxy)-5,6-dimethyl-[2,2']bipyridine (compound 341) (95 mg) was dissolved in methylene chloride (2 ml) to prepare a solution which was then brought to 0° C. Trifluoroacetic acid (1 ml) was added to the solution, the mixture was stirred at 0° C. for 30 min, and the mixture was then stirred at room temperature for 5 hr. The reaction solution was brought to 0° C., was stirred, and was made alkaline by the addition of a 10% aqueous sodium hydroxide solution. Water was added thereto, the mixture was extracted with chloroform, and the chloroform layer was then washed with saturated brine and was dried over anhydrous sodium sulfate. The solvent was removed by distillation under the reduced pressure, and the residue was purified by thin layer chromatography using chloroform-methanol to give the title compound (63 mg, yield 64%).

$^1$H-NMR (CD$_3$OD, 400 MHz): δ 2.45 (s, 3H), 2.63 (s, 3H), 3.69-3.77 (m, 2H), 4.02 (s, 3H), 4.06-4.15 (m, 2H), 4.20-4.24 (m, 1H), 6.36 (d, J=5.4 Hz, 1H), 7.23-7.26 (m, 1H), 7.28 (s, 1H), 7.64 (s, 1H), 7.65 (s, 1H), 7.72-7.82 (m, 2H), 8.27 (d, J=5.4 Hz, 1H), 8.39 (d, J=4.9 Hz, 1H)

Mass spectrometric value (ESI-MS, m/z): 448 (M+1)$^+$

Compound 343: 2-[4-(5,6-Dimethyl-[2,2']bipyridin-3-yloxy)-6-methoxy-quinolin-7-yloxymethyl]-propane-1,3-diol 4-(5,6-Dimethyl-[2,2']bipyridin-3-yloxy)-6-methoxy-quinolin-7-ol (compound 338) (80 mg) was dissolved in tetrahydrofuran (2 ml) to prepare a solution. Triphenylphosphine (112 mg), (2,2-dimethyl-[1,3]dioxan-5-yl)-methanol (38 mg), and diethylazodicarboxylate (0.078 ml) were added to the solution, and the mixture was stirred at room temperature for 6 hr. Further, 1 N sulfuric acid (4 ml) was added thereto, the mixture was stirred at room temperature overnight, and the reaction solution was brought to 0° C. and was stirred. The reaction solution was made alkaline by the addition of a 10% aqueous sodium hydroxide solution. Water was added thereto, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (50 mg, yield 52%).

$^1$H-NMR (CD$_3$OD, 400 MHz): δ 2.25-2.28 (m, 1H), 2.45 (s, 3H), 2.63 (s, 3H), 3.80 (d, J=5.9 Hz, 4H), 4.01 (s, 3H), 4.24 (d, J=5.9 Hz, 2H), 6.35 (d, J=5.6 Hz, 1H), 7.23-7.27 (m, 1H), 7.29 (s, 1H), 7.64 (s, 2H), 7.73-7.81 (m, 2H), 8.26 (d, J=5.4 Hz, 1H), 8.39-8.41 (m, 1H)

Mass spectrometric value (ESI-MS, m/z): 462 (M+1)$^+$

Compound 344: 3-(7-Benzyloxy-6-methoxy-quinolin-4-yloxy)-5,6-dimethyl-[2,3']bipyridine 5,6-Dimethyl-3-hydroxy-[2,3']bipyridine (400 mg), 7-benzyloxy-4-chloro-6-methoxyquinoline (1.80 g), and 4-dimethylaminopyridine (732 mg) were suspended in o-dichlorobenzene (8 ml), and the suspension was stirred at 140° C. for 6 hr. The reaction solution was cooled to room temperature, water was then added to the reaction solution, and the mixture was extracted with chloroform. The chloroform layer was washed with saturated brine and was dried over anhydrous sodium sulfate. The solvent was removed by distillation under the reduced pressure, and the residue was purified by column chromatography using chloroform-methanol to give the title compound (811 mg, yield 88%).

$^1$H-NMR (CDCl$_3$, 400 MHz): δ 2.36 (s, 3H), 2.63 (s, 3H), 4.03 (s, 3H), 5.32 (s, 2H), 6.36 (d, J=5.4 Hz, 1H), 7.22-7.52 (m, 9H), 8.15-8.18 (m, 1H), 8.41 (d, J=5.4 Hz, 1H), 8.50 (dd, J=1.7 Hz, 4.9 Hz, 1H), 9.13-9.16 (m, 1H)

Mass spectrometric value (ESI-MS, m/z): 464 (M+1)$^+$

Compound 345: 4-(5,6-Dimethyl-[2,3']bipyridin-3-yloxy)-6-methoxy-quinolin-7-ol 3-(7-Benzyloxy-6-methoxy-quinolin-4-yloxy)-5,6-dimethyl-[2,3']bipyridine (compound 344) (804 mg) was dissolved in trifluoroacetic acid (8 ml) to prepare a solution. Methanesulfonic acid (0.8 ml) was added to the solution, and the mixture was stirred at 70° C. for 1.5 hr. The reaction solution was cooled to room temperature, and the solvent was removed by distillation under the reduced pressure. An aqueous sodium hydrogencarbonate solution was then added to the residue, and the mixture was extracted with chloroform. The chloroform layer was washed with saturated brine and was dried over anhydrous sodium sulfate. The solvent was removed by distillation under the reduced pressure, and the residue was purified by column chromatography using chloroform-methanol to give the title compound (777 mg, yield 100%).

$^1$H-NMR (CDCl$_3$, 400 MHz): δ 2.37 (s, 3H), 2.64 (s, 3H), 4.01 (s, 3H), 6.34 (d, J=5.4 Hz, 1H), 7.25-7.30 (m, 1H), 7.32 (s, 1H), 7.49 (s, 2H), 8.18-8.21 (m, 1H), 8.43 (d, J=5.4 Hz, 1H), 8.50 (dd, J=1.5 Hz, 4.6 Hz, 1H), 9.16 (dd, J=1.0 Hz, 2.2 Hz, 1H)

Mass spectrometric value (ESI-MS, m/z): 374 (M+1)$^+$

Compound 346: 2-[4-(5,6-Dimethyl-[2,3']bipyridin-3-yloxy)-6-methoxy-quinolin-7-yloxy]-ethanol 4-(5,6-Dimethyl-[2,3']bipyridin-3-yloxy)-6-methoxy-quinolin-7-ol (compound 345) (150 mg) was dissolved in N,N-dimethylformamide (4 ml) to prepare a solution. Potassium carbonate (167 mg) and 2-bromoethanol (0.09 ml) were added to the solution, and the mixture was stirred at 70° C. overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (132 mg, yield 79%).

$^1$H-NMR (CDCl$_3$, 400 MHz): δ 2.37 (s, 3H), 2.64 (s, 3H), 4.01 (s, 3H), 4.09 (t, J=4.4 Hz, 2H), 4.30 (t, J=4.9 Hz, 2H), 6.38 (d, J=5.4 Hz, 1H), 7.22-7.25 (m, 1H), 7.32 (s, 1H), 7.45 (s, 1H), 7.49 (s, 1H), 8.15-8.18 (m, 1H), 8.44 (d, J=5.4 Hz, 1H), 8.50 (dd, J=1.7 Hz, 6.6 Hz, 1H), 9.14 (dd, J=0.7 Hz, 2.2 Hz, 1H)

Mass spectrometric value (ESI-MS, m/z): 418 (M+1)$^+$

Compound 347: 3-[4-(5,6-Dimethyl-[2,3']bipyridin-3-yloxy)-6-methoxy-quinolin-7-yloxy]-propan-1-ol 4-(5,6-Dimethyl-[2,3']bipyridin-3-yloxy)-6-methoxy-quinolin-7-ol (compound 345) (45 mg) was dissolved in N,N-dimethylformamide (2 ml) to prepare a solution, potassium carbonate (50 mg) and 3-bromo-1-propanol (0.03 ml) were added to the solution, and the mixture was stirred at room temperature overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (13 mg, yield 24%).

$^1$H-NMR (CDCl$_3$, 400 MHz): δ 2.16-2.22 (m, 2H), 2.37 (s, 3H), 2.64 (s, 3H), 3.93 (t, J=5.6 Hz, 2H), 4.01 (s, 3H), 4.38 (t, J=6.1 Hz, 2H), 6.38 (d, J=5.4 Hz, 1H), 7.22-7.25 (m, 1H), 7.32 (s, 1H), 7.47 (s, 1H), 7.48 (s, 1H), 8.15-8.18 (m, 1H), 8.43 (d, J=5.4 Hz, 1H), 8.50 (dd, J=1.7 Hz, 4.9 Hz, 1H), 9.13 (d, J=1.7 Hz, 1H)

Mass spectrometric value (ESI-MS, m/z): 432 (M+1)$^+$

Compound 348: 3-(6-Methoxy-7-oxiranylmethoxy-quinolin-4-yloxy)-5,6-dimethyl-[2,3']bipyridine 4-(5,6-Dimethyl-[2,3']bipyridin-3-yloxy)-6-methoxy-quinolin-7-ol (compound 345) (146 mg) was dissolved in N,N-dimethylformamide (4 ml) to prepare a solution, potassium carbonate (162 mg) and epibromohydrin (0.1 ml) were added to the solution, and the mixture was stirred at room temperature overnight. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (98 mg, yield 59%).

$^1$H-NMR (CDCl$_3$, 400 MHz): δ 2.37 (s, 3H), 2.63 (s, 3H), 2.83-2.85 (m, 1H), 2.95-2.97 (m, 1H), 3.48-3.52 (m, 1H), 4.02 (s, 3H), 4.18 (dd, J=5.6 Hz, 11.2 Hz, 1H), 4.43 (dd, J=3.2 Hz, 11.2 Hz, 1H), 6.37 (d, J=5.1 Hz, 1H), 7.22-7.29 (m, 1H), 7.31 (s, 1H), 7.43 (s, 1H), 7.49 (s, 1H), 8.15-8.18 (m, 1H), 8.44 (d, J=5.4 Hz, 1H), 8.50 (dd, J=1.7 Hz, 4.9 Hz, 1H), 9.14 (d, J=2.2 Hz, 1H)

Mass spectrometric value (ESI-MS, m/z): 430 (M+1)$^+$

Compound 349: 3-[4-(5,6-Dimethyl-[2,3']bipyridin-3-yloxy)-6-methoxy-quinolin-7-yloxy]-propane-1,2-diol 3-(6-Methoxy-7-oxiranylmethoxy-quinolin-4-yloxy)-5,6-dimethyl-[2,3']bipyridine (compound 348) (92 mg) was dissolved in methylene chloride (2 ml) to prepare a solution which was then brought to 0° C. Trifluoroacetic acid (1 ml) was added to the solution, and the mixture was stirred at 0° C. for 30 min. The mixture was then stirred at room temperature for 5 hr. The reaction solution was brought to 0° C., was stirred, and was made alkaline by the addition of a 10% aqueous sodium hydroxide solution. Water was added, and the mixture was extracted with chloroform. The chloroform layer was then washed with saturated brine and was dried over anhydrous sodium sulfate. The solvent was removed by distillation under the reduced pressure, and the residue was purified by thin layer chromatography using chloroform-methanol to give the title compound (34 mg, yield 36%).

¹H-NMR (CD₃OD, 400 MHz): δ 2.42 (s, 3H), 2.63 (s, 3H), 3.69-3.78 (m, 2H), 4.02 (s, 3H), 4.06-4.16 (m, 2H), 4.22-4.25 (m, 1H), 6.41 (d, J=5.4 Hz, 1H), 7.33 (s, 1H), 7.35-7.38 (m, 1H), 7.60 (s, 1H), 7.62 (s, 1H), 8.24-8.27 (m, 1H), 8.33 (d, J=5.4 Hz, 1H), 8.39 (dd, J=1.7 Hz, 4.9 Hz, 1H), 8.97-8.98 (m, 1H)

Mass spectrometric value (ESI-MS, m/z): 470 (M+Na)⁺

Compound 350: 2-[4-(5,6-Dimethyl-[2,3']bipyridin-3-yloxy)-6-methoxy-quinolin-7-yloxymethyl]-propane-1,3-diol 4-(5,6-Dimethyl-[2,3']bipyridin-3-yloxy)-6-methoxy-quinolin-7-ol (compound 345) (80 mg) was dissolved in tetrahydrofuran (2 ml) to prepare a solution. Triphenylphosphine (112 mg), (2,2-dimethyl-[1,3]dioxan-5-yl)-methanol (38 mg), and diethylazodicarboxylate (0.078 ml) were added to the solution, and the mixture was stirred at room temperature for 6 hr. Further, 1 N sulfuric acid (4 ml) was added thereto, and the mixture was stirred at room temperature overnight. The reaction solution was brought to 0° C., was stirred, and was made alkaline by the addition of a 10% aqueous sodium hydroxide solution. Water was added thereto, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (54 mg, yield 56%).

¹H-NMR (CD₃OD, 400 MHz): δ 2.26-2.28 (m, 1H), 2.43 (s, 3H), 2.63 (s, 3H), 3.79 (m, 2H), 3.81 (m, 2H), 4.01 (s, 3H), 4.25 (d, J=5.6 Hz, 2H), 6.40 (d, J=5.4 Hz, 1H), 7.34 (s, 1H), 7.35-7.39 (m, 1H), 7.60 (s, 1H), 7.60 (s, 1H), 8.24-8.26 (m, 1H), 8.32 (d, J=5.4 Hz, 1H), 8.40 (dd, J=1.7 Hz, 4.9 Hz, 1H), 8.96 (d, J=2.2 Hz, 1H)

Mass spectrometric value (ESI-MS, m/z): 462 (M+1)⁺

Compound 351: 7-Benzyloxy-6-methoxy-4-(2-methyl-quinolin-3-yloxy)-quinoline

3-Hydroxy-2-methyl-4-quinoline carboxylic acid (1.5 g), 7-benzyloxy-4-chloro-6-methoxyquinoline (2 g), and 4-(N,N-dimethylamino)-pyridine (2.4 g) were dissolved in 1,2-dichlorobenzene (70 ml) to prepare a solution which was then stirred at 150° C. overnight. The reaction solution was cooled to room temperature, and the solvent was then removed by distillation under the reduced pressure. Water was added to the residue, and the mixture was extracted with chloroform and was dried over anhydrous sodium sulfate. The solvent was removed by distillation under the reduced pressure. The residue was purified by column chromatography using hexane-acetone to give the title compound (2.4 g, yield 85%).

¹H-NMR (CDCl₃, 400 MHz): δ 2.66 (s, 3H), 4.07 (s, 3H), 5.35 (s, 2H), 6.37 (d, J=5.1 Hz, 1H), 7.29-7.37 (m, 1H), 7.37-7.44 (m, 2H), 7.49-7.57 (m, 4H), 7.61 (s, 1H), 7.72 (ddd, J=1.5, 6.8, 8.3 Hz, 1H), 7.75 (d, J=8.1 Hz, 1H), 7.80 (s, 1H), 8.10 (d, J=8.6 Hz, 1H), 8.48 (d, J=5.1 Hz, 1H)

Mass spectrometric value (ESI-MS, m/z): 423 (M+1)⁺

Compound 352: 6-Methoxy-4-(2-methyl-quinolin-3-yloxy)-quinolin-7-ol

7-Benzyloxy-6-methoxy-4-(2-methyl-quinolin-3-yloxy)-quinoline (compound 351) (1 g) was dissolved in N,N-dimethylformamide (15 ml) to prepare a solution. 20% Palladium hydroxide (100 mg) was added to the solution, and the mixture was stirred at room temperature under a hydrogen stream overnight. The reaction solution was filtered through Celite, and the solvent was removed from the filtrate by distillation under the reduced pressure. The residue was purified by column chromatography using chloroform-methanol to give the title compound (647 mg, yield 85%).

¹H-NMR (DMSO-d₆, 400 MHz): δ 2.54 (s, 3H), 3.93 (s, 3H), 6.43 (d, J=5.1 Hz, 1H), 7.31 (s, 1H), 7.52-7.62 (m, 2H), 7.73 (dd, J=7.1, 7.1 Hz, 1H), 7.92 (d, J=8.1 Hz, 1H), 8.00 (d, J=8.3 Hz, 1H), 8.13 (s, 1H), 8.40 (d, J=5.1 Hz, 1H)

Mass spectrometric value (ESI-MS, m/z): 333 (M+1)⁺

Compound 353: 7-(2-Chloro-ethoxy)-6-methoxy-4-(2-methyl-quinolin-3-yloxy)-quinoline 6-Methoxy-4-(2-methyl-quinolin-3-yloxy)-quinolin-7-ol (compound 352) (200 mg) was dissolved in N,N-dimethylformamide (10 ml) to prepare a solution. 1-Bromo-2-chloroethane (432 mg) and potassium carbonate (416 mg) were added to the solution, and the mixture was stirred at room temperature overnight. Water was added to the reaction solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (186 mg, yield 78%).

¹H-NMR (CDCl₃, 400 MHz): δ 2.66 (s, 3H), 3.98 (t, J=6.1 Hz, 2H), 4.06 (s, 3H), 4.48 (t, J=6.1 Hz, 2H), 6.39 (d, J=5.1 Hz, 1H), 7.47 (s, 1H), 7.52-7.58 (m, 1H), 7.62 (s, 1H), 7.72 (ddd, J=1.4, 7.1, 8.5 Hz, 1H), 7.76 (d, J=8.0 Hz, 1H), 7.82 (s, 1H), 8.11 (d, J=8.0 Hz, 1H), 8.51 (d, J=5.1 Hz, 1H)

Mass spectrometric value (ESI-MS, m/z): 395 (M+1)⁺

Compound 354: 2-[6-Methoxy-4-(2-methyl-quinolin-3-yloxy)-quinolin-7-yloxy]-ethylamine 2-{2-[6-Methoxy-4-(2-methyl-quinolin-3-yloxy)-quinolin-7-yloxy]-ethyl}-isoindole-1,3-dione (compound 367) (20 mg) was dissolved in N,N-dimethylformamide (2 ml) to prepare a solution, hydrazine (13 mg) was added to the solution, and the mixture was stirred at room temperature for 4 hr. The solvent was removed by distillation under the reduced pressure, and the residue was purified by thin layer chromatography using chloroform-methanol to give the title compound (16 mg, yield 98%).

¹H-NMR (CDCl₃, 400 MHz): δ 2.65 (s, 3H), 3.20-3.34 (m, 2H), 4.03 (s, 3H), 4.23 (t, J=4.9 Hz, 2H), 6.37 (d, J=5.2 Hz, 1H), 7.46 (s, 1H), 7.53 (dd, J=7.6, 7.6 Hz, 1H), 7.58 (s, 1H), 7.66-7.78 (m, 2H), 7.80 (s, 1H), 8.09 (d, J=8.6 Hz, 1H), 8.48 (d, J=5.4 Hz, 1H)

Mass spectrometric value (ESI-MS, m/z): 376 (M+1)⁺

Compound 355: {2-[6-Methoxy-4-(2-methyl-quinolin-3-yloxy)-quinolin-7-yloxy]-ethyl}-dimethyl-amine N,N-Dimethylformamide (2.5 ml) was added to 7-(2-chloro-ethoxy)-6-methoxy-4-(2-methyl-quinolin-3-yloxy)-quinoline (compound 353) (100 mg), potassium carbonate (500 mg), sodium iodide (20 mg), and water (0.05 ml), and the mixture was stirred at 80° C. for 3 days. The solvent was removed by distillation under the reduced pressure, water was added to the residue, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (34.2 mg, yield 33%).

$^1$H-NMR (CDCl$_3$, 400 MHz): δ 2.39 (s, 6H), 2.64 (s, 3H), 2.91 (t, J=5.6 Hz, 2H), 4.01 (s, 3H), 4.31 (t, J=5.9 Hz, 2H), 6.35 (d, J=5.4 Hz, 1H), 7.45 (s, 1H), 7.51 (dd, J=7.3, 7.3 Hz, 1H), 7.56 (s, 1H), 7.64-7.76 (m, 2H), 7.79 (s, 1H), 8.08 (d, J=8.3 Hz, 1H), 8.47 (d, J=5.4 Hz, 1H)

Mass spectrometric value (ESI-MS, m/z): 404 (M+1)$^+$

Compound 356: N-{2-[6-Methoxy-4-(2-methyl-quinolin-3-yloxy)-quinolin-7-yloxy]-ethyl}-guanidine A solution of 2-[6-methoxy-4-(2-methyl-quinolin-3-yloxy)-quinolin-7-yloxy]-ethylamine (compound 354) (340 mg) in dichloromethane (1 ml) and N,N-dimethylformamide (0.5 ml) were added to 1,3-diboc-2-(trifluoromethylsulfonyl) guanidine (355 mg), and the mixture was stirred at room temperature for 4 hr. The solvent was removed from the reaction solution under the reduced pressure, water was added to the residue, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give N-{2-[6-methoxy-4-(2-methyl-quinolin-3-yloxy)-quinolin-7-yloxy]-ethyl}-N',N"-diboc-guanidine (223 mg, yield 33%).

Trifluoroacetic acid (1 ml) was added to N-{2-[6-methoxy-4-(2-methyl-quinolin-3-yloxy)-quinolin-7-yloxy]-ethyl}-N',N"-diboc-guanidine (222 mg) at 0° C., and the mixture was then stirred at 0° C. for 2 hr. The reaction solution was made alkaline by the addition of a 1 N aqueous sodium hydroxide solution and was extracted with n-butanol. The n-butanol layer was washed with water and was then dried over anhydrous magnesium sulfate. The solvent was removed by distillation under the reduced pressure, and the residue was purified by thin layer chromatography using chloroform-methanol to give the title compound (150 mg, yield 100%).

$^1$H-NMR (CD$_3$OD, 400 MHz): δ 2.62 (s, 3H), 3.75 (t, J=5.4 Hz, 2H), 4.08 (s, 3H), 4.34 (t, J=5.4 Hz, 2H), 6.54 (d, J=5.2 Hz, 1H), 7.44 (s, 1H), 7.62 (dd, J=7.6, 7.6 Hz, 1H), 7.72-7.82 (m, 2H), 7.91 (d, J=8.6 Hz, 1H), 8.04 (d, J=8.3 Hz, 1H), 8.13 (s, 1H), 8.47 (d, J=5.4 Hz, 1H)

Mass spectrometric value (ESI-MS, m/z): 418 (M+1)$^+$

Compound 357: 4-{2-[6-Methoxy-4-(2-methyl-quinolin-3-yloxy)-quinolin-7-yloxy]-ethylcarbamoyl}-3,3-dimethyl-butanoic acid N,N-Dimethylformamide (1 ml) was added to 7-(2-chloro-ethoxy)-6-methoxy-4-(2-methyl-quinolin-3-yloxy)-quinoline (compound 353) (50 mg), potassium carbonate (53 mg), and 4,4-dimethylpiperidine-2,6-dione (54 mg), and the mixture was stirred at 80° C. overnight and then at 100° C. for one day. The reaction solution was cooled to room temperature, water was added to the reaction solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (3.5 mg, yield 5%).

$^1$H-NMR (CDCl$_3$, 400 MHz): δ 1.13 (s, 6H), 2.36 (s, 2H), 2.46 (s, 2H), 2.65 (s, 3H), 3.83-3.91 (m, 2H), 4.05 (s, 3H), 4.35 (t, J=4.9 Hz, 2H), 6.40 (d, J=5.4 Hz, 1H), 6.80 (brs, 1H), 7.50-7.60 (m, 2H), 7.62 (s, 1H), 7.68-7.82 (m, 2H), 7.83 (s, 1H), 8.11 (d, J=8.8 Hz, 1H), 8.49 (d, J=5.2 Hz, 1H)

Mass spectrometric value (ESI-MS, m/z): 516 (M–1)$^-$

Compound 358: 6-Methoxy-4-(2-methyl-quinolin-3-yloxy)-7-(2-piperidin-1-yl-ethoxy)-quinoline N,N-Dimethylformamide (1 ml) was added to 7-(2-chloro-ethoxy)-6-methoxy-4-(2-methyl-quinolin-3-yloxy)-quinoline (compound 353) (35 mg), potassium carbonate (37 mg), and piperidine (23 mg), and the mixture was stirred at 75° C. overnight. The reaction solution was cooled to room temperature, water was added to the reaction solution, and the mixture was extracted with chloroform. The chloroform layer was washed with water and was then dried over anhydrous magnesium sulfate. The solvent was removed by distillation under the reduced pressure, and the residue was purified by thin layer chromatography using chloroform-methanol to give the title compound (35 mg, yield 89%).

$^1$H-NMR (CDCl$_3$, 400 MHz): δ 1.45 (m, 2H), 1.60-1.81 (m, 4H), 2.57-2.77 (m, 7H), 2.95-3.10 (m, 2H), 4.04 (s, 3H), 4.41 (t, J=6.1 Hz, 2H), 6.38 (d, J=5.4 Hz, 1H), 7.47 (s, 1H), 7.54 (dd, J=7.1, 7.1 Hz, 1H), 7.59 (s, 1H), 7.68-7.79 (m, 2H), 7.81 (s, 1H), 8.10 (d, J=8.6 Hz, 1H), 8.50 (d, J=5.4 Hz, 1H)

Mass spectrometric value (ESI-MS, m/z): 444 (M+1)$^+$

Compound 359: (1-{2-[6-Methoxy-4-(2-methyl-quinolin-3-yloxy)-quinolin-7-yloxy]-ethyl}-piperidin-3-yl)-methanol N,N-Dimethylformamide (1 ml) was added to 7-(2-chloro-ethoxy)-6-methoxy-4-(2-methyl-quinolin-3-yloxy)-quinoline (compound 353) (50 mg), potassium carbonate (53 mg), and piperidin-3-yl-methanol (44 mg), and the mixture was stirred at 80° C. overnight. The reaction solution was then stirred at 100° C. for one day, and the reaction solution was cooled to room temperature. Water was added thereto, and the mixture was extracted with chloroform. The chloroform layer was washed with water and was then dried over anhydrous sodium sulfate. The solvent was removed by distillation under the reduced pressure. The residue was purified by thin layer chromatography using chloroform-methanol to give the title compound (33 mg, yield 55%).

$^1$H-NMR (CDCl$_3$, 400 MHz): δ 1.12-1.20 (m, 1H), 1.58-1.85 (m, 3H), 1.85-1.97 (m, 1H), 2.26-2.47 (m, 2H), 2.63-2.69 (m, 3H), 2.75-2.87 (m, 1H), 2.89-3.03 (m, 3H), 3.60-3.66 (m, 2H), 4.01-4.08 (m, 3H), 4.34-4.46 (m, 2H), 6.36-6.40 (m, 1H), 7.50-7.62 (m, 3H), 7.69-7.84 (m, 3H), 8.08-8.13 (m, 1H), 8.46-8.52 (m, 1H)

Mass spectrometric value (ESI-MS, m/z): 474 (M+1)$^+$

Compound 360: 1-{2-[6-Methoxy-4-(2-methyl-quinolin-3-yloxy)-quinolin-7-yloxy]-ethyl}-piperidine-3-carboxylic acid amide N,N-Dimethylformamide (1 ml) was added to 7-(2-chloro-ethoxy)-6-methoxy-4-(2-methyl-quinolin-3-yloxy)-quinoline (compound 353) (50 mg), potassium carbonate (53 mg), and piperidine-3-carboxamide (49 mg), and the mixture was stirred at 80° C. overnight. The reaction solution was cooled to room temperature, water was added to the reaction solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (45 mg, yield 72%).

$^1$H-NMR (CDCl$_3$, 400 MHz): δ 1.54-1.72 (m, 2H), 1.72-1.91 (m, 3H), 1.91-2.04 (m, 1H), 2.24-2.37 (m, 1H), 2.41-2.60 (m, 2H), 2.60-2.68 (m, 3H), 2.85-2.98 (m, 1H), 3.04-3.15 (m, 1H), 4.12-4.16 (m, 3H), 4.25-4.36 (m, 2H), 5.32-5.48 (m, 1H), 6.32-6.41 (m, 1H), 7.41-7.49 (m, 1H), 7.49-7.63 (m, 2H), 7.66-7.85 (m, 3H), 8.05-8.34 (m, 2H), 8.43-8.53 (m, 1H)

Mass spectrometric value (ESI-MS, m/z): 487 (M+1)$^+$

Compound 361: Ethyl 1-{2-[6-methoxy-4-(2-methyl-quinolin-3-yloxy)-quinolin-7-yloxy]-ethyl}-piperidine-3-carboxylate N,N-Dimethylformamide (1 ml) was added to 7-(2-chloro-ethoxy)-6-methoxy-4-(2-methyl-quinolin-3-yloxy)-quinoline (compound 353) (50 mg), potassium carbonate (53 mg), and ethyl piperidine-3-carboxylate (60 mg), and the mixture was stirred at 80° C. overnight. The reaction solution was cooled to room temperature, water was added to the reaction solution, and the mixture was extracted with chloroform. The chloroform layer was washed with water and was then dried over anhydrous sodium sulfate, the solvent was removed by distillation under the reduced pressure, and the residue was purified by thin layer chromatography using chloroform-methanol to give the title compound (36 mg, yield 54%).

$^1$H-NMR (CDCl$_3$, 400 MHz): δ 1.22-1.29 (m, 3H), 1.41-1.54 (m, 1H), 1.58-1.71 (m, 1H), 1.71-1.82 (m, 1H), 1.92-2.04 (m, 1H), 2.15-2.27 (m, 1H), 2.32-2.44 (m, 1H), 2.57-2.70 (m, 4H), 2.90-3.04 (m, 3H), 3.10-3.21 (m, 1H), 4.00-4.07 (m, 3H), 4.07-4.19 (m, 2H), 4.31-4.39 (m, 2H), 6.34-6.41 (m, 1H), 7.41-7.49 (m, 1H), 7.49-7.61 (m, 2H), 7.68-7.85 (m, 3H), 8.07-8.14 (m, 1H), 8.46-8.54 (m, 1H)

Mass spectrometric value (ESI-MS, m/z): 538 (M+Na)$^+$

Compound 362: 1-{2-[6-Methoxy-4-(2-methyl-quinolin-3-yloxy)-quinolin-7-yloxy]-ethyl}-piperidine 4-carboxylic Acid Amide N,N-Dimethylformamide (1 ml) was added to 7-(2-chloro-ethoxy)-6-methoxy-4-(2-methyl-quinolin-3-yloxy)-quinoline (compound 353) (50 mg), potassium carbonate (53 mg), and piperidine-4-carboxamide (49 mg), and the mixture was stirred at 80° C. overnight. The reaction solution was cooled to room temperature, water was added to the reaction solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (20 mg, yield 32%).

$^1$H-NMR (CDCl$_3$, 400 MHz): δ 1.74-2.32 (m, 7H), 2.61-2.70 (m, 3H), 2.92-3.04 (m, 2H), 3.06-3.19 (m, 2H), 3.97-4.10 (m, 3H), 4.29-4.41 (m, 2H), 5.37-5.73 (m, 2H), 6.32-6.43 (m, 1H), 7.43-7.63 (m, 3H), 7.66-7.85 (m, 3H), 8.07-8.15 (m, 1H), 8.45-8.55 (m, 1H)

Mass spectrometric value (ESI-MS, m/z): 487 (M+1)$^+$

Compound 363: Ethyl 1-{2-[6-methoxy-4-(2-methyl-quinolin-3-yloxy)-quinolin-7-yloxy]-ethyl}-piperidine-4-carboxylate N,N-Dimethylformamide (1 ml) was added to 7-(2-chloro-ethoxy)-6-methoxy-4-(2-methyl-quinolin-3-yloxy)-quinoline (compound 353) (50 mg), potassium carbonate (53 mg), and ethyl piperidine-4-carboxylate (60 mg), and the mixture was stirred at 80° C. overnight. The reaction solution was cooled to room temperature, water was added to the reaction solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (48 mg, yield 73%).

$^1$H-NMR (CDCl$_3$, 400 MHz): δ 1.29-2.39 (m, 10H), 2.54-2.64 (m, 3H), 2.90-3.10 (m, 4H), 4.01-4.41 (m, 7H), 6.33-6.43 (m, 1H), 7.42-7.66 (m, 3H), 7.66-7.85 (m, 3H), 8.05-8.15 (m, 1H), 8.45-8.54 (m, 1H)

Mass spectrometric value (ESI-MS, m/z): 538 (M+Na)$^+$

Compound 364: 1-{2-[6-Methoxy-4-(2-methyl-quinolin-3-yloxy)-quinolin-7-yloxy]-ethyl}-piperidin-4-ol N,N-Dimethylformamide (1 ml) was added to 7-(2-chloro-ethoxy)-6-methoxy-4-(2-methyl-quinolin-3-yloxy)-quinoline (compound 353) (50 mg), potassium carbonate (53 mg), and piperidin-4-ol (38 mg), and the mixture was stirred at 70° C. overnight. The reaction solution was cooled to room temperature, water was added to the reaction solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (24 mg, yield 41%).

$^1$H-NMR (CDCl$_3$, 400 MHz): δ 1.57-2.20 (m, 5H), 2.40-2.73 (m, 4H), 2.93-3.18 (m, 4H), 3.71-3.93 (m, 1H), 3.99-4.09 (m, 3H), 4.34-4.51 (m, 2H), 6.34-6.41 (m, 1H), 7.44-7.62 (m, 3H), 7.66-7.85 (m, 3H), 8.07-8.15 (m, 1H), 8.46-8.55 (m, 1H)

Mass spectrometric value (ESI-MS, m/z): 460 (M+1)$^+$

Compound 365: 6-Methoxy-4-(2-methyl-quinolin-3-yloxy)-7-(2-morpholin-4-yl-ethoxy)-quinoline N,N-Dimethylformamide (1.5 ml) was added to 7-(2-chloro-ethoxy)-6-methoxy-4-(2-methyl-quinolin-3-yloxy)-quinoline (compound 353) (50 mg), potassium carbonate (53 mg), and morpholine (33 mg), and the mixture was stirred at 80° C. for 3 days. The reaction solution was cooled to room temperature, water was added to the reaction solution, and the mixture was extracted with chloroform. The chloroform layer was washed with water and was then dried over anhydrous sodium sulfate, the solvent was removed by distillation under the reduced pressure, and the residue was purified by thin layer chromatography using chloroform-methanol to give the title compound (23 mg, yield 41%).

$^1$H-NMR (CDCl$_3$, 400 MHz): δ 2.66 (s, 3H), 3.40-3.74 (m, 8H), 4.05 (s, 3H), 4.43-4.52 (m, 2H), 4.56-4.66 (m, 2H), 6.39 (d, J=5.1 Hz, 1H), 7.50 (s, 1H), 7.55 (dd, J=7.6, 7.6 Hz, 1H), 7.61 (s, 1H), 7.69-7.79 (m, 2H), 7.82 (s, 1H), 8.11 (d, J=8.3 Hz, 1H), 8.50 (d, J=5.1 Hz, 1H)

Mass spectrometric value (ESI-MS, m/z): 446 (M+1)$^+$

Compound 366: 6-Methoxy-4-(2-methyl-quinolin-3-yloxy)-7-(2-morpholin-4-yl-ethoxy)-quinoline hydrochloride A hydrochloric acid/methanol solution (30 ml) was added to 6-methoxy-4-(2-methyl-quinolin-3-yloxy)-7-(2-morpholin-4-yl-ethoxy)-quinoline (compound 365) (748 mg), and the mixture was stirred at room temperature for one hr. The solvent was removed by distillation under the reduced pressure to give the title compound (900 mg, yield 59%).

¹H-NMR (CD₃OD, 400 MHz): δ 2.97 (s, 3H), 3.44-3.53 (m, 2H), 3.67-4.01 (m, 6H), 4.01-4.24 (m, 5H), 4.70-5.00 (m, 2H), 7.33 (d, J=5.6 Hz, 1H), 7.76 (s, 1H), 7.97 (dd, J=7.8, 7.8 Hz, 1H), 8.03 (s, 1H), 8.18 (dd, J=7.3, 7.3 Hz, 1H), 8.24-8.37 (m, 2H), 8.85 (d, J=5.6 Hz, 1H), 9.12 (s, 1H)

Mass spectrometric value (ESI-MS, m/z): 446 (M+1-3HCl)⁺

Compound 367: 2-{2-[6-Methoxy-4-(2-methyl-quinolin-3-yloxy)-quinolin-7-yloxy]-ethyl}-isoindole-1,3-dione N,N-Dimethylformamide (3 ml) was added to 6-methoxy-4-(2-methyl-quinolin-3-yloxy)-quinolin-7-ol (compound 352) (100 mg), 2-(2-bromo-ethyl)-isoindole-1,3-dione (229 mg) and potassium carbonate (125 mg), and the mixture was stirred at room temperature overnight. The solvent was removed by distillation under the reduced pressure, water was added to the residue, and the mixture was extracted with chloroform. The chloroform layer was washed with water and was then dried over anhydrous sodium sulfate. The solvent was removed by distillation under the reduced pressure, and the residue was purified by thin layer chromatography using acetone-hexane to give the title compound (83 mg, yield 55%).

¹H-NMR (CDCl₃, 400 MHz): δ 2.65 (s, 3H), 3.96 (s, 3H), 4.27 (t, J=5.9 Hz, 2H), 4.49 (t, J=5.9 Hz, 2H), 6.39 (d, J=5.1 Hz, 1H), 7.48-7.57 (m, 3H), 7.68-7.77 (m, 4H), 7.79 (s, 1H), 7.87-7.93 (m, 2H), 8.10 (d, J=8.6 Hz, 1H), 8.49 (d, J=5.4 Hz, 1H)

Mass spectrometric value (ESI-MS, m/z): 528 (M+Na)⁺

Compound 368: 7-(2-Imidazol-1-yl-ethoxy)-6-methoxy-4-(2-methyl-quinolin-3-yloxy)-quinoline N,N-Dimethylformamide (1.5 ml) was added to 7-(2-chloro-ethoxy)-6-methoxy-4-(2-methyl-quinolin-3-yloxy)-quinoline (compound 353) (50 mg), potassium carbonate (53 mg), and imidazole (26 mg), and the mixture was stirred at 80° C. for 3 days. The reaction solution was cooled to room temperature, water was added to the reaction solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (31 mg, yield 57%).

¹H-NMR (CDCl₃, 400 MHz): δ 2.65 (s, 3H), 4.06 (s, 3H), 4.41-4.54 (m, 4H), 6.38 (d, J=5.1 Hz, 1H), 7.09 (s, 1H), 7.16 (s, 1H), 7.40 (s, 1H), 7.55 (dd, J=7.6, 7.6 Hz, 1H), 7.61 (s, 1H), 7.68-7.80 (m, 3H), 7.81 (s, 1H), 8.10 (d, J=8.3 Hz, 1H), 8.49 (d, J=5.1 Hz, 1H)

Mass spectrometric value (ESI-MS, m/z): 427 (M+1)⁺

Compound 369: 2-[6-Methoxy-4-(2-methyl-quinolin-3-yloxy)-quinolin-7-yloxy]-ethanol A solution of 2-bromo-ethanol (226 mg) in N,N-dimethylformamide (6 ml) was added to 6-methoxy-4-(2-methyl-quinolin-3-yloxy)-quinolin-7-ol (compound 352) (100 mg) and potassium carbonate (250 mg), and the mixture was stirred at 70° C. overnight. The reaction solution was cooled to room temperature, water was added to the reaction solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-acetone to give the title compound (51.3 mg, yield 45%).

¹H-NMR (CDCl₃, 400 MHz): δ 2.66 (s, 3H), 4.05 (s, 3H), 4.11 (t, J=4.9 Hz, 2H), 4.33 (t, J=4.9 Hz, 2H), 6.39 (d, J=5.1 Hz, 1H), 7.49 (s, 1H), 7.55 (dd, J=7.1, 7.1 Hz, 1H), 7.61 (s, 1H), 7.67-7.79 (m, 2H), 7.82 (s, 1H), 8.10 (d, J=8.3 Hz, 1H), 8.50 (d, J=5.1 Hz, 1H)

Mass spectrometric value (ESI-MS, m/z): 377 (M+1)⁺

Compound 370: 2-[6-Methoxy-4-(2-methyl-quinolin-3-yloxy)-quinolin-7-yloxy]-acetamide N,N-Dimethylformamide (1.5 ml) was added to 6-methoxy-4-(2-methyl-quinolin-3-yloxy)-quinolin-7-ol (compound 352) (50 mg), bromoacetamide (62 mg), and potassium carbonate (62 mg), and the mixture was stirred at room temperature overnight. Water was added to the reaction solution, and the mixture was extracted with ethyl acetate. The ethyl acetate layer was washed with water and was then dried over anhydrous sodium sulfate. The solvent was removed by distillation under the reduced pressure, and the residue was purified by thin layer chromatography using chloroform-methanol to give the title compound (49 mg, yield 83%).

¹H-NMR (CDCl₃, 400 MHz): δ 2.65 (s, 3H), 4.09 (s, 3H), 4.76 (s, 2H), 5.72 (bs, 1H), 6.48 (d, J=5.4 Hz, 1H), 6.85 (bs, 1H), 7.58 (dd, J=8.0, 8.0 Hz, 1H), 7.68 (s, 1H), 7.72 (s, 1H), 7.73-7.81 (m, 2H), 7.87 (s, 1H), 8.13 (d, J=8.5 Hz, 1H), 8.53 (d, J=5.4 Hz, 1H)

Mass spectrometric value (ESI-MS, m/z): 412 (M+Na)⁺

Compound 371: Methyl [6-methoxy-4-(2-methyl-quinolin-3-yloxy)-quinolin-7-yloxy]-acetate N,N-Dimethylformamide (1.5 ml) was added to 6-methoxy-4-(2-methyl-quinolin-3-yloxy)-quinolin-7-ol (compound 352) (50 mg), methyl boromoacetate (69 mg), and potassium carbonate (62 mg), and the mixture was stirred at room temperature overnight. Water was added to the reaction solution, and the mixture was extracted with ethyl acetate. The ethyl acetate layer was washed with water and was then dried over anhydrous sodium sulfate. The solvent was removed by distillation under the reduced pressure, and the residue was purified by thin layer chromatography using chloroform-methanol to give the title compound (23 mg, yield 38%).

¹H-NMR (CDCl₃, 400 MHz): δ 2.64 (s, 3H), 3.82 (s, 3H), 4.06 (s, 3H), 4.88 (s, 2H), 6.37 (d, J=5.2 Hz, 1H), 7.34 (s, 1H), 7.52 (dd, J=8.3, 8.3 Hz, 1H), 7.62 (s, 1H), 7.69 (d, J=8.3, 8.3 Hz, 1H), 7.74 (d, J=8.0 Hz, 1H), 7.80 (s, 1H), 8.08 (d, J=8.5 Hz, 1H), 8.47 (d, J=5.1 Hz, 1H)

Mass spectrometric value (ESI-MS, m/z): 427 (M+Na)⁺

Compound 372: Ethyl [6-Methoxy-4-(2-methyl-quinolin-3-yloxy)-quinolin-7-yloxy]-acetate N,N-Dimethylformamide (1.5 ml) was added to 6-methoxy-4-(2-methyl-quinolin-3-yloxy)-quinolin-7-ol (compound 352) (50 mg), ethyl bromoacetate (75 mg), and potassium carbonate (62 mg), and the mixture was stirred at room temperature overnight. Water was added to the reaction solution, and the mixture was extracted with ethyl acetate. The ethyl acetate layer was washed with water and was then dried over anhydrous sodium sulfate. The solvent was removed by distillation under the reduced pressure, and the residue was purified by thin layer chromatography using chloroform-methanol to give the title compound (31 mg, yield 49%).

$^1$H-NMR (CDCl$_3$, 400 MHz): δ 1.31 (t, J=7.1 Hz, 3H), 2.64 (s, 3H), 4.06 (s, 3H), 4.29 (q, J=7.1 Hz, 2H), 4.87 (s, 2H), 6.38 (d, J=5.4 Hz, 1H), 7.36 (s, 1H), 7.53 (dd, J=8.3, 8.3 Hz, 1H), 7.62 (s, 1H), 7.70 (d, J=8.3, 8.3 Hz, 1H), 7.74 (d, J=8.1 Hz, 1H), 7.80 (s, 1H), 8.09 (d, J=8.3 Hz, 1H), 8.48 (d, J=5.1 Hz, 1H)

Mass spectrometric value (ESI-MS, m/z): 441 (M+Na)$^+$

Compound 373: Diethyl 2-[6-methoxy-4-(2-methyl-quinolin-3-yloxy)-quinolin-7-yloxy]-malonate N,N-Dimethylformamide (3 ml) was added to 6-methoxy-4-(2-methyl-quinolin-3-yloxy)-quinolin-7-ol (compound 352) (50 mg), diethyl 2-bromo-malonate (75 mg), and potassium carbonate (62 mg), and the mixture was stirred at room temperature overnight. Water was added to the reaction solution, and the mixture was extracted with ethyl acetate. The ethyl acetate layer was washed with water and was then dried over anhydrous sodium sulfate. The solvent was removed by distillation under the reduced pressure, and the residue was purified by thin layer chromatography using hexane-acetone to give the title compound (134 mg, yield 88%).

$^1$H-NMR (CDCl$_3$, 400 MHz): δ 1.33 (t, J=7.1 Hz, 6H), 2.64 (s, 3H), 4.05 (s, 3H), 4.28-4.42 (m, 4H), 5.35 (s, 1H), 6.37 (d, J=5.1 Hz, 1H), 7.43 (s, 1H), 7.53 (dd, J=7.6, 7.6 Hz, 1H), 7.62 (s, 1H), 7.70 (d, J=8.3, 8.3 Hz, 1H), 7.74 (d, J=8.1 Hz, 1H), 7.80 (s, 1H), 8.09 (d, J=8.3 Hz, 1H), 8.48 (d, J=5.1 Hz, 1H)

Mass spectrometric value (ESI-MS, m/z): 491 (M+1)$^+$

Compound 374: 2-[6-Methoxy-4-(2-methyl-quinolin-3-yloxy)-quinolin-7-yloxy]-propane-1,3-diol Diethyl 2-[6-methoxy-4-(2-methyl-quinolin-3-yloxy)-quinolin-7-yloxy]-malonate (compound 373) (50 mg) was dissolved in tetrahydrofuran (1 ml) to prepare a solution. Lithium aluminum hydride (10 mg) was added to the solution at 0° C., and the mixture was stirred at 0° C. for 3 hr and then at room temperature for 2 hr. Water was added to the reaction solution to stop the reaction. The mixture was filtered through Celite, water was then added to the filtrate, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (9.1 mg, yield 22%).

$^1$H-NMR (CDCl$_3$, 400 MHz): δ 2.64 (s, 3H), 4.02 (s, 3H), 4.03-4.10 (m, 4H), 4.65-4.71 (m, 1H), 6.37 (d, J=5.1 Hz, 1H), 7.55 (dd, J=7.6, 7.6 Hz, 1H), 7.61 (s, 1H), 7.67-7.79 (m, 3H), 7.82 (s, 1H), 8.10 (d, J=8.3 Hz, 1H), 8.47 (d, J=5.4 Hz, 1H)

Mass spectrometric value (ESI-MS, m/z): 407 (M+1)$^+$

Compound 375: 7-(3-Chloro-propoxy)-6-methoxy-4-(2-methyl-quinolin-3-yloxy)-quinoline 6-Methoxy-4-(2-methyl-quinolin-3-yloxy)-quinolin-7-ol (compound 352) (200 mg) was dissolved in N,N-dimethylformamide (10 ml) to prepare a solution. 1-Bromo-3-chloropropane (474 mg) and potassium carbonate (416 mg) were added to the solution, and the mixture was stirred at room temperature overnight. Water was added to the reaction solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (203 mg, yield 83%).

$^1$H-NMR (CDCl$_3$, 400 MHz): δ 2.36-2.46 (m, 2H), 2.66 (s, 3H), 3.83 (t, J=6.4 Hz, 2H), 4.04 (s, 3H), 4.38 (t, J=6.1 Hz, 2H), 6.38 (d, J=5.1 Hz, 1H), 7.49 (s, 1H), 7.52-7.58 (m, 1H), 7.59 (s, 1H), 7.72 (ddd, J=1.5, 7.1, 8.6 Hz, 1H), 7.76 (d, J=8.1 Hz, 1H), 7.81 (s, 1H), 8.11 (d, J=8.5 Hz, 1H), 8.50 (d, J=5.4 Hz, 1H)

Mass spectrometric value (ESI-MS, m/z): 409 (M+1)$^+$

Compound 376: 3-[6-Methoxy-4-(2-methyl-quinolin-3-yloxy)-quinolin-7-yloxy]-propylamine 2-{3-[6-Methoxy-4-(2-methyl-quinolin-3-yloxy)-quinolin-7-yloxy]-propyl}-isoindole-1,3-dione (compound 380) (21 mg) was dissolved in N,N-dimethylformamide (2 ml) to prepare a solution. Hydrazine (13 mg) was added to the solution, and the mixture was stirred at room temperature for 4 hr. The solvent was removed by distillation under the reduced pressure. The residue was purified by thin layer chromatography using chloroform-methanol to give the title compound (15 mg, yield 100%).

$^1$H-NMR (CDCl$_3$, 400 MHz): δ 2.03-2.16 (m, 2H), 2.65 (s, 3H), 2.98 (t, J=6.6 Hz, 2H), 4.03 (s, 3H), 4.31 (t, J=6.6 Hz, 2H), 6.36 (d, J=5.4 Hz, 1H), 7.46 (s, 1H), 7.53 (dd, J=8.0, 8.0 Hz, 1H), 7.57 (s, 1H), 7.66-7.78 (m, 2H), 7.80 (s, 1H), 8.09 (d, J=8.5 Hz, 1H), 8.48 (d, J=5.4 Hz, 1H)

Mass spectrometric value (ESI-MS, m/z): 390 (M+1)$^+$

Compound 377: N-{3-[6-Methoxy-4-(2-methyl-quinolin-3-yloxy)-quinolin-7-yloxy]-propyl}-guanidine N,N-Dimethylformamide (1 ml) was added to 7-(3-chloro-propoxy)-6-methoxy-4-(2-methyl-quinolin-3-yloxy)-quinoline (compound 375) (40 mg), potassium carbonate (41 mg), and guanidine hydrochloride (28 mg). Sodium hydride (39 mg) was added to the mixture, and the mixture was stirred at room temperature overnight. Water was added to the reaction solution, and the mixture was extracted with n-butanol. The n-butanol layer was washed with water and was then dried over anhydrous magnesium sulfate. The solvent was removed by distillation under the reduced pressure, and the residue was purified by thin layer chromatography using chloroform-methanol to give the title compound (7 mg, yield 17%).

$^1$H-NMR (CD$_3$OD, 400 MHz): δ 2.17-2.30 (m, 2H), 2.63 (s, 3H), 3.50 (t, J=6.8 Hz, 2H), 4.05 (s, 3H), 4.31 (t, J=5.9 Hz, 2H), 6.53 (dd, J=2.2, 5.4 Hz, 1H), 7.42 (d, J=3.2 Hz, 1H), 7.61 (dd, J=7.1, 7.1 Hz, 1H), 7.73 (d, J=3.4 Hz, 1H), 7.78 (dd, J=7.3, 7.3 Hz, 1H), 7.92 (d, J=8.3 Hz, 1H), 8.05 (d, J=8.5 Hz, 1H), 8.13 (s, 1H), 8.46 (d, J=5.1 Hz, 1H)

Mass spectrometric value (ESI-MS, m/z): 432 (M+1)$^+$

Compound 378: 6-Methoxy-4-(2-methyl-quinolin-3-yloxy)-7-(3-piperidin-1-yl-propoxy)-quinoline N,N-Dimethylformamide (1 ml) was added to 7-(3-chloro-propoxy)-6-methoxy-4-(2-methyl-quinolin-3-yloxy)-quinoline (compound 375) (40 mg), potassium carbonate (41 mg), and piperidine (25 mg), and the mixture was stirred at 75° C. overnight. The reaction solution was cooled to room temperature, water was added to the reaction solution, and the mixture was extracted with chloroform. The chloroform layer was washed with water and was then dried over anhydrous magnesium sulfate. The solvent was removed by distillation under the reduced pressure, and the residue was purified by thin layer chromatography using chloroform-methanol to give the title compound (32 mg, yield 72%).

¹H-NMR (CDCl₃, 400 MHz): δ 1.43-2.22 (m, 6H), 2.32-2.50 (m, 2H), 2.60-3.10 (m, 9H), 4.03 (s, 3H), 4.29 (t, J=6.1 Hz, 2H), 6.38 (d, J=5.4 Hz, 1H), 7.45 (s, 1H), 7.52-7.58 (m, 1H), 7.58 (s, 1H), 7.72 (ddd, J=1.4, 6.8, 8.3 Hz, 1H), 7.76 (d, J=8.0 Hz, 1H), 7.81 (s, 1H), 8.10 (d, J=7.8 Hz, 1H), 8.50 (d, J=5.4 Hz, 1H)

Mass spectrometric value (ESI-MS, m/z): 458 (M+1)⁺

Compound 379: 6-Methoxy-4-(2-methyl-quinolin-3-yloxy)-7-(3-morpholin-4-yl-propoxy)-quinoline N,N-Dimethylformamide (1.5 ml) was added to 7-(3-chloro-propoxy)-6-methoxy-4-(2-methyl-quinolin-3-yloxy)-quinoline (compound 375) (52 mg), potassium carbonate (53 mg), and morpholine (33 mg), and the mixture was stirred at 80° C. for 3 days. The reaction solution was cooled to room temperature, water was added to the reaction solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (31 mg, yield 53%).

¹H-NMR (CDCl₃, 400 MHz): δ 2.11-2.20 (m, 2H), 2.41-2.55 (m, 4H), 2.60 (t, J=7.1 Hz, 2H), 2.66 (s, 3H), 3.71-3.77 (m, 4H), 4.05 (s, 3H), 4.30 (t, J=6.6 Hz, 2H), 6.38 (d, J=5.4 Hz, 1H), 7.48 (s, 1H), 7.52-7.58 (m, 1H), 7.58 (s, 1H), 7.72 (ddd, J=1.5, 7.1, 8.6 Hz, 1H), 7.75 (d, J=8.0 Hz, 1H), 7.81 (s, 1H), 8.10 (d, J=8.6 Hz, 1H), 8.50 (d, J=5.4 Hz, 1H)

Mass spectrometric value (ESI-MS, m/z): 460 (M+1)⁺

Compound 380: 2-{3-[6-Methoxy-4-(2-methyl-quinolin-3-yloxy)-quinolin-7-yloxy]-propyl}-isoindole-1,3-dione N,N-Dimethylformamide (3 ml) was added to 6-methoxy-4-(2-methyl-quinolin-3-yloxy)-quinolin-7-ol (compound 352) (100 mg), 2-(3-bromo-propyl)-isoindole-1,3-dione (242 mg), and potassium carbonate (125 mg), and the mixture was stirred at room temperature overnight. The solvent was removed by distillation under the reduced pressure, water was added to the residue, and the mixture was extracted with chloroform. The chloroform layer was washed with water and was then dried over anhydrous sodium sulfate. The solvent was removed by distillation under the reduced pressure, and the residue was purified by thin layer chromatography using acetone-hexane to give the title compound (108 mg, yield 69%).

¹H-NMR (CDCl₃, 400 MHz): δ 2.29-2.43 (m, 2H), 2.66 (s, 3H), 3.80 (s, 3H), 3.99 (t, J=6.6 Hz, 2H), 4.29 (t, J=6.1 Hz, 2H), 6.37 (d, J=5.4 Hz, 1H), 7.41 (s, 1H), 7.49 (s, 1H), 7.52 (dd, J=7.1, 7.1 Hz, 1H), 7.65-7.78 (m, 4H), 7.79 (s, 1H), 7.81-7.88 (m, 2H), 8.10 (d, J=8.6 Hz, 1H), 8.48 (d, J=5.2 Hz, 1H)

Mass spectrometric value (ESI-MS, m/z): 542 (M+Na)⁺

Compound 381: 7-(3-Imidazol-1-yl-propoxy)-6-methoxy-4-(2-methyl-quinolin-3-yloxy)-quinoline N,N-Dimethylformamide (1.5 ml) was added to 7-(3-chloro-propoxy)-6-methoxy-4-(2-methyl-quinolin-3-yloxy)-quinoline (compound 375) (52 mg), potassium carbonate (53 mg), and imidazole (26 mg), and the mixture was stirred at 80° C. for 3 days. The reaction solution was cooled to room temperature, water was added to the reaction solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (31 mg, yield 81%).

¹H-NMR (CDCl₃, 400 MHz): δ 2.36-2.43 (m, 2H), 2.67 (s, 3H), 4.07 (s, 3H), 4.17 (t, J=5.0 Hz, 2H), 4.29 (t, J=6.8 Hz, 2H), 6.39 (d, J=5.4 Hz, 1H), 6.97 (s, 1H), 7.07 (s, 1H), 7.41 (s, 1H), 7.53 (s, 1H), 7.59 (dd, J=8.3, 8.3 Hz, 1H), 7.62 (s, 1H), 7.69-7.77 (m, 1H), 7.76 (d, J=8.1 Hz, 1H), 7.82 (s, 1H), 8.11 (d, J=8.5 Hz, 1H), 8.50 (d, J=5.4 Hz, 1H)

Mass spectrometric value (ESI-MS, m/z): 463 (M+Na)⁺

Compound 382: 3-[6-Methoxy-4-(2-methyl-quinolin-3-yloxy)-quinolin-7-yloxy]-propan-1-ol N,N-Dimethylformamide (2 ml) was added to 7-(3-chloro-propoxy)-6-methoxy-4-(2-methyl-quinolin-3-yloxy)-quinoline (compound 375) (69 mg), potassium carbonate (70 mg), and water (10 mg), and the mixture was stirred at 80° C. for 3 days. The reaction solution was cooled to room temperature, water was added to the reaction solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (40 mg, yield 61%).

¹H-NMR (CDCl₃, 400 MHz): δ 2.15-2.25 (m, 2H), 2.65 (s, 3H), 2.95 (t, J=5.4 Hz, 2H), 4.04 (s, 3H), 4.41 (t, J=6.1 Hz, 2H), 6.38 (d, J=5.4 Hz, 1H), 7.51 (s, 1H), 7.54 (dd, J=7.3, 7.3 Hz, 1H), 7.58 (s, 1H), 7.68-7.78 (m, 2H), 7.82 (s, 1H), 8.10 (d, J=8.5 Hz, 1H), 8.49 (d, J=5.1 Hz, 1H)

Mass spectrometric value (ESI-MS, m/z): 391 (M+1)⁺

Compound 383: 6-Methoxy-4-(2-methyl-quinolin-3-yloxy)-7-oxiranylmethoxy-quinoline N,N-Dimethylformamide (3 ml) was added to 6-methoxy-4-(2-methyl-quinolin-3-yloxy)-quinolin-7-ol (compound 352) (100 mg), potassium carbonate (125 mg), and epibromohydrin (124 mg), and the mixture was stirred at 80° C. overnight. The reaction solution was cooled to room temperature, water was added to the reaction solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (62 mg, yield 53%).

¹H-NMR (CDCl₃, 400 MHz): δ 2.66 (s, 3H), 2.83-2.89 (m, 1H), 2.94-3.01 (m, 1H), 3.49-3.57 (m, 1H), 4.06 (s, 3H), 4.21 (dd, J=5.6, 11.2 Hz, 1H), 4.46 (dd, J=3.4, 11.5 Hz, 1H), 6.38 (d, J=5.4 Hz, 1H), 7.48 (s, 1H), 7.55 (dd, J=7.8, 7.8 Hz, 1H), 7.60 (s, 1H), 7.69-7.80 (m, 2H), 7.82 (s, 1H), 8.10 (d, J=8.6 Hz, 1H), 8.50 (d, J=5.2 Hz, 1H)

Mass spectrometric value (ESI-MS, m/z): 389 (M+1)⁺

Compound 384: 3-[6-Methoxy-4-(2-methyl-quinolin-3-yloxy)-quinolin-7-yloxy]-propane-1,2-diol 6-Methoxy-4-(2-methyl-quinolin-3-yloxy)-7-oxiranyl-methoxy-quinoline (compound 383) (30 mg) was dissolved in dichloromethane (1.5 ml) to prepare a solution. Trifluoroacetic acid (1 ml) was added to the solution at 0° C., and the mixture was then stirred at 0° C. for 2 hr. The reaction solution was made alkaline by the addition of a 1 N aqueous sodium hydroxide solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (21 mg, yield 67%).

$^1$H-NMR (CDCl$_3$, 400 MHz): δ 2.65 (s, 3H), 3.86-3.97 (m, 2H), 4.04 (s, 3H), 4.22-4.35 (m, 2H), 4.39 (dd, J=3.9, 9.8 Hz, 1H), 6.41 (d, J=5.4 Hz, 1H), 7.55 (dd, J=7.6, 7.6 Hz, 1H), 7.57 (s, 1H), 7.60 (s, 1H), 7.72 (d, J=7.1 Hz, 1H), 7.76 (d, J=8.5 Hz, 1H), 7.83 (s, 1H), 8.11 (d, J=8.6 Hz, 1H), 8.50 (d, J=5.4 Hz, 1H)

Mass spectrometric value (ESI-MS, m/z): 407 (M+1)$^+$

Compound 385: (S)-3-[6-Methoxy-4-(2-methyl-quinolin-3-yloxy)-quinolin-7-yloxy]-propane-1,2-diol N,N-Dimethylformamide (2 ml) was added to 6-methoxy-4-(2-methyl-quinolin-3-yloxy)-quinolin-7-ol (compound 352) (50 mg), potassium carbonate (62 mg), and (S)-epichlorohydrin (42 mg), and the mixture was stirred at 90° C. overnight. The reaction solution was cooled to room temperature, water was added to the reaction solution, and the mixture was extracted with ethyl acetate. The ethyl acetate layer was washed with water and was then dried over anhydrous sodium sulfate. The solvent was removed by distillation under the reduced pressure, and the residue was purified by thin layer chromatography using hexane-acetone to give (S)-6-methoxy-4-(2-methyl-quinolin-3-yloxy)-7-oxiranylmethoxy-quinoline (33 mg, yield 54%).

(S)-6-Methoxy-4-(2-methyl-quinolin-3-yloxy)-7-oxiranylmethoxy-quinoline (30 mg) was dissolved in dichloromethane (1 ml) to prepare a solution. Trifluoroacetic acid (1 ml) was added dropwise to the solution at 0° C. The mixture was then stirred at room temperature for 3 hr. The reaction solution was made alkaline by the addition of a saturated aqueous sodium hydrogencarbonate solution and was extracted with ethyl acetate. The ethyl acetate layer was washed with water and was then dried over anhydrous sodium sulfate. The solvent was removed by distillation under the reduced pressure, and the residue was purified by thin layer chromatography using chloroform-methanol to give the title compound (24 mg, yield 76%).

$^1$H-NMR (CDCl$_3$, 400 MHz): δ 2.65 (s, 3H), 3.86-3.97 (m, 2H), 4.04 (s, 3H), 4.22-4.35 (m, 2H), 4.39 (dd, J=3.9, 9.8 Hz, 1H), 6.41 (d, J=5.4 Hz, 1H), 7.55 (dd, J=7.6, 7.6 Hz, 1H), 7.57 (s, 1H), 7.60 (s, 1H), 7.72 (d, J=7.1 Hz, 1H), 7.76 (d, J=8.5 Hz, 1H), 7.83 (s, 1H), 8.11 (d, J=8.6 Hz, 1H), 8.50 (d, J=5.4 Hz, 1H)

Mass spectrometric value (ESI-MS, m/z): 407 (M+1)$^+$

Compound 386: (R)-3-[6-Methoxy-4-(2-methyl-quinolin-3-yloxy)-quinolin-7-yloxy]-propane-1,2-diol N,N-Dimethylformamide (3 ml) was added to 6-methoxy-4-(2-methyl-quinolin-3-yloxy)-quinolin-7-ol (compound 352) (100 mg), potassium carbonate (125 mg), and (R)-epichlorohydrin (124 mg), and the mixture was stirred at 70° C. overnight. The reaction solution was cooled to room temperature, water was added to the reaction solution, and the mixture was extracted with ethyl acetate. The ethyl acetate layer was washed with water and was then dried over anhydrous sodium sulfate, and the solvent was removed by distillation under the reduced pressure. The residue was dissolved in dichloromethane (3 ml), trifluoroacetic acid (3 ml) was added dropwise to the solution at 0° C., and the mixture was then stirred at room temperature for 3 hr. The reaction solution was made alkaline by the addition of a 1 N aqueous sodium hydroxide solution, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (24 mg, yield 76%).

$^1$H-NMR (CDCl$_3$, 400 MHz): δ 2.65 (s, 3H), 3.86-3.97 (m, 2H), 4.04 (s, 3H), 4.22-4.35 (m, 2H), 4.39 (dd, J=3.9, 9.8 Hz, 1H), 6.41 (d, J=5.4 Hz, 1H), 7.55 (dd, J=7.6, 7.6 Hz, 1H), 7.57 (s, 1H), 7.60 (s, 1H), 7.72 (d, J=7.1 Hz, 1H), 7.76 (d, J=8.5 Hz, 1H), 7.83 (s, 1H), 8.11 (d, J=8.6 Hz, 1H), 8.50 (d, J=5.4 Hz, 1H)

Mass spectrometric value (ESI-MS, m/z): 407 (M+1)$^+$

Compound 387: 2-[6-Methoxy-4-(2-methyl-quinolin-3-yloxy)-quinolin-7-yloxymethyl]-propane-1,3-diol 6-Methoxy-4-(2-methyl-quinolin-3-yloxy)-quinolin-7-ol (compound 352) (50 mg) and triphenylphosphine (158 mg) were dissolved in tetrahydrofuran (1 ml) to prepare a solution. A solution of diethylazocarbodiimide (105 mg) in (2,2-dimethyl[1,3]dioxan-5-yl)-methanol (27 mg) and tetrahydrofuran (0.2 ml) was added to the solution, and the mixture was stirred at room temperature for 5 hr. A 1 N aqueous sulfuric acid solution (1 ml) was then added to the reaction solution, and the mixture was stirred at room temperature overnight. The reaction solution was made alkaline by the addition of 1 N sodium hydroxide, and the mixture was extracted with ethyl acetate. The ethyl acetate layer was washed with water and was dried over anhydrous sodium sulfate. The solvent was removed by distillation under the reduced pressure, and the residue was purified by thin layer chromatography using chloroform-methanol to give the title compound (29 mg, yield 45%).

$^1$H-NMR (CDCl$_3$, 400 MHz): δ 2.34-2.46 (m, 1H), 2.65 (s, 3H), 3.95-4.05 (m, 4H), 4.05 (s, 3H), 4.46 (d, J=5.6 Hz, 2H), 6.44 (dd, J=2.2, 5.6 Hz, 1H), 7.57 (dd, J=7.1, 7.1 Hz, 1H), 7.61 (s, 1H), 7.67-7.81 (m, 3H), 7.86 (s, 1H), 8.11 (d, J=8.5 Hz, 1H), 8.49 (d, J=5.6 Hz, 1H)

Mass spectrometric value (ESI-MS, m/z): 443 (M+Na)$^+$

Compound 388: 2,2-Bis-hydroxymethyl-3-[6-methoxy-4-(2-methyl-quinolin-3-yloxy)-quinolin-7-yloxy]-propan-1-ol N,N-Dimethylformamide (1.5 ml) was added to 6-methoxy-4-(2-methyl-quinolin-3-yloxy)-quinolin-7-ol (compound 352) (50 mg), potassium carbonate (62 mg), and 2-bromomethyl-2-hydroxymethyl-propane-1,3-diol (90 mg), and the mixture was stirred at 80° C. overnight. The reaction solution was cooled to room temperature, water was added to the reaction solution, and the mixture was extracted with ethyl acetate. The ethyl acetate layer was washed with water and was then dried over anhydrous sodium sulfate. The solvent was removed by distillation under the reduced pressure, and the residue was dissolved in dichloromethane (3 ml) to prepare a solution. Trifluoroacetic acid (3 ml) was added dropwise to the solution at 0° C., and the mixture was then stirred at room temperature for 3 hr. The reaction solution was made alkaline by the addition of a 1 N aqueous sodium hydroxide solution and was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (14 mg, yield 21%).

$^1$H-NMR (CDCl$_3$, 400 MHz): δ 2.64 (s, 3H), 3.91 (s, 6H), 4.00 (s, 3H), 4.35 (s, 2H), 6.37 (d, J=5.1 Hz, 1H), 7.50 (s, 1H), 7.51-7.59 (m, 2H), 7.68-7.80 (m, 2H), 7.82 (s, 1H), 8.10 (d, J=8.3 Hz, 1H), 8.47 (d, J=5.1 Hz, 1H)

Mass spectrometric value (ESI-MS, m/z): 473 (M+Na)$^+$

Compound 389: 2-Bromomethyl-2-[6-methoxy-4-(2-methyl-quinolin-3-yloxy)-quinolin-7-yloxymethyl]-propane-1,3-diol N,N-Dimethylformamide (9 ml) was added to 6-methoxy-4-(2-methyl-quinolin-3-yloxy)-quinolin-7-ol (compound 352) (300 mg), potassium carbonate (375 mg), and 2-bis(bromomethyl)-propane-1,3-diol (710 mg), and the mixture was stirred at 45° C. for 3 days. The reaction solution was cooled to room temperature, and the solvent was removed by distillation under the reduced pressure. Water was added to the residue, and the mixture was extracted with ethyl acetate. The ethyl acetate layer was washed with water and was then dried over anhydrous sodium sulfate. The solvent was removed by distillation under the reduced pressure, and the residue was purified by thin layer chromatography using chloroform-methanol to give the title compound (132 mg, yield 28%).

$^1$H-NMR (CDCl$_3$, 400 MHz): δ 2.58 (s, 3H), 3.70 (s, 3H), 4.08 (s, 2H), 4.47 (s, 2H), 4.57 (d, J=6.6 Hz, 2H), 4.59 (d, J=6.4 Hz, 2H), 6.32 (d, J=5.4 Hz, 1H), 7.43 (s, 1H), 7.45-7.51 (m, 1H), 7.51 (s, 1H), 7.63-7.72 (m, 2H), 7.76 (s, 1H), 8.03 (d, J=8.3 Hz, 1H), 8.42 (d, J=5.4 Hz, 1H)

Mass spectrometric value (ESI-MS, m/z): 535 (M+Na)$^+$

Compound 390: 1-[3-(7-Hydroxy-6-methoxy-quinolin-4-yloxy)-quinolin-2-yl]-ethanone 3-Hydroxy-quinoline-2-carbaldehyde (1.7 g) was dissolved in tetrahydrofuran (50 ml) to prepare a solution which was then cooled to −78° C. Methylmagnesium bromide (32 ml) was gradually added dropwise to the solution, and the mixture was stirred at room temperature overnight. Water was added to the reaction solution, and the mixture was neutralized with 10% hydrochloric acid and was extracted with chloroform. The chloroform layer was washed with saturated brine and was dried over anhydrous sodium sulfate. The solvent was removed by distillation under the reduced pressure, and the residue was used in the next reaction without purification.

The residue (1.73 g) was dissolved in methanol (8 ml) and dichloromethane (24 ml) to prepare a solution. Manganese dioxide (19.5 g) was added to the solution, and the mixture was stirred at room temperature for 2 days. The reaction solution was filtered through Celite and was then washed with chloroform and methanol. The solvent was removed by distillation under the reduced pressure, and the residue was purified by column chromatography using hexane-acetone to give (3-hydroxy-quinolin-2-yl)-ethanone (878 mg, yield 54%).

(3-Hydroxy-quinolin-2-yl)-ethanone (878 mg), 7-benzyloxy-4-chloro-6-methoxyquinoline (7.03 g), and 4-dimethylaminopyridine (3.44 g) were suspended in o-dichlorobenzene (20 ml), and the mixture was stirred at 130° C. overnight. The reaction solution was cooled to room temperature, water was then added thereto, and the mixture was extracted with chloroform. The chloroform layer was washed with saturated brine and was dried over anhydrous sodium sulfate. The solvent was removed by distillation under the reduced pressure, and the residue was purified by column chromatography using chloroform-acetone to give 1-[3-(7-benzyloxy-6-methoxy-quinolin-4-yloxy)-quinolin-2-yl]-ethanone (758 mg, yield 36%).

1-[3-(7-Benzyloxy-6-methoxy-quinolin-4-yloxy)-quinolin-2-yl]-ethanone (758 mg) was dissolved in trifluoroacetic acid (6 ml) to prepare a solution, methanesulfonic acid (0.6 ml) was added to the solution, and the mixture was stirred at 70° C. for 1.5 hr. The reaction solution was cooled to room temperature, and the solvent was removed by distillation under the reduced pressure. An aqueous sodium hydrogencarbonate solution was then added to the residue, and the mixture was extracted with chloroform. The chloroform layer was washed with saturated brine and was dried over anhydrous sodium sulfate, the solvent was removed by distillation under the reduced pressure, and the residue was purified by column chromatography using chloroform-methanol to give the title compound (609 mg, yield 100%).

$^1$H-NMR (CDCl$_3$, 400 MHz): δ 2.77 (s, 3H), 4.10 (s, 3H), 6.36 (d, J=5.4 Hz, 1H), 7.63 (s, 1H), 7.67 (s, 1H), 7.68-7.72 (m, 1H), 7.79-7.85 (m, 2H), 7.98 (s, 1H), 8.24 (d, J=8.5 Hz, 1H), 8.49 (d, J=5.4 Hz, 1H)

Mass spectrometric value (ESI-MS, m/z): 361 (M+1)$^+$

Compound 391: 1-{3-[6-Methoxy-7-(2-morpholin-4-yl-ethoxy)-quinolin-4-yloxy]-quinolin-2-yl}-ethanone 1-[3-(7-Hydroxy-6-methoxy-quinolin-4-yloxy)-quinolin-2-yl]-ethanone (compound 390) (86 mg) was dissolved in N,N-dimethylformamide (2 ml) to prepare a solution. Potassium carbonate (330 mg) and 1-bromo-2-chloroethane (1 ml) were added to the solution, and the mixture was stirred at room temperature overnight. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using acetone-chloroform to give 1-{3-[7-(2-chloro-ethoxy)-6-methoxy-quinolin-4-yloxy]-quinolin-2-yl}-ethanone (75 mg, yield 74%).

1-{3-[7-(2-Chloro-ethoxy)-6-methoxy-quinolin-4-yloxy]-quinolin-2-yl}-ethanone (37 mg) was dissolved in N,N-dimethylformamide (1 ml) to prepare a solution. Potassium carbonate (242 mg) and morpholine (0.1 ml) were added to the solution, and the mixture was stirred at 60° C. for 2 days. Water was added to the reaction solution and was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (11 mg, yield 27%).

$^1$H-NMR (CDCl$_3$, 400 MHz): δ 2.69 (s, 4H), 2.77 (s, 3H), 2.97-3.02 (m, 2H), 3.77-3.79 (m, 4H), 4.04 (s, 3H), 4.37-4.40 (m, 2H), 6.37 (d, J=5.4 Hz, 1H), 7.51 (s, 1H), 7.63 (s, 1H), 7.68-7.71 (m, 1H), 7.80-7.84 (m, 2H), 7.97 (s, 1H), 8.24 (d, J=8.5 Hz, 1H), 8.47 (d, J=5.4 Hz, 1H)

Mass spectrometric value (ESI-MS, m/z): 474 (M+1)$^+$

Compound 392: 1-{3-[7-(2-Hydroxy-ethoxy)-6-methoxy-quinolin-4-yloxy]-quinolin-2-yl}-ethanone 1-{3-[7-(2-Chloro-ethoxy)-6-methoxy-quinolin-4-yloxy]-quinolin-2-yl}-ethanone (37 mg) was dissolved in N,N-dimethylformamide (1 ml) to prepare a solution. Potassium carbonate (363 mg) and water (0.1 ml) were added to the solution, and the mixture was stirred at 60° C. for 5 days. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (2 mg, yield 6%).

$^1$H-NMR (CDCl$_3$, 400 MHz): δ 2.78 (s, 3H), 4.05 (s, 3H), 4.09-4.11 (m, 2H), 4.32-4.35 (m, 2H), 6.38 (d, J=5.4 Hz, 1H), 7.56 (s, 1H), 7.65 (s, 1H), 7.68-7.72 (m, 1H), 7.80-7.85 (m, 2H), 7.99 (s, 1H), 8.25 (d, J=8.3 Hz, 1H), 8.45 (d, J=5.4 Hz, 1H)

Mass spectrometric value (ESI-MS, m/z): 405 (M+1)$^+$

Compound 393: 1-(3-{7-[2-(3-Hydroxy-piperidin-1-yl)-ethoxy]-6-methoxy-quinolin-4-yloxy}-quinolin-2-yl)-ethanone 1-{3-[7-(2-Chloro-ethoxy)-6-methoxy-quinolin-4-yloxy]-quinolin-2-yl}-ethanone (46 mg) was dissolved in N,N-dimethylformamide (1 ml) to prepare a solution. Potassium carbonate (45 mg) and 3-hydroxypiperidine (33 mg) were added to the solution, and the mixture was stirred at 80° C. overnight. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (37 mg, yield 70%).

$^1$H-NMR (CDCl$_3$, 400 MHz): δ 1.63-2.77 (m, 8H), 2.77 (s, 3H), 3.04-3.06 (m, 2H), 3.92 (s, 1H), 4.04 (s, 3H), 4.39 (t, J=5.6 Hz, 2H), 6.36 (d, J=5.4 Hz, 1H), 7.47 (s, 1H), 7.63 (s, 1H), 7.67-7.71 (m, 1H), 7.79-8.32 (m, 2H), 7.96 (s, 1H), 8.24 (d, J=8.5 Hz, 1H), 8.48 (d, J=5.4 Hz, 1H)

Mass spectrometric value (ESI-MS, m/z): 488 (M+1)$^+$

Compound 394: 1-[3-(6-Methoxy-7-oxiranylmethoxy-quinolin-4-yloxy)-quinolin-2-yl]-ethanone 1-[3-(7-Hydroxy-6-methoxy-quinolin-4-yloxy)-quinolin-2-yl]-ethanone (compound 390) (200 mg) was dissolved in N,N-dimethylformamide (6 ml) to prepare a solution. Potassium carbonate (230 mg) and epibromohydrin (0.1 ml) were added to the solution, and the mixture was stirred at room temperature overnight. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (152 mg, yield 66%).

$^1$H-NMR (CDCl$_3$, 400 MHz): δ 2.78 (s, 3H), 2.85-2.88 (m, 1H), 2.96-2.99 (m, 1H), 3.50-3.54 (m, 1H), 4.06 (s, 3H), 4.21 (dd, J=5.9 Hz, 11.5 Hz, 1H), 4.48 (dd, J=3.2 Hz, 11.2 Hz, 1H), 6.38 (d, J=5.4 Hz, 1H), 7.57 (s, 1H), 7.65 (s, 1H), 7.69-7.73 (m, 1H), 7.80-7.85 (m, 2H), 7.99 (s, 1H), 8.25 (d, J=9.0 Hz, 1H), 8.47 (d, J=5.6 Hz, 1H)

Mass spectrometric value (ESI-MS, m/z): 417 (M+1)$^+$

Compound 395: 1-{3-[7-(2,3-Dihydroxy-propoxy)-6-methoxy-quinolin-4-yloxy]-quinolin-2-yl}-ethanone 1-[3-(6-Methoxy-7-oxiranylmethoxy-quinolin-4-yloxy)-quinolin-2-yl]-ethanone (compound 394) (150 mg) was dissolved in methylene chloride (2 ml) to prepare a solution which was brought to 0° C. Trifluoroacetic acid (1 ml) was added to the solution, and the mixture was stirred at 0° C. for 30 min. The mixture was then stirred at room temperature for 4 hr. The reaction solution was brought to 0° C. and was stirred. The reaction solution was made alkaline by the addition of a 10% aqueous sodium hydroxide solution. Water was added thereto, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (140 mg, yield 90%).

$^1$H-NMR (CDCl$_3$/CD$_3$OD, 400 MHz): δ 2.78 (s, 3H), 3.82-3.84 (m, 2H), 4.07 (s, 3H), 4.19-4.29 (m, 2H), 4.34-4.37 (m, 1H), 6.39 (d, J=5.6 Hz, 1H), 7.57 (s, 1H), 7.67 (s, 1H), 7.71-7.75 (m, 1H), 7.82-7.87 (m, 2H), 8.03 (s, 1H), 8.26 (d, J=9.3 Hz, 1H), 8.44 (d, J=5.6 Hz, 1H)

Mass spectrometric value (ESI-MS, m/z): 435 (M+1)

Compound 396: 1-{3-[7-(3-Hydroxy-2-hydroxymethyl-propoxy)-6-methoxy-quinolin-4-yloxy]-quinolin-2-yl}-ethanone 1-[3-(7-Hydroxy-6-methoxy-quinolin-4-yloxy)-quinolin-2-yl]-ethanone (compound 390) (50 mg) was dissolved in tetrahydrofuran (1 ml) to prepare a solution. Triphenylphosphine (73 mg), (2,2-dimethyl-[1,3]dioxan-5-yl)-methanol (24 mg), and diethylazodicarboxylate (0.05 ml) were added to the solution, and the mixture was stirred at room temperature for 4 hr. Further, 1 N sulfuric acid (3 ml) was added thereto, and the mixture was stirred at room temperature overnight. The reaction solution was brought to 0° C. and was stirred. The reaction solution was made alkaline by the addition of a 10% aqueous sodium hydroxide solution. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (47 mg, yield 75%).

$^1$H-NMR (CDCl$_3$/CD$_3$OD, 400 MHz): δ 2.35-2.41 (m, 1H), 2.78 (s, 3H), 3.90 (s, 2H), 3.91 (s, 2H), 4.04 (s, 3H), 4.38 (d, J=6.3 Hz, 2H), 6.38 (d, J=5.4 Hz, 1H), 7.51 (s, 1H), 7.65 (s, 1H), 7.71-7.74 (m, 1H), 7.82-7.88 (m, 2H), 8.03 (s, 1H), 8.26 (d, J=8.5 Hz, 1H), 8.42 (d, J=5.6 Hz, 1H)

Mass spectrometric value (ESI-MS, m/z): 449 (M+1)$^+$

Compound 397: 3-(7-Benzyloxy-6-methoxy-quinolin-4-yloxy)-2-methyl-[1,8]naphthyridine 3-Hydroxy-2-methyl-[1,8]naphthyridine (400 mg), 7-benzyloxy-4-chloro-6-methoxyquinoline (2.25 g), and 4-dimethylaminopyridine (915 mg) were suspended in o-dichlorobenzene (8 ml), and the mixture was stirred at 140° C. for 4 hr. The reaction solution was cooled to room temperature, water was then added to the reaction solution, and the mixture was extracted with chloroform. The chloroform layer was washed with saturated brine and was dried over anhydrous sodium sulfate. The solvent was removed by distillation under the reduced pressure, and the residue was purified by column chromatography using chloroform-methanol to give the title compound (736 mg, yield 70%).

$^1$H-NMR (CDCl$_3$, 400 MHz): δ 2.76 (s, 3H), 4.05 (s, 3H), 5.36 (s, 2H), 6.43 (d, J=5.1 Hz, 1H), 7.32-7.36 (m, 1H), 7.39-7.43 (m, 2H), 7.47-7.55 (m, 5H), 7.77 (s, 1H), 8.11 (dd, J=2.0 Hz, 8.3 Hz, 1H), 8.52 (d, J=5.1 Hz, 1H), 9.11 (dd, J=2.0 Hz, 4.1 Hz, 1H)

Mass spectrometric value (ESI-MS, m/z): 424 (M+1)$^+$

Compound 398: 3-[7-(2-Chloro-ethoxy)-6-methoxy-quinolin-4-yloxy]-2-methyl-[1,8]naphthyridine 3-(7-Benzyloxy-6-methoxy-quinolin-4-yloxy)-2-methyl-[1,8]naphthyridine (compound 397) (730 mg) was dissolved in trifluoroacetic acid (7 ml) to prepare a solution. Methanesulfonic acid (0.7 ml) was added to the solution, and the mixture was stirred at 70° C. for one hr. The reaction solution was cooled to room temperature, and the solvent was removed by distillation under the reduced pressure. An aqueous sodium hydrogencarbonate solution was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give 3-[7-hydroxy-6-methoxy-quinolin-4-yloxy]-2-methyl-[1,8]naphthyridine (604 mg, yield 100%).

3-[7-Hydroxy-6-methoxy-quinolin-4-yloxy]-2-methyl-[1,8]naphthyridine (45 mg) was dissolved in N,N-dimethylformamide (2 ml) to prepare a solution. Potassium carbonate (187 mg) and 1-bromo-2-chloroethane (0.06 ml) were added to the solution, and the mixture was stirred at room temperature overnight. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (46 mg, yield 90%).

$^1$H-NMR (CDCl$_3$, 400 MHz): δ 2.76 (s, 3H), 3.98 (t, J=6.1 Hz, 2H), 4.05 (s, 3H), 4.49 (t, J=6.1 Hz, 2H), 6.45 (d, J=5.4 Hz, 1H), 7.48-7.51 (m, 2H), 7.57 (s, 1H), 7.79 (s, 1H), 8.12 (dd, J=1.7 Hz, 8.1 Hz, 1H), 8.55 (d, J=5.4 Hz, 1H), 9.12 (dd, J=2.0 Hz, 4.4 Hz, 1H)

Mass spectrometric value (ESI-MS, m/z): 396 (M+1)$^+$

Compound 399: 1-{2-[6-Methoxy-4-(2-methyl-[1,8]naphthyridin-3-yloxy)-quinolin-7-yloxy]-ethyl}-piperidin-3-ol 3-[7-(2-Chloro-ethoxy)-6-methoxy-quinolin-4-yloxy]-2-methyl-[1,8]naphthyridine (compound 398) (42 mg) was dissolved in N,N-dimethylformamide (2 ml) to prepare a solution. Potassium carbonate (44 mg) and 3-hydroxypiperidine (32 mg) were added to the solution, and the mixture was stirred at 80° C. overnight. The reaction solution was cooled to room temperature, and the solvent was removed by distillation under the reduced pressure. Water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (29 mg, yield 56%).

$^1$H-NMR (CDCl$_3$, 400 MHz): δ 1.62-2.71 (m, 8H), 2.77 (s, 3H), 2.97-3.04 (m, 2H), 3.89 (s, 1H), 4.03 (s, 3H), 4.37 (t, J=5.9 Hz, 2H), 6.44 (d, J=5.1 Hz, 1H), 7.47-7.50 (m, 2H), 7.53 (s, 1H), 7.77 (s, 1H), 8.11 (dd, J=2.0 Hz, 8.3 Hz, 1H), 8.54 (d, J=5.4 Hz, 1H), 9.11 (dd, J=2.0 Hz, 4.1 Hz, 1H)

Mass spectrometric value (ESI-MS, m/z): 461 (M+1)$^+$

Compound 400: 2-[6-Methoxy-4-(2-methyl-[118]naphthyridin-3-yloxy)-quinolin-7-yloxy]-ethanol 3-[7-Hydroxy-6-methoxy-quinolin-4-yloxy]-2-methyl-[1,8]naphthyridine (162 mg) was dissolved in N,N-dimethylformamide (5 ml) to prepare a solution. Potassium carbonate (202 mg) and 2-bromoethanol (0.1 ml) were added to the solution, and the mixture was stirred at 70° C. overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (130 mg, yield 70%).

$^1$H-NMR (CDCl$_3$, 400 MHz): δ 2.77 (s, 3H), 4.04 (s, 3H), 4.10-4.14 (m, 2H), 4.34 (t, J=4.6 Hz, 2H), 6.45 (d, J=5.4 Hz, 1H), 7.48-7.51 (m, 1H), 7.53 (s, 1H), 7.55 (s, 1H), 7.79 (s, 1H), 8.12 (dd, J=2.0 Hz, 8.1 Hz, 1H), 8.54 (d, J=5.1 Hz, 1H), 9.11 (dd, J=2.0 Hz, 4.4 Hz, 1H)

Mass spectrometric value (ESI-MS, m/z): 378 (M+1)$^+$

Compound 401: 3-(6-Methoxy-7-oxiranylmethoxy-quinolin-4-yloxy)-2-methyl-[1,8]naphthyridine 3-[7-Hydroxy-6-methoxy-quinolin-4-yloxy]-2-methyl-[1,8]naphthyridine (130 mg) was dissolved in N,N-dimethylformamide (4 ml) to prepare a solution. Potassium carbonate (162 mg) and epibromohydrin (0.1 ml) were added to the solution, and the mixture was stirred at room temperature overnight. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (83 mg, yield 55%).

$^1$H-NMR (CDCl$_3$, 400 MHz): δ 2.77 (s, 3H), 2.85-2.87 (m, 1H), 2.96-2.99 (m, 1H), 3.50-3.54 (m, 1H), 4.05 (s, 3H), 4.21 (dd, J=5.9 Hz, 11.5 Hz, 1H), 4.48 (dd, J=3.4 Hz, 11.5 Hz, 1H), 6.45 (d, J=5.1 Hz, 1H), 7.48-7.52 (m, 2H), 7.55 (s, 1H), 7.78 (s, 1H), 8.12 (dd, J=2.0 Hz, 8.1 Hz, 1H), 8.54 (d, J=5.4 Hz, 1H), 9.11 (dd, J=2.0 Hz, 4.4 Hz, 1H)

Mass spectrometric value (ESI-MS, m/z): 390 (M+1)$^+$

Compound 402: 3-[6-Methoxy-4-(2-methyl-[1,8]naphthyridin-3-yloxy)-quinolin-7-yloxy]-propan-1-ol 3-[7-Hydroxy-6-methoxy-quinolin-4-yloxy]-2-methyl-[1,8]naphthyridine (45 mg) was dissolved in N,N-dimethylformamide (2 ml) to prepare a solution. Potassium carbonate (56 mg) and 3-bromo-1-propanol (0.04 ml) were added to the solution, and the mixture was stirred at room temperature overnight. The solvent was removed by distillation under the reduced pressure. Water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (36 mg, yield 71%).

$^1$H-NMR (CDCl$_3$, 400 MHz): δ 2.19-2.24 (m, 2H), 2.76 (s, 3H), 3.95 (t, J=5.4 Hz, 2H), 4.03 (s, 3H), 4.42 (t, J=5.9 Hz, 2H), 6.45 (d, J=5.4 Hz, 1H), 7.48-7.52 (m, 1H), 7.54 (s, 1H), 7.55 (s, 1H), 7.79 (s, 1H), 8.12 (dd, J=2.0 Hz, 8.1 Hz, 1H), 8.54 (d, J=5.4 Hz, 1H), 9.12 (dd, J=2.0 Hz, 4.4 Hz, 1H)

Mass spectrometric value (ESI-MS, m/z): 392 (M+1)$^+$

Compound 403: 3-[6-Methoxy-4-(2-methyl-[1,8]naphthyridin-3-yloxy)-quinolin-7-yloxy]-propane-1,2-diol 3-(6-Methoxy-7-oxiranylmethoxy-quinolin-4-yloxy)-2-methyl-[1,8]naphthyridine (compound 401) (76 mg) was dissolved in methylene chloride (2 ml) to prepare a solution which was then brought to 0° C. Trifluoroacetic acid (0.5 ml) was added to the solution, and the mixture was stirred at 0° C. for 30 min and then at room temperature for 3 hr. The reaction solution was brought to 0° C., was stirred, and was made alkaline by the addition of a 10% aqueous sodium hydroxide solution. Water was added thereto, and the mixture was extracted with chloroform. The chloroform layer was then washed with saturated brine and was dried over anhydrous sodium sulfate. The solvent was removed by distillation under the reduced pressure, and the residue was purified by thin layer chromatography using chloroform-methanol to give the title compound (46 mg, yield 56%).

1H-NMR (CDCl$_3$/CD$_3$OD, 400 MHz): δ 2.75 (s, 3H), 3.39-3.82 (m, 2H), 4.06 (s, 3H), 4.22-4.33 (m, 3H), 6.47 (d, J=5.4 Hz, 1H), 7.48 (s, 1H), 7.53-7.58 (m, 2H), 7.86 (s, 1H), 8.19 (d, J=6.6 Hz, 1H), 8.20-8.50 (m, 1H), 9.09 (s, 1H)

Mass spectrometric value (ESI-MS, m/z): 408 (M+1)

Compound 404: 2-[6-Methoxy-4-(2-methyl-[1,8]naphthyridin-3-yloxy)-quinolin-7-yloxymethyl]-propane-1,3-diol 3-[7-Hydroxy-6-methoxy-quinolin-4-yloxy]-2-methyl-[1,8]naphthyridine (85 mg) was dissolved in tetrahydrofuran (2 ml) to prepare a solution. Triphenylphosphine (134 mg), (2,2-dimethyl-[1,3]dioxan-5-yl)-methanol (45 mg), and diethylazodicarboxylic acid (0.1 ml) were added to the solution, and the mixture was stirred at room temperature for 4 hr. Further, 1 N sulfuric acid (4 ml) was added thereto, and the mixture was stirred at room temperature overnight. The reaction solution was brought to 0° C., was stirred, and was made alkaline by the addition of a 10% aqueous sodium hydroxide solution. Water was added thereto, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (41 mg, yield 39%).

$^1$H-NMR (CDCl$_3$, 400 MHz): δ 2.38-2.43 (m, 1H), 2.76 (s, 3H), 4.00-4.01 (m, 4H), 4.02 (s, 3H), 4.43 (d, J=5.9 Hz, 2H), 6.45 (d, J=5.1 Hz, 1H), 7.48-7.51 (m, 1H), 7.53 (s, 1H), 7.54 (s, 1H), 7.79 (s, 1H), 8.12 (dd, J=2.0 Hz, 8.3 Hz, 1H), 8.53 (d, J=5.4 Hz, 1H), 9.11 (dd, J=2.0 Hz, 4.4 Hz, 1H)

Mass spectrometric value (ESI-MS, m/z): 422 (M+1)$^+$

Compound 405: 4-[6-Methoxy-4-(2-methyl-[1,8]naphthyridin-3-yloxy)-quinolin-7-yloxy]-butan-1-ol 3-[7-Hydroxy-6-methoxy-quinolin-4-yloxy]-2-methyl-[1,8]naphthyridine (45 mg) was dissolved in N,N-dimethylformamide (2 ml) to prepare a solution. Potassium carbonate (56 mg) and 4-bromo-1-butanol (62 mg) were added to the solution, and the mixture was stirred at room temperature overnight. The solvent was removed by distillation under the reduced pressure. Water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (19 mg, yield 35%).

$^1$H-NMR (CDCl$_3$, 400 MHz): δ 1.81-1.88 (m, 2H), 2.05-2.12 (m, 2H), 2.76 (s, 3H), 3.78 (t, J=6.1 Hz, 2H), 4.03 (s, 3H), 4.28 (t, J=6.1 Hz, 2H), 6.44 (d, J=5.1 Hz, 1H), 7.48-7.51 (m, 2H), 7.53 (s, 1H), 7.78 (s, 1H), 8.12 (dd, J=2.0 Hz, 8.1 Hz, 1H), 8.53 (d, J=5.4 Hz, 1H), 9.11 (dd, J=2.0 Hz, 4.4 Hz, 1H)

Mass spectrometric value (ESI-MS, m/z): 404 (M−1)$^-$

Compound 406: 3-(7-Benzyloxy-6-methoxy-quinolin-4-yloxy)-2-methyl-[1,6]naphthyridine 3-Hydroxy-2-methyl-[1,6]naphthyridine (400 mg), 7-benzyloxy-4-chloro-6-methoxyquinoline (2.25 g), and 4-dimethylaminopyridine (915 mg) were suspended in o-dichlorobenzene (8 ml), and the suspension was stirred at 140° C. for 4 hr. The reaction solution was cooled to room temperature, water was then added to the reaction solution, and the mixture was extracted with chloroform. The chloroform layer was washed with saturated brine and was dried over anhydrous sodium sulfate. The solvent was removed by distillation under the reduced pressure, and the residue was purified by column chromatography using chloroform-methanol to give the title compound (597 mg, yield 56%).

$^1$H-NMR (CDCl$_3$, 400 MHz): δ 2.75 (s, 3H), 4.05 (s, 3H), 5.36 (s, 2H), 6.44 (d, J=5.1 Hz, 1H), 7.32-7.36 (m, 1H), 7.39-7.43 (m, 2H), 7.52 (s, 2H), 7.54 (s, 2H), 7.85 (s, 1H), 7.91 (d, J=6.1 Hz, 1H), 8.53 (d, J=5.4 Hz, 1H), 8.76 (d, J=6.1 Hz, 1H), 9.18 (d, J=1.0 Hz, 1H)

Mass spectrometric value (ESI-MS, m/z): 424 (M+1)$^+$

Compound 407: 2-[6-Methoxy-4-(2-methyl-[1,6]naphthyridin-3-yloxy)-quinolin-7-yloxy]-ethanol 3-(7-Benzyloxy-6-methoxy-quinolin-4-yloxy)-2-methyl-[1,6]naphthyridine (compound 406) (590 mg) was dissolved in trifluoroacetic acid (6 ml) to preapre a solution. Methanesulfonic acid (0.6 ml) was added to the solution, and the mixture was stirred at 70° C. for one hr. The reaction solution was cooled to room temperature, and the solvent was removed by distillation under the reduced pressure. An aqueous sodium hydrogencarbonate solution was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give 3-(7-hydroxy-6-methoxy-quinolin-4-yloxy)-2-methyl-[1,6]naphthyridine (456 mg, yield 98%).

3-(7-Hydroxy-6-methoxy-quinolin-4-yloxy)-2-methyl-[1,6]naphthyridine (157 mg) was dissolved in N,N-dimethylformamide (8 ml) to prepare a solution. Potassium carbonate (195 mg) and 2-bromoethanol (0.1 ml) were added to the solution, and the mixture was stirred at 70° C. overnight. The solvent was removed by distillation under the reduced pressure. Water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (147 mg, yield 83%).

$^1$H-NMR (CDCl$_3$, 400 MHz): δ 2.75 (s, 3H), 4.04 (s, 3H), 4.12 (t, J=4.4 Hz, 2H), 4.34 (t, J=4.9 Hz, 2H), 6.46 (d, J=5.4 Hz, 1H), 7.54 (d, J=1.5 Hz, 2H), 7.88 (s, 1H), 7.91 (d, J=6.1 Hz, 1H), 8.55 (d, J=5.1 Hz, 1H), 8.77 (d, J=5.9 Hz, 1H), 9.19 (s, 1H)

Mass spectrometric value (ESI-MS, m/z): 378 (M+1)$^+$

Compound 408: 3-[6-Methoxy-4-(2-methyl-[1,6] naphthyridin-3-yloxy)-quinolin-7-yloxy]-propane-1, 2-diol 3-(7-Hydroxy-6-methoxy-quinolin-4-yloxy)-2-methyl-[1,6]naphthyridine (126 mg) was dissolved in N,N-dimethylformamide (8 ml) to prepare a solution. Potassium carbonate (156 mg) and epibromohydrin (0.1 ml) were added to the solution, and the mixture was stirred at room temperature overnight. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give 3-(6-methoxy-7-oxiranylmethoxy-quinolin-4-yloxy)-2-methyl-[1,6]naphthyridine (48 mg, yield 33%).

3-(6-Methoxy-7-oxiranylmethoxy-quinolin-4-yloxy)-2-methyl-[1,6]naphthyridine (44 mg) was dissolved in methylene chloride (2 ml) to prepare a solution which was brought to 0° C. Trifluoroacetic acid (0.4 ml) was added thereto, and the mixture was stirred at 0° C. for 30 min and then at room temperature for 4 hr. The reaction solution was brought to 0° C., was stirred, and was made alkaline by the addition of a 10% aqueous sodium hydroxide solution. Water was added thereto, and the mixture was extracted with chloroform. The chloroform layer was then washed with saturated brine and was dried over anhydrous sodium sulfate. The solvent was removed by distillation under the reduced pressure, and the residue was purified by thin layer chromatography using chloroform-methanol to give the title compound (7 mg, yield 15%).

$^1$H-NMR (CD$_3$OD, 400 MHz): δ 2.74 (s, 3H), 3.71-3.80 (m, 2H), 4.03 (s, 3H), 4.11-4.31 (m, 3H), 6.66 (d, J=5.4 Hz, 1H), 7.45 (s, 1H), 7.68 (s, 1H), 7.96 (d, J=6.1 Hz, 1H), 8.26 (s, 1H), 8.49 (d, J=5.4 Hz, 1H), 8.70 (d, J=6.1 Hz, 1H), 9.26 (s, 1H)

Mass spectrometric value (ESI-MS, m/z): 408 (M+1)$^+$

Compound 409: 2-[6-Methoxy-4-(2-methyl-[1,6] naphthyridin-3-yloxy)-quinolin-7-yloxymethyl]-propane-1,3-diol 3-(7-Hydroxy-6-methoxy-quinolin-4-yloxy)-2-methyl-[1,6]naphthyridine (85 mg) was dissolved in tetrahydrofuran (2 ml) to prepare a solution. Triphenylphosphine (134 mg), (2,2-dimethyl-[1,3]dioxan-5-yl)-methanol (45 mg), and diethylazodicarboxylic acid (0.1 ml) were added to the solution, and the mixture was stirred at room temperature for 4 hr. Further, 1 N sulfuric acid (4 ml) was added thereto, and the mixture was stirred at room temperature overnight. The reaction solution was brought to 0° C., was stirred, and was made alkaline by the addition of a 10% aqueous sodium hydroxide solution. Water was added thereto, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (66 mg, yield 63%).

$^1$H-NMR (CDCl$_3$, 400 MHz): δ 2.38-2.43 (m, 1H), 2.74 (s, 3H), 4.00-4.01 (m, 4H), 4.02 (s, 3H), 4.43 (d, J=5.6 Hz, 2H), 6.46 (d, J=5.1 Hz, 1H), 7.52 (s, 1H), 7.55 (s, 1H), 7.87 (s, 1H), 7.91 (d, J=5.9 Hz, 1H), 8.55 (d, J=5.1 Hz, 1H), 8.77 (d, J=5.9 Hz, 1H), 9.19 (s, 1H)

Mass spectrometric value (ESI-MS, m/z): 422 (M+1)$^+$

Compound 410: [6-Methoxy-4-(2-methyl-quinolin-3-yloxy)-quinolin-7-yl]-(2-morpholin-4-yl-ethyl)-amine Palladium acetate (62 mg) and 2,2'-bis(diphenylphosphino)-1,1'-binaphthyl (170 mg) were dissolved in toluene (16 ml) to prepare a solution which was then stirred at room temperature for 5 min. 4-Chloro-6-methoxy-quinolin-7-yl trifluoro-methanesulfonate (400 mg) and 2-morpholin-4-yl-ethylamine (1.12 ml) were added thereto, and the mixture was further stirred at room temperature for 5 min. Cesium carbonate (1.97 g) was added to the reaction solution, and the mixture was stirred at 90° C. overnight. Water was added to the reaction solution, and the mixture was extracted with chloroform. The chloroform layer was then washed with water and was dried over anhydrous sodium sulfate. The solvent was removed by distillation under the reduced pressure, and the residue was purified by thin layer chromatography using methanol chloroform to give (4-chloro-6-methoxy-quinolin-7-yl)-(2-morpholin-4-yl-ethyl)-amine (53 mg, yield 14%).

(4-Chloro-6-methoxy-quinolin-7-yl)-(2-morpholin-4-yl-ethyl)-amine (53 mg), 3-hydroxy-2-methyl-quinolin-4-carboxylic acid (126 mg), and 4-dimethylaminopyridine (200 mg) were suspended in o-dichlorobenzene (8 ml). The suspension was stirred at 140° C. overnight. The reaction solution was cooled to room temperature, and the solvent was removed by distillation under the reduced pressure. Water was then added to the residue, and the mixture was extracted with ethyl acetate. The ethyl acetate layer was washed with water and was dried over anhydrous sodium sulfate. The solvent was removed by distillation under the reduced pressure, and the residue was purified by column chromatography using methanol-chloroform to give the title compound (12 mg, yield 16%).

$^1$H-NMR (CDCl$_3$, 400 MHz): δ 2.53 (s, 3H), 2.68 (s, 3H), 2.76 (m, 2H), 3.38 (m, 2H), 3.76 (m, 4H), 4.04 (s, 3H), 5.41 (m, 1H), 6.28 (d, J=5.4 Hz, 1H), 7.08 (s, 1H), 7.44 (s, 1H), 7.53 (m, 1H), 7.68-7.74 (m, 2H), 7.76 (s, 1H), 8.09 (d, J=8.6 Hz, 1H), 8.42 (d, J=5.4 Hz, 1H)

Mass spectrometric value (ESI-MS, m/z): 445 (M+1)$^+$

Compound 411: 3-[6-Methoxy-4-(2-methyl-quinolin-3-yloxy)-quinolin-7-yl]-propan-1-ol Ethyl 3-[6-methoxy-4-(2-methyl-quinolin-3-yloxy)-quinolin-7-yl]-acrylate (compound 413) (310 mg) was dissolved in triethylamine/N,N-dimethylformamide (2.5 ml/13 ml) to prepare a solution. 20% palladium hydroxide (1.27 g) was added to the solution, and the mixture was stirred under a hydrogen gas atmosphere at room temperature overnight. The reaction solution was filtered, and the solvent was then removed by distillation under the reduced pressure. Water was added to the residue, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using acetone-chloroform to give ethyl 3-[6-methoxy-4-(2-methyl-quinolin-3-yloxy)-quinolin-7-yl]-propionate (80 mg, yield 26%).

Ethyl 3-[6-methoxy-4-(2-methyl-quinolin-3-yloxy)-quinolin-7-yl]-propionate (80 mg) was dissolved in tetrahydrofuran (5 ml) to prepare a solution. A diisobutylaluminum hydride/0.93 M hexane solution (1 ml) was added to the solution under ice cooling, and the mixture was stirred at room temperature for 3 hr. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by column chromatography using acetone-chloroform to give the title compound (50 mg, yield 69%).

$^1$H-NMR (CDCl$_3$, 400 MHz): δ 2.02 (m, 2H), 2.67 (s, 3H), 2.96 (t, J=7.3 Hz, 2H), 3.74 (t, J=6.4 Hz, 2H), 4.02 (s, 3H), 6.42 (d, J=5.1 Hz, 1H), 7.55 (m, 1H), 7.58 (s, 1H), 7.70-7.77 (m, 2H), 7.81 (s, 1H), 7.91 (s, 1H), 8.10 (d, J=8.3 Hz, 1H), 8.53 (d, J=5.4 Hz, 1H)

Mass spectrometric value (ESI-MS, m/z): 375 (M+1)$^+$

Compound 412: 6-Methoxy-4-(2-methyl-quinolin-3-yloxy)-7-(3-morpholin-4-yl-propyl)-quinoline 3-[6-Methoxy-4-(2-methyl-quinolin-3-yloxy)-quinolin-7-yl]-propan-1-ol (compound 411) (23 mg) was dissolved in triethylamine/dichloromethane (1 ml/4 ml) to prepare a solution. Methanesulfonyl chloride (0.2 ml) was added to the solution, and the mixture was stirred at room temperature for 5 min. The solvent was removed by distillation under the reduced pressure, and the residue was used in the next reaction without purification.

The residue was dissolved in N,N-dimethylformamide (4 ml) to prepare a solution. Potassium carbonate (230 mg) and morpholine (0.2 ml) were added to the solution, and the mixture was stirred at 70° C. for 3 days. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using acetone-chloroform to give the title compound (17 mg, yield 63%).

$^1$H-NMR (CDCl$_3$, 400 MHz): δ 1.93 (m, 2H), 2.45-2.49 (m, 6H), 2.67 (s, 3H), 2.88 (t, J=7.6 Hz, 2H), 3.74 (m, 4H), 4.00 (s, 3H), 6.42 (d, J=5.1 Hz, 1H), 7.52-7.56 (m, 2H), 7.70-7.76 (m, 2H), 7.81 (s, 1H), 7.88 (s, 1H), 8.10 (d, J=8.6 Hz, 1H), 8.52 (d, J=4.9 Hz, 1H)

Mass spectrometric value (ESI-MS, m/z): 444 (M+1)$^+$

Compound 413: Ethyl 3-[6-methoxy-4-(2-methyl-quinolin-3-yloxy)-quinolin-7-yl]-acrylate Palladium acetate (28 mg), 2,2'-bis(diphenylphosphino)-1,1'-binaphthyl (80 mg) was dissolved in N,N-dimethylformamide (2 ml) to prepare a solution, and the mixture was stirred at room temperature for 5 min. 4-Chloro-6-methoxy-quinolin-7-yl trifluoro-methanesulfonate (100 mg) and ethyl acrylate (0.08 ml) were added thereto, and the mixture was further stirred at room temperature for 5 min. Triethylamine (0.12 ml) was added to the reaction solution, and the mixture was stirred at 80° C. for 6 hr. Water was added to the reaction solution, and the mixture was extracted with ethyl acetate. The ethyl acetate layer was then washed with water and was dried over anhydrous sodium sulfate. The solvent was removed by distillation under the reduced pressure, and the residue was used in the next reaction without purification.

The residue, 3-hydroxy-2-methyl-quinoline (63 mg), and 4-dimethylaminopyridine (175 mg) were suspended in o-dichlorobenzene (3 ml), and the mixture was stirred at 130° C. for 2 days. The reaction solution was cooled to room temperature, and the solvent was removed by distillation under the reduced pressure. Water was then added to the residue, and the mixture was extracted with ethyl acetate. The ethyl acetate layer was washed with water and was dried over anhydrous sodium sulfate. The solvent was removed by distillation under the reduced pressure, and the residue was purified by thin layer chromatography using acetone-chloroform to give the title compound (28 mg, yield 23%) (2 steps).

$^1$H-NMR (CDCl$_3$, 400 MHz): δ 1.38 (t, J=6.1 Hz, 3H), 2.66 (s, 3H), 4.07 (s, 3H), 4.32 (q, J=7.1 Hz, 2H), 6.44 (d, J=5.1 Hz, 1H), 6.77 (d, J=16.4 Hz, 1H), 7.56 (m, 1H), 7.65 (s, 1H), 7.71-7.78 (m, 3H), 7.84 (s, 1H), 8.14 (d, J=16.1 Hz, 1H), 8.29 (s, 1H), 8.57 (d, J=4.9 Hz, 1H)

Mass spectrometric value (ESI-MS, m/z): 415 (M+1)$^+$

Compound 414: 6-Methoxy-4-(2-methyl-quinolin-3-yloxy)-7-pyridin-4-yl-quinoline

4-Chloro-6-methoxy-quinolin-7-yl trifluoro-methanesulfonate (114 mg), 4-pyridine boranic acid (55 mg), and tetrakistriphenylphosphine palladium (30 mg) were dissolved in N,N-dimethylformamide (4 ml) to prepare a solution. A 2 M aqueous potassium carbonate solution (0.3 ml) was added to the reaction system, and the mixture was stirred at 80° C. for 2 hr. Water was added to the reaction solution, and the mixture was extracted with ethyl acetate. The ethyl acetate layer was then washed with water and was dried over anhydrous sodium sulfate. The solvent was removed by distillation under the reduced pressure, and the residue (84 mg) was used in the next reaction without purification.

A part (58 mg) of the residue, 3-hydroxy-2-methyl-quinoline-4-carboxylic acid (124 mg), and 4-dimethylaminopyridine (120 mg) were dissolved in o-dichlorobenzene (5 ml), and the solution was stirred at 130° C. overnight and further at 160° C. for 4 hr. The reaction solution was cooled to room temperature, water was then added to the reaction solution, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using acetone-chloroform to give the title compound (14 mg, yield 16%) (2 steps).

$^1$H-NMR (CDCl$_3$, 400 MHz): δ 2.68 (s, 3H), 4.03 (s, 3H), 6.49 (d, J=5.1 Hz, 1H), 7.55-7.62 (m, 3H), 7.73-7.81 (m, 3H), 7.87 (s, 1H), 8.12 (s, 1H), 8.13 (m, 1H), 8.60 (d, J=5.1 Hz, 1H), 8.72 (d, J=5.9 Hz, 2H)

Mass spectrometric value (ESI-MS, m/z): 394 (M+1)$^+$

Compound 415: 6-Benzyloxy-7-methoxy-4-(2-methyl-quinolin-3-yloxy)-quinoline

3-Hydroxy-2-methyl-4-quinoline carboxylic acid (549 mg), 6-benzyloxy-4-chloro-7-methoxyquinoline (810 mg), and 4-(N,N-dimethylamino)-pyridine (990 mg) were dissolved in 1,2-dichlorobenzene (40 ml) to prepare a solution. The mixture was stirred at 150° C. overnight. The reaction solution was cooled to room temperature, and the solvent was then removed by distillation under the reduced pressure. Water was added to the residue, and the mixture was extracted with chloroform. The chloroform layer was washed with water and was then dried over anhydrous sodium sulfate. The solvent was removed by distillation under the reduced pressure, and the residue was purified by column chromatography using hexane-acetone to give the title compound (718 mg, yield 63%).

$^1$H-NMR (CDCl$_3$, 400 MHz): δ 2.61 (s, 3H), 4.06 (s, 3H), 5.32 (s, 2H), 6.41 (d, J=5.1 Hz, 1H), 7.22-7.40 (m, 3H), 7.44-7.58 (m, 4H), 7.61 (s, 1H), 7.67-7.76 (m, 3H), 8.09 (d, J=8.3 Hz, 1H), 8.51 (d, J=5.1 Hz, 1H)

Mass spectrometric value (ESI-MS, m/z): 423 (M+1)$^+$

Compound 416: 6-(2-Imidazol-1-yl-ethoxy)-7-methoxy-4-(2-methyl-quinolin-3-yloxy)-quinoline Trifluoroacetic acid (5 ml) and methanesulfonic acid (0.2 ml) were added to 6-benzyloxy-7-methoxy-4-(2-methyl-quinolin-3-yloxy)-quinoline (compound 415) (700 mg), and the mixture was stirred at 100° C. for 2 hr. The reaction solution was cooled to room temperature, and the solvent was then removed by distillation under the reduced pressure. A saturated aqueous sodium hydrogencarbonate solution was added to the residue, and the mixture was extracted with chloroform. The chloroform layer was washed with a saturated aqueous sodium hydrogencarbonate solution and water and was then dried over anhydrous magnesium sulfate. The solvent was removed by distillation under the reduced pressure, and the residue was purified by column chromatography using chloroform-methanol to give 7-methoxy-4-(2-methyl-quinolin-3-yloxy)-quinolin-6-ol (26 mg, yield 5%).

7-Methoxy-4-(2-methyl-quinolin-3-yloxy)-quinolin-6-ol (25 mg) was dissolved in N,N-dimethylformamide (1 ml) to prepare a solution. 1-Bromo-2-chloroethane (54 mg) and potassium carbonate (52 mg) were added to the solution, and the mixture was stirred at room temperature overnight. Water was added to the reaction solution, and the mixture was extracted with chloroform. The chloroform layer was washed with water and was then dried over anhydrous magnesium sulfate. The solvent was removed by distillation under the reduced pressure. The residue was purified by thin layer chromatography using chloroform-methanol to give 6-(2-chloroethoxy)-7-methoxy-4-(2-methyl-quinolin-3-yloxy)-quinoline (24 mg, yield 79%).

N,N-Dimethylformamide (3 ml) was added to 6-(2-chloroethoxy)-7-methoxy-4-(2-methyl-quinolin-3-yloxy)-quinoline (24 mg), potassium carbonate (25 mg), imidazole (12 mg), and sodium iodide (1.8 mg), and the mixture was stirred at 75° C. overnight. The reaction solution was cooled to room temperature, and the solvent was removed by distillation under the reduced pressure. Water was added to the residue, and the mixture was extracted with chloroform. The chloroform layer was washed with water and was then dried over anhydrous sodium sulfate. The solvent was removed by distillation under the reduced pressure. The residue was purified by thin layer chromatography using chloroform-methanol to give the title compound (9.2 mg, yield 36%).

$^1$H-NMR (CDCl$_3$, 400 MHz): δ 2.62 (s, 3H), 4.06 (s, 3H), 4.39-4.54 (m, 4H), 6.36 (d, J=5.2 Hz, 1H), 7.08 (s, 1H), 7.15 (s, 1H), 7.48 (s, 1H), 7.50-7.59 (m, 2H), 7.68-7.78 (m, 3H), 7.79 (s, 1H), 8.10 (d, J=8.1 Hz, 1H), 8.51 (d, J=5.4 Hz, 1H)

Mass spectrometric value (ESI-MS, m/z): 449 (M+Na)$^+$

Compound 417: 3-[7-Methoxy-4-(2-methyl-quinolin-3-yloxy)-quinolin-6-yloxy]-propane-1,2-diol N,N-Dimethylformamide (6 ml) was added to 7-methoxy-4-(2-methyl-quinolin-3-yloxy)-quinolin-6-ol (189 mg), potassium carbonate (236 mg), and epibromohydrin (234 mg), and the mixture was stirred at room temperature overnight. Water was added to the reaction solution, and the mixture was extracted with ethyl acetate. The ethyl acetate layer was washed with water and was then dried over anhydrous sodium sulfate. The solvent was removed by distillation under the reduced pressure, and the residue was purified by thin layer chromatography using hexane-acetone to give 7-methoxy-4-(2-methyl-quinolin-3-yloxy)-6-oxiranylmethoxy-quinoline (59 mg, yield 27%).

7-Methoxy-4-(2-methyl-quinolin-3-yloxy)-6-oxiranylmethoxy-quinoline (59 mg) was dissolved in dichloromethane (2 ml) to prepare a solution. Trifluoroacetic acid (2 ml) was added dropwise to the solution at 0° C., and the mixture was then stirred at room temperature for 4 hr. The reaction solution was made alkaline by the addition of 1 N sodium hydroxide, and the mixture was extracted with chloroform. The chloroform layer was washed with water and was then dried over anhydrous sodium sulfate. The solvent was removed by distillation under the reduced pressure, and the residue was purified by thin layer chromatography using chloroform-methanol to give the title compound (18 mg, yield 29%).

$^1$H-NMR (CDCl$_3$, 400 MHz): δ 2.64 (s, 3H), 3.85-3.95 (m, 2H), 4.04 (s, 3H), 4.19-4.32 (m, 2H), 4.35 (dd, J=3.6, 9.3 Hz, 1H), 6.37 (d, J=5.4 Hz, 1H), 7.50 (s, 1H), 4.55 (dd, J=7.8, 7.8 Hz, 1H), 7.64 (s, 1H), 7.72 (dd, J=1.2, 8.3 Hz, 1H), 7.76 (d, J=8.5 Hz, 1H), 7.81 (s, 1H), 8.11 (d, J=8.3 Hz, 1H), 8.51 (d, J=5.2 Hz, 1H)

Mass spectrometric value (ESI-MS, m/z): 429 (M+Na)$^+$

Compound 418: (6,7-Dimethoxy-quinolin-4-yl)-quinolin-3-yl-amine

4-Chloro-6,7-dimethoxyquinoline (88 mg) and 3-aminoquinoline (72 mg) were dissolved in dimethylacetamide (1 ml) to prepare a solution. 60% sodium hydride (46 mg) was added to the solution under ice cooling. The mixture was stirred at 80° C. for 2 hr. Water was then added to the reaction solution, and the mixture was extracted with ethyl acetate. The ethyl acetate layer was dried over anhydrous sodium sulfate. The solvent was removed by distillation under the reduced pressure, and the residue was purified by column chromatography using methanol-chloroform to give the title compound (37 mg, yield 28%).

$^1$H-NMR (CDCl$_3$, 400 MHz): δ 3.98 (s, 3H), 3.99 (s, 3H), 6.96 (d, J=5.4 Hz, 1H), 7.24 (s, 1H), 7.39 (s, 1H), 7.54 (m, 1H), 7.64 (m, 1H), 7.73 (d, J=8.0 Hz, 1H), 7.96 (d, J=2.5 Hz, 1H), 8.08 (d, J=5.4 Hz, 1H), 8.43 (d, J=5.4 Hz, 1H), 8.90 (d, J=2.7 Hz, 1H)

Mass spectrometric value (ESI-MS, m/z): 332 (M+1)$^+$

Compound 419: Ethyl 2-(6,7-dimethoxy-quinolin-4-ylsulfanyl)-5-fluoro-benzoate

5-Fluoro-2-mercaptobenzoic acid (278 mg) and 4-chloro-6,7-dimethoxyquinoline (300 mg) were suspended in acetonitrile (6 ml), and the suspension was stirred at room temperature overnight. The solvent was removed by distillation under the reduced pressure. Water was added to the residue, the mixture was neutralized with sodium hydrogencarbonate and was then extracted with chloroform. The chloroform layer was washed with water and saturated brine and was dried over anhydrous magnesium sulfate. The solvent was removed by distillation under the reduced pressure, and the residue was purified by column chromatography using chloroform-methanol to give 2-(6,7-dimethoxy-quinolin-4-ylsulfanyl)-5-fluoro-benzoic acid (152 mg, yield 31%).

2-(6,7-Dimethoxy-quinolin-4-ylsulfanyl)-5-fluoro-benzoic acid (76 mg) was suspended in ethanol (387 mg), and the suspension was cooled at 0° C. Thionyl chloride (50 mg) was gradually added dropwise thereto, and the mixture was then heated under reflux for 20 min. The solvent was removed by distillation under the reduced pressure, water was added to the residue, and the mixture was neutralized with a 20% aqueous sodium hydroxide solution and was then extracted with ethyl acetate. Next, the ethyl acetate layer was washed with water and saturated brine and was dried over anhydrous sodium sulfate. The solvent was removed by distillation under the reduced pressure, and the residue was purified by column chromatography using acetone-hexane to give the title compound (68 mg, 84%).

$^1$H-NMR (CDCl$_3$, 400 MHz): δ 1.25 (t, J=7.2 Hz, 3H), 3.82 (s, 3H), 3.95 (s, 3H), 4.30 (q, J=7.2 Hz, 2H), 6.81-6.95 (m, 2H), 7.15 (d, J=4.8 Hz, 1H), 7.31 (s, 1H), 7.36 (s, 1H), 7.60 (dd, J=8.8 Hz, 3.2 Hz, 1H), 8.52 (d, J=4.8 Hz, 1H)

Mass spectrometric value (ESI-MS, m/z): 388 (M+1)$^+$

Compound 420:
6,7-Dimethoxy-4-(quinolin-2-ylsulfanyl)-quinoline

2-Quinolinethiol (87 mg) and 4-chloro-6,7-dimethoxyquinoline (100 mg) were suspended in acetonitrile (3 ml), and the suspension was stirred at room temperature overnight. The solvent was removed by distillation under the reduced pressure. Water was added to the residue, and the mixture was neutralized with sodium hydrogencarbonate and was then extracted with chloroform. The chloroform layer was washed with water and saturated brine and was dried over anhydrous magnesium sulfate. The solvent was removed by distillation under the reduced pressure, and the residue was purified by column chromatography using acetone-chloroform to give the title compound (15 mg, yield 10%).

$^1$H-NMR (CDCl$_3$, 400 MHz): δ 3.77 (s, 3H), 3.99 (s, 3H), 6.92 (d, J=8.8 Hz, 1H), 7.38-7.48 (m, 3H), 7.52 (d, J=4.8 Hz, 1H), 7.59-7.69 (m, 2H), 7.84 (d, J=8.4 Hz, 1H), 7.90 (d, J=8.4 Hz, 1H), 8.63 (d, J=4.8 Hz, 1H)

Mass spectrometric value (ESI-MS, m/z): 349 (M+1)$^+$

Compound 421: 3-(6,7-Dimethoxy-quinolin-4-yloxy)-2-pyridin-2-yl-[1,8]naphthyridine 2-Aminopyridine (14.1 g) and triethylamine (19.0 g) were dissolved in dichloromethane (200 ml) to prepare a solution which was cooled to 0° C. A solution of pivaloyl chloride (19.9 g) in dichloromethane (30 ml) was gradually added dropwise thereto, and the mixture was stirred at 0° C. for 15 min. Thereafter, the reaction solution was stirred at room temperature for 4 hr. The reaction solution was poured into water (150 ml), and the dichloromethane layer was washed with a dilute aqueous sodium hydrogencarbonate solution and was dried over anhydrous sodium sulfate. The solvent was removed by distillation under the reduced pressure, and the residue was purified by column chromatography using chloroform to give 2,2-dimethyl-N-pyridin-2-yl-propionamide (25.2 g, yield 95%).

2,2-Dimethyl-N-pyridin-2-yl-propionamide (20.3 g) was dissolved in tetrahydrofuran (230 ml) to prepare a solution which was cooled to −78° C. A 2.44 M n-butyllithium/n-hexane solution (100 ml) was gradually added dropwise thereto, and the mixture was stirred at −78° C. for 15 min. The reaction solution was stirred at 0° C. for 2 hr and was then again cooled to −78° C. A solution of N,N-dimethylformamide (25.0 g) in tetrahydrofuran (25 ml) was gradually added dropwise thereto. The temperature of the reaction solution was raised to room temperature. The reaction solution was then poured into a mixture of ice (50 g) with 6 N hydrochloric acid (150 ml), and the mixture was stirred at room temperature for 20 min. The aqueous layer was neutralized with potassium carbonate powder and was extracted with diethyl ether, and the diethyl ether layer was then washed with water and saturated brine and was dried over magnesium sulfate. The solvent was removed by distillation under the reduced pressure, and the residue was purified by column chromatography using acetone-chloroform to give N-(3-formyl-pyridin-2-yl)-2,2-dimethyl-propionamide (11.8 g, yield 50%).

N-(3-Formyl-pyridin-2-yl)-2,2-dimethyl-propionamide (9.68 g) was dissolved in 3 N hydrochloric acid (140 ml), and the solution was stirred under reflux overnight. The reaction solution was cooled to room temperature, was then washed with diethyl ether, and was neutralized with potassium carbonate powder. Diethyl ether was added thereto, and the mixture was extracted. The diethyl ether layer was dried over potassium carbonate, and the solvent was removed by distillation under the reduced pressure. The residue was purified by column chromatography using acetone-chloroform to give 2-amino-pyridine-3-carbaldehyde (5.03 g, yield 88%).

2-Amino-pyridine-3-carbaldehyde (200 mg) and 2-(bromoacetyl)pyridine hydrobromide (506 mg) were suspended in a 5 N aqueous sodium hydroxide solution (1 ml), and the suspension was hermetically sealed and, in this state, was allowed to stand for 2 days. The reaction solution was neutralized with 10% hydrochloric acid, dichloromethane was then added thereto, and the mixture was extracted. The dichloromethane layer was washed with water and saturated brine and was dried over magnesium sulfate. The solvent was removed by distillation under the reduced pressure, and the residue was purified by column chromatography using chloroform-methanol to give 2-pyridin-2-yl-[1,8]naphthyridin-3-ol (48 mg, yield 13%).

2-Pyridin-2-yl-[1,8]naphthyridin-3-ol (9 mg), 4-chloro-6,7-dimethoxyquinoline (27 mg), and 4-dimethylaminopyridine (16 mg) were suspended in o-dichlorobenzene (1.5 ml), and the mixture was stirred at 140° C. for 48 hr. The reaction solution was cooled to room temperature, water was then added to the reaction solution, and the mixture was extracted with chloroform. The chloroform layer was then washed with water and saturated brine and was dried over anhydrous magnesium sulfate. The solvent was removed by distillation under the reduced pressure, and the residue was purified by thin layer chromatography using chloroform-methanol to give the title compound (2 mg, yield 12%).

$^1$H-NMR (CDCl$_3$, 400 MHz): δ 3.97 (s, 3H), 3.98 (s, 3H), 6.39 (d, J=5.2 Hz, 1H), 7.12 (m, 1H), 7.35 (s, 1H), 7.50 (dd, J=8.0, 4.0 Hz, 1H), 7.61 (s, 1H), 7.69 (ddd, J=9.6, 8.0, 1.6 Hz, 1H), 7.98 (s, 1H), 8.14 (m, 2H), 8.29 (d, J=4.4 Hz, 1H), 8.36 (d, J=5.2 Hz, 1H), 9.12 (dd, J=4.0, 2.0 Hz, 1H)

Mass spectrometric value (ESI-MS, m/z): 433 (M+Na)$^+$

Compound 422: 3-(6,7-Dimethoxy-quinolin-4-yloxy)-2-phenyl-[1,8]naphthyridine

2-Amino-pyridine-3-carbaldehyde (100 mg) and 2-chloro-1-phenyl-ethanone (127 mg) were suspended in a 5 N aqueous sodium hydroxide solution (0.6 ml), and the suspension was hermetically sealed and, in this state, was allowed to stand for 3 days. The reaction solution was neutralized with 10% hydrochloric acid. Dichloromethane was then added thereto, and the mixture was extracted. The dichloromethane layer was washed with water and saturated brine and was dried over magnesium sulfate. The solvent was removed by distillation under the reduced pressure, and the residue was purified by column chromatography using chloroform-methanol to give 2-phenyl-[1,8]naphthyridin-3-ol (23 mg, yield 13%).

2-Phenyl-[1,8]naphthyridin-3-ol (23 mg), 4-chloro-6,7-dimethoxyquinoline (69 mg), and 4-dimethylaminopyridine (38 mg) were suspended in o-dichlorobenzene (2 ml), and the mixture was stirred at 140° C. for 5.5 hr. The reaction solution was cooled to room temperature. Water was then added to the reaction solution, and the mixture was extracted with chloroform. The chloroform layer was then washed with water and saturated brine and was dried over anhydrous magnesium sulfate. The solvent was removed by distillation under the reduced pressure, and the residue was purified by thin layer chromatography using chloroform-methanol to give the title compound (29 mg, yield 71%).

$^1$H-NMR (CDCl$_3$, 400 MHz): δ 3.93 (s, 3H), 3.97 (s, 3H), 6.44 (d, J=5.2 Hz, 1H), 7.29 (m, 3H), 7.37 (s, 1H), 7.40 (s, 1H), 7.50 (dd, J=8.0, 3.6 Hz, 1H), 7.85 (s, 1H), 8.08 (m, 3H), 8.41 (d, J=5.2 Hz, 1H), 9.08 (dd, J=4.0, 1.6 Hz, 1H)

Mass spectrometric value (ESI-MS, m/z): 410 (M+1)$^+$

Compound 423: 3-(6,7-Dimethoxy-quinolin-4-yloxy)-2-ethyl-[1,8]naphthyridine

2-Amino-pyridine-3-carbaldehyde (100 mg) and 1-bromo-butan-2-one (124 mg) were suspended in a 5 N aqueous sodium hydroxide solution (0.6 ml), and the suspension was hermetically sealed and, in this state, was allowed to stand for 3 days. The reaction solution was neutralized with 10% hydrochloric acid, and the precipitate was then filtered. The residue was washed with water and chloroform. The powder as the residue was dried under the reduced pressure to give 2-ethyl-[1,8]naphthyridin-3-ol (106 mg, yield 74%).

2-Ethyl-[1,8]naphthyridin-3-ol (30 mg), 4-chloro-6,7-dimethoxyquinoline (115 mg), and 4-dimethylaminopyridine (63 mg) were suspended in o-dichlorobenzene (2 ml), and the suspension was stirred at 140° C. for 2 hr. The reaction solution was cooled to room temperature, water was then added to the reaction solution, and the mixture was extracted with chloroform. The chloroform layer was then washed with water and saturated brine and was dried over anhydrous magnesium sulfate. The solvent was removed by distillation under the reduced pressure, and the residue was purified by thin layer chromatography using chloroform-methanol to give the title compound (35 mg, yield 57%).

$^1$H-NMR (CDCl$_3$, 400 MHz): δ 1.43 (t, J=7.2 Hz, 3H), 3.07 (q, J=7.2 Hz, 2H), 4.02 (s, 3H), 4.05 (s, 3H), 6.45 (d, J=5.2 Hz, 1H), 7.45 (m, 1H), 7.47 (s, 1H), 7.51 (s, 1H), 7.73 (s, 1H), 8.08 (dd, J=8.4, 2.0 Hz, 1H), 8.52 (d, J=5.2 Hz, 1H), 9.07 (dd, J=4.4, 2.0 Hz, 1H)

Mass spectrometric value (ESI-MS, m/z): 384 (M+Na)$^+$

Compound 424: 3-(6,7-Dimethoxy-quinolin-4-yloxy)-2-ethyl-[1,6]naphthyridine

4-Aminopyridine (4.70 g) and triethylamine (6.31 g) were dissolved in dichloromethane (75 ml) to prepare a solution which was then cooled to 0° C. A solution of pivaloyl chloride (6.63 g) in dichloromethane (10 ml) was gradually added dropwise thereto, and the mixture was stirred at 0° C. for 15 min. Thereafter, the reaction solution was stirred at room temperature overnight. The reaction solution was poured into water (50 ml). The dichloromethane layer was washed with a dilute aqueous sodium hydrogencarbonate solution and was dried over anhydrous sodium sulfate. The solvent was removed by distillation under the reduced pressure, and the residue was purified by column chromatography using chloroform to give 2,2-dimethyl-N-pyridin-4-yl-propionamide (7.70 g, yield 87%).

2,2-Dimethyl-N-pyridin-4-yl-propionamide (5.60 g) was dissolved in tetrahydrofuran (70 ml) to prepare a solution which was cooled to −78° C. A 1.57 M n-butyllithium/n-hexane solution (62 ml) was gradually added dropwise thereto, and the mixture was stirred at −78° C. for 15 min. The reaction solution was stirred at 0° C. for 4 hr and was then again cooled to −78° C. A solution of N,N-dimethylformamide (6.69 g) in tetrahydrofuran (7 ml) was gradually added dropwise thereto. The temperature was raised to room temperature. The reaction solution was then poured into a mixture of ice (10 g) with 6 N hydrochloric acid (30 ml), and the mixture was stirred for 15 min. The aqueous layer was neutralized with potassium carbonate powder and was extracted with diethyl ether. The diethyl ether layer was then washed with water and saturated brine and was dried over magnesium sulfate. The solvent was removed by distillation under the reduced pressure, and the residue was purified by column chromatography using acetone-chloroform to give N-(3-formyl-pyridin-4-yl)-2,2-dimethyl-propionamide (3.35 g, yield 52%).

N-(3-Formyl-pyridin-4-yl)-2,2-dimethyl-propionamide (3.35 g) was dissolved in 3 N hydrochloric acid (50 ml) to prepare a solution which was stirred under reflux for 5.5 hr. The reaction solution was cooled to room temperature, and the reaction solution was then washed with diethyl ether and was neutralized with potassium carbonate powder. Diethyl ether was added thereto, the mixture was extracted, and the diethyl ether layer was dried over potassium carbonate. The solvent was removed by distillation under the reduced pressure, and the residue was purified by column chromatography using acetone-chloroform to give 4-amino-pyridine-3-carbaldehyde (1.12 g, yield 58%).

4-Amino-pyridine-3-carbaldehyde (100 mg) and 1-bromo-butan-2-one (124 mg) were suspended in a 5 N aqueous sodium hydroxide solution (0.6 ml), and the suspension was hermetically sealed and, in this state, was allowed to stand for 3 days. The reaction solution was neutralized with 10% hydrochloric acid, the precipitate was then filtered, and the residue was washed with water and chloroform. The powder as the residue was dried under the reduced pressure to give 2-ethyl-[1,6]naphthyridin-3-ol (69 mg, yield 48%).

2-Ethyl-[1,6]naphthyridin-3-ol (69 mg), 4-chloro-6,7-dimethoxyquinoline (265 mg), and 4-dimethylaminopyridine (145 mg) were suspended in o-dichlorobenzene (3 ml), and the mixture was stirred at 140° C. for 4 hr. The reaction solution was cooled to room temperature, water was then added to the reaction solution, and the mixture was extracted with chloroform. The chloroform layer was then washed with water and saturated brine and was dried over anhydrous magnesium sulfate. The solvent was removed by distillation under the reduced pressure, and the residue was purified by thin layer chromatography using chloroform-methanol to give the title compound (9 mg, yield 6%).

$^1$H-NMR (CDCl$_3$, 400 MHz): δ 1.40 (t, J=7.6 Hz, 3H), 3.06 (q, J=7.6 Hz, 2H), 4.02 (s, 3H), 4.06 (s, 3H), 6.48 (d, J=5.2 Hz, 1H), 7.49 (s, 1H), 7.50 (s, 1H), 7.84 (s, 1H), 7.92 (d, J=6.0 Hz, 1H), 8.54 (d, J=5.2 Hz, 1H), 8.74 (d, J=6.0 Hz, 1H), 9.15 (s, 1H)

Mass spectrometric value (ESI-MS, m/z): 360 (M−1)$^-$

Compound 425: 3-(6,7-Dimethoxy-quinolin-4-yloxy)-naphthalen-2-ol

Naphthalene-2,3-diol (1.00 g), 4-chloro-6,7-dimethoxyquinoline (691 mg), and 4-dimethylaminopyridine (1.14 g) were suspended in o-dichlorobenzene (20 ml), and the mixture was stirred at 130° C. for one hr. The reaction solution was cooled to room temperature, water was then added to the reaction solution, and the mixture was extracted with chloroform. The chloroform layer was then washed with water and saturated brine and was dried over anhydrous magnesium sulfate. The solvent was removed by distillation under the reduced pressure, and the residue was purified by column chromatography using chloroform-methanol to give the title compound (627 mg, yield 58%).

$^1$H-NMR (CD$_3$OD, 400 MHz): δ 4.02 (s, 6H), 6.46 (d, J=5.2 Hz, 1H), 7.28-7.37 (m, 3H), 7.41 (m, 1H), 7.63 (s, 1H), 7.73 (m, 3H), 8.37 (d, J=5.2 Hz, 1H)

Mass spectrometric value (ESI-MS, m/z): 346 (M−1)$^−$

Compound 426: 2-Tert-butyl-3-(6,7-dimethoxy-quinolin-4-yloxy)-[1,8]naphthyridine 2-Amino-pyridine-3-carbaldehyde (100 mg) and 1-bromo-3,3-dimethyl-butan-2-one (147 mg) were suspended in a 5 N aqueous sodium hydroxide solution (0.6 ml), and the suspension was hermtically sealed and, in this state, was allowed to stand for 3 days. The reaction solution was neutralized with 10% hydrochloric acid, and the resultant precipitate was then collected by filtration and was washed with water and chloroform. The powder as the residue was dried under the reduced pressure to give 2-tert-butyl-[1,8]naphthyridin-3-ol (40 mg, yield 24%).

2-Tert-butyl-[1,8]naphthyridin-3-ol (40 mg), 4-chloro-6,7-dimethoxyquinoline (132 mg), and 4-dimethylaminopyridine (72 mg) were suspended in o-dichlorobenzene (3 ml), and the suspension was stirred at 140° C. for 5.5 hr. The reaction solution was cooled to room temperature, water was then added to the reaction solution, and the mixture was extracted with chloroform. The chloroform layer was then washed with water and saturated brine and was dried over anhydrous magnesium sulfate. The solvent was removed by distillation under the reduced pressure, and the residue was purified by column chromatography using chloroform-methanol to give the title compound (7 mg, yield 9%).

$^1$H-NMR (CDCl$_3$, 400 MHz): δ 1.61 (s, 9H), 3.99 (s, 3H), 4.06 (s, 3H), 6.64 (d, J=5.2 Hz, 1H), 7.44 (dd, J=8.4, 4.4 Hz, 1H), 7.49 (s, 1H), 7.52 (s, 1H), 7.64 (s, 1H), 8.01 (dd, J=8.4, 2.0 Hz, 1H), 8.58 (d, J=5.2 Hz, 1H), 9.07 (dd, J=4.4, 2.0 Hz, 1H)

Mass spectrometric value (ESI-MS, m/z): 412 (M+Na)$^+$

Compound 427: 3-(6,7-Dimethoxy-quinolin-4-yloxy)-[1,8]naphthyridine

2-Amino-pyridine-3-carbaldehyde (100 mg), 3-bromo-1,1,1-trifluoro-propan-2-one (157 mg) were suspended in a 5 N aqueous sodium hydroxide solution (0.6 ml), and the suspension was hermetically sealed and, in this state, was allowed to stand for 3 days. The reaction solution was neutralized with 10% hydrochloric acid, and the resultant precipitate was then collected by filtration and was washed with water and chloroform. The powder as the residue was dried under the reduced pressure to give 3-hydroxy-[1,8]naphthyridine-2-carboxylic acid (16 mg, yield 90%).

3-Hydroxy-[1,8]naphthyridine-2-carboxylic acid (15 mg), 4-chloro-6,7-dimethoxyquinoline (47 mg), and 4-dimethylaminopyridine (26 mg) were suspended in o-dichlorobenzene (1 ml), and the suspension was stirred at 140° C. for 24 hr. The reaction solution was cooled to room temperature, water was then added to the reaction solution, and the mixture was extracted with chloroform. The chloroform layer was then washed with water and saturated brine and was dried over anhydrous magnesium sulfate. The solvent was removed by distillation under the reduced pressure, and the residue was purified by column chromatography using chloroform-methanol to give the title compound (6 mg, yield 26%).

$^1$H-NMR (CDCl$_3$, 400 MHz): δ 4.02 (s, 3H), 4.05 (s, 3H), 6.59 (d, J=5.2 Hz, 1H), 7.48-7.58 (m, 3H), 7.85 (d, J=3.2 Hz, 1H), 8.15 (dd, J=8.4, 2.0 Hz, 1H), 8.55 (d, J=5.2 Hz, 1H), 9.10 (d, J=3.2 Hz, 1H), 9.13 (dd, J=4.0, 2.0 Hz, 1H)

Mass spectrometric value (ESI-MS, m/z): 356 (M+Na)$^+$

Compound 428: 3-(6,7-Dimethoxy-quinolin-4-yloxy)-2-p-tolyl-[1,8]naphthyridine 2-Amino-pyridine-3-carbaldehyde (100 mg) and 2-bromo-1-p-tolyl-ethanone (174 mg) were suspended in a 5 N aqueous sodium hydroxide solution (0.6 ml), and the suspension was hermetically sealed and, in this state, was allowed to stand for 3 days. The reaction solution was neutralized with 10% hydrochloric acid, and the resultant precipitate was then collected by filtration and was washed with water and chloroform. The powder as the residue was dried under the reduced pressure to give 2-p-toluyl-[1,8]naphthyridin-3-ol (2 mg, yield 1%).

2-p-Toluyl-[1,8]naphthyridin-3-ol (2 mg), 4-chloro-6,7-dimethoxyquinoline (6 mg), and 4-dimethylaminopyridine (3 mg) were suspended in o-dichlorobenzene (1 ml), and the suspension was stirred at 130° C. for 14.5 hr. The reaction solution was cooled to room temperature, water was then added to the reaction solution, and the mixture was extracted with chloroform. The chloroform layer was then washed with water and saturated brine and was dried over anhydrous magnesium sulfate. The solvent was removed by distillation under the reduced pressure, and the residue was purified by column chromatography using chloroform-methanol to give the title compound (0.7 mg, yield 20%).

$^1$H-NMR (CDCl$_3$, 400 MHz): δ 2.28 (s, 3H), 4.11 (s, 3H), 4.12 (s, 3H), 6.47 (d, J=5.2 Hz, 1H), 7.10 (m, 2H), 7.50 (s, 1H), 7.58 (m, 1H), 7.62 (s, 1H), 7.29 (m, 2H), 8.08 (s, 1H), 8.23 (m, 1H), 8.35 (d, J=5.2 Hz, 1H), 9.20 (m, 1H)

Mass spectrometric value (ESI-MS, m/z): 446 (M+Na)$^+$

Compound 429: 3-(6,7-Dimethoxy-quinolin-4-yloxy)-5,6,3'-trimethyl-[2,2']bipyridine 2-Bromo-3-methylpyridine (1.53 g) was dissolved in tetrahydrofuran (40 ml) under an argon atmosphere to prepare a solution. A 1.6M n-butyllithium/n-hexane solution (5.7 ml) was added dropwise to the solution at −78° C., and the mixture was then stirred at −78° C. for 30 min. A solution of 4,5-dimethylfurfural (1.00 g) in tetrahydrofuran (20 ml) was added dropwise thereto, and the temperature of the mixture was raised to room temperature while stirring. Water was added to the reaction solution to stop the reaction. The solvent was removed by distillation under the reduced pressure, water was added to the residue, and the mixture was extracted with ethyl acetate. The ethyl acetate layer was then washed with water and was dried over anhydrous sodium sulfate. The solvent was removed by distillation under the reduced pressure, and the residue was purified by column chromatography using hexane-ethyl acetate to give (4,5-dimethylfuran-2-yl)-(3-methyl-pyridin-2-yl)-methanol (1.17 g, yield 61%).

(4,5-Dimethylfuran-2-yl)-(3-methylpyridin-2-yl)-methanol (1.17 g) was dissolved in chloroform (30 ml) to prepare a solution. Manganese dioxide (4.69 g) was added to the solution, and the mixture was stirred at room temperature overnight. The reaction solution was filtered through Celite, and the solvent was removed from the filtrate by distillation under the reduced pressure to give (4,5-dimethylfuran-2-yl)-(3-methylpyridin-2-yl)-methanone (940 mg, yield 81%).

(4,5-Dimethylfuran-2-yl)-(3-methylpyridin-2-yl)-methanone (930 mg), methanol (7.5 ml), and a 28% aqueous ammonia solution (9 ml) were placed in a sealed tube and was stirred at 160° C. overnight. The reaction solution was cooled to room temperature, and the solvent was then removed by distillation under the reduced pressure, and the residue was purified by column chromatography using hexane-ethyl acetate to give 5,6,3'-trimethyl-[2,2']bipyridin-3-ol (109 mg, yield 86%).

Dimethyl sulfoxide (1.4 ml) was added to 5,6,3'-trimethyl-[2,2']bipyridin-3-ol (30 mg), 4-chloro-6,7-dimethoxyquinoline (94 mg), cesium carbonate (137 mg), and 4-(N,N-dimethylamino)-pyridine (51 mg), and the mixture was stirred at 140° C. overnight. The reaction solution was cooled to room temperature, water was then added to the reaction solution, and the mixture was extracted with ethyl acetate. The ethyl acetate layer was washed with water and was dried over anhydrous sodium sulfate. The solvent was removed by distillation under the reduced pressure, and the residue was purified by thin layer chromatography using hexane-acetone to give the title compound (29 mg, yield 52%).

$^1$H-NMR (CDCl$_3$, 400 MHz): δ 2.30 (s, 3H), 2.39 (s, 3H), 2.62 (s, 3H), 3.99 (s, 3H), 4.00 (s, 3H), 6.46 (d, J=5.4 Hz, 1H), 7.01 (dd, J=4.6, 7.8 Hz, 1H), 7.33 (s, 1H), 7.36-7.42 (m, 3H), 8.31-8.37 (m, 1H), 8.40 (d, J=5.4 Hz, 1H)

Mass spectrometric value (ESI-MS, m/z): 424 (M+Na)$^+$

Compound 430: 3-(6,7-Methoxyquinolin-4-yloxy)-6'-hydroxy-5,6-dimethyl-[2,3']bipyridine 3-Bromo-6-methoxypyridine (1.67 g) was dissolved in tetrahydrofuran (40 ml) under an argon atmosphere to prepare a solution. A 1.6 M n-butyllithium/hexane solution (5.7 ml) was added dropwise to the solution at −78° C., and the mixture was then stirred at −78° C. for 30 min. A solution of 4,5-dimethylfurfural (1.00 g) in tetrahydrofuran (20 ml) was added dropwise thereto, and the temperature of the mixture was raised to room temperature while stirring. Water was added to the reaction solution to stop the reaction, and the solvent was removed by distillation under the reduced pressure. Water was added to the residue, and the mixture was extracted with ethyl acetate. The ethyl acetate layer was then washed with water and was dried over anhydrous sodium sulfate. The solvent was removed by distillation under the reduced pressure, and the residue was purified by column chromatography using hexane-ethyl acetate to give (4,5-dimethylfuran-2-yl)-(6-methoxypyridin-3-yl)-methanol (1.24 g, yield 60%).

(4,5-Dimethylfuran-2-yl)-(6-methoxypyridin-3-yl)-methanol (1.24 g) was dissolved in chloroform (30 ml) to prepare a solution. Manganese dioxide (4.63 g) was added to the solution, and the mixture was stirred at room temperature overnight. Manganese dioxide (4.63 g) was then added to the reaction solution, and the mixture was stirred for 6 hr. The reaction solution was filtered through Celite, and the solvent was removed from the filtrate by distillation under the reduced pressure to give (4,5-dimethylfuran-2-yl)-(6-methoxypyridin-3-yl)-methanone (655 mg, yield 53%).

(4,5-Dimethylfuran-2-yl)-(6-methoxypyridin-3-yl)-methanone (650 mg), methanol (6 ml), and a 28% aqueous ammonia solution (6 ml) were placed in a sealed tube and was stirred at 160° C. overnight. The reaction solution was cooled to room temperature, the solvent was then removed by distillation under the reduced pressure, and the residue was purified by column chromatography using hexane-ethyl acetate to give 6'-methoxy-5,6-dimethyl-[2,3']bipyridin-3-ol (109 mg, yield 86%).

1,2-Dichlorobenzene (1.3 ml) was added to 6'-methoxy-5,6-dimethyl-[2,3']bipyridin-3-ol (30 mg), 4-chloro-6,7-dimethoxyquinoline (88 mg), and 4-(N,N-dimethylamino)pyridine (48 mg), and the mixture was stirred at 140° C. overnight. The reaction solution was cooled to room temperature, water was then added to the reaction solution, and the mixture was extracted with ethyl acetate. The ethyl acetate layer was washed with water and was dried over anhydrous sodium sulfate. The solvent was removed by distillation under the reduced pressure, and the residue was purified by thin layer chromatography using chloroform-methanol to give the title compound (12 mg, yield 23%).

$^1$H-NMR (CDCl$_3$, 400 MHz): δ 2.30 (s, 3H), 2.56 (s, 3H), 4.03 (s, 3H), 4.04 (s, 3H), 6.37 (d, J=5.4 Hz, 1H), 6.49 (d, J=9.5 Hz, 1H), 7.19 (s, 1H), 7.42 (s, 1H), 7.46 (s, 1H), 8.10-8.20 (m, 2H), 8.46 (d, J=5.1 Hz, 1H)

Mass spectrometric value (ESI-MS, m/z): 402 (M−1)$^-$

Compound 431: 5,6,5'-Trimethyl-3-(quinolin-4-yloxy)-[2,2']-bipyridine

Dimethyl sulfoxide (2 ml) was added to 5,6,5'-trimethyl-[2,2']bipyridin-3-ol (50 mg), 4-chloroquinoline (115 mg), and cesium carbonate (228 mg), and the mixture was stirred at 140° C. for 5 hr. The reaction solution was cooled to room temperature, water was then added to the reaction solution, and the mixture was extracted with ethyl acetate. The ethyl acetate layer was washed with water and was dried over anhydrous sodium sulfate. The solvent was removed by distillation under the reduced pressure, and the residue was purified by thin layer chromatography using chloroform-methanol to give the title compound (57 mg, yield 72%).

$^1$H-NMR (CDCl$_3$, 400 MHz): δ 2.22 (s, 3H), 2.38 (s, 3H), 2.66 (s, 3H), 6.42 (d, J=5.1 Hz, 1H), 7.34-7.39 (m, 2H), 7.54-7.60 (m, 1H), 7.72 (d, J=7.8 Hz, 1H), 7.74 (ddd, J=8.6, 7.1, 1.5 Hz, 1H), 8.05 (d, J=8.5 Hz, 1H), 8.32-8.39 (m, 2H), 8.56 (d, J=5.4 Hz, 1H)

Mass spectrometric value (ESI-MS, m/z): 342 (M+1)$^+$

Compound 432: 3-(7-Chloroquinolin-4-yloxy)-5,6,5'-trimethyl-[2,2']-bipyridine

Dimethyl sulfoxide (2 ml) was added to 5,6,5'-trimethyl-[2,2']bipyridin-3-ol (50 mg), 4,7-dichloroquinoline (139 mg), and cesium carbonate (228 mg), and the mixture was stirred at 140° C. for 5 hr. The reaction solution was cooled to room temperature, water was then added to the reaction solution, and the mixture was extracted with ethyl acetate. The ethyl acetate layer was washed with water and was dried over anhydrous sodium sulfate. The solvent was removed by distillation under the reduced pressure, and the residue was purified by thin layer chromatography using chloroform-methanol to give the title compound (77 mg, yield 94%).

$^1$H-NMR (CDCl$_3$, 400 MHz): δ 2.22 (s, 3H), 2.39 (s, 3H), 2.65 (s, 3H), 6.39 (d, J=5.4 Hz, 1H), 7.34-7.40 (m, 2H), 7.52

(dd, J=2.0, 8.8 Hz, 1H), 7.72 (d, J=8.0 Hz, 1H), 8.04 (d, J=2.2 Hz, 1H), 8.26-8.29 (m, 1H), 8.30 (d, J=9.0 Hz, 1H), 8.54 (d, J=5.4 Hz, 1H)

Mass spectrometric value (ESI-MS, m/z): 398 (M+Na)$^+$

Compound 433: 5,6,5'-Trimethyl-3-(7-trifluoromethylquinolin-4-yloxy)-[2,2']-bipyridine Dimethyl sulfoxide (2 ml) was added to 5,6,5'-trimethyl-[2,2']bipyridin-3-ol (50 mg), 4-chloro-7-trifluoromethylquinoline (162 mg), and cesium carbonate (228 mg), and the mixture was stirred at 140° C. for 5 hr. The reaction solution was cooled to room temperature, water was then added to the reaction solution, and the mixture was extracted with ethyl acetate. The ethyl acetate layer was washed with water and was dried over anhydrous sodium sulfate. The solvent was removed by distillation under the reduced pressure, and the residue was purified by thin layer chromatography using hexane-acetone to give the title compound (72 mg, yield 75%).

$^1$H-NMR (CDCl$_3$, 400 MHz): δ 2.21 (s, 3H), 2.39 (s, 3H), 2.65 (s, 3H), 6.50 (d, J=5.4 Hz, 1H), 7.36-7.42 (m, 2H), 7.72-7.79 (m, 2H), 8.22-8.27 (m, 1H), 8.35 (s, 1H), 8.50 (d, J=8.8 Hz, 1H), 8.64 (d, J=5.1 Hz, 1H)

Mass spectrometric value (ESI-MS, m/z): 432 (M+Na)$^+$

Compound 434: 6,7-Dimethoxy-4-[6-methyl-2-(1H-pyrazol-4-yl)-pyridin-3-yloxy]-quinoline N,N-Dimethylformamide (1.2 ml) and a 2 M aqueous potassium carbonate solution (1 ml) were added to 4-[(2-iodo-6-methyl-3-pyridyl)oxy]-6,7-dimethoxy-quinoline (compound 116) (50 mg), tetrakistriphenylphosphine palladium (70 mg), and 4-(4,4,5,5-tetramethyl-[1,3]dioxolan-2-ylboranyl)-1H-pyrazole (34 mg) under an argon atmosphere, and the mixture was stirred at 70° C. for 4 hr. The reaction solution was cooled to room temperature and was then filtered through Celite. The solvent was removed from the filtrate by distillation under the reduced pressure. Water was added to the residue, and the mixture was extracted with ethyl acetate. The ethyl acetate layer was then washed with water. The ethyl acetate layer was extracted with 1 N hydrochloric acid. The aqueous layer was then made alkaline by the addition of a 1 N aqueous sodium hydroxide solution and was extracted with ethyl acetate. The ethyl acetate layer was washed with water and was dried over anhydrous sodium sulfate. The solvent was removed by distillation under the reduced pressure, and the residue was purified by thin layer chromatography using hexane-acetone to give the title compound (19 mg, yield 44%).

$^1$H-NMR (CDCl$_3$, 400 MHz): δ 2.64 (s, 3H), 4.04 (s, 6H), 6.36 (d, J=5.4 Hz, 1H), 7.10 (d, J=8.3 Hz, 1H), 7.37 (d, J=8.3 Hz, 1H), 7.45 (s, 1H), 7.62 (s, 1H), 8.13 (s, 2H), 8.44 (d, J=5.4 Hz, 1H)

Mass spectrometric value (ESI-MS, m/z): 363 (M+1)$^+$

Compound 435: 3-(6,7-Methoxyquinolin-4-yloxy)-5,6,4'-trimethyl-[2,3']bipyridine

3-Bromo-4-methylpyridine (500 mg) was dissolved in tetrahydrofuran (15 ml) under an argon atmosphere to prepare a solution. A 1.6 M n-butyllithium/hexane solution (2 ml) was added dropwise to the solution at −78° C., and the mixture was then stirred at −78° C. for 30 min. A solution of 4,5-dimethylfurfural (350 mg) in tetrahydrofuran (2 ml) was added dropwise thereto, and the temperature of the reaction solution was raised to room temperature while stirring. Water was added to the reaction solution to stop the reaction, and the solvent was removed by distillation under the reduced pressure. Water was added to the residue, and the mixture was extracted with ethyl acetate. The ethyl acetate layer was then washed with water and was dried over anhydrous sodium sulfate. The solvent was removed by distillation under the reduced pressure, and the residue was purified by column chromatography using hexane-ethyl acetate to give (4,5-dimethylfuran-2-yl)-(4-methylpyridin-3-yl)-methanol (174 mg, yield 28%).

(4,5-Dimethylfuran-2-yl)-(4-methylpyridin-3-yl)-methanol (174 mg) was dissolved in chloroform (5 ml) to prepare a solution. Manganese dioxide (1.05 g) was added to the solution, and the mixture was stirred at room temperature overnight. The reaction solution was then filtered through Celite. The solvent was removed from the filtrate by distillation under the reduced pressure. The residue was purified by column chromatography using hexane-ethyl acetate to give (4,5-dimethylfuran-2-yl)-(4-methylpyridin-3-yl)-methanone (151 mg, yield 88%).

(4,5-Dimethylfuran-2-yl)-(4-methylpyridin-3-yl)-methanone (150 mg), methanol (2 ml), and a 28% aqueous ammonia solution (2 ml) were placed in a sealed tube and was stirred at 160° C. overnight. The reaction solution was cooled to room temperature, and the solvent was then removed by distillation under the reduced pressure, and the residue was purified by thin layer chromatography using hexane-acetone to give 5,6,4'-trimethyl-[2,3']bipyridin-3-ol (30 mg, yield 20%).

1,2-Dichlorobenzene (1.3 ml) was added to 5,6,4'-trimethyl-[2,3']bipyridin-3-ol (27 mg), 4-chloro-6,7-dimethoxyquinoline (85 mg), and 4-(N,N-dimethylamino)-pyridine (46 mg), and the mixture was stirred at 130° C. overnight. The reaction solution was cooled to room temperature, and the solvent was then removed by distillation under the reduced pressure. The residue was purified by thin layer chromatography using chloroform-methanol to give the title compound (44 mg, yield 87%).

$^1$H-NMR (CDCl$_3$, 400 MHz): δ 2.31 (s, 3H), 2.40 (s, 3H), 2.61 (s, 3H), 3.99 (s, 3H), 4.00 (s, 3H), 6.36 (d, J=5.1 Hz, 1H), 7.04 (d, J=5.1 Hz, 1H), 7.30 (s, 1H), 7.34 (s, 1H), 7.39 (s, 1H), 8.30 (d, J=5.1 Hz, 1H), 8.42 (d, J=5.4 Hz, 1H), 8.33 (s, 1H)

Mass spectrometric value (ESI-MS, m/z): 402 (M+1)$^+$

Compound 436: 6,7-Dimethoxy-4-(2-phenyl-[1,8] naphthyridin-3-yloxy-quinazoline 1,2-Dichlorobenzene (1 ml) was added to 2-phenyl-[1,8] naphthyridin-3-ol (10 mg), 4-chloro-6,7-dimethoxyquinazoline (30 mg), and 4-(N,N-dimethylamino)-pyridine (17 mg), and the mixture was stirred at 120° C. overnight. The reaction solution was cooled to room temperature, water was then added to the reaction solution, and the mixture was extracted with chloroform. The chloroform layer was washed with water and was dried over anhydrous sodium sulfate. The solvent was removed by distillation under the reduced pressure, and the residue was purified by thin layer chromatography using hexane-acetone to give the title compound (18 mg, yield 97%).

$^1$H-NMR (CDCl$_3$, 400 MHz): δ 4.04 (s, 3H), 4.06 (s, 3H), 7.30-7.34 (m, 4H), 7.46 (s, 1H), 7.54 (dd, J=4.2, 8.0 Hz, 1H), 7.97-8.03 (m, 2H), 8.26 (dd, J=2.0, 8.3 Hz, 1H), 8.32 (s, 1H), 8.52 (s, 1H), 9.17 (dd, J=2.0, 4.2 Hz, 1H)

Mass spectrometric value (ESI-MS, m/z): 433 (M+Na)$^+$

Compound 437: 6,7-Dimethoxy-4-(5,6,5'-trimethyl-[2,2']bipyridin-3-yloxy)-quinazoline Dimethyl sulfoxide (1.4 ml) was added to 5,6,5'-trimethyl-[2,2']bipyridin-3-ol (30 mg), 4-chloro-6,7-dimethoxyquinazoline (94 mg), and cesium carbonate (137 mg), and the mixture was stirred at 130° C. for 4 hr. The reaction solution was cooled to room temperature, water was then added to the reaction solution, the mixture was filtered, and the residue was washed with chloroform/methanol. The solvent was removed from the filtrate by distillation under the reduced pressure, water was added to the residue, and the mixture was extracted with chloroform. The chloroform layer was washed with water and was then dried over anhydrous sodium sulfate. The solvent was removed by distillation under the reduced pressure, and the residue was purified by thin layer chromatography using hexane-acetone to give the title compound (51 mg, yield 91%).

$^1$H-NMR (CDCl$_3$, 400 MHz): δ 2.20 (s, 3H), 2.39 (s, 3H), 2.62 (s, 3H), 4.04 (s, 3H), 4.05 (s, 3H), 7.27-7.30 (m, 1H), 7.40-7.45 (m, 1H), 7.47 (s, 1H), 7.57 (s, 1H), 7.80 (d, J=8.0 Hz, 1H), 8.08-8.12 (m, 1H), 8.48 (s, 1H)

Mass spectrometric value (ESI-MS, m/z): 425 (M+Na)$^+$

Compound 438: 6,7-Dimethoxy-4-[6-methyl-2-(1-methyl-1H-pyrazol-4-yl)-pyridin-3-yloxy]-quinoline 6,7-Dimethoxy-4-[6-methyl-2-(1H-pyrazol-4-yl)-pyridin-3-yloxy]-quinoline (compound 434) (30 mg) was suspended in N,N-dimethylformamide (1 ml), 60% sodium hydride (9.9 mg) was added to the suspension, and the mixture was then stirred for 30 min. Methyl iodide (18 mg) was added to the reaction solution, and the mixture was stirred for one hr. Water was added to the reaction solution to stop the reaction, and the mixture was extracted with ethyl acetate. The ethyl acetate layer was washed with water and was then dried over anhydrous sodium sulfate. The solvent was removed by distillation under the reduced pressure. The residue was purified by thin layer chromatography using hexane-acetone to give the title compound (23 mg, yield 73%).

$^1$H-NMR (CDCl$_3$, 400 MHz): δ 2.63 (s, 3H), 3.82 (s, 3H), 4.06 (s, 3H), 4.07 (s, 3H), 6.37 (d, J=5.4 Hz, 1H), 7.07 (d, J=8.3 Hz, 1H), 7.34 (d, J=8.3 Hz, 1H), 7.46 (s, 1H), 7.63 (s, 1H), 7.91 (s, 1H), 8.02 (s, 1H), 8.45 (d, J=5.1 Hz, 1H)

Mass spectrometric value (ESI-MS, m/z): 377 (M+1)$^+$

Compound 439: 6,7-Dimethoxy-4-[2-(3-methyl-butyl)-quinolin-3-yloxy]-quinoline 4-[2-(5-Chloro-4-methyl-thiophen-2-yl)-quinolin-3-yloxy]-6,7-dimethoxy-quinoline (compound 290) (7 mg) was dissolved in triethylamine/N,N-dimethylformamide (0.5 ml/1.5 ml) to prepare a solution, 20% palladium hydroxide (68 mg) was added to the solution, and the mixture was stirred under a hydrogen gas atmosphere at room temperature overnight. The reaction solution was filtered, and the solvent was then removed by distillation under the reduced pressure. Water was added to the residue, and the mixture was extracted with ethyl acetate. The ethyl acetate layer was then washed with water and was dried over anhydrous sodium sulfate. The solvent was removed by distillation under the reduced pressure, and the residue was purified by thin layer chromatography using acetone-chloroform to give the title compound (3.6 mg, yield 56%).

$^1$H-NMR (CDCl$_3$, 400 MHz): δ 0.85 (d, J=6.6 Hz, 6H), 1.46-1.84 (m, 3H), 2.96 (m, 2H), 4.06 (s, 3H), 4.08 (s, 3H), 6.45 (d, J=5.4 Hz, 1H), 7.48 (s, 1H), 7.53 (m, 1H), 7.59 (s, 1H), 7.69-7.75 (m, 2H), 7.79 (s, 1H), 8.12 (d, J=8.6 Hz, 1H), 8.52 (d, J=5.1 Hz, 1H)

Mass spectrometric value (ESI-MS, m/z): 403 (M+1)$^+$

Compound 440: 3-[6-Methoxy-7-(2-piperidin-1-yl-ethoxy)-quinolin-4-yloxy]-2-methyl-[1,8]naphthyridine 3-[7-Hydroxy-6-methoxy-quinolin-4-yloxy]-2-methyl-[1,8]naphthyridine (67 mg) was dissolved in N,N-dimethylformamide (5 ml) to prepare a solution. Potassium carbonate (225 mg) and 1-bromo-2-chloroethane (0.15 ml) were added to the solution, and the mixture was stirred at room temperature overnight. Potassium carbonate (300 mg) and piperidine (0.5 ml) were added to the reaction solution, and the mixture was further stirred at 70° C. overnight. The reaction solution was cooled to room temperature, water was then added to the reaction solution, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (69 mg, yield 78%) (2 steps).

$^1$H-NMR (CDCl$_3$, 400 MHz): δ 1.49 (m, 2H), 1.62-1.68 (m, 4H), 2.59 (m, 4H), 2.77 (s, 3H), 2.95 (t, J=6.1 Hz, 2H), 4.03 (s, 3H), 4.36 (t, J=6.1 Hz, 2H), 6.44 (d, J=5.1 Hz, 1H), 7.48 (s, 1H), 7.49 (m, 1H), 7.52 (s, 1H), 7.77 (s, 1H), 8.11 (dd, J=1.9 Hz, 8.0 Hz, 1H), 8.54 (d, J=5.1 Hz, 1H), 9.10 (dd, J=1.9 Hz, 4.2 Hz, 1H)

Mass spectrometric value (ESI-MS, m/z): 467 (M+Na)$^+$

Compound 441: 3-[6-Methoxy-7-(2-morpholin-4-yl-ethoxy)-quinolin-4-yloxy]-2-methyl-[1,8]naphthyridine 3-[7-Hydroxy-6-methoxy-quinolin-4-yloxy]-2-methyl-[1,8]naphthyridine (67 mg) was dissolved in N,N-dimethylformamide (5 ml) to prepare a solution. Potassium carbonate (225 mg) and 1-bromo-2-chloroethane (0.15 ml) were added to the solution, and the mixture was stirred at room temperature overnight. Morpholine (0.3 ml) was added to the reaction solution, and the mixture was further stirred overnight at 70° C. Potassium carbonate (354 mg) and morpholine (0.2 ml) were further added to the reaction solution, and the mixture was stirred at 70° C. overnight. The reaction solution was cooled to room temperature, water was then added to the reaction solution, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (11 mg, yield 12%) (2 steps).

$^1$H-NMR (CDCl$_3$, 400 MHz): δ 2.65 (m, 4H), 2.76 (s, 3H), 2.97 (t, J=5.9 Hz, 2H), 3.76 (m, 4H), 4.03 (s, 3H), 4.36 (t, J=6.1 Hz, 2H), 6.44 (d, J=5.2 Hz, 1H), 7.48 (s, 1H), 7.49 (m, 1H), 7.53 (s, 1H), 7.77 (s, 1H), 8.11 (dd, J=1.7 Hz, 8.1 Hz, 1H), 8.54 (d, J=5.1 Hz, 1H), 9.11 (dd, J=2.0 Hz, 4.4 Hz, 1H)

Mass spectrometric value (ESI-MS, m/z): 469 (M+Na)$^+$

Compound 442: 3-(7-Benzyloxy-6-methoxy-quinolin-4-yloxy)-5,6,6'-trimethyl-[2,2']bipyridine 5,6,6'-Trimethyl-[2,2']bipyridin-3-ol (300 mg), 7-benzyloxy-4-chloro-6-methoxyquinoline (1.26 g), 4-dimethylaminopyridine (513 mg), and cesium carbonate (1.37 g) were suspended in dimethyl sulfoxide (6 ml), and the suspension was stirred at 130° C. overnight. The reaction solution was cooled to room temperature, water was then added to the reaction solution, and the mixture was extracted with chloroform. The chloroform layer was washed with saturated brine and was dried over anhydrous sodium sulfate. The solvent was removed by distillation under the reduced pressure, and the residue was purified by column chromatography using chloroform-methanol to give the title compound (483 mg, yield 72%).

$^1$H-NMR (CDCl$_3$, 400 MHz): δ 2.19 (s, 3H), 2.38 (s, 3H), 2.64 (s, 3H), 4.03 (s, 3H), 5.31 (s, 2H), 6.31 (d, J=5.4 Hz, 1H), 6.93 (d, J=7.3 Hz, 1H), 7.30-7.65 (m, 10H), 8.33 (d, J=5.4 Hz, 1H)

Mass spectrometric value (ESI-MS, m/z): 478 (M+1)$^+$

Compound 443: 6-Methoxy-4-(5,6,6'-trimethyl-[2,2']bipyridin-3-yloxy)-quinolin-7-ol 3-(7-Benzyloxy-6-methoxy-quinolin-4-yloxy)-5,6,6'-trimethyl-[2,2']bipyridine (compound 442) (475 mg) was dissolved in trifluoroacetic acid (4.7 ml) to prepare a solution. Methanesulfonic acid (0.47 ml) was added to the solution, and the mixture was stirred at 70° C. for one hr. The reaction solution was cooled to room temperature, and the solvent was removed by distillation under the reduced pressure. An aqueous sodium hydrogencarbonate solution was then added to the residue, and the mixture was extracted with chloroform. The chloroform layer was washed with saturated brine and was dried over anhydrous sodium sulfate. The solvent was removed by distillation under the reduced pressure, and the residue was purified by column chromatography using chloroform-methanol to give the title compound (433 mg, yield 100%).

$^1$H-NMR (CDCl$_3$, 400 MHz): δ 2.17 (s, 3H), 2.39 (s, 3H), 2.64 (s, 3H), 4.06 (s, 3H), 6.31 (d, J=5.4 Hz, 1H), 6.93 (d, J=7.6 Hz, 1H), 7.38 (s, 1H), 7.47-7.66 (m, 4H), 8.36 (d, J=5.4 Hz, 1H)

Mass spectrometric value (ESI-MS, m/z): 388 (M+1)$^+$

Compound 444: 4-[4-(5,6-Dimethyl-[2,3']bipyridin-3-yloxy)-6-methoxy-quinolin-7-yloxy]-butan-1-ol 4-(5,6-Dimethyl-[2,3']bipyridin-3-yloxy)-6-methoxy-quinolin-7-ol (compound 345) (45 mg) was dissolved in N,N-dimethylformamide (2 ml) to prepare a solution. Potassium carbonate (50 mg) and 4-bromo-1-butanol (55 mg) were added to the solution, and the mixture was stirred at room temperature overnight. Water was added to the reaction solution, the mixture was extracted with ethyl acetate, and the ethyl acetate layer was then washed with saturated brine and was dried over anhydrous sodium sulfate. The solvent was removed by distillation under the reduced pressure, and the residue was purified by thin layer chromatography using chloroform-acetone to give the title compound (19 mg, yield 35%).

$^1$H-NMR (CDCl$_3$, 400 MHz): δ 1.79-1.85 (m, 2H), 2.03-2.09 (m, 2H), 2.37 (s, 3H), 2.63 (s, 3H), 3.77 (t, J=6.1 Hz, 2H), 4.01 (s, 3H), 4.25 (t, J=6.3 Hz, 2H), 6.37 (d, J=5.1 Hz, 1H), 7.21-7.25 (m, 1H), 7.31 (s, 1H), 7.44 (s, 1H), 7.46-7.48 (m, 1H), 8.16 (d, J=7.8 Hz, 1H), 8.43 (d, J=5.4 Hz, 1H), 8.49 (d, J=4.9 Hz, 1H), 9.13-9.14 (m, 1H)

Mass spectrometric value (ESI-MS, m/z): 446 (M+1)$^+$

Compound 445: 4-[4-(5,6-Dimethyl-[2,2']bipyridin-3-yloxy)-6-methoxy-quinolin-7-yloxy]-butan-1-ol 4-(5,6-Dimethyl-[2,2']bipyridin-3-yloxy)-6-methoxy-quinolin-7-ol (compound 338) (45 mg) was suspended in N,N-dimethylformamide (4 ml). Potassium carbonate (50 mg) and 4-bromo-1-butanol (55 mg) were added to the suspension, and the mixture was stirred at room temperature overnight. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-acetone to give the title compound (26 mg, yield 48%).

$^1$H-NMR (CDCl$_3$, 400 MHz): δ 1.78-1.85 (m, 2H), 2.03-2.09 (m, 2H), 2.39 (s, 3H), 2.66 (s, 3H), 3.77 (t, J=6.1 Hz, 2H), 4.01 (s, 3H), 4.25 (t, J=6.3 Hz, 2H), 6.38 (d, J=5.4 Hz, 1H), 7.10-7.13 (m, 1H), 7.37 (s, 1H), 7.42-7.61 (m, 3H), 7.79-7.83 (m, 1H), 8.38 (d, J=5.4 Hz, 1H), 8.48-8.51 (m, 1H)

Mass spectrometric value (ESI-MS, m/z): 446 (M+1)$^+$

Compound 446: 3-(6-Methoxy-7-oxiranylmethoxy-quinolin-4-yloxy)-5,6,6'-trimethyl-[2,2']bipyridine 6-Methoxy-4-(5,6,6'-trimethyl-[2,2']bipyridin-3-yloxy)-quinolin-7-ol (compound 443) (87 mg) was dissolved in N,N-dimethylformamide (4 ml) to prepare a solution, and potassium carbonate (93 mg) and epibromohydrin (0.06 ml) were added to the solution. The mixture was stirred at room temperature overnight. Water was added to the reaction solution, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (97 mg, yield 99%).

$^1$H-NMR (CDCl$_3$, 400 MHz): δ 2.17 (s, 3H), 2.39 (s, 3H), 2.64 (s, 3H), 2.83-2.85 (m, 1H), 2.95-2.97 (m, 1H), 3.49-3.53 (m, 1H), 4.02 (s, 3H), 4.14-4.20 (m, 1H), 4.43 (dd, J=3.4 Hz, 11.5 Hz, 1H), 6.32 (d, J=5.4 Hz, 1H), 6.93 (d, J=7.8 Hz, 1H), 7.38-7.67 (m, 5H), 8.35 (d, J=5.4 Hz, 1H)

Mass spectrometric value (ESI-MS, m/z): 444 (M+1)$^+$

Compound 447: 3-[6-Methoxy-4-(5,6,6'-trimethyl-[2,2']bipyridin-3-yloxy)-quinolin-7-yloxy]-propan-1-ol 6-Methoxy-4-(5,6,6'-trimethyl-[2,2']bipyridin-3-yloxy)-quinolin-7-ol (compound 443) (50 mg) was dissolved in N,N-dimethylformamide (2 ml) to prepare a solution. Potassium carbonate (54 mg) and 3-bromo-1-propanol (0.03 ml) were added to the solution, and the mixture was stirred at room temperature overnight. The solvent was removed by distillation under the reduced pressure. Water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (36 mg, yield 62%).

$^1$H-NMR (CDCl$_3$, 400 MHz): δ 2.16-2.22 (m, 2H), 2.18 (s, 3H), 2.39 (s, 3H), 2.64 (s, 3H), 3.92-3.94 (m, 2H), 4.00 (s, 3H), 4.37 (t, J=6.1 Hz, 2H), 6.33 (d, J=5.4 Hz, 1H), 6.93 (d,

J=7.6 Hz, 1H), 7.38 (s, 1H), 7.43 (s, 1H), 7.48 (t, J=7.8 Hz, 1H), 7.57 (s, 1H), 7.65-7.67 (m, 1H), 8.35 (d, J=5.4 Hz, 1H)

Mass spectrometric value (ESI-MS, m/z): 446 (M+1)$^+$

Compound 448: 2-[6-Methoxy-4-(5,6,6'-trimethyl-[2,2']bipyridin-3-yloxy)-quinolin-7-yloxymethyl]-propane-1,3-diol 6-Methoxy-4-(5,6,6'-trimethyl-[2,2']bipyridin-3-yloxy)-quinolin-7-ol (compound 443) (75 mg) was dissolved in tetrahydrofuran (2 ml) to prepare a solution. Triphenylphosphine (102 mg), (2,2-dimethyl-[1,3]dioxan-5-yl)-methanol (34 mg), and diethylazodicarboxylate (0.07 ml) were added to the solution, and the mixture was stirred at room temperature for 7 hr. Further, 1N-sulfuric acid (4 ml) was added to the reaction solution, and the mixture was stirred at room temperature overnight. The reaction solution was brought to 0° C., was stirred, and was made alkaline by the addition of a 10% aqueous sodium hydroxide solution. Water was added thereto, and the mixture was extracted with ethyl acetate. The ethyl acetate layer was then washed with saturated brine and was dried over anhydrous sodium sulfate. The solvent was removed by distillation under the reduced pressure, and the residue was purified by thin layer chromatography using chloroform-methanol to give the title compound (56 mg, yield 62%).

$^1$H-NMR (CD$_3$OD, 400 MHz): δ 2.19 (s, 3H), 2.23-2.29 (m, 1H), 2.45 (s, 3H), 2.63 (s, 3H), 3.80 (d, J=5.9 Hz, 4H), 4.00 (s, 3H), 4.24 (d, J=5.6 Hz, 2H), 6.32 (d, J=5.4 Hz, 1H), 7.04-7.06 (m, 1H), 7.30 (s, 1H), 7.57-7.65 (m, 4H), 8.24 (d, J=5.4 Hz, 1H)

Mass spectrometric value (ESI-MS, m/z): 476 (M+1)$^+$

Compound 449: 3-[6-Methoxy-4-(5,6,6'-trimethyl-[2,2']bipyridin-3-yloxy)-quinolin-7-yloxy]-propane-1,2-diol 3-(6-Methoxy-7-oxiranylmethoxy-quinolin-4-yloxy)-5,6,6'-trimethyl-[2,2']bipyridine (compound 446) (75 mg) was dissolved in methylene chloride (2 ml) to prepare a solution. The solution was brought to 0° C., trifluoroacetic acid (1 ml) was added thereto, and the mixture was stirred at 0° C. for 30 min and then at room temperature for 4 hr. The reaction solution was brought to 0° C., was stirred and was made alkaline by the addition of a 10% aqueous sodium hydroxide solution. Water was added thereto, and the mixture was extracted with chloroform. The chloroform layer was then washed with saturated brine and was dried over anhydrous sodium sulfate. The solvent was removed by distillation under the reduced pressure, and the residue was purified by thin layer chromatography using chloroform-methanol to give the title compound (48 mg, yield 61%).

$^1$H-NMR (CD$_3$OD, 400 MHz): δ 2.18 (s, 3H), 2.45 (s, 3H), 2.63 (s, 3H), 3.69-3.78 (m, 2H), 4.01 (s, 3H), 4.07-4.15 (m, 2H), 4.21-4.24 (m, 1H), 6.33 (d, J=5.4 Hz, 1H), 7.03-7.06 (m, 1H), 7.29 (s, 1H), 7.58-7.65 (m, 4H), 8.25 (d, J=5.6 Hz, 1H)

Mass spectrometric value (ESI-MS, m/z): 462 (M+1)$^+$

Compound 450: 2-[6-Methoxy-4-(5,6,6'-trimethyl-[2,2']bipyridin-3-yloxy)-quinolin-7-yloxy]-ethanol 6-Methoxy-4-(5,6,6'-trimethyl-[2,2']bipyridin-3-yloxy)-quinolin-7-ol (compound 443) (50 mg) was dissolved in N,N-dimethylformamide (2 ml) to prepare a solution. Potassium carbonate (54 mg) and 2-bromoethanol (0.03 ml) were added to the solution, and the mixture was stirred at 70° C. overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (29 mg, yield 51%).

$^1$H-NMR (CDCl$_3$, 400 MHz): δ 2.17 (s, 3H), 2.39 (s, 3H), 2.64 (s, 3H), 4.01 (s, 3H), 4.09 (t, J=4.1 Hz, 2H), 4.29 (t, J=4.9 Hz, 2H), 6.33 (d, J=5.4 Hz, 1H), 6.93 (d, J=8.1 Hz, 1H), 7.39 (s, 1H), 7.43 (s, 1H), 7.46-7.50 (m, 1H), 7.58 (s, 1H), 7.65-7.67 (m, 1H), 8.35 (d, J=5.4 Hz, 1H)

Mass spectrometric value (ESI-MS, m/z): 432 (M+1)$^+$

Compound 451: 1-{2-[6-Methoxy-4-(2-methyl-[1,8]naphthyridin-3-yloxy)-quinolin-7-yloxy]-ethyl}-piperidine 4-ol 3-[7-(2-Chloro-ethoxy)-6-methoxy-quinolin-4-yloxy]-2-methyl-[1,8]naphthyridine (compound 398) (32 mg) was suspended in N,N-dimethylformamide (2 ml). Potassium carbonate (34 mg) and 4-hydroxypiperidine (25 mg) were added to the suspension, and the mixture was stirred at 80° C. overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (22 mg, yield 60%).

$^1$H-NMR (CDCl$_3$, 400 MHz): δ 1.25-2.48 (m, 8H), 2.77 (s, 3H), 3.03 (s, 2H), 3.80 (s, 1H), 4.02 (s, 3H), 4.40 (s, 2H), 6.44 (d, J=5.1 Hz, 1H), 7.47-7.51 (m, 2H), 7.53 (s, 1H), 7.77 (s, 1H), 8.11 (dd, J=2.0 Hz, 8.3 Hz, 1H), 8.54 (d, J=5.1 Hz, 1H), 9.11 (dd, J=2.0 Hz, 4.4 Hz, 1H)

Mass spectrometric value (ESI-MS, m/z): 461 (M+1)$^+$

Compound 452: 3-(7-Benzyloxy-6-methoxy-quinolin-4-yloxy)-5,6,5'-trimethyl-[2,2']bipyridine 5,6,5'-Trimethyl-[2,2']bipyridin-3-ol (300 mg), 7-benzyloxy-4-chloro-6-methoxyquinoline (1.26 g), 4-dimethylaminopyridine (513 mg), and cesium carbonate (1.37 g) were suspended in dimethyl sulfoxide (6 ml), and the suspension was stirred at 130° C. overnight. The reaction solution was cooled to room temperature, water was then added to the reaction solution, and the mixture was extracted with chloroform. The chloroform layer was then washed with saturated brine and was dried over anhydrous sodium sulfate. The solvent was removed by distillation under the reduced pressure, and the residue was purified by column chromatography using chloroform-methanol to give the title compound (504 mg, yield 75%).

$^1$H-NMR (CDCl$_3$, 400 MHz): δ 2.24 (s, 3H), 2.37 (s, 3H), 2.65 (s, 3H), 4.04 (s, 3H), 5.32 (s, 2H), 6.35 (d, J=5.4 Hz, 1H), 7.31-7.53 (m, 8H), 7.58 (s, 1H), 7.72 (d, J=7.8 Hz, 1H), 8.33 (s, 1H), 8.35 (d, J=5.4 Hz, 1H)

Mass spectrometric value (ESI-MS, m/z): 478 (M+1)$^+$

Compound 453: 6-Methoxy-4-(5,6,5'-trimethyl-[2,2']bipyridin-3-yloxy)-quinolin-7-ol 3-(7-Benzyloxy-6-methoxy-quinolin-4-yloxy)-5,6,5'-trimethyl-[2,2']bipyridine (compound 452) (500 mg) was dissolved in trifluoroacetic acid (5 ml) to prepare a solution. Methanesulfonic acid (0.5 ml) was added to the solution, and the mixture was stirred at 70° C. for 1.5 hr. The reaction solution was cooled to room temperature, and the solvent was removed by distillation under the reduced pressure. An aqueous sodium hydrogencarbonate solution was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (358 mg, yield 88%).

$^1$H-NMR (CDCl$_3$, 400 MHz): δ 2.24 (s, 3H), 2.37 (s, 3H), 2.65 (s, 3H), 4.06 (s, 3H), 6.33 (d, J=5.4 Hz, 1H), 7.34 (s, 1H), 7.38-7.41 (m, 1H), 7.55 (s, 1H), 7.59 (s, 1H), 7.70-7.72 (m, 1H), 8.33 (s, 1H), 8.39 (d, J=5.4 Hz, 1H)

Mass spectrometric value (ESI-MS, m/z): 388 (M+1)$^+$

Compound 454: 7-Benzyloxy-4-[2-(4,5-dimethyl-thiazol-2-yl)-5,6-dimethyl-pyridin-3-yloxy]-6-methoxy-quinoline 2-(4,5-Dimethyl-thiazol-2-yl)-5,6-dimethyl-pyridin-3-ol (200 mg), 7-benzyloxy-4-chloro-6-methoxyquinoline (768 mg), 4-dimethylaminopyridine (313 mg), and cesium carbonate (313 mg) were suspended in dimethyl sulfoxide (4 ml), and the mixture was stirred at 130° C. for 9 hr. The reaction solution was cooled to room temperature, water was then added to the reaction solution, and the mixture was extracted with chloroform. The chloroform layer was washed with saturated brine and was dried over anhydrous sodium sulfate. The solvent was removed by distillation under the reduced pressure, and the residue was purified by column chromatography using chloroform-methanol to give the title compound (94 mg, yield 22%).

$^1$H-NMR (CDCl$_3$, 400 MHz): δ 2.10 (s, 3H), 2.27 (d, J=0.7 Hz, 3H), 2.35 (s, 3H), 2.63 (s, 3H), 4.07 (s, 3H), 5.35 (s, 2H), 6.32 (d, J=5.4 Hz, 1H), 7.32-7.35 (m, 2H), 7.39-7.42 (m, 2H), 7.53-7.55 (m, 3H), 7.72 (s, 1H), 8.39 (d, J=5.4 Hz, 1H)

Mass spectrometric value (ESI-MS, m/z): 498 (M+1)$^+$

Compound 455: 4-[2-(4,5-Dimethyl-thiazol-2-yl)-5,6-dimethyl-pyridin-3-yloxy]-6-methoxy-quinolin-7-ol 7-Benzyloxy-4-[2-(4,5-dimethyl-thiazol-2-yl)-5,6-dimethyl-pyridin-3-yloxy]-6-methoxy-quinoline (compound 454) (254 mg) was dissolved in trifluoroacetic acid (3 ml) to prepare a solution. Methanesulfonic acid (0.3 ml) was added to the solution, and the mixture was stirred at 70° C. for one hr. The reaction solution was cooled to room temperature, and the solvent was removed by distillation under the reduced pressure. An aqueous sodium hydrogencarbonate solution was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (189 mg, yield 91%).

$^1$H-NMR (CDCl$_3$, 400 MHz): δ 2.10 (s, 3H), 2.27 (s, 3H), 2.36 (s, 3H), 2.63 (s, 3H), 4.10 (s, 3H), 6.31 (d, J=5.4 Hz, 1H), 7.33 (s, 1H), 7.61 (s, 1H), 7.73 (s, 1H), 8.42 (d, J=5.4 Hz, 1H)

Mass spectrometric value (ESI-MS, m/z): 408 (M+1)$^+$

Compound 456: 1-{3-[7-(3-Hydroxy-propoxy)-6-methoxy-quinolin-4-yloxy]-quinolin-2-yl}-ethanone 1-[3-(7-Hydroxy-6-methoxy-quinolin-4-yloxy)-quinolin-2-yl]-ethanone (compound 390) (50 mg) was dissolved in N,N-dimethylformamide (2 ml) to prepare a solution. Potassium carbonate (58 mg) and 3-bromo-1-propanol (0.03 ml) were added to the solution, and the mixture was stirred at room temperature overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (44 mg, yield 74%).

$^1$H-NMR (CDCl$_3$, 400 MHz): δ 2.18-2.23 (m, 2H), 2.77 (s, 3H), 3.94 (t, J=5.4 Hz, 2H), 4.04 (s, 3H), 4.41 (t, J=5.8 Hz, 2H), 6.37 (d, J=5.4 Hz, 1H), 7.52 (s, 1H), 7.63 (s, 1H), 7.68-7.72 (m, 1H), 7.79-7.84 (m, 2H), 7.98 (s, 1H), 8.24 (d, J=8.5 Hz, 1H), 8.47 (d, J=5.4 Hz, 1H)

Mass spectrometric value (ESI-MS, m/z): 419 (M+1)$^+$

Compound 457: 3-(6-Methoxy-7-oxiranylmethoxy-quinolin-4-yloxy)-5,6,5'-trimethyl-[2,2']bipyridine 6-Methoxy-4-(5,6,5'-trimethyl-[2,2']bipyridin-3-yloxy)-quinolin-7-ol (compound 453) (50 mg) was suspended in N,N-dimethylformamide (2 ml). Potassium carbonate (54 mg) and epibromohydrin (0.03 ml) were added to the suspension, and the mixture was stirred at room temperature overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (58 mg, yield 100%).

$^1$H-NMR (CDCl$_3$, 400 MHz): δ 2.24 (s, 3H), 2.38 (s, 3H), 2.65 (s, 3H), 2.84-2.85 (m, 1H), 2.95-2.98 (m, 1H), 3.48-3.52 (m, 1H), 4.03 (s, 3H), 4.14-4.19 (m, 1H), 4.45 (dd, J=3.2 Hz, 11.5 Hz, 1H), 6.36 (d, J=5.4 Hz, 1H), 7.35 (s, 1H), 7.38-7.40 (m, 1H), 7.45 (s, 1H), 7.58 (s, 1H), 7.73 (d, J=8.1 Hz, 1H), 8.30 (s, 1H), 8.37 (d, J=5.4 Hz, 1H)

Mass spectrometric value (ESI-MS, m/z): 444 (M+1)$^+$

Compound 458: 4-[2-(4,5-Dimethyl-thiazol-2-yl)-5,6-dimethyl-pyridin-3-yloxy]-6-methoxy-7-oxiranyl-methoxy-quinoline 4-[2-(4,5-Dimethyl-thiazol-2-yl)-5,6-dimethyl-pyridin-3-yloxy]-6-methoxy-quinolin-7-ol (compound 455) (41 mg) was suspended in N,N-dimethylformamide (2 ml). Potassium carbonate (42 mg) and epibromohydrin (0.03 ml) were added to the supension, and the mixture was stirred at room temperature overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (44 mg, yield 94%).

¹H-NMR (CDCl₃, 400 MHz): δ 2.08 (s, 3H), 2.27 (s, 3H), 2.36 (s, 3H), 2.64 (s, 3H), 2.85-2.87 (m, 1H), 2.97-2.99 (m, 1H), 3.51-3.55 (m, 1H), 4.06 (s, 3H), 4.17-4.22 (m, 1H), 4.48 (dd, J=3.2 Hz, 11.2 Hz, 1H), 6.33 (d, J=5.4 Hz, 1H), 7.34 (s, 1H), 7.50 (s, 1H), 7.72 (s, 1H), 8.40 (d, J=5.4 Hz, 1H)

Mass spectrometric value (ESI-MS, m/z): 486 (M+Na)⁺

Compound 459: 2-[6-Methoxy-4-(5,6,5'-trimethyl-[2,2']bipyridin-3-yloxy)-quinolin-7-yloxy]-ethanol 6-Methoxy-4-(5,6,5'-trimethyl-[2,2']bipyridin-3-yloxy)-quinolin-7-ol (compound 453) (50 mg) was suspended in N,N-dimethylformamide (2 ml). Potassium carbonate (54 mg) and 2-bromoethanol (0.03 ml) were added to the suspension, and the mixture was stirred at 70° C. overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (34 mg, yield 61%).

¹H-NMR (CDCl₃, 400 MHz): δ 2.24 (s, 3H), 2.38 (s, 3H), 2.65 (s, 3H), 4.02 (s, 3H), 4.09-4.10 (m, 2H), 4.30 (t, J=4.6 Hz, 2H), 6.36 (d, J=5.4 Hz, 1H), 7.35 (s, 1H), 7.37-7.40 (m, 1H), 7.44 (s, 1H), 7.58 (s, 1H), 7.72 (d, J=8.1 Hz, 1H), 8.32 (s, 1H), 8.38 (d, J=5.1 Hz, 1H)

Mass spectrometric value (ESI-MS, m/z): 432 (M+1)⁺

Compound 460: 3-[6-Methoxy-4-(5,6,5'-trimethyl-[2,2']bipyridin-3-yloxy)-quinolin-7-yloxy]-propan-1-ol 6-Methoxy-4-(5,6,5'-trimethyl-[2,2']bipyridin-3-yloxy)-quinolin-7-ol (compound 453) (50 mg) was suspended in N,N-dimethylformamide (2 ml). Potassium carbonate (54 mg) and 3-bromo-1-propanol (0.03 ml) were added to the suspension, and the mixture was stirred at room temperature overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (26 mg, yield 46%).

¹H-NMR (CDCl₃, 400 MHz): δ 2.16-2.22 (m, 2H), 2.24 (s, 3H), 2.38 (s, 3H), 2.65 (s, 3H), 3.93 (s, 2H), 4.01 (s, 3H), 4.38 (t, J=5.9 Hz, 2H), 6.36 (d, J=5.4 Hz, 1H), 7.35 (s, 1H), 7.38-7.44 (m, 2H), 7.56 (s, 1H), 7.72 (d, J=8.1 Hz, 1H), 8.32 (s, 1H), 8.37 (d, J=5.4 Hz, 1H)

Mass spectrometric value (ESI-MS, m/z): 446 (M+1)⁺

Compound 461: 2-{4-[2-(4,5-Dimethyl-thiazol-2-yl)-5,6-dimethyl-pyridin-3-yloxy]-6-methoxy-quinolin-7-yloxy}-ethanol 4-[2-(4,5-Dimethyl-thiazol-2-yl)-5,6-dimethyl-pyridin-3-yloxy]-6-methoxy-quinolin-7-ol (compound 455) (41 mg) was suspended in N,N-dimethylformamide (2 ml). Potassium carbonate (42 mg) and 2-bromoethanol (0.02 ml) were added to the suspension, and the mixture was stirred at 70° C. overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (47 mg, yield 100%).

¹H-NMR (CDCl₃, 400 MHz): δ 2.08 (s, 3H), 2.27 (s, 3H), 2.36 (s, 3H), 2.64 (s, 3H), 4.05 (s, 3H), 4.11 (t, J=4.4 Hz, 2H), 4.33 (t, J=4.4 Hz, 2H), 6.34 (d, J=5.4 Hz, 1H), 7.34 (s, 1H), 7.52 (s, 1H), 7.72 (s, 1H), 8.41 (d, J=5.4 Hz, 1H)

Mass spectrometric value (ESI-MS, m/z): 452 (M+1)⁺

Compound 462: 3-{4-[2-(4,5-Dimethyl-thiazol-2-yl)-5,6-dimethyl-pyridin-3-yloxy]-6-methoxy-quinolin-7-yloxy}-propan-1-ol 4-[2-(4,5-Dimethyl-thiazol-2-yl)-5,6-dimethyl-pyridin-3-yloxy]-6-methoxy-quinolin-7-ol (compound 455) (41 mg) was suspended in N,N-dimethylformamide (2 ml). Potassium carbonate (42 mg) and 3-bromo-1-propanol (0.03 ml) were added to the supension, and the mixture was stirred at room temperature overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-acetone to give the title compound (32 mg, yield 68%).

¹H-NMR (CDCl₃, 400 MHz): δ 2.09 (s, 3H), 2.18-2.24 (m, 2H), 2.27 (s, 3H), 2.36 (s, 3H), 2.64 (s, 3H), 3.94-3.95 (m, 2H), 4.04 (s, 3H), 4.41 (t, J=5.9 Hz, 2H), 6.34 (d, J=5.4 Hz, 1H), 7.34 (s, 1H), 7.51 (s, 1H), 7.70 (s, 1H), 8.40 (d, J=5.4 Hz, 1H)

Mass spectrometric value (ESI-MS, m/z): 466 (M+1)⁺

Compound 463: 3-[6-Methoxy-4-(5,6,5'-trimethyl-[2,2']bipyridin-3-yloxy)-quinolin-7-yloxy]-propane-1,2-diol 3-(6-Methoxy-7-oxiranylmethoxy-quinolin-4-yloxy)-5,6,5'-trimethyl-[2,2']bipyridine (compound 457) (54 mg) was dissolved in methylene chloride (2 ml) to prepare a solution which was then brought to 0° C. Trifluoroacetic acid (1 ml) was added thereto, and the mixture was stirred at 0° C. for 30 min and then at room temperature for 5 hr. The reaction solution was brought to 0° C., was stirred and was made alkaline by the addition of a 10% aqueous sodium hydroxide solution. Water was added to the reaction solution, the mixture was extracted with chloroform, and the chloroform layer was then washed with saturated brine and was dried over anhydrous sodium sulfate. The solvent was removed by distillation under the reduced pressure, and the residue was purified by thin layer chromatography using chloroform-methanol to give the title compound (35 mg, yield 63%).

¹H-NMR (CD₃OD, 400 MHz): δ 2.24 (s, 3H), 2.44 (s, 3H), 2.62 (s, 3H), 3.69-3.78 (m, 2H), 4.02 (s, 3H), 4.06-4.15 (m, 2H), 4.21-4.24 (m, 1H), 6.34 (d, =5.4 Hz, 1H), 7.29 (s, 1H), 7.56-7.58 (m, 1H), 7.61 (s, 1H), 7.66 (s, 1H), 7.69-7.71 (m, 1H), 8.24 (s, 1H), 8.27 (d, J=5.4 Hz, 1H)

Mass spectrometric value (ESI-MS, m/z): 484 (M+Na)⁺

Compound 464: 3-{4-[2-(4,5-Dimethyl-thiazol-2-yl)-5,6-dimethyl-pyridin-3-yloxy]-6-methoxy-quinolin-7-yloxy}-propane-1,2-diol 4-[2-(4,5-Dimethyl-thiazol-2-yl)-5,6-dimethyl-pyridin-3-yloxy]-6-methoxy-7-oxiranylmethoxy-quinoline (compound 458) (40 mg) was dissolved in methylene chloride (2 ml) to prepare a solution which was then brought to 0° C. Trifluoroacetic acid (0.4 ml) was added thereto, the mixture was stirred at 0° C. for 30 min, and the mixture was then stirred at room temperature for 5 hr. The reaction solution was brought to 0° C., was stirred, and was made alkaline by the addition of a 10% aqueous sodium hydroxide solution. Water was added to the reaction solution, the mixture was extracted with chloroform, and the chloroform layer was then washed with saturated brine and was dried over anhydrous sodium sulfate. The solvent was removed by distillation under the reduced pressure, and the residue was purified by thin layer chromatography using chloroform-methanol to give the title compound (41 mg, yield 100%).

$^1$H-NMR (CD$_3$OD, 400 MHz): δ 1.98 (s, 3H), 2.27 (s, 3H), 2.40 (s, 3H), 2.60 (s, 3H), 3.71-3.80 (m, 2H), 4.04 (s, 3H), 4.10-4.19 (m, 2H), 4.25-4.28 (m, 1H), 6.34 (d, J=5.4 Hz, 1H), 7.37 (s, 1H), 7.56 (s, 1H), 7.81 (s, 1H), 8.31 (d, J=5.4 Hz, 1H)

Mass spectrometric value (ESI-MS, m/z): 504 (M+Na)

Compound 465: 3-[7-(2-Chloro-ethoxy)-6-methoxy-quinolin-4-yloxy]-5,6,6'-trimethyl-[2,2']bipyridine 6-Methoxy-4-(5,6,6'-trimethyl-[2,2']bipyridin-3-yloxy)-quinolin-7-ol (compound 443) (30 mg) was dissolved in N,N-dimethylformamide (2 ml) to prepare a solution. Potassium carbonate (107 mg) and 1-bromo-2-chloroethane (0.03 ml) were added to the solution, and the mixture was stirred at room temperature overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (37 mg, yield 100%).

$^1$H-NMR (CDCl$_3$, 400 MHz): δ 2.14 (s, 3H), 2.39 (s, 3H), 2.65 (s, 3H), 3.96 (t, J=6.1 Hz, 2H), 4.03 (s, 3H), 4.45 (t, J=5.9 Hz, 2H), 6.35 (d, J=5.4 Hz, 1H), 6.93 (d, J=7.3 Hz, 1H), 7.39 (s, 1H), 7.46-7.52 (m, 2H), 7.60 (s, 1H), 7.68 (d, J=7.8 Hz, 1H), 8.35 (d, J=5.6 Hz, 1H)

Mass spectrometric value (ESI-MS, m/z): 472 (M+Na)$^+$

Compound 466: 3-[7-(2-Chloro-ethoxy)-6-methoxy-quinolin-4-yloxy]-5,6,5'-trimethyl-[2,2']bipyridine 6-Methoxy-4-(5,6,5'-trimethyl-[2,2']bipyridin-3-yloxy)-quinolin-7-ol (compound 453) (30 mg) was suspended in N,N-dimethylformamide (2 ml). Potassium carbonate (107 mg) and 1-bromo-2-chloroethane (0.03 ml) were added to the suspension, and the mixture was stirred at room temperature overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (36 mg, yield 100%).

$^1$H-NMR (CDCl$_3$, 400 MHz): δ 2.24 (s, 3H), 2.38 (s, 3H), 2.65 (s, 3H), 3.96 (t, J=6.1 Hz, 2H), 4.03 (s, 3H), 4.45 (t, J=6.1 Hz, 2H), 6.37 (d, J=5.4 Hz, 1H), 7.35 (s, 1H), 7.38-7.40 (m, 1H), 7.44 (s, 1H), 7.59 (s, 1H), 7.73 (d, J=7.8 Hz, 1H), 8.30 (s, 1H), 8.38 (d, J=5.6 Hz, 1H)

Mass spectrometric value (ESI-MS, m/z): 472 (M+Na)$^+$

Compound 467: 1-{3-[6-Methoxy-7-(2-piperidin-1-yl-ethoxy)-quinolin-4-yloxy]-quinolin-2-yl}-ethanone 1-{3-[7-(2-Chloro-ethoxy)-6-methoxy-quinolin-4-yloxy]-quinolin-2-yl}-ethanone (41 mg) was dissolved in N,N-dimethylformamide (2 ml) to prepare a solution. Potassium carbonate (268 mg) and piperidine (0.1 ml) were added to the solution, and the mixture was stirred at 80° C. for 2 days. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (24 mg, yield 53%).

$^1$H-NMR (CDCl$_3$, 400 MHz): δ 1.23-2.64 (m, 10H), 2.77 (s, 3H), 3.01 (s, 2H), 4.03 (s, 3H), 4.39 (s, 2H), 6.36 (d, J=5.1 Hz, 1H), 7.45 (s, 1H), 7.62 (s, 1H), 7.66-7.70 (m, 1H), 7.78-7.82 (m, 2H), 7.95 (s, 1H), 8.24 (d, J=8.5 Hz, 1H), 8.48 (d, J=5.1 Hz, 1H)

Mass spectrometric value (ESI-MS, m/z): 472 (M+1)$^+$

Compound 468: 2-{2-[6-Methoxy-4-(5,6,6'-trimethyl-[2,2']bipyridin-3-yloxy)-quinolin-7-yloxy]-ethylamino}-ethanol 3-[7-(2-Chloro-ethoxy)-6-methoxy-quinolin-4-yloxy]-5,6,6'-trimethyl-[2,2']bipyridine (compound 465) (35 mg) was dissolved in N,N-dimethylformamide (2 ml) to prepare a solution. Potassium carbonate (108 mg) and 2-aminoethanol (0.14 ml) were added to the solution, and the mixture was stirred at 70° C. overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (24 mg, yield 64%).

$^1$H-NMR (CDCl$_3$, 400 MHz): δ 2.20 (s, 3H), 2.39 (s, 3H), 2.64 (s, 3H), 2.95 (t, J=5.9 Hz, 2H), 3.22 (t, J=5.1 Hz, 2H), 3.73 (t, J=5.6 Hz, 2H), 4.00 (s, 3H), 4.31 (t, J=5.1 Hz, 2H), 6.31 (d, J=5.1 Hz, 1H), 6.93 (d, J=7.6 Hz, 1H), 7.38 (d, J=4.6 Hz, 2H), 7.48 (t, J=7.6 Hz, 1H), 7.57 (s, 1H), 7.64 (d, J=7.8 Hz, 1H), 8.35 (d, J=5.1 Hz, 1H)

Mass spectrometric value (ESI-MS, m/z): 475 (M+1)$^+$

Compound 469: 2-{2-[6-Methoxy-4-(5,6,5'-trimethyl-[2,2']bipyridin-3-yloxy)-quinolin-7-yloxy]-ethylamino}-ethanol 3-[7-(2-Chloro-ethoxy)-6-methoxy-quinolin-4-yloxy]-5,6,5'-trimethyl-[2,2']bipyridine (compound 466) (33 mg) was dissolved in N,N-dimethylformamide (2 ml) to prepare a solution. Potassium carbonate (101 mg) and 2-aminoethanol (0.13 ml) were added to the solution, and the mixture was stirred at 70° C. overnight. The solvent was removed by distillation under the reduced pressure, water was then added to the residue, and the mixture was extracted with chloroform. The chloroform layer was washed with saturated brine and was dried over anhydrous sodium sulfate. The solvent was removed by distillation under the reduced pressure, and the residue was purified by thin layer chromatography using chloroform-methanol to give the title compound (25 mg, yield 71%).

$^1$H-NMR (CDCl$_3$, 400 MHz): δ 2.24 (s, 3H), 2.37 (s, 3H), 2.65 (s, 3H), 2.95 (t, J=5.1 Hz, 2H), 3.22 (t, J=5.1 Hz, 2H), 3.73 (t, J=5.1 Hz, 2H), 4.01 (s, 3H), 4.32 (t, J=5.4 Hz, 2H), 6.34 (d, J=5.1 Hz, 1H), 7.34 (s, 1H), 7.37-7.40 (m, 2H), 7.56 (s, 1H), 7.70 (d, J=8.1 Hz, 1H), 8.35-8.36 (m, 1H), 8.38 (d, J=5.4 Hz, 1H)

Mass spectrometric value (ESI-MS, m/z): 475 (M+1)$^+$

Evaluation Tests

Test Example 1

TGFβ Signal Inhibitory Activity (in vitro Test)

The TGFβ signal inhibitory activity of compounds according to the present invention was evaluated according to the method described in *J. Boil. Chem.*, 273, 21145-21152 (1998).

Specifically, a luciferase gene driving by four tandem binding sequences of Smad2/3, which are TGFβ signal transfer factors was used as a reporter gene ((SBE)4-Luc). This reporter gene was introduced into human lung cancer epithelial cells (A549) (available from ATCC) to establish a stable cell line expressing its gene.

A test compound and TGFβ-1 (2 ng/ml) were added to the cells, and the mixture was cultured for 4 hr. Compounds according to the present invention synthesized in the above working examples were used as the test compound. After the culture, the luciferase activity of cells was measured by a chemiluminescence method (Steady Glo (trademark) luciferase assay system available from Promega).

Likewise, the luciferase activity was measured for control cells, that is, cells which had been cultured with the addition of TGFβ only, and cells which had been cultured without the addition of TGFβ and the test compound.

The TGFβ inhibition rate (%) was calculated based on the results of measurement according to the following equation:

$$TGF\beta \text{ inhibition rate } (\%) = (A-B)/(A-C) \times 100$$

wherein A, B and C have the following respective meanings:

A: luciferase activity in the case where TGFβ1 was added and the test compound was not added (relative luciferase unit);

B: luciferase activity in the case where both TGFβ1 and the test compound were added (relative luciferase unit); and C: luciferase activity in the case where neither TGFβ1 nor the test compound was added (relative luciferase unit).

The test was carried out for each of a test compound concentration of 3 μM and a test compound concentration of 10 μM. For given test compounds, the test was further carried out for a test compound concentration of 1 μM.

The results were as shown in Table 1.

The results show that the compounds according to the present invention have activity which counteracts the action of TGFβ.

TABLE 1

| Compound | Molecular structure | TGFβ inhibition, % 10 μM | 3 μM |
|---|---|---|---|
| 1 | 6,7-dimethoxy-4-(2-benzylphenoxy)quinoline | 53 | 5 |
| 2 | 6,7-dimethoxy-4-[2-(prop-1-enyl)phenoxy]quinoline | 88 | 13 |
| 3 | 6,7-dimethoxy-4-(2-chloro-4-methylphenoxy)quinoline | 75 | 0 |

TABLE 1-continued

| | | | |
|---|---|---|---|
| 4 | (structure: 6,7-dimethoxyquinoline-4-yloxy linked to 2-bromo-4-methylphenyl) | 78 | 20 |
| 5 | (structure: 6,7-dimethoxyquinoline-4-yloxy linked to 2,4-dimethylphenyl; ClH) | 56 | 13 |
| 6 | (structure: 6,7-dimethoxyquinoline-4-yloxy linked to 2-(piperidinylmethyl)-4-methylphenyl) | 72 | 30 |
| 7 | (structure: 6,7-dimethoxyquinoline-4-yloxy linked to 2-styryl-4-methoxyphenyl) | 54 | 13 |
| 8 | (structure: 6,7-dimethoxyquinoline-4-yloxy linked to 2-[ethyl 2-methylacrylate]-5-methoxyphenyl) | 59 | 10 |

TABLE 1-continued
| | | | | |
|---|---|---|---|---|
| 9 | 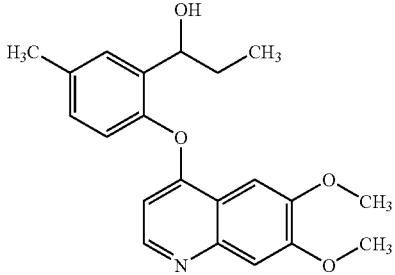 | | 77 | 29 |
| 10 | 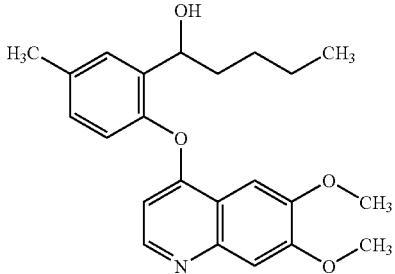 | | 87 | 38 |
| 11 | 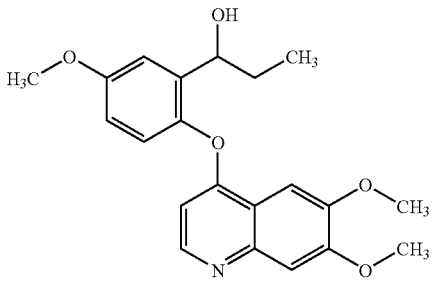 | | 66 | 28 |
| 12 | 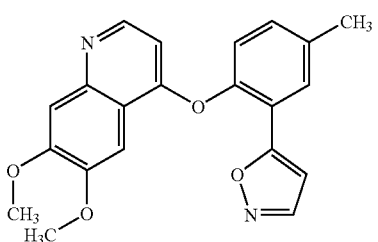 | | 89 | 21 |
| 13 | 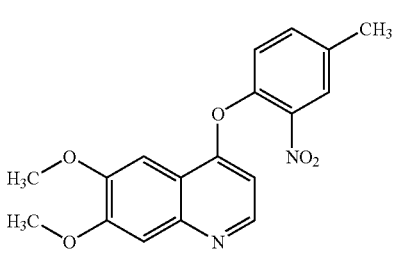 | | 78 | 28 |
| 14 | 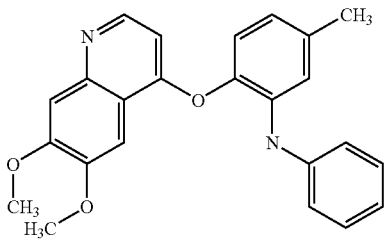 | | 64 | 15 |

TABLE 1-continued

| | | | |
|---|---|---|---|
| 15 | [structure: 6,7-dimethoxyquinoline-4-oxy-3,4-dimethylphenyl · ClH] | 84 | 41 |
| 16 | [structure: 6,7-dimethoxyquinoline-4-oxy-naphthalen-1-yl] | 62 | 0 |
| 17 | [structure: 6,7-dimethoxyquinoline-4-oxy-naphthalen-2-yl] | 80 | 15 |
| 18 | [structure: 6,7-dimethoxyquinoline-4-oxy-6-bromonaphthalen-2-yl] | 69 | 15 |
| 19 | [structure: 6,7-dimethoxyquinoline-4-oxy-fluoren-9-one-2-yl] | 95 | 73 |
| 20 | [structure: 6,7-dimethoxyquinoline-4-oxy-1-methylindol-5-yl] | 69 | 19 |

TABLE 1-continued

| | | | |
|---|---|---|---|
| 21 | (structure) | 71 | 16 |
| 22 | (structure) | 81 | 11 |
| 23 | (structure) | 91 | 56 |
| 24 | (structure) | 91 | 66 |
| 25 | | | |
| 26 | (structure) | 73 | 20 |
| 27 | (structure) | 93 | 0 |

TABLE 1-continued
| | | | |
|---|---|---|---|
| 28 | 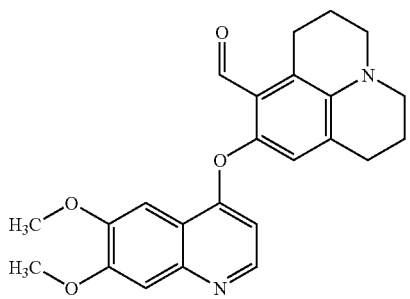 | 53 | 0 |
| 29 | 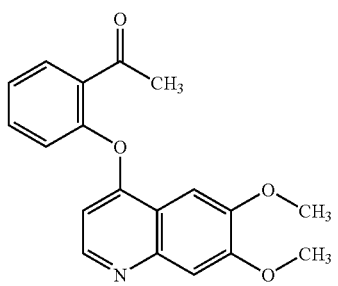 | 67 | 0 |
| 30 | 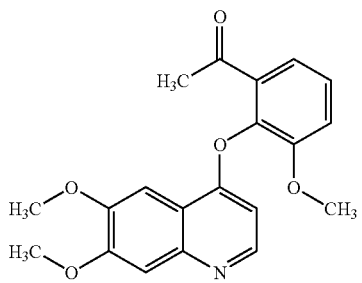 | 61 | 0 |
| 31 | 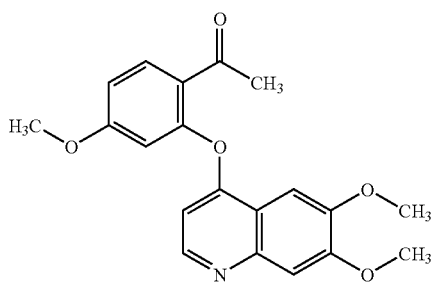 | 98 | 49 |
| 32 | 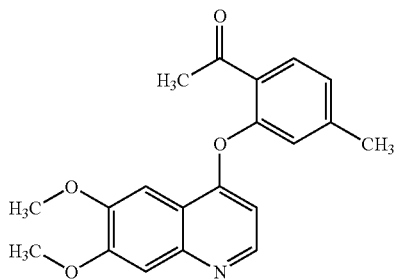 | 98 | 81 |

TABLE 1-continued

| | | | |
|---|---|---|---|
| 33 | (structure) | 94 | 27 |
| 34 | (structure) | 78 | 0 |
| 35 | (structure) | 89 | 49 |
| 36 | (structure) | 100 | 95 |
| 37 | (structure) | 100 | 94 |

TABLE 1-continued
| | | | |
|---|---|---|---|
| 38 | 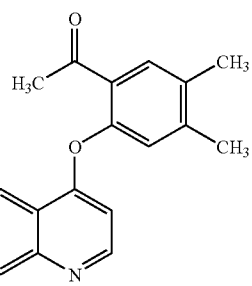 | 100 | 98 |
| 39 | 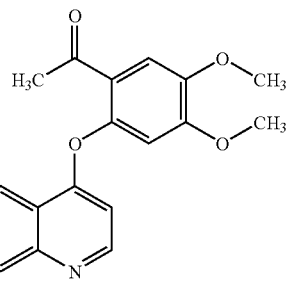 | 91 | 0 |
| 40 | 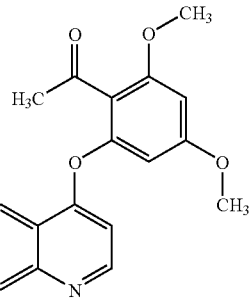 | 83 | 12 |
| 41 | 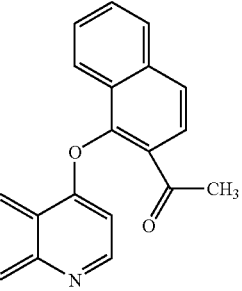 | 97 | 57 |
| 42 | 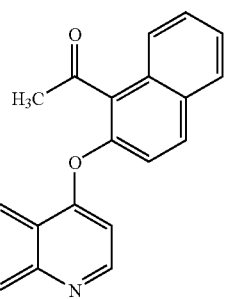 | 93 | 90 |

TABLE 1-continued

| | Structure | | |
|---|---|---|---|
| 43 | (6,7-dimethoxyquinolin-4-yl)oxy phenyl propan-1-one, 3-F | 66 | 0 |
| 44 | (6,7-dimethoxyquinolin-4-yl)oxy phenyl propan-1-one, 4-OCH3 | 100 | 97 |
| 45 | (6,7-dimethoxyquinolin-4-yl)oxy phenyl propan-1-one, 4-OBn | 67 | 0 |
| 46 | (6,7-dimethoxyquinolin-4-yl)oxy phenyl propan-1-one, 4-Cl | 100 | 70 |
| 47 | (6,7-dimethoxyquinolin-4-yl)oxy phenyl propan-1-one, 4-I | 98 | 45 |

TABLE 1-continued

| # | Structure | | |
|---|---|---|---|
| 48 | (structure) | 100 | 98 |
| 49 | (structure) | 62 | 0 |
| 50 | (structure) | 100 | 100 |
| 51 | (structure) | 99 | 71 |
| 52 | (structure) | 100 | 97 |

TABLE 1-continued
| | | | |
|---|---|---|---|
| 53 | 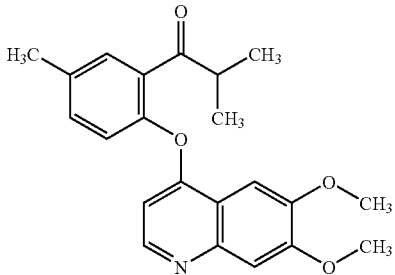 | 100 | 97 |
| 54 | 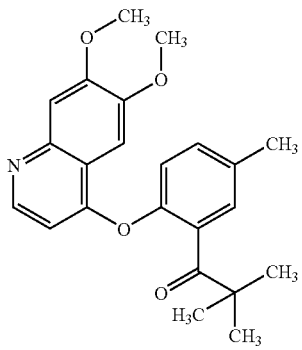 | 73 | 13 |
| 55 | 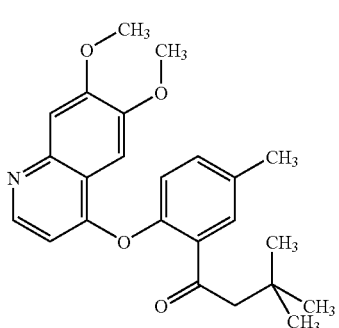 | 98 | 53 |
| 56 | 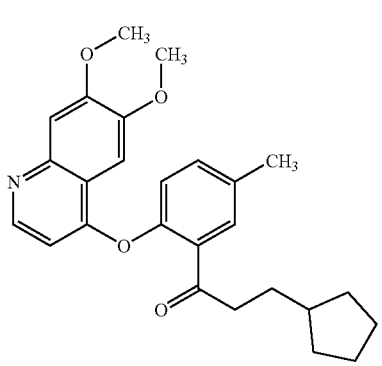 | 84 | 0 |
| 57 | 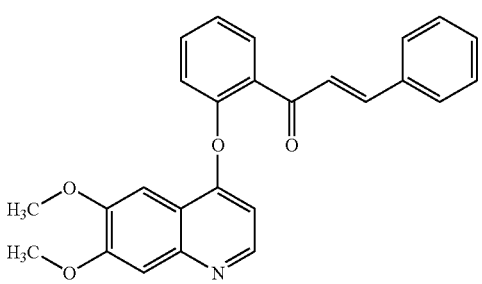 | 55 | 10 |

TABLE 1-continued
| | | | |
|---|---|---|---|
| 58 | 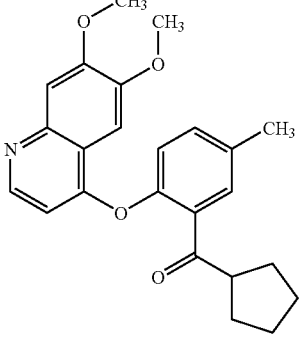 | 100 | 90 |
| 59 | 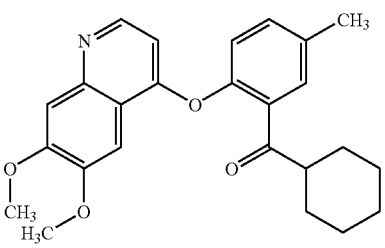 | 99 | 65 |
| 60 | 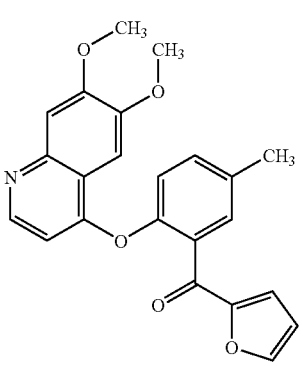 | 98 | 63 |
| 61 | 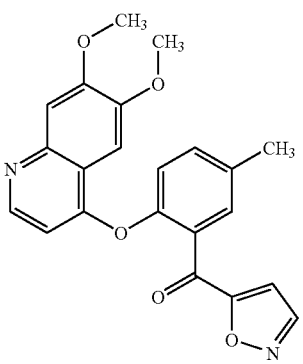 | 98 | 61 |
| 62 | 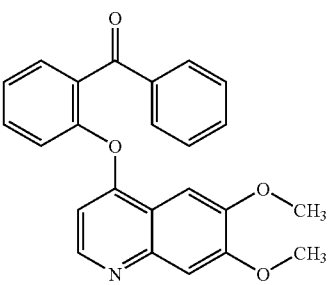 | 85 | 43 |

TABLE 1-continued

| | | | |
|---|---|---|---|
| 63 | (structure) ClH | 91 | 57 |
| 64 | (structure) | 98 | 67 |
| 65 | (structure) | 100 | 58 |
| 66 | (structure) | 86 | 22 |
| 67 | (structure) | 93 | 4 |

TABLE 1-continued
| | | | |
|---|---|---|---|
| 68 | 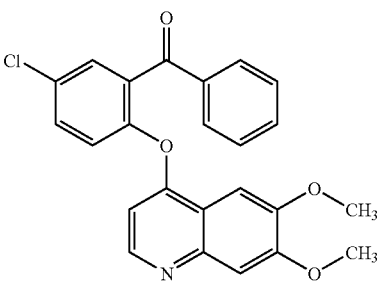 | 100 | 89 |
| 69 | 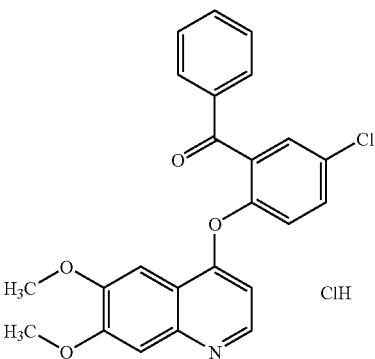 ClH | 100 | 100 |
| 70 | 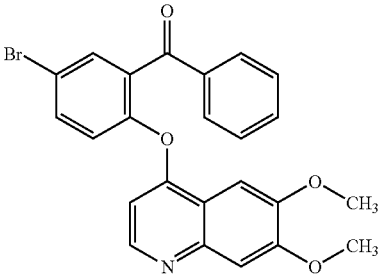 | 100 | 73 |
| 71 | 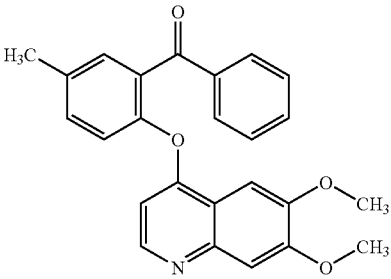 | 100 | 79 |
| 72 | 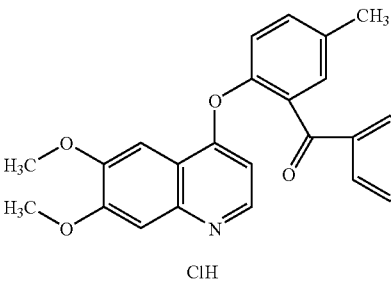 ClH | 100 | 98 |

TABLE 1-continued

| | | | |
|---|---|---|---|
| 73 | [structure] | 81 | 24 |
| 74 | [structure] | 84 | 27 |
| 75 | [structure] | 100 | 97 |
| 76 | [structure] ClH | 100 | 95 |
| 77 | [structure] | 46 | 0 |

TABLE 1-continued
| 78 | 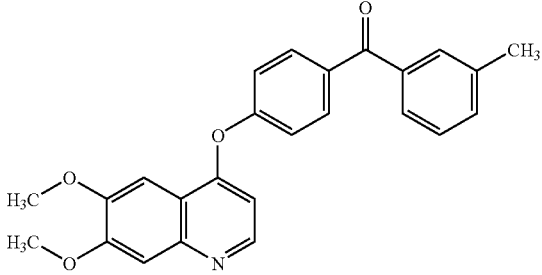 | 57 | 0 |
| 79 | 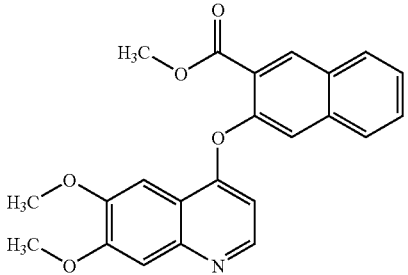 | 100 | 97 |
| 80 | 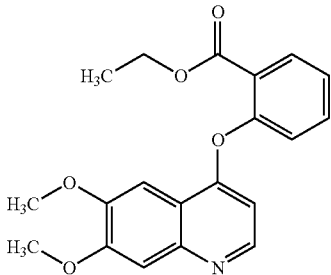 | 95 | 62 |
| 81 | 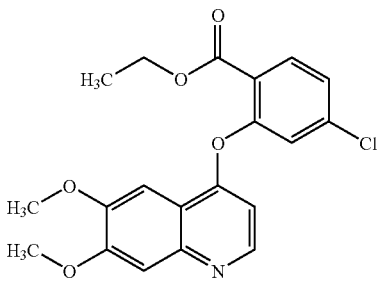 | 100 | 91 |
| 82 | 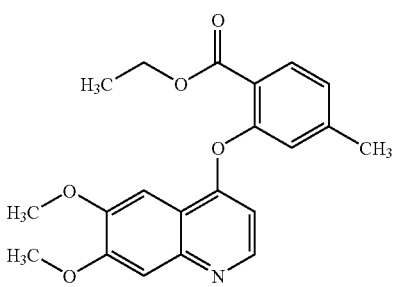 | 99 | 90 |

TABLE 1-continued

| | | | |
|---|---|---|---|
| 83 | [structure: ethyl 5-fluoro-2-((6,7-dimethoxyquinolin-4-yl)oxy)benzoate] | 81 | 41 |
| 84 | [structure: ethyl 5-chloro-2-((6,7-dimethoxyquinolin-4-yl)oxy)benzoate] | 100 | 84 |
| 85 | [structure: ethyl 5-bromo-2-((6,7-dimethoxyquinolin-4-yl)oxy)benzoate] | 100 | 87 |
| 86 | [structure: ethyl 5-iodo-2-((6,7-dimethoxyquinolin-4-yl)oxy)benzoate] | 99 | 68 |
| 87 | [structure: ethyl 5-methyl-2-((6,7-dimethoxyquinolin-4-yl)oxy)benzoate] | 99 | 84 |

TABLE 1-continued
| | | | |
|---|---|---|---|
| 88 | 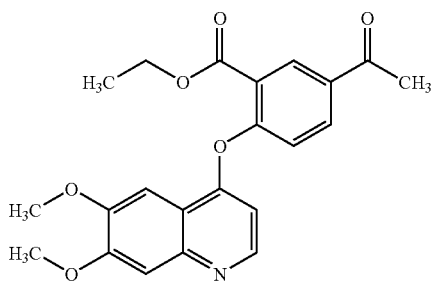 | 94 | 70 |
| 89 | 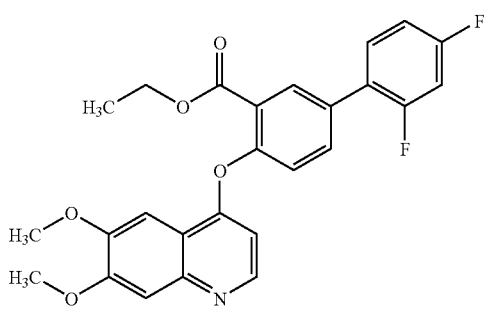 | 63 | 20 |
| 90 | 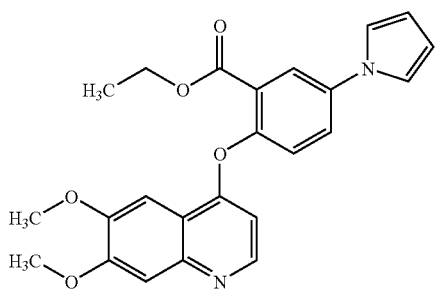 | 95 | 54 |
| 91 | 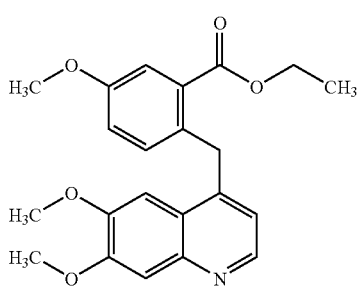 | 100 | 96 |
| 92 | 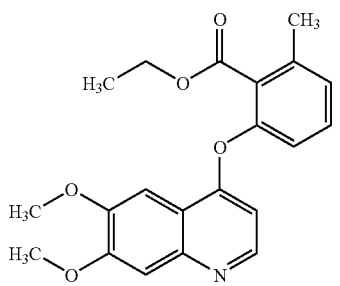 | 82 | 25 |

TABLE 1-continued

| # | Structure | | |
|---|---|---|---|
| 93 | [isopropyl 2-((6,7-dimethoxyquinolin-4-yl)oxy)benzoate] | 88 | 44 |
| 94 | [propyl 2-((6,7-dimethoxyquinolin-4-yl)oxy)benzoate] | 97 | 39 |
| 95 | [propyl 5-acetyl-2-((6,7-dimethoxyquinolin-4-yl)oxy)benzoate] | 96 | 67 |
| 96 | [propyl 4-((6,7-dimethoxyquinolin-4-yl)oxy)-2',4'-difluoro-[1,1'-biphenyl]-3-carboxylate] | 65 | 19 |
| 97 | [isobutyl 2-((6,7-dimethoxyquinolin-4-yl)oxy)benzoate] | 92 | 14 |

TABLE 1-continued

| # | Structure | A | B |
|---|---|---|---|
| 98 | 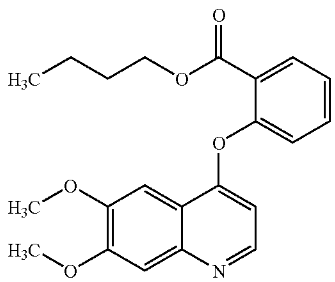 | 93 | 4 |
| 99 | 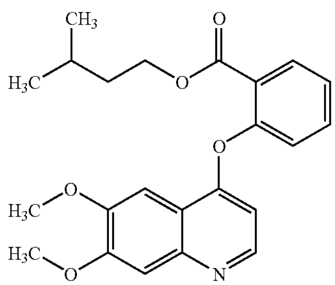 | 92 | 7 |
| 100 | 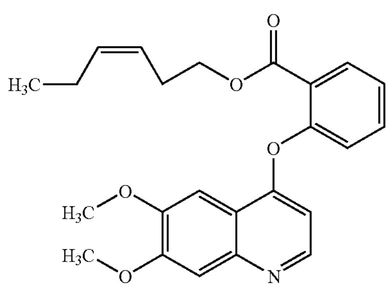 | 82 | 0 |
| 101 | 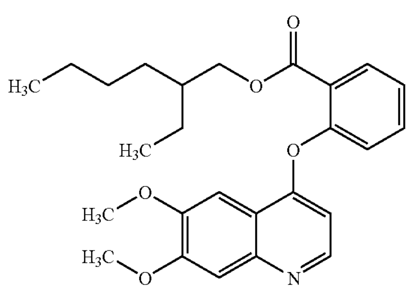 | 64 | 0 |
| 102 | 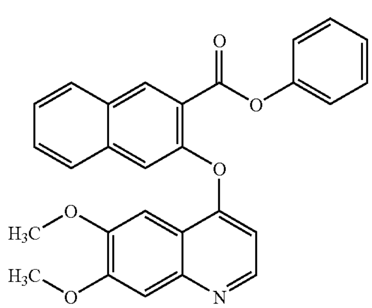 | 95 | 33 |

TABLE 1-continued

| | | | |
|---|---|---|---|
| 103 | [structure] | 84 | 20 |
| 104 | [structure] | 58 | 0 |
| 105 | [structure] | 88 | 17 |
| 106 | [structure] | 80 | 9 |
| 107 | [structure] | 82 | 0 |

TABLE 1-continued

| | | | |
|---|---|---|---|
| 108 | (structure) | 73 | 0 |
| 109 | (structure) | 66 | 5 |
| 110 | (structure) | 93 | 55 |
| 111 | (structure) | 92 | 29 |
| 112 | (structure) | 91 | 44 |

TABLE 1-continued

| | | | |
|---|---|---|---|
| 113 | (structure) | 96 | 0 |
| 114 | (structure) | 96 | 0 |
| 115 | (structure) | 97 | 74 |
| 116 | (structure) | 100 | 99 |
| 117 | (structure) | 98 | 84 |

TABLE 1-continued
| | | | |
|---|---|---|---|
| 118 | 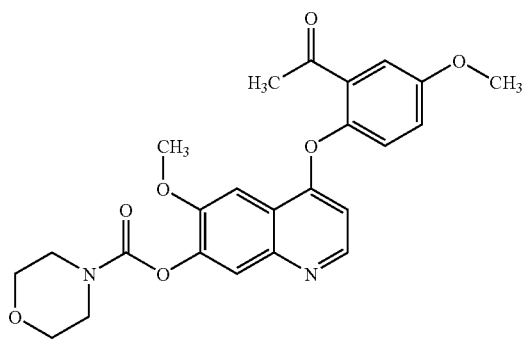 | 100 | 97 |
| 119 | 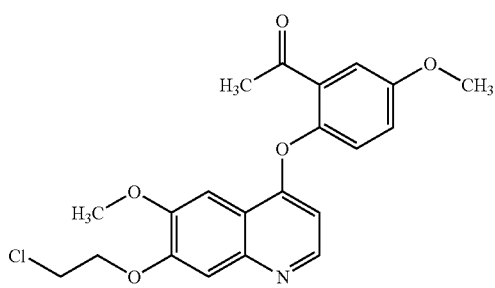 | 97 | 96 |
| 120 | 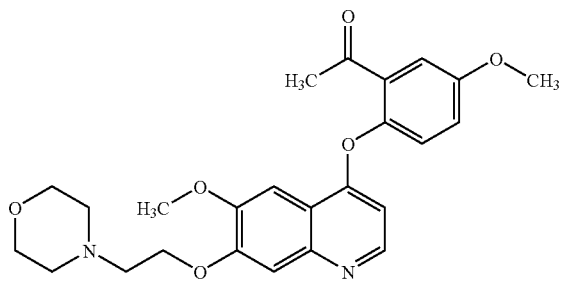 | 100 | 94 |
| 121 | 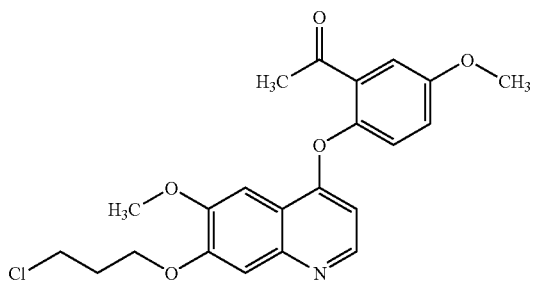 | 100 | 100 |
| 122 | 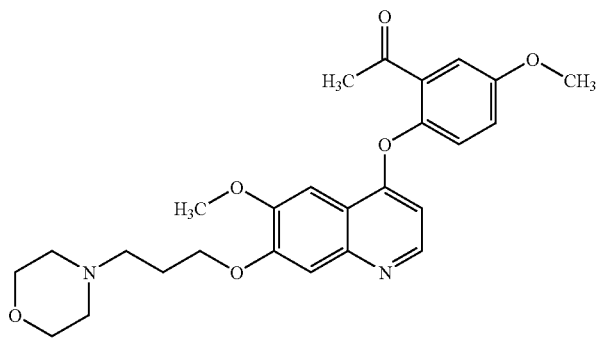 | 100 | 100 |

TABLE 1-continued
| | | | |
|---|---|---|---|
| 123 | 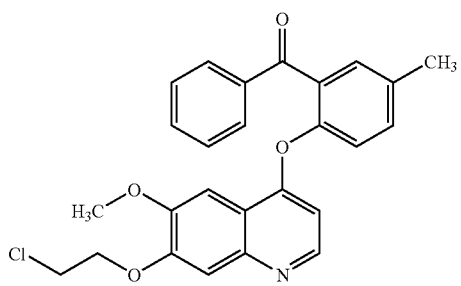 | 100 | 98 |
| 124 | 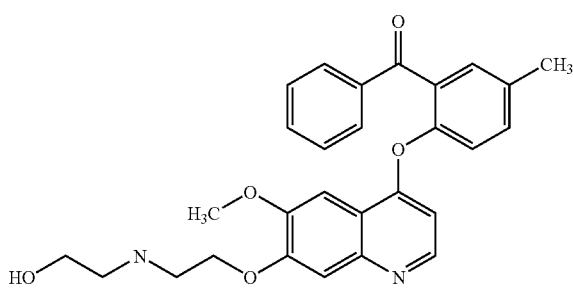 | 100 | 99 |
| 125 | 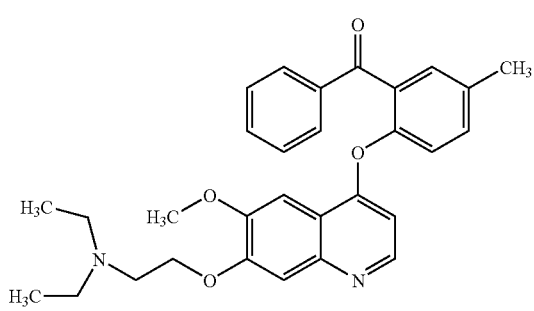 | 100 | 98 |
| 126 | 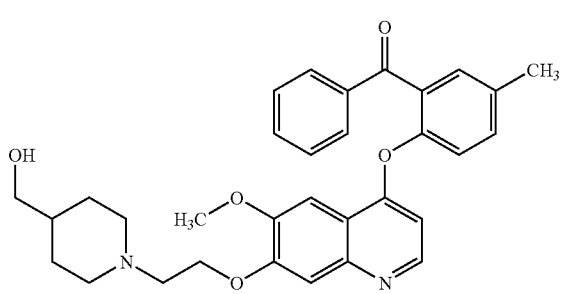 | 100 | 100 |
| 127 | 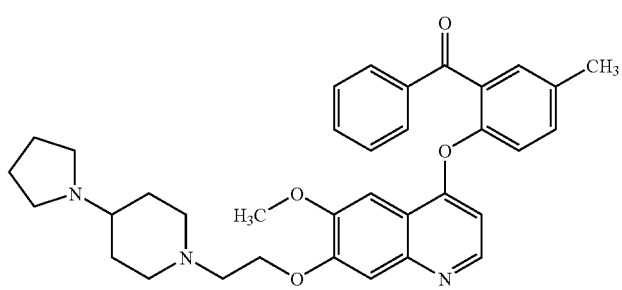 | 100 | 99 |

TABLE 1-continued
| | | | | |
|---|---|---|---|---|
| 128 | 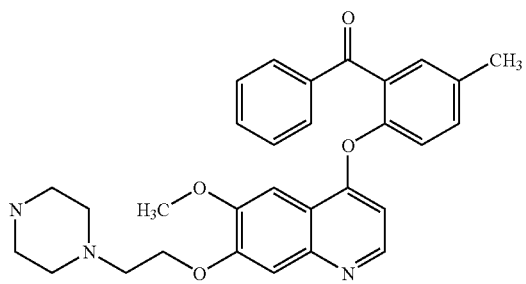 | | 100 | 100 |
| 129 | 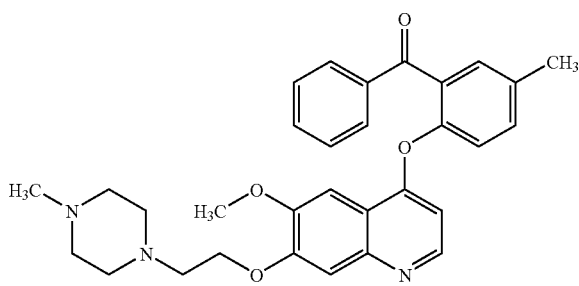 | | 100 | 100 |
| 130 | 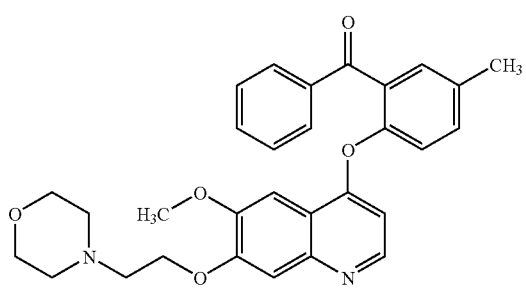 | | 100 | 90 |
| 131 | 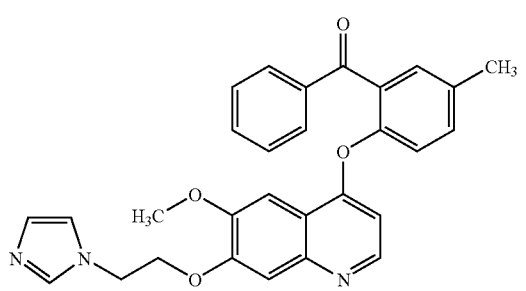 | | 100 | 96 |
| 132 | 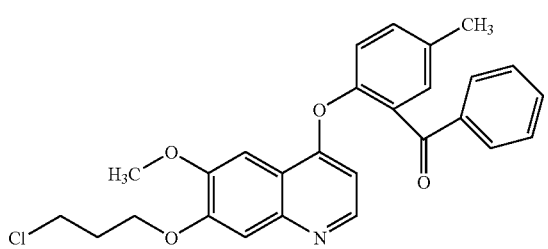 | | 99 | 72 |

TABLE 1-continued

| | | | |
|---|---|---|---|
| 133 | (structure) | 100 | 100 |
| 134 | (structure) | 100 | 100 |
| 135 | (structure) | 100 | 100 |
| 136 | (structure) | 100 | 90 |
| 137 | (structure) | 100 | 100 |

TABLE 1-continued
| 138 | 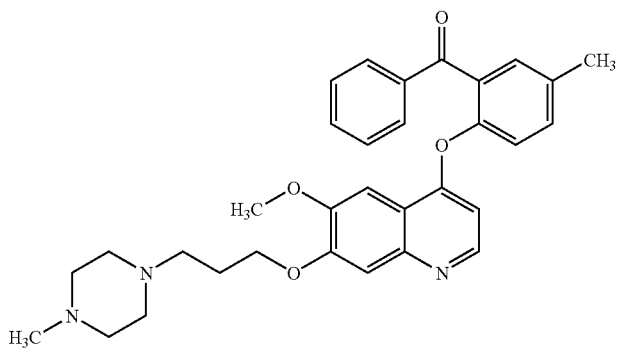 | 100 | 96 |
| 139 | 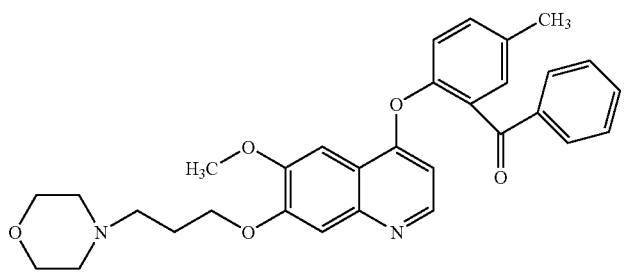 | 100 | 99 |
| 140 | 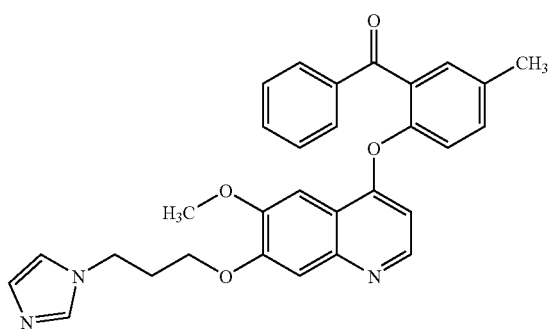 | 100 | 85 |
| 141 | 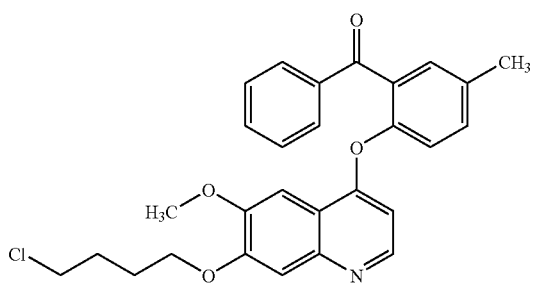 | 89 | 55 |
| 142 | 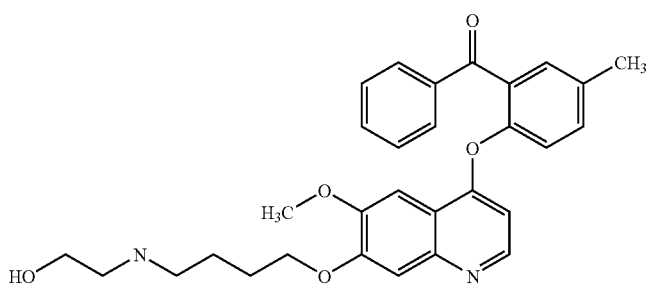 | 100 | 100 |

TABLE 1-continued

| | | | |
|---|---|---|---|
| 143 | (structure) | 100 | 97 |
| 144 | (structure) | 100 | 99 |
| 145 | (structure) | 100 | 87 |
| 146 | (structure) | 100 | 64 |
| 147 | (structure) | 100 | 98 |
| 148 | (structure) | 100 | 99 |

TABLE 1-continued
| | | | |
|---|---|---|---|
| 149 | 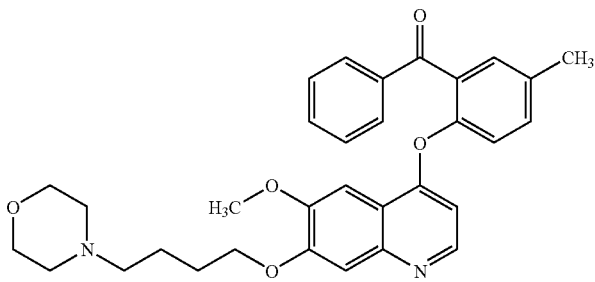 | 100 | 96 |
| 150 | 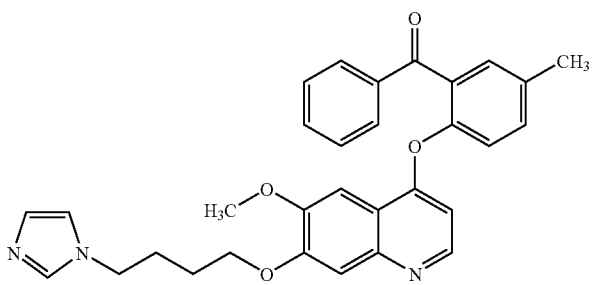 | 100 | 97 |
| 151 | 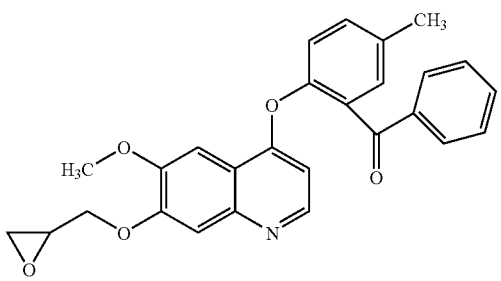 | 100 | 95 |
| 152 | 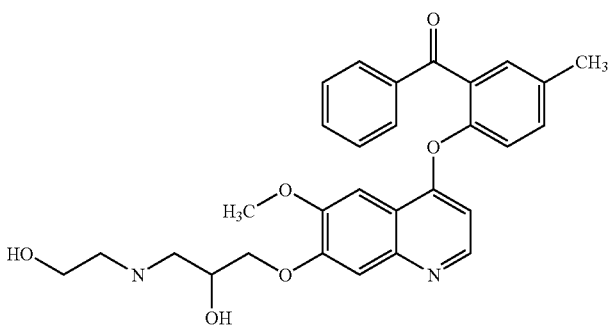 | 100 | 99 |
| 153 | 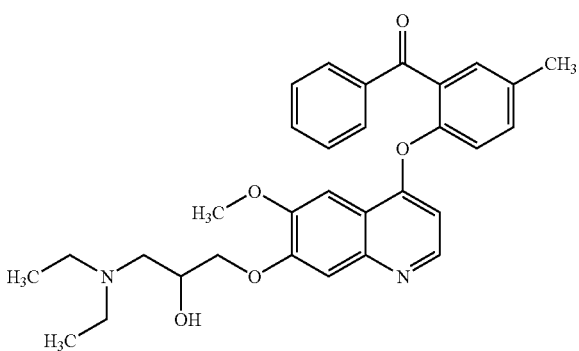 | 100 | 100 |

TABLE 1-continued
| | | | |
|---|---|---|---|
| 154 | 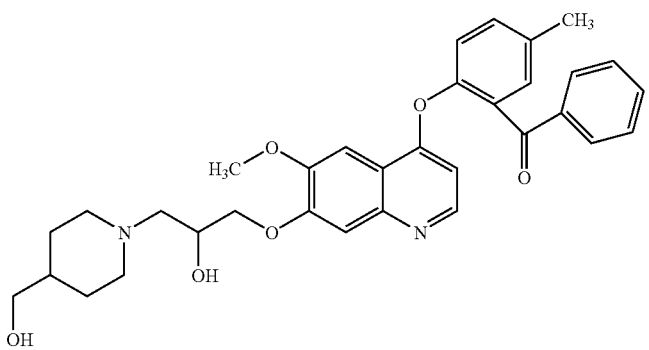 | 100 | 99 |
| 155 | 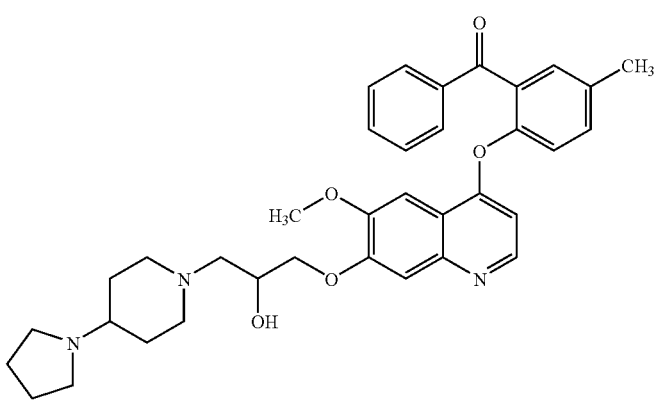 | 100 | 100 |
| 156 | 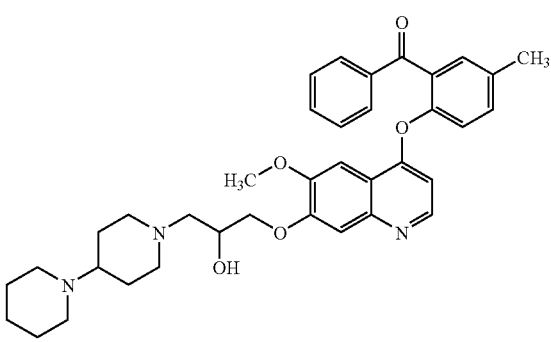 | 100 | 99 |
| 157 | 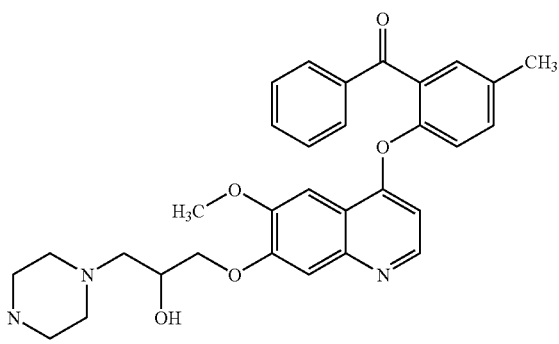 | 100 | 100 |

TABLE 1-continued
| | | | |
|---|---|---|---|
| 158 | 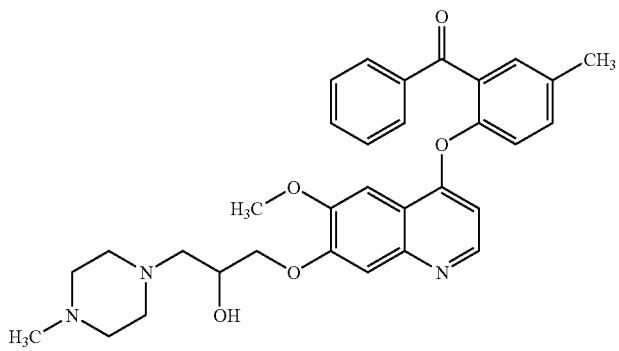 | 100 | 100 |
| 159 | 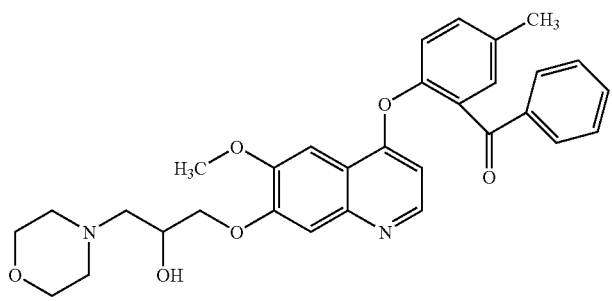 | 100 | 98 |
| 160 | 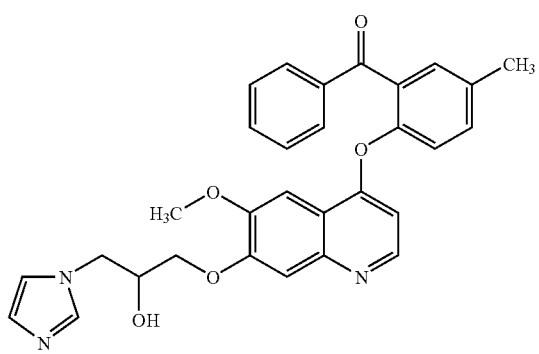 | 100 | 98 |
| 161 | 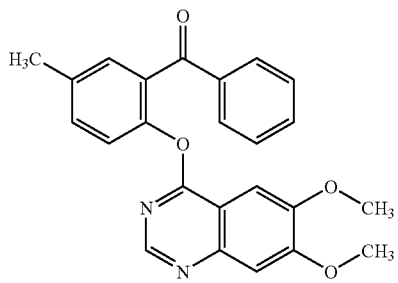 | 83 | 25 |
| 162 | 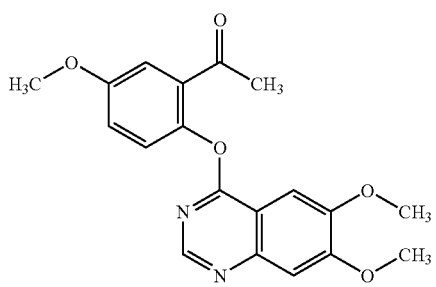 | 54 | 5 |

TABLE 1-continued

| Compound | Molecular structure | TGFβ inhibition, % | | |
|---|---|---|---|---|
| | | 10 μM | 3 μM | 1 μM |
| 163 | | | 67 | 3 |
| 164 | 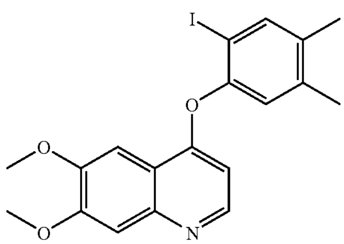 | 98 | 54 | |
| 165 | 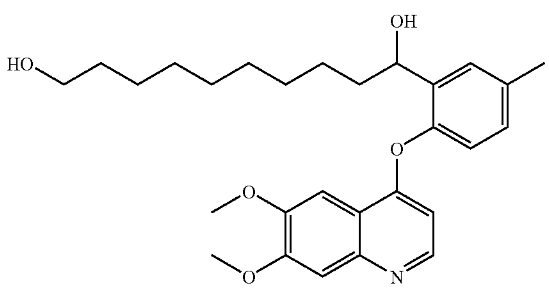 | 89 | 38 | |
| 166 | 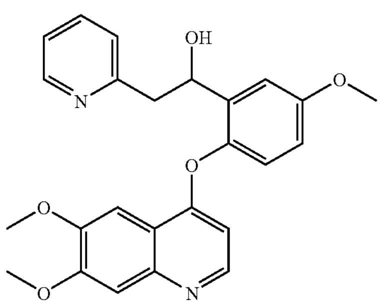 | 67 | 24 | |
| 167 | 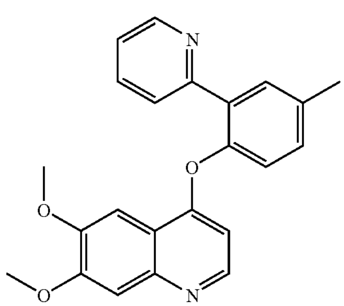 | 100 | 98 | |

TABLE 1-continued
| 168 | 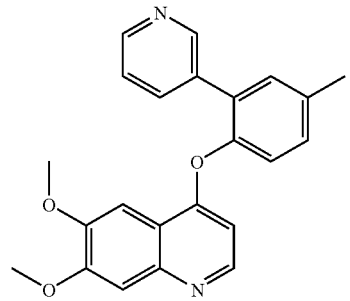 | 74 | 22 |
| 169 | 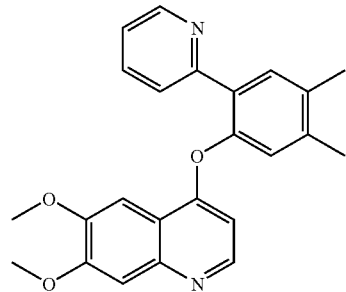 | 100 | 99 |
| 170 | 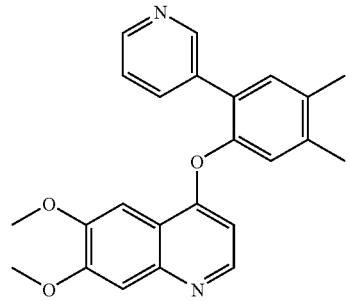 | 100 | 76 |
| 171 | 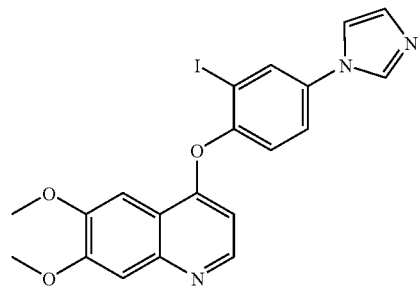 | 76 | 11 |
| 172 | 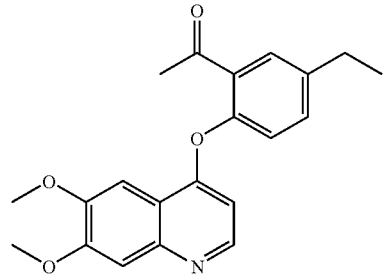 | 99 | 82 |

TABLE 1-continued

| Compound | Molecular structure | 10 μM | 3 μM |
|---|---|---|---|
| 173 | [6,7-dimethoxyquinolin-4-yloxy linked to 2-acetyl-4-propylphenyl] | 100 | 83 |
| 174 | [6,7-dimethoxyquinolin-4-yloxy linked to 2-acetyl-4-butylphenyl] | 96 | 57 |
| 175 | [6,7-dimethoxyquinolin-4-yloxy linked to 2-acetyl-4-benzyloxyphenyl] | 60 | 13 |

| | | TGFβ inhibition, % | | |
|---|---|---|---|---|
| Compound | Molecular structure | 10 μM | 3 μM | 1 μM |
| 176 | [6,7-dimethoxyquinolin-4-yloxy linked to 2-acetyl-4-hydroxyphenyl] | 67 | 32 | |

-continued

| Compound | Molecular structure | TGFβ inhibition, % | | |
|---|---|---|---|---|
| | | 10 μM | 3 μM | 1 μM |
| 177 | 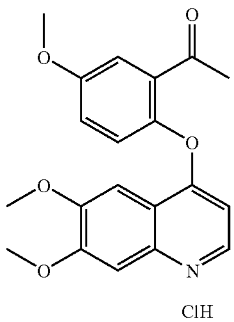 | 100 | 94 | |
| 178 | 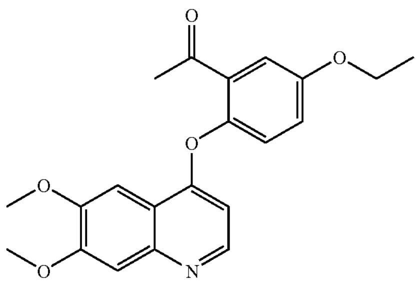 | 97 | 66 | |
| 179 | 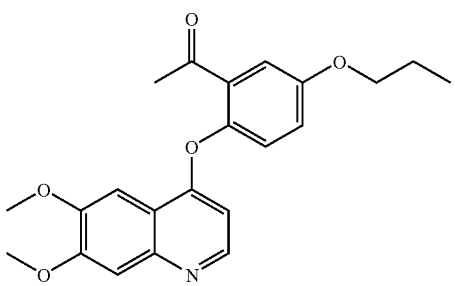 | 68 | 18 | |
| 180 | 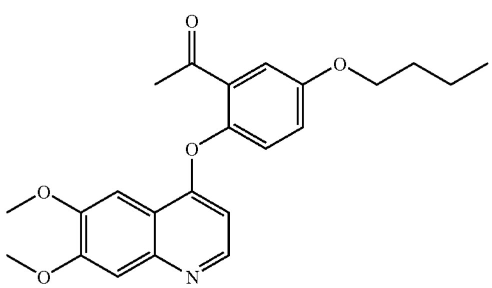 | 55 | −2 | |
| 181 | 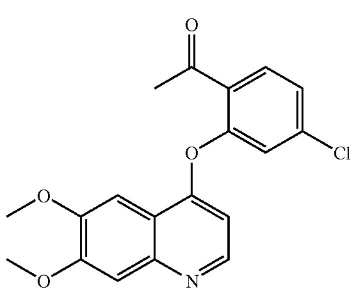 | 82 | 42 | |

-continued

| Compound | Molecular structure | TGFβ inhibition, % | | |
|---|---|---|---|---|
| | | 10 μM | 3 μM | 1 μM |
| 182 | 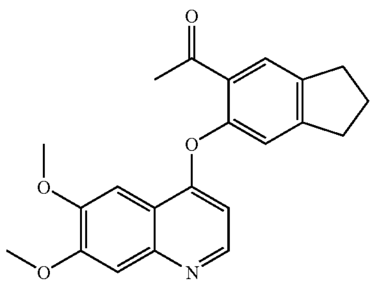 | 96 | 57 | |
| 183 | 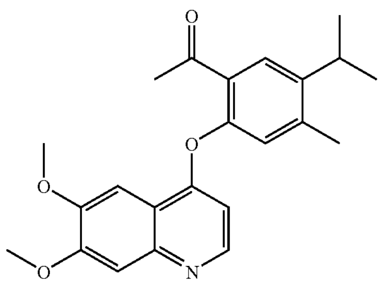 | 100 | 82 | |
| 184 | 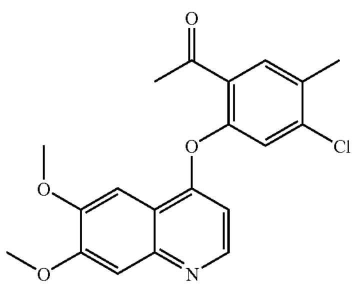 | 100 | 100 | |
| 185 | 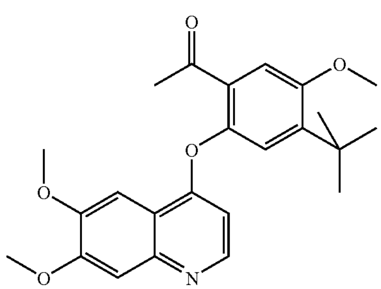 | 59 | 11 | |
| 186 | 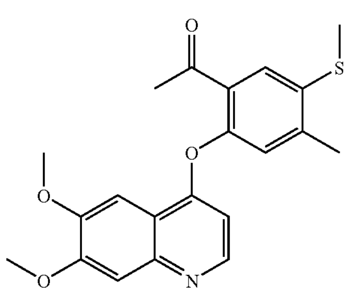 | 100 | 76 | |

-continued

| Compound | Molecular structure | TGFβ inhibition, % | | |
|---|---|---|---|---|
| | | 10 μM | 3 μM | 1 μM |
| 187 | 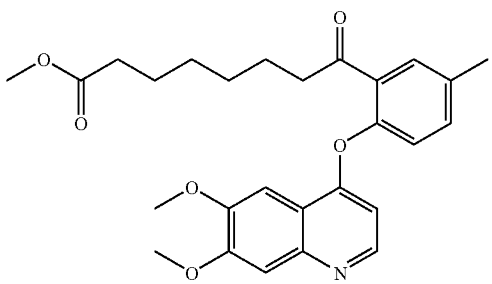 | 91 | 35 | |
| 188 | 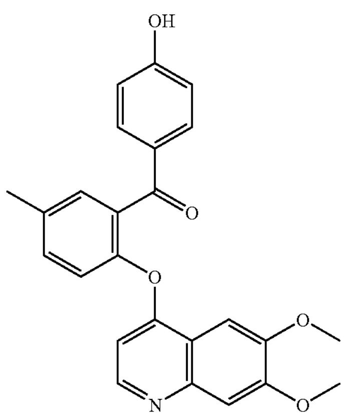 | 100 | 80 | |
| 189 | 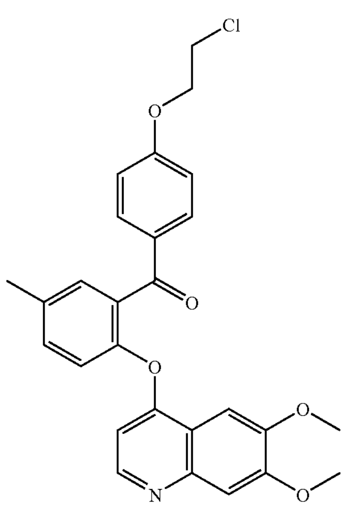 | 100 | 86 | |

| Compound | Molecular structure | TGFβ inhibition, % | | |
|---|---|---|---|---|
| | | 10 μM | 3 μM | 1 μM |
| 190 | 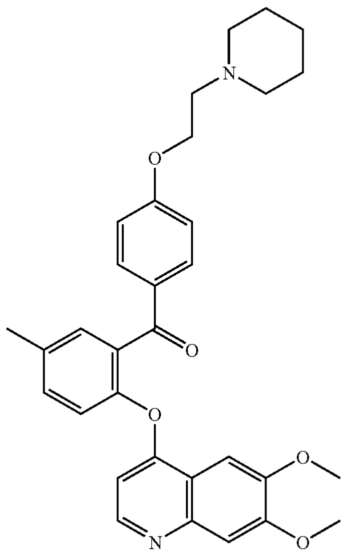 | 86 | 30 | |
| 191 | 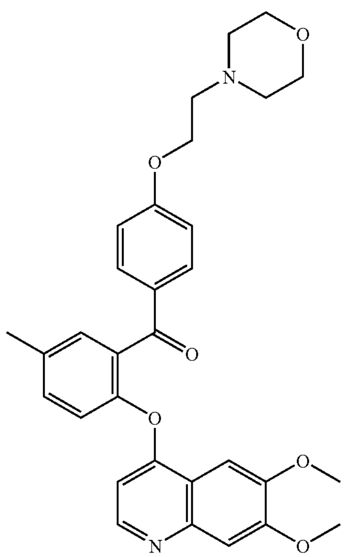 | 93 | 39 | |
| 192 | 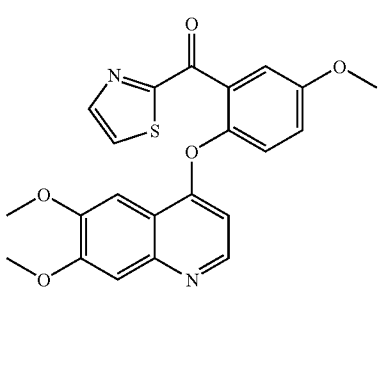 | 99 | 79 | |

-continued

| Compound | Molecular structure | TGFβ inhibition, % | | |
|---|---|---|---|---|
| | | 10 μM | 3 μM | 1 μM |
| 193 | 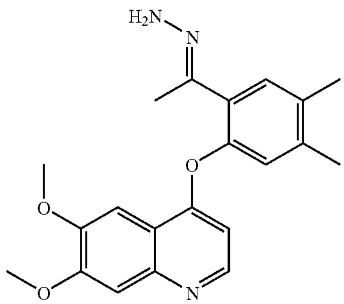 | 99 | 74 | |
| 194 | 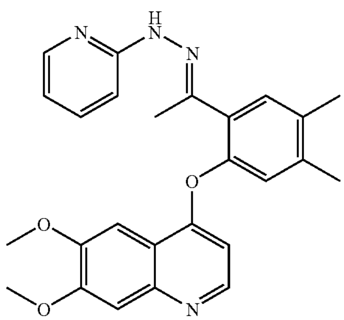 | 94 | 47 | |
| 195 | 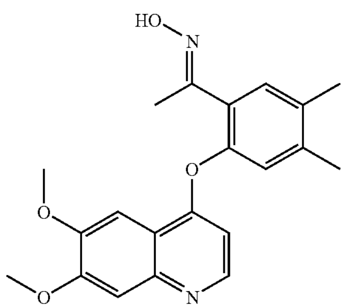 | 100 | 99 | |
| 196 | 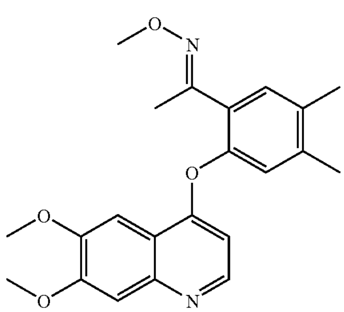 | 83 | 41 | |
| 197 | 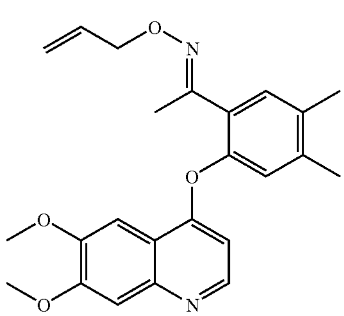 | 88 | 40 | |

-continued
| Compound | Molecular structure | TGFβ inhibition, % | | |
|---|---|---|---|---|
| | | 10 μM | 3 μM | 1 μM |
| 198 | 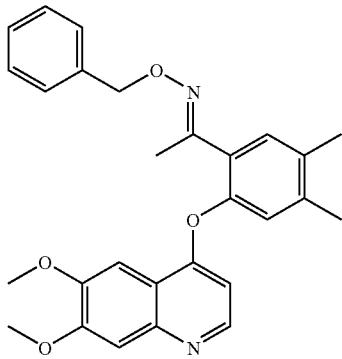 | 80 | 32 | |
| 199 | 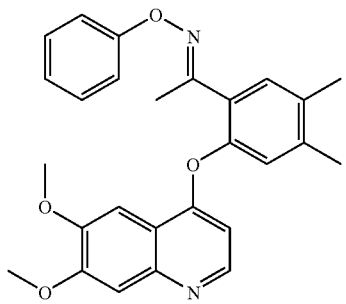 | 59 | 14 | |
| 200 | 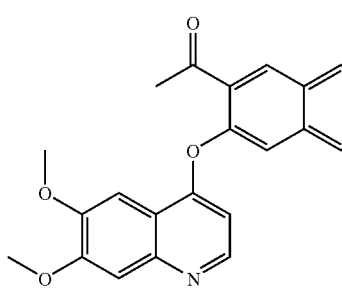 | 100 | 94 | |
| 201 | 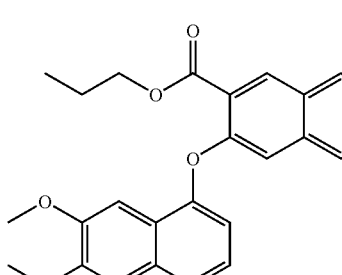 | 100 | 79 | |
| 202 | 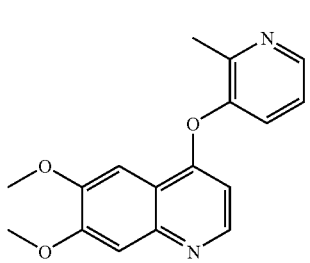 | 54 | 20 | |

-continued

| Compound | Molecular structure | TGFβ inhibition, % | | |
|---|---|---|---|---|
| | | 10 μM | 3 μM | 1 μM |
| 203 | 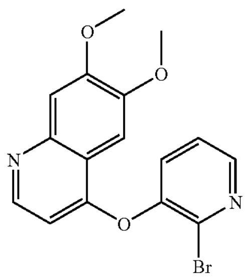 | 52 | 19 | |
| 204 | 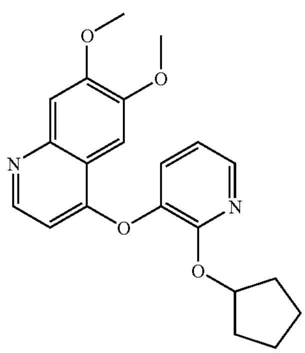 | 77 | 14 | |
| 205 | 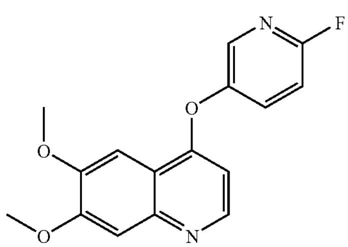 | 57 | 26 | |
| 206 | 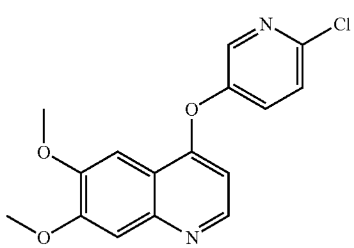 | 94 | 69 | |
| 207 | 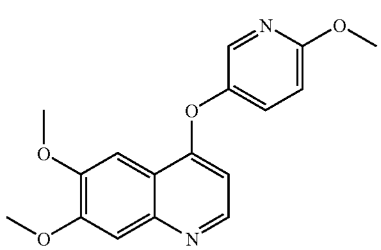 | 99 | 77 | |

-continued

| Compound | Molecular structure | TGFβ inhibition, % | | |
|---|---|---|---|---|
| | | 10 μM | 3 μM | 1 μM |
| 208 | 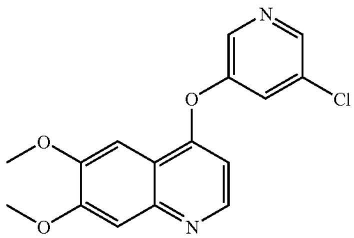 | 73 | 18 | |
| 209 | 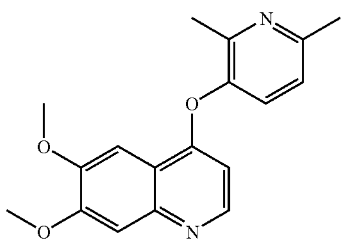 | 100 | 99 | |
| 210 | 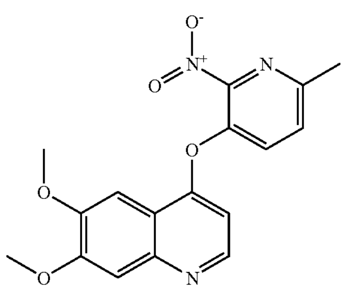 | 80 | 45 | |
| 211 | 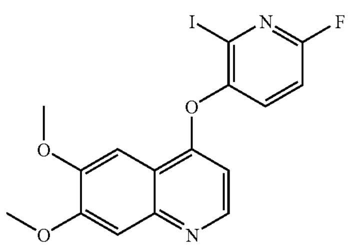 | 100 | 87 | |
| 212 | 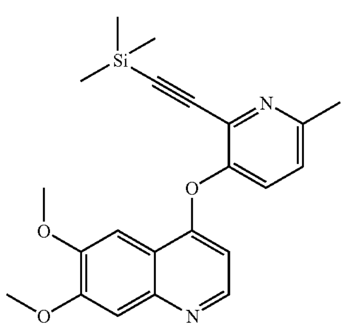 | 100 | 94 | |

-continued
| Compound | Molecular structure | TGFβ inhibition, % | | |
|---|---|---|---|---|
| | | 10 μM | 3 μM | 1 μM |
| 213 | 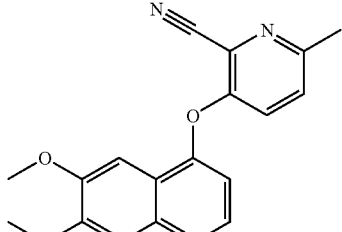 | 65 | 28 | |
| 214 | 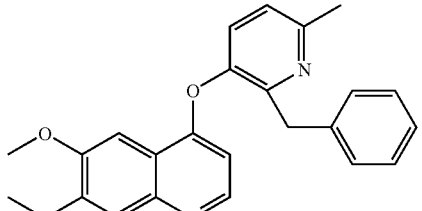 | 100 | 99 | |
| 215 | 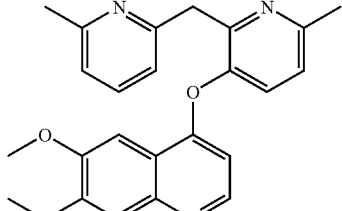 | 99 | 72 | |
| 216 | 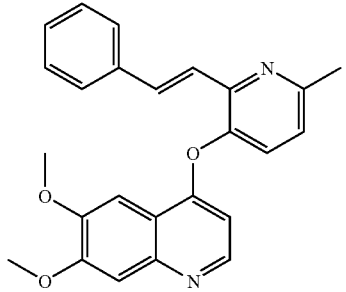 | 73 | 22 | |
| 217 | 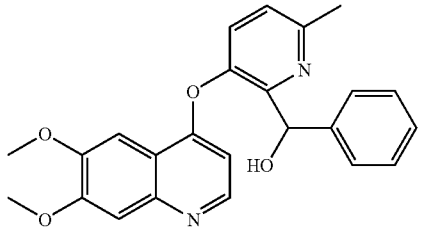 | 100 | 91 | |
| 218 | 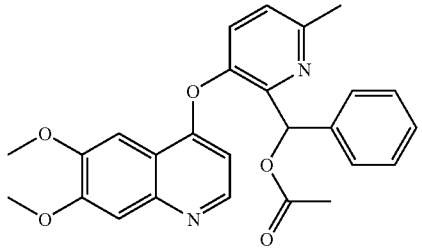 | 56 | 21 | |

-continued

| Compound | Molecular structure | TGFβ inhibition, % | | |
|---|---|---|---|---|
| | | 10 μM | 3 μM | 1 μM |
| 219 | 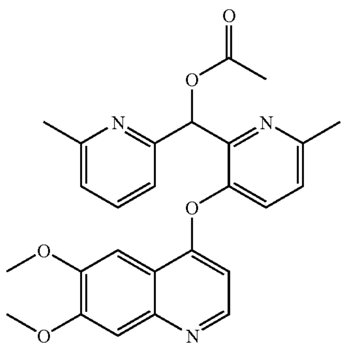 | 67 | 20 | |
| 220 | 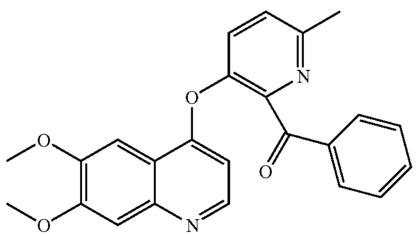 | 100 | 99 | |
| 221 | 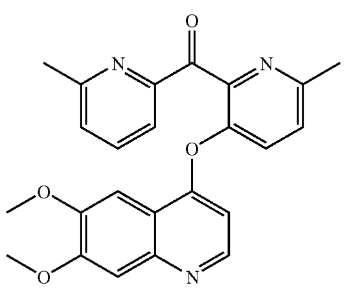 | 98 | 71 | |
| 222 | 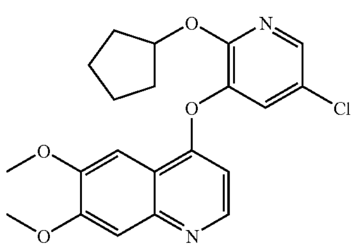 | 100 | 44 | |
| 223 | 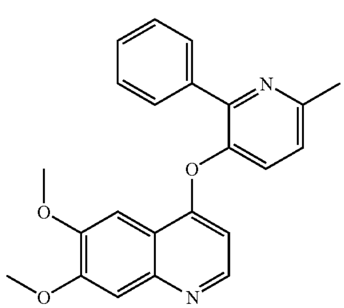 | 100 | 99 | |

-continued

| Compound | Molecular structure | TGFβ inhibition, % | | |
|---|---|---|---|---|
| | | 10 μM | 3 μM | 1 μM |
| 224 | 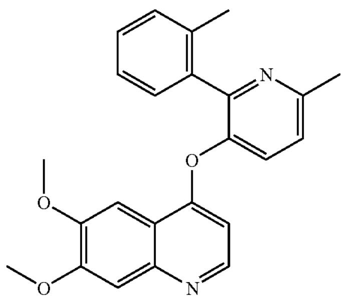 | 96 | 69 | |
| 225 | 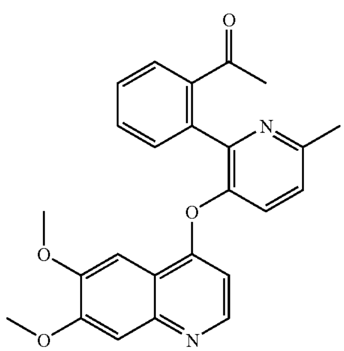 | 78 | 39 | |
| 226 | 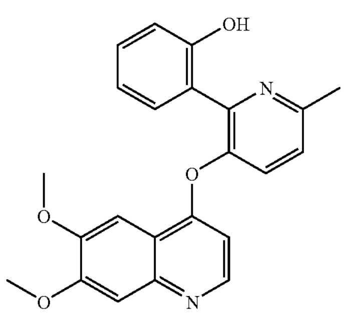 | 96 | 60 | |
| 227 | 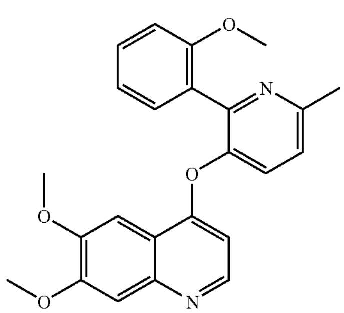 | 87 | 50 | |

-continued

| | | TGFβ inhibition, % | | |
|---|---|---|---|---|
| Compound | Molecular structure | 10 μM | 3 μM | 1 μM |
| 228 | | 100 | 88 | |
| 229 | | 100 | 99 | |
| 230 | | 97 | 60 | |
| 231 | | 100 | 100 | |

-continued

| Compound | Molecular structure | TGFβ inhibition, % | | |
|---|---|---|---|---|
| | | 10 μM | 3 μM | 1 μM |
| 232 | 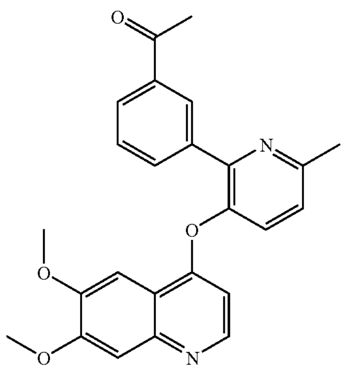 | 79 | 66 | |
| 233 | 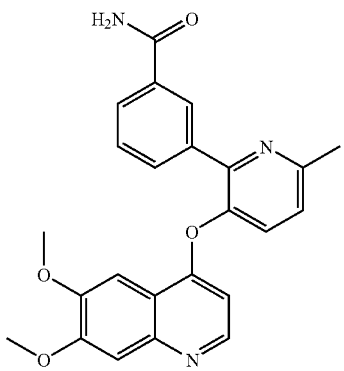 | 100 | 98 | |
| 234 | 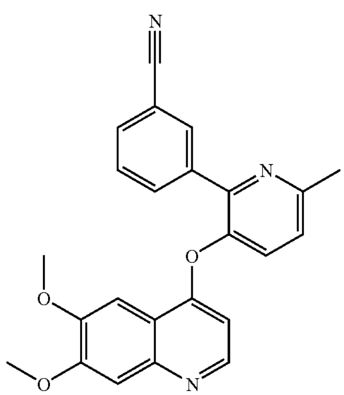 | 100 | 87 | |
| 235 | 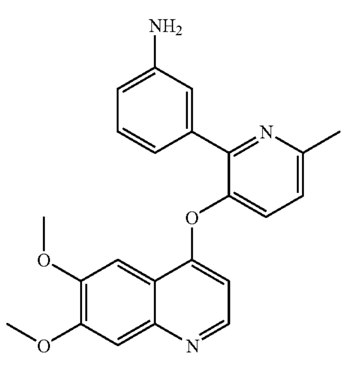 | 100 | 100 | |

-continued

| Compound | Molecular structure | TGFβ inhibition, % | | |
|---|---|---|---|---|
| | | 10 μM | 3 μM | 1 μM |
| 236 | 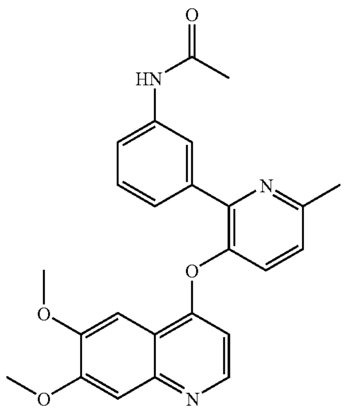 | 100 | 90 | |
| 237 | 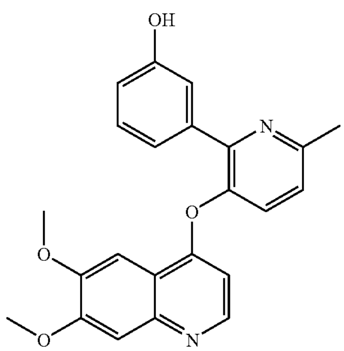 | 100 | 100 | |
| 238 | 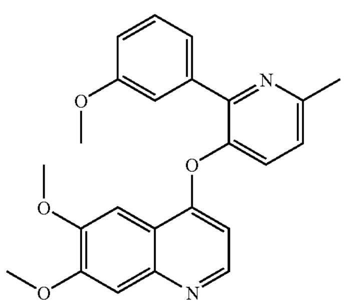 | 100 | 92 | |
| 239 | 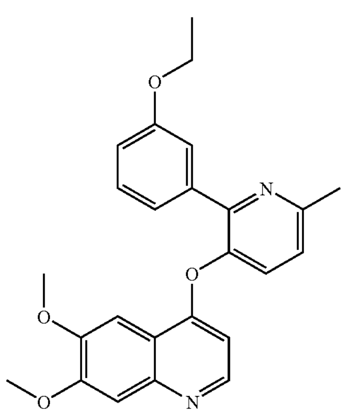 | 100 | 83 | |

-continued
| Compound | Molecular structure | TGFβ inhibition, % | | |
|---|---|---|---|---|
| | | 10 μM | 3 μM | 1 μM |
| 240 | 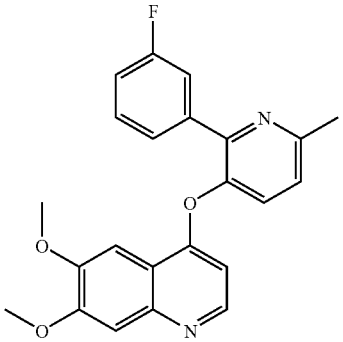 | 100 | 100 | |
| 241 | 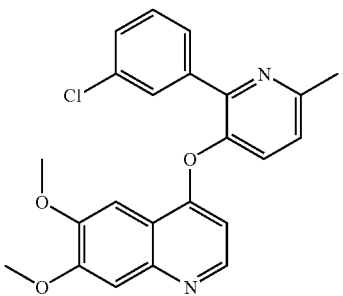 | 100 | 96 | |
| 242 | 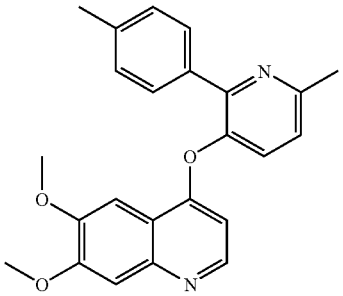 | 99 | 68 | |
| 243 | 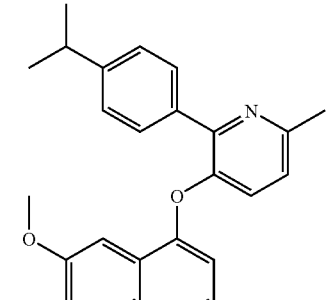 | 62 | −7 | |

| Compound | Molecular structure | TGFβ inhibition, % | | |
|---|---|---|---|---|
| | | 10 μM | 3 μM | 1 μM |
| 244 | 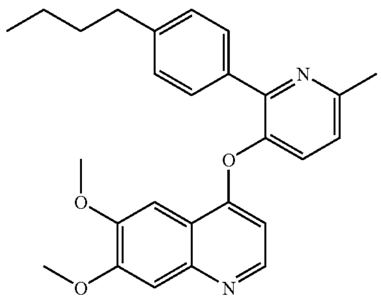 | 63 | −3 | |
| 245 | 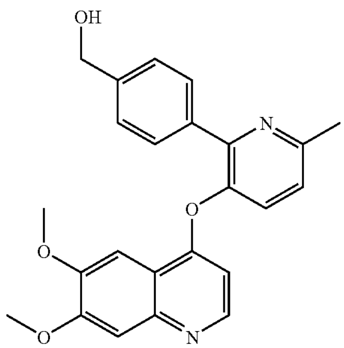 | 99 | 80 | |
| 246 | 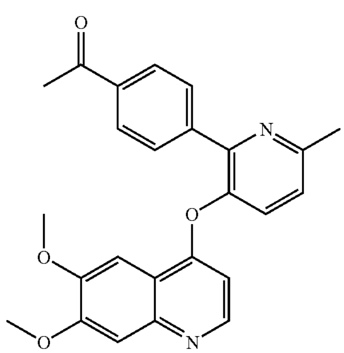 | 93 | 64 | |
| 247 | 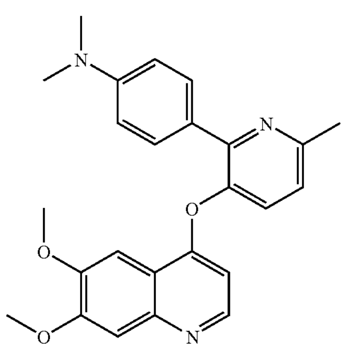 | 100 | 93 | |

-continued
| Compound | Molecular structure | TGFβ inhibition, % | | |
|---|---|---|---|---|
| | | 10 μM | 3 μM | 1 μM |
| 248 | 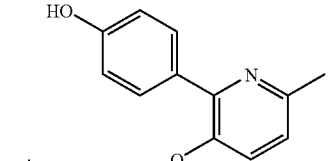 | 100 | 99 | |
| 249 | 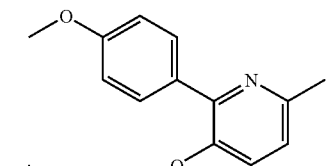 | 98 | 52 | |
| 250 | 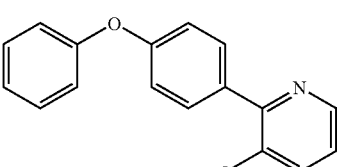 | 81 | 34 | |
| 251 | 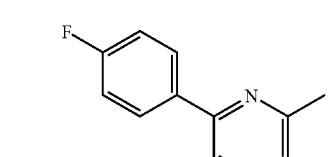 | 100 | 84 | |
| 252 | 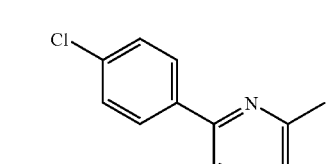 | 78 | 16 | |

| Compound | Molecular structure | TGFβ inhibition, % | | |
|---|---|---|---|---|
| | | 10 μM | 3 μM | 1 μM |
| 253 | 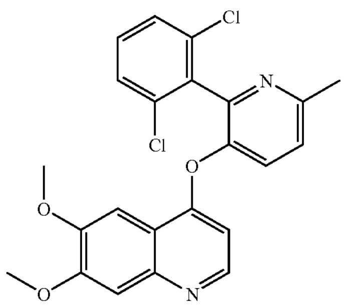 | 97 | 68 | |
| 254 | 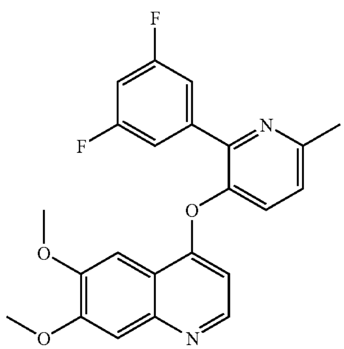 | 100 | 100 | |
| 255 | 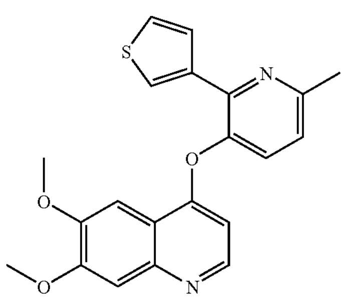 | 100 | 93 | |
| 256 | 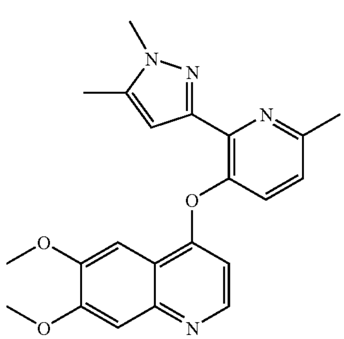 | 100 | 98 | |

-continued

| Compound | Molecular structure | TGFβ inhibition, % | | |
|---|---|---|---|---|
| | | 10 μM | 3 μM | 1 μM |
| 257 | 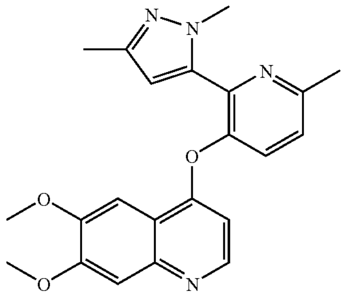 | 62 | 15 | |
| 258 | 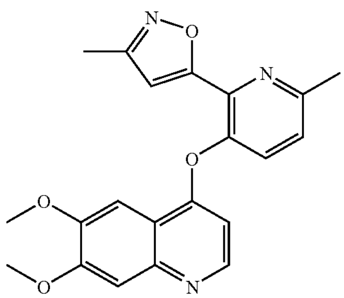 | 100 | 99 | |
| 259 | 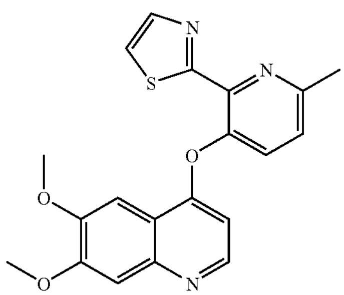 | | | 100 |
| 260 | 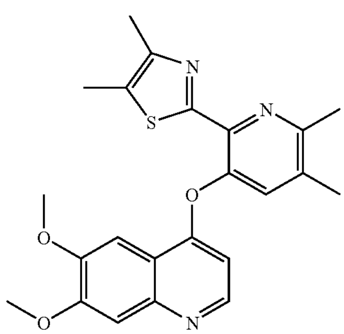 | 100 | 96 | |
| 261 | 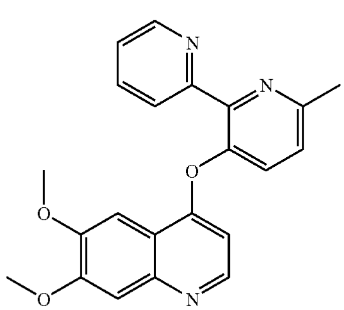 | 100 | 100 | |

-continued

| Compound | Molecular structure | TGFβ inhibition, % | | |
|---|---|---|---|---|
| | | 10 μM | 3 μM | 1 μM |
| 262 | 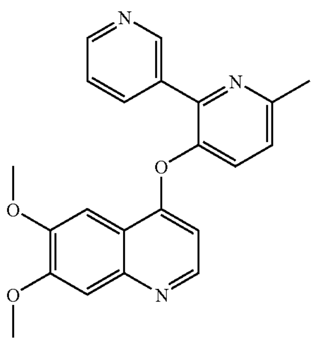 | 100 | 91 | |
| 263 | 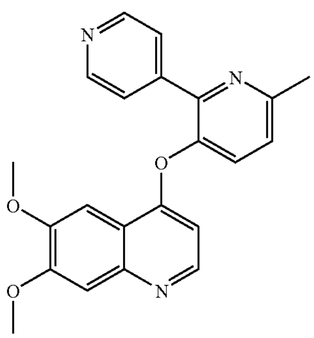 | 99 | 82 | |
| 264 | 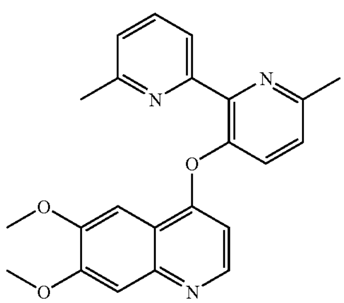 | 100 | 88 | |
| 265 | 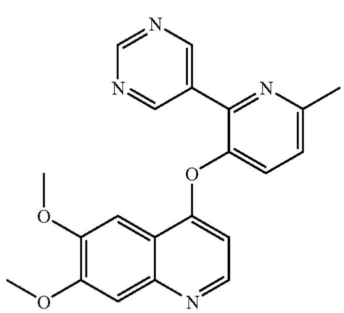 | 85 | 45 | |

-continued

| Compound | Molecular structure | TGFβ inhibition, % | | |
|---|---|---|---|---|
| | | 10 μM | 3 μM | 1 μM |
| 266 | 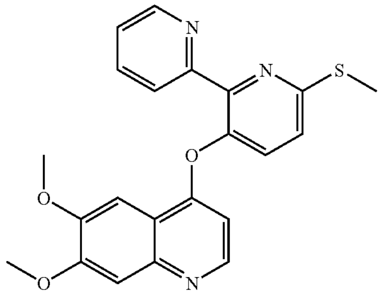 | 100 | 92 | |
| 267 | 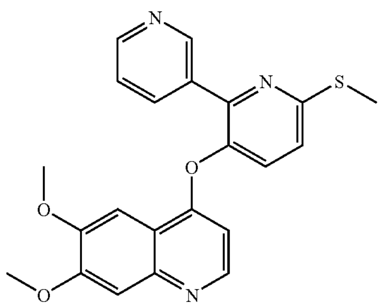 | 83 | 34 | |
| 268 | 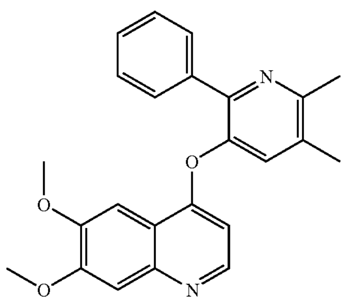 | 100 | 100 | |
| 269 | 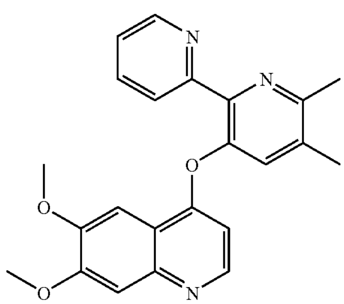 | | | 97 |
| 270 | 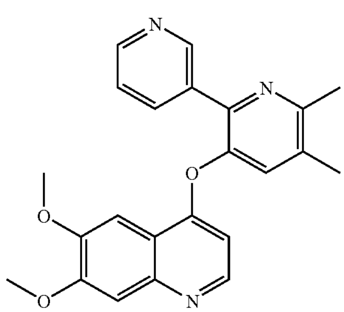 | | | 100 |

-continued

| Compound | Molecular structure | TGFβ inhibition, % | | |
|---|---|---|---|---|
| | | 10 μM | 3 μM | 1 μM |
| 271 | 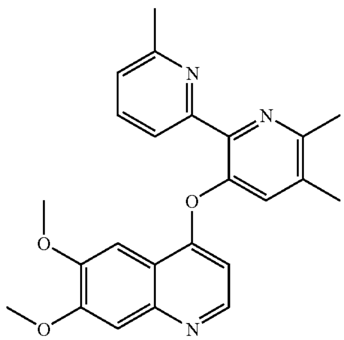 | 100 | 94 | |
| 272 | 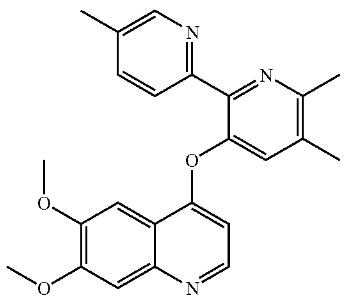 | 100 | 98 | |
| 273 | 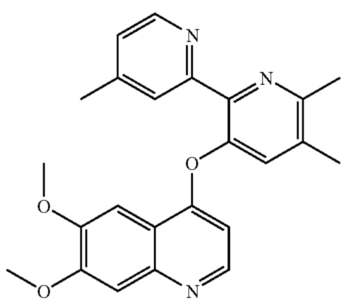 | 100 | 99 | |
| 274 | 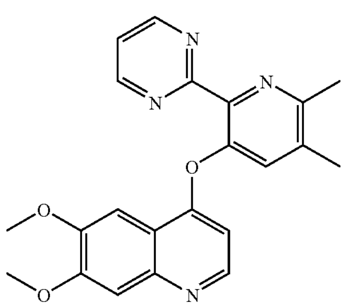 | | 97 | |
| 275 | 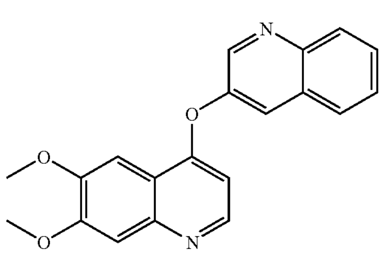 | 90 | 45 | |

-continued

| Compound | Molecular structure | TGFβ inhibition, % | | |
|---|---|---|---|---|
| | | 10 μM | 3 μM | 1 μM |
| 276 | 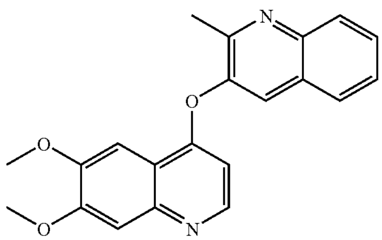 | 100 | 89 | |
| 277 | 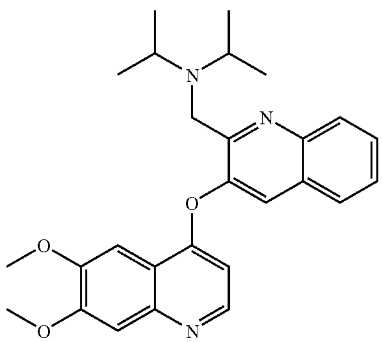 | 89 | 32 | |
| 278 | 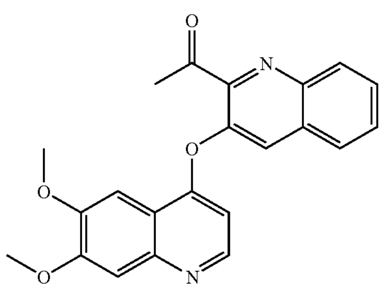 | 99 | 90 | |
| 279 | 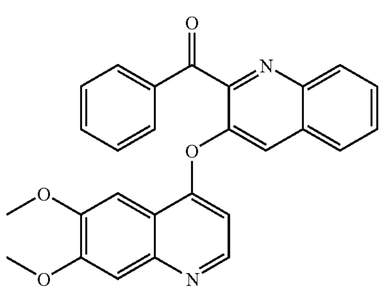 | 100 | 98 | |
| 280 | 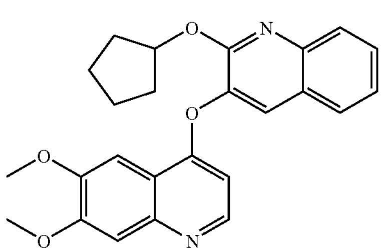 | 88 | 45 | |

| Compound | Molecular structure | TGFβ inhibition, % | | |
|---|---|---|---|---|
| | | 10 μM | 3 μM | 1 μM |
| 281 | 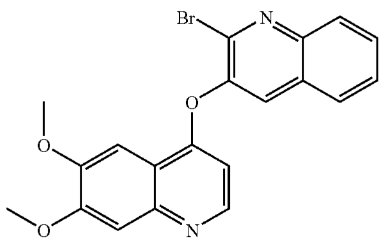 | 100 | 88 | |
| 282 | 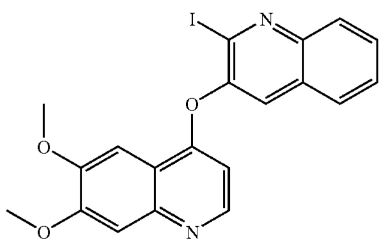 | 100 | 96 | |
| 283 | 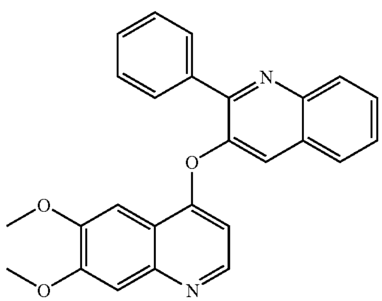 | 100 | 99 | |
| 284 | 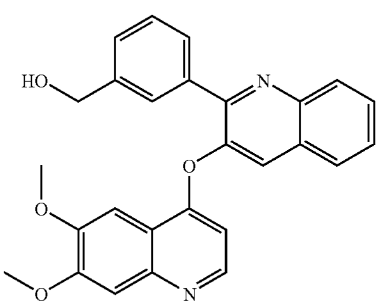 | 100 | 96 | |
| 285 | 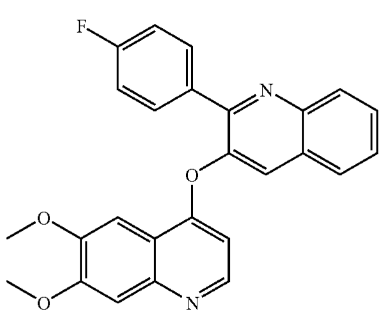 | 100 | 65 | |

-continued
| Compound | Molecular structure | TGFβ inhibition, % | | |
|---|---|---|---|---|
| | | 10 μM | 3 μM | 1 μM |
| 286 | 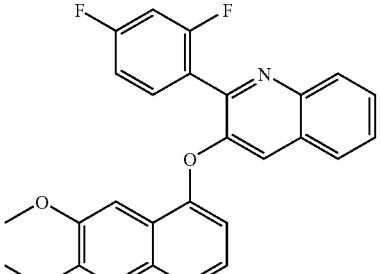 | 100 | 93 | |
| 287 | 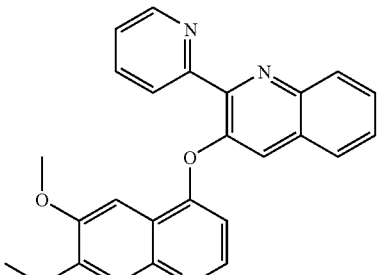 | 100 | 100 | |
| 288 | 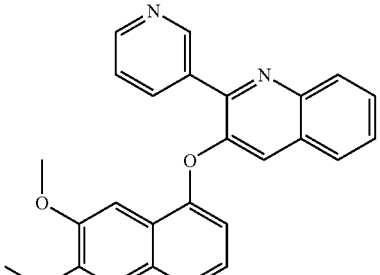 | 100 | 94 | |
| 289 | 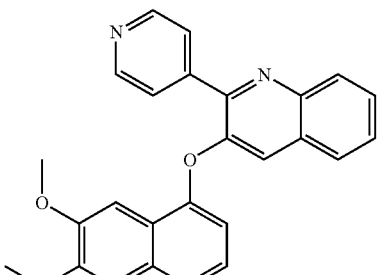 | 99 | 80 | |
| 290 | 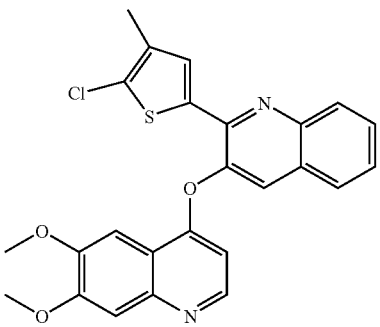 | 57 | 18 | |

-continued

| Compound | Molecular structure | TGFβ inhibition, % | | |
|---|---|---|---|---|
| | | 10 μM | 3 μM | 1 μM |
| 291 | 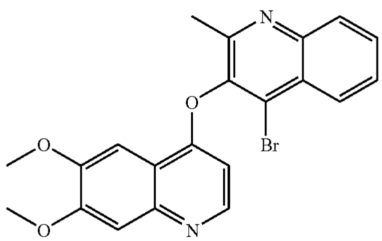 | 78 | 14 | |
| 292 | 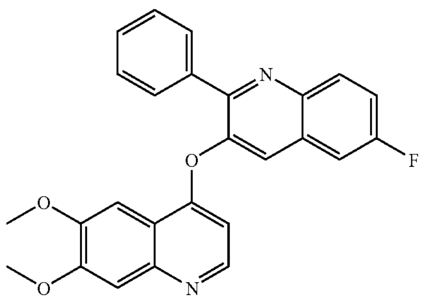 | 100 | 86 | |
| 293 | 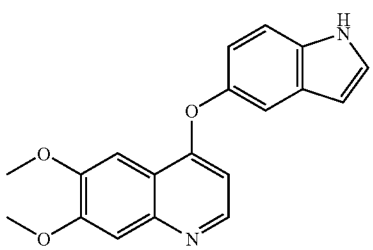 | 95 | 65 | |
| 294 | 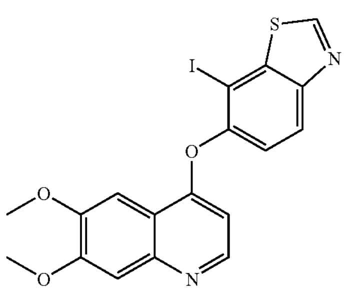 | 77 | 53 | |
| 295 | 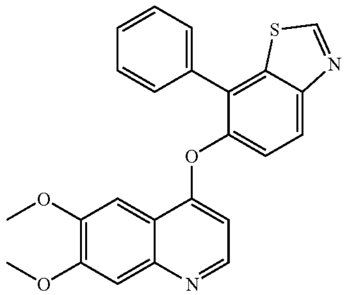 | 96 | 47 | |

-continued
| Compound | Molecular structure | TGFβ inhibition, % | | |
|---|---|---|---|---|
| | | 10 μM | 3 μM | 1 μM |
| 296 | 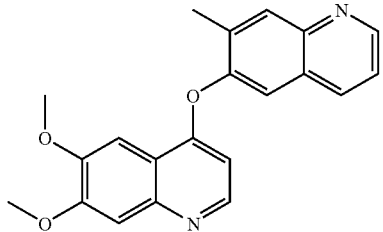 | 100 | 86 | |
| 297 | 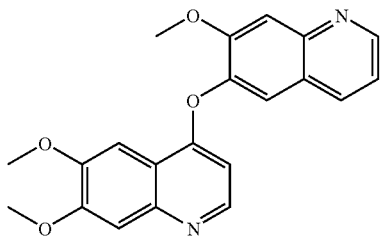 | 94 | 61 | |
| 298 | 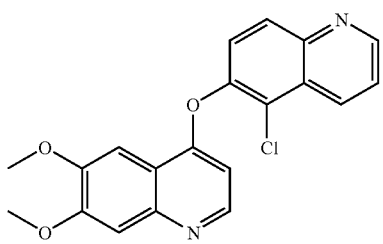 | 75 | 30 | |
| 299 | 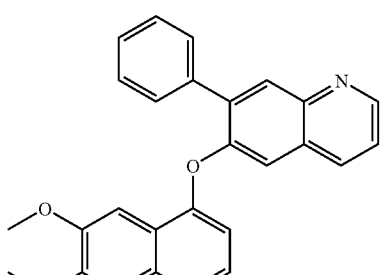 | 100 | 99 | |
| 300 | 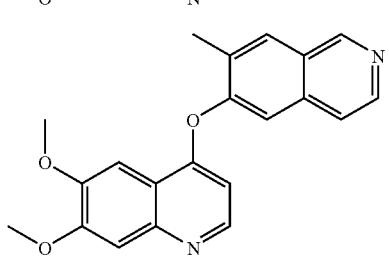 | 63 | 9 | |
| 301 | 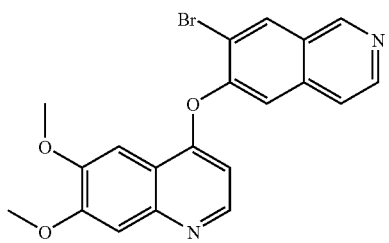 | 75 | 20 | |

-continued

| Compound | Molecular structure | TGFβ inhibition, % | | |
|---|---|---|---|---|
| | | 10 μM | 3 μM | 1 μM |
| 302 | 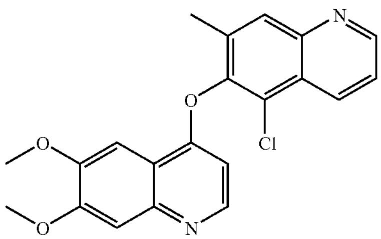 | 90 | 30 | |
| 303 | 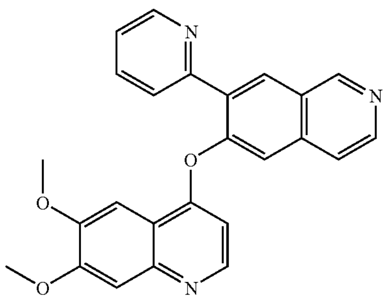 | 96 | | |
| 304 | 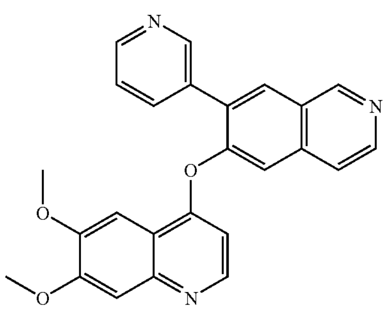 | 64 | 26 | |
| 305 | 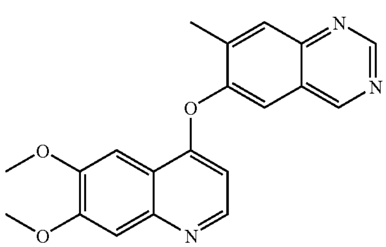 | 64 | 28 | |
| 306 | 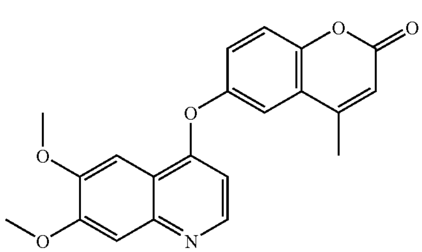 | 53 | 20 | |

| Compound | Molecular structure | TGFβ inhibition, % | | |
|---|---|---|---|---|
| | | 10 μM | 3 μM | 1 μM |
| 307 | 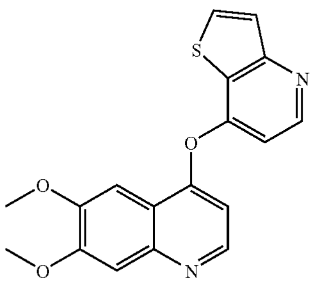 | 69 | 26 | |
| 308 | 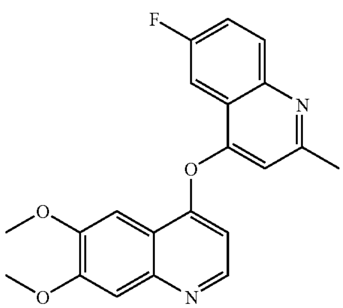 | 56 | 21 | |
| 309 | 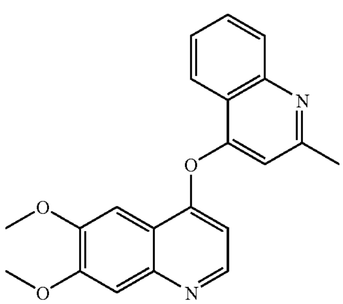 | 79 | 41 | |
| 310 | 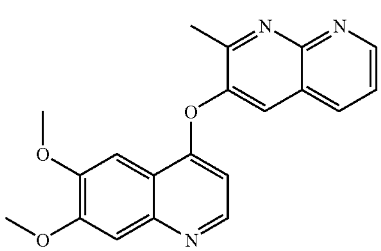 | 97 | 72 | |
| 311 | 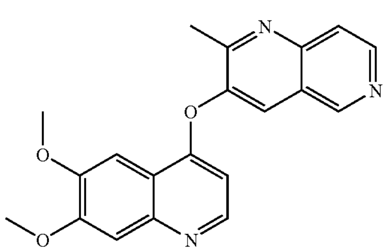 | 90 | 53 | |

-continued

| Compound | Molecular structure | TGFβ inhibition, % | | |
|---|---|---|---|---|
| | | 10 μM | 3 μM | 1 μM |
| 312 | 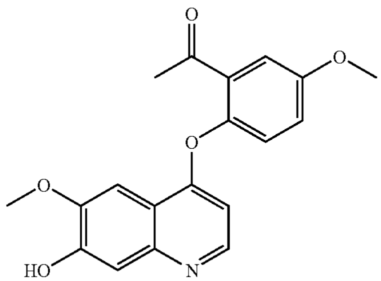 | 76 | 50 | |
| 313 | 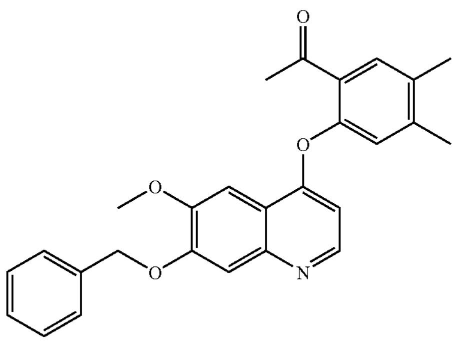 | 94 | 56 | |
| 314 | 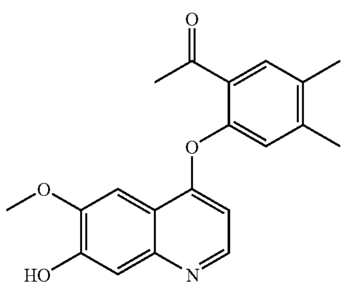 | 89 | 50 | |
| 315 | 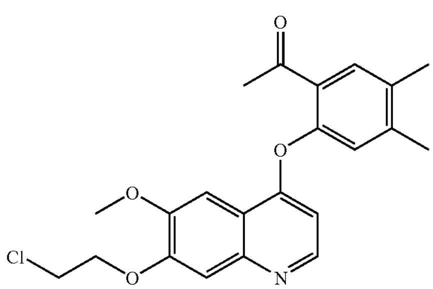 | 100 | 98 | |
| 316 | 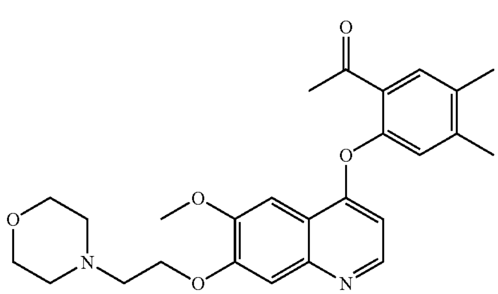 | 100 | 99 | |

-continued

| Compound | Molecular structure | TGFβ inhibition, % | | |
|---|---|---|---|---|
| | | 10 μM | 3 μM | 1 μM |
| 317 | 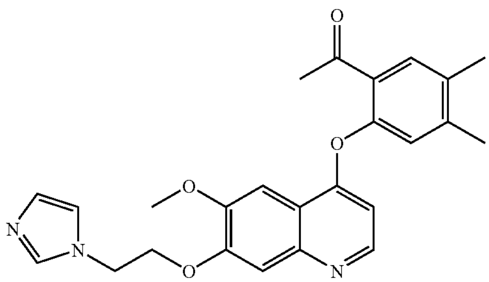 | 100 | 100 | |
| 318 | 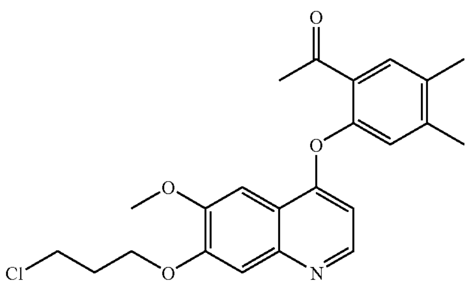 | 100 | 82 | |
| 319 | 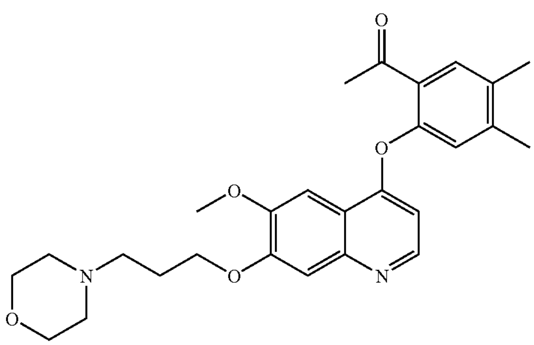 | 100 | 100 | |
| 320 | 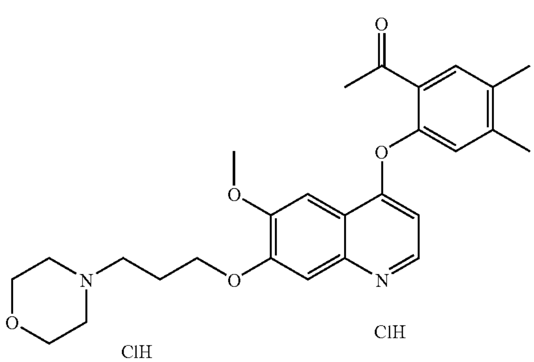 | 100 | 100 | |

-continued

| Compound | Molecular structure | TGFβ inhibition, % | | |
|---|---|---|---|---|
| | | 10 μM | 3 μM | 1 μM |
| 321 | 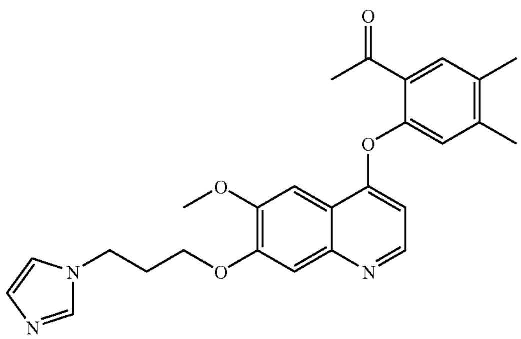 | 100 | 100 | |
| 322 | 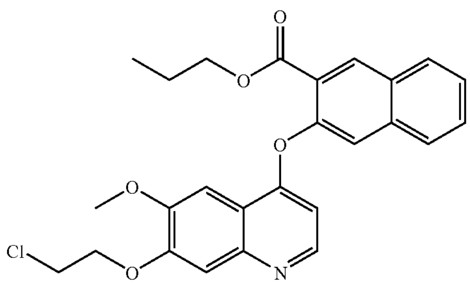 | 88 | 50 | |
| 323 | 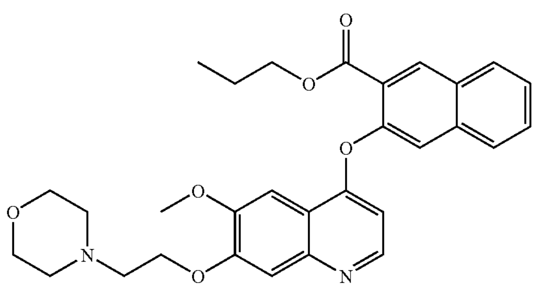 | 100 | 89 | |
| 324 | 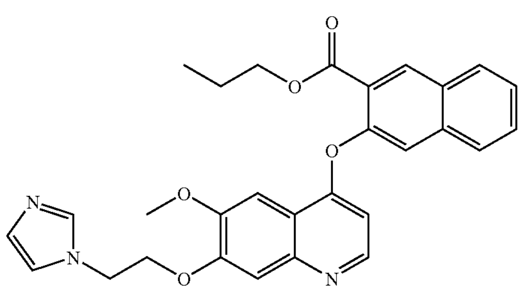 | 100 | 86 | |
| 325 | 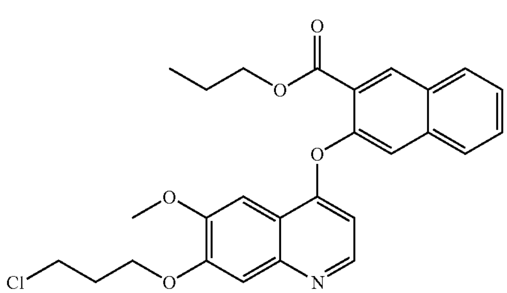 | 60 | 19 | |

-continued
| Compound | Molecular structure | TGFβ inhibition, % | | |
|---|---|---|---|---|
| | | 10 μM | 3 μM | 1 μM |
| 326 | 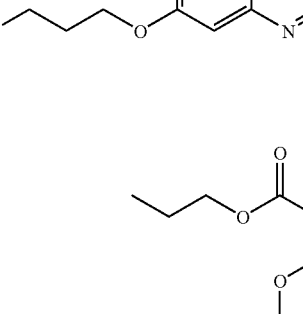 | 100 | 83 | |
| 327 | 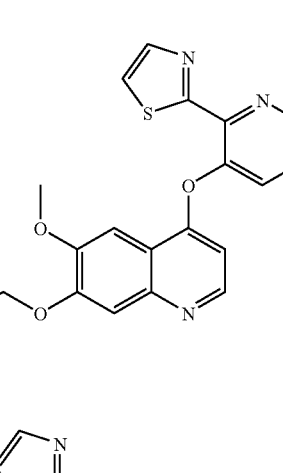 | 100 | 89 | |
| 328 | 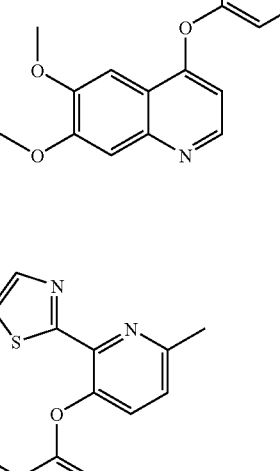 | 100 | 100 | |
| 329 | 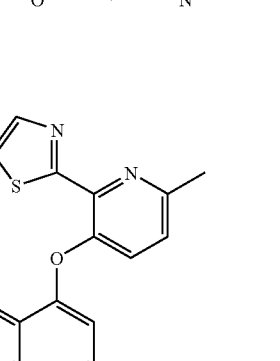 | 100 | 100 | |

| | | TGFβ inhibition, % | | |
|---|---|---|---|---|
| Compound | Molecular structure | 10 μM | 3 μM | 1 μM |
| 330 | | 100 | 100 | |
| 331 | | 90 | 73 | |
| 332 | | 100 | 97 | |
| 333 | | | 100 | |

-continued

| Compound | Molecular structure | TGFβ inhibition, % | | |
|---|---|---|---|---|
| | | 10 μM | 3 μM | 1 μM |
| 334 | 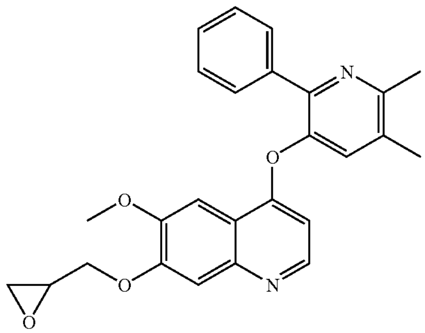 | 99 | | |
| 335 | 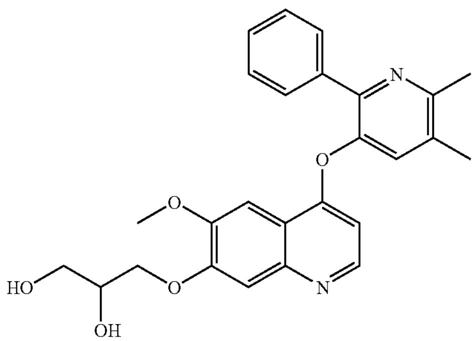 | 100 | | |
| 336 | 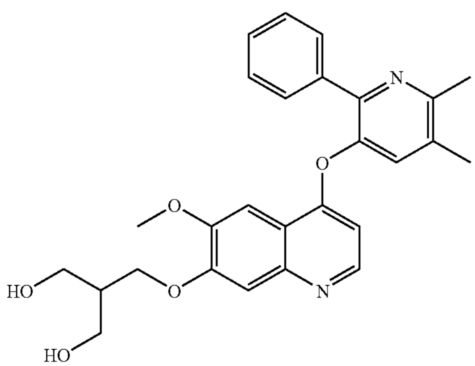 | 100 | | |
| 337 | 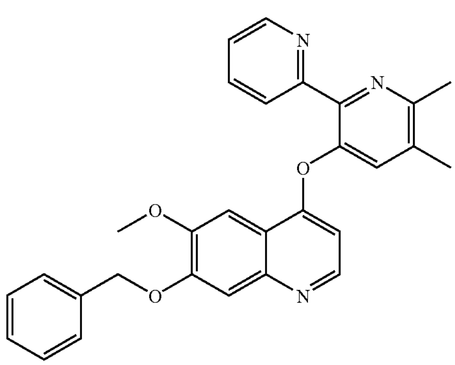 | 98 | | |

-continued

| Compound | Molecular structure | TGFβ inhibition, % | | |
|---|---|---|---|---|
| | | 10 μM | 3 μM | 1 μM |
| 338 | 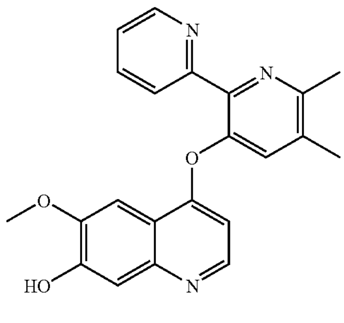 | 100 | 92 | |
| 339 | 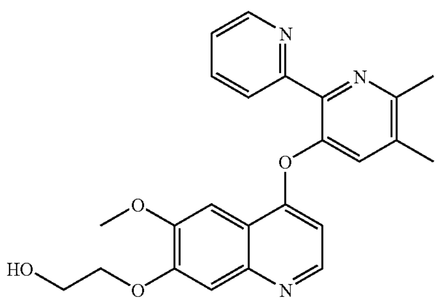 | 100 | | |
| 340 | 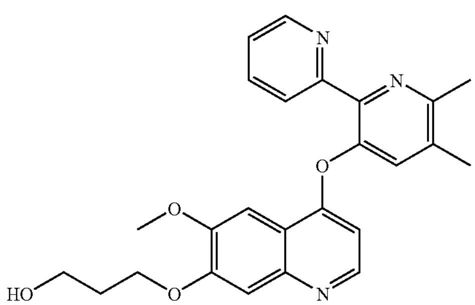 | 99 | | |
| 341 | 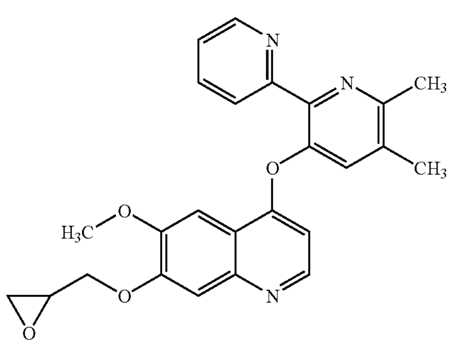 | 99 | | |

-continued

| Compound | Molecular structure | TGFβ inhibition, % | | |
|---|---|---|---|---|
| | | 10 μM | 3 μM | 1 μM |
| 342 | 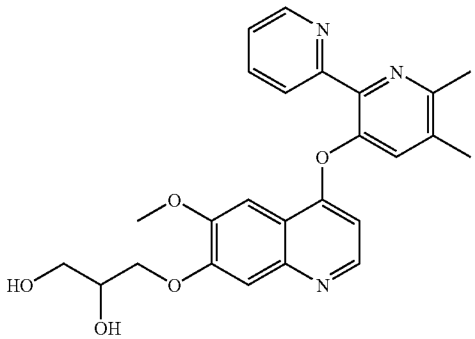 | 89 | | |
| 343 | 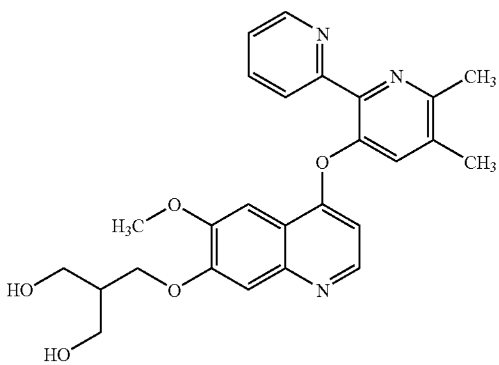 | 93 | | |
| 344 | 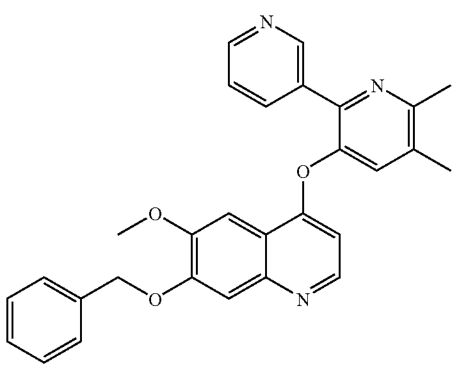 | 92 | | |
| 345 | 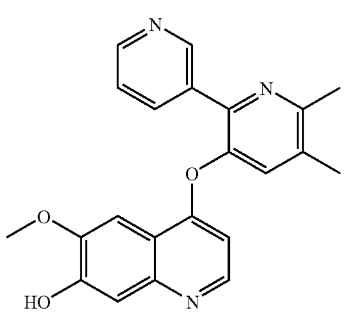 | 93 | 61 | |

-continued

| Compound | Molecular structure | TGFβ inhibition, % | | |
|---|---|---|---|---|
| | | 10 μM | 3 μM | 1 μM |
| 346 | 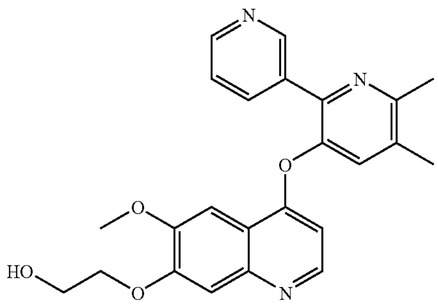 | 99 | | |
| 347 | 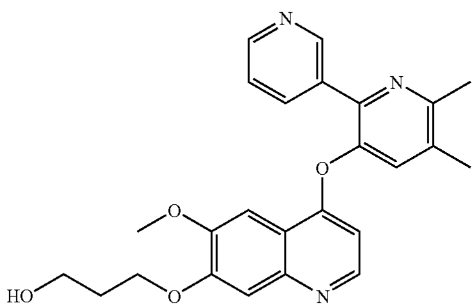 | 100 | | |
| 348 | 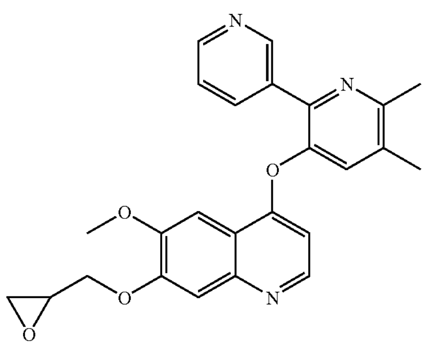 | 76 | | |
| 349 | 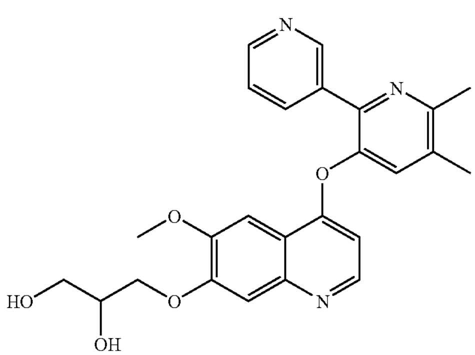 | 96 | | |

-continued

| Compound | Molecular structure | TGFβ inhibition, % | | |
|---|---|---|---|---|
| | | 10 μM | 3 μM | 1 μM |
| 350 | 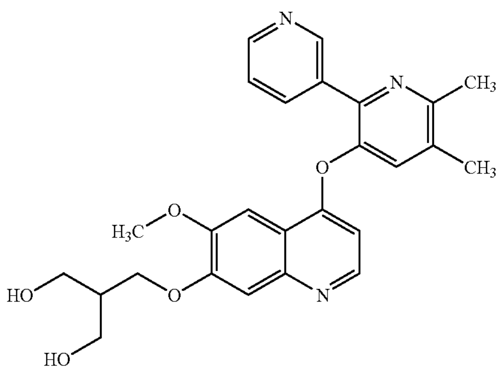 | | 96 | |
| 351 | 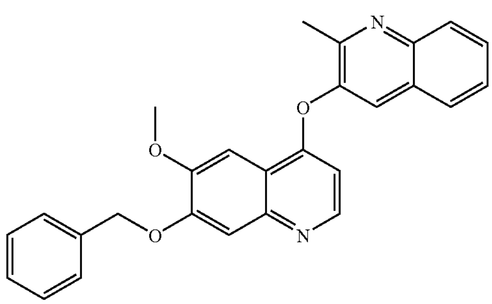 | 90 | 42 | |
| 352 | 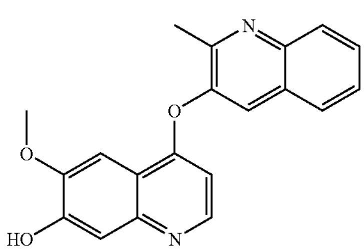 | 68 | 14 | |
| 353 | 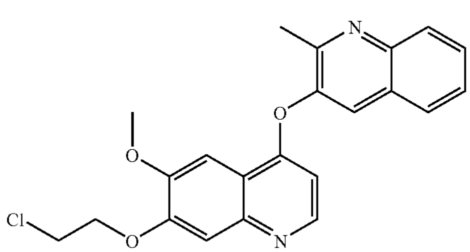 | 86 | 54 | |
| 354 | 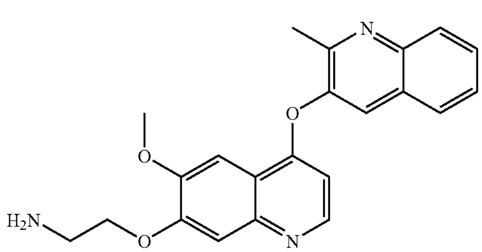 | 100 | 100 | |

| Compound | Molecular structure | TGFβ inhibition, % | | |
|---|---|---|---|---|
| | | 10 μM | 3 μM | 1 μM |
| 355 | 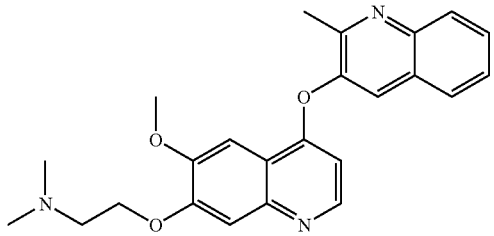 | 100 | 100 | |
| Compound | Molecular structure | TGFβ inhibition, % | | |
|---|---|---|---|---|
| | | 10 μM | 3 μM | 1 μM |
| 356 | 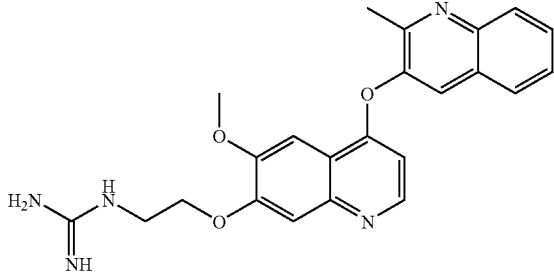 | 54 | −2 | |
| 357 | 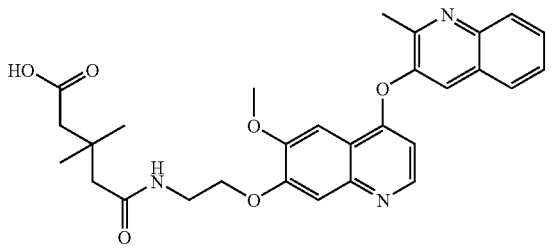 | 60 | 27 | |
| 358 | 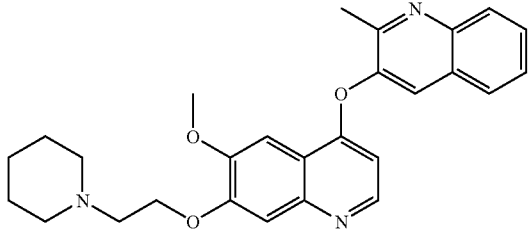 | 100 | 100 | |
| 359 | 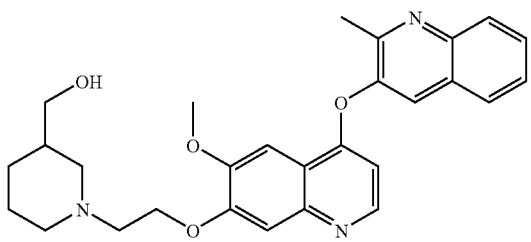 | 100 | 100 | |

-continued

| Compound | Molecular structure | TGFβ inhibition, % | | |
|---|---|---|---|---|
| | | 10 μM | 3 μM | 1 μM |
| 360 | 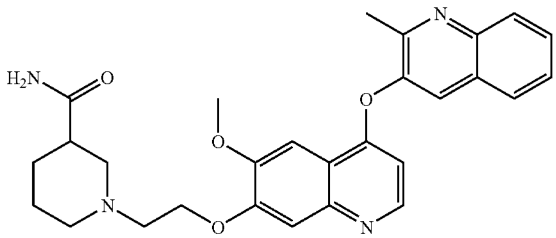 | 100 | 100 | |
| 361 | 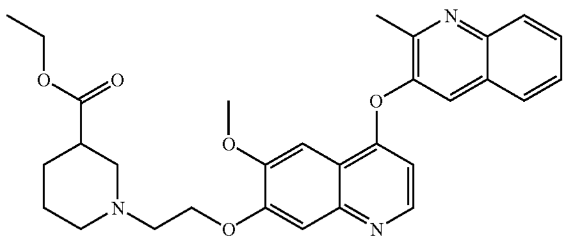 | 100 | 96 | |
| 362 | 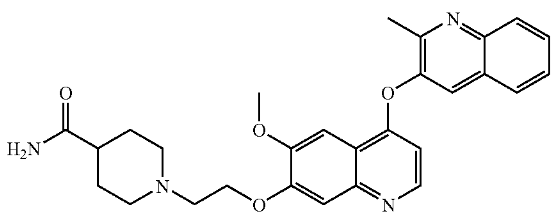 | 100 | 100 | |
| 363 | 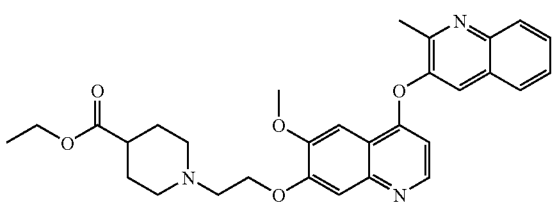 | 100 | 100 | |
| 364 | 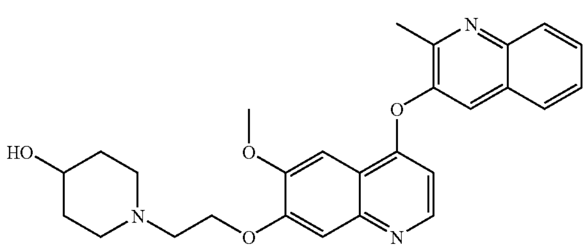 | 100 | 100 | |
| 365 | 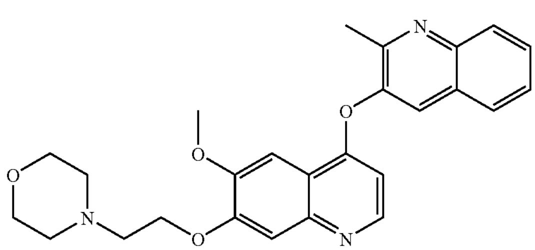 | 100 | 100 | |

-continued

| Compound | Molecular structure | TGFβ inhibition, % | | |
|---|---|---|---|---|
| | | 10 μM | 3 μM | 1 μM |
| 366 | 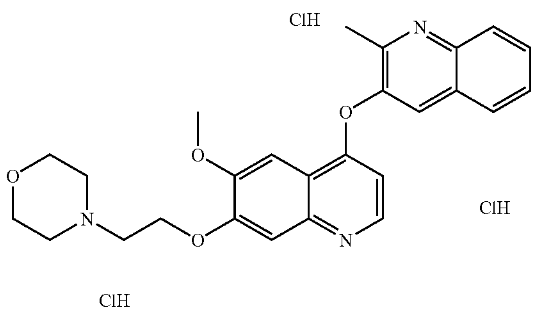 | 100 | 100 | |
| 367 | 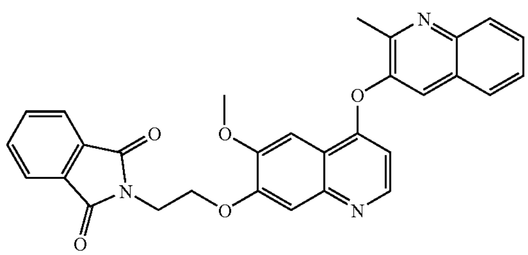 | 98 | 95 | |
| 368 | 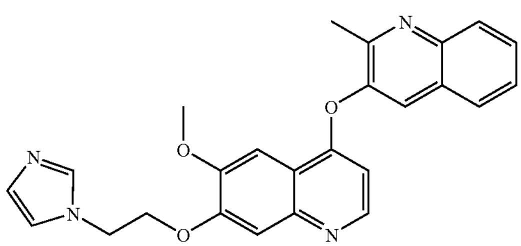 | 100 | 100 | |
| 369 | 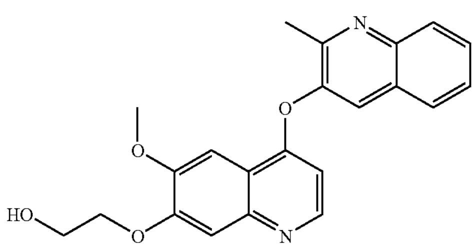 | 100 | 99 | |
| 370 | 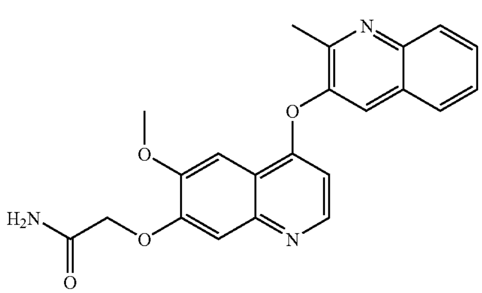 | 99 | 85 | |

| Compound | Molecular structure | TGFβ inhibition, % | | |
|---|---|---|---|---|
| | | 10 μM | 3 μM | 1 μM |
| 371 | 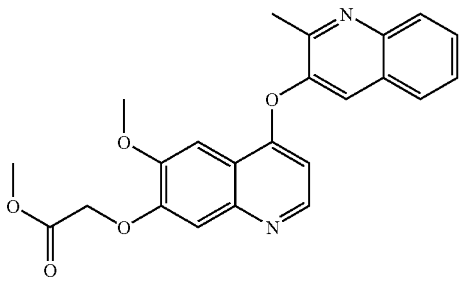 | 90 | 28 | |
| 372 | 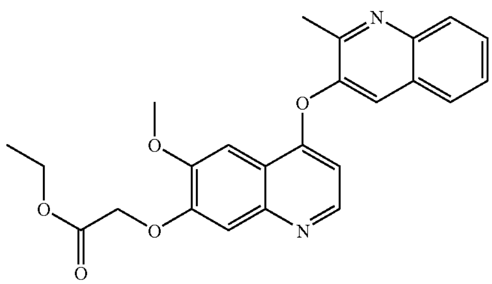 | 93 | 14 | |
| 373 | 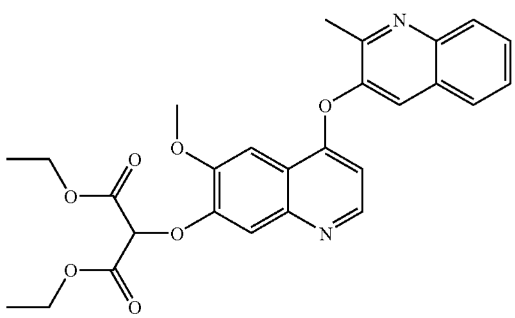 | 86 | 48 | |
| 374 | 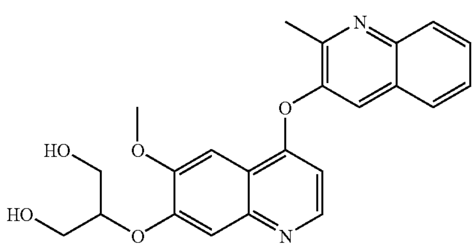 | 79 | 26 | |
| 375 | 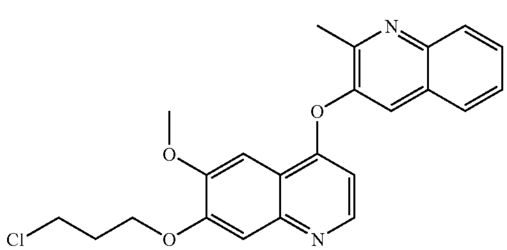 | 100 | 84 | |

-continued

| Compound | Molecular structure | TGFβ inhibition, % | | |
|---|---|---|---|---|
| | | 10 μM | 3 μM | 1 μM |
| 376 | 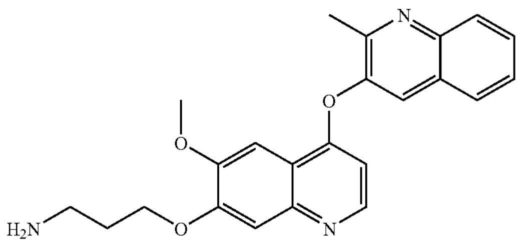 | 100 | 100 | |
| 377 | 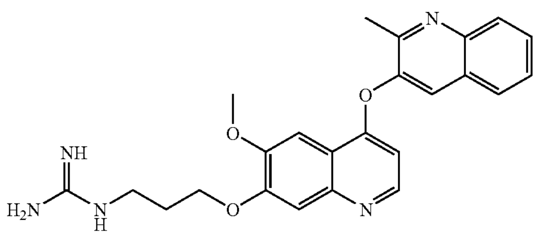 | 100 | 93 | |
| 378 | 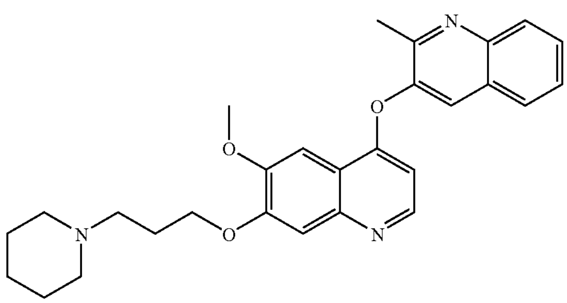 | 100 | 100 | |
| 379 | 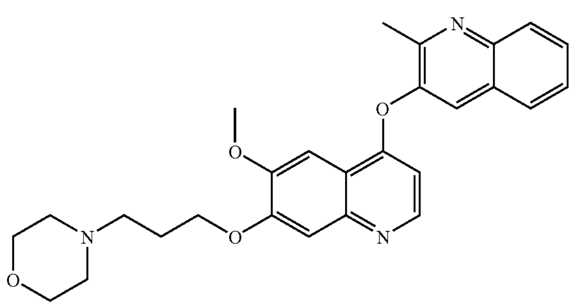 | 100 | 100 | |
| 380 | 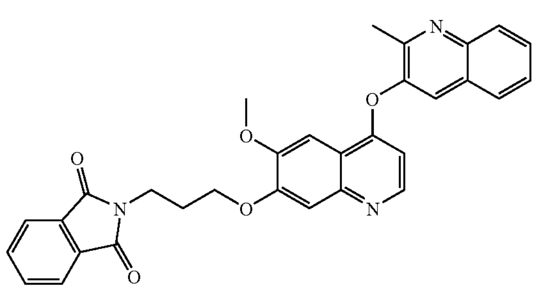 | 89 | 50 | |

-continued

| Compound | Molecular structure | TGFβ inhibition, % | | |
|---|---|---|---|---|
| | | 10 μM | 3 μM | 1 μM |
| 381 | 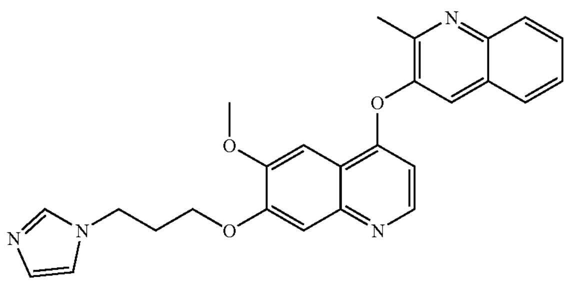 | 100 | 100 | |
| 382 | 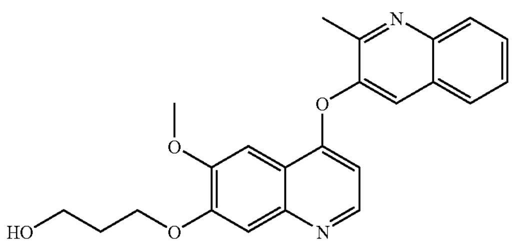 | 100 | 100 | |
| 383 | 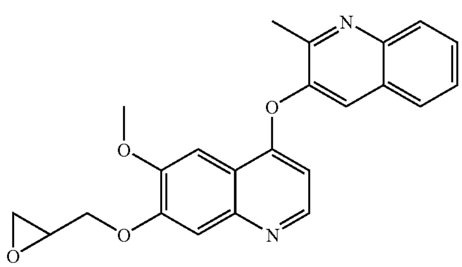 | 100 | 97 | |
| 384 | 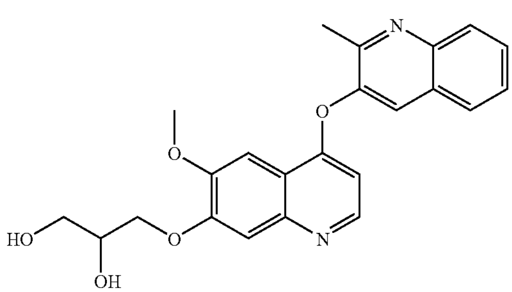 | 100 | 100 | |
| 385 | (Chiral) | 100 | 100 | |

-continued

| Compound | Molecular structure | TGFβ inhibition, % | | |
|---|---|---|---|---|
| | | 10 μM | 3 μM | 1 μM |
| 386 | 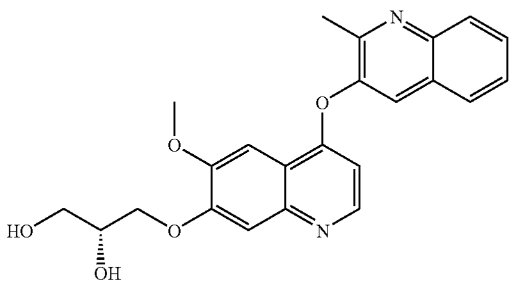 | | 99 | |
| 387 | 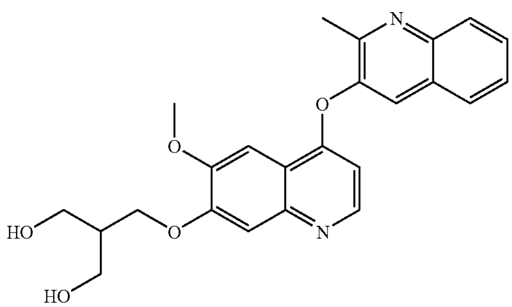 | 100 | 99 | |
| 388 | 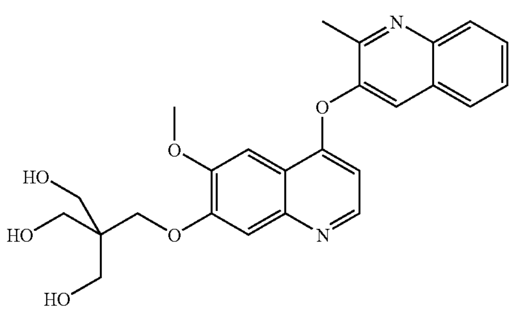 | 100 | 88 | |
| 389 | 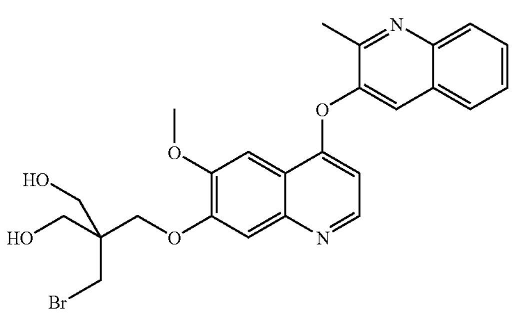 | 100 | 100 | |
| 390 | 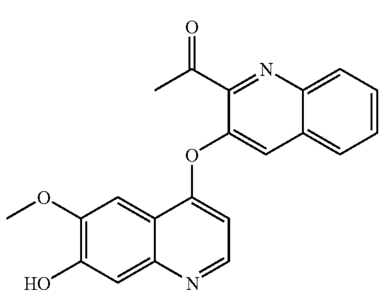 | 64 | 16 | |

-continued

| Compound | Molecular structure | TGFβ inhibition, % | | |
|---|---|---|---|---|
| | | 10 μM | 3 μM | 1 μM |
| 391 | 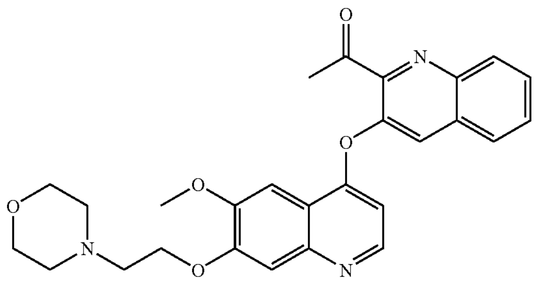 | 100 | 99 | |
| 392 | 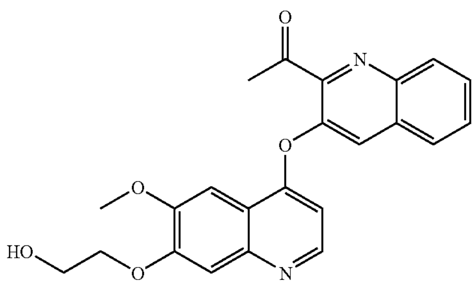 | 100 | 93 | |
| 393 | 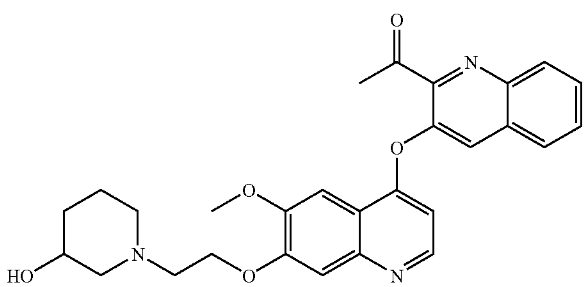 | | 100 | |
| 394 | 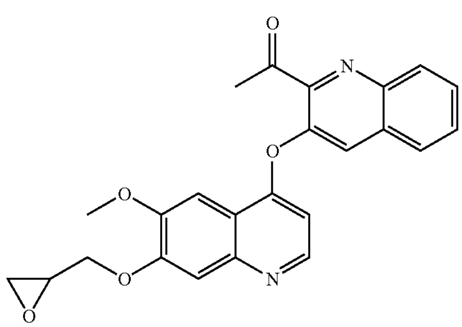 | 100 | 83 | |
| 395 | 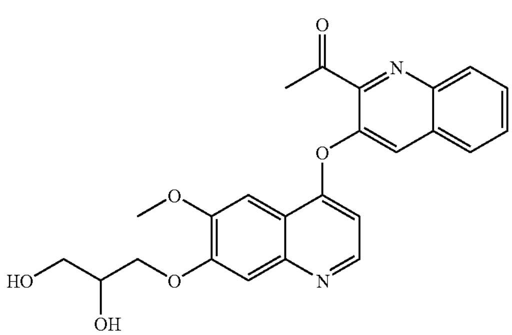 | 100 | 96 | |

-continued

| Compound | Molecular structure | TGFβ inhibition, % | | |
|---|---|---|---|---|
| | | 10 μM | 3 μM | 1 μM |
| 396 | 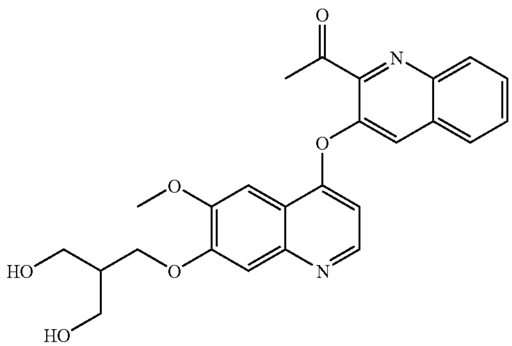 | | 96 | |
| 397 | 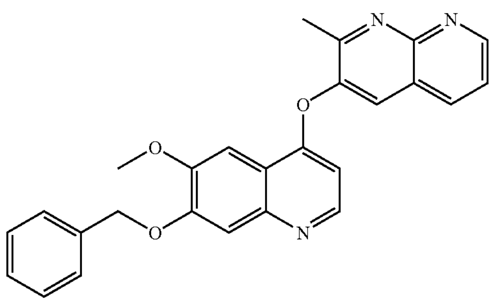 | 100 | 71 | |
| 398 | 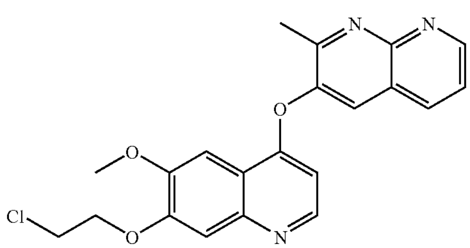 | 97 | 78 | |
| 399 | 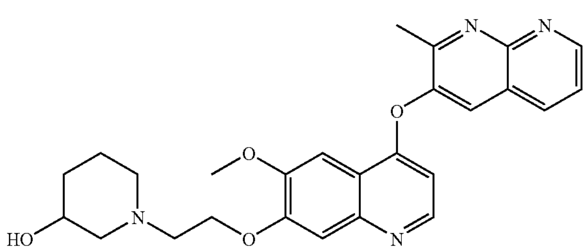 | 100 | 99 | |
| 400 | 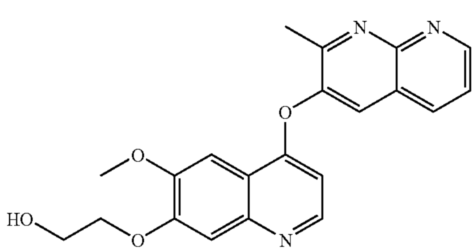 | 100 | 82 | |

-continued

| Compound | Molecular structure | TGFβ inhibition, % | | |
|---|---|---|---|---|
| | | 10 μM | 3 μM | 1 μM |
| 401 | 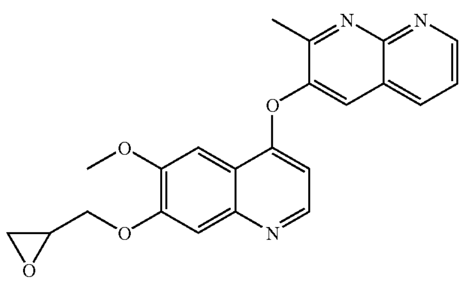 | 76 | 24 | |
| 402 | 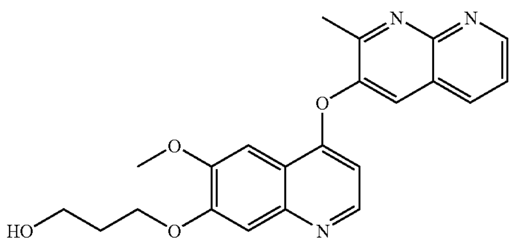 | 100 | 90 | |
| 403 | 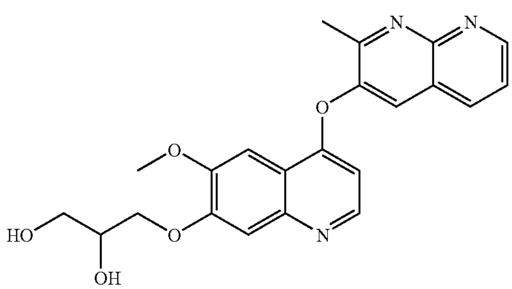 | 66 | 27 | |
| 404 | 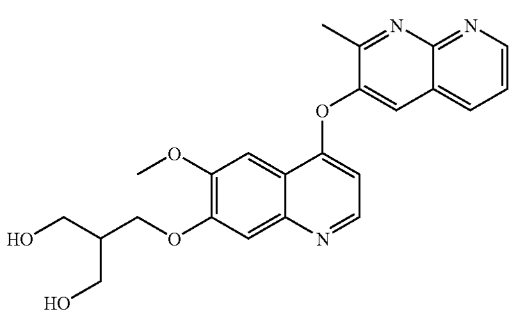 | 72 | 29 | |
| 405 | 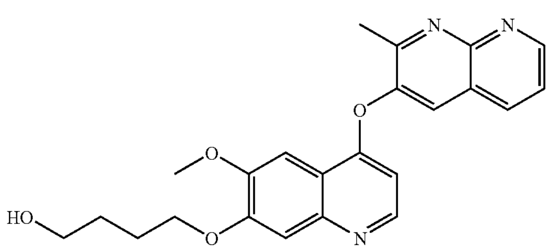 | 100 | 92 | |

-continued

| Compound | Molecular structure | TGFβ inhibition, % | | |
|---|---|---|---|---|
| | | 10 μM | 3 μM | 1 μM |
| 406 | 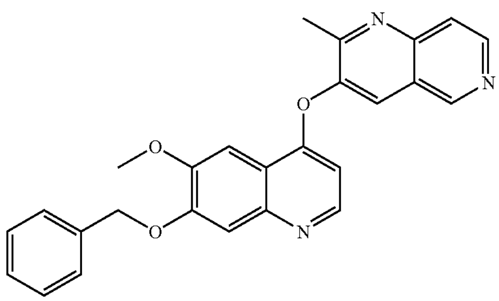 | 96 | 56 | |
| 407 | 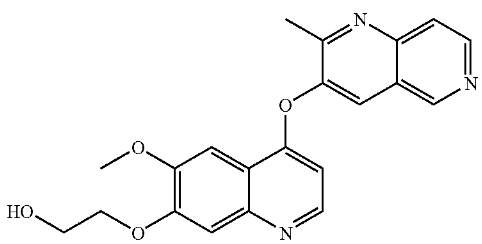 | 97 | 71 | |
| 408 | 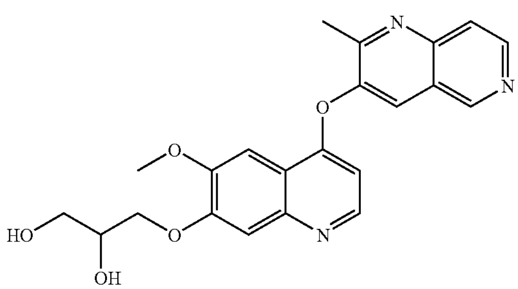 | 79 | 38 | |
| 409 | 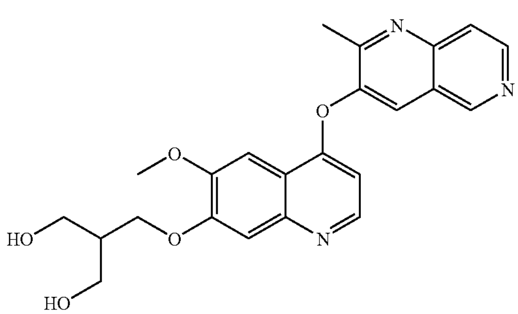 | 88 | 41 | |
| 410 | 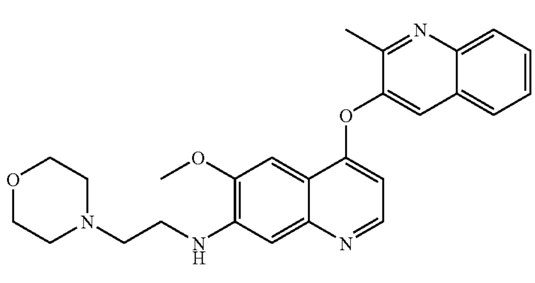 | 100 | 91 | |

-continued

| Compound | Molecular structure | TGFβ inhibition, % | | |
|---|---|---|---|---|
| | | 10 μM | 3 μM | 1 μM |
| 411 | 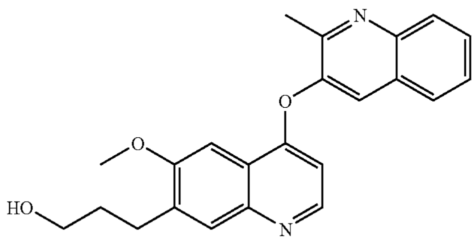 | 85 | 50 | |
| 412 | 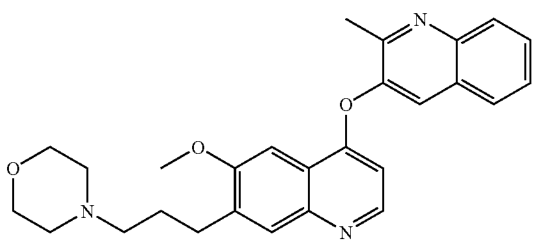 | 99 | 77 | |
| 413 | 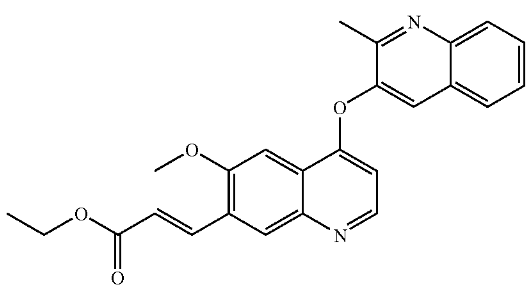 | 76 | 31 | |
| 414 | 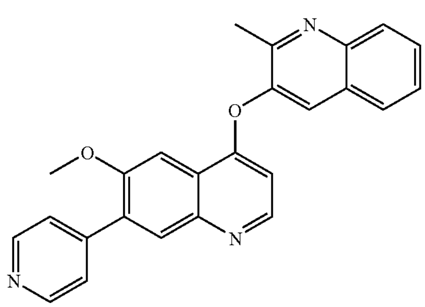 | 100 | 82 | |
| 415 | 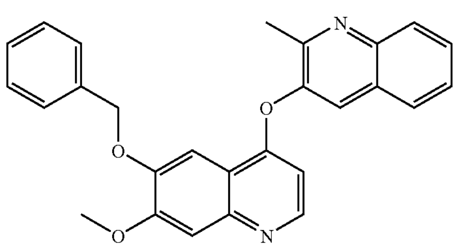 | 100 | 77 | |

| Compound | Molecular structure | TGFβ inhibition, % | | |
|---|---|---|---|---|
| | | 10 μM | 3 μM | 1 μM |
| 416 | 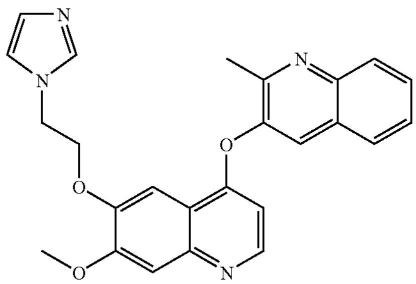 | 100 | 92 | |
| 417 | 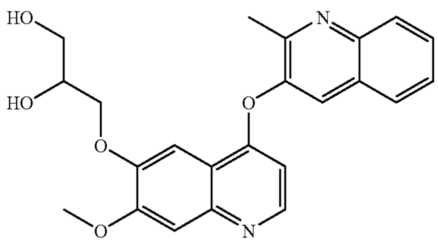 | 100 | 98 | |
| 418 | 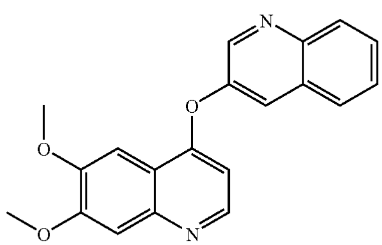 | 73 | 46 | |
| 419 | 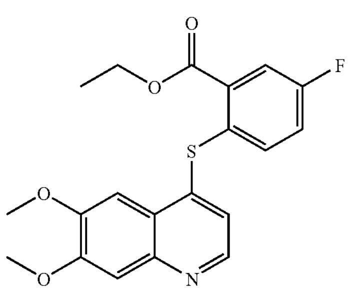 | 67 | 7 | |
| 420 | 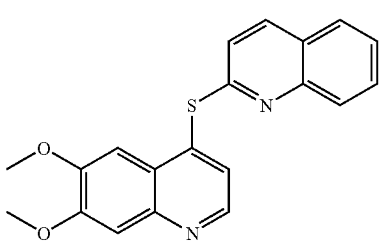 | 62 | 2 | |

-continued

| Compound | Molecular structure | TGFβ inhibition, % | | |
|---|---|---|---|---|
| | | 10 μM | 3 μM | 1 μM |
| 421 | 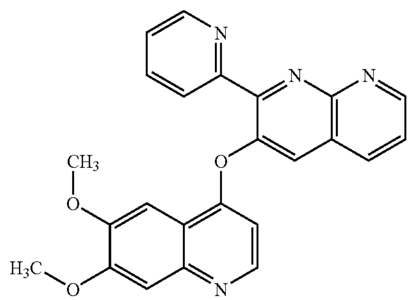 | 100 | 94 | |
| 422 | 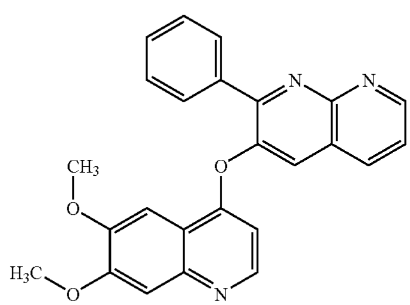 | 100 | 100 | |
| 423 | 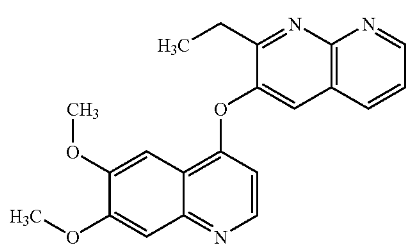 | 100 | 88 | |
| 424 | 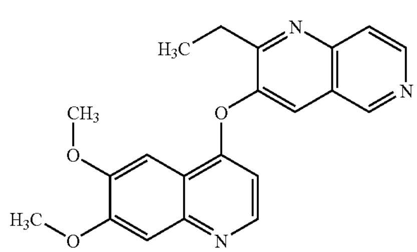 | 79 | 28 | |
| 425 | 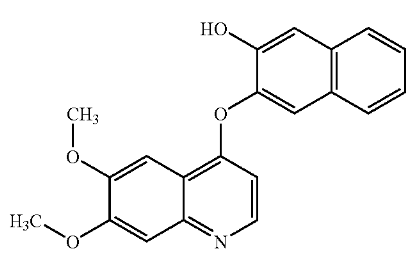 | 100 | 72 | |

-continued

| Compound | Molecular structure | TGFβ inhibition, % | | |
|---|---|---|---|---|
| | | 10 μM | 3 μM | 1 μM |
| 426 | 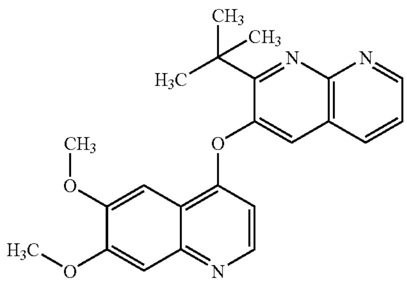 | | 100 | |
| 427 | 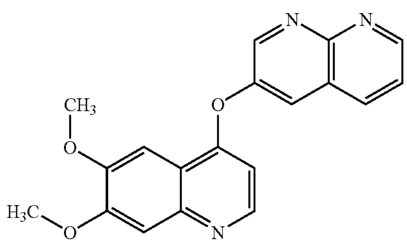 | 80 | 44 | |
| 428 | 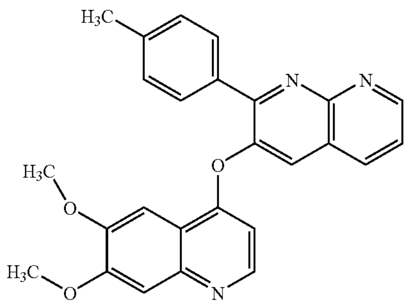 | | 67 | |
| 429 | 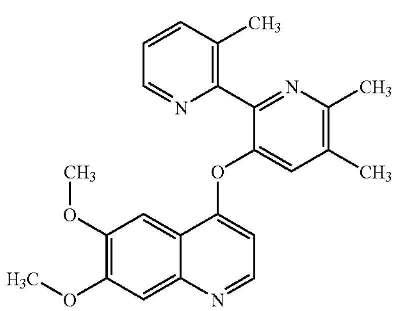 | 94 | 52 | |
| 430 | 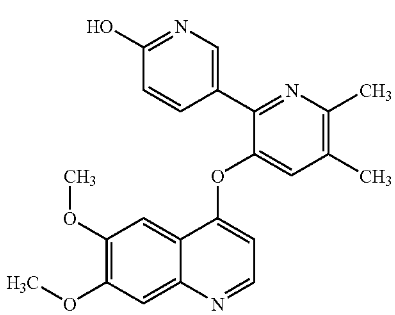 | 78 | 19 | |

| | | TGFβ inhibition, % | | |
|---|---|---|---|---|
| Compound | Molecular structure | 10 μM | 3 μM | 1 μM |
| 431 | | 99 | 97 | |
| 432 | | 100 | 99 | |
| 433 | | 100 | 91 | |
| 434 | | 100 | 100 | |

-continued

| Compound | Molecular structure | TGFβ inhibition, % | | |
|---|---|---|---|---|
| | | 10 μM | 3 μM | 1 μM |
| 435 | 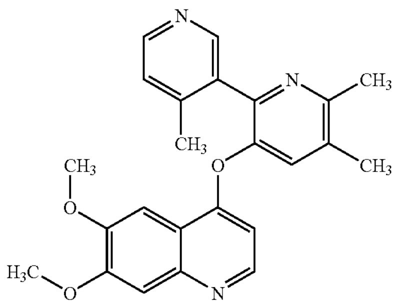 | 79 | 29 | |
| 436 | 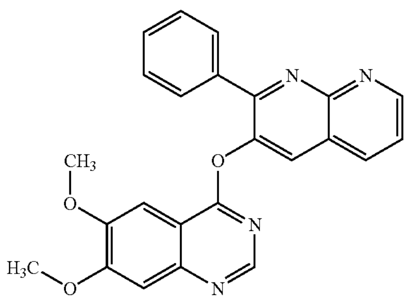 | 100 | 99 | |
| 437 | 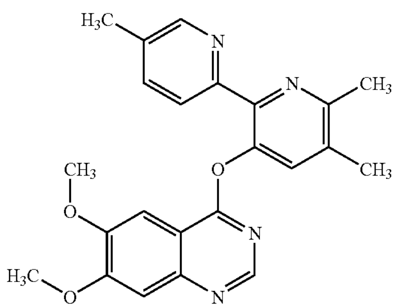 | 100 | 95 | |
| 438 | 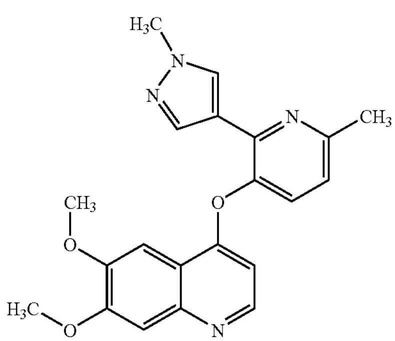 | 100 | 99 | |
| 439 | 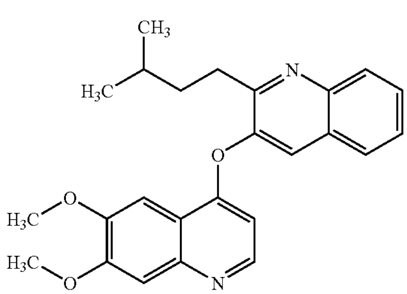 | 95 | 43 | |

| Compound | Molecular structure | TGFβ inhibition, % | | |
|---|---|---|---|---|
| | | 10 μM | 3 μM | 1 μM |
| 440 | 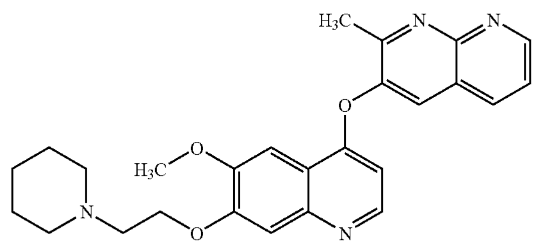 | 100 | 100 | |
| 441 | 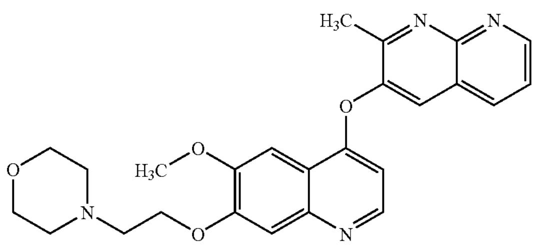 | 100 | 97 | |
| 442 | 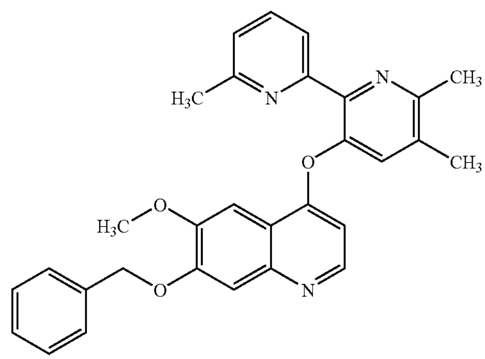 | 100 | 70 | |
| 443 | 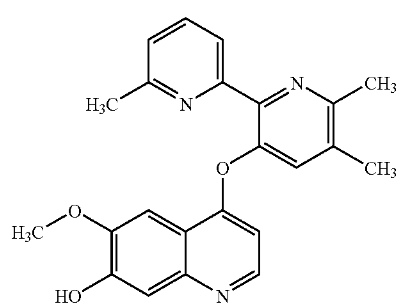 | 97 | 60 | |
| 444 | 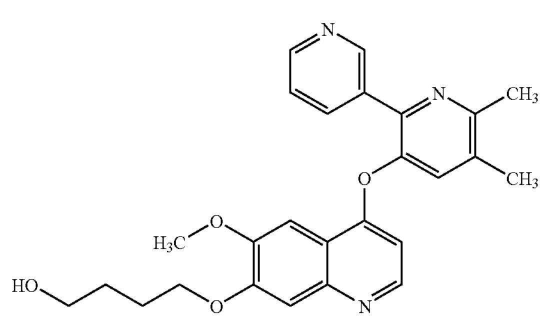 | 100 | | |

-continued

| Compound | Molecular structure | TGFβ inhibition, % | | |
|---|---|---|---|---|
| | | 10 μM | 3 μM | 1 μM |
| 445 | 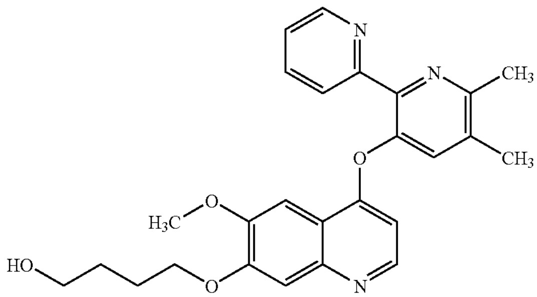 | | 99 | |
| 446 | 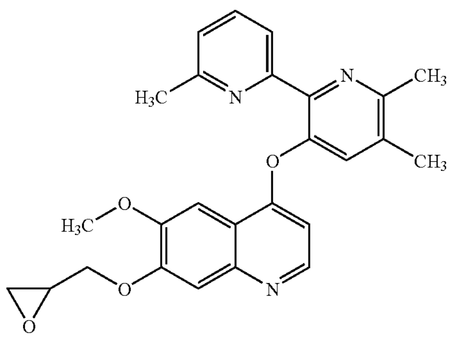 | 89 | 35 | |
| 447 | 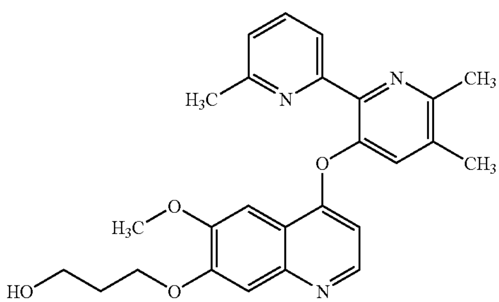 | 100 | 94 | |
| 448 | 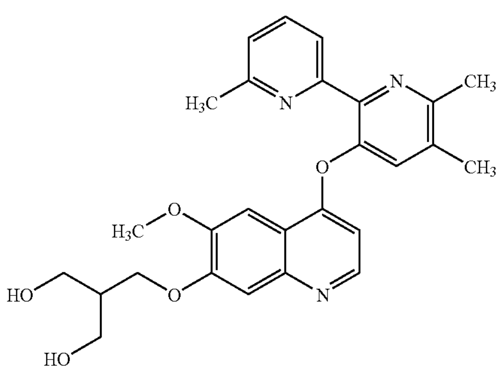 | 97 | 70 | |

-continued

| Compound | Molecular structure | TGFβ inhibition, % | | |
|---|---|---|---|---|
| | | 10 μM | 3 μM | 1 μM |
| 449 | 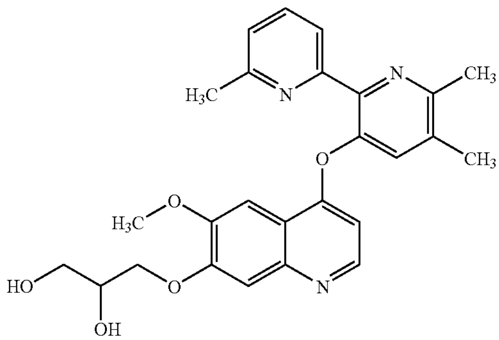 | 98 | 74 | |
| 450 | 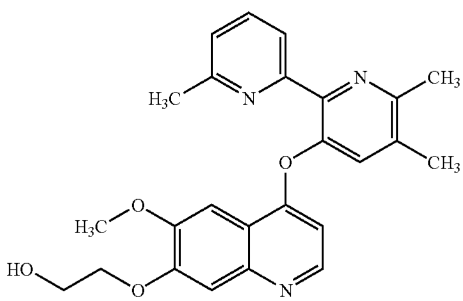 | 100 | 94 | |
| 451 | 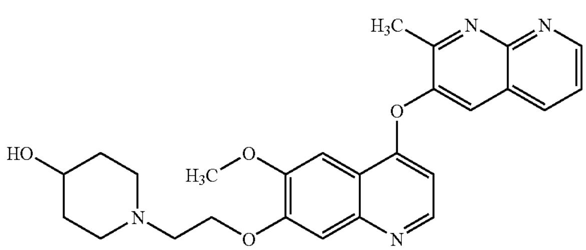 | 100 | 99 | |
| 452 | 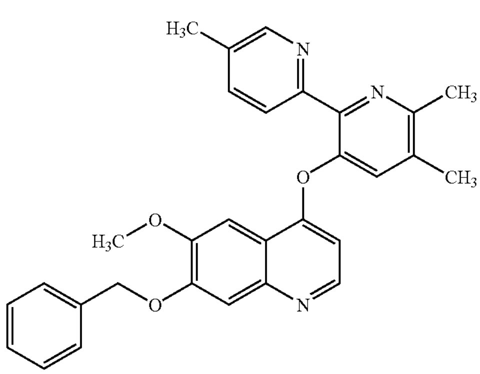 | 99 | 67 | |

-continued

| Compound | Molecular structure | TGFβ inhibition, % | | |
|---|---|---|---|---|
| | | 10 μM | 3 μM | 1 μM |
| 453 | 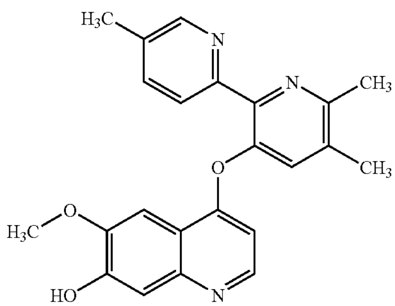 | 98 | 72 | |
| 454 | 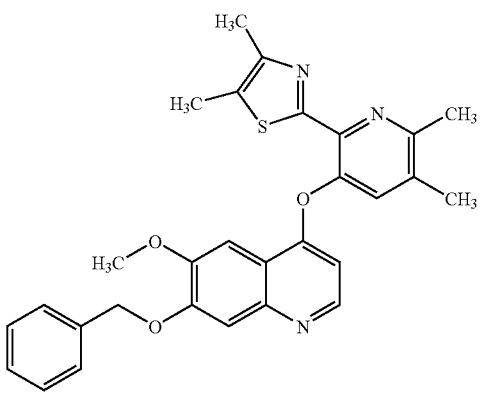 | 75 | 41 | |
| 455 | 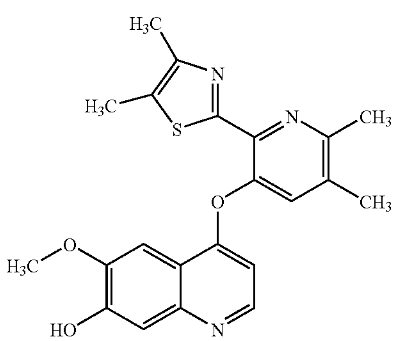 | 99 | 76 | |
| 456 | 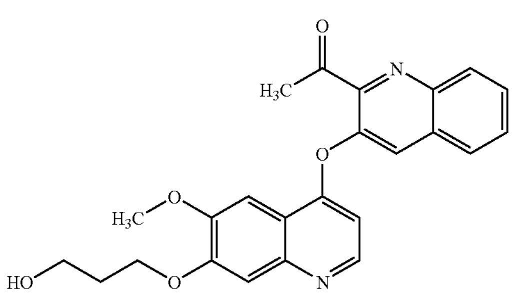 | 100 | 99 | |

-continued

| Compound | Molecular structure | TGFβ inhibition, % | | |
|---|---|---|---|---|
| | | 10 μM | 3 μM | 1 μM |
| 457 | 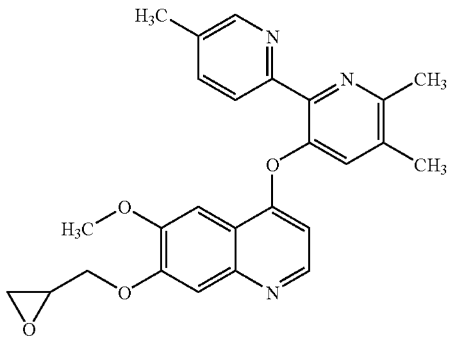 | 100 | 97 | |
| 458 | 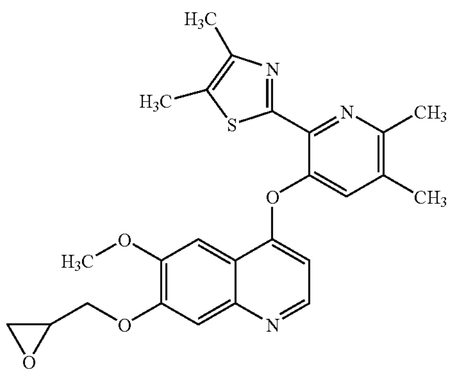 | 100 | 94 | |
| 459 | 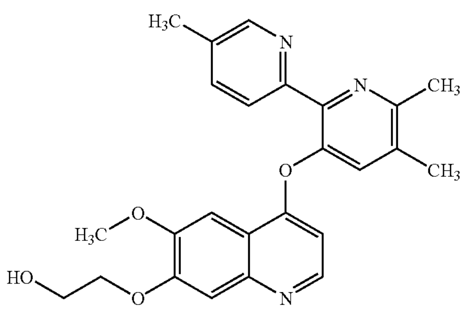 | | 98 | |
| 460 | 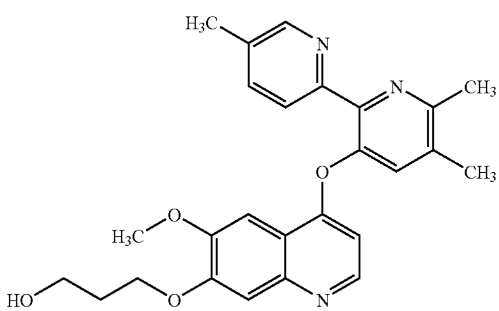 | | 97 | |

-continued
| Compound | Molecular structure | TGFβ inhibition, % | | |
|---|---|---|---|---|
| | | 10 μM | 3 μM | 1 μM |
| 461 | 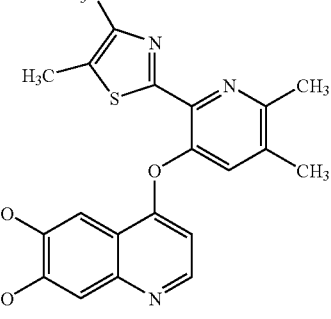 | 82 | | |
| 462 | 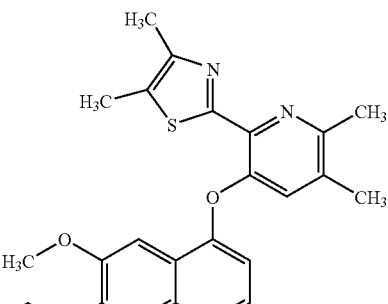 | 99 | | |
| 463 | 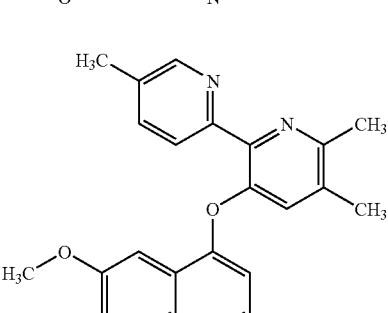 | 99 | 77 | |
| 464 | 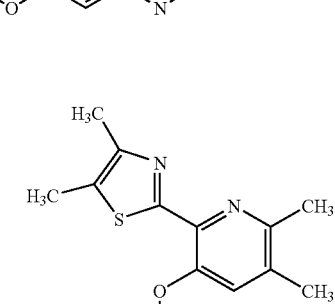 | 100 | 97 | |

-continued

| Compound | Molecular structure | TGFβ inhibition, % | | |
|---|---|---|---|---|
| | | 10 μM | 3 μM | 1 μM |
| 465 | 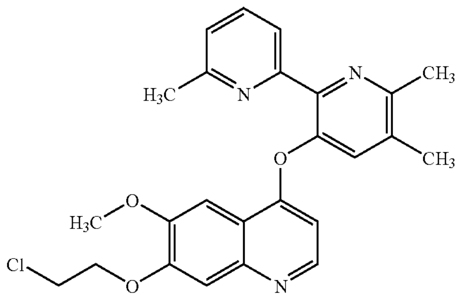 | 100 | 98 | |
| 466 | 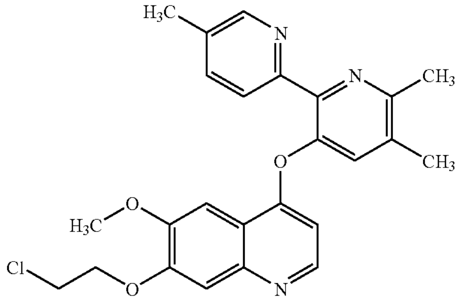 | 100 | 99 | |
| 467 | 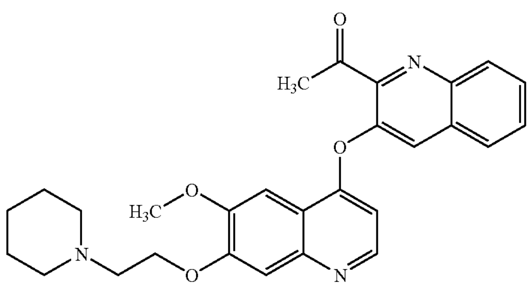 | 100 | | |
| 468 | 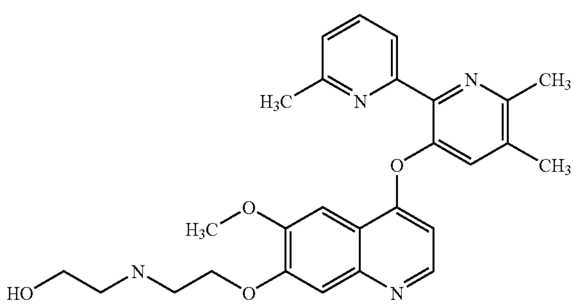 | 99 | | |
| 469 | 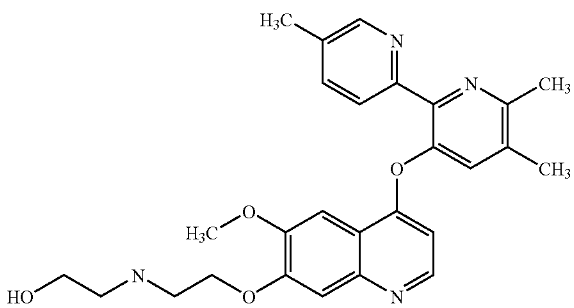 | 100 | | |

Test Example 2

Measurement of Fibrotic Inhibitory Activity Using Mouse Unilateral Ureteral Obstruction (UUO) Model The fibrotic inhibitory activity of a compound according to the present invention was evaluated using a mouse unilateral ureteral obstruction (UUO) model which is a renal fibrosis model. Compound 384 prepared in the working example was used as the test compound.

Seven-week-old male BALB/c mice (available from Charles River Japan, Inc.) were purchased and were pre-raised before use in experiments. Regarding diets and drinking water, pellets CE-2 (available from CLEA JAPAN INC.) and sterile tap water were freely fed.

The mice underwent laparotomy under pentobarbital anesthesia, and the left renal urinary duct was ligated. Thereafter, the mice underwent suturing operation and were divided into a vehicle administration group (n=7) and a test compound administration group (n=7) using the weight as an index.

The test compound was weighed, and then one drop of 1 N HCl was added to the test compound to prepare a solution. The solution was then suspended in 0.5% carboxymethylcellulose (solvent). The suspension was forcibly orally administered twice a day with an oral sonde from the day of urinary duct ligation (5, 15, or 50 mg/kg). The solvent was administered to the vehicle administration group in the same manner as described just above.

After administration for 4 days, the mouse left kidney was excised, and the hydroxyproline content as an index of organ fibrosis was measured by the following method.

Renal pieces were placed in 6 N HCl, were homogenized, and were then heated on a heat block at 130° C. for 3 hr to hydrolyze protein. Thereafter, the suspension of renal pieces was neutralized by the addition of an appropriate amount of 4 N NaOH. The neutralized suspension was centrifuged (1000 rpm, 5 min, room temperature) to obtain the supernatant as a kidney extract. A chloramine T liquid, a perchloric acid solution (a solution prepared by adding distilled water to 31.5 ml of 60% perchloric acid to bring the total volume to 100 ml), and a p-dimethylaminobenzaldehyde solution (a solution prepared by adding methylcellulose to 20 g of p-dimethylaminobenzaldehyde to bring the total volume to 100 ml) were added to the kidney extract, and a reaction was allowed to proceed at 60° C. for 20 min. The absorbance at 557 nm was then measured. The content of hydroxyproline was determined from the measured data based on a calibration curve for hydroxyproline prepared using control. Further, the content of hydroxyproline thus determined was corrected according to the weight of the homogenized kidney.

The results were as shown in Table 2. The values in the table are average of data on 7 mice for each group±standard deviation.

As a result, it was found that, as compared with the kidney of normal mice, for the mouse kidney for which the left renal urinary duct had been ligated, the content of hydroxyproline was increased and extracellular substrate accumulated within the kidney. As compared with the solvent administration group, for the group to which the compound according to the present invention had been administered, the content of hydroxyproline was lowered, indicating that the compound according to the present invention could suppress the accumulation of extracellular matrix poteins in the kidney.

TABLE 2

| Administration group | Hydroxyproline content (mg/g) |
|---|---|
| Normal mice | 392.9 ± 10.8 |
| UUO treatment + solvent | 549.4 ± 15.2 ### |
| UUO treatment + compound 384 (5 mg/kg) | 514.4 ± 20.8 |
| UUO treatment + compound 384 (15 mg/kg) | 487.7 ± 10.9 ** |
| UUO treatment + compound 384 (50 mg/kg) | 425.7 ± 14.2 *** |

In the table, ### indicates that $p < 0.001$ in Student's t-test against the normal mouse group, and  and * respectively indicate that $p < 0.01$ and $p < 0.001$ in Student's t-test against UUO treatment + solvent group.

Test Example 3

Measurement of Fibrotic Inhibitory Activity Using Mouse Unilateral Ureteral Obstruction (UUO) Model The fibrotic inhibitory activity of a compound according to the present invention was evaluated using the same model as used in Test Example 2. Compound 320 prepared in the working example was used as the test compound.

The experiment method and evaluation method were the same as those in Test Example 2, except that the compound administration was carried out by feeding a diet mixed with the compound for 10 days and the correction of hydroxyproline content was changed to the content of protein in the kidney extract.

The results were as shown in Table 3. The values in the table are average of data on five mice for each group±standard deviation.

As a result, it was found that, as compared with the solvent administration group, for the group to which the compound according to the present invention had been administered, the content of hydroxyproline was significantly lowered, indicating that the compound according to the present invention could suppress the accumulation of extracellular matrix proteins in the kidney.

TABLE 3

| Administration group | Hydroxyproline content (mg/g protein) |
|---|---|
| Normal mice | 6.7 ± 1.26 |
| UUO treatment + solvent | 12.7 ± 1.14 # |
| UUO treatment + compound 320 (0.1% mixed diet) | 9.44 ± 0.53 * |
| UUO treatment + compound 320 (0.3% mixed diet) | 9.19 ± 0.38 * |

In the table, # indicates that $p < 0.05$ in Student's t-test against the normal mouse group, and ** indicates that $p < 0.05$ in Student's t-test against UUO treatment + solvent group.

Test Example 4

Measurement of Fibrotic Inhibitory Activity Using Mouse DMN Hepatic Fibrosis Model The fibrotic inhibitory activity of a compound according to the present invention was evaluated using a mouse DMN hepatic fibrosis model as a liver fibrosis model. Compound 384 prepared in the working example was used as the test compound.

Six-week-old male BALB/c mice (available from Charles River Japan, Inc.) were purchased and were pre-raised before use in experiments.

The mice were divided into a vehicle administration group (n=6) and a test compound administration group (n=7) using the weight as an index. Thereafter, dimethylnitrosoamine (DMN) diluted with physiological saline was intraperitoneally administered at 15 mg/kg three times per week for 3 weeks to induce hepatic fibrosis.

The administration of the test compound was carried out from the first day of the DMN administration. The test compound was mixed in amounts of 0.015, 0.03, and 0.06% in powder diet CE-2 (available from CLEA JAPAN INC.), and the mixtures were fed as a diet to each mouse group.

After 21 days, the mice underwent laparotomy under ether anesthesia, and blood was collected from the heart, followed by measurement of the level of hyaluronic acid in blood as an index of hepatic fibrosis with a hyaluronic acid plate (Chugai Pharmaceutical Co., Ltd.).

The results were as shown in Table 3. The values in the table are average of data on 6 mice for each group±standard deviation.

As a result, it was found that, as compared with the liver of normal mice, for the mouse liver to which DMN had been administered, the hyaluronic acid level of blood was increased and extracellular matrix proteins accumulated within the liver. As compared with the solvent administration group, for the group to which the compound according to the present invention had been administered, the hyaluronic acid level of blood was lowered, indicating that the compound according to the present invention could suppress the accumulation of extracellular matrix proteins in the liver.

TABLE 4

| Administration group | Hyaluronic acid level of blood (ng/ml) |
| --- | --- |
| Normal mice | 113.8 ± 14.9 |
| DMN administration + solvent | 326.4 ± 47.1 ## |
| DMN administration + compound 384 (0.015% mixed diet) | 167.8 ± 25.0 * |
| DMN administration + compound 384 (0.03% mixed diet) | 108.5 ± 9.0 ** |
| DMN administration + compound 384 (0.06% mixed diet) | 97.2 ± 11.0 ** |

In the table, ## indicates that $p < 0.01$ in Student's t-test against the normal mouse group, and * and ** respectively indicate that $p < 0.05$ and $p < 0.01$ in Student's t-test against UUO treatment + solvent group.

What is claimed is:

1. A compound represented by formula (I) or a pharmaceutically acceptable salt or solvate thereof:

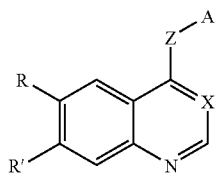

(I)

wherein
X represents CH,
Z represents —O— or —S—,
R and R', which may be the same or different, represent
1) a hydrogen atom,
2) a halogen atom, or OR" wherein R" represents a hydrogen atom, or —(CH$_2$)m-R$^a$ wherein R$^a$ represents a hydrogen atom, a halogen atom, hydroxyl, a saturated or unsaturated three- to six-membered carbocyclic or heterocyclic group, C$_{1-4}$ alkoxy, C$_{1-4}$ alkoxycarbonyl, or —NR$^b$R$^c$ wherein R$^b$ and R$^c$, which may be the same or different, represent a hydrogen atom or C$_{1-6}$ alkyl, in which the C$_{1-6}$ alkyl group is optionally substituted by hydroxyl, an oxygen atom, amino, a nitrogen atom, or C$_{1-4}$ alkyl, and R$^b$ and R$^c$ may combine with a nitrogen atom attached thereto to form a saturated or unsaturated five- or six-membered heterocyclic group, which may further comprise one or more heteroatoms, and in which the heterocyclic group is optionally substituted by C$_{1-4}$ alkyl optionally substituted by hydroxyl, hydroxyl, an oxygen atom, aminocarbonyl, C$_{1-4}$ alkoxy, C$_{1-4}$ alkoxycarbonyl, or a saturated or unsaturated five- or six-membered heterocyclic group, and the heterocyclic group may condense with another saturated or unsaturated five- or six-membered carbocyclic or heterocyclic group to form a bicyclic group; m is an integer of 1 to 6; and the alkyl chain part in this group, —(CH$_2$)m-, is optionally substituted by hydroxyl, an oxygen atom, —OR$^d$ group, wherein R$^d$ represents C$_{1-4}$ alkyl or C$_{1-4}$ alkylcarbonyl, or C$_{1-4}$ alkyl optionally substituted by hydroxyl or a halogen atom and A represents
a group of formula (b1):

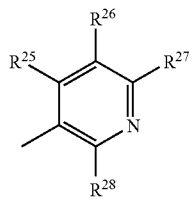

(b1)

wherein
R$^{25}$ to R$^{27}$, which may be the same or different, represent
a hydrogen atom,
a halogen atom,
C$_{1-6}$ alkyl,
C$_{1-8}$ alkoxy,
C$_{1-4}$ alkylcarbonyl
C$_{1-4}$ alkylthio, or
phenylcarbonyl,
R$^{25}$ and R$^{26}$, and R$^{26}$ and R$^{27}$ each may combine with a carbon atom attached thereto to form a saturated or unsaturated five- or six-membered carbocyclic or heterocyclic group,
R$^{28}$ represents
a hydrogen atom,
a halogen atom,
nitro,
cyano,
C$_{1-6}$ alkyl in which the alkyl group is optionally substituted by hydroxyl; phenyl; amino optionally substituted by C$_{1-4}$ alkyl; C$_{1-4}$ alkylcarbonyloxy; or a saturated or unsaturated six-membered heterocyclic group optionally substituted by C$_{1-4}$ alkyl,
C$_{1-8}$ alkoxy,
C$_{1-4}$ alkylcarbonyl,
C$_{2-6}$ alkenyl optionally substituted by a saturated or unsaturated six-membered carbocyclic group, $C_{2-6}$ alkynyl optionally substituted by $C_{1-2}$ alkylsilyl, a saturated or unsaturated three- to eight-membered carbocyclic oxy group, a saturated or unsaturated six-membered carbocyclic carbonyl or heterocyclic carbonyl group optionally substituted by $C_{1-4}$ alkyl, or a saturated or unsaturated three- to eight-membered carbocyclic or heterocyclic group in which the carbocyclic or heterocyclic group is optionally substituted by hydroxyl; cyano; a halogen atom; $C_{1-4}$ alkoxy; phenyloxy; $C_{1-4}$ alkylcarbonyl; amino optionally substituted by $C_{1-4}$ alkyl or $C_{1-4}$ alkylcarbonyl; aminocarbonyl optionally substituted by $C_{1-4}$ alkyl; or $C_{1-4}$ alkyl optionally substituted by hydroxyl or a halogen atom.

2. The compound according to claim 1, represented by formula (II), or a pharmaceutically acceptable salt or solvate thereof:

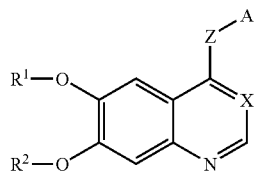

(II)

wherein

X, Z, and A are as defined in claim 1, $R^1$ and $R^2$, which may be the same or different, represent a hydrogen atom, or —$(CH_2)m$-$R^a$ wherein $R^a$ represents a hydrogen atom, a halogen atom, hydroxyl, a saturated or unsaturated three- to six-membered carbocyclic or heterocyclic group, $C_{1-4}$ alkoxy, $C_{1-4}$ alkoxycarbonyl, or —$NR^bR^c$ wherein $R^b$ and $R^c$, which may be the same or different, represent a hydrogen atom or $C_{1-6}$ alkyl, in which the $C_{1-6}$ alkyl group is optionally substituted by hydroxyl, an oxygen atom, amino, a nitrogen atom, or $C_{1-4}$ alkyl, and $R^b$ and $R^c$ may combine with a nitrogen atom attached thereto to form a saturated or unsaturated five- or six-membered heterocyclic group, which may further comprise one or more heteroatoms, and in which the heterocyclic group is optionally substituted by $C_{1-4}$ alkyl, optionally substituted by hydroxyl, hydroxyl, an oxygen atom, aminocarbonyl, $C_{1-4}$ alkoxy, $C_{1-4}$ alkoxycarbonyl, or a saturated or unsaturated five- or six-membered heterocyclic group, and the heterocyclic group may condense with another saturated or unsaturated five- or six-membered carbocyclic or heterocyclic group to form a bicyclic group; m is an integer of 1 to 6; and the alkyl chain part in this group, —$(CH_2)m$-, is optionally substituted by hydroxyl, an oxygen atom, —$OR^d$ group, wherein $R^d$ represents $C_{1-4}$ alkyl or $C_{1-4}$ alkylcarbonyl, or $C_{1-4}$ alkyl optionally substituted by hydroxyl or a halogen atom.

3. The compound according to claim 2, wherein $R^1$ and $R^2$, which may be the same or different, represent any group selected from the group consisting of a hydrogen atom, $C_{1-6}$ alkyl optionally substituted by phenyl, and groups of formulae (i) to (vi):

(i) a group of formula (i):

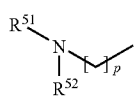

(i)

wherein $R^{51}$ and $R^{52}$, which may be the same or different, represent a hydrogen atom, or $C_{1-8}$ alkyl optionally substituted by hydroxyl, an oxygen atom, amino, or a nitrogen atom, $R^{51}$ and $R^{52}$ may combine with a nitrogen atom attached thereto to form a saturated or unsaturated five- or six-membered heterocyclic group which may further comprise one or more heteroatoms, and in which the heterocyclic group is optionally substituted by $C_{1-4}$ alkyl optionally substituted by hydroxyl, hydroxyl, an oxygen atom, aminocarbonyl, $C_{1-4}$ alkoxy, $C_{1-4}$ alkoxycarbonyl, or a saturated or unsaturated five- or six-membered heterocyclic group, and the heterocyclic group optionally formed by allowing $R^{51}$ to combine with $R^{52}$ may condense with another saturated or unsaturated five- or six-membered carbocyclic or heterocyclic group to form a bicyclic group, p is an integer of 2 to 4, and the alkyl chain part in this group is optionally substituted by hydroxyl, or —$OR^e$ group wherein $R^e$ represents $C_{1-4}$ alkyl or $C_{1-4}$ alkylcarbonyl, (ii) a group of formula (ii):

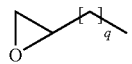

(ii)

wherein q is an integer of 1 to 4, (iii) a group of formula (iii):

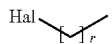

(iii)

wherein Hal represents a halogen atom, and r represents an integer of 2 to 4, (iv) a group of formula (iv):

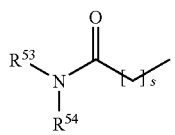

(iv)

wherein $R^{53}$ and $R^{54}$, which may be the same or different, represent a hydrogen atom, or $C_{1-6}$ alkyl optionally substituted by hydroxyl, $R^{53}$ and $R^{54}$ may combine with a nitrogen atom attached thereto to form a saturated or unsaturated five- or six-membered heterocyclic group which may further comprise one or more heteroatoms and in which the heterocyclic group is optionally substituted by $C_{1-4}$ alkyl optionally substituted by hydroxyl, or a saturated or unsaturated five- or six-membered heterocyclic group, and the heterocyclic group optionally formed by allowing $R^{53}$ to combine with $R^{54}$ may condense with another saturated or unsaturated five- or six-membered carbocyclic or heterocyclic group to form a bicyclic group, and s is an integer of 0 to 3, (v) a group of formula (v):

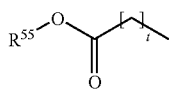

(v)

wherein $R^{55}$ represents $C_{1-4}$ alkyl and t is an integer of 0 (zero) to 3, and (vi) a group of formula (vi):

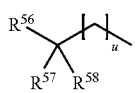

(vi)

wherein $R^{56}$, $R^{57}$ and $R^{58}$, which may be the same or different, represent a hydrogen atom, $C_{1-4}$ alkoxycarbonyl, or $C_{1-4}$ alkyl optionally substituted by hydroxyl or a halogen atom, and u is an integer of 0 (zero) to 4.

4. The compound according to claim 3, wherein formula (i) is represented by formula (i-a):

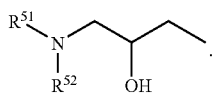

(i-a)

5. The compound according to claim 3 or 4, wherein $R^1$ and $R^2$, which may be the same or different, represent any group selected from the group consisting of a hydrogen atom, $C_{1-6}$ alkyl, benzyl, groups of formulae (i), (v), and (vi) according to claim 3, and groups of formulae (ii-a), (iii-a), and (iv-a):

formula (ii-a):

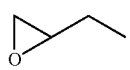

(ii-a)

formula (iii-a):

(iii-a)

wherein r1 is an integer of 2 to 4, and formula (iv-a):

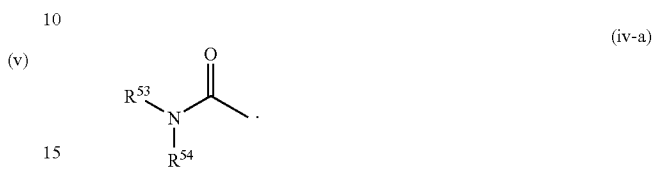

(iv-a)

6. The compound according to claim 5, wherein one of $R^1$ and $R^2$ is selected from $C_{1-6}$ alkyl, and the other substituent is selected from the group consisting of a hydrogen atom, benzyl, groups of formulae (i), (v), and (vi) according to claim 3, and groups of formulae (ii-a), (iii-a), and (iv-a) according to claim 5.

7. The compound according to claim 1, wherein at least one of R and R' is selected from the group consisting of a hydrogen atom, and a halogen atom.

8. The compound according to claim 1, wherein

R' is selected from the group consisting of a hydrogen atom, and a halogen atom.

9. The compound according to claim 1, wherein

A represents a group of formula (b1) and, in formula (b1), $R^{25}$ represents a hydrogen atom, $R^{26}$ represents a hydrogen atom, a halogen atom, or $C_{1-4}$ alkyl, $R^{27}$ represents a hydrogen atom, a halogen atom, $C_{1-4}$ alkyl, $C_{1-4}$ alkoxy, or $C_{1-4}$ alkylthio, $R^{26}$ and $R^{27}$ may combine with a carbon atom attached thereto to form an unsaturated six-membered carbocyclic or heterocyclic group, and $R^{28}$ represents a saturated or unsaturated four- to seven-membered carbocyclic or heterocyclic group in which the carbocyclic or heterocyclic group is optionally substituted by hydroxyl; cyano; a halogen atom; $C_{1-4}$ alkoxy; phenyloxy; $C_{1-4}$ alkylcarbonyl; amino optionally substituted by $C_{1-4}$ alkyl or $C_{1-4}$ alkylcarbonyl; aminocarbonyl optionally substituted by $C_{1-4}$ alkyl; or $C_{1-4}$ alkyl optionally substituted by hydroxyl or a halogen atom.

10. The compound according to claim 1, wherein when one of $R^1$ and $R^2$ is selected from $C_{1-6}$ alkyl, and the other substituent is selected from the group consisting of a hydrogen atom, benzyl, groups of formulae (i), (v), and (vi) according to claim 3, and groups of formulae (ii), (iii-a), and (iv-a) according to claim 5, A is selected from groups of formula.

11. The compound according to claim 1 or pharmaceutically acceptable salt or solvate thereof, wherein formula (I) is represented by formula (600):

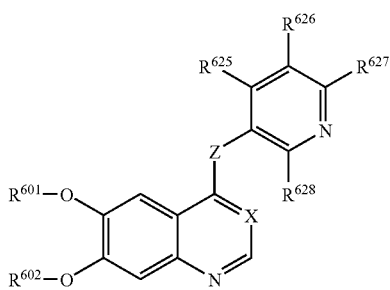
(600)

wherein
X represents CH,
Z represents —O—, or —S—,
$R^{601}$ and $R^{602}$, which may be the same or different, represent any group selected from the group consisting of
a hydrogen atom,
$C_{1-6}$ alkyl,
benzyl, and
groups of formulae (i), (ii-a), (iii-a), (iv-a), (v), and (vi),
(i) a group of formula (i):

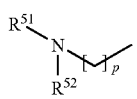

wherein
$R^{51}$ and $R^{52}$, which may be the same or different, represent
a hydrogen atom, or
$C_{1-8}$ alkyl optionally substituted by hydroxyl, an oxygen atom, amino, or a nitrogen atom,
$R^{51}$ and $R^{52}$ may combine with a nitrogen atom attached thereto to form a saturated or unsaturated five- or six-membered heterocyclic group which may further comprise one or more heteroatoms and in which the heterocyclic group is optionally substituted by $C_{1-4}$ alkyl, optionally substituted by hydroxyl, hydroxyl, an oxygen atom, aminocarbonyl, $C_{1-4}$ alkoxy, $C_{1-4}$ alkoxycarbonyl, or a saturated or unsaturated five- or six-membered heterocyclic group, and the heterocyclic group optionally formed by allowing $R^{51}$ to combine with $R^{52}$ may condense with another saturated or unsaturated five- or six-membered carbocyclic or heterocyclic group to form a bicyclic group,
p is an integer of 2 to 4, and
the alkyl chain part in this group is optionally substituted by hydroxyl, or —$OR^e$ group wherein $R^e$ represents $C_{1-4}$ alkyl or $C_{1-4}$ alkylcarbonyl,
(ii) a group of formula (ii-a):

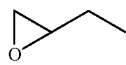

(iii) a group of formula (iii-a):

wherein r1 represents an integer of 2 to 4,
(iv) a group of formula (iv-a):

wherein
$R^{53}$ and $R^{54}$, which may be the same or different, represent
a hydrogen atom, or
$C_{1-6}$ alkyl optionally substituted by hydroxyl, and
$R^{53}$ and $R^{54}$ may combine with a nitrogen atom attached thereto to form a saturated or unsaturated five- or six-membered heterocyclic group which may further comprise one or more heteroatoms and in which the heterocyclic group is optionally substituted by $C_{1-4}$ alkyl, optionally substituted by hydroxyl, or a saturated or unsaturated five- or six-membered heterocyclic group, and the heterocyclic group optionally formed by allowing $R^{53}$ to combine with $R^{54}$ may condense with another saturated or unsaturated five- or six-membered carbocyclic or heterocyclic group to form a bicyclic group,
(v) a group of formula (v):

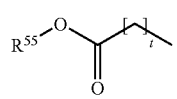

wherein
$R^{55}$ represents $C_{1-4}$ alkyl and
t is an integer of 0 (zero) to 3, and
(vi) a group of formula (vi):

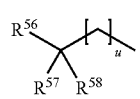

wherein
$R^{56}$, $R^{57}$ and $R^{58}$, which may be the same or different, represent
a hydrogen atom,
$C_{1-4}$ alkoxycarbonyl, or
$C_{1-4}$ alkyl optionally substituted by hydroxyl or a halogen atom, and
u is an integer of 0 (zero) to 4,
$R^{625}$ represents a hydrogen atom,
$R^{626}$ represents a hydrogen atom, a halogen atom, or $C_{1-4}$ alkyl,
$R^{627}$ represents a hydrogen atom, a halogen atom, $C_{1-4}$ alkyl, $C_{1-4}$ alkoxy, or $C_{1-4}$ alkylthio, $R^{626}$ and $R^{627}$ may combine with a carbon atom attached thereto to form an unsaturated six-membered carbocyclic or heterocyclic group, $R^{628}$ represents a hydrogen atom, a halogen atom, nitro, cyano, $C_{1-6}$ alkyl in which the alkyl group is optionally substituted by hydroxyl; phenyl; amino optionally substituted by $C_{1-4}$ alkyl; $C_{1-4}$ alkylcarbonyloxy; or a saturated or unsaturated six-membered heterocyclic group optionally substituted by $C_{1-4}$ alkyl, $C_{1-8}$ alkoxy, $C_{1-4}$ alkylcarbonyl, $C_{2-6}$ alkenyl optionally substituted by a saturated or unsaturated six-membered carbocyclic group, $C_{2-6}$ alkynyl optionally substituted by $C_{1-2}$ alkylsilyl, a saturated or unsaturated three- to eight-membered carbocyclic oxy group, a saturated or unsaturated six-membered carbocyclic carbonyl or heterocyclic carbonyl group optionally substituted by $C_{1-4}$ alkyl, or a saturated or unsaturated three- to eight-membered carbocyclic or heterocyclic group in which the carbocyclic or heterocyclic group is optionally substituted by hydroxyl; cyano; a halogen atom; $C_{1-4}$ alkoxy; phenyloxy; $C_{1-4}$ alkylcarbonyl; amino optionally substituted by $C_{1-4}$ alkyl or $C_{1-4}$ alkylcarbonyl; aminocarbonyl optionally substituted by $C_{1-4}$ alkyl; or $C_{1-4}$ alkyl optionally substituted by hydroxyl or a halogen atom.

12. The compound according to claim 11, wherein $R^{628}$ represents a saturated or unsaturated four- to seven-membered carbocyclic or heterocyclic group in which the carbocyclic or heterocyclic group is optionally substituted by hydroxyl; cyano; a halogen atom; $C_{1-4}$ alkoxy; phenyloxy; $C_{1-4}$ alkylcarbonyl; amino optionally substituted by $C_{1-4}$ alkyl or $C_{1-4}$ alkylcarbonyl; aminocarbonyl optionally substituted by $C_{1-4}$ alkyl; or $C_{1-4}$ alkyl optionally substituted by hydroxyl or a halogen atom.

13. A pharmaceutical composition comprising as an active ingredient the compound according to claim 1 or a pharmaceutically acceptable salt or solvate thereof; and a pharmaceutically acceptable carrier.

\* \* \* \* \*